United States Patent
Johns et al.

(10) Patent No.: US 8,691,991 B2
(45) Date of Patent: *Apr. 8, 2014

(54) 2-OXONAPHTHYRIDINE-3-CARBOXAMIDES HIV INTEGRASE INHIBITORS

(75) Inventors: Brian Alvin Johns, Durham, NC (US); Eric Eugene Boros, Durham, NC (US); Takshi Kawasuji, Osaka (JP); Cecilia S. Koble, Durham, NC (US); Noriyuki Kurose, Osaka (JP); Hitoshi Murai, Osaka (JP); Ronald George Sherrill, Durham, NC (US); Jason Gordon Weatherhead, Durham, NC (US)

(73) Assignees: Shionogi & Co., Ltd., Osaka (JP); ViiV Healthcare Company, Research Triangle Park, NC (US)

( * ) Notice: Subject to any disclaimer, the term of this patent is extended or adjusted under 35 U.S.C. 154(b) by 852 days.

This patent is subject to a terminal disclaimer.

(21) Appl. No.: 10/597,902

(22) PCT Filed: Feb. 10, 2005

(86) PCT No.: PCT/US2005/004085
§ 371 (c)(1),
(2), (4) Date: Aug. 11, 2006

(87) PCT Pub. No.: WO2005/077050
PCT Pub. Date: Aug. 25, 2005

(65) Prior Publication Data
US 2007/0124152 A1    May 31, 2007

Related U.S. Application Data

(60) Provisional application No. 60/543,670, filed on Feb. 11, 2004.

(51) Int. Cl.
*C07D 471/04* (2006.01)
*A61K 31/4375* (2006.01)

(52) U.S. Cl.
USPC .......................................... 546/123; 514/300

(58) Field of Classification Search
USPC .......................................... 514/300; 546/123
See application file for complete search history.

(56) References Cited

U.S. PATENT DOCUMENTS

| | | |
|---|---|---|
| 2004/0186148 A1 | 9/2004 | Shankar et al. |
| 2006/0128669 A1 | 6/2006 | Murai et al. |

FOREIGN PATENT DOCUMENTS

| | | |
|---|---|---|
| WO | 02/30931 | 4/2002 |
| WO | WO 02/30426 | 4/2002 |
| WO | WO 02/30930 | 4/2002 |
| WO | 02/36734 | 5/2002 |
| WO | 02/055079 | 7/2002 |
| WO | 02/070486 | 9/2002 |
| WO | WO 03/062204 | 7/2003 |
| WO | WO 2004/024693 | 3/2004 |
| WO | WO 2005/023189 | 3/2005 |
| WO | WO 2005/028478 | 3/2005 |
| WO | 2005/077050 | 8/2005 |

OTHER PUBLICATIONS

Zdzislaw Brzozowsk et. al. "Synthesis, anti-HIV-1 integrase, and cytotoxic activities of 4-chloro-N-(4-oxopyrimidin-2-yl)-2-mercaptobenzenesulfonamide derivatives" European Journal of Medicinal Chemistry 2007 in press doi:10.1016/j.ejmech. Aug. 13, 2007.*
Alessia Petrocchi et. al. "From dihydroxypyrimidine carboxylic acids to carboxamide HIV-1 integrase inhibitors: SAR around the amide moiety" Bioorganic & Medicinal Chemistry Letters 2007, 17, 350-353.*
Jones, M. Organic Chemistry Norton: New York, 1997, pp. 578-591.*

* cited by examiner

*Primary Examiner* — David K O Dell
(74) *Attorney, Agent, or Firm* — Wenderoth, Lind & Ponack, L.L.P.

(57) ABSTRACT

The present invention features compounds that are HIV integrase inhibitors and therefore are useful in the inhibition of HIV replication, the prevention and/or treatment of infection by HIV, and in the treatment of AIDS and/or ARC.

22 Claims, No Drawings

2-OXONAPHTHYRIDINE-3-CARBOXAMIDES HIV INTEGRASE INHIBITORS

This application is filed pursuant to 35 U.S.C. §371 as a United States National Phase Application of International Application No. PCT/U.S.2005/004085 filed Feb. 10, 2005 which claims priority from U.S. 60/543,670 filed Feb. 11, 2004.

BACKGROUND OF THE INVENTION

The Names of Parties to a Joint Research Agreement

This invention was made under a Joint Research Agreement between Shionogi & Co, Ltd. and SmithKline Beecham Corporation.

The human immunodeficiency virus ("HIV") is the causative agent for acquired immunodeficiency syndrome ("AIDS"), a disease characterized by the destruction of the immune system, particularly of CD4+ T-cells, with attendant susceptibility to opportunistic infections, and its precursor AIDS-related complex ("ARC"), a syndrome characterized by symptoms such as persistent generalized lymphadenopathy, fever and weight loss. HIV is a retrovirus; the conversion of its RNA to DNA is accomplished through the action of the enzyme reverse transcriptase. Compounds that inhibit the function of reverse transcriptase inhibit replication of HIV in infected cells. Such compounds are useful in the prevention or treatment of HIV infection in humans.

A required step in HIV replication in human T-cells is the insertion by virally-encoded integrase of proviral DNA into the host cell genome. Integration is believed to be mediated by integrase in a process involving assembly of a stable nucleoprotein complex with viral DNA sequences, cleavage of two nucleotides from the 3' termini of the linear proviral DNA and covalent joining of the recessed 3' OH termini of the proviral DNA at a staggered cut made at the host target site. The repair synthesis of the resultant gap may be accomplished by cellular enzymes.

There is continued need to find new therapeutic agents to treat human diseases. HIV integrase is an attractive target for the discovery of new therapeutics due to its important role in viral infections, particularly HIV infections. Integrase inhibitors are disclosed in WO03/062204. The compounds of the present invention exhibit advantages over previously disclosed integrase inhibitors, for example increased potency, metabolic stability, increased therapeutic index, or other pharmaceutical properties.

SUMMARY OF THE INVENTION

The present invention features compounds that are HIV integrase inhibitors and therefore are useful in the inhibition of HIV replication, the prevention and/or treatment of infection by HIV, and in the treatment of AIDS and/or ARC. The present invention features compounds of formula (I):

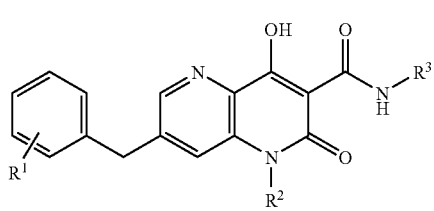

wherein:
$R^1$ is one or more substituents independently selected from hydrogen, hydroxy, CN, $N(R^aR^b)$, $C_{1-8}$alkyl, $C_{3-7}$ cycloalkyl, halogen and $C_{1-8}$ alkoxy;

$R^2$ is selected from hydrogen, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl, heterocycle, each of which may be optionally substituted with one or more substituents independently selected from the group consisting of $C_{1-8}$ alkyl, $C_{1-8}$ haloalkyl, $C_{3-7}$ cycloalkyl, $C_{2-6}$ alkenyl, $C_{3-7}$cycloalkenyl, $C_{3-6}$ alkynyl, halogen, CN, $NO_2$, $OR^a$, $N(R^aR^b)$, $S(O)_m R^a$, $SR^a$, $OS(O)_m R^a$, $S(O)_m OR^a$, $OS(O)_m OR^a$, $N(R^a)S(O)_m R^b$, $S(O)_m N(R^aR^b)$, $N(R^a)S(O)_m N(R^aR^b)$, $OS(O)_m N(R^aR^b)$, $N(R^a)S(O)_m OR^b$, $C(O)R^a$, $OC(O)R^a$, $C(O)OR^a$, $OC(O)OR^a$, $N(R^a)C(O)R^b$, $C(O)N(R^aR^b)$, $N(R^a)C(O)N(R^aR^b)$, $OC(O)N(R^aR^b)$, $N(R^a)C(O)OR^b$, $C(NR^aR^b)=N(R^a)$, $N(R^a)C(NR^aR^b)=N(R^a)$, $C(SR^a)=N(R^b)$, $C(OR^a)=N(R^b)$, $N(R^a)C(SR^a)=N(R^b)$ and heterocycle optionally substituted with oxo or $R^a$;

or optionally when $R^2$ is $C_{5-7}$ cycloalkyl, $C_{6-14}$ aralkyl, $C_{-57}$ cycloalkenyl, $C_{6-14}$ aryl or heterocycle $R^2$ may be fused to 5-7 membered carbocyclic or heterocyclic rings;

$R^a$ and $R^b$ are independently hydrogen, $NO_2$, $OR^c$, CN, $N(R^cR^d)$, $C(O)R^c$, $C(O)C(O)R^c$, $C(O)N(R^cR^d)$, $C(O)C(O)N(R^cR^d)$, $S(O)_m R^c$, $SR^c$, $S(O)_m N(R^cR^d)$, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl or heterocycle, each of which may be optionally substituted with one or more substituents independently selected from the group consisting of $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl, CN, $NO_2$, $OR^c$, $N(R^cR^d)$, $S(O)_m R^c$, $SR^c$, $OS(O)_m R^c$, $S(O)_m OR^c$, $OS(O)_m OR^c$, $N(R^c)S(O)_m R^d$, $S(O)_m N(R^cR^d)$, $N(R^c)S(O)_m N(R^cR^d)$, $OS(O)_m N(R^cR^d)$, $N(R^c)S(O)_m OR^d$, $C(O)R^c$, $OC(O)R^c$, $C(O)OR^c$, $OC(O)OR^c$, $N(R^c)C(O)R^d$, $C(O)N(R^cR^d)$, $N(R^c)C(O)N(R^cR^d)$, $OC(O)N(R^cR^d)$, $N(R^c)C(O)OR^d$, $C(NR^cR^d)=N(R^c)$, $C(SR^c)=N(R^d)$, $C(OR^c)N(R^d)$ and heterocycle;

Optionally, $R^a$ and $R^b$ may be linked together through one or more ring carbon atoms and/or ring heteroatoms including N, O, $C(R^cR^d)$, C(O), $S(O)_m$, or S to form a saturated or unsaturated 3 to 8 membered carbocyclic or heterocyclic ring;

$R^c$ and $R^d$ are independently hydrogen, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl or heterocycle;

Optionally, $R^c$ and $R^d$ may be linked together through one or more ring carbon atoms and/or ring heteroatoms including N, O, C(O) and $S(O)_m$, or S to form a saturated or unsaturated 3 to 8 membered carbocyclic or heterocyclic ring;

$R^3$ is hydrogen, hydroxy, $C_{1-8}$ alkyl, $C_{1-8}$ haloalkyl, $C_{3-7}$ cycloalkyl, $C_{2-6}$ alkenyl, $C_{3-7}$ cycloalkenyl, $C_{3-6}$ alkynyl, $N(R^aR^b)$, or heterocycle, each of which may be optionally substituted with one or more substituents independently selected from the group consisting of $C_{1-8}$ alkyl, $C_{1-8}$ haloalkyl, $C_{3-7}$ cycloalkyl, $C_{2-6}$ alkenyl, $C_{3-}$ cycloalkenyl, $C_{3-6}$ alkynyl, halogen, oxo, CN, $NO_2$, $OR^a$, $N(R^aR^b)$, $S(O)_m R^a$, $SR^a$, $OS(O)_m R^a$, $S(O)_m OR^a$, $OS(O)_m OR^a$, $N(R^a)S(O)_m R^b$, $S(O)_m N(R^aR^b)$, $N(R^a)S(O)_m N(R^aR^b)$, $OS(O)_m N(R^aR^b)$, $N(R^a)S(O)_m OR^b$, $C(O)R^a$, $OC(O)R^a$, $C(O)OR^a$, $OC(O)OR^a$, $N(R^a)C(O)R^b$, $C(O)N(R^aR^b)$, $N(R^a)C(O)N(R^aR^b)$, $OC(O)N(R^aR^b)$, $N(R^a)C(O)OR^b$, $C(NR^a)=N(R^b)$, $C(SR^a)=N(R^b)$, $C(OR^a)=N(R^b)$, $N(R^a)C(NR^aR^b)=N(R^a)$, $N(R^a)C(SR^a)=N(R^b)$, $N(R^a)C(OR^a)=N(R^b)$, and heterocycle optionally substituted by oxo or $R^a$;

m is 1 or 2;
or a pharmaceutically acceptable derivative thereof, provided that:
(a) when $R^1$ and $R^2$ are both hydrogen, then $R^3$ cannot be $C_{1-8}$ alkyl substituted with $N(R^aR^b)$ where $R^a$ and $R^b$ are both $C_{1-8}$ alkyl;
(b) when $R^1$ is halogen and $R^2$ is $C_{1-8}$ alkyl, $C_{1-8}$ alkyl substituted with $C(O)R^a$ where $R^a$ is $C_{1-8}$ alkyl, or $R^2$ is $C_{1-8}$ alkyl substituted with $S(O)_m R^a$ where $R^a$ is $C_{1-8}$ alkyl and m is 2, then $R^3$ cannot be $C_{1-8}$ alkyl or $C_{1-8}$ alkyl substituted with $OR^a$ where $R^a$ is $C_{1-8}$ alkyl.

DETAILED DESCRIPTION OF THE INVENTION

The present invention includes the compounds of Formula (I), useful in treating or preventing viral infections, particularly HIV infections, pharmaceutical compositions comprising compounds of Formula (I), and processes for preparing the compounds.

The present invention features compounds of formula (I):

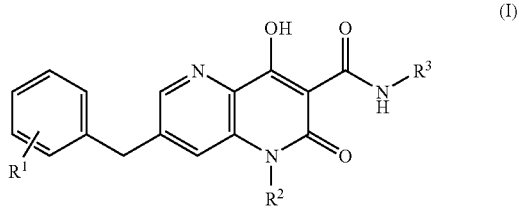

wherein:
$R^1$ is one or more substituents independently selected from hydrogen, hydroxy, CN, $N(R^aR^b)$, $C_{1-8}$ alkyl, $C_{3-7}$ cycloalkyl, halogen and $C_{1-8}$ alkoxy;
$R^2$ is selected from hydrogen, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl, heterocycle, each of which may be optionally substituted with one or more substituents independently selected from the group consisting of $C_{1-8}$ alkyl, $C_{1-8}$ haloalkyl, $C_{3-7}$ cycloalkyl, $C_{2-6}$ alkenyl, $C_{3-7}$ cycloalkenyl, $C_{3-6}$ alkynyl, halogen, CN, $NO_2$, $OR^a$, $N(R^aR^b)$, $S(O)_m R^a$, $SR^a$, $OS(O)_m R^a$, $S(O)_m OR^a$, $OS(O)_m OR^a$, $N(R^a)S(O)_m R^b$, $S(O)_m N(R^aR^b)$, $N(R^a)S(O)_m N(R^aR^b)$, $OS(O)_m N(R^aR^b)$, $N(R^a)S(O)_m OR^b$, $C(O)R^a$, $OC(O)R^a$, $C(O)OR^a$, $OC(O)OR^a$, $N(R^a)C(O)R^b$, $C(O)N(R^aR^b)$, $N(R^a)C(O)N(R^aR^b)$, $OC(O)N(R^aR^b)$, $N(R^a)C(O)OR^b$, $C(NR^aR^b)=N(R^a)$, $N(R^a)C(NR^aR^b)=N(R^a)$, $C(SR^a)=N(R^b)$, $C(OR^a)=N(R^b)$, $N(R^a)C(SR^a)=N(R^b)$ and heterocycle optionally substituted with oxo or $R^a$;
or optionally when $R^2$ is $C_{5-7}$ cycloalkyl, $C_{6-14}$ aralkyl, $C_{5-7}$ cycloalkenyl, $C_{6-14}$ aryl or heterocycle $R^2$ may be fused to 5-7 membered carbocyclic or heterocyclic rings;
$R^a$ and $R^b$ are independently hydrogen, $NO_2$, $OR^c$, CN, $N(R^cR^d)$, $C(O)R^c$, $C(O)C(O)R^c$, $C(O)N(R^cR^d)$, $C(O)C(O)N(R^cR^d)$, $S(O)_m R^c$, $SR^c$, $S(O)_m N(R^cR^d)$, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl or heterocycle, each of which may be optionally substituted with one or more substituents independently selected from the group consisting of $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl, CN, $NO_2$, $OR^c$, $N(R^cR^d)$, $S(O)_m R^c$, $SR^c$, $OS(O)_m R^c$, $S(O)_m OR^c$, $OS(O)_m OR^c$, $N(R^cR^d)$, $S(O)_m R^d$, $S(O)_m N(R^cR^d)$, $N(R^c)S(O)_m N(R^cR^d)$, $OS(O)_m N(R^cR^d)$, $N(R^c)S(O)_m OR^d$, $C(O)R^c$, $OC(O)R^c$, $C(O)OR^c$, $OC(O)OR^c$, $N(R^c)C(O)R^d$, $C(O)N(R^cR^d)$, $N(R^c)C(O)N(R^cR^d)$, $OC(O)N(R^cR^d)$, $N(R^c)C(O)OR^d$, $C(NR^cR^d)=N(R^c)$, $C(SR^c)=N(R^d)$, $C(OR^c)=N(R^d)$ and heterocycle;
Optionally, $R^a$ and $R^b$ may be linked together through one or more ring carbon atoms and/or ring heteroatoms including N, O, $C(R^cR^d)$, C(O), $S(O)_m$, or S to form a saturated or unsaturated 3 to 8 membered carbocyclic or heterocyclic ring;
$R^c$ and $R^d$ are independently hydrogen, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl or heterocycle;
Optionally, $R^c$ and $R^d$ may be linked together through one or more ring carbon atoms and/or ring heteroatoms including N, O, C(O) and $S(O)_m$, or S to form a saturated or unsaturated 3 to 8 membered carbocyclic or heterocyclic ring;
$R^3$ is hydrogen, hydroxy, $C_{1-8}$ alkyl, $C_{1-8}$ haloalkyl, $C_{3-7}$ cycloalkyl, $C_{2-6}$ alkenyl, $C_{3-7}$ cycloalkenyl, $C_{3-6}$ alkynyl, $N(R^aR^b)$, or heterocycle, each of which may be optionally substituted with one or more substituents independently selected from the group consisting of $C_{1-8}$ alkyl, $C_{1-8}$ haloalkyl, $C_{3-7}$ cycloalkyl, $C_{2-6}$ alkenyl, $C_{3-7}$ cycloalkenyl, $C_{3-6}$ alkynyl, halogen, oxo, CN, $NO_2$, $OR^a$, $N(R^aR^b)$, $S(O)_m R^a$, $SR^a$, $OS(O)_m R^a$, $S(O)_m OR^a$, $OS(O)_m OR^a$, $N(R^a)S(O)_m R^b$, $S(O)_m N(R^aR^b)$, $N(R^a)S(O)_m N(R^aR^b)$, $OS(O)_m N(R^aR^b)$, $N(R^a)S(O)_m OR^b$, $C(O)R^a$, $OC(O)R^a$, $C(O)OR^a$, $OC(O)OR^a$, $N(R^a)C(O)R^b$, $C(O)N(R^aR^b)$, $N(R^a)C(O)N(R^aR^b)$, $OC(O)N(R^aR^b)$, $N(R^a)C(O)OR^b$, $C(NR^a)N(R^b)$, $C(SR^a)=N(R^b)$, $C(OR^a)=N(R^b)$, $N(R^a)C(NR^aR^b)=N(R^a)$, $N(R^a)C(SR^a)=N(R^b)$, $N(R^a)C(OR^a)=N(R^b)$, and heterocycle optionally substituted by oxo or $R^a$;
m is 1 or 2;
or a pharmaceutically acceptable derivative thereof, provided that:
(a) when $R^1$ and $R^2$ are both hydrogen, then $R^3$ cannot be $C_{1-8}$ alkyl substituted with $N(R^aR^b)$ where $R^a$ and $R^b$ are both $C_{1-8}$ alkyl;
(b) when $R^1$ is halogen and $R^2$ is $C_{1-8}$ alkyl, $C_{1-8}$ alkyl substituted with $C(O)R^a$ where $R^a$ is $C_{1-8}$ alkyl, or $R^2$ is $C_{1-8}$ alkyl substituted with $S(O)_m R^a$ where $R^a$ is $C_{1-8}$ alkyl and m is 2, then $R^3$ cannot be $C_{1-8}$ alkyl or $C_{1-8}$ alkyl substituted with $OR^a$ where $R^a$ is $C_{1-8}$ alkyl.

The term "alkyl", alone or in combination with any other term, refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "cycloalkyl" refers to a saturated or partially saturated carbocyclic ring composed of 3-6 carbons in any chemically stable configuration. Examples of suitable carbocyclic groups include cyclopropyl, cyclobutyl, cyclopentyl, cyclohexyl, and cyclohexenyl.

The term "alkenyl," alone or in combination with any other term, refers to a straight-chain or branched-chain alkyl group with at least one carbon-carbon double bond. Examples of alkenyl radicals include, but are not limited to, ethenyl, propenyl, isopropenyl, butenyl, isobutenyl, pentenyl, hexenyl, hexadienyl and the like.

The term "alkynyl" refers to hydrocarbon groups of either a straight or branched configuration with one or more carbon-carbon triple bonds which may occur in any stable point along the chain, such as ethynyl, propynyl, butynyl, pentynyl, and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl" alone or in combination with any other term, refers to a carbocyclic aromatic moiety (such as phenyl or naphthyl) containing the specified number of carbon atoms, preferably from 6-14 carbon atoms, and more preferably from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like.

The term "aralkyl" refers to an alkyl group substituted by an aryl group. Examples of aralkyl groups include, but are not limited to, benzyl, phenethyl and the like.

The term "heterocycle," "heterocyclic," and "heterocyclyl" as used herein, refer to a 3- to 7-membered monocyclic heterocyclic ring or 8- to 11-membered bicyclic heterocyclic ring system any ring of which is either saturated, partially saturated or unsaturated, and which may be optionally benzofused if monocyclic. Each heterocycle consists of one or more carbon atoms and from one to four heteroatoms selected from the group consisting of N, O and S, and wherein the nitrogen and sulfur heteroatoms may optionally be oxidized, and the nitrogen atom may optionally be quaternized, and including any bicyclic group in which any of the above-defined heterocyclic rings is fused to a benzene ring. The heterocyclic ring may be attached at any carbon or heteroatom, provided that the attachment results in the creation of a stable structure. Preferred heterocycles include 5-7 membered monocyclic heterocycles and 8-10 membered bicyclic heterocycles. When the heterocyclic ring has substituents, it is understood that the substituents may be attached to any atom in the ring, whether a heteroatom or a carbon atom, provided that a stable chemical structure results. "Heteroaromatics" or "heteroaryl" are included within the heterocycles as defined above and generally refers to a heterocycle in which the ring system is an aromatic monocyclic or polycyclic ring radical containing five to twenty carbon atoms, preferably five to ten carbon atoms, in which one or more ring carbons, preferably one to four, are each replaced by a heteroatom such as N, O, S and P. Preferred heteroaryl groups include 5-6 membered monocyclic heteroaryls and 8-10 membered bicyclic heteroaryls. Also included within the scope of the term "heterocycle", "heterocyclic" or "heterocyclyl" is a group in which a non-aromatic heteroatom-containing ring is fused to one or more aromatic rings, such as in an indolinyl, chromanyl, phenanthridinyl or tetrahydro-quinolinyl, where the radical or point of attachment is on the non-aromatic heteroatom-containing ring. Unless otherwise indicated, the term "heterocycle", "heterocyclic" or "heterocyclyl" also included each possible positional isomer of a heterocyclic radical, such as in 1-indolinyl, 2-indolinyl, 3-indolinyl. Examples of heterocycles include imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, oxadiazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

The term "heteroatom" means nitrogen, oxygen, or sulfur and includes any oxidized form of nitrogen, such as N(O) {N$^+$—O$^-$} and sulfur such as S(O) and S(O)$_2$, and the quaternized form of any basic nitrogen.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure, i.e., the R and S configurations for each asymmetric center. Therefore, racemates and racemic mixtures, single enantiomers, diastereomeric mixtures and individual diastereoisomers of the present compounds are expressly included within the scope of the invention. Although the specific compounds exemplified herein may be depicted in a particular stereochemical configuration, compounds having either the opposite stereochemistry at any given chiral center or mixtures thereof are also envisioned.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are also within the scope of this invention.

It will be apparent to one skilled in the art that certain compounds of this invention may exist in alternative tautomeric forms. All such tautomeric forms of the present compounds are within the scope of the invention. Unless otherwise indicated, the representation of either tautomer is meant to include the other.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylactically effective amount" refers to an amount effective in preventing a virus infection, for example an HIV infection, or preventing the occurrence of symptoms of such an infection, in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiviral agent.

The term "treatment" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. Treatment includes prophylaxis which refers to preventing a disease or condition or preventing the occurrence of symptoms of such a disease or condition, in a patient. As used herein, the term "patient" refers to a mammal, including a human.

As used herein, the term "subject" refers to a patient, animal or a biological sample. The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

Throughout this specification, the word "comprise" or variations such as "comprises" or "comprising" will be understood to imply the inclusion of a stated integer or groups of integers but not the exclusion of any other integer or group of integers.

As used herein, the compounds according to the invention are defined to include pharmaceutically acceptable derivatives thereof. A "pharmaceutically acceptable derivative" means any pharmaceutically acceptable salt, ester, salt of an ester, ether, or other derivative of a compound of this invention which, upon administration to a recipient, is capable of providing directly or indirectly a compound of this invention or an inhibitorily active metabolite or residue thereof. Particularly favored derivatives and prodrugs are those that increase the bioavailability of the compounds of this invention when such compounds are administered to a mammal, for example, by allowing an orally administered compound to be more readily absorbed into the blood, or which enhance delivery of the parent compound to a biological compartment, for example, the brain or lymphatic system, relative to the parent species.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium, $NW_4^+$ (wherein W is $C_{1-4}$ alkyl) and other amine salts. Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$ alkyl group). Preferred salts include sodium, calcium, potassium, magnesium, choline, meglumine, hydrochloride, and quaternary ammonium.

Other compounds of this invention may be prepared by one skilled in the art following the teachings of the specification coupled with knowledge in the art using reagents that are readily synthesized or commercially available.

Any reference to any of the above compounds also includes a reference to a pharmaceutically acceptable salt thereof.

Salts of the compounds of the present invention may be made by methods known to a person skilled in the art. For example, treatment of a compound of the present invention with an appropriate base or acid in an appropriate solvent will yield the corresponding salt.

Esters of the compounds of the present invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group.

Ethers of the compounds of the present invention include, but are not limited to methyl, ethyl, butyl and the like.

The present invention features a compound of formula (I) wherein:

$R^1$ is hydrogen or halogen;

$R^2$ is
(a) hydrogen;
(b) $C_{1-8}$ alkyl optionally substituted with $C_{3-7}$cycloalkyl, $OR^a$, $N(R^a R^b)$, $C(O)R^a$, $C(O)N(R^a R^b)$, or heterocycle optionally substituted with oxo or $R^a$; or
(c) $C_{6-14}$ aralkyl optionally substituted with $S(O)_m R^a$ or $R^a$; wherein m is 2;

$R^3$ is
(a) $C_{1-8}$ alkyl optionally substituted with $C_{1-8}$ alkyl, $C_{3-7}$ cycloalkyl, $OR^a$, $SR^a$, $C(O)N(R^a R^b)$, $NR^a C(O)R^b$, or heterocycle optionally substituted with oxo or $R^a$;
(b) $C_{3-7}$ cycloalkyl;
(c) $C_{1-8}$ haloalkyl;
(d) heterocycle optionally substituted with oxo; or
(e) $N(R^a R^b)$;

wherein $R^a$ and $R^b$ are independently hydrogen, $OR^c$, $SR^c$, $C_{1-8}$ alkyl, $C_{6-14}$ aryl or heterocycle, each of which each of which may be optionally substituted with one or more substituents independently selected from the group consisting of $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl, CN, $NO_2$, $OR^c$, $N(R^c R^d)$, $S(O)_m R^c$, $SR^c$, $OS(O)_m R^c$, $S(O)_m OR^c$, $OS(O)_m OR^c$, $N(R^c)S(O)_m R^d$, $S(O)_m N(R^c R^d)$, $N(R^c)S(O)_m N(R^c R^d)$, $OS(O)_m N(R^c R^d)$, $N(R^c)S(O)_m OR^d$, $C(O)R^c$, $OC(O)R^c$, $C(O)OR^c$, $OC(O)OR^c$, $N(R^c)C(O)R^d$, $C(O)N(R^c R^d)$, $N(R^c)C(O)N(R^c R^d)$, $OC(O)N(R^c R^d)$, $N(R^c)C(O)OR^d$, $C(NR^c R^d)=N(R^c)$, $C(SR^c)N(R^d)$, $C(OR^c)=N(R^d)$ and heterocycle;

wherein $R^c$ is hydrogen, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl or heterocycle;

$R^c$ and $R^d$ are independently hydrogen, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl or heterocycle;

or a pharmaceutically acceptable derivative thereof provided that
(a) when $R^1$ and $R^2$ are both hydrogen, then $R^3$ cannot be $C_{1-8}$ alkyl substituted with $N(R^aR^b)$ where $R^a$ and $R^b$ are both $C_{1-8}$ alkyl;
(b) when $R^1$ is halogen and $R^2$ is $C_{1-8}$ alkyl, $C_{1-8}$ alkyl substituted with $C(O)R^a$ where $R^a$ is $C_{1-8}$ alkyl, then $R^3$ cannot be $C_{1-8}$ alkyl or $C_{1-8}$ alkyl substituted with $OR^a$ where $R^a$ is $C_{1-8}$ alkyl.

The present invention features a compound of formula (I) wherein
$R^1$ is hydrogen or halogen;
$R^2$ is
  (a) hydrogen;
  (b) $C_{1-8}$ alkyl optionally substituted with $C_{3-7}$ cycloalkyl, $OR^a$, $N(R^aR^b)$, $C(O)R^a$, $C(O)N(R^aR^b)$, or heterocycle optionally substituted with oxo or $R^a$; or
  (c) $C_{6-14}$ aralkyl optionally substituted with $S(O)_mR^a$ or $R^a$; wherein m is 2;
$R^3$ is
  (a) $C_{1-8}$ alkyl optionally substituted with $C_{1-8}$ alkyl, $C_{3-7}$ cycloalkyl, $OR^a$, $SR^a$, $C(O)N(R^aR^b)$, $NR^aC(O)R^b$, or heterocycle optionally substituted with oxo or $R^a$;
  (b) $C_{3-7}$ cycloalkyl;
  (c) $C_{1-8}$ haloalkyl;
  (d) heterocycle optionally substituted with oxo; or
  (e) $N(R^aR^b)$;
wherein $R^a$ and $R^b$ are independently hydrogen, $NO_2$, $OR^c$, $C(O)R^c$, $C_{1-8}$ alkyl optionally substituted with $OR^c$, $C_{6-14}$ aryl or heterocycle;
wherein $R^c$ is hydrogen, $C_{1-8}$ alkyl or $C_{6-14}$ aryl;
or a pharmaceutically acceptable derivative thereof provided that
(a) when $R^1$ and $R^2$ are both hydrogen, then $R^3$ cannot be $C_{1-8}$ alkyl substituted with $N(R^aR^b)$ where $R^a$ and $R^b$ are both $C_{1-8}$ alkyl;
(b) when $R^1$ is halogen and $R^2$ is $C_{1-8}$ alkyl, $C_{1-8}$ alkyl substituted with $C(O)R^a$ where $R^a$ is $C_{1-8}$ alkyl, then $R^3$ cannot be $C_{1-8}$ alkyl or $C_{1-8}$ alkyl substituted with $OR^a$ where $R^a$ is $C_{1-8}$ alkyl.

The present invention further features a compound of formula (I) wherein
$R^1$ is hydrogen or halogen;
$R^2$ is
  (a) hydrogen;
  (b) $C_{1-8}$ alkyl substituted with $C_{3-7}$ cycloalkyl, $C(O)R^a$ wherein $R^a$ is heterocycle, or heterocycle optionally substituted with oxo; or
  (c) $C_{6-14}$ aralkyl optionally substituted with $S(O)_mR^a$ wherein $R^a$ is $C_{1-8}$ alkyl and m is 2;
$R^3$ is
  (a) $C_{1-8}$ alkyl optionally substituted with $C_{1-8}$ alkyl, $C_{3-7}$ cycloalkyl, $OR^a$, $SR^a$, $C(O)N(R^aR^b)$, $NR^aC(O)R^b$, or heterocycle optionally substituted with oxo or $R^a$; wherein $R^a$ and $R^b$ are independently hydrogen, $NO_2$, $OR^c$, $C(O)R^c$, $C_{1-8}$ alkyl optionally substituted with $OR^c$, $C_{6-14}$ aryl or heterocycle;
  (b) $C_{3-7}$ cycloalkyl;
  (c) $C_{1-8}$ haloalkyl;
  (d) heterocycle optionally substituted with oxo; or
  (e) $N(R^aR^b)$ wherein $R^a$ and $R^b$ are independently hydrogen, $NO_2$, $OR^c$, $C(O)R^c$, $C_{1-8}$ alkyl optionally substituted with $OR^c$, $C_{6-14}$ aryl or heterocycle;
wherein $R^c$ is hydrogen, $C_{1-8}$ alkyl or $C_{6-14}$ aryl
or a pharmaceutically acceptable derivative thereof.

The present invention features a compound of formula (Ia)

(Ia)

wherein:
$R^2$ is selected from hydrogen, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl, heterocycle, each of which may be optionally substituted with one or more substituents independently selected from the group consisting of $C_{1-8}$ alkyl, $C_{1-8}$ haloalkyl, $C_{3-7}$ cycloalkyl, $C_{2-6}$ alkenyl, $C_{3-7}$ cycloalkenyl, $C_{3-6}$ alkynyl, halogen, CN, $NO_2$, $OR^a$, $N(R^aR^b)$, $S(O)_m R^a$, $SR^a$, $OS(O)_mR^a$, $S(O)_mOR^a$, $OS(O)_mOR^a$, $N(R^a)S(O)_mR^b$, $S(O)_mN(R^aR^b)$, $N(R^a)S(O)_mN(R^aR^b)$, $OS(O)_mN(R^aR^b)$, $N(R^a)S(O)_mOR^b$, $C(O)R^a$, $OC(O)R^a$, $C(O)OR^a$, $OC(O)OR^a$, $N(R^a)C(O)R^b$, $C(O)N(R^aR^b)$, $N(R^a)C(O)N(R^aR^b)$, $OC(O)N(R^aR^b)$, $N(R^a)C(O)OR^b$, $C(NR^aR^b)=N(R^a)$, $N(R^a)C(NR^aR^b)=N(R^a)$, $C(SR^a)=N(R^b)$, $C(OR^a)=N(R^b)$, $N(R^a)C(SR^a)=N(R^b)$ and heterocycle optionally substituted with oxo or $R^a$;
or optionally when $R^2$ is $C_{5-7}$ cycloalkyl, $C_{6-14}$ aralkyl, $C_{5-7}$ cycloalkenyl, $C_{6-14}$ aryl or heterocycle $R^2$ may be fused to 5-7 membered carbocyclic or heterocyclic rings;

$R^a$ and $R^b$ are independently hydrogen, $NO_2$, $OR^c$, CN, $N(R^cR^d)$, $C(O)R^c$, $C(O)C(O)R^c$, $C(O)N(R^cR^d)$, $C(O)C(O)N(R^cR^d)$, $S(O)_mR^c$, $SR^c$, $S(O)_mN(R^cR^d)$, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl or heterocycle, each of which may be optionally substituted with one or more substituents independently selected from the group consisting of $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl, CN, $NO_2$, $OR^c$, $N(R^cR^d)$, $S(O)_mR^c$, $SR^c$, $OS(O)_mR^c$, $S(O)_mOR^c$, $OS(O)_mOR^c$, $N(R^c)S(O)_mR^d$, $S(O)_mN(R^cR^d)$, $N(R^c)S(O)_mN(R^cR^d)$, $OS(O)_mN(R^cR^d)$, $N(R^c)S(O)_mOR^d$, $C(O)R^c$, $OC(O)R^c$, $C(O)OR^c$, $OC(O)OR^c$, $N(R^c)C(O)R^d$, $C(O)N(R^cR^d)$, $N(R^c)C(O)N(R^cR^d)$, $OC(O)N(R^cR^d)$, $N(R^c)C(O)OR^d$, $C(NR^cR^d)=N(R^c)$, $C(SR^c)=N(R^d)$, $C(OR^c)=N(R^d)$ and heterocycle;

Optionally, $R^a$ and $R^b$ may be linked together through one or more ring carbon atoms and/or ring heteroatoms including N, O, $C(R^cR^d)$, $C(O)$, $S(O)_m$, or S to form a saturated or unsaturated 3 to 8 membered carbocyclic or heterocyclic ring;

$R^c$ and $R^d$ are independently hydrogen, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl or heterocycle;

Optionally, $R^c$ and $R^d$ may be linked together through one or more ring carbon atoms and/or ring heteroatoms including N, O, $C(O)$ and $S(O)_m$, or S to form a saturated or unsaturated 3 to 8 membered carbocyclic or heterocyclic ring;

$R^3$ is hydrogen, hydroxy, $C_{1-8}$ alkyl, $C_{1-8}$ haloalkyl, $C_{3-7}$ cycloalkyl, $C_{2-6}$ alkenyl, $C_{3-7}$ cycloalkenyl, $C_{3-6}$ alkynyl, $NR^aR^b$), or heterocycle, each of which may be optionally substituted with one or more substituents independently selected from the group consisting of $C_{1-8}$ alkyl, $C_{1-8}$ haloalkyl, $C_{3-7}$ cycloalkyl, $C_{2-6}$ alkenyl, $C_{3-7}$ cycloalkenyl, $C_{3-6}$ alkynyl, halogen, oxo, CN, $NO_2$, $OR^a$, $N(R^aR^b)$, $S(O)_m R^a$, $SR^a$, $OS(O)_mR^a$, $S(O)_mOR^a$, $OS(O)_mOR^a$, $N(R^a)S(O)_mR^b$, $S(O)_mN(R^aR^b)$, $N(R^a)S(O)_mN(R^aR^b)$, $OS(O)_mN(R^aR^b)$, $N(R^a)S(O)_mOR^b$, $C(O)R^a$, $OC(O)R^a$, $C(O)OR^a$, $OC(O)OR^a$, $N(R^a)C(O)R^b$, $C(O)N(R^aR^b)$, $N(R^a)C(O)N(R^aR^b)$, $OC(O)N(R^aR^b)$, $N(R^a)C(O)OR^b$, $C(NR^a)=N(R^b)$, $C(SR^a)=N(R^b)$, $C(OR^a)=N(R^b)$, $N(R^a)C(NR^aR^b)=N(R^a)$, $N(R^a)C(SR^a)=N(R^b)$, $N(R^a)C(OR^a)=N(R^b)$, and heterocycle optionally substituted by oxo or $R^a$;

m is 1 or 2;

or a pharmaceutically acceptable derivative thereof, provided that:

when $R^1$ is halogen and $R^2$ is $C_{1-8}$ alkyl, $C_{1-8}$ alkyl substituted with $C(O)R^a$ where $R^a$ is $C_{1-8}$ alkyl, or $R^2$ is $C_{1-8}$ alkyl substituted with $S(O)_mR^a$ where $R^a$ is $C_{1-8}$ alkyl and m is 2, then $R^3$ cannot be $C_{1-8}$ alkyl or $C_{1-8}$ alkyl substituted with $OR^a$ where $R^a$ is $C_{1-8}$ alkyl.

The present invention features a compound of formula (Ia) wherein:

$R^2$ is
- (a) hydrogen;
- (b) $C_{1-8}$ alkyl optionally substituted with $C_{3-7}$ cycloalkyl, $OR^a$, $N(R^aR^b)$, $C(O)R^a$, $C(O)N(R^aR^b)$, or heterocycle optionally substituted with oxo or $R^a$; or
- (c) $C_{6-14}$ aralkyl optionally substituted with $S(O)_mR^a$ or $R^a$; wherein m is 2;

$R^3$ is
- (a) $C_{1-8}$ alkyl optionally substituted with $C_{1-8}$ alkyl, $C_{3-7}$ cycloalkyl, $OR^a$, $SR^a$, $C(O)N(R^aR^b)$, $NR^aC(O)R^b$, or heterocycle optionally substituted with oxo or $R^a$;
- (b) $C_{3-7}$ cycloalkyl;
- (c) $C_{1-8}$ haloalkyl;
- (d) heterocycle optionally substituted with oxo; or
- (e) $N(R^aR^b)$;

wherein $R^a$ and $R^b$ are independently hydrogen, $OR^c$, $SR^c$, $C_{1-8}$ alkyl, $C_{6-14}$ aryl or heterocycle, each of which each of which may be optionally substituted with one or more substituents independently selected from the group consisting of $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl, CN, $NO_2$, $OR^c$, $N(R^cR^d)$, $S(O)_mR^c$, $SR^c$, $OS(O)_mR^c$, $S(O)_mOR^c$, $OS(O)_mOR^c$, $N(R^c)S(O)_mR^d$, $S(O)_mN(R^cR^d)$, $N(R^c)S(O)_mN(R^cR^d)$, $OS(O)_mN(R^cR^d)$, $N(R^c)S(O)_mOR^d$, $C(O)R^c$, $OC(O)R^c$, $C(O)OR^c$, $OC(O)OR^c$, $N(R^c)C(O)R^d$, $C(O)N(R^cR^d)$, $N(R^c)C(O)N(R^cR^d)$, $OC(O)N(R^cR^d)$, $N(R^c)C(O)OR^d$, $C(NR^cR^d)=N(R^c)$, $C(SR^c)=N(R^d)$, $C(OR^c)=N(R^d)$ and heterocycle;

wherein $R^c$ is hydrogen, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl or heterocycle;

$R^c$ and $R^d$ are independently hydrogen, $C_{1-8}$ alkyl, $C_{1-8}$ haloalkyl, $C_{3-7}$ cycloalkyl, $C_{6-14}$ aralkyl, $C_{2-6}$ alkenyl, $C_{3-7}$ cycloalkenyl, $C_{3-6}$ alkynyl, $C_{6-14}$ aryl or heterocycle;

or a pharmaceutically acceptable derivative thereof provided that when $R^1$ is halogen and $R^2$ is $C_{1-8}$ alkyl, $C_{1-8}$ alkyl substituted with $C(O)R^a$ where $R^a$ is $C_{1-8}$ alkyl, then $R^3$ cannot be $C_{1-8}$ alkyl or $C_{1-8}$ alkyl substituted with $OR^a$ where $R^a$ is $C_{1-8}$ alkyl.

The present invention features a compound of formula (Ia) wherein:

$R^2$ is
- (a) hydrogen;
- (b) $C_{1-8}$ alkyl optionally substituted with $C_{3-7}$ cycloalkyl, $OR^a$, $N(R^aR^b)$, $C(O)R^a$, $C(O)N(R^aR^b)$, or heterocycle optionally substituted with oxo or $R^a$; or
- (c) $C_{6-14}$ aralkyl optionally substituted with $S(O)_mR^a$ or $R^a$; wherein m is 2;

$R^3$ is
- (a) $C_{1-8}$ alkyl optionally substituted with $C_{1-8}$ alkyl, $C_{3-7}$ cycloalkyl, $OR^a$, $SR^a$, $C(O)N(R^aR^b)$, $NR^aC(O)R^b$, or heterocycle optionally substituted with oxo or $R^a$;
- (b) $C_{3-7}$ cycloalkyl;
- (c) $C_{1-8}$ haloalkyl;
- (d) heterocycle optionally substituted with oxo; or
- (e) $N(R^aR^b)$;

wherein $R^a$ and $R^b$ are independently hydrogen, $NO_2$, $OR^c$, $C(O)R^c$, $C_{1-8}$ alkyl optionally substituted with $OR^c$, $C_{6-14}$ aryl or heterocycle;

wherein $R^c$ is hydrogen, $C_{1-8}$ alkyl or $C_{6-14}$ aryl;

or a pharmaceutically acceptable derivative thereof provided that when $R^1$ is halogen and $R^2$ is $C_{1-8}$ alkyl, $C_{1-8}$ alkyl substituted with $C(O)R^a$ where $R^a$ is $C_{1-8}$ alkyl, then $R^3$ cannot be $C_{1-8}$ alkyl or $C_{1-8}$ alkyl substituted with $OR^a$ where $R^a$ is $C_{1-8}$ alkyl.

The present invention further features a compound of formula (Ia) wherein:

$R^2$ is
- (a) hydrogen;
- (b) $C_{1-8}$ alkyl substituted with $C_{3-7}$ cycloalkyl, $C(O)R^a$ wherein $R^a$ is heterocycle, or heterocycle optionally substituted with oxo; or
- (c) $C_{6-14}$ aralkyl optionally substituted with $S(O)_mR^a$ wherein $R^a$ is $C_{1-8}$ alkyl and m is 2;

$R^3$ is
- (a) $C_{1-8}$ alkyl optionally substituted with $C_{1-8}$ alkyl, $C_{3-7}$ cycloalkyl, $OR^a$, $SR^a$, $C(O)N(R^aR^b)$, $NR^aC(O)R^b$, or heterocycle optionally substituted with oxo or $R^a$; wherein $R^a$ and $R^b$ are independently hydrogen, $NO_2$, $OR^c$, $C(O)R^c$, $C_{1-8}$alkyl optionally substituted with $OR^c$, $C_{6-14}$ aryl or heterocycle;
- (b) $C_{3-7}$ cycloalkyl;
- (c) $C_{1-8}$ haloalkyl;
- (d) heterocycle optionally substituted with oxo; or
- (e) $N(R^aR^b)$ wherein $R^a$ and $R^b$ are independently hydrogen, $NO_2$, $OR^c$, $C(O)R^c$, $C_{1-8}$ alkyl optionally substituted with $OR^c$, $C_{6-14}$ aryl or heterocycle;

wherein $R^c$ is hydrogen, $C_{1-8}$ alkyl or $C_{6-14}$aryl;

or a pharmaceutically acceptable derivative thereof.

The present invention also features a compound of formula (I) as described above wherein $R^1$ is one or more substituents independently selected from hydroxy, CN, $N(R^aR^b)$, $C_{1-8}$ alkyl, $C_{3-7}$ cycloalkyl, halogen and $C_{1-8}$ alkoxy; and pharmaceutically acceptable salts thereof. The present invention also features a compound of formula (I) as described above wherein $R^1$ is halogen or a pharmaceutically acceptable salt thereof.

The present invention also features a compound of formula (Ia) as described above wherein $R^2$ is $C_{1-8}$ alkyl optionally substituted with $C(O)N(R^aR^b)$, wherein $R^a$ and $R^b$ are hydrogen or $C_{1-8}$ alkyl and $R^3$ is $C_{1-8}$ alkyl optionally substituted with $OR^a$, wherein $OR^a$ is hydrogen or $C_{1-8}$ alkyl, or a pharmaceutically acceptable salt thereof.

The present invention features a compound selected from the group consisting of:
Ethyl 7-(4-fluorobenzyl)-4-hydroxy-2-oxo-1,2-dihydro-1,5-naphthyridine-3-carboxylate;
7-(4-fluorobenzyl)-4-hydroxy-N-(2-methoxyethyl)-2-oxo-1,2-dihydro-1,5-naphthyridine-3-carboxamide;
7-benzyl-N-(cyclopropylmethyl)-4-hydroxy-2-oxo-1,2-dihydro-1,5-naphthyridine-3-carboxamide;
Ethyl 7-benzyl-4-hydroxy-1-[4-(methylsulfonyl)benzyl]-2-oxo-1,2-dihydro- 1,5-naphthyridine-3-carboxylate;
7-Benzyl-4-hydroxy-1-[4-(methylsulfonyl)benzyl]-2-oxo-N-(pyridine-4-ylmethyl)-1,2-dihydro-1,5-naphthyridine-3-carboxamide;
Methyl 7-benzyl-4-hydroxy-2-oxo-1,2-dihydro-1,5-naphthyridine-3-carboxylate;
7-Benzyl-N,4-dihydroxy-2-oxo-1,2-dihydro-1,5-naphthyridine-3-carboxamide;
Ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate;
N-Cyclopropyl-7-(4-fluorobenzyl)-4-hydroxy-2-oxo-1-[2-(2-oxopyrrolidin-1-yl)ethyl]-1,2-dihydro-1,5-naphthyridine-3-carboxamide;
7-(4-Fluorobenzyl)-4-hydroxy-N-(2-morpholin-4-ylethyl)-2-oxo-1-[2-(2-oxopyrrolidin-1-yl)ethyl]-1,2-dihydro-1,5-naphthyridine-3-carboxamide;
Ethyl 7-benzyl-4-hydroxy-1-(2-morpholin-4-yl-2-oxoethyl)-2-oxo-1,2-dihydro-1,5-naphthyridine-3-carboxylate;
7-Benzyl-4-hydroxy-N-(2-methoxyethyl)-1-(2-morpholin-4-yl-2-oxoethyl)-2-oxo-1,2-dihydro-1,5-naphthyridine-3-carboxamide;
4-Hydroxy-N-(2-methylpropyl)-2-oxo-7-(phenylmethyl)-1,2-dihydro-1,5-naphthyridine-3-carboxamide;
N-Cycloheptyl-4-hydroxy-2-oxo-7-(phenylmethyl)-1,2-dihydro-1,5-naphthyridine-3-carboxamide;
N-Cyclopentyl-4-hydroxy-2-oxo-7-(phenylmethyl)-1,2-dihydro-1,5-naphthyridine-3-carboxamide;
N-Cyclobutyl-4-hydroxy-2-oxo-7-(phenylmethyl)-1,2-dihydro-1,5-naphthyridine-3-carboxamide;
4-Hydroxy-N-[2-(methyloxy)ethyl]-2-oxo-7-(phenylmethyl)-1,2-dihydro-1,5-naphthyridine-3-carboxamide;
4-Hydroxy-2-oxo-N-(2-phenylethyl)-7-(phenylmethyl)-1,2-dihydro-1,5-naphthyridine-3-carboxamide;
4-Hydroxy-2-oxo-N-(1-phenylethyl)-7-(phenylmethyl)-1,2-dihydro-1,5-naphthyridine-3-carboxamide;
N-(Cyclohexylmethyl)-4-hydroxy-2-oxo-7-(phenylmethyl)-1,2-dihydro-1,5-naphthyridine-3-carboxamide;
N-(2-Furanylmethyl)-4-hydroxy-2-oxo-7-(phenylmethyl)-1,2-dihydro-1,5-naphthyridine-3-carboxamide;
N-Cyclohexyl-4-hydroxy-2-oxo-7-(phenylmethyl)-1,2-dihydro-1,5-naphthyridine-3-carboxamide;
4-Hydroxy-2-oxo-7-(phenylmethyl)-N-(2-thienylmethyl)-1,2-dihydro-1,5-naphthyridine-3-carboxamide;
N-Cyclopropyl-4-hydroxy-2-oxo-7-(phenylmethyl)-1,2-dihydro-1,5-naphthyridine-3-carboxamide;
N-Cyclobutyl-7-[(4-fluorophenyl)methyl]-4-hydroxy-2-oxo-1,2-dihydro-1,5-naphthyridine-3-carboxamide;
N-Cyclopropyl-7-[(4-fluorophenyl)methyl]-4-hydroxy-2-oxo-1,2-dihydro-1,5-naphthyridine-3-carboxamide;
7-[(4-Fluorophenyl)methyl]-N-(2-furanylmethyl)-4-hydroxy-2-oxo-1,2-dihydro-1,5-naphthyridine-3-carboxamide;
7-[(4-Fluorophenyl)methyl]-4-hydroxy-2-oxo-N-[3-(2-oxo-1-pyrrolidinyl)propyl]-1,2-dihydro-1,5-naphthyridine-3-carboxamide;
7-[(4-Fluorophenyl)methyl]-4-hydroxy-2-oxo-N-[2-(1-pyrrolidinyl)ethyl]-1,2-dihydro-1,5-naphthyridine-3-carboxamide;
(±)-7-[(4-Fluorophenyl)methyl]-4-hydroxy-2-oxo-N-(tetrahydro-2-furanylmethyl)-1,2-dihydro-1,5-naphthyridine-3-carboxamide;
7-[(4-Fluorophenyl)methyl]-4-hydroxy-2-oxo-N-[2-(1-piperidinyl)ethyl]1,2-dihydro-1,5-naphthyridine-3-carboxamide;
7-[(4-Fluorophenyl)methyl]-4-hydroxy-2-oxo-N-(4-pyridinylmethyl)-1,2-dihydro-1,5-naphthyridine-3-carboxamide;
7-[(4-Fluorophenyl)methyl]-4-hydroxy-2-oxo-N-(2-pyridinylmethyl)-1,2-dihydro-1,5-naphthyridine-3-carboxamide;
7-[(4-Fluorophenyl)methyl]-4-hydroxy-2-oxo-N-(3-pyridinylmethyl)-1,2-dihydro-1,5-naphthyridine-3-carboxamide;
7-[(4-Fluorophenyl)methyl]-N-(hexahydro-1H-azepin-1-yl)-4-hydroxy-2-oxo-1,2-dihydro-1,5-naphthyridine-3-carboxamide;
7-[(4-Fluorophenyl)methyl]-4-hydroxy-N-[2-(4-morpholinyl)ethyl]-2-oxo-1,2-dihydro-1,5-naphthyridine-3-carboxamide;
7-[(5-Fluoro-2-pyridinyl)methyl]-4-hydroxy-N-[3-(4-morpholinyl)propyl]-2-oxo-1,2-dihydro-1,5-naphthyridine-3-carboxamide;
7-[(4-Fluorophenyl)methyl]-4-hydroxy-2-oxo-N-[2-(2-pyridinyl)ethyl]-1,2-dihydro-1,5-naphthyridine-3-carboxamide;
7-[(4-Fluorophenyl)methyl]-4-hydroxy-2-oxo-1,2-dihydro-1,5-naphthyridine-3-carboxamide;
7-[(4-Fluorophenyl)methyl]-4-hydroxy-N-[2-(1H-imidazol-4-yl)ethyl]-2-oxo-1,2-dihydro-1,5-naphthyridine-3-carboxamide;
Ethyl 7-benzyl-4-hydroxy-2-oxo-1-[2-(2-oxopyrrolidin-1-yl)ethyl]-1,2-dihydro-1,5-naphthyridine-3-carboxylate;
Benzyl-N-cyclobutyl-4-hydroxy-2-oxo-1-[2-(2-oxopyrrolidin-1-yl)ethyl]-1,2-dihydro-1,5-naphthyridine-3-carboxamide;
7-Benzyl-N-cyclopropyl-4-hydroxy-1-[4-(methylsulfonyl)benzyl]-2-oxo-1,2-dihydro-1,5-naphthyridine-3-carboxamide;
7-Benzyl-N-cyclobutyl-4-hydroxy-1-[4-(methylsulfonyl)benzyl]-2-oxo-1,2-dihydro-1,5-naphthyridine-3-carboxamide;
7-Benzyl-4-hydroxy-N-(2-methoxyethyl)-1-[4-(methylsulfonyl)benzyl]-2-oxo-1,2dihydro-1,5-naphthyridine-3-carboxamide;
7-Benzyl-N-(2-furylmethyl)-4-hydroxy-1-[4-(methylsulfonyl)benzyl]-2-oxo-1,2-dihydro-1,5-naphthyridine-3-carboxamide;
Ethyl 7-benzyl-4-hydroxy-1-[(1-methyl-1H-imidazol-2-yl)methyl]-2-oxo-1,2-dihydro-1,5-naphthyridine-3-carboxylate;
7-Benzyl-N-cyclopropyl-4-hydroxy-1-[(1-methyl-1H-imidazol-2-yl)methyl]-2-oxo-1,2-dihydro-1,5-naphthyridine-3-carboxamide;
7-(4-Fluorobenzyl)-4-hydroxy-N-(2-methoxyethyl)-2-oxo-1-[2-(2-oxopyrrolidin-1-yl)ethyl]-1,2-dihydro-1,5-naphthyridine-3-carboxamide;
7-Benzyl-4-hydroxy-N-(2-methoxyethyl)-1-[(1-methyl-1H-imidazol-2-yl)methyl]-2-oxo-1,2-dihydro-1,5-naphthyridine-3-carboxamide;
7-Benzyl-4-hydroxy-1-(2-morpholin-4-yl-2-oxoethyl)-2-oxo-N-(pyridin-4-ylmethyl)-1,2-dihydro-1,5-naphthyridine-3-carboxamide;

7-(4-Fluorobenzyl)-4-hydroxy-2-oxo-1-[2-(2-oxopyrrolidin-1-yl)ethyl]-N-(pyridin-4-ylmethyl)-1,2-dihydro-1,5-naphthyridine-3-carboxamide;

Ethyl 7-benzyl-1-(cyclopropylmethyl)-4-hydroxy-2-oxo-1,2-dihydro-1,5-naphthyridine-3-carboxylate;

7-Benzyl-1-(cyclopropylmethyl)-4-hydroxy-N-(2-methoxyethyl)-2-oxo-1,2-dihydro-1,5-naphthyridine-3-carboxamide;

7-Benzyl-N-cyclobutyl-1-(cyclopropylmethyl)-4-hydroxy-2-oxo-1,2-dihydro-1,5-naphthyridine-3-carboxamide;

Ethyl 7-benzyl-4-hydroxy-1-(2-morpholin-4-ylethyl)-2-oxo-1,2-dihydro-1,5-naphthyridine-3-carboxylate;

7-Benzyl-N-cyclobutyl-4-hydroxy-1-(2-morpholin-4-ylethyl)-2-oxo-1,2-dihydro-1,5-naphthyridine-3-carboxamide;

7-Benzyl-4-hydroxy-1-[4-(methylsulfonyl)benzyl]-N-(3-morpholin-4-ylpropyl)-2-oxo-1,2-dihydro-1,5-naphthyridine-3-carboxamide;

7-Benzyl-4-hydroxy-1-[4-(methylsulfonyl)benzyl]-2-oxo-N-(2-pyrrolidin-1-ylethyl)-1,2-dihydro-1,5-naphthyridine-3-carboxamide;

Ethyl 7-benzyl-4-hydroxy-2-oxo-1-(1,3-thiazol-2-ylmethyl)-1,2-dihydro-1,5-naphthyridine-3-carboxylate;

7-Benzyl-N-cyclobutyl-4-hydroxy-2-oxo-1-(1,3-thiazol-2-ylmethyl)-1,2-dihydro-1,5-naphthyridine-3-carboxamide;

7-Benzyl-4-hydroxy-N-(2-methoxyethyl)-2-oxo-1-(1,3-thiazol-2-ylmethyl)-1,2-dihydro-1,5-naphthyridine-3-carboxamide;

Ethyl 7-(4-fluorobenzyl)-4-hydroxy-1-[4-(methylsulfonyl)benzyl]-2-oxo-1,2-dihydro-1,5-naphthyridine-3-carboxylate;

7-(4-Fluorobenzyl)-4-hydroxy-N-(2-methoxyethyl)-1-[4-(methylsulfonyl)benzyl]-2-oxo-1,2-dihydro-1,5-naphthyridine-3-carboxamide;

7-(4-Fluorobenzyl)-4-hydroxy-1-[4-(methylsulfonyl)benzyl]-2-oxo-N-(pyridin-4-ylmethyl)-1,2-dihydro-1,5-naphthyridine-3-carboxamide;

7-(4-Fluorobenzyl)-4-hydroxy-1-[4-(methylsulfonyl)benzyl]-2-oxo-N-(pyridin-3-ylmethyl)-1,2-dihydro-1,5-naphthyridine-3-carboxamide;

7-(4-Fluorobenzyl)-4-hydroxy-1-[4-(methylsulfonyl)benzyl]-N-(2-morpholin-4-ylethyl)-2-oxo-1,2-dihydro-1,5-naphthyridine-3-carboxamide;

Ethyl 4-hydroxy-1-[(4-nitrophenyl)methyl]-2-oxo-7-(phenylmethyl)-1,2-dihydro-1,5-naphthyridine-3-carboxylate;

N-(2-Furanylmethyl)-4-hydroxy-1-[(4-nitrophenyl)methyl]-2-oxo-7-(phenylmethyl)-1,2-dihydro-1,5-naphthyridine-3-carboxamide;

4-Hydroxy-N-[2-(methyloxy)ethyl]-1-[(4-nitrophenyl)methyl]-2-oxo-7-(phenylmethyl)-1,2-dihydro-1,5-naphthyridine-3-carboxamide;

N-Cyclobutyl-4-hydroxy-1-[(4-nitrophenyl)methyl]-2-oxo-7-(phenylmethyl)-1,2-dihydro-1,5-naphthyridine-3-carboxamide;

1-[(4-Aminophenyl)methyl]-N-cyclobutyl-4-hydroxy-2-oxo-7-(phenylmethyl)-1,2-dihydro-1,5-naphthyridine-3-carboxamide;

and pharmaceutically acceptable salts thereof.

The present invention features a compound selected from the group consisting of:

7-(4-fluorobenzyl)-4-hydroxy-N-(2-methoxyethyl)-2-oxo-1,2-dihydro-1,5-naphthyridine-3-carboxamide;

N-Cyclopropyl-7-(4-fluorobenzyl)-4-hydroxy-2-oxo-1-[2-(2-oxopyrrolidin-1-yl)ethyl]-1,2-dihydro-1,5-naphthyridine-3-carboxamide;

7-(4-Fluorobenzyl)-4-hydroxy-N-(2-morpholin-4-ylethyl)-2-oxo-1-[2-(2-oxopyrrolidin-1-yl)ethyl]-1,2-dihydro-1,5-naphthyridine-3-carboxamide;

7-Benzyl-4-hydroxy-N-(2-methoxyethyl)-1-(2-morpholin-4-yl-2-oxoethyl)-2-oxo-1,2-dihydro-1,5-naphthyridine-3-carboxamide;

4-Hydroxy-N-[2-(methyloxy)ethyl]-2-oxo-7-(phenylmethyl)-1,2-dihydro-1,5-naphthyridine-3-carboxamide;

7-[(4-Fluorophenyl)methyl]-4-hydroxy-2-oxo-N-[3-(2-oxo-1-pyrrolidinyl)propyl]-1,2-dihydro-1,5-naphthyridine-3-carboxamide;

7-[(4-Fluorophenyl)methyl]-4-hydroxy-N-[2-(4-morpholinyl)ethyl]-2-oxo-1,2-dihydro-1,5-naphthyridine-3-carboxamide;

7-[(5-Fluoro-2-pyridinyl)methyl]-4-hydroxy-N-[3-(4-morpholinyl)propyl]-2-oxo-1,2-dihydro-1,5-naphthyridine-3-carboxamide;

7-Benzyl-4-hydroxy-N-(2-methoxyethyl)-1-[4-(methylsulfonyl)benzyl]-2-oxo-1,2-dihydro-1,5-naphthyridine-3-carboxamide;

7-(4-Fluorobenzyl)-4-hydroxy-N-(2-methoxyethyl)-2-oxo-1-[2-(2-oxopyrrolidin-1-yl)ethyl]-1,2-dihydro-1,5-naphthyridine-3-carboxamide;

7-Benzyl-4-hydroxy-N-(2-methoxyethyl)-1-[(1-methyl-1H-imidazol-2-yl)methyl]-2-oxo-1,2-dihydro-1,5-naphthyridine-3-carboxamide;

7-Benzyl-1-(cyclopropylmethyl)-4-hydroxy-N-(2-methoxyethyl)-2-oxo-1,2-dihydro-1,5-naphthyridine-3-carboxamide;

7-Benzyl-4-hydroxy-N-(2-methoxyethyl)-2-oxo-1-(1,3-thiazol-2-ylmethyl)-1,2-dihydro-1,5-naphthyridine-3-carboxamide;

7-(4-Fluorobenzyl)-4-hydroxy-N-(2-methoxyethyl)-1-[4-(methylsulfonyl)benzyl]-2-oxo-1,2-dihydro-1,5-naphthyridine-3-carboxamide;

and pharmaceutically acceptable salts thereof.

The present invention also features a compound selected from the group consisting of:

7-[(4-Fluorophenyl)methyl]-4-hydroxy-N-(2-hydroxyethyl)-1-methyl-2-oxo-1,2-dihydro-1,5-naphthyridine-3-carboxamide;

7-[(4-fluorophenyl)methyl]-4-hydroxy-N-(2-hydroxyethyl)-1-methyl-2-oxo-1,2-dihydro-1,5-naphthyridine-3-carboxamide sodium salt;

1-[2-(Dimethylamino)-2-oxoethyl]-7-(4-fluorobenzyl)-4-hydroxy-N-methyl-2-oxo-1,2-dihydro-1,5-naphthyridine-3-carboxamide;

Sodium 1-[2-(Dimethylamino)-2-oxoethyl]-7-(4-fluorobenzyl)-3-[(methylamino)carbonyl]-2-oxo-1,2-dihydro-1,5-naphthyridine-4-olate;

7-[(4-Fluorophenyl)methyl]-4-hydroxy-1-[2-(methylamino)-2-oxoethyl]-N-[2-(methyloxy)ethyl]-2-oxo-1,2-dihydro-1,5-naphthyridine-3-carboxamide;

1-[2-(Dimethylamino)-2-oxoethyl]-7-[(4-fluorophenyl)methyl]-4-hydroxy-N-[2-(methyloxy)ethyl]-2-oxo-1,2-dihydro-1,5-naphthyridine-3-carboxamide;

Sodium 1-[2-(dimethylamino)-2-oxoethyl]-7-[(4-fluorophenyl)methyl]-3-({[2-(methyloxy)ethyl]amino}carbonyl)-2-oxo-1,2-dihydro-1,5-naphthyridine-4-olate;

7-(4-Fluorobenzyl)-4-hydroxy-N-[(2R)-2-hydroxypropyl]-2-oxo-1-[2-(2-oxopyrrolidin-1-yl)ethyl]-1,2-dihydro-1,5-naphthyridine-3-carboxamide;

Sodium 7-[(4-fluorophenyl)methyl]-3-({[(2R)-2-hydroxypropyl]amino}carbonyl)-2-oxo-1-[2-(2-oxo-1-pyrrolidinyl)ethyl]-1,2-dihydro-1,5-naphthyridine-4-olate;

7-(4-Fluorobenzyl)-4-hydroxy-N-[(2S)-2-hydroxypropyl]-2-oxo-1-[2-(2-oxopyrrolidin-1-yl)ethyl]-1,2-dihydro-1,5-naphthyridine-3-carboxamide;

1-(2-Amino-2-oxoethyl)-7-[(4-fluorophenyl)methyl]-4-hydroxy-N-[2-(methyloxy)ethyl]-2-oxo-1,2-dihydro-1,5-naphthyridine-3-carboxamide;

1-(4-Fluorophenyl)-7-[(4-fluorophenyl)methyl]-4-hydroxy-N-(2-hydroxyethyl)-2-oxo-1,2-dihydro-1,5-naphthyridine-3-carboxamide;

Sodium 1-(4-fluorophenyl)-7-[(4-fluorophenyl)methyl]-3-{[(2-hydroxyethyl)amino]carbonyl}-2-oxo-1,2-dihydro-1,5-naphthyridine-4-olate;

N-[(2R)-2,3-Dihydroxypropyl]-7-[(4-fluorophenyl)methyl]-4-hydroxy-1-methyl-2-oxo-1,2-dihydro-1,5-naphthyridine-3-carboxamide;

7-(4-Fluorobenzyl)-4-hydroxy-N-(2-methoxyethyl)-2-oxo-1-[2-(2-oxopyrrolidin-1-yl)ethyl]-1,2-dihydro-1,5-naphthyridine-3-carboxamide;

7-[(4-Fluorophenyl)methyl]-4-hydroxy-1-[(1-methyl-1H-imidazol-2-yl)methyl]-N-[2-(methyloxy)ethyl]-2-oxo-1,2-dihydro-1,5-naphthyridine-3-carboxamide;

Sodium 7-[(4-fluorophenyl)methyl]-1-[(1-methyl-1H-imidazol-2-yl)methyl]-3-({[2-(methyloxy)ethyl]amino}carbonyl)-2-oxo-1,2-dihydro-1,5-naphthyridine-4-olate;

1-Ethyl-7-[(4-fluorophenyl)methyl]-4-hydroxy-N-[(1S)-2-hydroxy-1-methylethyl]-2-oxo-1,2-dihydro-1,5-naphthyridine-3-carboxamide;

Sodium 1-ethyl-7-[(4-fluorophenyl)methyl]-3-({[(1S)-2-hydroxy-1-methylethyl]amino}carbonyl)-2-oxo-1,2-dihydro-1,5-naphthyridine-4-olate;

and pharmaceutically acceptable salts thereof.

The present invention also features a compound selected from the group consisting of:

7-Benzyl-4-hydroxy-N-(2-methoxyethyl)-1-(2-morpholin-4-yl-2-oxoethyl)-2-oxo-1,2-dihydro-1,5-naphthyridine-3-carboxamide;

7-[(4-Fluorophenyl)methyl]-4-hydroxy-N-[2-(methyloxy)ethyl]-1-[2-(4-morpholinyl)-2-oxoethyl]-2-oxo-1,2-dihydro-1,5-naphthyridine-3-carboxamide;

1-[2-(Dimethylamino)-2-oxoethyl]-7-[(4-fluorophenyl)methyl]-4-hydroxy-N-[2-(methyloxy)ethyl]-2-oxo-1,2-dihydro-1,5-naphthyridine-3-carboxamide;

7-(4-Fluorobenzyl)-4-hydroxy-N-(2-hydroxy-1-methylethyl)-2-oxo-1-[2-(2-oxopyrrolidin-1-yl)ethyl]-1,2-dihydro-1,5-naphthyridine-3-carboxamide;

7-(4-Fluorobenzyl)-4-hydroxy-N-(2-hydroxypropyl)-2-oxo-1-[2-(2-oxopyrrolidin-1-yl)ethyl]-1,2-dihydro-1,5-naphthyridine-3-carboxamide;

N-[2-(Ethyloxy)ethyl]-7-[(4-fluorophenyl)methyl]-4-hydroxy-1-[2-(4-morpholinyl)-2-oxoethyl]-2-oxo-1,2-dihydro-1,5-naphthyridine-3-carboxamide;

7-[(4-Fluorophenyl)methyl]-4-hydroxy-1-methyl-2-oxo-N-[2-(2-oxo-1-imidazolidinyl)ethyl]-1,2-dihydro-1,5-naphthyridine-3-carboxamide;

7-[(4-Fluorophenyl)methyl]-4-hydroxy-1-methyl-N-{2-[methyl(methylsulfonyl)amino]ethyl}-2-oxo-1,2-dihydro-1,5-naphthyridine-3-carboxamide;

(±)-1-[2-(Dimethylamino)-2-oxoethyl]-7-[(4-fluorophenyl)methyl]-4-hydroxy-N-(2-hydroxy-1-methylethyl)-2-oxo-1,2-dihydro-1,5-naphthyridine-3-carboxamide;

7-[(4-Fluorophenyl)methyl]-4-hydroxy-N-(2-hydroxyethyl)-1-(3-hydroxypropyl)-2-oxo-1,2-dihydro-1,5-naphthyridine-3-carboxamide;

7-[(4-Fluorophenyl)methyl]-4-hydroxy-1-(3-hydroxypropyl)-N-{2-[methyl(methylsulfonyl)amino]ethyl}-2-oxo-1,2-dihydro-1,5-naphthyridine-3-carboxamide;

1-[2-(Dimethylamino)-2-oxoethyl]-7-[(4-fluorophenyl)methyl]-4-hydroxy-N-(2-hydroxy-1,1-dimethylethyl)-2-oxo-1,2-dihydro-1,5-naphthyridine-3-carboxamide;

7-[(4-Fluorophenyl)methyl]-4-hydroxy-1-(3-hydroxypropyl)-N-{2-[(1-methylethyl)sulfonyl]ethyl}-2-oxo-1,2-dihydro-1,5-naphthyridine-3-carboxamide;

1-[2-(Cyclopropylamino)-2-oxoethyl]-7-[(4-fluorophenyl)methyl]-4-hydroxy-N-methyl-2-oxo-1,2-dihydro-1,5-naphthyridine-3-carboxamide;

1-{2-[[(Dimethylamino)carbonyl](methyl)amino]ethyl}-7-[(4-fluorophenyl)methyl]-4-hydroxy-N-(2-hydroxyethyl)-2-oxo-1,2-dihydro-1,5-naphthyridine-3-carboxamide;

7-[(4-fluorophenyl)methyl]-4-hydroxy-N-(2-hydroxyethyl)-2-oxo-1-[2-(2-oxo-1-piperidinyl)ethyl]-1,2-dihydro-1,5-naphthyridine-3-carboxamide;

7-[(4-Fluorophenyl)methyl]-4-hydroxy-N-(2-hydroxy-1-methylethyl)-2-oxo-1-[2-(2-oxo-1-piperidinyl)ethyl]-1,2-dihydro-1,5-naphthyridine-3-carboxamide;

7-(4-Fluorobenzyl)-4-hydroxy-N-(2-methoxyethyl)-2-oxo-1-[2-oxo-2-(1,3-thiazolidin-3-yl)ethyl]-1,2-dihydro-1,5-naphthyridine-3-carboxamide;

7-[(4-fluorophenyl)methyl]-4-hydroxy-N-(3-hydroxypropyl)-2-oxo-1-[2-(2-oxo-1-piperidinyl)ethyl]-1,2-dihydro-1,5-naphthyridine-3-carboxamide;

7-[(4-Fluorophenyl)methyl]-4-hydroxy-N-[(2S)-2-hydroxypropyl]-1-[3-(methyloxy)propyl]-2-oxo-1,2-dihydro-1,5-naphthyridine-3-carboxamide;

7-[(4-fluorophenyl)methyl]-4-hydroxy-N-(3-hydroxybutyl)-2-oxo-1-[2-(2-oxo-1-piperidinyl)ethyl]-1,2-dihydro-1,5-naphthyridine-3-carboxamide;

7-(4-Fluorobenzyl)-4-hydroxy-1-{2-[(2-methoxyethyl)amino]-2-oxoethyl}-N-methyl-2-oxo-1,2-dihydro-1,5-naphthyridine-3-carboxamide;

7-[(4-fluorophenyl)methyl]-4-hydroxy-N-(2-hydroxyethyl)-2-oxo-1-[3-(2-oxo-1-piperidinyl)propyl]-1,2-dihydro-1,5-naphthyridine-3-carboxamide;

7-[(4-fluorophenyl)methyl]-4-hydroxy-N-(3-hydroxypropyl)-2-oxo-1-[3-(2-oxohexahydro-1H-azepin-1-yl)propyl]-1,2-dihydro-1,5-naphthyridine-3-carboxamide;

7-[(4-fluorophenyl)methyl]-4-hydroxy-N-[(1S)-2-hydroxy-1-methylethyl]-2-oxo-1-[3-(2-oxohexahydro-1H-azepin-1-yl)propyl]-1,2-dihydro-1,5-naphthyridine-3-carboxamide;

7-[(4-fluorophenyl)methyl]-4-hydroxy-N-(2-hydroxyethyl)-2-oxo-1-[3-(2-oxohexahydro-1H-azepin-1-yl)propyl]-1,2-dihydro-1,5-naphthyridine-3-carboxamide;

and pharmaceutically acceptable salts thereof.

The present invention also features a compound selected from 7-[(4-Fluorophenyl)methyl]-4-hydroxy-N-(2-hydroxyethyl)-1-methyl-2-oxo-1,2-dihydro-1,5-naphthyridine-3-carboxamide; 1-[2-(Dimethylamino)-2-oxoethyl]-7-(4-fluorobenzyl)-4-hydroxy-N-methyl-2-oxo-1,2-dihydro-1,5-naphthyridine-3-carboxamide; and pharmaceutically acceptable salts thereof. Examples of pharmaceutically acceptable salts are 7-[(4-fluorophenyl)methyl]-4-hydroxy-N-(2-hydroxyethyl)-1-methyl-2-oxo-1,2-dihydro-1,5-naphthyridine-3-carboxamide sodium salt and Sodium 1-[2-(Dimethylamino)-2-oxoethyl]-7-(4-fluorobenzyl)-3-[(methylamino)carbonyl]-2-oxo-1,2-dihydro-1,5-naphthyridine-4-olate.

The present invention features a compound selected from the group consisting of examples numbers 2, 9, 10, 12, 17, 28, 36, 37, 45, 49, 50, 54, 62, 64, 83, 84, 85, 86, 89, 91, 93, 94, 95, 96, 97, 98, 99, 101, 102, 104, 105, 106, 107, 237 and pharmaceutically acceptable salts thereof. The present invention features a compound selected from the group consisting of example numbers 73, 114, 116, 122, 125, 145, 146, 148, 149, 153, 154, 155, 156, 162, 168, 169, 170, 173, 180, 185, 186, 188, 189, 190, 203, 206, 208, 209, 210, 227, 231, 234, 237, 245, 253, 260, 261, 262, 279, 292, 296, 297, 301, 302, 310, 327, 339, 340, 343, 359, 360, 363, 366, 367, 377, 380, 381, 382, 383, 394, 408, 409, 410, 411, 428, 429, 431, 434, 463, 465, 471, 472, 473, 476, 477, 484, 495, 515, 516, 519, 521, 522, 524, 525, 528, 535, 548, 549, 554, 557, 564, 566, 568, 569, 574, 576, 577, 579, 580, 581, 582, 583, 584, 588, 589, 591, 593, 595, 596, 598, 599, 601, 602, 603, 604, 624, 626, 627, 628, 629, 631, 633, 634, 636, 637, 638, 642, 646, 657, 660, 662, 663, 665, 669, 671, 673, 674, 677, 680, 681, 684, 688, 690, 691, 693, 694, 696, 697, and 698 and pharmaceutically acceptable salts thereof.

The present invention further features a compound selected from the group consisting of examples numbers 12, 36, 37, 49, 84, 89, 91, 93, 95, 96, 101, 237 and pharmaceutically acceptable salts thereof.

Compounds of the present invention are useful as integrase inhibitors. One aspect of the instant invention relates to methods of treating or preventing viral infection, for example an HIV infection, in a biological sample comprising contacting the biological sample with compounds of formula (I) or (Ia) or pharmaceutically acceptable derivatives thereof. Another aspect of the instant invention relates to methods of treating or preventing viral infection, for example, an HIV infection, in a patient comprising administering to the patient a therapeutically effective amount of compounds of formula (I) or (Ia) or pharmaceutically acceptable derivatives thereof.

The compounds according to the invention are particularly suited to the treatment or prophylaxis of HIV infections and associated conditions. Reference herein to treatment extends to prophylaxis as well as the treatment of established infections, symptoms, and associated clinical conditions such as AIDS related complex (ARC), Kaposi's sarcoma, and AIDS dementia.

The compounds of the present invention exhibit advantages over previously disclosed integrase inhibitors, for example increased potency, metabolic stability, increased therapeutic index, or other pharmaceutical properties.

According to one embodiment of the invention, compounds of formula (I) or (Ia) or salts thereof may be formulated into compositions. In a preferred embodiment, the composition is a pharmaceutical composition, which comprises a compound of formula (I) or (Ia) and pharmaceutically acceptable carrier, adjuvant or vehicle. In one embodiment, the composition comprises an amount of a compound of the present invention effective to treat or prevent viral infection, for example an HIV infection, in a biological sample or in a patient. In another embodiment, compounds of this invention and pharmaceutical compositions thereof, which comprise an amount of a compound of the present innovation effective to inhibit viral replication or to treat or prevent a viral infection or disease or disorder, for example an HIV infection, and a pharmaceutically acceptable carrier, adjuvant or vehicle, may be formulated for administration to a patient, for example, for oral administration.

The present invention features compounds according to the invention for use in medical therapy, for example for the treatment or prophylaxis of a viral infection, for example an HIV infection and associated conditions. The compounds according to the invention are especially useful for the treatment of AIDS and related clinical conditions such as AIDS related complex (ARC), progressive generalized lymphadenopathy (PGL), Kaposi's sarcoma, thromobocytopenic purpura, AIDS-related neurological conditions such as AIDS dementia complex, multiple sclerosis or tropical paraperesis, anti-HIV antibody-positive and HIV-positive conditions, including such conditions in asymptomatic patients.

According to another aspect, the present invention provides a method for the treatment or prevention of the symptoms or effects of a viral infection in an infected patient, for example, a mammal including a human, which comprises administering to said patient a pharmaceutically effective amount of a compound according to the invention. According to one aspect of the invention, the viral infection is a retroviral infection, in particular an HIV infection.

The present invention further includes the use of a compound according to the invention in the manufacture of a medicament for administration to a subject for the treatment of a viral infection, in particular and HIV infection.

The compounds according to the invention may also be used in adjuvant therapy in the treatment of HIV infections or HIV-associated symptoms or effects, for example Kaposi's sarcoma.

The present invention further provides a method for the treatment of a clinical condition in a patient, for example, a mammal including a human which clinical condition includes those which have been discussed hereinbefore, which comprises treating said patient with a pharmaceutically effective amount of a compound according to the invention. The present invention also includes a method for the treatment or prophylaxis of any of the aforementioned diseases or conditions.

Reference herein to treatment extends to prophylaxis as well as the treatment of established conditions, disorders and infections, symptoms thereof, and associated. The above compounds according to the invention and their pharmaceutically acceptable derivatives may be employed in combination with other therapeutic agents for the treatment of the above infections or conditions. Combination therapies according to the present invention comprise the administration of a compound of the present invention or a pharmaceutically acceptable derivative thereof and another pharmaceutically active agent. The active ingredient(s) and pharmaceutically active agents may be administered simultaneously (i.e., concurrently) in either the same or different pharmaceutical compositions or sequentially in any order. The amounts of the active ingredient(s) and pharmaceutically active agent(s) and the relative timings of administration will be selected in order to achieve the desired combined therapeutic effect.

Examples of such therapeutic agents include, but are not limited to, agents that are effective for the treatment of viral infections or associated conditions. Among these agents are (1-alpha, 2-beta, 3-alpha)-9-[2,3-bis(hydroxymethyl)cyclobutyl]guanine [(−)BHCG, SQ-34514, lobucavir]; 9-[(2R, 3R,4S)-3,4-bis(hydroxy methyl)-2-oxetanosyl]adenine (oxetanocin-G); acyclic nucleosides, for example acyclovir, valaciclovir, famciclovir, ganciclovir, and penciclovir; acyclic nucleoside phosphonates, for example (S)-1-(3-hydroxy-2-phosphonyl-methoxypropyl) cytosine (HPMPC), [[[2-(6-amino-9H-purin-9-yl)ethoxy]methyl]phosphinylidene]bis (oxymethylene)-2,2-dimethyl propanoic acid (bis-POM PMEA, adefovir dipivoxil), [[(1R)-2-(6-amino-9H-purin-9-yl)-1-methylethoxy]methyl]phosphonic acid (tenofovir), and (R)-[[2-(6-Amino-9H-purin-9-yl)-1-methylethoxy]methyl] phosphonic acid bis-(isopropoxycarbonyloxymethyl)ester (bis-POC-PMPA); ribonucleotide reductase inhibitors, for example 2-acetylpyridine 5-[(2-chloroanilino)thiocarbonyl) thiocarbonohydrazone and hydroxyurea; nucleoside reverse transcriptase inhibitors, for example 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-dideohydrothymidine (d4T, stavudine), (−)-beta-D-2,6-diaminopurine dioxolane (DAPD), 3'-azido-2',3'-dideoxythymidine-5'-H-phosphophonate (phosphonovir), 2'-deoxy-5-iodo-uridine (idoxuridine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluoropuridine, (−)-cis-4-[2-amino-6-(cyclo-propylamino)-9H-purin-9-yl]-2-cyclopentene-1-methanol (abacavir), 9-[4-hydroxy-2-(hydroxymethyl)but-1-yl]-guanine(H2G), ABT-606 (2HM-H2G) and ribavirin; protease inhibitors, for example indinavir, ritonavir, nelfinavir, amprenavir, saquinavir, fosamprenavir,(R)-N-tert-butyl-3-[(2S,3S)-2-hydroxy-3-N-[(R)-2-N-(isoquinolin-5-yloxyacetyl)amino-3-methylthio-propanoyl]amino-4-phenylbutanoyl]-5,5-dimethyl-1,3-thiazolidine-4-carboxamide (KNI-272), 4R-(4alpha, 5alpha, 6beta)]-1,3-bis[(3-aminophenyl)methyl]hexahydro-5,6-dihydroxy-4,7-bis (phenylmethyl)-2H-1,3-diazepin-2-onedimethanesulfonate (mozenavir), 3-[1-[3-[2-(5-trifluoromethylpyridinyl)-sulfonylamino]phenyl]propyl]-4-hydroxy-6alpha-phenethyl-6beta-propyl-5,6-dihydro-2-pyranone(tipranavir), N'-[2(S)-Hydroxy-3(S)-[N-(methoxycarbonyl)-1-tert-leucylamino]-4-phenylbutyl-N$^{alpha}$-(methoxycarbonyl)-N'[4-(2-pyridyl) benzyl]-L-tert-leucylhydrazide(BMS-232632), 3-(2(S)-Hydroxy-3(S)-(3-hydroxy-2-methylbenzamido)-4-phenylbutanoyl)-5,5-dimethyl-N-(2-methylbenzyl) thiazolidine-4(R)-carboxamide(AG-1776), N-(2(R)-hydroxy-1(S)-indanyl)-2(R)-phenyl-methyl-4(S)-hydroxy-5-(1-(1-(4-benzo[b]furanylmethyl)-2(S)-N'-(tert-butylcarboxamido)piperazinyl)pentanamide (MK-944A); interferons such as α-interferon; renal excretion inhibitors such as probenecid; nucleoside transport inhibitors such as dipyridamole, pentoxifylline, N-acetylcysteine (NAC), Procysteine, α-trichosanthin, phosphonoformic acid; as well as immunomodulators such as interleukin II or thymosin, granulocyte macrophage colony stimulating factors, erythropoetin, soluble $CD_4$ and genetically engineered derivatives thereof; non-nucleoside reverse transcriptase inhibitors (NNRTIs), for example nevirapine(BI-RG-587), alpha-((2-acetyl-5-methylphenyl)amino)-2,6-dichloro-benzeneacetamide (loviride), 1-[3-(isopropyl amino)-2-pyridyl]-4-[5-(methanesulfonamido)-1H-indol-2-ylcarbonyl]piperazine monomethanesulfonate (delavirdine), (10R,11S,12S)-12-Hydroxy-6,6,10,11-tetramethyl-4-propyl-11,12-dihydro-2H,6H,10H-benzo(1,2-b:3,4-b':5,6-b")tripyran-2-one((+) calanolide A), (4S)-6-Chloro-4-[1E)-cyclopropyl ethenyl)-3,4-dihydro-4-(trifluoromethyl)-2(1H)-quinazolinone (DPC-083),(S)-6-chloro-4-(cyclopropyl ethynyl)-1,4-dihydro-4-(trifluoromethyl)-2H-3,1-benzoxazin-2-one(efavirenz, DMP 266), 1-(ethoxymethyl)-5-(1-methylethyl)-6-(phenylmethyl)-2,4(1H,3H)-pyrimidinedione (MKC-442), and 5-(3,5-dichlorophenyl)thio-4-isopropyl-1-(4-pyridyl)methyl-1H-imidazol-2-ylmethyl carbamate (capravirine); glycoprotein 120 antagonists, for example PRO-2000, PRO-542 and 1,4-bis[3-[(2,4-dichlorophenyl)carbonyl amino]-2-oxo-5,8-disodiumsulfanyl]naphthalyl-2,5-dimethoxyphenyl-1,4-dihydrazone(FP-21399); cytokine antagonists, for example reticulose (Product-R), 1,1'-azobis-formamide (ADA), 1,11-(1,4-phenylenebis (methylene))bis-1,4,8,11-tetraazacyclotetradecane octahydrochloride (AMD-3100); integrase inhibitors; and fusion inhibitors, for example T-20 and T-1249.

The present invention further includes the use of a compound according to the invention in the manufacture of a medicament for simultaneous or sequential administration with at least another therapeutic agent, such as those defined hereinbefore.

Compounds of the present invention may be administered with an agent known to inhibit or reduce the metabolism of compounds, for example ritonavir. Accordingly, the present invention features a method for the treatment or prophylaxis of a disease as hereinbefore described by administration of a compound of the present invention in combination with a metabolic inhibitor. Such combination may be administered simultaneously or sequentially.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. Unless otherwise indicated; all weights of active ingredient are calculated as the parent compound of formula (I) or (Ia); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, preferably 20 to 500 mg, and most preferably 50 to 400 mg of active ingredient per unit dosage form.

While it is possible for the active ingredient to be administered alone, it is preferable to present it as a pharmaceutical composition. The compositions of the present invention comprise at least one active ingredient, as defined above, together with one or more acceptable carriers thereof and optionally other therapeutic agents. Each carrier must be acceptable in the sense of being compatible with the other ingredients of the composition and not injurious to the patient.

Pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable derivative thereof and another therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3(6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray. Pharmaceutical compositions may contain in addition to the active ingredient such carriers as are known in the art to be appropriate.

Pharmaceutical compositions for rectal administration may be presented as a suppository with a suitable carrier comprising, for example, cocoa butter or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

The compounds of the present invention may be prepared according to the following reactions schemes and examples, or modifications thereof using readily available starting materials, reagents and conventional synthesis procedures. In these reactions, it is also possible to make use of variants which are known to those of ordinary skill in the art.

The compounds of the present invention are readily prepared by methods outlined in Schemes 1-9 or by methods known to one skilled in the art. Compounds of formula (I) and (Ia) as defined above may be prepared by treating compounds such as 1c with amines ($R^3NH_2$). These and other methods for the conversion of carboxylic esters and acid derivatives to amides are well known to those skilled in the art. For examples, see: March, J., Advanced Organic Chemistry, $4^{th}$ Edition; John Wiley & Sons, 1992, pp 419-424. Compounds such as 1c are prepared by treating 3-oxopropanoyl derivatives 1b with base (e.g. NaOMe or NaOEt) in protic solvents such as MeOH or EtOH. Oxopropanoyl derivatives 1b may be prepared by reacting amines 1a with malonylchloride derivatives in the presence of base. Alternatively, compounds 1b are prepared by heating a solution of amine 1a with a malonylchloride derivatives in a nonprotic solvent.

SCHEME 1

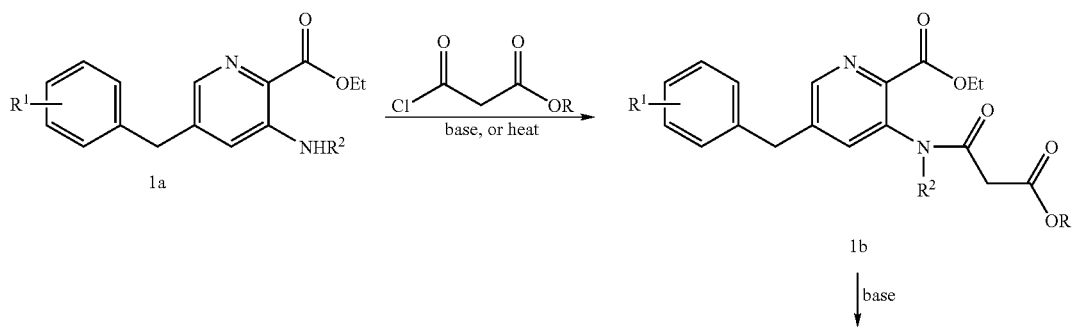

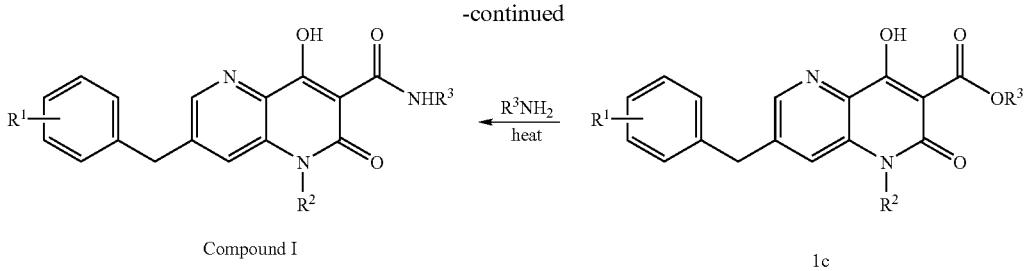

Amines 1a may be prepared by reductive amination of amines 2a with aldehydes and ketones as outlined in Scheme 2. For examples, of reductive amination reactions, see: March, J., Advanced Organic Chemistry, 4th Edition; John Wiley & Sons, 1992, pp 898-900.

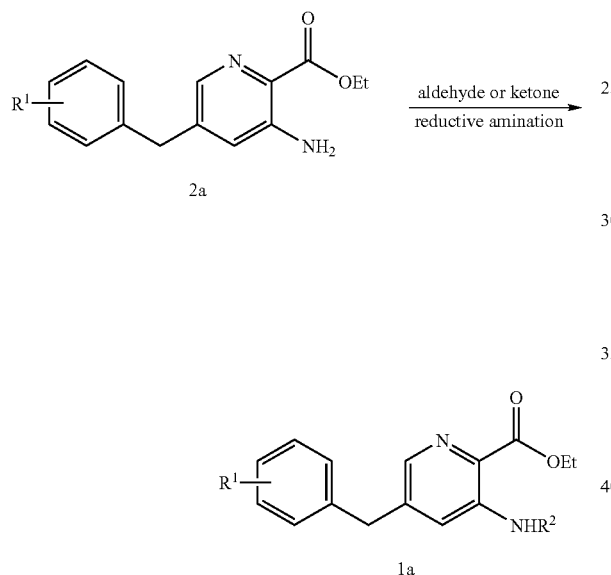

Amines 2a are readily prepared by methods outlined in Scheme 3. Heck reaction of aryl iodides 3a with allyl alcohol generates 3-arylproponals 3b. For examples of Heck reactions in the preparation of 3b, see: March, J., Advanced Organic Chemistry, 4th Edition; John Wiley & Sons, 1992, pp 717-718. Treatment of 3b with formaldehyde in the presence of diethylamine hydrochloride affords requisite 2-benzylpropenals 3c. Reaction of 3c with diethyl 2-aminofamarate provides a pyridine diethyl ester 3d which may be hydrolyzed under basic conditions (e.g. NaOH) to the corresponding pyridine dicarboxylic acid 3e. For synthesis of diethyl 2-aminofumarate, see: Isobe, K.; Mohiri, C.; Sano, H.; Mohri, K.; Enomoto, H., Chem. Pharm. Bull., Vol. 37, 1989, pp 3236-3238. Treatment of 3e with acetic anhydride yields the corresponding cyclic anhydride 3f which is treated with EtOH at reflux to generate the pyridine carboxylic acid monoester 3g. Curtius rearrangement of 3g in the presence of t-BuOH yields the BOC-protected 3-aminopyridine derivative 3h which may be deprotected with TFA to afford the desired 3-aminopyridine compound 2a. For an example of a Curtius rearrangement of this type, see: Feiser, M., Reagents for Organic Synthesis, Vol. 11; John Wiley & Sons, 1984, p 222.

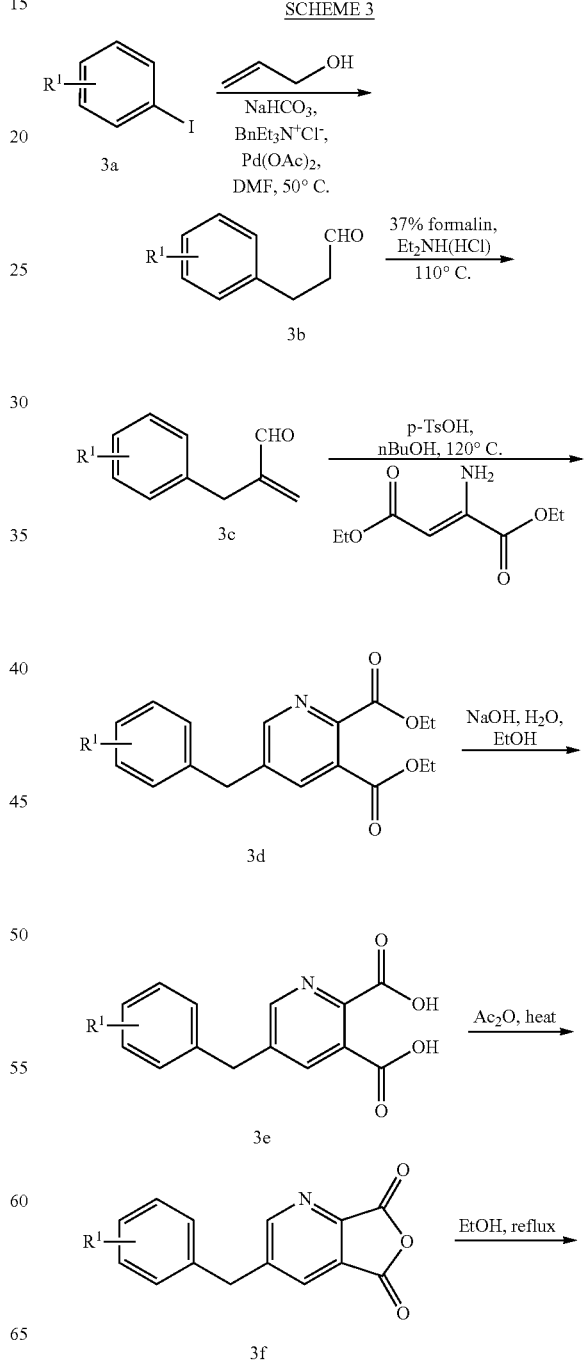

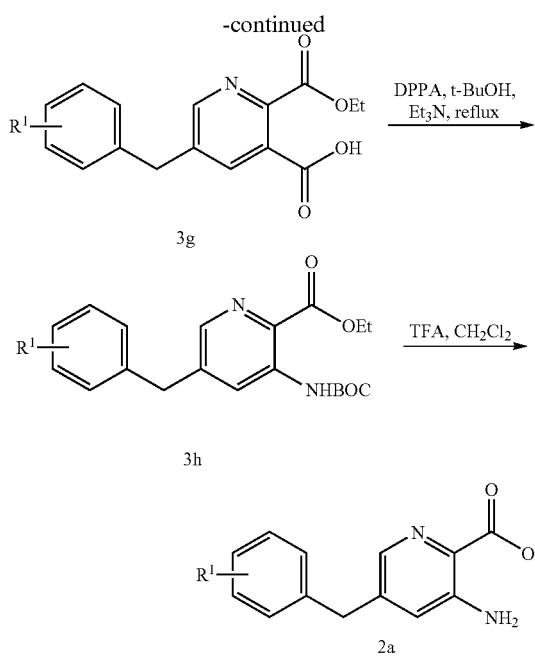

A particularly useful synthesis of a compound similar to 1a (4h) is shown in Scheme 4. Disubstituted pyridines such as 4a can be metallated and reacted with electrophiles such as aldehydes. Conditions for metallation can include by way of example treating a heteroaryl bromide such as 4a with alkyllithium reagents or magnesium in the case of forming Grignard intermediates. The reactive metallated species can then be exposed to an optionally substituted benzaldehyde (4b) at low temperature to form a diaryl carbinol such as 4c. Specific reaction conditions such as temperature and solvent can effect the results of this type of reaction. A particularly useful solvent for this type of chemistry is methyl tert-butyl ether (MTBE). Low temperature condition involve reaction temperature from −78° C. to ambient temperature by way of example. The resultant benzylic alcohol can be converted to the corresponding diarylmethane derivative 4d by way of reduction. Typically conditions for reduction of an alcohol such as 4c involve catalytic hydrogenation or hydride reduction conditions. Catalytic hydrogenation conditions can typically involve the use of Pd/C in an alcoholic solvent or ethyl acetate as an example. A particularly useful reduction protocol well know to those skilled in the art for the reduction of benzylic alcohols involves treatment of 4c with triethylsilane in trifluoroacetic acid. Similarly, triethylsilane and a Lewis acid such as boron trifluoride etherate and the like can also be used in an inert solvent optionally with heating. The methyl ether in 4c is also able to be removed to produce the 2 hydroxypyridine moiety in the same pot as the reduction transformation. In cases where the methyl ether is not sufficiently cleaved, acidic conditions can be used to deblock the phenol. Typically these conditions include a strong acid such as HBr and the like optionally in a solvent such as acetic acid in some cases with heating. Pyrridone 4d can be nitrated regioselectively to produce nitrophenol 4e. This type of transformation is commonly known to one skilled in the art, however a particularly useful set of conditions to obtain the desired regiochemistry involve an acidic solvent such as TFA and a nitrating agent such as fuming nitric acid. This material can then be converted to a 2-bromo-pyridine derivative 4f by treatment with phosphorous oxybromide in an inert solvent. Typical solvents of choice include but are not limited to toluene and 1,2-dichloroethane and the like. In some cases the corresponding chloro derivative produced by use of phosphorous oxychloride may also be useful in the same reaction sequence. In some cases a base may be added. Suitable bases may include diethylaniline by means of example. Compounds such as 4f can be converted to a compound such as 4g by carbonylation. Typically these conditions involve the use of a source of palladium (0) and an atmosphere of carbon monoxide optionally at ambient or increased pressures in the presence of a base. hi many cases these reactions are best run at elevated temperatures. The catalyst can be tetrakistriphenylphosphine palladium (0) or palladium acetate and the like be way of example. Suitable bases such as triethylamine and the like are typically added. An alcohol is typically added to form the resultant ester. A particularly useful alcohol is methanol. The nitro group in 4g can be reduced to form the aniline 4h using methods well known to those skilled in the art. Typical conditions involve catalytic hydrogenation. Suitable conditions may involve the use of palladium on carbon with an atmosphere of hydrogen at ambient or elevated pressures. In some cases the addition of iron metal can be particularly useful.

SCHEME 4

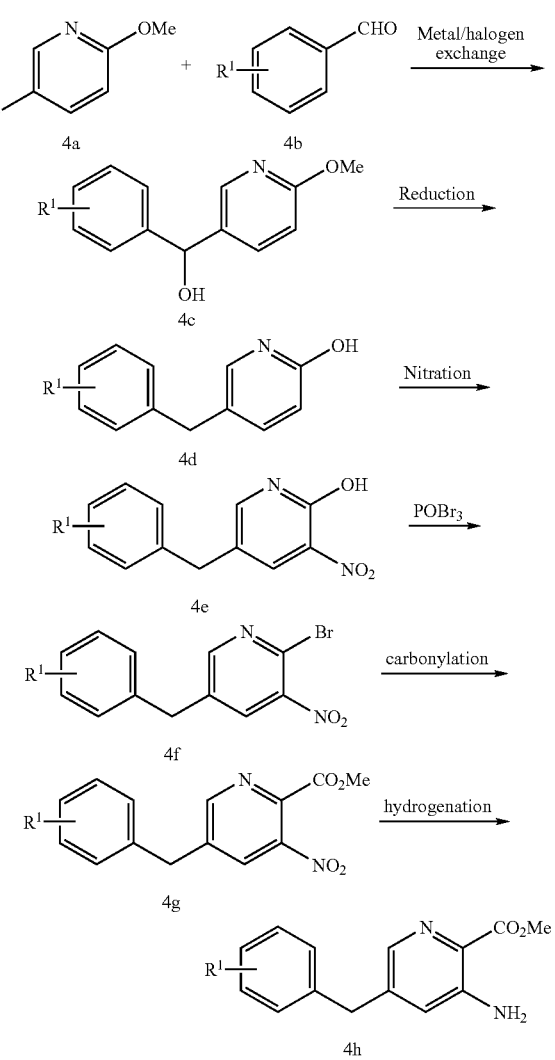

A particularly useful route to produce a compound similar to 1a is shown is Scheme 5. This strategy begins with a 3-fluoro-pyridine such as 5a. It is well precedented in the literature how to oxidize the pyridine 5a to form the corresponding pyridine N-oxide 5b (Sharpless, K. B. et. al. *J. Org. Chem.* 1998, 63, 1740). The literature method of Sakamoto et. al. (*Chem. Pharm. Bull.* 1985, 33, 565) can be used to form 2-cyano-3-fluoropyridine 5c by treatment of N-oxide 5b with TMSCN. This method is well known to regioselectively form the 2-nitrile. This material is able to be lithiated according to a modifications of methods described in the literature (WO 2004/019868) and treated with elemental iodine to form the 4-iodo derivative 5d. The 4-iodo derivative 5d can then be rearranged to the 5-iodo derivative 5e again according to a modification of the procedure outlined in the literature (WO 2004/019868). This 5-iodopyridine derivative can be subjected to a palladium mediated cross-coupling known to those skilled in the art as a Negishi-type coupling. Typically these cross-coupling reactions involve the reaction of an aryl halide with a alkyl zinc reagent. In this case reaction of iodide 5e with a benzyl zinc halide in the presence of a catalytic amount of a palladium (0) source resulted in formation of the 5-benzyl derivative 5g. The benzyl zinc halide can be prepared by literature methods or purchased from commercial sources. Typically, the catalyst is Pd(PPh$_3$)$_4$ and the like and the solvent is THF. The reaction optionally may be heated. An optionally substituted amine can be used to displace the 3-fluoro substituent in 5g to produce 5h. Typically this can be done by heating optionally in a microwave a mixture of the amine and 3-fluoropyridine 5g in the amine neat or in an inert solvent to provide the 3-amino-2-cyano derivative 5h. The nitrile functionality may be hydrolyzed under acidic or basic conditions. A particularly useful method involves heating the nitrile in ethanolic sodium hydroxide to give the corresponding carboxylic acid 5i. The acid may then be converted to the corresponding ester using several methods well known in the literature. By way of example, particularly useful conditions involve the use of diazomethane, TMS-diazomethane and the like in a solvent such as ether or methanol/benzene respectively. Another particularly useful method for conversion of the acid to ester 5j involves the use of a base and alkylating agent. Typically, the alkylating agent is methyl iodide and the like and the base is potassium carbonate, triethylamine, sodium hydroxide and the like by way of example. This reaction can be performed optionally in an inert solvent such as DMF and the like.

SCHEME 5

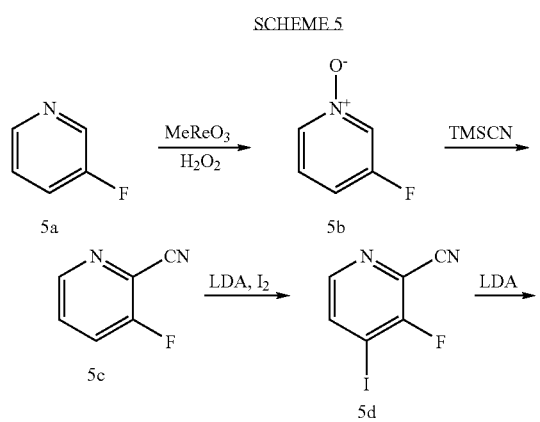

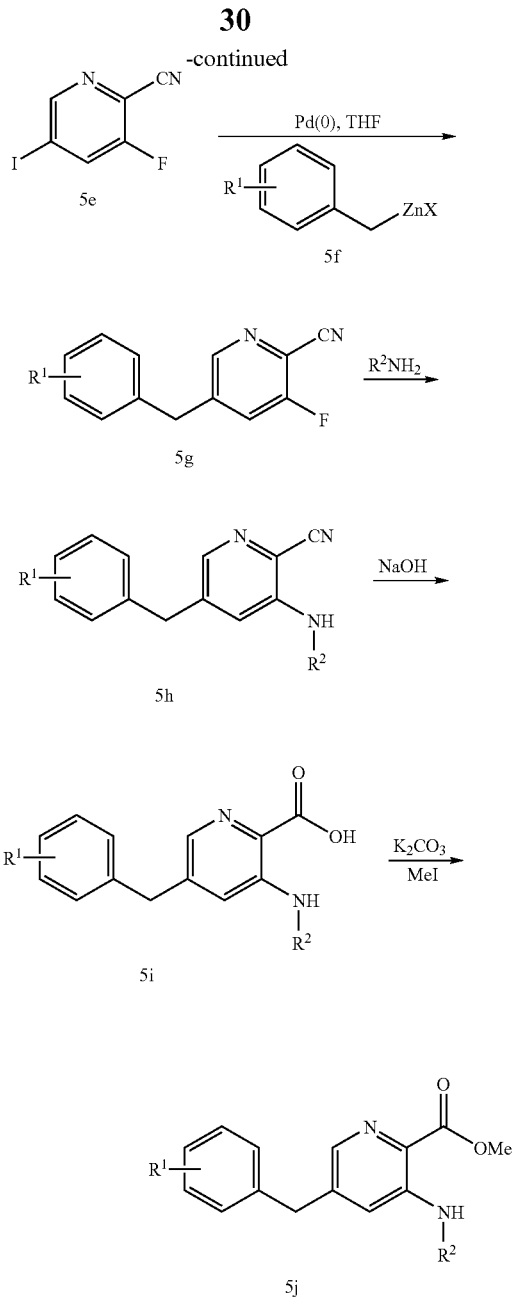

An analogous method to that shown in Scheme 5 can be used to form an intermediate 3,5-dibromo-2-cyanopyridine 6c (Scheme 6). A unique discovery with this system is the selective Negishi coupling to form intermediate 6e with a high level of selectivity. Dibromo derivative 6c can be treated with an optionally substituted benzyl zinc derivative 6d resulting in selective formation of the 5-benzyl product 6e. Typical conditions involved the use of Pd(PPh$_3$)$_4$ in an inert solvent such as THF and the like. The 3-bromo substituent is particularly useful since it is well known that aryl bromides can be used for palladium mediated amination reactions known to those skilled in the art as Buchwald-Hartwig type couplings. This was particularly useful for the formation of compounds where R$^2$ was an optionally substituted aryl group however can be used in a general sense to form a wide variety of R$^2$ substituted compounds of the formula I. The remainder of the synthesis can proceed as shown in the previous Schemes.

SCHEME 6

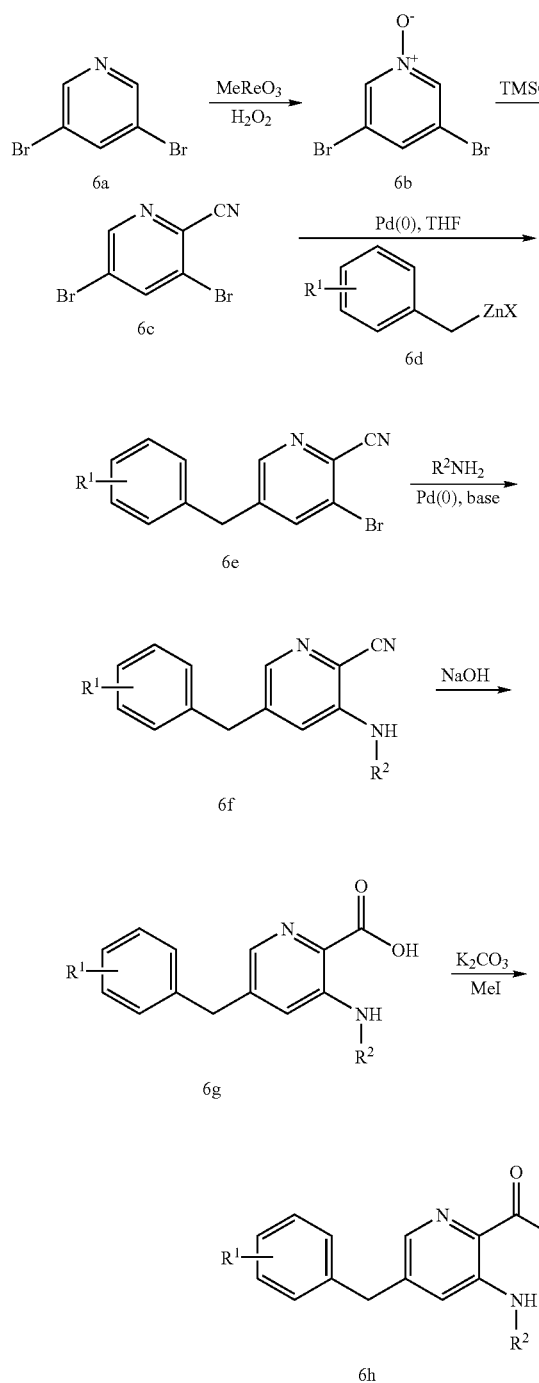

SCHEME 7

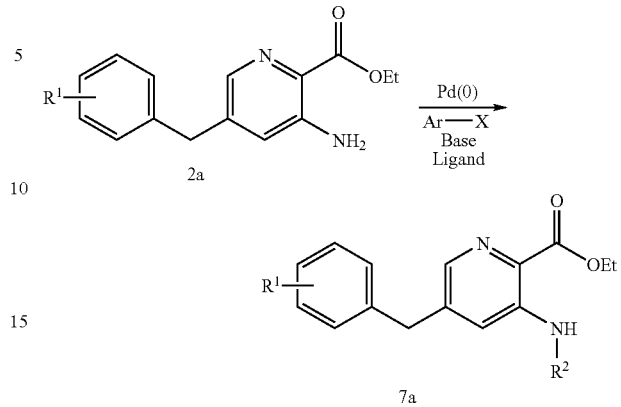

A useful method for conversion of a compound of formula 8a to one of the formula 1c involved the use of an alkylation (Scheme 8). Typically these type of reactions employ a base and an alkylating agent in an inert solvent. By way of example suitable bases include but are not limited to LDA, lithium hexamethyldisilazide, sodium hydride and the like. Alkylating agents include but are not limited to alkyl halides, triflates, mesylates, tosylates and the like.

SCHEME 8

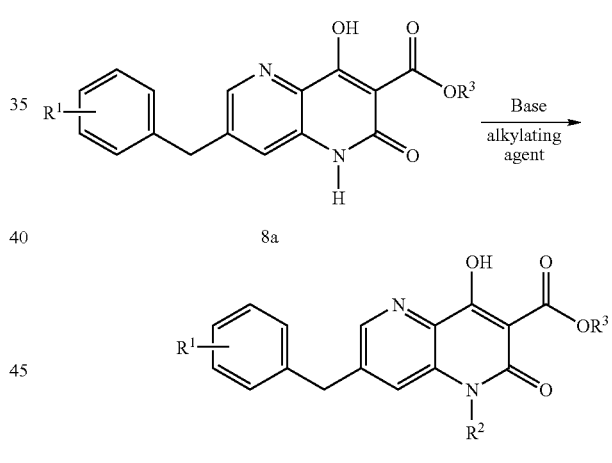

A useful method for conversion of a compound such as 2a to a higher substituted version such as 1a involves the method shown in Scheme 9. The 3 amino group can be activated for alkylation by conversion to a trifluoroacetamide or similar group such as shown in structure 9a. Typically this can be formed using trifluoroacetic anhydride or a similar reagent optionally with heating neat or in an inert solvent. Trifluoroacetamide 9a can be alkylated using conditions known to those skilled in the art. Typical conditions may include the use of a base such as potassium carbonate and the like in an inert solvent such as acetonitrile or DMF. Alkylating agents include but are not limited to alkyl halides, triflates, mesylates and the like. Typically removal of the trifluoroacetamide can be accomplished by subjecting 9a to hydrolysis conditions. Suitable conditions typically include heating in an alcohol optionally in the presence of a base.

Another noteworthy method to convert a compound such as 2a to a selected group of compounds such as 7a where $R^2$ is aryl or heteroaryl involves the use of palladium mediated Buchwald-Hartwig reaction. Typically conditions for this type of reaction involve the use of a source of palladium (0) catalyst, a ligand and a base. By way of example conditions may use palladium acetate and the like as a catalyst. Suitable ligand may include but are not limited to phosphine ligands such as Xantphos. Bases include but are not limited to cesium carbonate and sodium tert-butoxide and the like.

SCHEME 9

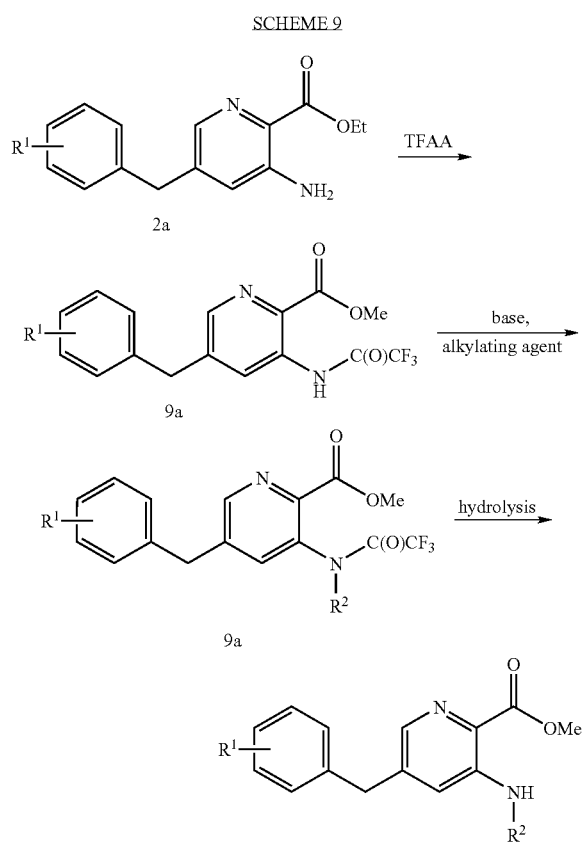

The following examples are intended for illustration only and are not intended to limit the scope of the invention in any way.

EXAMPLE 1

Ethyl 7-(4-fluorobenzyl)-4-hydroxy-2-oxo-1,2-dihydro-1,5-naphthyridine-3-carboxylate

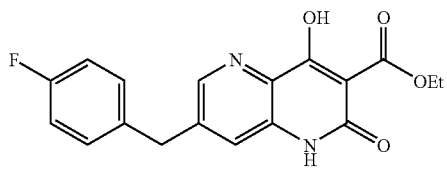 [SMILES: CCOC(=O)c1c(O)c2ncc(Cc3ccc(F)cc3)cc2[nH]c1=O]

Step 1: Synthesis of 3-(4-fluorophenyl)propanol

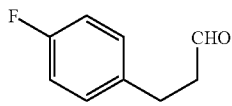

To a mixture of 1-fluoro-4-iodobenzene (300 g, 1.35 mol), benzyltriethylammonium chloride (300 g, 1.35 mol), NaHCO₃ (283 g, 3.4 mol) and allyl alcohol (138 mL, 2.0 mol) in DMF (300 mL) was added palladium acetate (3.0 g, 13.5 mmol). The mixture was heated at 50° C. for 5 h with stirring. Water (1 L) and Et₂O (1 L) were added at rt. After filtration through Celite, the filtrate was extracted with Et₂O. The extracts were washed with H₂O and brine, then dried and concentrated to yield the product: $^1$H NMR (CDCl₃) δ 9.81 (1H, s), 7.16 (2H, m), 6.97 (2H, m), 2.93 (2H, t, J=7.5 Hz), 2.77 (2H, t, J=7.5 Hz).

Step 2: Synthesis of 2-(4-fluorobenzyl)propenyl

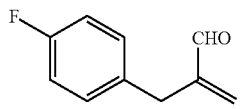

A mixture of 3-(4-fluorophenyl)propanal (205 g, 1.3 mol), diethylamine hydrochloride (148 g, 1.3 mol) and 37% formalin (ca. 1.2 eq.) was heated at 110° C. for 2 h. Water (600 mL) was added and the mixture was extracted with EtOAc. The extract was washed with H₂O and brine, then dried and concentrated to afford the product: $^1$H NMR (CDCl₃) δ 9.59 (1H, s), 7.13 (2H, m), 6.98 (2H, m), 6.10 (2H, m), 3.55 (2H, s).

Steps 3 and 4: Synthesis of 5-(4-fluorobenzyl)-2,3-pyridinedicarboxylic acid

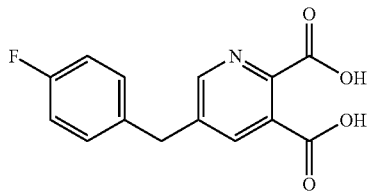 [SMILES: O=C(O)c1cc(Cc2ccc(F)cc2)cnc1C(=O)O]

To a solution of diethyl 2-aminofumarate (153 g, 0.81 mol) and p-TsOH.H₂O (1.5 g, 8.1 mmol) in n-BuOH (325 mL) was added 2-(4-fluorobenzyl)propenal (162 g, 0.98 mol) dropwise at 120° C. The mixture was stirred for 17 h at 120° C. and at rt for ca. 24 h. The mixture was filtered and concentrated under vacuum to yield the crude diethyl 5-(4-fluorobenzyl)-2,3-pyridinedicarboxylate. This material was dissolved in EtOH (400 mL) and an ice-cold solution of NaOH (88 g, 2.2 mol) in water (300 mL) was added. The mixture was stirred for 2 h at rt. After removal of EtOH in vacuo, water (400 mL) and 6N HCl (200 mL) were added and the mixture was extracted with EtOAc. The EtOAc layer was washed with water and the combined aqueous layers adjusted to pH 2 with 6N HCl (175 mL). The mixture was stirred for 1 h at ice-bath temperature and the product was collected by filtration: $^1$H NMR (d₆-DMSO) δ 8.64 (1H, d, J=2 Hz), 8.01 (1H, d, J=2

Hz), 7.32 (2H, dd, J~9, 6 Hz), 7.12 (2H, t, J~9 Hz), 4.05 (2H, s); ES+ MS: 276 (M+H+, 100).

Steps 5 and 6: Synthesis of 5-(4-fluorobenzyl)-2,3-pyridinedicarboxylic acid 2-ethyl ester

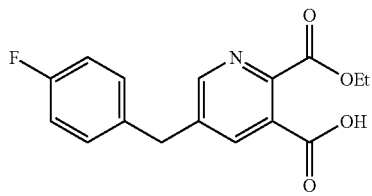 [SMILES: CCOC(=O)c1ncc(Cc2ccc(F)cc2)cc1C(=O)O]

A mixture of 5-(4-fluorobenzyl)-2,3-pyridinedicarboxylic acid (25.3 g, 92 mmol) and Ac$_2$O (200 mL) was stirred for 3 h at 120° C. The reaction mixture was concentrated in vacuo, dissolved in toluene (200 mL) and re-concentrated in vacuo again to give 5-(4-fluorobenzyl)-2,3-pyridinedicarboxylic anhydride. This material was dissolved in EtOH (200 mL) and the mixture was heated at reflux for 3 h and then stored at rt overnight. The reaction mixture was concentrated in vacuo, dissolved in toluene and concentrated again to afford the product as the major isomer. This material contained ca. 30% of the corresponding 3-ethyl ester 2-carboxylic acid isomer. Major isomer: $^1$H NMR (d$_6$-DMSO) δ 13.5 (1H, br), 8.67 (1H, d, J=2 Hz), 8.06 (1H, d, J=2 Hz), 7.31 (2H, dd, J~9, 6 Hz), 7.11 (2H, t, J~9 Hz), 4.25 (2H, q, J=7 Hz), 1.24 (3H, t, J=7 Hz); ES+ MS: 304 (M+H+, 80), 326 (M+Na+, 30).

Step 7: Synthesis of ethyl 5-(4-fluorobenzyl)-3-[(tert-butoxy)carbonyl]amino-2-pyridinecarboxylate

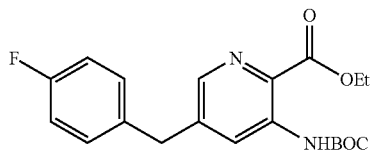

A solution of 5-(4-fluorobenzyl)-2,3-pyridinedicarboxylic acid 2-ethyl ester (28 g, 92 mmol), diphenylphosphoryl azide (29.7 mL, 138 mmol) and Et$_3$N (38.5 mL, 276 mmol) in t-BuOH (250 mL) was heated at reflux for 5 h and stored at rt for 3 d. After removal of solvent in vacuo, EtOAc was added and the mixture was washed with NH$_4$Cl solution, NaHCO$_3$ solution and brine, and then dried and concentrated. The crude material was purified by column chromatography on silica gel eluting with 30% EtOAc/hexanes to afford the product as the major isomer. This material contained ca. 30% of the corresponding 3-ethyl ester 2-(tert-butoxy)carbonylamino isomer. Major isomer: $^1$H NMR (d$_6$-DMSO) δ 9.96 (1H, s), 8.30 (1H, d, J=2 Hz), 8.24 (1H, d, J=2 Hz), 7.27 (2H, m), 7.11 (2H, m), 4.28 (2H, q, J=7 Hz), 4.01 (2H, s), 1.43 (9H, s), 1.28 (3H, t, J=7 Hz); AP+ MS: 375 (M+H+, 100).

Step 8: Synthesis of ethyl 3-amino-5-(4-fluorobenzyl)-2-pyridinecarboxylate

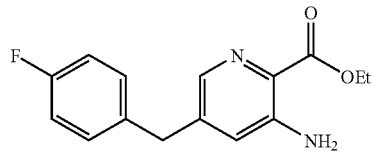 [SMILES: CCOC(=O)c1ncc(Cc2ccc(F)cc2)cc1N]

A solution of 5-(4-fluorobenzyl)-3-[(tert-butoxy)carbonyl]amino-2-pyridinecarboxylate (29 g, 77 mmol) in CH$_2$Cl$_2$ (200 mL) and trifluoroacetic acid (60 mL) was stirred at rt overnight. The solvent was removed in vacuo and the crude material was dissolved in EtOAc and washed with NaHCO$_3$ solution and brine. The organic layer was dried, concentrated and chromatographed on silica gel eluting with 20-60% EtOAc/hexanes to yield the product as a light yellow solid: $^1$H NMR (d$_6$-DMSO) δ 7.76 (1H, d, J=1.7 Hz), 7.25 (2H, m), 7.15 (2H, t, J=9 Hz), 6.92 (1H, d,J=1.7 Hz), 6.62 (2H, br s), 4.23 (2H, q, J=7 Hz), 3.87 (2H, s), 1.26 (3H, t, J=7 Hz), AP+ MS: 275 (M+H+, 100); HRMS calcd for C$_{15}$H$_{15}$FN$_2$O$_2$+H+: 275.1196. Found: 275.1206.

Step 9: Synthesis of ethyl 3-[(3-ethoxy-3-oxopropanoyl)amino]-5-(4-fluorobenzyl)pyridine-2-carboxylate

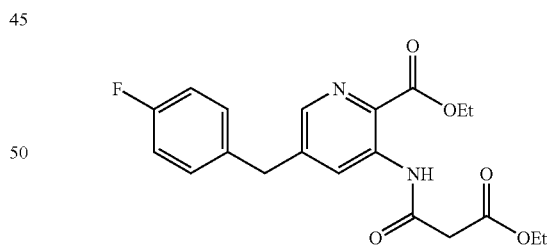

Ethyl 3-chloro-3-oxopropionate (1.32 g, 8.75 mmol) was added to a solution of ethyl 3-amino-5-(4-fluorobenzyl)-2-pyridinecarboxylate (2 g, 7.29 mmol) in DCE (20 mL) and the solution was heated at reflux for 1 h. The solvent was removed in vacuo and silica gel chromatography eluting with 0-5% MeOH/CH$_2$Cl$_2$ provide the product as an amber oil: $^1$H NMR (CDCl$_3$) δ 8.96 (1H, br s), 8.32 (1H, d, J=1.8 Hz), 7.17 (2H, dd, J~9, 6 Hz), 7.00 (2H, t, J~9 Hz), 4.53 (2H, t, J=7 Hz), 4.29 (2H, t, J=7 Hz), 4.02 (2H, s), 3.54 (2H, s), 1.48 (3H, t, J=7 Hz), 1.33 (3H, t, J=7 Hz).

Step 10: Synthesis of ethyl 7-(4-fluorobenzyl)-4-hydroxy-2-oxo-1,2-dihydro-1,5-naphthyridine-3-carboxylate

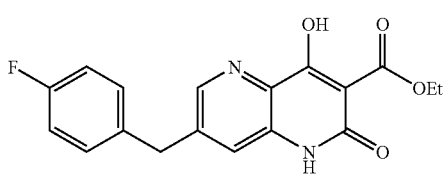 [SMILES: CCOC(=O)c1c(O)c2ncc(Cc3ccc(F)cc3)cc2[nH]c1=O]

A 2M solution of NaOEt in EtOH (5.87 mL, 11.74 mmol) was added to a solution of ethyl 3-[(3-ethoxy-3-oxopropanoyl)amino]-5-(4-fluorobenzyl)pyridine-2-carboxylate (2.28 g, 5.87 mmol) in EtOH (23 mL) and the mixture was stirred at rt for 1 h. The mixture was neutralized with conc. HCl and concentrated in vacuo. Trituration of the resulting material with a mixture of EtOH and 1:1 brine/water followed by filtration afforded the product as a beige solid: $^1$H NMR (d$_6$-DMSO) δ 11.54 (1H, br s), 8.54 (1H, d, J=1.4 Hz), 7.44 (1H, s), 7.32 (2H, dd, J=8, 6 Hz), 7.17 (2H, t, J~9 Hz), 4.23 (2H, q, J=7 Hz), 4.12 (2H, s), 1.26 (3H, t, J=7 Hz); HRMS calcd for C$_{18}$H$_{15}$FN$_2$O$_4$+H$^+$: 343.1094. Found: 343.1088.

EXAMPLE 2

7-(4-Fluorobenzyl)-4-hydroxy-N-(2-methoxyethyl)-2-oxo-1,2-dihydro-1,5-naphthyridine-3-carboxamide

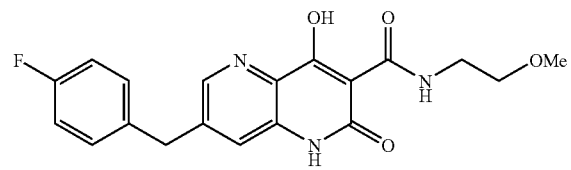 [SMILES: COCCNC(=O)c1c(O)c2ncc(Cc3ccc(F)cc3)cc2[nH]c1=O]

A mixture of ethyl 7-(4-fluorobenzyl)-4-hydroxy-2-oxo-1,2-dihydro-1,5-naphthyridine-3-carboxylate (35 mg, 0.102 mmol) and 2-methoxyethylamine (384 mg, 5.11 mmol) was heated at 120° C. in a sealed tube for 18 h. The material was triturated with hot EtOH and filtered to give the product as a white solid: $^1$H NMR (d$_6$-DMSO) δ 8.37 (1H, br), 7.39 (1H, br), 7.31 (2H, br t, J~8 Hz), 7.15 (2H, br t, J~9 Hz), 4.07 (2H, br), 3.47 (4H, br), 3.33 (3H, s); HRMS calcd for C$_{19}$H$_{18}$FN$_3$O$_4$+H$^+$: 372.1360. Found: 372.1372.

EXAMPLE 3

7-Benzyl-N-(cyclopropylmethyl)-4-hydroxy-2-oxo-1,2-dihydro-1,5-naphthyridine-3-carboxamide

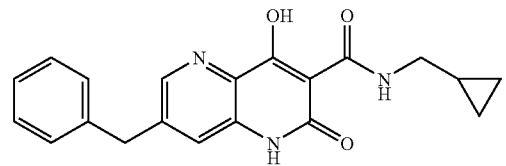 [SMILES: O=C(NCC1CC1)c1c(O)c2ncc(Cc3ccccc3)cc2[nH]c1=O]

Steps 1-8. Synthesis of ethyl 3-amino-5-benzylpyridine-2-carboxylate

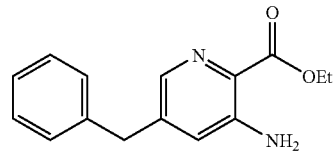 [SMILES: CCOC(=O)c1ncc(Cc2ccccc2)cc1N]

This compound was prepared from 3-phenylpropanal and diethyl 2-aminofumarate employing methods similar to those described in Example 1, Steps 2-8. The product was obtained as a beige solid: $^1$H NMR (d$_6$-DMSO) δ 7.77 (1H, d, J=1.6 Hz), 7.30 (2H, d, J=8 Hz), 7.21 (3H, m), 6.94 (1H, d, J=1.6 Hz), 6.62 (2H, br s), 4.23 (2H, q, J=7 Hz), 3.97 (2H, s), 1.26 (3H, t, J=7 Hz); HRMS calcd for C$_{15}$H$_{16}$N$_2$O$_2$+H$^+$: 257.1290. Found: 257.1286.

Steps 9-10: Ethyl 7-benzyl-4-hydroxy-2-oxo-1,2-dihydro-1,5-naphthyridine-3-carboxylate

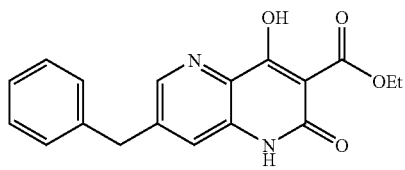 [SMILES: CCOC(=O)c1c(O)c2ncc(Cc3ccccc3)cc2[nH]c1=O]

This compound was prepared from ethyl 3-amino-5-benzylpyridine-2-carboxylate and ethyl 3-chloro-3-oxopropionate employing methods similar to those described in Example 1, Steps 9-10. The product was obtained as a white solid: $^1$H NMR (d$_6$-DMSO) δ 10.72 (1H, br s), 8.24 (1H, br s), 7.36-7.23 (6H, m), 4.14 (2H, q, J=7 Hz), 4.06 (2H, s), 1.22 (3H, t, J=7 Hz); ES$^+$ MS: 325 (M+H$^+$, 75), 347 (M+Na$^+$, 26);

Anal. Calcd for $C_{18}H_{16}N_2O_4$: C, 53.61; H, 3.99; N, 6.94. Found: C, 53.40; H, 3.92; N, 6.92.

Synthesis of 7-Benzyl-N-(cyclopropylmethyl)-4-hydroxy-2-oxo-1,2-dihydro-1,5-naphthyridine-3-carboxamide

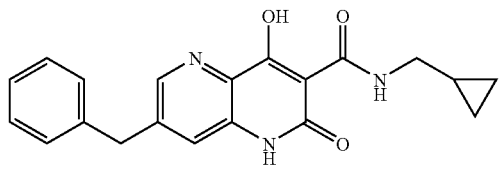 [SMILES: O=C(NCC1CC1)c1c(O)c2ncc(Cc3ccccc3)cc2[nH]c1=O]

Ethyl 7-benzyl-4-hydroxy-2-oxo-1,2-dihydro-1,5-naphthyridine-3-carboxylate was treated with cyclopropylmethyl amine in a manner similar to that described in Example 2. The product was obtained as a white solid: $^1$H NMR ($d_6$-DMSO) δ 11.85 (1H, br), 10.85 (1H, br), 10.11 (1H, br), 8.20 (1H, br m), 7.39-7.25 (6H, br m), 4.01 (2H, br s), 3.33-3.13 (2H, br m), 1.20-0.90 (1H, m), 0.44 (2H, m), 0.19 (2H, m); HRMS calcd for $C_{20}H_{19}N_3O_3+H^+$: 350.1505. Found: 350.1517.

EXAMPLE 4

Ethyl 7-benzyl-4-hydroxy-1-[4-(methylsulfonyl)benzyl]-2-oxo-1,2-dihydro-1,5-naphthyridine-3-

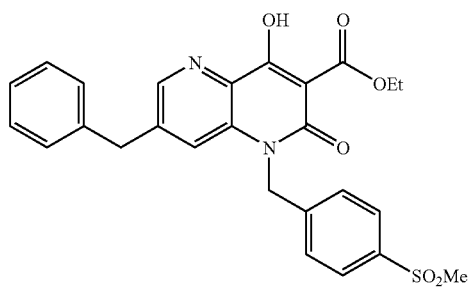

Step 1: Synthesis of ethyl 5-benzyl-3-{[4-(methylsulfonyl)benzyl]amino}pyridine-2-carboxylate

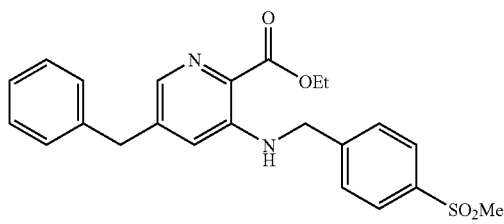 [SMILES: CCOC(=O)c1ncc(Cc2ccccc2)cc1NCc1ccc(S(C)(=O)=O)cc1]

A solution of 1M $BH_3.SMe_2$ in $CH_2Cl_2$ (7 mL, 7 mmol) was added dropwise to a solution of ethyl 3-amino-5-benzylpyridine-2-carboxylate (600 mg, 2.34 mmol) and 4-methylsulfonyl benzaldehyde (647 mg, 3.51 mmol) in $CH_2Cl_2$ (8 mL) and HOAc (4 mL). The mixture was stirred at rt for 30 min and additional amounts of 1M $BH_3.SMe_2$ (2 mL, 2 mmol) and 4-methylsulfonyl benzaldehyde (160 mg, 3.51 mmol) were added. After stirring overnight at rt, the solution was concentrated in vacuo, dissolved in $CH_2Cl_2$ and washed with $NaHCO_3$ solution. The organic layer was dried, concentrated and chromatographed on silica gel eluting with 0-5% MeOH/$CH_2Cl_2$. This afforded the product as an amber foam: $^1$H NMR ($CDCl_3$) δ 8.31 (1H, br m), 7.97 (1H, s), 7.86 (2H, d, J=8 Hz), 7.42 (2H, d, J=8 Hz), 7.22 (3H, m), 7.02 (2H, dd, J=8, 2 Hz), 6.58 (1H, s), 4.46 (2H, br), 4.46 (2H, q, J=7 Hz), 3.87 (2H, s), 3.04 (3H, s), 1.45 (3H, t, J=7 Hz); HRMS calcd for $C_{23}H_{24}N_2O_4S+H^+$: 425.1535. Found: 425.1524.

Step 2: Synthesis of ethyl 5-benzyl-3-{(3-ethoxy-3-oxopropanoyl)[4-(methylsulfonyl)benzyl]amino}pyridine-2-carboxylate

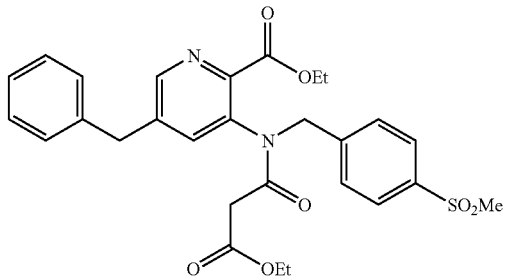 [SMILES: CCOC(=O)CC(=O)N(Cc1ccc(S(C)(=O)=O)cc1)c1cc(Cc2ccccc2)cnc1C(=O)OCC]

A solution of ethyl 5-benzyl-3-{[4-(methylsulfonyl)benzyl]amino}pyridine-2-carboxylate (0.54 g, 1.27 mmol) and ethyl 3-chloro-3-oxopropionate (0.21 mL, 1.67 mmol) in DCE (6 mL) was heated at reflux for 2.5 h. After cooling to rt, the solution was diluted with $CH_2Cl_2$ and washed with $NaHCO_3$ solution. The organic layer was dried and concentrated to give the product: $^1$H NMR ($CDCl_3$) δ 8.62 (1H, d, J=2 Hz), 7.82 (2H, d, J=8 Hz), 7.37 (2H, d, J=8 Hz), 7.28 (3H, m), 7.06 (1H, d, J=2 Hz), 6.97 (2H, dd, J=8, 2 Hz), 5.52 (1H, d, J=15 Hz), 4.38 (2H, m), 4.22 (1H, d, J=15 Hz), 4.01 (2H, m), 3.92 (2H, m), 3.24 (1H, d, J=16 Hz), 3.11 (1H, d, J=16 Hz), 3.02 (3H, s), 1.39 (3H, t, J=7 Hz), 1.17 (3H, t, J=7 Hz); HRMS calcd for $C_{28}H_{30}N_2O_7S+H^+$: 539.1852. Found: 539.1854.

Step 3: Synthesis of ethyl 7-benzyl-4-hydroxy-1-[4-(methylsulfonyl)benzyl]-2-oxo-1,2-dihydro-1,5-naphthyridine-3-carboxylate

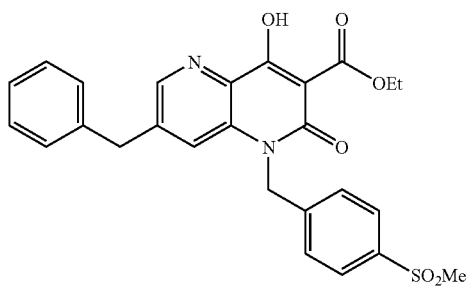 [SMILES: CCOC(=O)c1c(O)c2ncc(Cc3ccccc3)cc2n(Cc2ccc(S(C)(=O)=O)cc2)c1=O]

A solution of 1M NaOEt in EtOH (2.5 mL, 2.5 mmol) was added dropwise to a solution of ethyl 5-benzyl-3-{(3-ethoxy-3-oxopropanoyl)[4-(methylsulfonyl)benzyl]-amino}-pyridine-2-carboxylate (690 mg, 1.26 mmol) in EtOH (6 mL). The mixture was stirred at rt for 30 min, neutralized with 1M HCl (2.5 mL) and the resulting precipitate was collected by filtration washing with 1:1 water/EtOH. This procedure afforded the product as an off-white solid: $^1$H NMR (CDCl$_3$) δ 14.07 (1H, br s), 8.56 (1H, s), 7.79 (2H, d, J=8 Hz), 7.30 (3H, m), 7.19 (2H, d, J=8 Hz), 7.02 (3H, m), 5.40 (2H, br s), 4.53 (2H, q, J=7 Hz), 4.04 (2H, s), 3.01 (3H, s), 1.48 (3H, s); HRMS calcd for C$_{26}$H$_{24}$N$_2$O$_6$S+H$^+$: 493.1433. Found: 493.1422.

EXAMPLE 5

7-Benzyl-4-hydroxy-1-[4-(methylsulfonyl)benzyl]-2-oxo-N-(pyridin-4-ylmethyl)-1,2-dihydro-1,5-naphthyridine-3-carboxamide

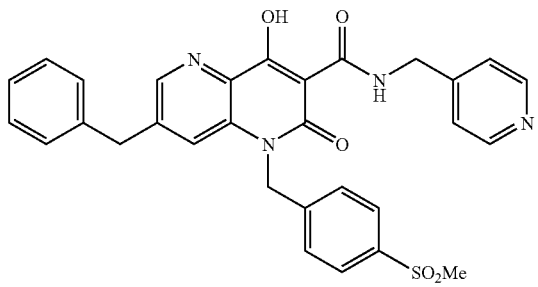 [SMILES: CS(=O)(=O)c1ccc(Cn2c(=O)c(C(=O)NCc3ccncc3)c(O)c3ncc(Cc4ccccc4)cc32)cc1]

A mixture of ethyl 7-benzyl-4-hydroxy-1-[4-(methylsulfonyl)benzyl]-2-oxo-1,2-dihydro-1,5-naphthyridine-3-carboxylate (40 mg, 0.080 mmol) and 4-(aminomethyl)pyridine (122 μL, 1.2 mmol) in EtOH (1 mL) was heated at 120° C. in a sealed tube in a microwave for 30 min. The reaction mixture was concentrated at reduced pressure, reconstituted in CH$_2$Cl$_2$ and washed with a mixture of 1N HCl and brine. Drying and evaporation of the organic phase gave the product as a pale green solid: $^1$H NMR (CDCl$_3$) δ 10.81 (1H, br t, J=6 Hz), 8.69 (2H, d, J=7 Hz), 8.65 (1H, d, J=1 Hz), 7.83 (2H, d, J=8 Hz), 7.76 (2H, d, J=6 Hz), 7.31 (3H, m), 7.19 (2H, d, J=8 Hz), 7.11 (1H, s), 7.03 (2H, m), 5.43 (2H, br s), 4.86 (2H, d, J=6 Hz), 4.08 (2H, s), 3.03 (3H, s); HRMS calcd for C$_{30}$H$_{26}$N$_4$O$_5$S+H$^+$: 555.1702. Found: 555.1699.

EXAMPLE 6

Methyl 7-benzyl-4-hydroxy-2-oxo-1,2-dihydro-1,5-naphthyridine-3-carboxylate

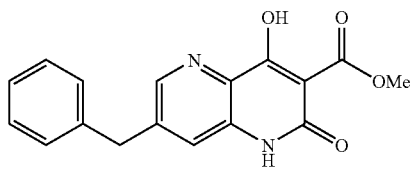 [SMILES: COC(=O)c1c(O)c2ncc(Cc3ccccc3)cc2[nH]c1=O]

This compound was prepared from ethyl 3-amino-5-benzylpyridine-2-carboxylate and methyl 3-chloro-3-oxopropionate employing methods similar to those described in Example 1, Steps 10-11. The product was obtained as a tan solid: $^1$H NMR (d$_6$-DMSO) δ 11.9 (1H, br), 11.59 (1H, s), 8.46 (1H, d, J=1.6 Hz), 7.43 (1H, d, J=1.6 Hz), 7.33-7.20 (5H, m), 4.11 (2H, s), 3.74 (3H, s); HRMS calcd for C$_{17}$H$_{14}$N$_2$O$_4$+H$^+$: 311.1032. Found: 311.1025.

EXAMPLE 7

7-Benzyl-N,4-dihydroxy-2-oxo-1,2-dihydro-1,5-naphthyridine-3-carboxamide

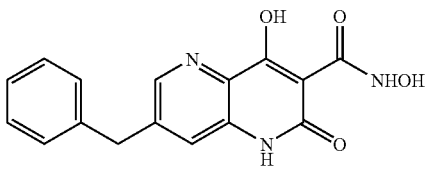

A mixture of methyl 7-benzyl-4-hydroxy-2-oxo-1,2-dihydro-1,5-naphthyridine-3-carboxylate (21 mg, 68 μmol), hydroxylamine hydrochloride (75 mg, 1.1 mmol) and 4.63 M NaOMe/MeOH (0.1 mL, 463 μmol) in 4:1 EtOH/water (1.25 mL) was heated at reflux for 2 h. The mixture was neutralized with conc. HCl, diluted with water and the resulting solids were collected by filtration. Trituration of the filter cake with EtOAc/MeOH provided the product as a beige solid: $^1$H NMR (d$_6$-DMSO) δ 11.86 (2H, br), 9.78 (1H, br), 8.50 (1H, br), 7.50-7.10 (6H, m), 4.10 (2H, br s); HRMS calcd for C$_{16}$H$_{13}$N$_3$O$_4$+H$^+$: 312.0984. Found: 312.0987.

EXAMPLE 8

Ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate

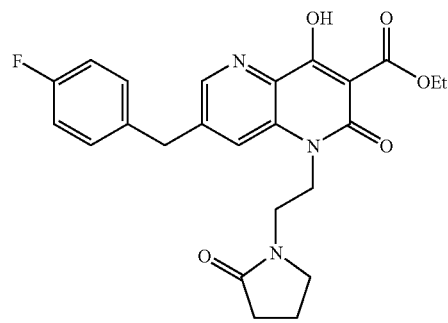 [SMILES: CCOC(=O)c1c(O)c2ncc(Cc3ccc(F)cc3)cc2n(CCN2CCCC2=O)c1=O]

Step 1: Synthesis of (2-oxopyrrolidin-1-yl)acetaldehyde

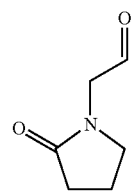

Oxalyl chloride (0.87 mL, 10 mmol) was added dropwise to a solution of DMSO (0.71 mL, 10 mmol) in CH$_2$Cl$_2$ (7 mL)

cooled to −78° C. After stirring 15 min at this temperature, 1-(2-hydroxyethyl)-2-pyrrolidinone (1 g, 7.7 mmol) was added dropwise. The mixture was stirred 30 min at −78° C. and Et$_3$N (2.8 mL, 20 mmol) was added dropwise. After allowing the reaction to warm to rt, a solution of NaHCO$_3$ was added and the mixture was extracted with CH$_2$Cl$_2$ (6×). The combined organic layers were dried and concentrated to give the product as an oil: $^1$H NMR (CDCl$_3$) δ 9.60 (1H, s), 4.16 (2H, s), 3.46 (2H, t, J=7 Hz), 2.45 (2H, t, J=8 Hz), 2.11 (2H, m).

Step 2: Synthesis of ethyl 5-(4-fluorobenzyl)-3-{[2-(2-oxopyrrolidin-1-yl)ethyl]amino}pyridine-2-carboxylate

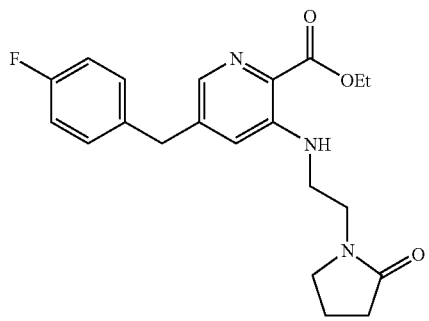 [SMILES: CCOC(=O)c1ncc(Cc2ccc(F)cc2)cc1NCCN1CCCC1=O]

(2-Oxopyrrolidin-1-yl)acetaldehyde and ethyl 3-amino-5-(4-fluorobenzyl)-2-pyridinecarboxylate were treated in a manner similar to that described in Example 5, Step 1 to yield the product as an amber oil: $^1$H NMR (CDCl$_3$) δ 7.89 (1H, d, J=1.4 Hz), 7.83 (1H, br t, J~6 Hz), 7.15 (2H, dd, J~9, 6 Hz), 6.98 (2H, t, J~9 Hz), 6.92 (1H, s), 4.42 (2H, q, J=7 Hz), 3.92 (2H, s), 3.49 (2H, m), 3.41 (2H, t, J=7 Hz), 3.35 (2H, q, J=6 Hz), 2.36 (2H, t, J=8 Hz), 1.99 (2H, m), 1.42 (3H, t, J=7 Hz); HRMS calcd for C$_{21}$H$_{24}$FN$_3$O$_3$+H$^+$: 386.1880. Found: 386.1880.

Steps 3-4: Synthesis of ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate

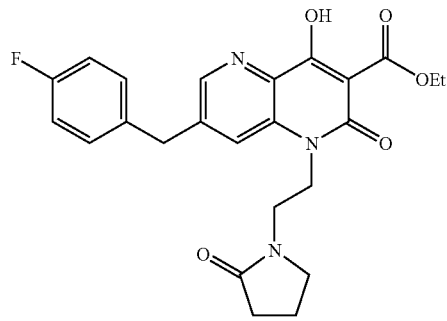 [SMILES: CCOC(=O)c1c(O)c2ncc(Cc3ccc(F)cc3)cc2n(CCN2CCCC2=O)c1=O]

This compound was prepared from ethyl 5-(4-fluorobenzyl)-3-{[2-(2-oxopyrrolidin-1-yl)ethyl]amino}pyridine-2-carboxylate and ethyl 3-chloro-3-oxopropionate in a manner similar to that described in Example 1, Steps 10-11 and was obtained as a white solid: $^1$H NMR (CDCl$_3$) δ 8.50 (1H, d, J=1.4 Hz), 8.11 (1H, s), 7.26 (2H, m), 7.00 (2H, ddd, J~9, 9, 2 Hz), 4.52 (2H, q, J=7 Hz), 4.33 (2H, br t, J~7 Hz), 4.14 (2H, s), 3.52-3.44 (4H, m), 2.35 (2H, t, J=8 Hz), 2.00 (2H, m), 1.48 (3H, t, J=7 Hz); HRMS calcd for C$_{24}$H$_{24}$FN$_3$O$_5$+H$^+$: 454.1778. Found: 454.1787.

EXAMPLE 9

N-Cyclopropyl-7-(4-fluorobenzyl)-4-hydroxy-2-oxo-1-[2-(2-oxopyrrolidin-1-yl)ethyl]-1,2-dihydro-1,5-naphthyridine-3-carboxamide

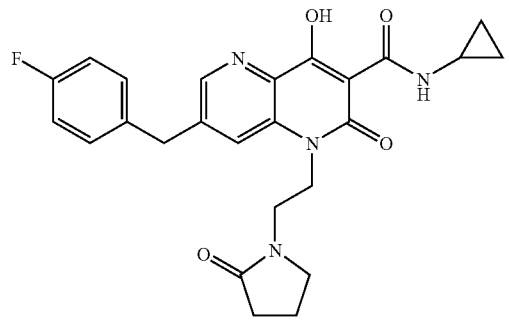 [SMILES: O=C(NC1CC1)c1c(O)c2ncc(Cc3ccc(F)cc3)cc2n(CCN2CCCC2=O)c1=O]

A mixture of ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate (47 mg, 104 μmol) and cyclopropylamine (0.1 mL, 1.44 mmol) in EtOH (3 mL) was heated at 120° C. in a microwave for 20 min. The mixture was concentrated in vacuo, triturated with EtOH and the product was collected by filtration as a white solid: $^1$H NMR (CDCl$_3$) δ 10.06 (1H, d, J=3 Hz), 8.57 (1H, d, J=1.2 Hz), 8.08 (1H, s), 7.25 (2H, dd, J=8.5, 5.5 Hz), 7.00 (2H, t, J=8.5 Hz), 4.32 (2H, q, J=7 Hz), 4.14 (2H, s), 3.49 (2H, t, J=7.4 Hz), 3.41 (2H, t, J=7 Hz), 2.95 (1H, m), 2.32 (2H, t, J=8 Hz), 1.97 (2H, m), 0.90 (2H, m), 0.69 (2H, m); HRMS calcd for C$_{25}$H$_{25}$FN$_4$O$_4$+H$^+$: 465.1938. Found: 465.1932.

EXAMPLE 10

7-(4-Fluorobenzyl)-4-hydroxy-N-(2-morpholin-4-ylethyl)-2-oxo-1-[2-(2-oxopyrrolidin-1-yl)ethyl]-1,2-dihydro-1,5-naphthyridine-3-carboxamide

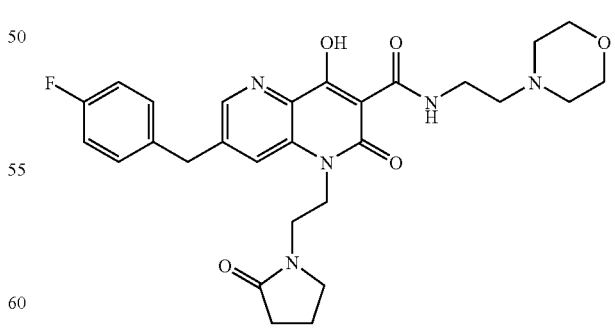

This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 2-(4-morpholino)ethylamine employing methods similar to those described in Example 5. The reaction mixture was concentrated in vacuo and purified by reverse phase preparative HPLC (C-18 stationary phase; 10-100% CH₃CN/water/0.1% formic acid mobile phase). This procedure gave the product as an off-white rigid foam: ¹H NMR (CDCl₃) δ 10.46 (1H, br t, J~6 Hz), 8.59 (1H, d, J=1.3 Hz), 8.12 (1H, s), 7.24 (2H, dd, J=8.6, 5.4 Hz), 7.00 (2H, t, J=8.6 Hz), 4.32 (2H, br t, J=7 Hz), 4.16 (2H, s), 3.98 (4H, br), 3.91 (2H, q, J=6 Hz), 3.77 (2H, br), 3.50 (4H, m), 3.39 (2H, t, J=6 Hz), 2.92 (2H, br), 2.41 (2H, t, J=8 Hz), 2.05 (2H, m); ES⁺ MS: 538 (M+H⁺, 100).

EXAMPLE 11

Ethyl 7-benzyl-4-hydroxy-1-(2-morpholin-4-yl-2-oxoethyl)-2-oxo-1,2-dihydro-1,5-naphthyridine-3-carboxylate

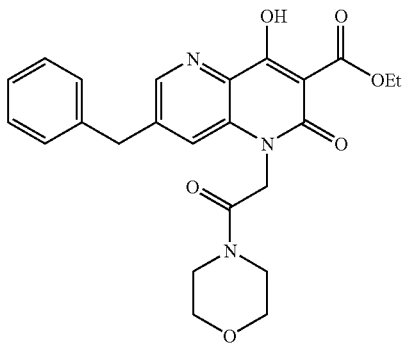 [SMILES: CCOC(=O)c1c(O)c2ncc(Cc3ccccc3)cc2n(CC(=O)N2CCOCC2)c1=O]

Step 1: Synthesis of N-[5-benzyl-2-(ethoxycarbonyl)pyridin-3-yl]glycine

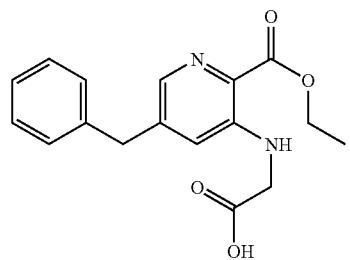 [SMILES: CCOC(=O)c1ncc(Cc2ccccc2)cc1NCC(=O)O]

A mixture of ethyl 3-amino-5-benzylpyridine-2-carboxylate (0.543 g, 2.12 mmol) and glyoxylic acid monohydrate (0.254 g, 2.76 mmol) in EtOH (6 mL) was heated at reflux for 1 h. The mixture was allowed to cool to rt and NaCNBH₃ (266 mg, 4.23 mmol) was added. After stirring 2 h at rt, the reaction was quenched with water and the EtOH was removed at reduced pressure. The aqueous mixture was extracted with CH₂Cl₂ and the organic layers were dried and concentrated. Trituration of the remaining material with EtOAc/hexanes and filtration afforded the product as a beige solid: ¹H NMR (d₆-DMSO) δ 13.2 (1H, br), 7.92 (1H, br t, J=4.8 Hz), 7.76 (1H, s), 7.26 (4H, m), 7.17 (1H, t, J=7 Hz), 7.00 (1H, s), 4.24 (2H, q, J=7 Hz), 3.90 (2H, s), 3.86 (2H, br), 1.27 (3H, t, J=7 Hz).

Step 2: Synthesis of 5-benzyl-2-(ethoxycarbonyl)-N-(2-morpholin-4-yl-2-oxoethyl)pyridin-3-amine

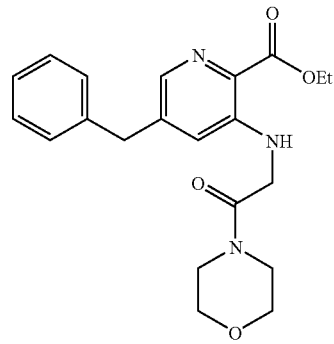 [SMILES: CCOC(=O)c1ncc(Cc2ccccc2)cc1NCC(=O)N1CCOCC1]

HATU (494 mg, 1.3 mmol) was added via spatula to a solution of N-[5-benzyl-2-(ethoxycarbonyl)pyridin-3-yl]glycine (328 mg, 1.04 mmol), morpholine (0.113 mL, 1.3 mmol) and Et₃N (0.18 mL, 1.3 mmol) in DMF (6 mL). After stirring for 45 min at rt, the solvent was removed in vacuo and the resulting material was dissolved in CH₂Cl₂ and washed with water. The organic layer was dried and concentrated. Purification of the crude material by silica gel chromatography eluting with 0-5% MeOH/CH₂Cl₂ afforded the product: ¹H NMR (CDCl₃) δ 8.57 (1H, br), 7.94 (1H, s), 7.23 (3H, m), 7.15 (2H, m), 6.68 (1H, s), 4.46 (2H, q, J=7 Hz), 3.95 (2H, s), 3.90 (2H, d, J=4.2 Hz), 3.68 (6H, br), 3.43 (2H, br), 1.42 (3H, t, J=7 Hz); ES⁺ MS: 384 (M+H⁺, 70).

Steps 3-4: Synthesis of ethyl 7-benzyl-4-hydroxy-1-(2-morpholin-4-yl-2-oxoethyl)-2-oxo-1,2-dihydro-1,5-naphthyridine-3-carboxylate

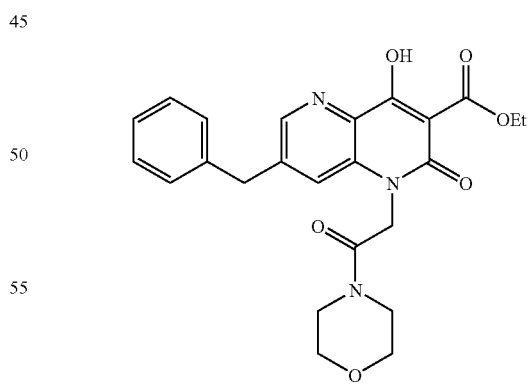

This compound was prepared in two steps from 5-benzyl-2-(ethoxycarbonyl)-N-(2-morpholin-4-yl-2-oxoethyl)pyridin-3-amine and ethyl 3-chloro-3-oxopropionate employing methods similar to those described in Example 5, Steps 2-3. The product was obtained as a white solid: ¹H NMR (CDCl₃) δ 14.2 (1H, br), 8.53 (1H, s), 7.32 (3H, m), 7.18 (2H, d, J=7 Hz), 7.05 (1H, s), 4.93 (2H, s), 4.49 (2H, q, J=7 Hz), 4.13 (2H, s), 3.70 (2H, m), 3.66 (2H, m), 3.54 (4H, m), 1.45 (3H, t, J=7 Hz); ES⁺ MS: 452 (M+H⁺, 100).

EXAMPLE 12

7-Benzyl-4-hydroxy-N-(2-methoxyethyl-1-(2-morpholin-4-yl-2-oxoethyl)-2-oxo-1,2-dihydro-1,5-naphthyridine-3-carboxamide

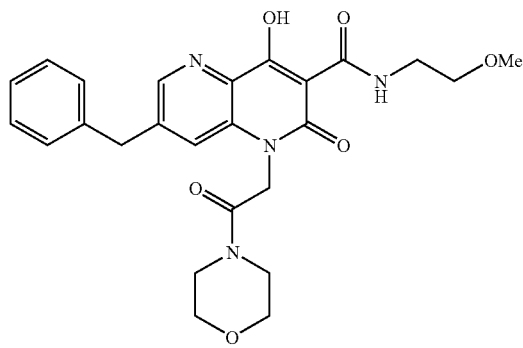 [SMILES: COCCNC(=O)c1c(O)c2ncc(Cc3ccccc3)cc2n(CC(=O)N2CCOCC2)c1=O]

This compound was prepared from ethyl 7-benzyl-4-hydroxy-1-(2-morpholin-4-yl-2-oxoethyl)-2-oxo-1,2-dihydro-1,5-naphthyridine-3-carboxylate and 2-methoxyethylamine employing methods similar to those described in Example 5. The product was obtained as a white solid: ¹H NMR (CDCl₃) δ 10.14 (1H, br), 8.59 (1H, s), 7.37-7.27 (3H, m), 7.18 (2H, d, J=7 Hz), 7.01 (1H, s), 4.93 (2H, s), 4.15 (2H, s), 3.70-3.61 (6H, m), 3.56 (4H, m), 3.52 (2H, m), 3.39 (3H, s); ES⁺ MS: 481 (M+H⁺, 100).

EXAMPLE 13

4-Hydroxy-N-(2-methylpropyl)-2-oxo-7-(phenylmethyl)-1,2-dihydro-1,5-naphthyridine-3-carboxamide

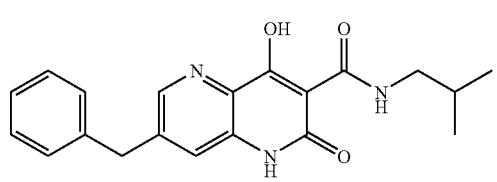 [SMILES: CC(C)CNC(=O)c1c(O)c2ncc(Cc3ccccc3)cc2[nH]c1=O]

This compound was prepared from ethyl 4-hydroxy-2-oxo-7-(phenylmethyl)-1,2-dihydro-1,5-naphthyridine-3-carboxylate and isobutylamine employing methods similar to those described in Example 2 and was obtained as a white solid; ¹H NMR (d₆-DMSO) δ 10.82 (1H, br), 8.22 (1H, s), 7.35-7.22 (6H, m), 4.03 (2H, s), 3.11 (2H, br), 1.77 (1H, m), 0.92 (6H, d, J=6.5 Hz); HRMS calcd for $C_{20}H_{21}N_3O_3+H^+$: 352.1661. Found: 352.1645.

EXAMPLE 14

N-Cycloheptyl-4-hydroxy-2-oxo-7-(phenylmethyl)-1,2-dihydro-1,5-naphthyridine-3-carboxamide

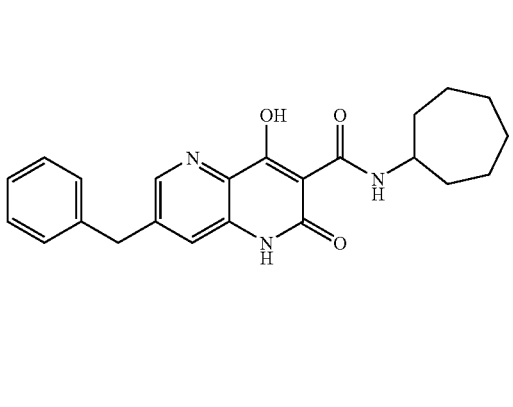 [SMILES: O=C(NC1CCCCCC1)c1c(O)c2ncc(Cc3ccccc3)cc2[nH]c1=O]

This compound was prepared from ethyl 4-hydroxy-2-oxo-7-(phenylmethyl)-1,2-dihydro-1,5-naphthyridine-3-carboxylate and cycloheptylamine employing methods similar to those described in Example 2 and was obtained as a white solid; ¹H NMR (d₆-DMSO) δ 10.75 (1H, br), 8.23 (1H, s), 7.38 (1H, s), 7.35-7.20 (5H, m), 4.04 (2H, s), 4.00 (1H, m), 1.88-1.34 (12H, m); HRMS calcd for $C_{23}H_{25}N_3O_3+H^+$: 392.1974. Found: 392.1956.

EXAMPLE 15

N-Cyclopentyl-4-hydroxy-2-oxo-7-(phenylmethyl)-1,2-dihydro-1,5-naphthyridine-3-carboxamide

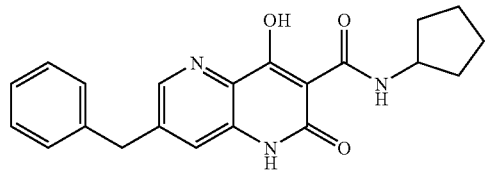 [SMILES: O=C(NC1CCCC1)c1c(O)c2ncc(Cc3ccccc3)cc2[nH]c1=O]

This compound was prepared from ethyl 4-hydroxy-2-oxo-7-(phenylmethyl)-1,2-dihydro-1,5-naphthyridine-3-carboxylate and cyclopentylamine employing methods similar to those described in Example 2 and was obtained as a white solid: ¹H NMR (d₆-DMSO) δ 10.75 (1H, br), 8.24 (1H, s), 7.35 (1H, s), 7.32-7.20 (5H, m), 4.21 (1H, m, J=6.7 Hz), 4.04

(2H, s), 1.93-1.35 (8H, m); Anal. Calcd for $C_{21}H_{21}N_3O_3 \cdot 1.90$ HCl: C, 58.29; H, 5.33; N, 9.71. Found: C, 58.31; H, 5.33; N, 9.85.

EXAMPLE 16

N-Cyclobutyl-4-hydroxy-2-oxo-7-(phenylmethyl)-1,2-dihydro-1,5-naphthyridine-3-carboxamide

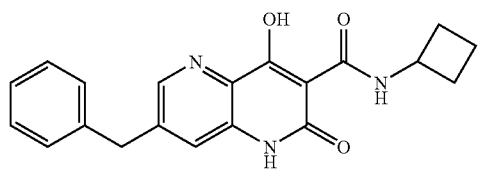 [SMILES: O=C(NC1CCC1)c1c(O)c2ncc(Cc3ccccc3)cc2[nH]c1=O]

This compound was prepared from ethyl 4-hydroxy-2-oxo-7-(phenylmethyl)-1,2-dihydro-1,5-naphthyridine-3-carboxylate and cyclobutylamine employing methods similar to those described in Example 2 and was obtained as a white solid: $^1$H NMR (d$_6$-DMSO) δ 12.00 (1H, br), 8.23 (1H, br), 7.38-7.25 (6H, m), 4.41 (1H, m, J=7.7 Hz), 4.04 (2H, br s), 2.27 (2H, br m), 1.93 (2H, br m), 1.71 (2H, br m); Anal. Calcd for $C_{20}H_{19}N_3O_3 \cdot 0.45$ $CH_2Cl_2$: C, 63.37; H, 5.18; N, 10.84. Found: C, 63.62; H, 5.29; N, 10.97.

EXAMPLE 17

4-Hydroxy-N-[2-(methyloxy)ethyl]-2-oxo-7-(phenylmethyl-1,2-dihydro-1,5-naphthyridine-3-carboxamide

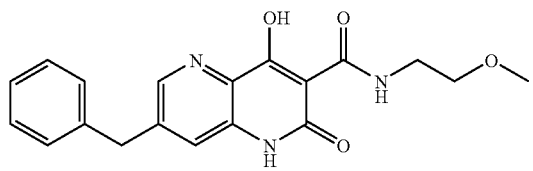 [SMILES: COCCNC(=O)c1c(O)c2ncc(Cc3ccccc3)cc2[nH]c1=O]

This compound was prepared from ethyl 4-hydroxy-2-oxo-7-(phenylmethyl)-1,2-dihydro-1,5-naphthyridine-3-carboxylate and 2-methoxyethylamine employing methods similar to those described in Example 2 and was obtained as a white solid: $^1$H NMR (d$_6$-DMSO) δ 11.85 (1H, br), 10.80 (1H, br), 9.23 (1H, br), 7.35-7.22 (6H, m), 4.03 (2H, br s), 3.45 (4H, br m), 3.28 (3H, s); Anal. Calcd for $C_{19}H_{19}N_3O_4 \cdot 0.25$ $CH_2Cl_2$: C, 61.72; H, 5.25; N, 11.22. Found: C, 61.44; H, 4.90; N, 11.28.

EXAMPLE 18

4-Hydroxy-2-oxo-N-(2-phenylethyl)-7-(phenylmethyl)-1,2-dihydro-1,5-naphthyridine-3-carboxamide

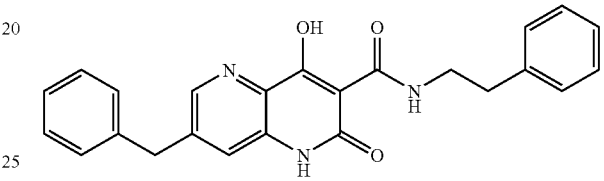

This compound was prepared from ethyl 4-hydroxy-2-oxo-7-(phenylmethyl)-1,2-dihydro-1,5-naphthyridine-3-carboxylate and phenethylamine employing methods similar to those described in Example 2 and was obtained as a white solid: $^1$H NMR (d$_6$-DMSO) δ 11.90 (1H, br), 10.65 (1H br), 8.30 (1H, br), 7.37-7.22 (1H, m), 4.04 (2H, br s), 3.53 (2H, m, J~5 Hz), 2.83 (2H, t, J=7 Hz); Anal. Calcd for $C_{24}H_{21}N_3O_3 \cdot 0.25$ $CH_2Cl_2$: C, 69.45; H, 5.12; N, 9.92. Found: C, 69.40; H, 4.92; N, 10.11.

EXAMPLE 19

4-Hydroxy-2-oxo-N-(1-phenylethyl)-7-(phenylmethyl)-1,2-dihydro-1,5-naphthyridine-3-carboxamide

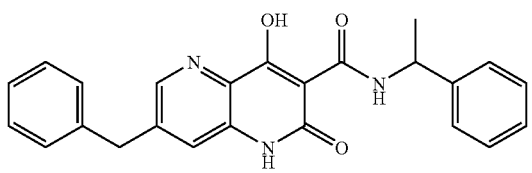 [SMILES: CC(NC(=O)c1c(O)c2ncc(Cc3ccccc3)cc2[nH]c1=O)c1ccccc1]

This compound was prepared from ethyl 4-hydroxy-2-oxo-7-(phenylmethyl)-1,2-dihydro-1,5-naphthyridine-3-carboxylate and α-methylbenzylamine employing methods similar to those described in Example 2 and was obtained as a white solid: $^1$H NMR (d$_6$-DMSO) δ 12.40 (1H, br), 10.80

(1H, br), 8.35 (1H, br), 7.35-7.24 (1H, m), 5.14 (1H, m), 4.05 (2H, br s), 1.46 (3H, br); HRMS calcd for $C_{24}H_{21}N_3O_3+H^+$: 400.1661. Found: 400.1670.

EXAMPLE 20

N-(Cyclohexylmethyl)-4-hydroxy-2-oxo-7-(phenylmethyl)-1,2-dihydro-1,5-naphthyridine-3-carboxamide

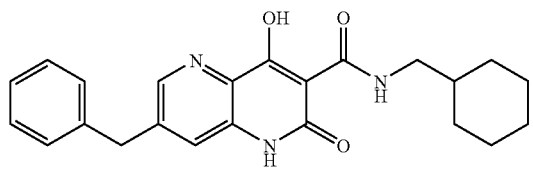 [SMILES: O=C(NCC1CCCCC1)c1c(O)c2ncc(Cc3ccccc3)cc2[nH]c1=O]

This compound was prepared from ethyl 4-hydroxy-2-oxo-7-(phenylmethyl)-1,2 dihydro-1,5-naphthyridine-3-carboxylate and cyclohexylmethylamine employing methods similar to those described in Example 2 and was obtained as a white solid: $^1$H NMR (d$_6$-DMSO) δ 10.80 (1H, br), 8.32 (1H, br s), 7.39 (1H, s), 7.35-7.22 (5H, m), 4.05 (2H, br s), 3.17 (2H, t, J=6 Hz), 1.71-0.79 (11H, m); HRMS calcd for $C_{23}H_{25}N_3O_3+H^+$: 392.1974. Found: 392.1956.

EXAMPLE 21

N-(2-Furanylmethyl)-4-hydroxy-2-oxo-7-(phenylmethyl)-1,2-dihydro-1,5-naphthyridine-3-carboxamide

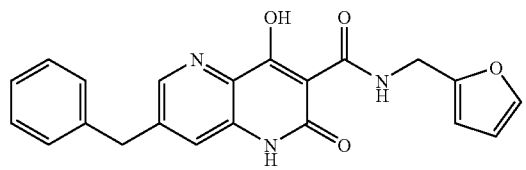 [SMILES: O=C(NCc1ccco1)c1c(O)c2ncc(Cc3ccccc3)cc2[nH]c1=O]

This compound was prepared from ethyl 4-hydroxy-2-oxo-7-(phenylmethyl)-1,2-dihydro-1,5-naphthyridine-3-carboxylate and furfurylamine employing methods similar to those described in Example 2 and was obtained as a white solid; $^1$H NMR (d$_6$-DMSO) δ 12.13 (1H, br), 11.12 (1H, br), 10.15 (1H, br), 8.20 (1H, br s), 7.57 (1H, s), 7.31-7.20 (6H, m), 6.38 (1H, s), 6.27 (1H, br s), 4.48 (2H, br), 4.01 (2H, br s); HRMS calcd for $C_{21}H_{17}N_3O_4+H^+$: 376.1297. Found: 376.1286.

EXAMPLE 22

N-Cyclohexyl-4-hydroxy-2-oxo-7-(phenylmethyl)-1,2-dihydro-1,5-naphthyridine-3-carboxamide

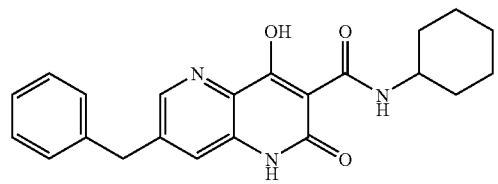 [SMILES: O=C(NC1CCCCC1)c1c(O)c2ncc(Cc3ccccc3)cc2[nH]c1=O]

This compound was prepared from ethyl 4-hydroxy-2-oxo-7-(phenylmethyl)-1,2-dihydro-1,5-naphthyridine-3-carboxylate and cyclohexylamine employing methods similar to those described in Example 2 and was obtained as a white solid: $^1$H NMR (d$_6$-DMSO) δ 11.85 (1H, br), 10.60 (1H, br), 8.33 (1H, br), 7.39 (1H, s), 7.35-7.22 (5H, m), 4.05 (2H, br s), 3.82 (1H, m), 1.85 (2H, m), 1.67 (2H, m), 1.56 (1H, m), 1.38-1.27 (5H, m); HRMS calcd for $C_{22}H_{23}N_3O_3+H^+$: 378.1810. Found: 378.1822.

EXAMPLE 23

4-Hydroxy-2-oxo-7-(phenylmethyl)-N-(2-thienylmethyl)-1,2-dihydro-1,5-naphthyridine-3-carboxamide

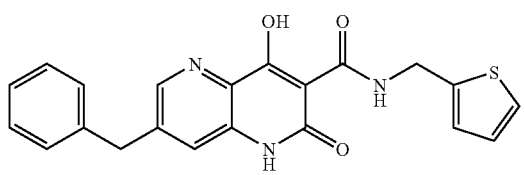

This compound was prepared from ethyl 4-hydroxy-2-oxo-7-(phenylmethyl)-1,2-dihydro-1,5-naphthyridine-3-carboxylate and thiophene-2-methylamine employing methods similar to those described in Example 2 and was obtained as a white solid: $^1$H NMR (d$_6$-DMSO) δ 12.25 (1H, br), 11.10 (1H, br), 10.2 (1H, br), 8.28 (1H, br s), 7.38 (1H, br s), 7.34-7.22 (6H, m), 7.04 (1H, s), 6.97 (1H, d, J=4.3 Hz), 4.68 (2H, br), 4.04 (2H, br s); HRMS calcd for $C_{21}H_{17}N_3O_3S+H^+$: 392.1069. Found: 392.1070.

EXAMPLE 24

N-Cyclopropyl-4-hydroxy-2-oxo-7-(phenylmethyl)-1,2-dihydro-1,5-naphthyridine-3-carboxamide

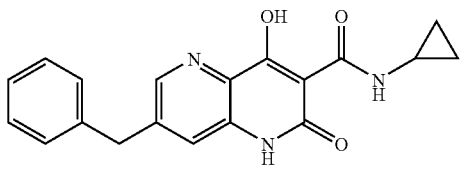 [SMILES: O=C(NC1CC1)c1c(O)c2ncc(Cc3ccccc3)cc2[nH]c1=O]

This compound was prepared from ethyl 4-hydroxy-2-oxo-7-(phenylmethyl)-1,2-dihydro-1,5-naphthyridine-3-carboxylate and cyclopropylamine employing methods similar to those described in Example 5 and using dimethylacetamide as the reaction solvent. The product was obtained as a white solid: $^1$H NMR ($d_6$-DMSO) δ 11.86 (1H, s), 10.87 (1H, s), 10.14 (1H, s), 8.20 (1H, s), 7.38-7.25 (6H, m), 4.01 (2H, br s), 2.79 (1H, m), 0.70 (2H, m), 0.45 (2H, m); HRMS calcd for $C_{19}H_{17}N_3O_3+H^+$: 336.1348. Found: 336.1347.

EXAMPLE 25

N-Cyclobutyl-7-[(4-fluorophenyl)methyl]-4-hydroxy-2-oxo-1,2-dihydro-1,5-naphthyridine-3-carboxamide

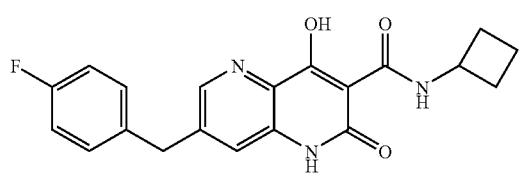 [SMILES: O=C(NC1CCC1)c1c(O)c2ncc(Cc3ccc(F)cc3)cc2[nH]c1=O]

This compound was prepared from ethyl 7-[(4-fluorophenyl)methyl]-4-hydroxy-2-oxo-1,2-dihydro-1,5-naphthyridine-3-carboxylate and cyclobutylamine employing methods similar to those described in Example 2 and was obtained as an off-white solid: $^1$H NMR ($d_6$-DMSO) δ 11.90 (1H, br), 10.50 (1H, br), 8.33 (1H, br), 7.39 (1H, br s), 7.31 (2H, m), 7.15 (2H, t, J~9 Hz), 4.42 (1H, m, J=8 Hz), 4.06 (2H, br s), 2.29 (2H, m), 1.95 (2H, m), 1.71 (2H, m); HRMS calcd for $C_{20}H_{18}FN_3O_3+H^+$: 368.1410. Found: 368.1410.

EXAMPLE 26

N-Cyclopropyl-7-[(4-fluorophenyl)methyl]-4-hydroxy-2-oxo-1,2-dihydro-1,5-naphthyridine-3-carboxamide

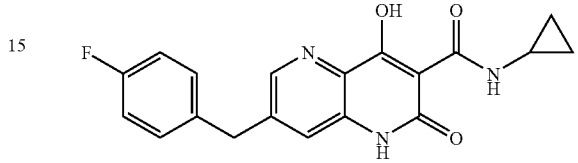

This compound was prepared from ethyl 7-[(4-fluorophenyl)methyl]-4-hydroxy-2-oxo-1,2-dihydro-1,5-naphthyridine-3-carboxylate and cyclopropylamine employing methods similar to those described in Example 2 and was obtained as a white solid: $^1$H NMR ($d_6$-DMSO) δ 11.80 (1H, br), 10.35 (1H, br), 8.35 (1H, br), 7.38 (1H, s), 7.30 (2H, m), 7.15 (2H, t, J=8.7 Hz), 4.06 (2H, br s), 2.85 (1H, m), 0.74 (2H, m), 0.51 (2H, m); HRMS calcd for $C_{19}H_{16}FN_3O_3+H^+$: 354.1254. Found: 354.1255.

EXAMPLE 27

7-[(4-Fluorophenyl)methyl]-N-(2-furanylmethyl)-4-hydroxy-2-oxo-1,2-dihydro-1,5-naphthyridine-3-carboxamide

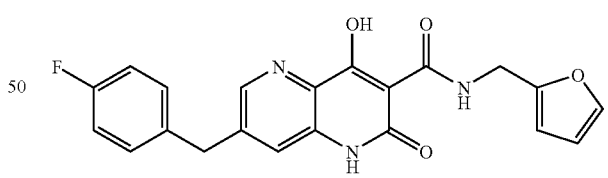

This compound was prepared from ethyl 7-[(4-fluorophenyl)methyl]-4-hydroxy-2-oxo-1,2-dihydro-1,5-naphthyridine-3-carboxylate and furfurylamine employing methods similar to those described in Example 2 and was obtained as an off-white solid: $^1$H NMR ($d_6$-DMSO) δ 11.85 (1H, br), 10.70 (1H, br), 8.39 (1H, br s), 7.61 (1H, s), 7.40 (1H, s), 7.31

(2H, m), 7.15 (2H, t, J=8.5 Hz), 6.42 (1H, s), 6.33 (1H, s), 4.54 (2H, s), 4.08 (2H, s); HRMS calcd for $C_{21}H_{16}FN_3O_4+H^+$: 394.1202. Found: 394.1195.

EXAMPLE 28

7-[(4-Fluorophenyl)methyl]-4-hydroxy-2-oxo-N-[3-(2-oxo-1-pyrrolidinyl-propyl]-1,2-dihydro-1,5-naphthyridine-3-carboxamide

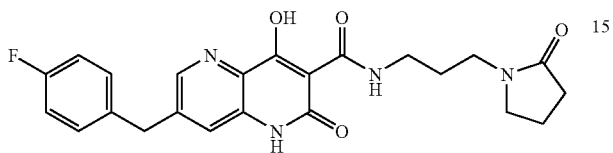

This compound was prepared from ethyl 7-[(4-fluorophenyl)methyl]-4-hydroxy-2-oxo-1,2-dihydro-1,5-naphthyridine-3-carboxylate and 1-(3-aminopropyl)-2-pyrrolidinone employing methods similar to those described in Example 2 and was obtained as a white solid: $^1$H NMR (d$_6$-DMSO) δ 1.88 (1H, br), 10.82 (1H, br), 10.12 (1H, br), 8.20 (1H, m), 7.38 (1H, s), 7.29 (2H, m), 7.17 (2H, m), 4.01 (2H, s), 3.27-3.22 (6H, m), 2.21 (2H, t, J=8 Hz), 1.91 (2H, m), 1.69 (2H, m); HRMS calcd for $C_{23}H_{23}FN_4O_4+H^+$: 439.1782. Found: 439.1774.

EXAMPLE 29

7-[(4-Fluorophenyl)methyl]-4-hydroxy-2-oxo-N-[2-(1-pyrrolidinyl)ethyl]-1,2-dihydro-1,5-naphthyridine-3-carboxamide

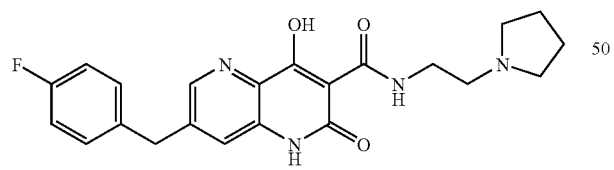

This compound was prepared from ethyl 7-[(4-fluorophenyl)methyl]-4-hydroxy-2-oxo-1,2-dihydro-1,5-naphthyridine-3-carboxylate and 2-(1-pyrrolidinyl)ethylamine employing methods similar to those described in Example 2 and was obtained as a white solid: $^1$H NMR (d$_6$-DMSO) δ 10.61 (1H, br), 8.28 (1H, br s), 7.36 (1H, s), 7.30 (2H, m), 7.14 (2H, t, J=8.8 Hz), 4.04 (2H, s), 3.41 (2H, m), 2.56 (2H, t, J=6.4 Hz), 2.54-2.48 (4H, m), 1.68 (4H, m); ES$^+$ MS: 411 (M+H$^+$, 100).

EXAMPLE 30

(±)-7-[(4-Fluorophenyl)methyl]-4-hydroxy-2-oxo-N-(tetrahydro-2-furanylmethyl)-1,2-dihydro-1,5-naphthyridine-3-carboxamide

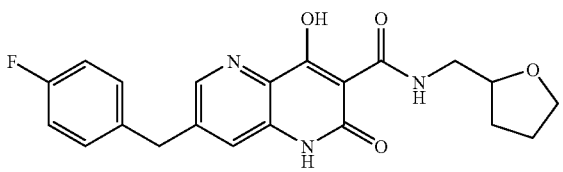 [SMILES: O=C(NCC1CCCO1)c1c(O)c2ncc(Cc3ccc(F)cc3)cc2[nH]c1=O]

This compound was prepared from ethyl 7-[(4-fluorophenyl)methyl]-4-hydroxy-2-oxo-1,2-dihydro-1,5-naphthyridine-3-carboxylate and (±)-(tetrahydro-2-furanylmethyl) amine employing methods similar to those described in Example 2 and was obtained as a white solid: $^1$H NMR (d$_6$-DMSO) δ 11.9 (1H, br), 10.60 (1H, br), 8.37 (1H, br), 7.39 (1H, s), 7.30 (2H, m), 7.15 (2H, t, J=8.6 Hz), 4.06 (2H, br s), 3.96 (1H, m), 3.80 (1H, q, J~7 Hz), 3.64 (1H, q, J~7 Hz), 3.50-3.20 (2H, m), 2.00-1.52 (4H, m); ES$^+$ MS: 398 (M+H$^+$, 100).

EXAMPLE 31

7-[(4-Fluorophenyl)methyl]-4-hydroxy-2-oxo-N-[2-(1-piperidinyl)ethyl]-1,2-dihydro-1,5-naphthyridine-3-carboxamide

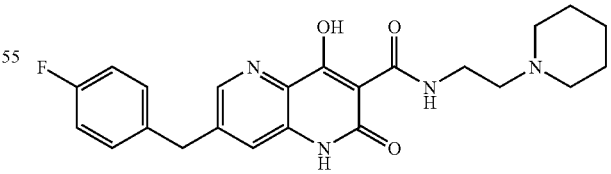

This compound was prepared from ethyl 7-[(4-fluorophenyl)methyl]-4-hydroxy-2-oxo-1,2-dihydro-1,5-naphthyridine-3-carboxylate and 2-(1-piperidinyl)ethylamine employing methods similar to those described in Example 2 and was obtained as a white solid: $^1$H NMR (d$_6$-DMSO) δ 11.75 (1H, br), 10.70 (1H, br), 10.15 (1H, br), 8.20 (1H, m), 7.38-7.11

(5H, m), 4.01 (2H, s), 3.39 (2H, m), 2.38 (6H, m), 1.50 (4H, m), 1.39 (2H, m); ES +MS: 425 (M+H$^+$, 100).

EXAMPLE 32

7-[(4-Fluorophenyl)methyl]-4-hydroxy-2-oxo-N-(4-pyridinylmethyl)-1,2-dihydro-1,5-naphthyridine-3-carboxamide

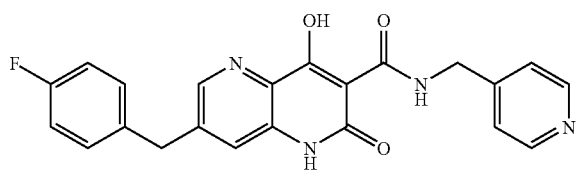

This compound was prepared from ethyl 7-[(4-fluorophenyl)methyl]-4-hydroxy-2-oxo-1,2-dihydro-1,5-naphthyridine-3-carboxylate and 4-(aminomethyl)pyridine employing methods similar to those described in Example 2 and was obtained as a white solid: $^1$H NMR (d$_6$-DMSO) δ 12.40 (1H, br), 11.31 (1H, br), 10.15 (1H, br), 8.48 (2H, br m), 8.20 (1H, br s), 7.29 (5H, m), 7.14 (2H, t, J=8.7 Hz), 4.52 (2H, br m), 4.01 (2H, s); ES$^+$ MS: 405 (M+H$^+$, 100).

EXAMPLE 33

7-[(4-Fluorophenyl)methyl]-4-hydroxy-2-oxo-N-(2-pyridinylmethyl)-1,2-dihydro-1,5-naphthyridine-3-carboxamide

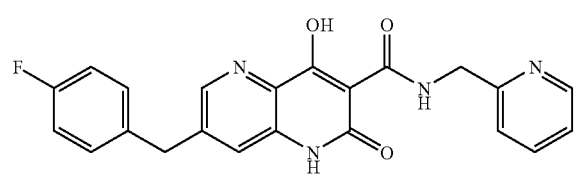 [SMILES: O=C(NCc1ccccn1)c1c(O)c2ncc(Cc3ccc(F)cc3)cc2[nH]c1=O]

This compound was prepared from ethyl 7-[(4-fluorophenyl)methyl]-4-hydroxy-2-oxo-1,2-dihydro-1,5-naphthyridine-3-carboxylate and 2-(aminomethyl)pyridine employing methods similar to those described in Example 2 and was obtained as a white solid: $^1$H NMR (d$_6$-DMSO) δ 12.30 (1H, br), 11.21 (1H, br), 10.20 (1H, br), 8.52 (1H, d, J=4.2 Hz), 8.26 (1H, br s), 7.75 (1H, t, J=7.6 Hz), 7.36-7.24 (5H, m), 7.15 (2H, t, J=8.9 Hz), 4.62 (2H, br m), 4.04 (2H, s); ES$^+$ MS: 405 (M+H, 100).

EXAMPLE 34

7-[(4-Fluorophenyl)methyl]-4-hydroxy-2-oxo-N-(3-pyridinylmethyl)-1,2-dihydro-1,5-naphthyridine-3-carboxamide

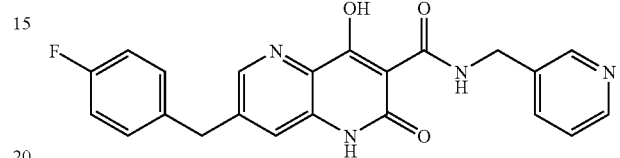

This compound was prepared from ethyl 7-[(4-fluorophenyl)methyl]-4-hydroxy-2-oxo-1,2-dihydro-1,5-naphthyridine-3-carboxylate and 3-(aminomethyl)pyridine employing methods similar to those described in Example 2 and was obtained as a white solid: $^1$H NMR (d$_6$-DMSO) δ 12.32 (1H, br), 11.29 (1H, br), 10.17 (1H, br), 8.56 (1H, s), 8.44 (1H, br), 8.18 (1H, br), 7.73 (1H, m), 7.30-7.27 (4H, m), 7.14 (2H, t, J=8.6 Hz), 4.55 (2H, m), 4.01 (2H, s); ES$^+$ MS: 405 (M+H$^+$, 100).

EXAMPLE 35

7-[(4-Fluorophenyl)methyl]-N-(hexahydro-1H-azepin-1-yl)-4-hydroxy-2-oxo-1,2-dihydro-1,5-naphthyridine-3-carboxamide

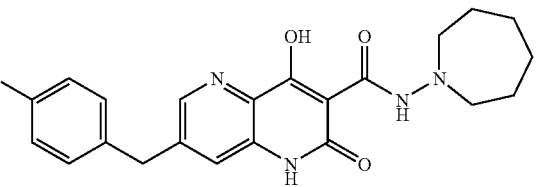

This compound was prepared from ethyl 7-[(4-fluorophenyl)methyl]-4-hydroxy-2-oxo-1,2-dihydro-1,5-naphthyridine-3-carboxylate and hexahydro-1-H-azepin-1-amine employing methods similar to those described in Example 2 and was obtained as a white solid: $^1$H NMR (d$_6$-DMSO) δ 12.90 (1H, br), 11.80 (1H, br), 10.13 (1H, br), 8.15 (1H, br s), 7.23 (3H, m), 7.11 (2H, t, J=8.8 Hz), 3.97 (2H, s), 2.94 (4H, m), 1.59 (8H, m); ES⁺ MS: 411 (M+H⁺, 100).

EXAMPLE 36

7-[(4-Fluorophenyl)methyl]-4-hydroxy-N-[2-(4-morpholinyl)ethyl]-2-oxo-1,2-dihydro-1,5-naphthyridine-3-carboxamide

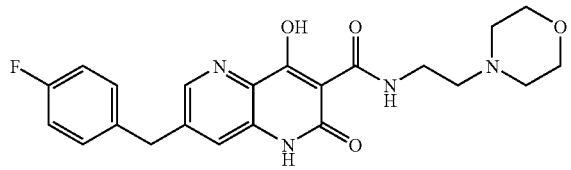 [SMILES: O=C(NCCN1CCOCC1)c1c(O)c2ncc(Cc3ccc(F)cc3)cc2[nH]c1=O]

This compound was prepared from ethyl 7-[(4-fluorophenyl)methyl]-4-hydroxy-2-oxo-1,2-dihydro-1,5-naphthyridine-3-carboxylate and 2-(4-morpholino)ethylamine employing methods similar to those described in Example 2 and was obtained as a white solid: ¹H NMR (d₆-DMSO) δ 11.79 (1H, s), 10.76 (1H, br s), 10.12 (1H, br), 8.18 (1H, m), 7.35-7.24 (3H, m), 7.12 (2H, br m), 3.98 (2H, br s), 3.56 (4H, m), 3.40 (2H, m), 2.39 (6H, m); ES⁺ MS: 427 (M+H⁺, 100).

EXAMPLE 37

7-[(5-Fluoro-2-pyridinyl)methyl]-4-hydroxy-N-[3-(4-morpholinyl)propyl]-2-oxo-1,2-dihydro-1,5-naphthyridine-3-carboxamide

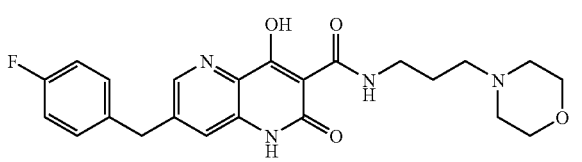 [SMILES: O=C(NCCCN1CCOCC1)c1c(O)c2ncc(Cc3ccc(F)cc3)cc2[nH]c1=O]

This compound was prepared from ethyl 7-[(4-fluorophenyl)methyl]-4-hydroxy-2-oxo-1,2-dihydro-1,5-naphthyridine-3-carboxylate and 4-(3-aminopropyl)morpholine employing methods similar to those described in Example 2 and was obtained as a white solid: ¹H NMR (CF₃CO₂D) δ 8.71 (1H, s), 8.47 (1H, s), 7.28 (2H, dd, J=8.5, 5.3 Hz), 7.13 (2H, t, J=8.5 Hz), 4.41 (2H, s), 4.38 (2H, m), 4.13 (2H, m), 3.82 (4H, m), 3.54 (2H, t, J=8 Hz), 3.43 (2H, m), 2.41 (2H, m); ES⁺ MS: 441 (M+H, 100).

EXAMPLE 38

7-[(4-Fluorophenyl)methyl]-4-hydroxy-2-oxo-N-[2-(2-pyridinyl)ethyl]-1,2-dihydro-1,5-naphthyridine-3-carboxamide

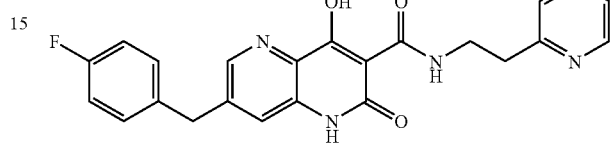

This compound was prepared from ethyl 7-[(4-fluorophenyl)methyl]-4-hydroxy-2-oxo-1,2-dihydro-1,5-naphthyridine-3-carboxylate and 2-(2-aminoethyl)pyridine employing methods similar to those described in Example 2 and was obtained as a white solid: ¹H NMR (CF₃CO₂D) δ 8.84 (1H, d, J=6 Hz), 8.79 (1H, s), 8.71 (1H, t, J=8 Hz), 8.55 (1H s), 8.20 (1H, d, J=8 Hz), 8.11 (1H, t, J=7 Hz), 7.35 (2H, dd, J=8.6, 5.3 Hz), 7.20 (2H, t, J=8.6 Hz), 4.48 (2H, s), 4.26 (2H, t, J=7 Hz), 3.75 (2H, t, J=7 Hz); ES⁺ MS: 4419 (M+H⁺, 100).

EXAMPLE 39

7-[(4-Fluorophenyl)methyl]-4-hydroxy-2-oxo-1,-dihydro-1,5-naphthyridine-3-carboxamide

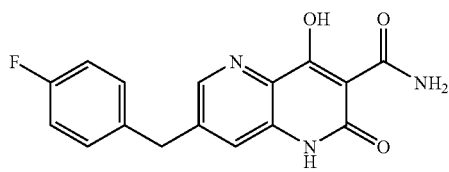 [SMILES: NC(=O)c1c(O)c2ncc(Cc3ccc(F)cc3)cc2[nH]c1=O]

This compound was prepared from ethyl 7-[(4-fluorophenyl)methyl]-4-hydroxy-2-oxo-1,2-dihydro-1,5-naphthyridine-3-carboxylate and ammonium hydroxide employing methods similar to those described in Example 11 and was obtained as a light yellow solid: ¹H NMR (CF₃CO₂D) δ 8.77

(1H, s), 8.51 (1H, s), 7.29 (2H, dd, J=8.6, 5.1 Hz), 7.13 (2H, t, J=8.6 Hz), 4.43 (2H, s); ES+ MS: 314 (M+H+, 100).

EXAMPLE 40

7-[(4-Fluorophenyl)methyl]-4-hydroxy-N-[2-(1H-imidazol-4-yl)ethyl]-2-oxo-1,2-dihydro-1,5-naphthyridine-3-carboxamide

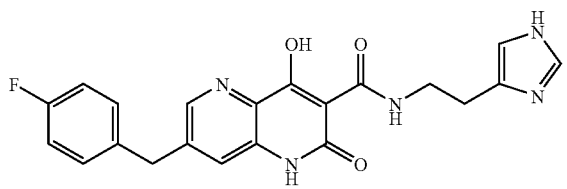 [SMILES: O=C(NCCc1c[nH]cn1)c1c(O)c2ncc(Cc3ccc(F)cc3)cc2[nH]c1=O]

This compound was prepared from ethyl 7-[(4-fluorophenyl)methyl]-4-hydroxy-2-oxo-1,2-dihydro-1,5-naphthyridine-3-carboxylate and 2-(1H-imidazol-4-yl)ethylamine employing methods similar to those described in Example 11 and was obtained as an off-white solid: $^1$H NMR (CF$_3$CO$_2$D) δ 8.66 (1H, s), 8.60 (1H, s), 8.43 (1H, s), 7.39 (1H, s), 7.22 (2H, m), 7.08 (2H, t, J=8.4 Hz), 4.36 (2H, s), 4.00 (2H, br, t, J=6 Hz), 3.29 (2H, br t, J=6 Hz); ES+ MS: 408 (M+H+, 100).

EXAMPLE 41

Ethyl 7-benzyl-4-hydroxy-2-oxo-1-[2-(2-oxopyrrolidin-1-yl)ethyl]-1,2-dihydro-1,5-naphthyridine-3-carboxylate

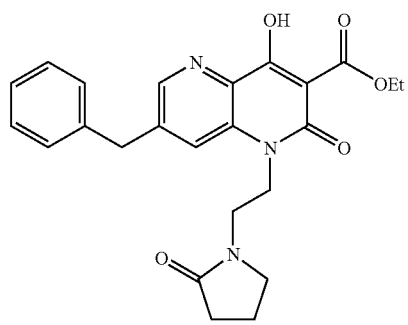 [SMILES: CCOC(=O)c1c(O)c2ncc(Cc3ccccc3)cc2n(CCN2CCCC2=O)c1=O]

This compound was prepared from ethyl 3-amino-5-benzylpyridine-2-carboxylate and (2-oxopyrrolidin-1-yl)acetaldehyde employing methods similar to those described in Example 10, Steps 1-4 and was obtained as a white solid: $^1$H NMR (CDCl$_3$) δ 13.9 (1H, br), 8.54 (1H, s), 8.11 (1H, s), 7.52-7.21 (5H, m), 4.52 (2H, q, J=7 Hz), 4.34 (2H, br t, J=7 Hz), 4.18 (2H, s), 3.52 (2H, br t, J=7 Hz), 3.44 (2H, t, J=7 Hz), 2.33 (2H, t, J=8 Hz), 1.98 (2H, m), 1.48 (3H, t, J=7 Hz); ES+ MS: 458 (M+Na+, 100).

EXAMPLE 42

Benzyl-N-cyclobutyl-4-hydroxy-2-oxo-1-[2-(2-oxopyrrolidin-1-yl)ethyl]-1,2-dihydro-1,5-naphthyridine-3-carboxamide

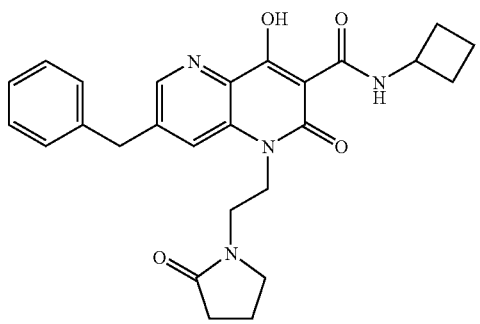 [SMILES: O=C(NC1CCC1)c1c(O)c2ncc(Cc3ccccc3)cc2n(CCN2CCCC2=O)c1=O]

This compound was prepared from ethyl 7-benzyl-4-hydroxy-2-oxo-1-[2-(2-oxopyrrolidin-1-yl)ethyl]-1,2-dihydro-1,5-naphthyridine-3-carboxylate and cyclobutylamine employing methods similar to those described in Example 2 and was obtained as an off-white solid: $^1$H NMR (CDCl$_3$) δ 10.23 (1H, br d, J=7 Hz), 8.58 (1H, s), 8.02 (1H, s), 7.33-7.20 (5H, m), 4.53 (1H, m), 4.35 (2H, br t, J=7 Hz), 4.17 (2H, s), 3.52 (2H, t, J=7 Hz), 3.37 (2H, t, J=7 Hz), 2.41 (2H, m), 2.28 (2H, t, J=8 Hz), 2.08 (2H, m), 1.93 (2H, m), 1.80 (2H, m); HRMS calcd for C$_{26}$H$_{28}$N$_4$O$_4$+H+: 461.2189. Found: 461.2205.

EXAMPLE 43

7-Benzyl-N-cyclopropyl-4-hydroxy-1-[4-(methylsulfonyl)benzyl]-2-oxo-1,2-dihydro-1,5-naphthyridine-3-carboxamide

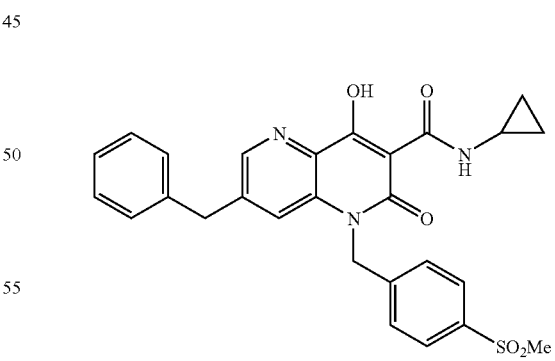

This compound was prepared from ethyl 7-benzyl-4-hydroxy-1-[4-(methylsulfonyl)benzyl]-2-oxo-1,2-dihydro-1,5-naphthyridine-3-carboxylate and cyclopropylamine employing methods similar to those described in Example 2. The product was obtained as a white solid: $^1$H NMR (CDCl$_3$) δ 10.04 (1H, br d, J=3.4 Hz), 8.61 (1H, s), 7.81 (2H, d, J=8.4 Hz), 7.29 (3H, m), 7.17 (2H, d, J=8.4 Hz), 7.05 (1H, s), 7.03 (2H, m), 5.39 (2H, br), 4.05 (2H, s), 3.01 (3H, s), 2.97 (1H, m), 0.90 (2H, m), 0.70 (2H, m); HRMS calcd for $C_{27}H_{25}N_3O_5S+H^+$: 504.1593. Found: 504.1581.

EXAMPLE 44

7-Benzyl-N-cyclobutyl-4-hydroxy-1-[4-(methylsulfonyl)benzyl]-2-oxo-1,2-dihydro-1,5-naphthyridine-3-carboxamide

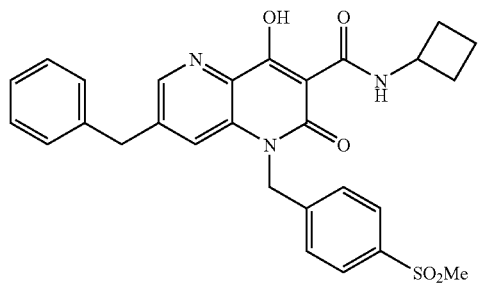 [SMILES: CS(=O)(=O)c1ccc(Cn2c(=O)c(C(=O)NC3CCC3)c(O)c3ncc(Cc4ccccc4)cc32)cc1]

This compound was prepared from ethyl 7-benzyl-4-hydroxy-1-[4-(methylsulfonyl)benzyl]-2-oxo-1,2-dihydro-1,5-naphthyridine-3-carboxylate and cyclobutylamine employing methods similar to those described in Example 2. The product was obtained as a white solid: $^1$H NMR (CDCl$_3$) δ 10.19 (1H, br d, J=7.4 Hz), 8.61 (1H, d, J=1.1 Hz), 7.82 (2H, d, J=8.4 Hz), 7.30 (3H, m), 7.18 (2H, d, J=8.4 Hz), 7.06 (1H, s), 7.03 (2H, m), 5.41 (2H, br), 4.54 (1H, m), 4.05 (2H, s), 3.02 (3H, s), 2.44 (2H, m), 2.08 (2H, m), 1.83 (2H, m); HRMS calcd for $C_{28}H_{27}N_3O_5S+H^+$: 518.1740. Found: 518.1741.

Example 45

7-Benzyl-4-hydroxy-N-(2-methoxyethyl)-1-[4-(methylsulfonyl)benzyl]-2-oxo-1,2-dihydro-1,5-naphthyridine-3-carboxamide

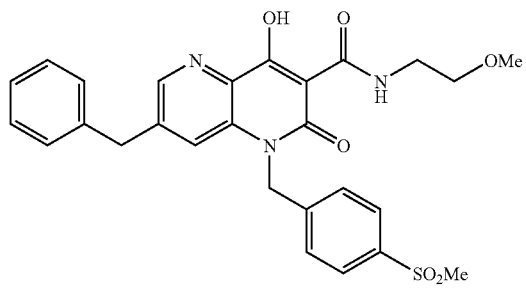 [SMILES: COCCNC(=O)c1c(O)c2ncc(Cc3ccccc3)cc2n(Cc2ccc(S(C)(=O)=O)cc2)c1=O]

This compound was prepared from ethyl 7-benzyl-4-hydroxy-1-[4-(methylsulfonyl)benzyl]-2-oxo-1,2-dihydro-1,5-naphthyridine-3-carboxylate and 2-methoxyethylamine employing methods similar to those described in Example 2. The product was obtained as a white solid: $^1$H NMR (CDCl$_3$) δ 10.22 (1H, br m), 8.61 (1H, s), 7.81 (2H, d, J=8 Hz), 7.29 (3H, m), 7.17 (2H, d, J=8 Hz), 7.06 (1H, s), 7.02 (2H, m), 5.41 (2H, br), 4.05 (2H, s), 3.67 (2H, m), 3.60 (2H, m), 3.40 (3H, s), 3.01 (3H, s); HRMS calcd for $C_{27}H_{27}N_3O_6S+H^+$: 522.1699. Found: 522.1686.

EXAMPLE 46

7-Benzyl-N-(2-furylmethyl)-4-hydroxy-1-[4-(methylsulfonyl)benzyl]-2-oxo-1,2-dihydro-1,5-naphthyridine-3-carboxamide

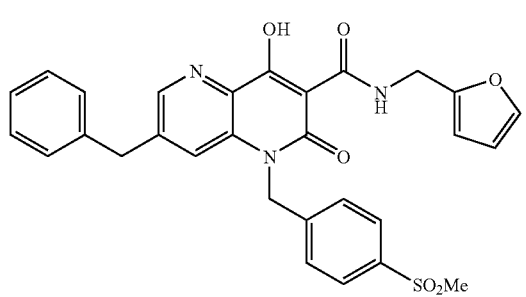 [SMILES: CS(=O)(=O)c1ccc(Cn2c(=O)c(C(=O)NCc3ccco3)c(O)c3ncc(Cc4ccccc4)cc32)cc1]

This compound was prepared from ethyl 7-benzyl-4-hydroxy-1-[4-(methylsulfonyl)benzyl]-2-oxo-1,2-dihydro-1,5-naphthyridine-3-carboxylate and furfurylamine employing methods similar to those described in Example 2. The product was obtained as a light beige solid: $^1$H NMR (CDCl$_3$) δ 10.37 (1H, br t, J=5.5 Hz), 8.62 (1H, s), 7.81 (2H, d, J=8 Hz), 7.39 (1H, s), 7.30 (3H, m), 7.17 (2H, d, J=8 Hz), 7.06 (1H, s), 7.03 (2H, m), 6.33 (2H, m), 5.40 (2H, br), 4.66 (2H, br d, J=5.5 Hz), 4.05 (2H, s), 3.01 (3H, s); HRMS calcd for $C_{29}H_{25}N_3O_6S+H^+$: 544.1542. Found: 544.1534.

EXAMPLE 47

Ethyl 7-benzyl-4-hydroxy-1-[(1-methyl-1H-imidazol-2-yl)methyl]-2-oxo-1,2-dihydro-1,5-naphthyridine-3-carboxylate

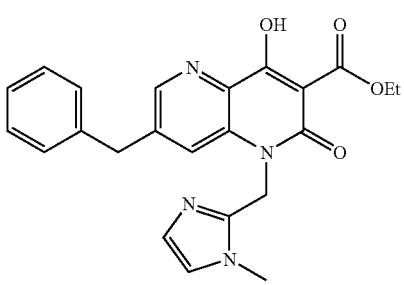 [SMILES: CCOC(=O)c1c(O)c2ncc(Cc3ccccc3)cc2n(Cc2nccn2C)c1=O]

This compound was prepared from ethyl 3-amino-5-benzylpyridine-2-carboxylate and 1-methyl-2-imidazolecarboxaldehyde employing methods similar to those describe in Example 5, Steps 1-3. The product was obtained as an off-white solid: $^1$H NMR (CDCl$_3$) δ 13.7 (1H, br), 8.50 (2H, s), 7.28-7.21 (5H, m), 6.99 (1H, br s), 6.81 (1H, s), 5.66 (2H, br), 4.52 (2H, q, J=7 Hz), 4.17 (2H, s), 3.72 (3H, s), 1.46 (3H, t, J=7 Hz); HRMS calcd for $C_{23}H_{22}N_4O_4+H^+$: 419.1719. Found: 419.1711.

EXAMPLE 48

7-Benzyl-N-cyclopropyl-4-hydroxy-1-[(1-methyl-1H-imidazol-2-yl)methyl]-2-oxo-1,2-dihydro-1,5-naphthyridine-3-carboxamide

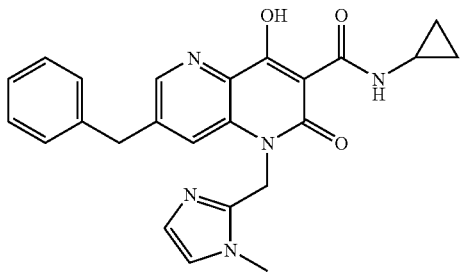 [SMILES: Cn1ccnc1Cn1c(=O)c(C(=O)NC2CC2)c(O)c2ncc(Cc3ccccc3)cc21]

This compound was prepared from ethyl 7-benzyl-4-hydroxy-1-[(1-methyl-1H-imidazol-2-yl)methyl]-2-oxo-1,2-dihydro-1,5-naphthyridine-3-carboxylate and cyclopropylamine using methods similar to those described in Example 11. The product was obtained as a white solid: $^1$H NMR (CDCl$_3$) δ 10.02 (1H, br), 8.57 (1H, s), 8.45 (1H, br s), 7.30-7.21 (5H, m), 7.01 (1H, br s), 6.83 (1H, s), 5.69 (2H, br), 4.17 (2H, s), 3.67 (3H, s), 2.95 (1H, m), 0.91 (2H, m), 0.71 (2H, m); HRMS calcd for $C_{24}H_{23}N_5O_3+H^+$: 430.1879. Found: 430.1877.

EXAMPLE 49

7-(4-Fluorobenzyl)-4-hydroxy-N-(2-methoxyethyl)-2-oxo-1-[2-(2-oxopyrrolidin-1-yl)ethyl]-1,2-dihydro-1,5-naphthyridine-3-carboxamide

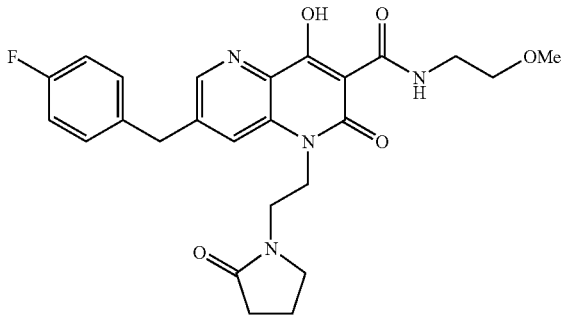 [SMILES: COCCNC(=O)c1c(O)c2ncc(Cc3ccc(F)cc3)cc2n(CCN2CCCC2=O)c1=O]

This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 2-methoxyethylamine by methods similar to those described in Example 6. The product was obtained as a white solid: $^1$H NMR (CDCl$_3$) δ 10.27 (1H, br m), 8.55 (1H, s), 8.06 (1H, s), 7.24 (2H, m), 6.99 (2H, t, J=8.6 Hz), 4.35 (2H, t, J=7 Hz), 4.14 (2H, s), 3.65 (2H, m), 3.59 (2H, m), 3.50 (2H, t, J=7 Hz), 3.44 (2H, m), 3.42 (3H, s), 2.31 (2H, t, J=8 Hz), 1.97 (2H, m); ES$^+$ MS: 483 (M+H$^+$, 100).

EXAMPLE 50

7-Benzyl-4-hydroxy-N-(2-methoxyethyl)-1-[(1-methyl-1H-imidazol-2-yl)methyl]-2-oxo-1,2-dihydro-1,5-naphthyridine-3-carboxamide

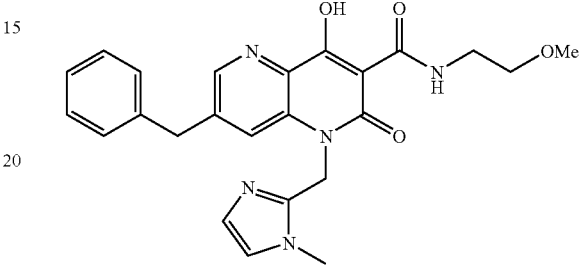

This compound was prepared from ethyl 7-benzyl-4-hydroxy-1-[(1-methyl-1H-imidazol-2-yl)methyl]-2-oxo-1,2-dihydro-1,5-naphthyridine-3-carboxylate and 2-methoxyethylamine employing methods similar to those described in Example 6. The product was obtained as a beige powder: $^1$H NMR (CDCl$_3$) δ 10.14 (1H, br), 8.58 (2H, br), 7.32-7.15 (5H, m), 7.12 (1H, br), 6.88 (1H, br s), 5.97 (2H, br), 4.22 (2H, s), 3.70 (3H, s), 3.67 (2H, q, J~5 Hz), 3.60 (2H, t, J~5 Hz), 3.42 (3H, s); ES$^+$ MS: 483 (M+H$^+$, 100).

EXAMPLE 51

7-Benzyl-4-hydroxy-1-(2-morpholin-4-yl-2-oxoethyl)-2-oxo-N-(pyridin-4-ylmethyl)-1,2-dihydro-1,5-naphthyridine-3-carboxamide

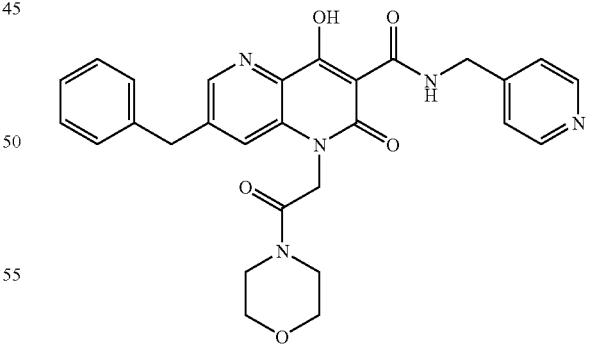

This compound was prepared from ethyl 7-benzyl-4-hydroxy-1-(2-morpholin-4-yl-2-oxoethyl)-2-oxo-1,2-dihydro-1,5-naphthyridine-3-carboxylate and 4-(aminomethyl)pyridine employing methods similar to those employed in Example 11. The product was obtained as a white solid: $^1$H NMR (CDCl$_3$) δ 10.48 (1H, br t, J=6 Hz), 8.62 (1H, d, J=1.1 Hz), 8.58 (2H, d, J=6 Hz), 7.38-7.29 (3H, m), 7.27 (2H, d, J=6 Hz), 7.19 (2H, d, J=7 Hz), 7.02 (1H, s), 4.93 (2H, s), 4.65 (2H, d, J=6 Hz), 4.16 (2H, s), 3.69 (4H, m), 3.57 (2H, m), 3.51 (2H, m); ES+ MS: 514 (M+H+, 100).

EXAMPLE 52

7-(4-Fluorobenzyl)-4-hydroxy-2-oxo-1-[2-(2-oxopyrrolidin-1-ylethyl]-N-(pyridin-4-ylmethyl)-1,2-dihydro-1,5-naphthyridine-3-carboxamide

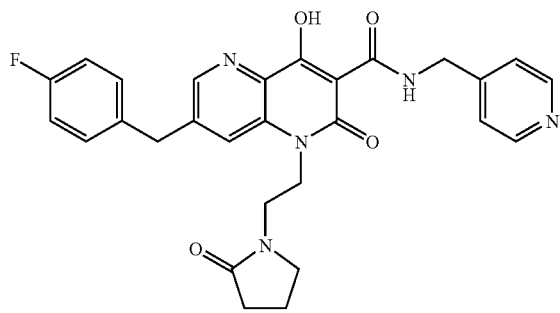 [SMILES: O=C(NCc1ccncc1)c1c(O)c2ncc(Cc3ccc(F)cc3)cc2n(CCN2CCCC2=O)c1=O]

This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 4-(aminomethyl)pyridine employing procedures similar to those described in Example 12. The product was obtained as a white solid: $^1$H NMR (CDCl$_3$) δ 14.4 (1H, br), 10.84 (1H, br t, J=6 Hz), 8.83 (2H, d, J=6.5 Hz), 8.63 (1H, s), 8.10 (1H, s), 7.79 (2H, d, J=6.5 Hz), 7.24 (2H, m), 7.01 (2H, t, J=8.6 Hz), 4.86 (2H, d, J=6 Hz), 4.38 (2H, t, J=7 Hz), 4.17 (2H, s), 3.54-3.47 (4H, m), 2.40 (2H, t, J=8 Hz), 2.04 (2H, m); ES+ MS: 516 (M+H+).

EXAMPLE 53

Ethyl 7-benzyl-1-(cyclopropylmethyl)-4-hydroxy-2-oxo-1,2-dihydro-1,5-naphthyridine-3-carboxylate

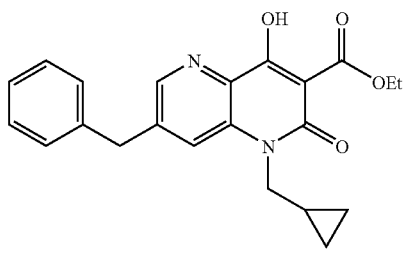 [SMILES: CCOC(=O)c1c(O)c2ncc(Cc3ccccc3)cc2n(CC2CC2)c1=O]

This compound was prepared from ethyl 3-amino-5-benzylpyridine-2-carboxylate and cyclopropanecarboxaldehyde employing methods similar to those described in Example 5, Steps 1-3 and was obtained as a tan wax: $^1$H NMR (d$_6$-DMSO) δ 11.65 (1H, br), 8.47 (1H, s), 8.03 (1H, s), 7.34-7.28 (4H, m), 7.20 (1H, t, J=7 Hz), 4.22 (2H, q, J=7 Hz), 4.17 (2H, s), 4.07 (2H, d, J=7 Hz), 1.23 (3H, t, J=7 Hz), 1.10 (1H, m), 0.38 (4H, m); HRMS calcd for C$_{22}$H$_{22}$N$_2$O$_4$+H+: 379.1658. Found: 379.1673.

EXAMPLE 54

7-Benzyl-1-(cyclopropylmethyl)-4-hydroxy-N-(2-methoxyethyl)-2-oxo-1,2-dihydro-1,5-naphthyridine-3-carboxamide

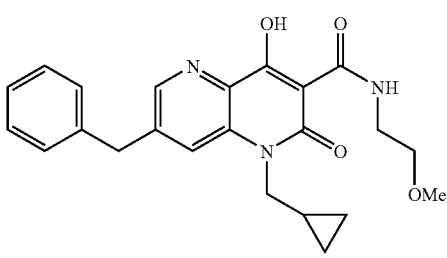 [SMILES: COCCNC(=O)c1c(O)c2ncc(Cc3ccccc3)cc2n(CC2CC2)c1=O]

This compound was prepared from ethyl 7-benzyl-1-(cyclopropylmethyl)-4-hydroxy-2-oxo-1,2-dihydro-1,5-naphthyridine-3-carboxylate and 2-methoxyethylamine employing methods similar to those described in Example 5 and was obtained as an off-white solid: $^1$H NMR (CDCl$_3$) δ 10.36 (1H, br t, J=5 Hz), 8.59 (1H, d, J=1.3 Hz), 7.46 (1H, s), 7.34 (2H, m), 7.26 (1H, m), 7.20 (2H, d, J=7 Hz), 4.16 (2H, s), 4.08 (2H, d, J=7 Hz), 3.64 (2H, q, J~5 Hz), 3.58 (2H, t, J~5 Hz), 3.40 (3H, s), 1.00 (1H, m), 0.46 (2H, m), 0.39 (2H, m); HRMS calcd for C$_{23}$H$_{25}$N$_3$O$_4$+H+: 408.1923. Found: 408.1914.

EXAMPLE 55

7-Benzyl-N-cyclobutyl-1-(cyclopropylmethyl)-4-hydroxy-2-oxo-1,2-dihydro-1,5-naphthyridine-3-carboxamide

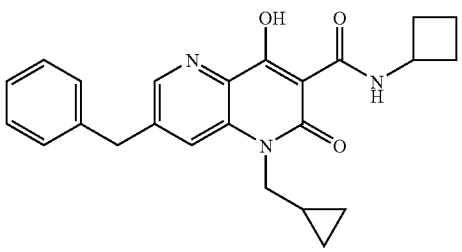 [SMILES: O=C(NC1CCC1)c1c(O)c2ncc(Cc3ccccc3)cc2n(CC2CC2)c1=O]

This compound was prepared from ethyl 7-benzyl-1-(cyclopropylmethyl)-4-hydroxy-2-oxo-1,2-dihydro-1,5-naphthyridine-3-carboxylate and cyclobutylamine employing methods similar to those described in Example 5 and was obtained as an off-white solid: $^1$H NMR (CDCl$_3$) δ 10.34 (1H, br d, J=7 Hz), 8.59 (1H, s), 7.46 (1H, s), 7.35 (2H, t, J=7 Hz), 7.28 (1H, t, J=7 Hz), 7.21 (2H, d, J=7 Hz), 4.53 (1H, m), 4.17 (2H, s), 4.08 (2H, d, J=7 Hz), 2.42 (2H, m), 2.09 (2H, m), 1.80

(2H, m), 1.01 (1H, m), 0.50 (2H, m), 0.40 (2H, m); HRMS calcd for $C_{24}H_{25}N_3O_3+H^+$: 404.1974. Found: 404.1971.

EXAMPLE 56

Ethyl 7-benzyl-4-hydroxy-1-(2-morpholin-4-ylethyl-2-oxo-1,2-dihydro-1,5-naphthyridine-3-carboxylate

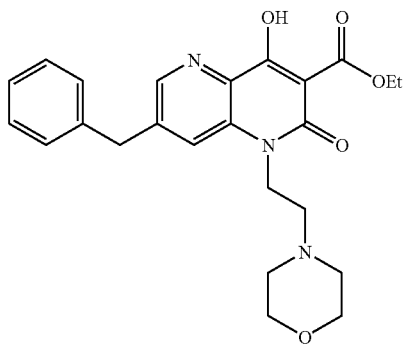 [SMILES: CCOC(=O)c1c(O)c2ncc(Cc3ccccc3)cc2n(CCN2CCOCC2)c1=O]

This compound was prepared from ethyl 3-amino-5-benzylpyridine-2-carboxylate and morpholin-4-ylacetaldehyde (Duhamel, L. et al.; Bull. Soc. Chim. Fr.; 1968; 4423-4428) employing methods similar to those described in Example 5, Steps 1-3 and was obtained as an amber glass: $^1$H NMR (CDCl$_3$) δ 8.54 (1H, d, J=1 Hz), 8.45 (1H, br), 7.35-7.26 (4H, m), 7.20 (1H, t, J=7 Hz), 4.72 (2H, br), 4.51 (2H, q, J=7 Hz), 4.22 (2H, s), 4.02 (6H, br), 3.06 (4H, br), 1.46 (3H, t, J=7 Hz); HRMS calcd for $C_{24}H_{27}N_3O_5+H^+$: 438.2029. Found: 438.2021.

EXAMPLE 57

7-Benzyl-N-cyclobutyl-4-hydroxy-1-(2-morpholin-4-ylethyl)-2-oxo-1,2-dihydro-1,5-naphthyridine-3-carboxamide

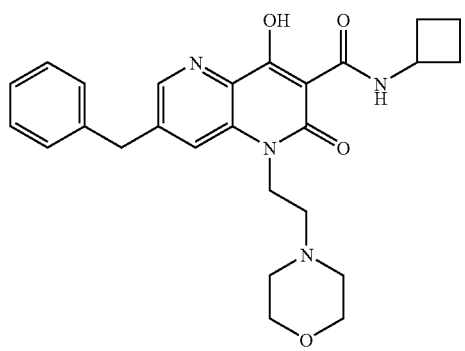 [SMILES: O=C(NC1CCC1)c1c(O)c2ncc(Cc3ccccc3)cc2n(CCN2CCOCC2)c1=O]

This compound was prepared from ethyl 7-benzyl-4-hydroxy-1-(2-morpholin-4-ylethyl)-2-oxo-1,2-dihydro-1,5-naphthyridine-3-carboxylate and cyclobutylamine employing methods similar to those described in Example 5 and was obtained as an off-white solid: $^1$H NMR (CDCl$_3$) δ 10.01 (1H, br d, J=5 Hz), 8.70 (1H, s), 8.61 (1H, s), 7.39 (2H, d, J=7.7 Hz), 7.30 (2H, t, J=7.7 Hz), 7.21 (1H, m), 4.89 (2H, m), 4.52 (1H, m), 4.26 (4H, m), 4.07 (2H, m), 3.50 (2H, m), 3.18 (2H, m), 3.09 (2H, m), 2.43 (2H, m), 2.06 (2H, m), 1.81 (2H, m); HRMS calcd for $C_{26}H_{30}N_4O_4+H^+$: 463.2345. Found: 463.2343.

EXAMPLE 58

7-Benzyl-4-hydroxy-1-[4-(methylsulfonyl)benzyl]-N-(3-morpholin-4-ylpropyl)-2-oxo-1,2-dihydro-1,5-naphthyridine-3-carboxamide

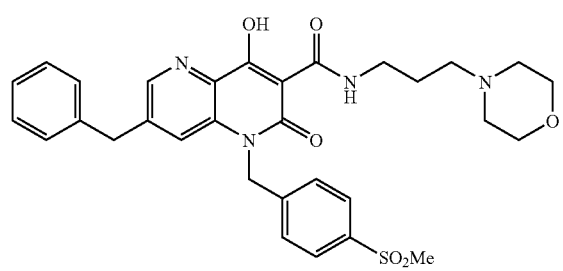 [SMILES: CS(=O)(=O)c1ccc(Cn2c(=O)c(C(=O)NCCCN3CCOCC3)c(O)c3ncc(Cc4ccccc4)cc32)cc1]

This compound was prepared from ethyl 7-benzyl-4-hydroxy-1-[4-(methylsulfonyl)benzyl]-2-oxo-1,2-dihydro-1,5-naphthyridine-3-carboxylate and N-(3-aminopropyl)morpholine employing methods similar to those described in Example 5 and was obtained as a white solid: $^1$H NMR (CDCl$_3$) δ 13.29 (1H, br), 10.31 (1H, t, J=6 Hz), 8.62 (1H, d, J=1 Hz), 7.82 (2H, d, J=8.3 Hz), 7.30 (3H, m), 7.18 (2H, d, J=8.3 Hz), 7.07 (1H, s), 7.03 (2H, m), 5.40 (2H, br), 4.32 (2H, m), 4.06 (2H, s), 3.97 (2H, m), 3.60 (2H, m), 3.46 (2H, m), 3.08 (2H, m), 3.02 (3H, s), 2.87 (2H, m), 2.34 (2H, m); HRMS calcd for $C_{31}H_{34}N_4O_6S+H^+$: 591.2277. Found: 591.2277.

EXAMPLE 59

7-Benzyl-4-hydroxy-1-[4-(methylsulfonyl)benzyl]-2-oxo-N-(2-pyrrolidin-1-ylethyl)-1,2-dihydro-1,5-naphthyridine-3-carboxamide

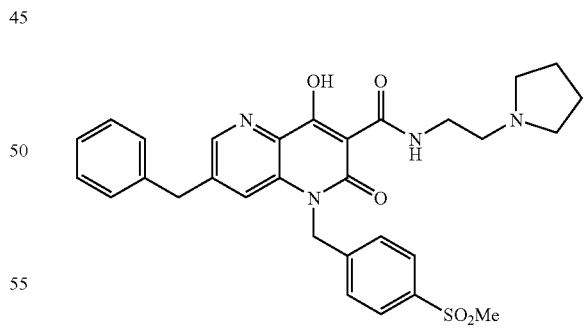

This compound was prepared from ethyl 7-benzyl-4-hydroxy-1-[4-(methylsulfonyl)benzyl]-2-oxo-1,2-dihydro-1,5-naphthyridine-3-carboxylate and N-(2-aminoethyl)pyrrolidine employing methods similar to those described in Example 5 and was obtained as a white solid: $^1$H NMR (CDCl$_3$) δ 12.80 (1H, br), 10.44 (1H, t, J=6 Hz), 8.60 (1H, d, J=1 Hz), 7.81 (2H, d, J=8.2 Hz), 7.30 (3H, m), 7.19 (2H, d, J=8.2 Hz), 7.06 (1H, s), 7.01 (2H, m), 5.41 (2H, br), 4.05 (2H, s), 4.02 (2H, q, J=6.6 Hz), 3.87 (2H, br), 3.36 (2H, t, J=7 Hz), 3.02 (3H, s), 2.89 (2H, m), 2.24 (2H, br), 2.10 (2H, br); HRMS calcd for $C_{30}H_{32}N_4O_5S+H^+$: 561.2172. Found: 561.2166.

EXAMPLE 60

Ethyl 7-benzyl-4-hydroxy-2-oxo-1-(1,3-thiazol-2-ylmethyl)-1,2-dihydro-1,5-naphthyridine-3-carboxylate

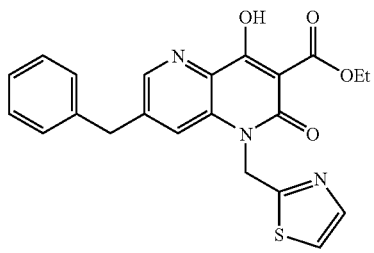 [SMILES: CCOC(=O)c1c(O)c2ncc(Cc3ccccc3)cc2n(Cc2nccs2)c1=O]

This compound was prepared from ethyl 3-amino-5-benzylpyridine-2-carboxylate and 2-thiazolecarboxaldehyde employing methods similar to those described in Example 5, Steps 1-3 and was obtained as a white solid; $^1$H NMR (d$_6$-DMSO) δ 8.49 (1H, s), 8.05 (1H, s), 7.68 (1H, d, J=3.3 Hz), 7.65 (1H, d, J=3.3 Hz), 7.28-7.15 (5H, m), 5.69 (2H, s), 4.23,(2H, q, J=7 Hz), 4.09 (2H, s), 1.24 (3H, t, J=7 Hz); HRMS calcd for $C_{22}H_{19}N_3O_4S+H^+$: 422.1175. Found: 422.1164.

EXAMPLE 61

7-Benzyl-N-cyclobutyl-4-hydroxy-2-oxo-1-(1,3-thiazol-2-ylmethyl)-1,2-dihydro-1,5-naphthyridine-3-carboxamide

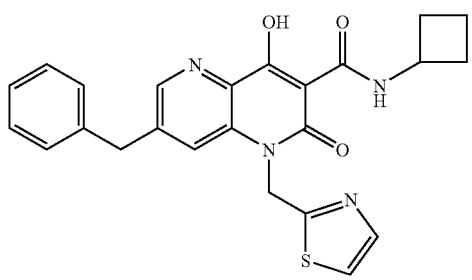 [SMILES: O=C(NC1CCC1)c1c(O)c2ncc(Cc3ccccc3)cc2n(Cc2nccs2)c1=O]

This compound was prepared from ethyl 7-benzyl-4-hydroxy-2-oxo-1-(1,3-thiazol-2-ylmethyl)-1,2-dihydro-1,5-naphthyridine-3-carboxylate and cyclobutylamine employing methods similar to those described in Example 5 and was obtained as a white solid: $^1$H NMR (d$_6$-DMSO) δ 10.27 (1H, d, J=7), 8.56 (1H, s), 8.13 (1H, s), 7.70 (1H, d, J=3.2 Hz), 7.67 (1H, d, J=3.2 Hz), 7.28-7.16 (5H, m), 5.78 (2H, s), 4.41 (1H, m), 4.09 (2H, s), 2.29 (2H, m), 2.05 (2H, m), 1.71 (2H, m); HRMS calcd for $C_{24}H_{22}N_4O_3S+H^+$: 447.1491. Found: 447.1487.

EXAMPLE 62

7-Benzyl-4-hydroxy-N-(2-methoxyethyl)-2-oxo-1-(1,3-thiazol-2-ylmethyl)-1,2-dihydro-1,5-naphthyridine-3-carboxamide

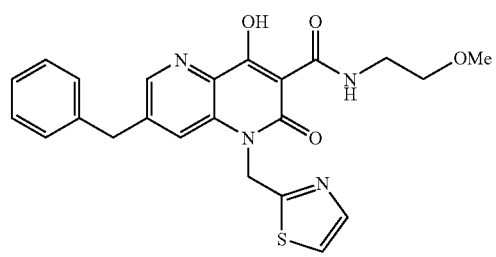 [SMILES: COCCNC(=O)c1c(O)c2ncc(Cc3ccccc3)cc2n(Cc2nccs2)c1=O]

This compound was prepared from ethyl 7-benzyl-4-hydroxy-2-oxo-1-(1,3-thiazol-2-ylmethyl)-1,2-dihydro-1,5-naphthyridine-3-carboxylate and 2-methoxyethylamine employing methods similar to those described in Example 5 and was obtained as a white solid: $^1$H NMR (d$_6$-DMSO) δ 10.21 (1H, t, J=5 Hz), 8.56 (1H, s), 8.12 (1H, s), 7.69 (1H, d, J=3.2 Hz), 7.67 (1H, d, J=3.2 Hz) 7.28-7.22 (4H, m), 7.18 (1H, t, J=7 Hz), 5.78 (2H, s), 4.09 (2H, s), 3.56-3.48 (4H, m), 3.28 (3H, s); HRMS calcd for $C_{23}H_{22}N_4O_4S+H^+$: 451.1440. Found: 451.1428.

EXAMPLE 63

Ethyl 7-(4-fluorobenzyl)-4-hydroxy-1-[4-(methylsulfonyl)benzyl]-2-oxo-1,2-dihydro-1,5-naphthyridine-3-carboxylate

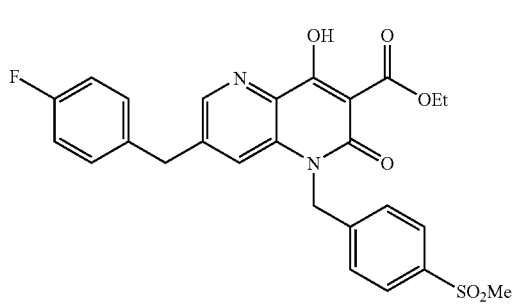 [SMILES: CCOC(=O)c1c(O)c2ncc(Cc3ccc(F)cc3)cc2n(Cc2ccc(S(C)(=O)=O)cc2)c1=O]

This compound was prepared from ethyl 3-amino-5-(4-fluorobenzyl)-2-pyridinecarboxylate and 4-methylsulfonyl benzaldehyde employing methods similar to those described in Example 5, Steps 1-3 and was obtained as a white solid; $^1$H NMR (d$_6$-DMSO) δ 8.49 (1H, s), 7.83 (2H, d, J=8.3 Hz), 7.73 (1H, s), 7.38 (2H, d, J=8.3 Hz), 7.18 (2H, dd, J=8.2, 6 Hz), 7.04 (2H, t, J=9 Hz), 5.51 (2H, s), 4.25 (2H, q, J=7 Hz), 4.04 (2H, s), 3.15 (3H, s), 1.25 (3H, t, J=7 Hz); ES+ MS: 511 (M+H+, 100).

EXAMPLE 64

7-(4-Fluorobenzyl)-4-hydroxy-N-(2-methoxyethyl)-1-[4-(methylsulfonyl)benzyl]-2-oxo-1,2-dihydro-1,5-naphthyridine-3-carboxamide

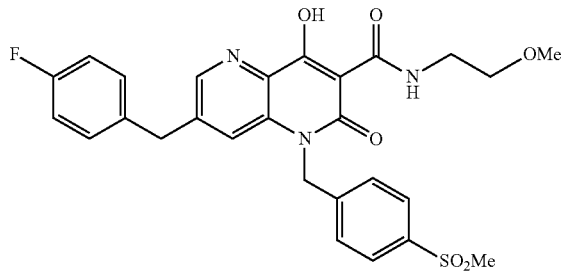 [SMILES: COCCNC(=O)c1c(O)c2ncc(Cc3ccc(F)cc3)cc2n(Cc2ccc(S(C)(=O)=O)cc2)c1=O]

This compound was prepared from ethyl 7-(4-fluorobenzyl)-4-hydroxy-1-[4-(methylsulfonyl)benzyl]-2-oxo-1,2-dihydro-1,5-naphthyridine-3-carboxylate and 2-methoxyethylamine employing methods similar to those described in Example 5 and was obtained as a white solid; $^1$H NMR (CDCl$_3$) δ 10.22 (1H, br t, J=5 Hz), 8.58 (1H, d, J=1.2 Hz), 7.85 (2H, d, J=8.3 Hz), 7.21 (2H, d, J=8.3 Hz), 7.01-6.98 (5H, m), 5.44 (2H, br), 4.02 (2H, s), 3.68 (2H, q, J=5.2 Hz), 3.60 (2H, t, J=5.2 Hz); 3.41 (3H, s), 3.03 (3H, s); ES+ MS: 540 (M+H+, 100).

EXAMPLE 65

7-(4-Fluorobenzyl)-4-hydroxy-1-[4-(methylsulfonyl)benzyl]-2-oxo-N-(pyridin-4-ylmethyl)-1,2-dihydro-1,5-naphthyridine-3-carboxamide

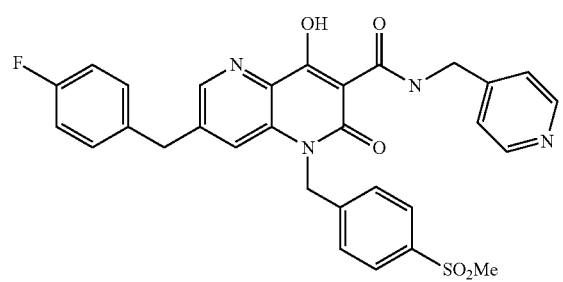 [SMILES: CS(=O)(=O)c1ccc(Cn2c(=O)c(C(=O)NCc3ccncc3)c(O)c3ncc(Cc4ccc(F)cc4)cc32)cc1]

This compound was prepared from ethyl 7-(4-fluorobenzyl)-4-hydroxy-1-[4-(methylsulfonyl)benzyl]-2-oxo-1,2-dihydro-1,5-naphthyridine-3-carboxylate and 4-(aminomethyl)pyridine employing methods similar to those described in Example 5 and was obtained as a white solid; $^1$H NMR (CDCl$_3$) δ 10.59 (1H, t, J~6 Hz), 8.64 (2H, d, J=6 Hz), 8.62 (1H, d, J=1.2 Hz), 7.86 (2H, d, J=8 Hz), 7.55 (2H, d, J=6 Hz), 7.22 (2H, d, J=8 Hz), 7.06 (1H, s), 7.00 (4H, m), 5.43 (2H, br), 4.78 (2H, d, J=6 Hz), 4.05 (2H, s), 3.04 (3H, s); ES+ MS: 573 (M+H+, 100).

EXAMPLE 66

7-(4-Fluorobenzyl)-4-hydroxy-1-[4-(methylsulfonyl)benzyl]-2-oxo-N-(pyridin-3-ylmethyl)-1,2-dihydro-1,5-naphthyridine-3-carboxamide

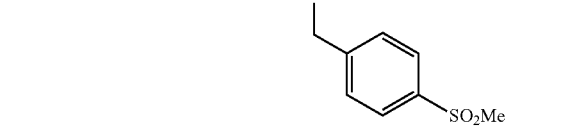

This compound was prepared from ethyl 7-(4-fluorobenzyl)-4-hydroxy-1-[4-(methylsulfonyl)benzyl]-2-oxo-1,2-dihydro-1,5-naphthyridine-3-carboxylate and 3-(aminomethyl)pyridine employing methods similar to those described in Example 5 and was obtained as a white solid; $^1$H NMR (CDCl$_3$) δ 10.82 (1H, br t, J=6 Hz), 8.79 (1H, s), 8.67 (1H, d, J=5 Hz), 8.61 (1H, s), 8.44 (1H, d, J=8 Hz), 7.90 (1H, m), 7.86 (2H, d, J=8.2 Hz), 7.22 (2H, d, J=8.2 Hz), 7.07 (1H, s), 7.00 (4H, m), 5.44 (2H, br), 4.83 (2H, d, J=6 Hz), 4.05 (2H, s), 3.04 (3H, s); ES+ MS: 573 (M+H+, 100).

EXAMPLE 67

7-(4-Fluorobenzyl)-4-hydroxy-1-[4-(methylsulfonyl)benzyl]-N-(2-morpholin-4-ylethyl)-2-oxo-1,2-dihydro-1,5-naphthyridine-3-carboxamide

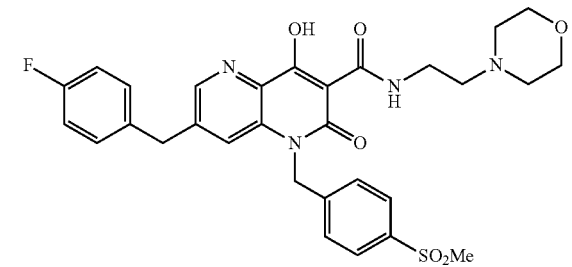 [SMILES: CS(=O)(=O)c1ccc(Cn2c(=O)c(C(=O)NCCN3CCOCC3)c(O)c3ncc(Cc4ccc(F)cc4)cc32)cc1]

This compound was prepared from ethyl 7-(4-fluorobenzyl)-4-hydroxy-1-[4-(methylsulfonyl)benzyl]-2-oxo-1,2-dihydro-1,5-naphthyridine-3-carboxylate and 2-(4-morpholino)ethylamine employing methods similar to those described in Example 5 and was obtained as a white solid; $^1$H NMR (CDCl$_3$) δ 13.49 (1H, br), 10.45 (1H, t, J=6 Hz), 8.57 (1H, s), 7.84 (2H, d, J=8.3 Hz), 7.23 (2H, d, J=8.3 Hz), 7.04 (1H, s), 7.00 (4H, m), 5.43 (2H, br), 4.31 (2H, m), 4.08 (2H, m), 4.02 (2H, s), 3.99 (2H, m), 3.58 (2H, m), 3.29 (2H, m), 3.03 (3H, s), 2.97 (2H, m); ES+ MS: 595 (M+H+, 100).

EXAMPLE 68

Ethyl 4-hydroxy-1-[(4-nitrophenyl)methyl]-2-oxo-7-(phenylmethyl)-1,2-dihydro-1,5-naphthyridine-3-carboxylate

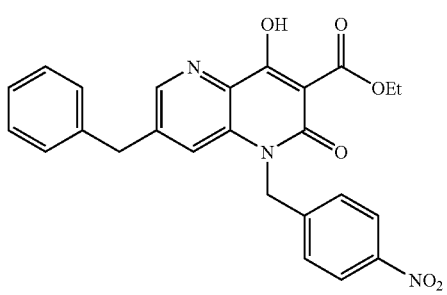 [SMILES: CCOC(=O)c1c(O)c2ncc(Cc3ccccc3)cc2n(Cc2ccc([N+](=O)[O-])cc2)c1=O]

This compound was prepared from ethyl 3-amino-5-benzylpyridine-2-carboxylate and 4-nitrobenzaldehyde employing methods similar to those described in Example 5, Steps 1-3 and was obtained as a beige solid: $^1$H NMR (d$_6$-DMSO) δ 8.14 (2H, d, J=8.6 Hz), 8.10 (1H, s), 7.36 (2H, d, J=8.6 Hz), 7.29 (1H, s), 7.14 (3H, m), 7.07 (2H, m), 5.43 (2H, br), 4.08 (2H, q, J=7 Hz), 3.92 (2H, s), 1.21 (3H, t, J=7 Hz); ES+ MS: 460 (M+H+, 30).

EXAMPLE 69

N-(2-Furanylmethyl-4-hydroxy-1-[(4-nitrophenyl)methyl]-2-oxo-7-(phenylmethyl)-1,2-dihydro-1,5-naphthyridine-3-carboxamide

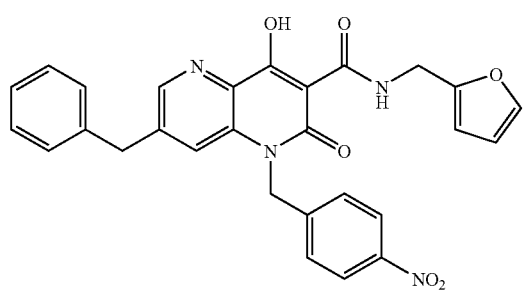 [SMILES: O=C(NCc1ccco1)c1c(O)c2ncc(Cc3ccccc3)cc2n(Cc2ccc([N+](=O)[O-])cc2)c1=O]

This compound was prepared from ethyl 4-hydroxy-1-[(4-nitrophenyl)methyl]-2-oxo-7-(phenylmethyl)-1,2-dihydro-1,5-naphthyridine-3-carboxylate and furfurylamine employing methods similar to those described in Example 2 and was obtained as a beige solid: $^1$H NMR (d$_6$-DMSO) δ 11.10 (1H, br m), 8.21 (1H, s), 8.10 (2H, d, J=8.6 Hz), 7.57 (1H, s), 7.35 (2H, d, J=8.6 Hz), 7.30 (1H, s), 7.13 (3H, m), 7.06 (2H, m), 6.39 (1H, br s), 6.27 (1H, d, J=3 Hz), 5.48 (2H, br), 4.45 (2H, d, J=5 Hz), 3.91 (2H, s); HRMS calcd for C$_{28}$H$_{22}$N$_4$O$_6$+H+: 511.1618. Found: 511.1609.

EXAMPLE 70

4-Hydroxy-N-[2-(methyloxy)ethyl]-1-[(4-nitrophenyl)methyl]-2-oxo-7-(phenylmethyl)-1,2-dihydro-1,5-naphthyridine-3-carboxamide

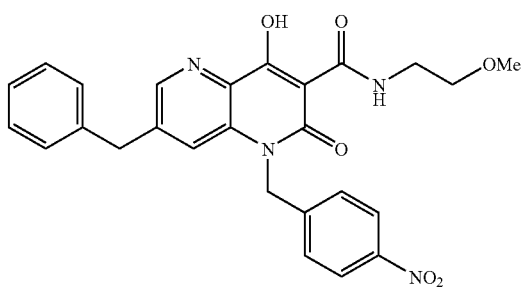 [SMILES: COCCNC(=O)c1c(O)c2ncc(Cc3ccccc3)cc2n(Cc2ccc([N+](=O)[O-])cc2)c1=O]

This compound was prepared from ethyl 4-hydroxy-1-[(4-nitrophenyl)methyl]-2-oxo-7-(phenylmethyl)-1,2-dihydro-1,5-naphthyridine-3-carboxylate and 2-methoxyethylamine employing methods similar to those described in Example 2 and was obtained as a light yellow solid: $^1$H NMR (d$_6$-DMSO) δ 10.69 (1H, br), 8.21 (1H, s), 8.10 (2H, d, J=8.7 Hz), 7.35 (2H, d, J=8.7 Hz), 7.31 (1H, s), 7.13 (3H, m), 7.07 (2H, m), 5.49 (2H, br s), 3.91 (2H, s), 3.41 (4H, m), 3.27 (3H, s); HRMS calcd for C$_{26}$H$_{24}$N$_4$O$_6$+H+: 489.1774. Found: 489.1778.

EXAMPLE 71

N-Cyclobutyl-4-hydroxy-1-[(4-nitrophenyl)methyl]-2-oxo-7-(phenylmethyl)-1,2-dihydro-1,5-naphthyridine-3-carboxamide

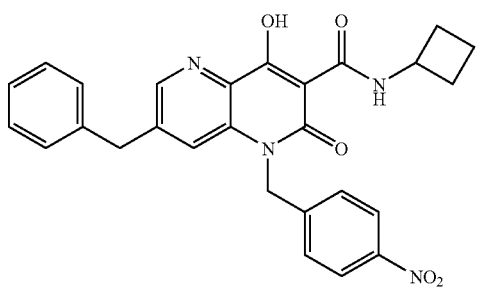 [SMILES: O=C(NC1CCC1)c1c(O)c2ncc(Cc3ccccc3)cc2n(Cc2ccc([N+](=O)[O-])cc2)c1=O]

This compound was prepared from ethyl 4-hydroxy-1-[(4-nitrophenyl)methyl]-2-oxo-7-(phenylmethyl)-1,2-dihydro-1,5-naphthyridine-3-carboxylate and cyclobutylamine employing methods similar to those described in Example 2 and was obtained as a white solid: $^1$H NMR (d$_6$-DMSO) δ 10.91 (1H, d, J=7.6 Hz), 8.21 (1H, s), 8.10 (2H, d, J=8.6 Hz), 7.35 (2H, d, J=8.6 Hz), 7.29 (1H, s), 7.14 (3H, m), 7.08 (2H, m), 5.47 (2H, br s), 4.40 (1H, m), 3.91 (2H, s), 2.24 (2H, m), 1.86 (2H, m), 1.67 (2H, m); HRMS calcd for C$_{27}$H$_{24}$N$_4$O$_5$+H$^+$: 485.1825. Found: 485.1815.

EXAMPLE 72

1-[(4-Aminophenyl)methyl]-N-cyclobutyl-4-hydroxy-2-oxo-7-(phenylmethyl)-1,2-dihydro-1,5-naphthyridine-3-carboxamide

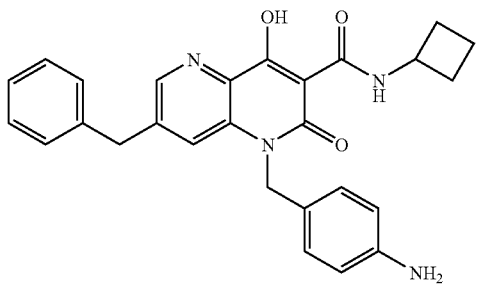

This compound was prepared by hydrogenation of N-cyclobutyl-4-hydroxy-1-[(4-nitrophenyl)methyl]-2-oxo-7-(phenylmethyl)-1,2-dihydro-1,5-naphthyridine-3-carboxamide in THF in the presence of 3% Pt-C. The catalyst was removed by filtration and the filtrate was concentrated in vacuo. The product was obtained as a tan solid by addition of one equivalent of conc. HCl followed by concentration in vacuo and trituration with Et$_2$O: $^1$H NMR (CD$_3$OD) δ 7.76 (1H, br), 7.32-7.27 (8H, m), 7.16 (2H, d, J=7.5 Hz), 5.57 (2H, s), 4.57 (1H, m), 4.19 (2H, s), 2.44 (2H, m), 2.13 (2H, m), 1.86 (2H, m); HRMS calcd for C$_{27}$H$_{26}$N$_4$O$_3$+H$^+$: 455.2083. Found: 455.2088.

EXAMPLE 73

7-[(4-Fluorophenyl)methyl]-4-hydroxy-N-(2-hydroxyethyl)-2-oxo-1-[2-(2-oxo-1-pyrrolidinyl)ethyl]-1,2-dihydro-1,5-naphthyridine-3-carboxamide

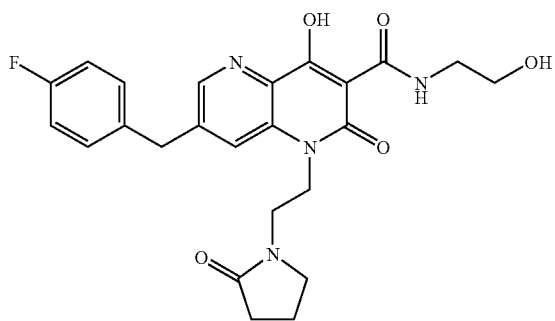 [SMILES: O=C(NCCO)c1c(O)c2ncc(Cc3ccc(F)cc3)cc2n(CCN2CCCC2=O)c1=O]

This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 2-hydroxyethylamine by methods similar to those described in Example 6. The product was obtained as a white solid: $^1$H NMR (CDCl$_3$) δ 10.38 (1H, br m), 8.60 (1H, s), 8.07 (1H, s), 7.24 (2H, m), 7.00 (2H, t, J=8.6 Hz), 4.36 (2H, t, J=7 Hz), 4.15 (2H, s), 3.87 (2H, t, J=5 Hz), 3.66 (2H, m), 3.51 (2H, t, J=8 Hz), 3.45 (2H, t, J=7 Hz), 2.37 (2H, t, J=8 Hz), 2.00 (2H, m).

EXAMPLE 74

7-[(4-fluorophenylmethyl]-4-hydroxy-N-(3-methylbutyl)-2-oxo-1,2-dihydro-1,5-naphthyridine-3-carboxamide

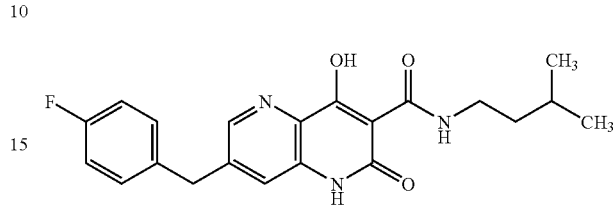

$^1$H NMR (d$_6$-DMSO) tautomers are observed δ 11.75 (1H, br s), 10.30 (1H, br s), 8.39 (0.47H, br s), 8.20 (0.53H, br s), 7.36 (1H, s), 7.30-7.26 (2H, m), 7.14-7.10 (2H, m), 4.00 (2H, br s), 3.26-3.28 (2H, m), 1.62 (1H, t, J=6.3 Hz), 1.43-1.37 (2H, m), 0.90 (3H, s), 0.88 (3H, s); HRMS calcd for C$_{21}$H$_{22}$FN$_3$O$_3$+H$^+$: 384.1723. Found 384.1721.

EXAMPLE 75

7-[(4-fluorophenyl)methyl]-4-hydroxy-N-(2-methylpropyl)-2-oxo-1,2-dihydro-1,5-naphthyridine-3-carboxamide

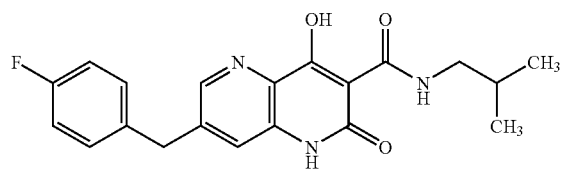 [SMILES: CC(C)CNC(=O)c1c(O)c2ncc(Cc3ccc(F)cc3)cc2[nH]c1=O]

$^1$H NMR (d$_6$-DMSO) tautomers are observed δ 11.90 (1H, br s), 10.40 (1H, br s), 8.44 (0.51H, br s), 8.20 (0.49H, br s), 7.37 (1H, br s), 7.31-7.27 (2H, m), 7.15-7.13 (2H, m), 4.01 (2H, br s), 3.15 (2H, br s), 1.79 (1H, br s), 0.91 (3H, s), 0.89 (3H, s); HRMS calcd for C$_{20}$H$_{20}$F$_2$N$_3$O$_3$+H$^+$: 370.1567. Found: 370.1559.

EXAMPLE 76

7-[(4-Fluorophenyl)methyl]-4-hydroxy-N-4-morpholinyl-2-oxo-1,2-dihydro-1,5-naphthyridine-3-carboxamide

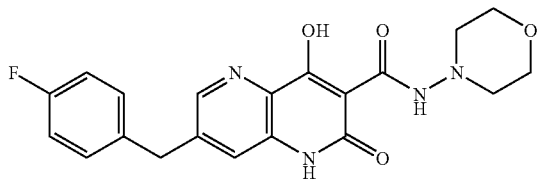 [SMILES: O=C(NN1CCOCC1)c1c(O)c2ncc(Cc3ccc(F)cc3)cc2[nH]c1=O]

$^1$H NMR (d$_6$-DMSO) tautomers are observed δ 12.94 (1H, br s), 11.77 (1H, br s), 10.10 (1H, br s), 8.20 (0.42H, br s), 8.16 (0.58H, br s), 7.35-7.23 (3H, m), 7.14-7.09 (2H, m), 3.98 (2H, s), 3.67-3.61 (4H, m), 2.85-2.75 (4H, m); HRMS calcd for C$_{20}$H$_{19}$F$_2$N$_4$O$_4$+H$^+$: 399.1469. Found: 399.1459.

EXAMPLE 77

7-[(4-fluorophenyl)methyl]-4-hydroxy-N-[3-(4-methyl-1-piperazinyl)propyl]-2-oxo-1,2-dihydro-1,5-naphthyridine-3-carboxamide

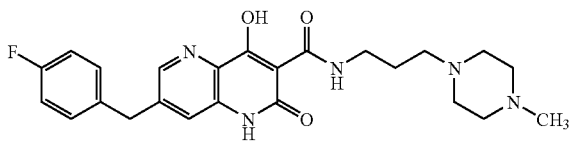 [SMILES: CN1CCN(CCCNC(=O)c2c(O)c3ncc(Cc4ccc(F)cc4)cc3[nH]c2=O)CC1]

$^1$H NMR (d$_6$-DMSO) δ 11.81 (1H, br s), 10.76 (1H, br s), 10.11 (1H, br s), 8.17 (1H, br s), 7.35-7.25 (3H, m), 7.16-7.09 (2H, m), 3.98 (2H, s), 3.29-3.21 (2H, m), 2.48 (2H, br s), 2.40-2.29 (8H, m), 2.11 (3H, s) 1.65-1.56 (2H, m); HRMS calcd for C$_{24}$H$_{28}$FN$_5$O$_3$+H$^+$: 454.2254. Found: 454.2242.

EXAMPLE 78

7-[(4-Fluorophenyl)methyl]-4-hydroxy-2-oxo-N-[2-(3-pyridinyl)ethyl-]-1,2-dihydro-1,5-naphthyridine-3-carboxamide

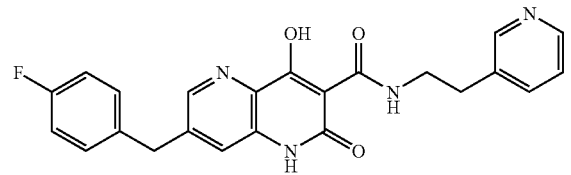 [SMILES: O=C(NCCc1cccnc1)c1c(O)c2ncc(Cc3ccc(F)cc3)cc2[nH]c1=O]

$^1$H NMR (d$_6$-DMSO) δ 11.91 (1H, br s), 10.90 (1H, br s), 10.10 (1H, br s), 8.42 (1H, s), 8.39 (1H, br s), 8.20-8.15 (1H, m), 7.69-7.64 (H, m), 7.35-7.25 (4H, m), 7.15-7.09 (2H, m), 3.98 (2H, s), 3.55-3.51 (2H, m), 2.85-2.79 (2H, m); HRMS calcd for C$_{23}$H$_{19}$FN$_4$O$_3$+H$^+$: 419.1519. Found: 419.1512.

EXAMPLE 79

Ethyl 7-[(4-Fluorophenyl)methyl]-4-hydroxy-1-[2-(4-morpholinyl)-2-oxoethyl]-2-oxo-1,2-dihydro-1,5-naphthyridine-3-carboxylate

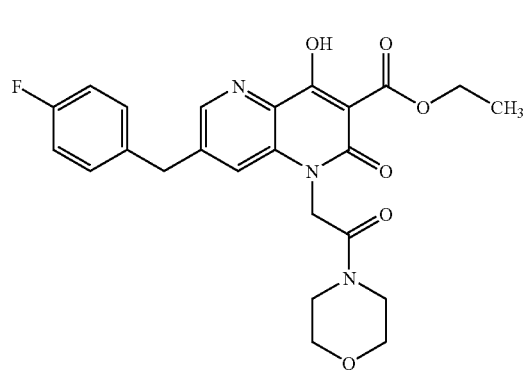 [SMILES: CCOC(=O)c1c(O)c2ncc(Cc3ccc(F)cc3)cc2n(CC(=O)N2CCOCC2)c1=O]

HRMS calcd for C$_{24}$H$_{24}$FN$_3$O$_6$+H$^+$: 470.1727. Found: 470.1743.

EXAMPLE 80

N-(1,1-Dioxidotetrahydro-3-thienyl)-7-[(4-fluorophenyl)methyl]-4-hydroxy2-oxo-1,2-dihydro-1,5-naphthyridine-3-carboxamide

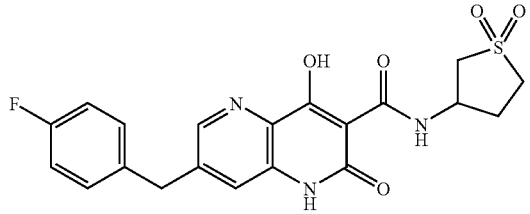 [SMILES: O=C(NC1CCS(=O)(=O)C1)c1c(O)c2ncc(Cc3ccc(F)cc3)cc2[nH]c1=O]

$^1$H NMR (d-TFA) δ 11.60 (1H, br s), 8.73 (1H, s), 8.45 (1H, s), 7.26-7.22 (2H, m), 7.11-7.07 (2H, m), 5.16-5.11 (1H, m), 4.38 (2H, m), 3.84-3.73 (1H, m), 3.65-3.44 (3H, m), 2.95-

2.85 (1H, m), 2.69-2.59 (1H, m); HRMS calcd for $C_{20}H_{18}FN_3O_5S+H^+$: 432.1029. Found: 432.1049.

EXAMPLE 81

7-[(4-fluorophenyl)methyl]-4-hydroxy-N-[2-(methylthio)ethyl]-2-oxo-1,2-dihydro-1,5-naphthyridine-3-carboxamide

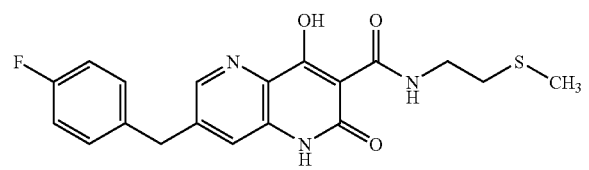 [SMILES: CSCCNC(=O)c1c(O)c2ncc(Cc3ccc(F)cc3)cc2[nH]c1=O]

$^1$H NMR ($d_6$-DMSO) δ; 10.45 (1H, br s), 8.45 (1H br s), 7.41 (1H, s), 7.31-7.28 (2H, m) 7.16-7.12 (2H, m), 4.08 (2H, s), 3.56-3.51 (2H, m), 2.66 (2H, t, J=6.6 Hz), 2.09 (3H, s); HRMS calcd for $C_{19}H_{18}FN_3O_3S+H^+$: 388.1131. Found: 388.1125.

EXAMPLE 82

7-[(4-fluorophenyl)methyl]-4-hydroxy-N-methyl-2-oxo-1,2-dihydro-1,5-naphthyridine-3-carboxamide

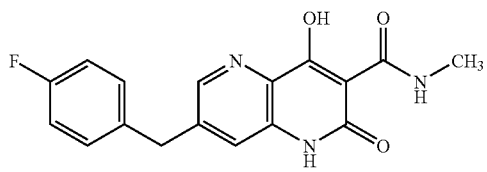 [SMILES: CNC(=O)c1c(O)c2ncc(Cc3ccc(F)cc3)cc2[nH]c1=O]

$^1$H NMR ($d_6$-DMSO) δ 11.62 (1H, br s), 10.41 (1H, br s), 8.22 (1H, br s), 7.30-7.20 (3H, m), 7.14-7.05 (2H, m), 4.01 (2H, br s), 2.78 (3H, br s); HRMS calcd for $C_{17}H_{14}FN_3O_3+H^+$: 328.1097. Found: 328.1084.

EXAMPLE 83

7-[(4-Fluorophenyl)methyl]-4-hydroxy-N-[2-(4-morpholinyl)ethyl]-1-[2-(4-morpholinyl)-2-oxoethyl]-2-oxo-1,2-dihydro-1,5-naphthyridine-3-carboxamide

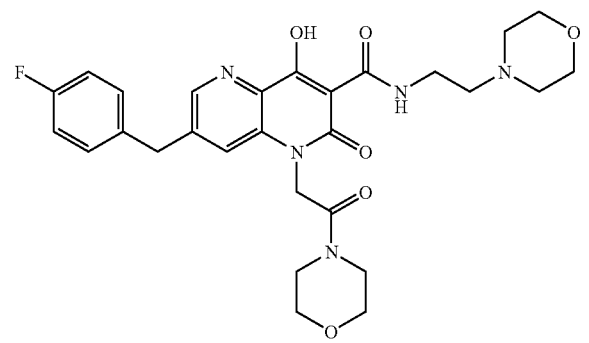 [SMILES: O=C(NCCN1CCOCC1)c1c(O)c2ncc(Cc3ccc(F)cc3)cc2n(CC(=O)N2CCOCC2)c1=O]

The title compound was made from ethyl 7-[(4-fluorophenyl)methyl]-4-hydroxy-1-[2-(4-morpholinyl)-2-oxoethyl]-2-oxo-1,2-dihydro-1,5-naphthyridine-3-carboxylate in a manner similar to example 9 using 2-(4-morpholino)ethylamine to give a white solid:
$^1$H NMR (CDCl$_3$) δ 10.34 (1H, m), 8.58 (1H, s), 7.14 (3H, m), 7.03 (2H, m), 4.93 (2H, s), 4.12 (2H, s), 3.86-3.99 (8H, m), 3.75 (2H, m), 3.68 (2H, m), 3.56 (4H, m), 3.40 (2H, t, J=5 Hz), 2.93 (2H, m); HRMS calcd for $C_{28}H_{32}FN_5O_6+H^+$: 554.2415. Found: 554.140.

EXAMPLE 84

7-[(4-Fluorophenyl)methyl]-4-hydroxy-N-[2-(methyloxy)ethyl]-1-[2-(4-morpholinyl)-2-oxoethyl]-2-oxo-1,2-dihydro-1,5-naphthyridine-3-carboxamide

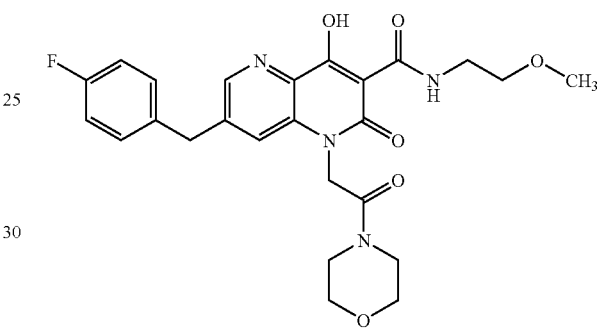

The title compound was made in a manner similar to example 83 using 2-methoxyethylamine to give a white solid:
$^1$H NMR (CDCl$_3$) δ 10.10 (1H, m), 8.59 (1H, s), 7.14 (2H, m), 7.09 (1H, s), 7.03 (2H, m), 4.95 (2H, s), 4.12 (2H, s), 3.73 (2H, m), 3.68 (2H, m), 3.63 (2H, m), 3.57 (6H, m), 3.39 (3H, s); HRMS calcd for $C_{25}H_{27}FN_4O_6+H^+$: 499.1993. Found: 499.1996.

EXAMPLE 85

7-[(4-Fluorophenyl)methyl]-4-hydroxy-N-(3-hydroxy-2,2-dimethylpropyl)-2-oxo-1,2-dihydro-1,5-naphthyridine-3-carboxamide

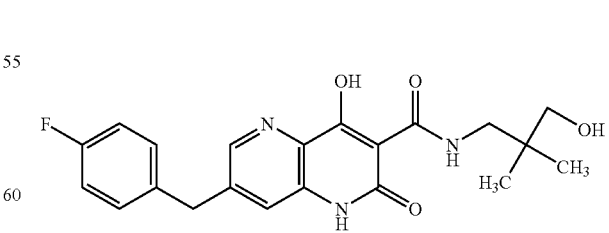

$^1$H NMR ($d_6$-DMSO) tautomers are observed δ 11.97 (1H, t, J=5.8 Hz), 11.04 (1H, brs), 9.89 (1H, s), 8.18 (0.44H, s), 8.15 (0.56H, s), 7.36-7.23 (3H, m), 7.14-7.08 (2H, m), 4.67 (0.57H, t, J=6.2 Hz), 4.56 (0.43H, t, J=5.6 Hz), 3.98 (2H, s), 3.16-3.13 (2H, m), 3.08-3.03 (2H, m), 0.84 (3H, s), 0.81 (3H, s); HRMS calcd for $C_{21}H_{22}FN_3O_4+H^+$: 400.1672. Found: 400.1665.

EXAMPLE 86

7-[(4-Fluorophenyl)methyl]-4-hydroxy-N-{2-[(2-hydroxyethyl)oxy]ethyl}-2-oxo-1,2-dihydro-1,5-naphthyridine-3-carboxamide

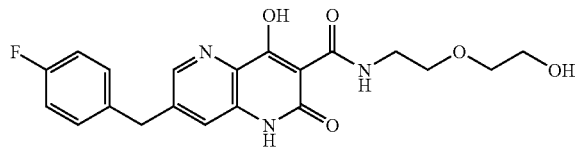 [SMILES: O=C(NCCOCCO)c1c(O)c2ncc(Cc3ccc(F)cc3)cc2[nH]c1=O]

$^1$H NMR ($d_6$-DMSO) tautomers are observed δ 12.09 (1H, br s), 11.07 (1H, br s), 10.36 (1H, br s), 8.75 (0.5H, br s), 8.65 (0.5H, br s), 7.60-7.48 (3H, m), 7.38-7.34 (2H, m), 4.85 (1H, br s), 4.23 92H, s), 3.74-3.56 (8H, M); HRMS calcd for $C_{20}H_{20}FN_3O_5+H^+$: 402.1465. Found: 402.1469.

EXAMPLE 87

7-[(4-Fluorophenyl)methyl]-4-hydroxy-N',N!-dimethyl-2-oxo-1,2-dihydro-1,5-naphthyridine-3-carbohydrazide

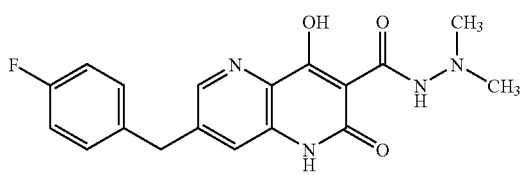 [SMILES: CN(C)NC(=O)c1c(O)c2ncc(Cc3ccc(F)cc3)cc2[nH]c1=O]

$^1$H NMR ($d_6$-TFA) δ 8.80 (1H, s), 8.47 (1H, s), 7.26-7.22 (2H, m), 7.13-7.08 (2H, m), 4.40 (2H, s), 3.62 (3H, s), 3.61 (3H, s); HRMS calcd for $C_{18}H_{17}FN_4O_3+H^+$: 357.1363. Found: 357.1351.

EXAMPLE 88

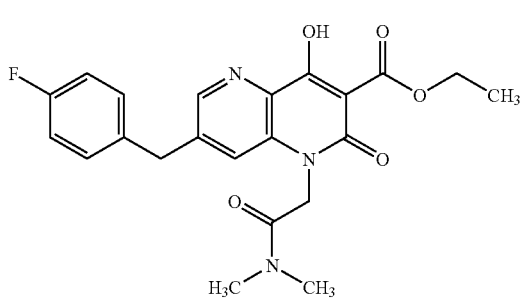 [SMILES: CCOC(=O)c1c(O)c2ncc(Cc3ccc(F)cc3)cc2n(CC(=O)N(C)C)c1=O]

M+H calcd: 428.1622. M+H found: 428.1616.

EXAMPLE 89

1-[2-(Dimethylamino)-2-oxoethyl]-7-[(4-fluorophenyl)methyl]-4-hydroxy-N-[2-(methyloxy)ethyl]-2-oxo-1,2-dihydro-1,5-naphthyridine-3-carboxamide Step 1: Synthesis of (4-fluorophenyl[6-(methyloxy)-3-pyridinyl]methanol

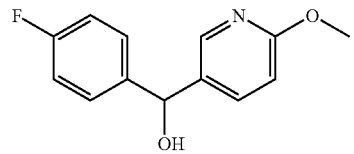 [SMILES: COc1ccc(C(O)c2ccc(F)cc2)cn1]

A 2.5M solution of n-BuLi in THF (181 mL, 0.452 mol) was added slowly to a stirred solution of 5-bromo-2-(methyloxy)pyridine (85 g, 0.452 mol) in THF (500 mL) cooled to −65° C. The internal temperature was maintained at or below −55° C. during the addition; when the addition was complete, a solution of 4-fluorobenzaldehyde (51 g, 0.411 mol) in THF (120 mL) was added slowly maintaining the temperature at or below −50° C. Saturated ammonium chloride solution (200 mL) was added and the mixture was warmed to −15° C. and concentrated at reduced pressure. The mixture was diluted with EtOAc (1 L) and washed twice with saturated ammonium chloride solution. The aqueous layers were back-extracted with EtOAc and the combined organic layers were washed with brine, dried and concentrated to afford the product as a light amber oil: $^1$H NMR (CDCl$_3$) δ 8.14 (1H, d, J=2.5 Hz), 7.54 (1H, dd, J=8.6, 2.5 Hz), 7.36 (2H, dd, J=8.6, 5.4 Hz), 7.05 (2H, m), 6.73 (1H, d, J=8.6 Hz), 5.82 (1H, s), 3.94 (3H, s), 2.40 (1H, br).

Steps 2-3 : Synthesis of 5-[(4-fluorophenyl)methyl]-2(1H)-pyridinone

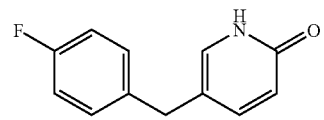 [SMILES: O=c1ccc(Cc2ccc(F)cc2)c[nH]1]

A stirred mixture of (4-fluorophenyl)[6-(methyloxy)-3-pyridinyl]methanol (293 g, 1.26 mol), DCE (650 mL), TFA (650 mL) and triethylsilane (650 mL) was heated at reflux for 5 h; the DCE was removed by distillation and glacial acetic acid (250 mL, 4.4 mol) and 48% HBr (250 mL, 2.2 mol) were added. The resulting solution was heated at reflux for 6.5 h during which time additional 48% HBr (100 mL, 0.88 mol) was added. The mixture was partially concentrated at reduced pressure and the remaining bi-phasic mixture was separated. The upper phase, containing silane bi-products from the previous step, was discarded and the lower phase was cooled in an ice bath and neutralized with 4N NaOH solution to pH 8-9. The resulting precipitate was collected by filtration, washed with water and dried in a vacuum oven to afford the product as a white solid: $^1$H NMR (d$_6$-DMSO) δ 11.39 (1H, br), 7.23 (4H, m), 7.08 (2H, m), 6.24 (1H, d, J=9 Hz), 3.62 (2H, s); ES$^+$ MS: 204 (M+H$^+$, 100).

Step 4: Synthesis of 5-[(4-fluorophenyl)methyl]-3-nitro-2(1H)-pyridinone

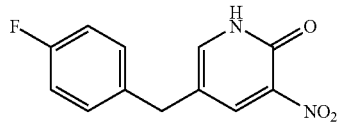 [SMILES: O=c1[nH]cc(Cc2ccc(F)cc2)cc1[N+](=O)[O-]]

A solution of 90% HNO$_3$ (57 mL, 1.22 mol) was added slowly to a stirred solution of 5-[(4-fluorophenyl)methyl]-2(1H)-pyridinone (249 g, 1.22 mol) in TFA (750 mL). The solution was heated at 75° C. for 2 h during which time additional 90% HNO$_3$ (25 mL, 0.5 mol) was added. Water (1L) was added slowly and most of the TFA was removed by distillation. The mixture was allowed to cool to rt and the product was isolated by filtration as a yellow solid: $^1$H NMR (d$_6$-DMSO) δ 12.76 (1H, br), 8.31 (1H, d, J=2.4 Hz), 7.80 (1H, d, J=2.4 Hz), 7.30 (2H, dd, J=8.6, 5.7 Hz), 7.11 (2H, t, J=8.6 Hz), 3.76 (2H, s); ES$^+$ MS: 249 (M+H$^+$, 100).

Step 5: Synthesis of 2-bromo-5-[(4-fluorophenyl)methyl]-3-nitropyridine

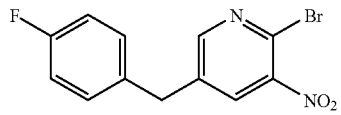 [SMILES: O=[N+]([O-])c1cc(Cc2ccc(F)cc2)cnc1Br]

A solution of POBr$_3$ (227 g, 0.79 mol) in toluene (900 mL) was added slowly to a stirred suspension of 5-[(4-fluorophenyl)methyl]-3-nitro-2(1H)-pyridinone (179 g, 0.72 mol) in toluene (900 mL). The mixture was heated to reflux; then cooled to rt and DMF (56 mL, 0.72 mol) was added slowly; the mixture was again heated to reflux and then allowed to cool to rt overnight. After cooling the mixture in an ice-bath, water (500 mL) was added slowly followed by dropwise addition 4 N NaOH (450 mL, 1.76 mol). All insoluble material was removed by filtration and the two liquid phases were separated. The organic layer was concentrated at reduced pressure to afford the product as a beige solid: $^1$H NMR (d$_6$-DMSO) δ 8.62 (1H, d, J=2 Hz), 8.37 (1H, d, J=2 Hz), 7.33 (2H, m), 7.12 (2H, m), 4.05 (2H, s); ES$^+$ MS: 313 (M+H$^+$, 100), 311 (M+H$^+$, 100).

Step 6: Synthesis of methyl 5-[(4-fluorophenyl)methyl]-3-nitro-2-pyridinecarboxylate

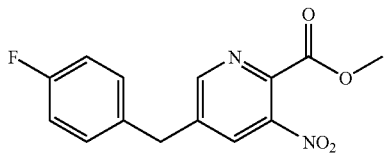

A mixture of bromo-5-[(4-fluorophenyl)methyl]-3-nitropyridine (206 g, 0.66 mol), TEA (230 mL, 1.66 mol), (o-tol)$_3$P (5 g, 16.4 mmol), and Pd(OAc)$_2$ (3.7 g, 16.6 mmol) in MeOH (2 L) was heated at 60-65° C. under a CO$_{(g)}$ atmosphere for 33 h. During this time additional (o-tol)$_3$P (5 g, 16.4 mmol), and Pd(OAc)$_2$ (5.2 g, 23 mmol) were added. The mixture was filtered through celite, concentrated at reduced pressure, reconstituted in EtOAc and washed with saturated NaHCO$_3$ solution and brine. The organic phase was dried and concentrated to provide the product as a dark oil: $^1$H NMR (d$_6$-DMSO) δ 8.71 1H, d, J=1.5 Hz), 8.03 (1H, d, J=1.5 Hz), 7.14 (2H, m), 7.06 (2H, m), 4.10 (2H, s), 3.99 (3H, s); ES$^+$ MS: 291 (M+H$^+$, 100).

Step 7: Synthesis of methyl 3-amino-5-[(4-fluorophenyl)methyl]-2-pyridinecarboxylate

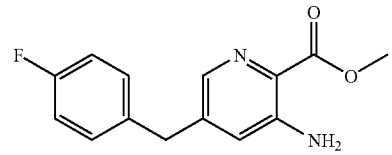 [SMILES: COC(=O)c1ncc(Cc2ccc(F)cc2)cc1[N+](=O)[O-]]

A mixture of methyl 5-[(4-fluorophenyl)methyl]-3-nitro-2-pyridinecarboxylate (200 g, 0.66 mol) and Degussa 10% Pd on carbon (50% by weight water, 20 g) in THF (1.5 L) was stirred under an atmosphere of H$_2$ for 2 d. The mixture was filtered through celite and the filtrate was re-subjected to similar hydrogenation conditions with 10% Pd on carbon (30 g) at 45° C. for 7 d. During this time, conc. HCl (14 mL, 0.17 mol) in MeOH (75 mL) and 10% Pd on carbon (18 g) were added in approximately three portions each. The mixture was filtered through celite, concentrated at reduced pressure, reconstituted in CH$_2$Cl$_2$ and washed with saturated NaHCO$_3$ solution. The organic phase was concentrated and the resulting material was triturated with EtOAc to provide the product as an off-white solid: $^1$H NMR (CDCl$_3$) δ 7.94 (1H, d, J=1.5 Hz), 7.11 (2H, m), 6.98 (2H, m), 6.72 (1H, 1.5 Hz), 5.67 (2H, br s), 3.95 (3H, s), 3.89 (2H, s); ES$^+$ MS: 261 (M+H$^+$, 100).

Steps 8-10: Synthesis of methyl 3-{[2-(dimethylamino)-2-oxoethyl]amino}-5-[(4-fluorophenyl)methyl]-2-pyridinecarboxylate

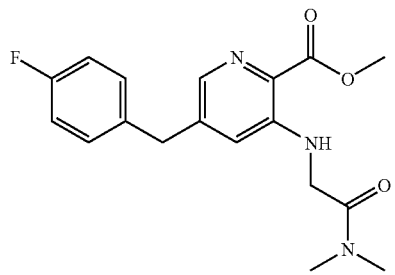 [SMILES: COC(=O)c1ncc(Cc2ccc(F)cc2)cc1NCC(=O)N(C)C]

A stirring suspension of methyl 3-amino-5-[(4-fluorophenyl)methyl]-2-pyridinecarboxylate (60 g, 0.23 mol) in i-PrOAc (400 mL) was heated to 30° C. and trifluoroacetic anhydride (35.3 mL, 0.254 mol) was added dropwise. The reaction mixture was stirred 15 min at 30° C.; then cooled to rt and quenched slowly with 0.6 M NaHCO$_3$ solution (512 mL, 0.32 mol). The resulting biphasic mixture was separated and the organic phase was washed twice with water; then diluted with CH₃CN (700 mL) and distilled to about half its initial volume. To the remaining solution (ca. 600 mL) was added K₂CO₃ (34.6 g, 0.255 mol), NaI (5.18 g, 34.6 mol) and 2-chloro-N,N-dimethylacetamide (26.1 mL, 0.254 mol) and the resulting mixture was heated to 80° C. for 3.5 h. The reaction was cooled to 60° C., diluted with MeOH (200 mL), heated at reflux for 2 h and then distilled to approximately half its original volume. The remaining mixture was cooled to 37° C. and water (650 mL) was added over 2 h with gradual cooling to 15° C. A precipitate formed which was collected by filtration and washed with water. Drying of the filter cake in a vacuum oven afforded the product as an off-white solid: $^1$H NMR (CDCl₃) δ 8.56 (1H, br), 7.89 (1H, s), 7.12 (2H, dd, J=8.5, 5.5 Hz), 6.98 (2H, t, J=8.5 Hz), 6.68 (1H, s), 3.96 (3H, s), 3.93 (2H, s), 3.88 (2H, d, J=4.2 Hz), 3.02 (3H, s), 3.01 (3H, s).

Steps 11-12: Synthesis of ethyl 1-[2-(dimethylamino)-2-oxoethyl]-7-[(4-fluorophenyl)methyl]-4-hydroxy-2-oxo-1,2-dihydro-1,5-naphthyridine-3-carboxylate

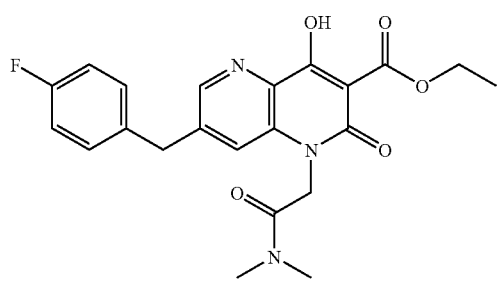 [SMILES: CCOC(=O)c1c(O)c2ncc(Cc3ccc(F)cc3)cc2n(CC(=O)N(C)C)c1=O]

Ethyl malonyl chloride (27 mL, 0.21 mol) was added slowly to a solution of methyl 3-{[2-(dimethylamino)-2-oxoethyl]amino}-5-[(4-fluorophenyl)methyl]-2-pyridinecarboxylate (65.8 g, 0.19 mol) in DCE (350 mL) at rt. The mixture was heated at reflux for 3 h during which time additional ethyl malonyl chloride (10 mL, 78 mmol) was added. When the reaction was complete, the mixture was cooled to rt; washed three times with 0.8 M NaHCO₃ solution and once with water. The organic phase was diluted with EtOH (50 mL), distilled to approximately 30% of its original volume and cooled to rt. A solution of 2.68 M NaOEt in EtOH (70 mL, 0.188 mol) was added and after stirring 10 min at rt, the mixture was acidified with 1N HCl (190 mL, 190 mmol) and diluted with EtOH (600 mL). The mixture was heated to 70° C.; then cooled to 50° C. and filtered. The filter cake was washed with water and dried in a vacuum oven to afford the product as a white solid: $^1$H NMR (d₆-DMSO) δ 8.44 (1H, d, J=1 Hz), 7.67 (1H, s), 7.31 (2H, dd, J=8.7, 5.6 Hz), 7.12 (2H, t, J=8.7 Hz), 5.04 (2H, s), 4.21 (2H, q, J=7 Hz), 4.11 (2H, s), 3.10 (3H, s), 2.80 (3H, s), 1.23 (3H, t, J=7 Hz); ES⁻ MS: 426 (M−1, 100).

Step 13: Synthesis of 1-[2-(dimethylamino)-2-oxoethyl]-7-[(4-fluorophenyl)methyl]-4-hydroxy-N-[2-(methyloxy)ethyl]-2-oxo-1,2-dihydro-1,5-naphthyridine-3-carboxamide

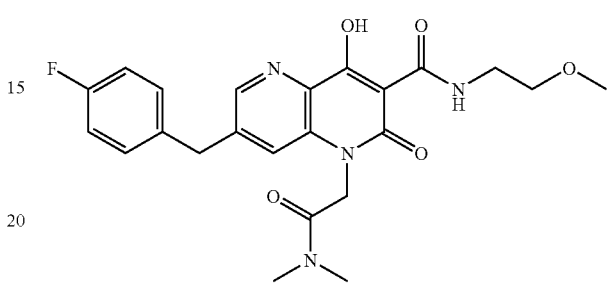

A mixture of ethyl 1-[2-(dimethylamino)-2-oxoethyl]-7-[(4-fluorophenyl)methyl]-4-hydroxy-2-oxo-1,2-dihydro-1,5-naphthyridine-3-carboxylate(49.2 g, 115 mmol) and 2-methoxyethylamine (14.8 mL, 172 mmol) in NMP (400 mL) was heated at 95-115° C. for 1-2 h. The mixture was cooled to rt, diluted with water (600 mL) and acidified with 1N HCl (72 mL). The precipitate was collected by filtration, washed with water and dried overnight in a vacuum oven to afford the product as a white solid: $^1$H NMR (d₆-DMSO) δ 10.23 (1H, br t, J=5 Hz), 8.51 (1H, s), 7.75 (1H, s), 7.32 (2H, dd, J=9, 6 Hz), 7.12 (2H, t, J=9 Hz), 5.12 (2H, s), 4.11 (2H, s), 3.54-3.44 (4H, m), 3.27 (3H, s), 3.12 (3H, s), 2.82 (3H, s); HRMS calcd for C₂₃H₂₅FN₄O₅+H⁺: 457.1887.Found: 457.1884.

EXAMPLE 90

N-Cyclopropyl-1-[2-(dimethylamino)-2-oxoethyl]-7-[(4-fluorophenyl)methyl]-4-hydroxy-2-oxo-1,2-dihydro-1,5-naphthyridine-3-carboxamide

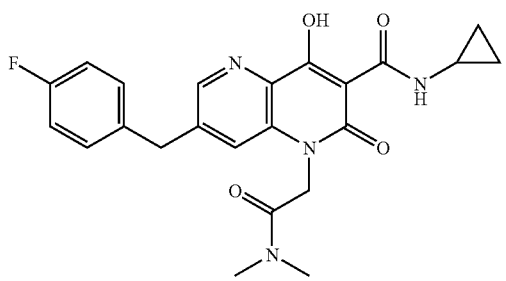 [SMILES: CN(C)C(=O)Cn1c(=O)c(C(=O)NC2CC2)c(O)c2ncc(Cc3ccc(F)cc3)cc21]

This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and cyclopropylamine employing methods similar to those described in Example 9. The product was obtained as a white solid: $^1$H NMR (CDCl₃) δ 9.96 (1H, br), 8.54 (1H, d, J=1.4 Hz), 7.13 (2H, m), 7.04-7.00 (3H, m), 4.92 (2H, s), 4.10 (2H, s), 3.11 (3H, s), 2.96 (3H, s), 2.93 (1H, m), 0.86 (2H, m, J=13, 7), 0.66 (2H, m); HRMS calcd for $C_{23}H_{23}FN_4O_4$+H$^+$: 439.1781. Found: 439.1774.

EXAMPLE 91

1-[2-(Dimethylamino)-2-oxoethyl]-7-[(4-fluorophenyl)methyl]-4-hydroxy-N-[2-(4-morpholinyl)ethyl]-2-oxo-1,2-dihydro-1,5-naphthyridine-3-carboxamide

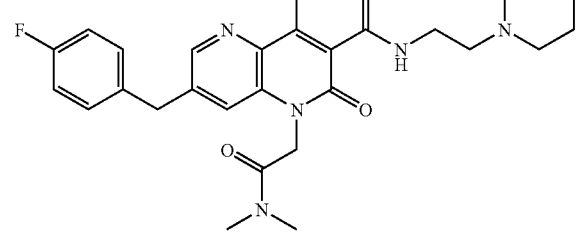

This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and 4-(2-aminoethyl)morpholine employing methods similar to those described in Example 9. The product was obtained as a white solid: $^1$H NMR (CDCl$_3$) δ 10.15 (1H, br t), 8.54 (1H, s), 7.15 (2H, dd, J=9, 6 Hz), 7.05-7.01 (3H, m), 4.96 (2H, s), 4.11 (2H, s), 3.74 (4H, m), 3.56 (2H, q, J=6 Hz), 3.13 (3H, s), 2.97 (3H, s), 2.59 (2H, t, J=6 Hz), 2.52 (4H, m); HRMS calcd for $C_{26}H_{30}FN_5O_5$+H$^+$: 512.2309. Found: 512.2296.

EXAMPLE 92

Ethyl 7-[(4-Fluorophenyl)methyl]-4-hydroxy-1-methyl-2-oxo-1,2-dihydro-1,5-naphthyridine-3-carboxylate

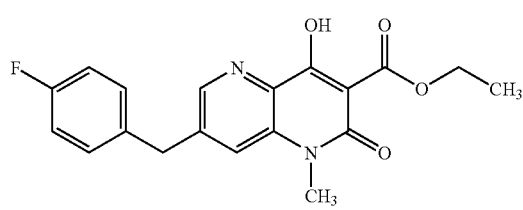 [SMILES: CCOC(=O)c1c(O)c2ncc(Cc3ccc(F)cc3)cc2n(C)c1=O]

HRMS calcd for $C_{19}H_{17}FN_2O_4$+H$^+$: 357.1250. Found: 357.1244.

EXAMPLE 93

7-[(4-Fluorophenyl)methyl]-4-hydroxy-1-[2-(4-morpholinyl)-2-oxoethyl]-N-[3-(4-morpholinyl)propyl]-2-oxo-1,2-dihydro-1,5-naphthyridine-3-carboxamide

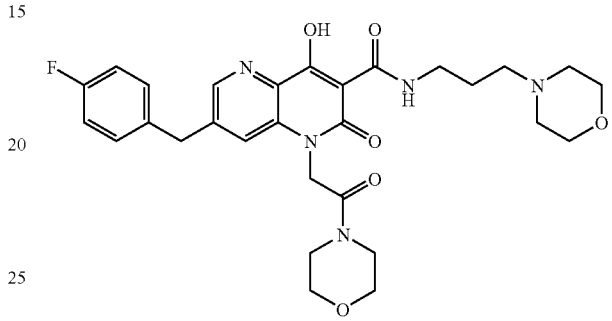

The title compound was made in a manner similar to example 83 using N-(3-aminopropyl)morpholine to give a pale lemon solid: $^1$H NMR (CDCl$_3$) δ 10.14 (1H, m), 8.60 (1H, s), 7.15 (2H, m), 7.07 (1H, s), 7.04 (2H, m), 4.94 (2H, s), 4.14 (2H, s), 4.00 (4H, m), 3.76 (2H, m), 3.70 (2H, m), 3.59 (8H, m), 3.14 (2H, t, J=8 Hz), 2.89 (2H, m), 2.17 (2H, m); HRMS calcd for $C_{29}H_{34}FN_5O_6$+H$^+$: 568.2571. Found: 568.2571.

EXAMPLE 94

7-[(4-Fluorophenyl)methyl]-4-hydroxy-1-[2-(4-morpholinyl)-2-oxoethyl]-2-oxo-N-[3-(2-oxo-1-pyrrolidinyl)propyl]-1,2-dihydro-1,5-naphthyridine-3-carboxamide

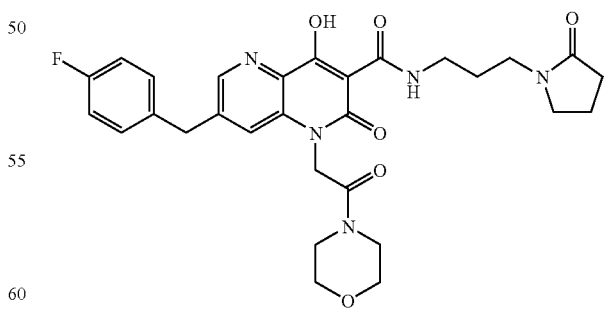

The title compound was made in a manner similar to example 83 using 1-(3-aminopropyl)-2-pyrrolidinone to give a white solid: $^1$H NMR (CDCl$_3$) δ 10.15 (1H, m), 8.58 (1H, s), 7.14 (2H, m), 7.04 (3H, m), 4.96 (2H, s), 4.13 (2H, s), 3.74 (2H, m), 3.68 (2H, m), 3.57 (4H, m), 3.43 (6H, m), 2.49 (2H, t, J=8 Hz), 2.06 (2H, m), 1.87 (2H, m); HRMS calcd for $C_{29}H_{32}FN_5O_6+H^+$: 566.2415. Found: 566.2411.

EXAMPLE 95

7-[(4-Fluorophenyl)methyl]-4-hydroxy-N-(2-hydroxyethyl)-1-[2-(4-morpholinyl)-2-oxoethyl]-2-oxo-1,2-dihydro-1,5-naphthyridine-3-carboxamide

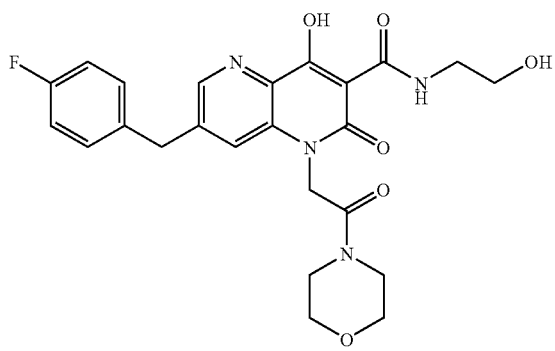 [SMILES: O=C(NCCO)c1c(O)c2ncc(Cc3ccc(F)cc3)cc2n(CC(=O)N2CCOCC2)c1=O]

The title compound was made in a manner similar to example 83 using ethanolamine to give a white solid: $^1$H NMR ($d_6$-DMSO) δ 10.26 (1H, m), 8.52 (1H, s), 7.71 (1H, s), 7.31 (2H, m), 7.13 (2H, m), 5.17 (2H, s), 4.93 (1H, m), 4.13 (2H, s), 3.67 (2H, m), 3.60 (2H, m), 3.54 (4H, m), 3.40 (4H, m); HRMS calcd for $C_{24}H_{25}FN_4O_6+H^+$: 485.1836. Found: 485.1828.

EXAMPLE 96

7-[(4-Fluorophenyl)methyl]-4-hydroxy-1-methyl-N-[2-(4-morpholinyl)ethyl]-2-oxo-1,2-dihydro-1,5-naphthyridine-3-carboxamide

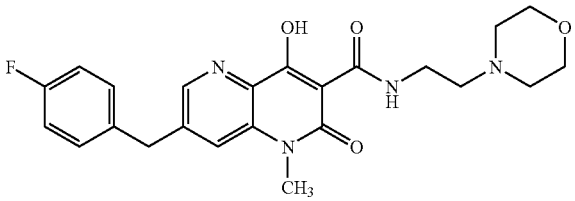 [SMILES: Cn1c(=O)c(C(=O)NCCN2CCOCC2)c(O)c2ncc(Cc3ccc(F)cc3)cc21]

The title compound was made from ethyl 7-[(4-fluorophenyl)methyl]-4-hydroxy-1-methyl-2-oxo-1,2-dihydro-1,5-naphthyridine-3-carboxylate in a manner similar to example 9 using 2-(4-morpholino)ethylamine to give a glass: $^1$H NMR (CDCl$_3$) δ 10.55 (1H, m), 8.63 (1H, s), 7.46 (1H, s), 7.16 (2H, m), 7.04 (2H, m), 4.16 (2H, s), 3.90-3.99 (6H, m), 3.80 (2H, m), 3.57 (3H, s), 3.41 (2H, t, J=5 Hz), 2.93 (2H, m); HRMS calcd for $C_{23}H_{25}FN_4O_4+H^+$: 441.1938. Found: 441.1927.

EXAMPLE 97

7-[(4-Fluorophenyl)methyl]-4-hydroxy-1-methyl-N-[3-(4-morpholinyl)propyl]-2-oxo-1,2-dihydro-1,5-naphthyridine-3-carboxamide

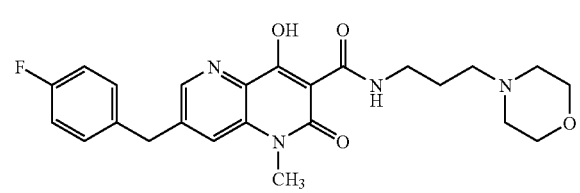 [SMILES: Cn1c(=O)c(C(=O)NCCCN2CCOCC2)c(O)c2ncc(Cc3ccc(F)cc3)cc21]

The title compound was made in a manner similar to example 96 using N-(3-aminopropyl)morpholine to give a glass: $^1$H NMR (CDCl$_3$) δ 10.36 (1H, m), 8.60 (1H, s), 7.44 (1H, s), 7.16 (2H, m), 7.04 (2H, m), 4.15 (2H, s), 3.99 (4H, m), 3.59 (3H, s), 3.56 (4H, m), 3.14 (2H, m), 2.88 (2H, m), 2.15 (2H, m); HRMS calcd for $C_{24}H_{27}FN_4O_4+H^+$: 455.2095. Found: 455.2089.

EXAMPLE 98

7-[(4-Fluorophenyl)methyl]-4-hydroxy-1-methyl-N-[2-(methyloxy)ethyl]-2-oxo-1,2-dihydro-1,5-naphthyridine-3-carboxamide

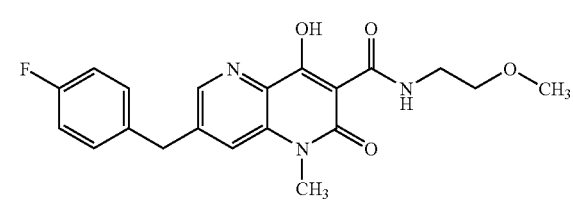 [SMILES: COCCNC(=O)c1c(O)c2ncc(Cc3ccc(F)cc3)cc2n(C)c1=O]

The title compound was made in a manner similar to example 96 using 2-methoxyethylamine to give a white solid: $^1$H NMR (CDCl$_3$) δ 10.34 (1H, m), 8.59 (1H, s), 7.41 (1H, s), 7.17 (2H, m), 7.03 (2H, m), 4.14 (2H, s), 3.67 (2H, m), 3.60 (2H, m), 3.59 (3H, s), 3.42 (3H, s); HRMS calcd for $C_{20}H_{20}FN_3O_4+H^+$: 386.1516. Found: 386.1531.

EXAMPLE 99

7-[(4-Fluorophenyl)methyl]-4-hydroxy-1-methyl-2-oxo-N-[3-(2-oxo-1-pyrrolidinyl)propyl]-1,2-dihydro-1,5-naphthyridine-3-carboxamide

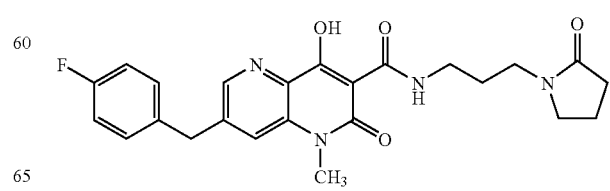

The title compound was made in a manner similar to example 96 using 1-(3-aminopropyl)-2-pyrrolidinone to give a glass: $^1$H NMR (CDCl$_3$) δ 10.29 (1H, m), 8.66 (1H, s), 7.49 (1H, s), 7.17 (2H, m), 7.04 (2H, m), 4.17 (2H, s), 3.60 (3H, s), 3.42-3.51 (6H, m), 2.56 (2H, t, J=8 Hz), 2.10 (2H, m), 1.91 (2H, m); HRMS calcd for C$_{24}$H$_{25}$FN$_4$O$_4$+H$^+$: 453.1938. Found: 453.1927.

EXAMPLE 100

Ethyl 7-[(4-Fluorophenyl)methyl]-4-hydroxy-1-[2-(4-methyl-1-piperazinyl)-2-oxoethyl]-2-oxo-1,2-dihydro-1,5-naphthyridine-3-carboxylate

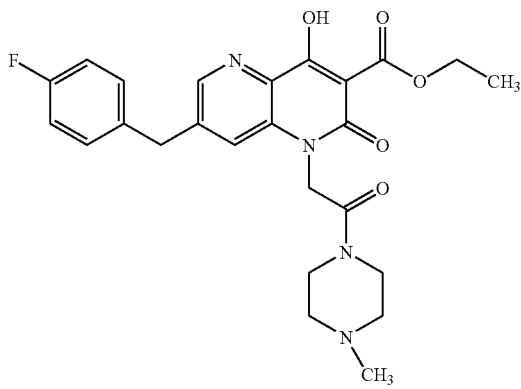 [SMILES: CCOC(=O)c1c(O)c2ncc(Cc3ccc(F)cc3)cc2n(CC(=O)N2CCN(C)CC2)c1=O]

HRMS calcd for C$_{25}$H$_{27}$FN$_4$O$_5$+H$^+$: 483.2043. Found: 483.2035

EXAMPLE 101

7-[(4-Fluorophenyl)methyl]-4-hydroxy-N-(2-hydroxyethyl)-1-methyl-2-oxo-1,2-dihydro-1,5-naphthyridine-3-carboxamide

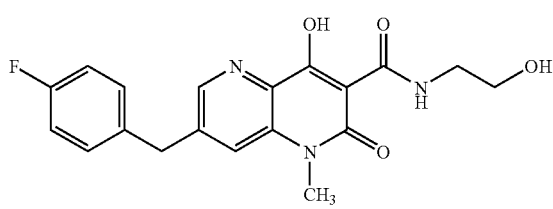 [SMILES: Cn1c(=O)c(C(=O)NCCO)c(O)c2ncc(Cc3ccc(F)cc3)cc21]

The title compound was made in a manner similar to example 96 using ethanolamine to give a lemon solid: $^1$H NMR (CDCl$_3$) δ 10.47 (1H, m), 8.58 (1H, s), 7.40 (1H, s), 7.16 (2H, m), 7.03 (2H, m), 4.14 (2H, s), 3.86 (2H, m), 3.65 (2H, m), 3.59 (3H, s); HRMS calcd for C$_{19}$H$_{18}$FN$_3$O$_4$+H$^+$: 372.1359. Found: 372.1355.

EXAMPLE 102

7-[(4-Fluorophenyl)methyl]-4-hydroxy-N-[2-(methyloxy)ethyl]-1-[2-(4-methyl-1-piperazinyl)-2-oxoethyl]-2-oxo-1,2-dihydro-1,5-naphthyridine-3-carboxamide

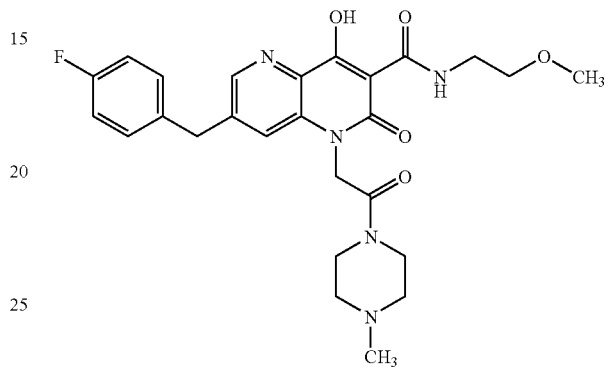

The title compound was made from ethyl 7-[(4-fluorophenyl)methyl]-4-hydroxy-1-[2-(4-methyl-1-piperazinyl)-2-oxoethyl]-2-oxo-1,2-dihydro-1,5-naphthyridine-3-carboxylate in a manner similar to example 9 using 2-methoxyethylamine to give a glass: $^1$H NMR (CDCl$_3$) δ 10.00 (1H, m), 8.59 (1H, s), 7.31 (1H, s), 7.13 (2H, m), 7.02 (2H, m), 5.30 (1H, br s), 4.62 (2H, br s), 4.12 (2H, s), 3.57-3.66 (12H, m), 3.39 (3H, s), 2.90 (3H, s); HRMS calcd for C$_{26}$H$_{30}$FN$_5$O$_5$+H$^+$: 512.2309. Found: 512.2307.

EXAMPLE 103

7-[(4-Fluorophenyl)methyl]-4-hydroxy-1-[2-(4-methyl-1-piperazinyl)-2-oxoethyl]-2-oxo-N-[3-(2-oxo-1-pyrrolidinyl)propyl]-1,2-dihydro-1,5-naphthyridine-3-carboxamide

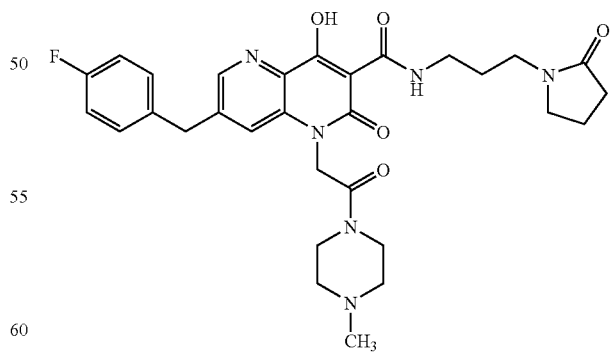

The title compound was made in a manner similar to example 102 using 1-(3-aminopropyl)-2-pyrrolidinone to give a pale yellow viscous oil: $^1$H NMR (CDCl$_3$) δ 10.09 (2H, m), 8.56 (1H, s), 7.37 (1H, s), 7.13 (2H, m), 7.01 (2H, m), 5.37 (1H, m), 4.60 (2H, m), 4.22 (1H, m), 4.11 (2H, s), 3.91 (1H, m), 3.65 (2H, m), 3.45 (7H, m), 3.31 (2H, m), 2.90 (3H, s), 2.46 (2H, m), 2.08 (2H, m), 1.86 (2H, m); HRMS calcd for $C_{30}H_{35}FN_6O_5+H^+$: 579.2734. Found: 579.2731.

EXAMPLE 104

7-[(4-Fluorophenyl)methyl]-4-hydroxy-1-(2-{methyl[2-(methyloxy)ethyl]amino}-2-oxoethyl)-N-[2-(methyloxy)ethyl]-2-oxo-1,2-dihydro-1,5-naphthyridine-3-carboxamide

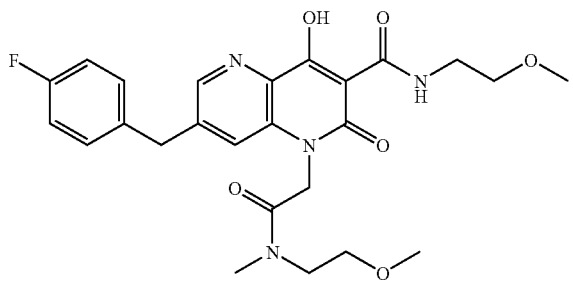 [SMILES: COCCNC(=O)c1c(O)c2ncc(Cc3ccc(F)cc3)cc2n(CC(=O)N(C)CCOC)c1=O]

This compound was prepared from ethyl 7-[(4-fluorophenyl)methyl]-4-hydroxy-1-(2-{methyl[2-(methyloxy)ethyl]amino}-2-oxoethyl)-2-oxo-1,2-dihydro-1,5-naphthyridine-3-carboxylate and 2-methoxyethylamine employing methods similar to those described in Example 9 and was purified by reverse phase preparative HPLC (C-18 stationary phase; 10-100% CH$_3$CN/water/0.1% formic acid mobile phase). The product was obtained as an off-white solid: $^1$H NMR (CDCl$_3$) mixture of rotamers δ 10.20 (1H, br), 8.55 and 8.50 (1H, s), 7.34 and 7.10 (1H, s), 7.15-6.97 (4H, m), 5.21 and 4.98 (2H, s), 4.10 (2H, s), 3.64-3.41 (8H, m), 3.40 and 3.39 (3H, s), 3.34 and 3.32 (3H, s), 3.17 and 2.97 (3H, s); HRMS calcd for $C_{25}H_{29}FN_4O_6+H^+$: 501.2149. Found: 501.2140.

EXAMPLE 105

(±)-7-[(4-Fluorophenyl)methyl]-4-hydroxy-N-[2-hydroxy-1-methylethyl]-1-(2-{methyl[2-(methyloxy)ethyl]amino}-2-oxoethyl)-2-oxo-1,2-dihydro-1,5-naphthyridine-3-carboxamide

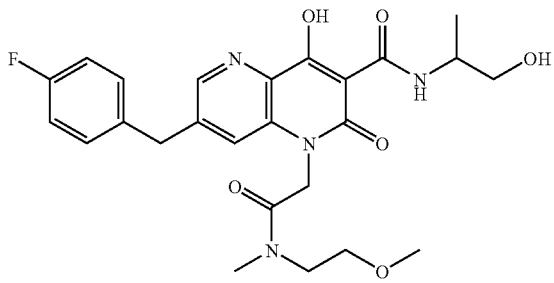 [SMILES: COCCN(C)C(=O)Cn1c(=O)c(C(=O)NC(C)CO)c(O)c2ncc(Cc3ccc(F)cc3)cc21]

This compound was prepared from 7-[(4-fluorophenyl)methyl]-4-hydroxy-1-(2-{methyl[2-(methyloxy)ethyl]amino}-2-oxoethyl)-2-oxo-1,2-dihydro-1,5naphthyridine-3-carboxylate and (±)-2-amino-1-propanol employing methods similar to those described in Example 5, Step 4 and was obtained as an off-white solid: $^1$H NMR (CDCl$_3$) mixture of rotamers δ 10.21 and 10.19 (1H, br d), 8.55 and 8.49 (1H, s), 7.33 and 7.10 (1H, s), 7.12-6.97 (4H, m), 5.21 and 4.97 (2H, m), 4.27 (1H, m), 4.09 (2H, s), 3.80-3.50 (6H, m), 3.34 and 3.32 (3H, s), 3.17 and 2.97 (3H, s), 1.30 and 1.29 (3H, d, J=7 Hz); HRMS calcd for $C_{25}H_{29}FN_4O_6+H^+$: 501.2149. Found: 501.2160.

EXAMPLE 106

(±)-7-[(4-Fluorophenyl)methyl]-4-hydroxy-N-[(2-hydroxypropyl]-1-(2-{methyl[2-(methyloxy)ethyl]amino}-2-oxoethyl)-2-oxo-1,2-dihydro-1,5-naphthyridine-3-carboxamide

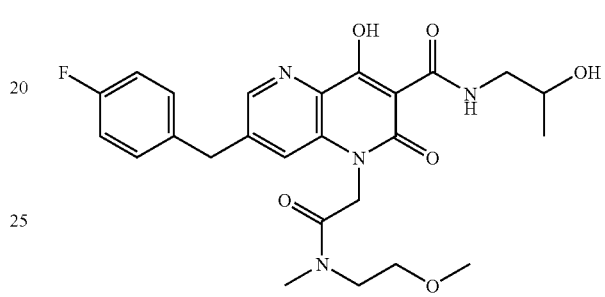

This compound was prepared from 7-[(4-fluorophenyl)methyl]-4-hydroxy-1-(2-{methyl[2-(methyloxy)ethyl]amino}-2-oxoethyl)-2-oxo-1,2-dihydro-1,5-naphthyridine-3-carboxylate and (±)-1-amino-2-propanol employing methods similar to those described in Example 9 and was purified by reverse phase preparative HPLC (C-18 stationary phase; 10-100% CH$_3$CN/water/0.1% formic acid mobile phase). The product was obtained as an off-white solid: $^1$H NMR (CDCl$_3$) mixture of rotamers δ 10.35 and 10.30 (1H, brt), 8.54 and 8.49 (1H, s), 7.33 and 7.10 (1H, s), 7.15-6.97 (4H, m), 5.21 and 4.98 (2H, m), 4.09 (2H, s), 4.05 (1H, m), 3.50-3.30 (7H, m), 3.34 and 3.32 (3H, s), 3.17 and 2.97 (3H, s), 1.26 (3H, d, J=6 Hz); HRMS calcd for $C_{25}H_{29}FN_4O_6+H^+$: 501.2149. Found: 501.2141.

EXAMPLE 107

N-[2-(ethyloxy)ethyl]-7-[(4-fluorophenyl)methyl]-4-hydroxy-1-(2-{methyl[2-(methyloxy)ethyl]amino}-2-oxoethyl)-2-oxo-1,2-dihydro-1,5-naphthyridine-3-carboxamide

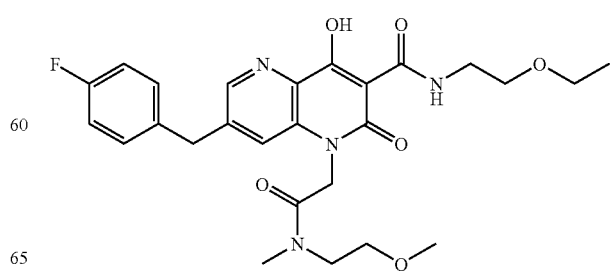

Step 1: Synthesis of N-{2-[(ethyloxy)carbonyl]-5-[(4-fluorophenyl)methyl]-3-pyridinyl}glycine

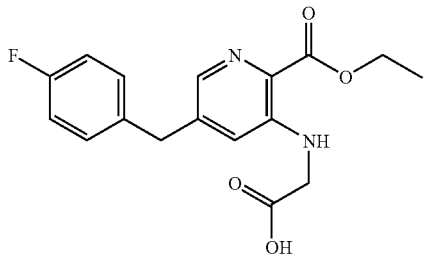 [SMILES: CCOC(=O)c1ncc(Cc2ccc(F)cc2)cc1NCC(=O)O]

This compound was prepared from ethyl 3-amino-5-[(4-fluorophenyl)methyl]-2-pyridinecarboxylate and glyoxylic acid monohydrate employing methods similar to those described in Example 11, Step 1 and was obtained as a white solid: $^1$H NMR (d$_6$-DMSO) δ 13.1 (1H, br), 7.91 (1H, t, J=5 Hz), 7.78 (1H, d, J=1 Hz), 7.29 (2H, dd, J=9, 6 Hz), 7.09 (1H, t, J=9 Hz), 7.02 (1H, s), 4.25 (2H, q, J=7 Hz), 3.92 (2H, d, J=5 Hz), 3.90 (2H, s), 1.27 (3H, t, J=7 Hz); ES$^+$ MS: 333 (M+1).

Steps 2-4: Synthesis of ethyl 7-[(4-fluorophenyl)methyl]-4-hydroxy-1-(2-{methyl[2-(methyloxy)ethyl]amino}-2-oxoethyl)-2-oxo-1,2-dihydro-1,5-naphthyridine-3-carboxylate

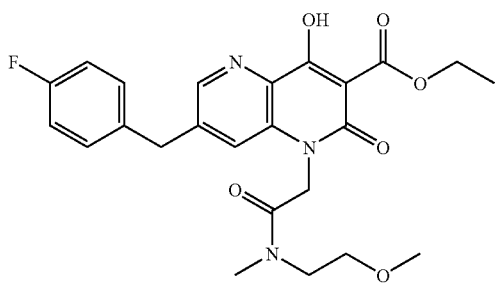 [SMILES: CCOC(=O)c1c(O)c2ncc(Cc3ccc(F)cc3)cc2n(CC(=O)N(C)CCOC)c1=O]

This compound was prepared from N-{2-[(ethyloxy)carbonyl]-5-[(4-fluorophenyl)methyl]-3-pyridinyl}glycine and methyl[2-(methyloxy)ethyl]amine employing methods similar to those described in Example 11, Steps 2-4. The product was obtained as an off-white solid: AP$^-$ MS: 470 (M−1, 100).

Step 5: Synthesis of N-[2-(ethyloxy)ethyl]-7-[(4-fluorophenyl)methyl]-4-hydroxy-1-(2-{methyl[2-(methyloxy)ethyl]amino}-2-oxoethyl)-2-oxo-1,2-dihydro-1,5-naphthyridine-3-carboxamide

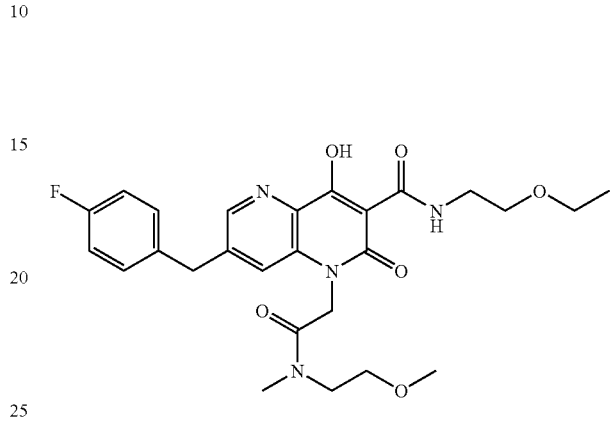

This compound was prepared from ethyl 7-[(4-fluorophenyl)methyl]-4-hydroxy-1-(2-{methyl[2-(methyloxy)ethyl]amino}-2-oxoethyl)-2-oxo-1,2-dihydro-1,5-naphthyridine-3-carboxylate and 2-ethoxyethylamine employing methods similar to those described in Example 9 and was purified by reverse phase preparative HPLC (C-18 stationary phase; 10-100% CH$_3$CN/water/0.1% formic acid mobile phase). The product was obtained as an off-white solid: $^1$H NMR (CDCl$_3$) mixture of rotamers δ 10.20 (1H, br), 8.56 and 8.52 (1H, s), 7.38 and 7.10 (1H, s), 7.16-7.09 (2H, m), 7.04-6.98 (2H, m), 5.21 and 4.98 (2H, s), 4.11 (2H, s), 3.74-3.50 (10H, m), 3.34 and 3.32 (3H, s), 3.18 and 2.97 (3H, s), 1.22 and 1.23 (3H, t, J=7 Hz); HRMS calcd for C$_{26}$H$_{31}$FN$_4$O$_6$+H$^+$: 515.2306. Found: 515.2293.

EXAMPLE 108

N-[2-(Dimethylamino)-2-oxoethyl]-7-[(4-fluorophenyl)methyl]-4-hydroxy-1-methyl-2-oxo-1,2-dihydro-1,5-naphthyridine-3-carboxamide

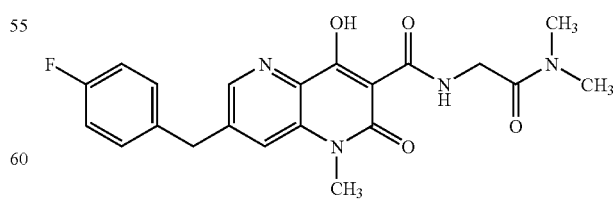

The title compound was made in a manner similar to example 96 using N',N'-dimethylglycinamide to give an off-white solid: $^1$H NMR (CDCl$_3$) δ 10.89 (1H, m), 8.58 (1H, s), 7.43 (1H, s), 7.16 (2H, m), 7.02 (2H, m), 4.26 (2H, d, J=5 Hz), 4.14 (2H, s), 3.59 (3H, s), 3.05 (3H, s), 3.03 (3H, s); HRMS calcd for $C_{21}H_{21}FN_4O_4+H^+$: 413.1625. Found: 413.1617.

EXAMPLE 109

N-(2,2-Difluoroethyl)-7-[(4-fluorophenyl)methyl]-4-hydroxy-1-methyl-2-oxo-1,2-dihydro-1,5-naphthyridine-3-carboxamide

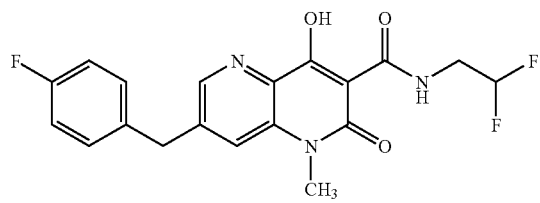 [SMILES: Cn1c(=O)c(C(=O)NCC(F)F)c(O)c2ncc(Cc3ccc(F)cc3)cc21]

The title compound was made in a manner similar to example 96 using 2,2-difluoroethylamine to give an off-white solid: $^1$H NMR (CDCl$_3$) δ 10.45 (1H, m), 8.65 (1H, s), 7.47 (1H, s), 7.16 (2H, m), 7.04 (2H, m), 5.97 (1H, m), 4.16 (2H, s), 3.84 (2H, m), 3.61 (3H, s); HRMS calcd for $C_{19}H_{16}F_3N_3O_3+H^+$: 392.1222. Found: 392.1222.

EXAMPLE 110

7-[(4-Fluorophenyl)methyl]-4-hydroxy-1-(2-{methyl[2-(methyloxy)ethyl]amino}-2-oxoethyl)-2-oxo-N-(2,2,2-trifluoroethyl)-1,2-dihydro-1,5-naphthyridine-3-carboxamide

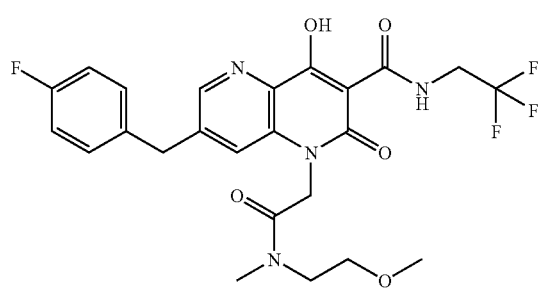 [SMILES: COCCN(C)C(=O)Cn1c(=O)c(C(=O)NCC(F)(F)F)c(O)c2ncc(Cc3ccc(F)cc3)cc21]

This compound was prepared from ethyl 7-[(4-fluorophenyl)methyl]-4-hydroxy-1-(2-{methyl[2-(methyloxy)ethyl]amino}-2-oxoethyl)-2-oxo-1,2-dihydro-1,5-naphthyridine-3-carboxylate and 2,2,2-trifluoroethylamine employing methods similar to those described in Example 9 and was recrystallized from a mixture of DMSO and EtOH. The product was obtained as a white solid: $^1$H NMR (d$_6$-DMSO) mixture of rotamers δ 10.53 (1H, m), 8.55 (1H, s), 7.77 and 7.59 (1H, s), 7.29 (2H, m), 7.12 (2H, br t, J=8 Hz), 5.20 and 5.16 (2H, s), 4.27 (2H, br), 4.12 (2H, s), 3.63 and 3.57 (2H, br m), 3.40-3.20 (2H, m), 3.33 and 3.22 (3H, s), 3.16 and 2.81 (3H, s); AP$^+$ MS: 525 (M+H$^+$, 100).

EXAMPLE 111

N-[3-(Ethyloxy)propyl]-7-[(4-fluorophenyl)methyl]-4-hydroxy-2-oxo-1,2-dihydro-1,5-naphthyridine-3-carboxamide

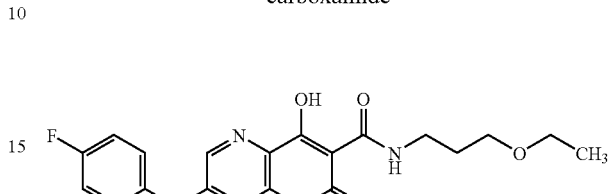

$^1$H NMR (d$_6$-DMSO) tautomers are observed δ 11.83 (1H, t, J=5.3 Hz), 10.80 (1H, br s), 10.10 (1H, br s), 8.18 (0.47H, s), 8.14 (0.53H, s), 7.36-7.23 93H, m), 7.14-7.07 (2H, m), 3.98 (2H, s), 3.43-3.23 (6H, m), 1.75-1.64 (2H, m), 1.09 (3H, m); HRMS calcd for $C_{21}H_{22}FN_3O_4+H^+$: 400.1673. Found: 400.1681.

EXAMPLE 112

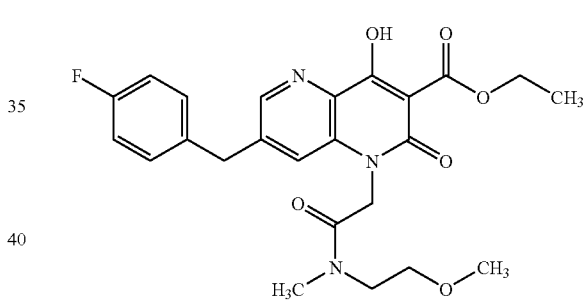

AP– MS: 470 (M–H, 100)

EXAMPLE 113

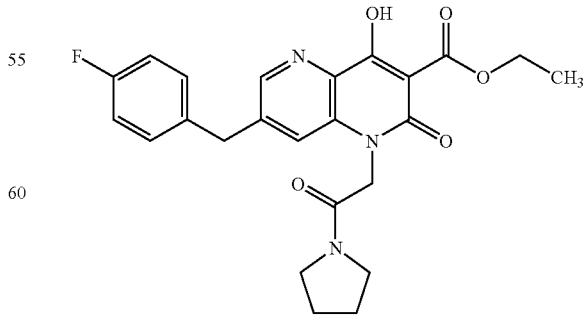

AP– MS: 452 (M–H, 100)

EXAMPLE 114

7-[(4-Fluorophenyl)methyl]-4-hydroxy-N-[2-(methyloxy)ethyl]-2-oxo-1-[2-oxo-2-(1-pyrrolidinyl)ethyl]-1,2-dihydro-1,5-naphthyridine-3-carboxamide

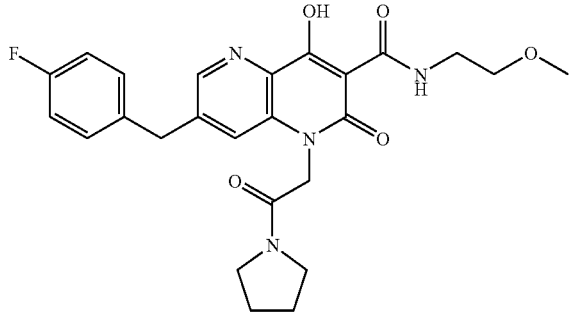 [SMILES: COCCNC(=O)c1c(O)c2ncc(Cc3ccc(F)cc3)cc2n(CC(=O)N2CCCC2)c1=O]

Steps 1-4: Synthesis of ethyl 7-[(4-fluorophenyl)methyl]-4-hydroxy-2-oxo-1-[2-oxo-2-(1-pyrrolidinyl)ethyl]-1,2-dihydro-1,5-naphthyridine-3-carboxylate

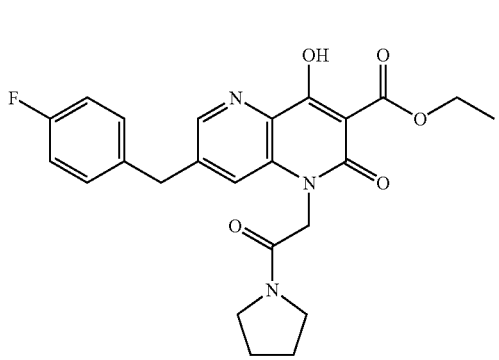 [SMILES: CCOC(=O)c1c(O)c2ncc(Cc3ccc(F)cc3)cc2n(CC(=O)N2CCCC2)c1=O]

This compound was prepared from N-{2-[(ethyloxy)carbonyl]-5-[(4-fluorophenyl)methyl]-3-pyridinyl}glycine and pyrrolidine employing methods similar to those described in Example 11, Steps 2-4 and was obtained as an off-white solid: AP⁻ MS: 452 (M−1, 100).

Step 5: Synthesis of 7-[(4-fluorophenyl)methyl]-4-hydroxy-N-[2-(methyloxy)ethyl]-2-oxo-1-[2-oxo-2-(1-pyrrolidinyl)ethyl]-1,2-dihydro-1,5-naphthyridine-3-carboxamide

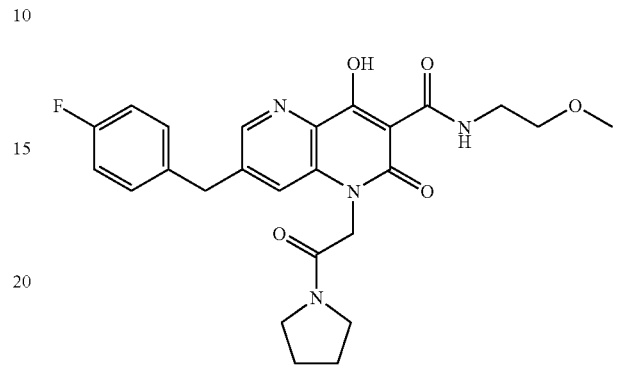

This compound was prepared from ethyl 7-[(4-fluorophenyl)methyl]-4-hydroxy-2-oxo-1-[2-oxo-2-(1-pyrrolidinyl)ethyl]-1,2-dihydro-1,5-naphthyridine-3-carboxylate and 2-methoxyethylamine employing methods similar to those described in Example 110 and was obtained as a white solid: $^1$H NMR (CDCl$_3$) δ 10.18 (1H, br t, J=5 Hz), 8.54 (1H, d, J=1 Hz), 7.15 (2H, dd, J=9, 5 Hz), 7.07 (1H, s), 7.02 (2H, t, J=9 Hz), 4.88 (2H, s), 4.11 (2H, s), 3.64 (2H, m), 3.57 (2H, m), 3.51 (2H, m), 3.45 (2H, m), 3.39 (3H, s), 2.03 (2H, m), 1.90 (2H, m); HRMS calcd for $C_{25}H_{27}FN_4O_5$+H⁺: 483.2044. Found: 483.2055.

EXAMPLE 115

7-[(4-Fluorophenyl)methyl]-4-hydroxy-N-[2-(4-morpholinyl)ethyl]-2-oxo-1-[2-oxo-2-(1-pyrrolidinyl)ethyl]-1,2-dihydro-1,5-naphthyridine-3-carboxamide

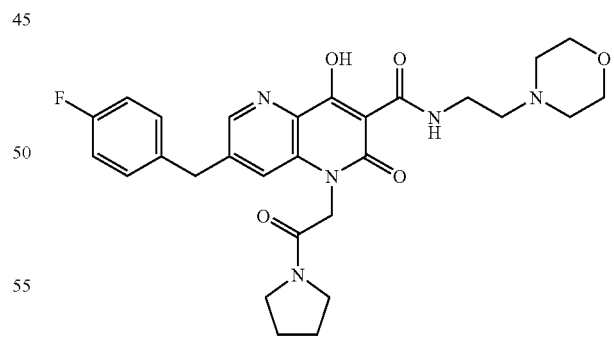

This compound was prepared from ethyl 7-[(4-fluorophenyl)methyl]-4-hydroxy-2-oxo-1-[2-oxo-2-(1-pyrrolidinyl)ethyl]-1,2-dihydro-1,5-naphthyridine-3-carboxylate and 4-(2-aminoethyl)morpholine employing methods similar to those those described in Example 9 and was purified by reverse phase preparative HPLC (C-18 stationary phase; 10-100% CH$_3$CN/water/0.1% formic acid mobile phase). The product was obtained as a white rigid foam: $^1$H NMR (CDCl$_3$) δ 10.39 (1H, br m), 8.55 (1H, s), 7.15 (3H, m), 7.02

(2H, t, J=9 Hz), 4.85 (2H, s), 4.12 (2H, s), 3.98 (4H, br), 3.88 (2H, q, J=6 Hz), 3.72 (2H, br), 3.54 (2H, t, J=7 Hz), 3.45 (2H, t, J=7 Hz), 3.35 (2H, t, J=6 Hz), 2.92 (2H, br), 2.06 (2H, m, J=7 Hz), 1.90 (2H, m, J=7 Hz); HRMS calcd for $C_{28}H_{32}FN_5O_5+H^+$: 538.2466. Found: 538.2460.

EXAMPLE 116

7-[(4-Fluorophenyl)methyl]-4-hydroxy-N-(2-hydroxyethyl)-2-oxo-1-[2-oxo-2-(1-pyrrolidinyl)ethyl]-1,2-dihydro-1,5-naphthyridine-3-carboxamide

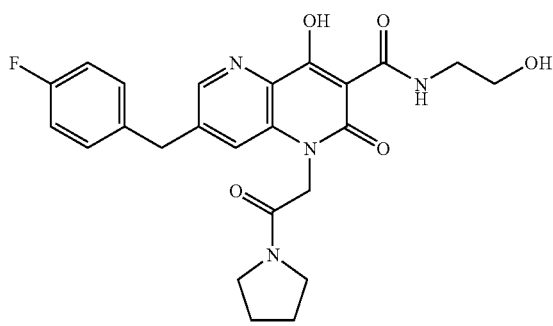 [SMILES: O=C(NCCO)c1c(O)c2ncc(Cc3ccc(F)cc3)cc2n(CC(=O)N2CCCC2)c1=O]

This compound was prepared from ethyl 7-[(4-fluorophenyl)methyl]-4-hydroxy-2-oxo-1-[2-oxo-2-(1-pyrrolidinyl) ethyl]-1,2-dihydro-1,5-naphthyridine-3-carboxylate and ethanolamine employing methods similar to those those described in Example 9 and was purified by reverse phase preparative HPLC (C-18 stationary phase; 10-100% $CH_3CN$/water/0.1% formic acid mobile phase). The product was obtained as a white solid: $^1H$ NMR ($d_6$-DMSO) δ 10.27 (1H, t, J=5 Hz), 8.51 (1H, s), 7.75 (1H, s), 7.31 (2H, dd, J=9, 6 Hz), 7.12 (2H, t, J=9 Hz), 5.03 (2H, s), 4.90 (1H, br), 4.12 (2H, s), 3.58 (2H, t, J=6 Hz), 3.54 (2H, m), 3.42 (2H, t, J=7 Hz), 3.40 (2H, t, J=7 Hz), 1.96 (2H, m, J=7 Hz), 1.80 (2H, m, J=7 Hz); HRMS calcd for $C_{24}H_{25}FN_4O_5+H^+$: 469.1887. Found: 469.1896.

EXAMPLE 117A

Biological Activity

MT4 Cell Assay
Experimental Procedure

Antiviral HIV activity and compound-induced cytotoxicity were measured in parallel by means of a propidium iodide based procedure in the human T-cell lymphotropic virus transformed cell line MT4. Aliquots of the test compounds were serially diluted in medium (RPMI 1640, 10% fetal calf serum (FCS), and gentamycin) in 96-well plates (Costar 3598) using a Cetus Pro/Pette. Exponentially growing MT4 cells were harvested and centrifuged at 1000 rpm for 10 min in a Jouan centrifuge (model CR 4 12). Cell pellets were resuspended in fresh medium (RPMI 1640, 20% FCS, 20% IL-2, and gentamycin) to a density of 5×105 cells/ml. Cell aliquots were infected by the addition of HIV-1 (strain IIIB) diluted to give a viral multiplicity of infection of 100× TCID50. A similar cell aliquot was diluted with medium to provide a mock-infected control. Cell infection was allowed to proceed for 1 hr at 37° C. in a tissue culture incubator with humidified 5% $CO_2$ atmosphere. After the 1 hr incubation the virus/cell suspensions were diluted 6-fold with fresh medium, and 125 μl of the cell suspension was added to each well of the plate containing pre-diluted compound. Plates were then placed in a tissue culture incubator with humidified 5% $CO_2$ for 5 days. At the end of the incubation period, cell number and hence HIV-induced cytopathy was estimated by either (A) propidium iodide staining, or by an (B) MTS tetrazolium staining method (ref. 5).

For propidium iodide readout, 27 μl of 5% Nonidet-40 was added to each well of the incubation plate. After thorough mixing with a Costar multitip pipetter, 60 μl of the mixture was transferred to filter-bottomed 96-well plates. The plates were analyzed in an automated assay instrument (Screen Machine, Idexx Laboratories). The control and standard used was 3'-azido-3'-deoxythymidine tested over a concentration range of 0.01 to 1 μM in every assay. The expected range of $IC_{50}$ values for 3'-azido-3'-deoxythymidine is 0.04 to 0.12 μM. The assay makes use of a propidium iodide dye to estimate the DNA content of each well.

For MTS readout, 20 μl CellTiter 96 AQ One Solution reagent (Promega #G3582) was added to each well. At 75 minutes following the addition of MTS reagent, absorbance was read at 492 μM using a Tecan Sunrise 96-well plate reader.

Analysis

The antiviral effect of a test compound is reported as an $IC_{50}$, i.e. the inhibitory concentration that would produce a 50% decrease in the HIV-induced cytopathic effect. This effect is measured by the amount of test compound required to restore 50% of the cell growth of HIV-infected MT4 cells, compared to uninfected MT4 cell controls. $IC_{50}$ was calculated by RoboSage, Automated Curve Fitting Program, version 5.00, 10 Jul. 1995.

For each assay plate, the results (relative fluorescence units, rfU, or OD values) of wells containing uninfected cells or infected cells with no compound were averaged, respectively. For measurements of compound-induced cytotoxicity, results from wells containing various compound concentrations and uninfected cells were compared to the average of uninfected cells without compound treatment. Percent of cells remaining is determined by the following formula:

Percent of cells remaining=(compound-treated uninfected cells, rfU, or OD values/untreated uninfected cells)×100.

A level of percent of cells remaining of 79% or less indicates a significant level of direct compound-induced cytotoxicity for the compound at that concentration. When this condition occurs the results from the compound-treated infected wells at this concentration are not included in the calculation of $IC_{50}$.

For measurements of compound antiviral activity, results from wells containing various compound concentrations and infected cells are compared to the average of uninfected and infected cells without compound treatment. Percent inhibition of virus is determined by the following formula:

Percent inhibition of virus=(1−((ave. untreated uninfected cells−treated infected cells)/(ave. untreated uninfected cells−ave. untreated infected cells)))×100

References
1. Averett, D. R., Anti-HIV compound assessment by two novel high capacity assays, *J. Virol. Methods* 23: 263-276, 1989.
2. Schwartz, O., et al., A rapid and simple colorimetric test for the study of anti-HIV agents, *AIDS Res. and Human Retroviruses* 4 (6): 441-447, 1988.

3. Daluge, S. M., et al., 5-chloro-2',3'-deoxy-3'fluorouridine (935U83), a selective anti-human immunodeficiency virus agent with an improved metabolic and toxicological profile. *Antimicro. Agents and Chemother.* 38 (7): 1590-1603, 1994.
4. Dormsife, R. E., et al., Anti-human immunodeficiency virus synergism by zidovudine (3'-azidothymidine) and didanosine (dideoxyinosine) contrasts with the additive inhibition of normal human marrow progenitor cells, *Antimicro. Agents and Chemother.* 35 (2): 322-328, 1991.
5. Promega Technical Bulletin #TB245. CellTiter 96 AQ One Solution Cell Proliferation Assay.

Results

Compounds of the present invention have anti-HIV activity in the range $IC_{50}$=1-1000 nM.

EXAMPLE 117B

Biological Activity

Pseudotyped HIV Vector Expressing Luciferase Reporter Assay

Expression of luciferase reporter following viral integration was performed essentially as described in Jármy, G. et al., J. Medical Virology, 64:223-231, 2001.

Results

Compounds of the present invention have anti-HIV activity in this assay in the range $IC_{50}$=1-1000 nM.

TABLE 1

$IC_{50}$ values for representative compounds

| Example number | $IC_{50}$ (nM) |
|---|---|
| 2 | a* |
| 9 | a |
| 10 | a |
| 12 | a |
| 17 | b** |
| 28 | a |
| 36 | a |
| 37 | a |
| 45 | a |
| 49 | a |
| 50 | a |
| 54 | a |
| 62 | a |
| 64 | a |
| 83 | b |
| 84 | a |
| 85 | a |
| 86 | a |
| 89 | a |
| 91 | b |
| 93 | b |
| 94 | b |
| 95 | b |
| 96 | a |
| 97 | a |
| 98 | a |
| 99 | a |
| 101 | a |
| 102 | a |
| 104 | a |
| 105 | a |
| 106 | a |
| 107 | a |
| 124 | a |
| 162 | a |
| 200 | a |
| 237 | a |
| 428 | a |
| 429 | a |
| 465 | a |

TABLE 1-continued $IC_{50}$ values for representative compounds

| Example number | $IC_{50}$ (nM) |
|---|---|
| 467 | a |
| 516 | a |
| 576 | a |

*$IC_{50}$ < 10 nM
**$IC_{50}$ = 10-25 nM

The $IC_{50}$ for N-[2-(Diethylamino)ethyl]-4-hydroxy-2-oxo-7-(phenylmethyl)-1,2-dihydro-1,5-naphthyridine-3-carboxamide (WO 2004024693) in this assay was >150 nM.

EXAMPLE 118

7-[(4-Fluorophenyl)methyl]-4-hydroxy-N-[2-(methyloxy)ethyl]-1-[4-(4-morpholinyl)phenyl]-2-oxo-1,2-dihydro-1,5-naphthyridine-3-carboxamide In a manner similar to that described in example 681, the title compound was prepared in 94% yield as a white solid. $^1$H NMR (DMSO-$d_6$) δ 10.24 (m, 1 H), 8.49 (s, 1 H), 7.16-7.02 (m, 8 H), 6.79 (s, 1 H), 3.99 (s, 2 H), 3.75 (m, 4 H), 3.50-3.44 (m, 4 H), 3.23 (s, 3 H), 3.18 (m, 4 H); MS m/z 423 (M+1).

EXAMPLE 119

Methyl 7-Benzyl-4-hydroxy-1-isopropyl-2-oxo-1,2-dihydro-1,5-naphthyridine-3-carboxylate The title compound was made in a manner similar to example 8, steps 2-4 using actone in place of (2-oxopyrrolidin-1-yl)acetaldehyde and ethyl 3-amino-5-benzyl-2-pyridinecarboxylate in place of ethyl 3-amino-5-(4-fluorobenzyl)-2-pyridinecarboxylate to give an oil: $^1$H NMR (CDCl$_3$) δ 8.62 (1H, s), 7.61 (1H, s), 7.20-7.39 (5H, m), 5.39 (1H, br), 4.18 (2H, s), 4.02 (3H, s), 1.45 (6H, d, J=7 Hz); HRMS calcd for $C_{20}H_{20}N_2O_4$+H$^+$: 353.1501. Found: 353.1504.

EXAMPLE 121

7-[(4-Fluorophenyl)methyl]-4-hydroxy-N-(2-hydroxyethyl)-1-[4-(4-morpholinyl)phenyl]-2-oxo-1,2-dihydro-1,5-naphthyridine-3-carboxamide The title compound was prepared in a manner similar to that described in example 681 as a white solid in 98% yield. $^1$H NMR (DMSO-$d_6$) δ 10.26 (m, 2 H), 8.48 (s, 1 H), 7.16-7.02 (m, 8 H), 6.79 (s, 1 H), 4.86 (t, J=4.8, 1 H), 3.99 (s, 2 H), 3.75 (m, 4 H), 3.50 (m, 2 H), 3.39 (m, 2 H), 3.18 (m, 4 H); MS m/z 519 (M+1).

EXAMPLE 122

7-[(4-fluorophenyl)methyl]-4-hydroxy-N-(2-hydroxybutyl)-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and 1-amino-2-butanol using methods similar to Example 563 to provide an off-white solid: $^1$H NMR (300 MHz, DMSO-$d_6$) δ ppm 0.89 (t, J=7.48 Hz, 3 H), 1.33-1.48

(m, 2 H), 1.49-1.59 (m, 4 H), 1.60-1.75 (m, 4 H), 2.37-2.44 (m, 2 H), 3.17-3.27 (m, 1 H), 3.33-3.42 (m, 4 H), 3.45-3.59 (m, 2 H), 4.16-4.24 (m, 4 H), 4.96 (d, J=5.26 Hz, 1 H), 7.14 (ddd, J=8.95, 6.63, 2.11 Hz, 2 H), 7.38-7.44 (m, 2 H), 8.00 (d, J=1.47 Hz, 1 H), 8.56 (d, J=1.47 Hz, 1 H), 10.44 (t, J=5.16 Hz, 1 H), 17.22 (s, 1 H); ES$^+$ MS: 539 (M+H$^+$).

EXAMPLE 123

7-[(4-fluorophenyl)methyl]-4-hydroxy-N-[(1R)-1-(hydroxymethyl)-3-methylbutyl]-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and (2R)-2-amino-4-methyl-1-pentanol using methods similar to Example 563 to provide a pink solid: $^1$H NMR (300 MHz, DMSO-d$_6$) δ ppm 0.90 (dd, J=6.42, 1.79 Hz, 6 H), 1.39-1.49 (m, 2 H), 1.55 (d, J=5.48 Hz, 4 H), 1.59-1.75 (m, 5 H), 2.35-2.45 (m, 2 H), 3.37 (d, J=8.00 Hz, 2 H), 3.40 (s, 2 H), 3.48 (s, 2 H), 4.04-4.13 (m, 1 H), 4.19 (s, 4 H), 4.93 (s, 1 H), 7.11-7.18 (m, 2 H), 7.41 (dd, J=8.74, 5.58 Hz, 2 H), 7.99 (s, 1 H), 8.56 (d, J=1.47 Hz, 1 H), 10.31 (d, J=8.63 Hz, 1 H), 17.26 (s, 1 H); ES$^+$ MS: 567 (M+H$^+$).

EXAMPLE 124

Sodium 1-ethyl-7-[(4-fluorophenyl)methyl]-3-({[(1S)-2-hydroxy-1-methylethyl]amino}carbonyl)-2-oxo-1,2-dihydro-1,5-naphthyridin-4-olate In manner similar to that described in example 474, from 1-ethyl-7-[(4-fluorophenyl)methyl]-4-hydroxy-N-[(1S)-2-hydroxy-1-methylethyl]-2-oxo-1,2-dihydro-1,5-naphthyridine-3-carboxamide (757 mg, 1.90 mmol described in example 576) and 1 N sodium hydroxide (1.84 mL) was prepared sodium 1-ethyl-7-[(4-fluorophenyl)methyl]-3-({[(1S)-2-hydroxy-1-methylethyl]amino}carbonyl)-2-oxo-1,2-dihydro-1,5-naphthyridine-4-olate (626 mg, 78% yield) as a white solid. $^1$H NMR (DMSO-d$_6$) δ 10.43 (d, J=7.2 Hz, 1 H), 8.14 (s, 1 H), 7.59 (s, 1 H), 7.33-7.29 (m, 2 H), 7.12-7.07 (m, 2 H), 4.83 (m, 1 H), 4.10-4.03 (m, 4 H), 3.91 (m, 1 H), 3.40 (m, 1 H), 3.25-3.22 (m, 2 H), 1.07-1.03 (m, 5 H); MS m/z 422 (M+23).

EXAMPLE 125

7-[(4-Fluorophenyl)methyl]-4-hydroxy-N-(2-hydroxyethyl)-1-[3-(methyloxy)propyl]-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 10.45 (m, 1 H), 8.53 (s, 1 H), 7.59 (s, 1 H), 7.17 (dd, J=8.5, 5.3 Hz, 2 H), 7.02 (t, J=8.7 Hz, 2 H), 4.21 (t, J=7.4 Hz, 2 H), 4.12 (s, 2 H), 3.86 (t, J=5.0 Hz, 2 H), 3.63 (m, 2 H), 3.37 (t, J=5.4 Hz, 2 H), 3.29 (s, 3 H), 1.86 (m, 2 H); MS m/z 430 (M+1).

EXAMPLE 126

7-[(4-Fluorophenyl)methyl]-4-hydroxy-N-methyl-1-[3-(methyloxy)propyl]-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 8.53 (s, 1 H), 7.57 (s, 1 H), 7.15 (dd, J=8.4, 5.6 Hz, 2 H), 7.00 (t, J=8.6 Hz, 1 H), 4.23 (t, J=7.5 Hz, 2 H), 4.11 (s, 2 H), 3.37 (t, J=5.6 Hz, 2 H), 3.28 (s, 3 H), 2.99 (d, J=4.8 Hz, 3 H), 1.87 (m, 2 H); MS m/z 400 (M+1).

EXAMPLE 127

7-[(4-Fluorophenyl)methyl]-4-hydroxy-N-[2-(methyloxy)ethyl]-1-[3-(methyloxy)propyl]-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 10.35 (m, 1H), 8.54 (s, 1 H), 7.60 (s, 1 H), 7.17 (m, 2 H), 7.02 (m, 2 H), 4.24 (m, 2 H), 4.12 (s, 2 H), 3.65 (m, 2 H), 3.58 (m, 2 H), 3.41 (s, 3 H), 3.38 (m, 2 H), 3.30 (s, 3 H), 1.89 (m, 2 H); MS m/z 444 (M+1).

EXAMPLE 128

Ethyl 7-(4-fluorobenzyl)-1-(4-fluorophenyl)-4-hydroxy-2-oxo-1,2-dihydro-1,5-naphthyridine-3-carboxylate Step 1: Synthesis of ethyl 5-(4-fluorobenzyl)-3-[(4-fluorophenyl)amino]pyridine-2-carboxylate.

To a dry 100 mL flask under a nitrogen atmosphere was added ethyl 3-amino-5-(4-fluorobenzyl)pyridine-2-carboxylate (200 mg, 0.73 mmol) described in example 1, Cs$_2$CO$_3$ (333 mg, 1.02 mmol), Pd$_2$dba$_3$ (20.1 mg, 0.022 mmol), and Xantphos (38.2 mg, 0.066 mmol). Dioxane (15 mL) and 1-fluoro-4-iodobenzene (0.25 mL, 2.19 mmol) were added and the resulting solution was refluxed for 3 hrs or until judged complete by TLC (7:3 hexanes:ethyl acetate). The mixture was allowed to cool to ambient temperature, filtered through Celite eluting with dichloromethane and concentrated under reduced pressure. Purification by silica gel chromatography (0-45% ethyl acetate/hexanes gradient elution) afforded ethyl 5-(4-fluorobenzyl)-3-[(4-fluorophenyl)amino]pyridine-2-carboxylate (193 mg, 72% yield) as a yellow solid. $^1$H NMR (CDCl$_3$) δ 9.35 (s, 1 H), 7.95 (s, 1 H), 7.14 (, s, 1 H), 7.10-6.99 (m, 6 H), 6.96-6.93 (m, 2 H), 4.46 (q, J=7.2 Hz, 2 H), 3.83 (s, 2 H), 1.44 (t, J=7.2 Hz, 3 H); MS m/z 369 (M+1).

Step 2: Synthesis of ethyl 1-(4-fluorophenyl)-7-[(4-fluorophenyl)methyl]-4-hydroxy-2-oxo-1,2-dihydro-1,5-naphthyridine-3-carboxylate.

To a solution of ethyl 5-(4-fluorobenzyl)-3-[(4-fluorophenyl)amino]pyridine-2-carboxylate (456 mg, 1.24 mmol) in 1,2-dichloroethane was added ethyl 3-chloro-3-oxopropanoate (0.18 mL, 2.36 mmol) and the resulting yellow solution was refluxed for 1 hour or until determined complete by TLC (5% methanol/dichloromethane). The mixture was cooled to ambient temperature, quenched with water and extracted with dichloromethane. The organics were washed with saturated aqueous sodium bicarbonate, brine, and dried over sodium sulfate to yield ethyl 3-[[3-(ethyloxy)-3-oxopropanoyl](4-fluorophenyl)amino]-5-[(4-fluorophenyl)methyl]-2-pyridinecarboxylate (477 mg, 80% yield) as mixture of rotamers. The yellow oil can be carried on without further purification or purified by silica gel chromatography (0-12% methanol/dichloromethane gradient elution). Spectral data was consistent with the expected product as mixture of rotamers. MS m/z 505 (M+23).

Ethyl 3-[(3-ethoxy-3-oxopropanoyl)(4-fluorophenyl) amino]-5-(4-fluorobenzyl)pyridine-2-carboxylate (477 mg, 0.99 mmol) was dissolved in ethanol (50 mL) and sodium ethoxide (0.91 mL of a 2.4 M solution) was added. The solution was stirred until reaction was determined complete by LC-MS and the suspension was concentrated under reduced pressure. A small amount of water was added and the mixture was acidified with 1 N hydrochloric acid to a pH of 3 and the resulting white solid was collected by vacuum filtration to yield ethyl 1-(4-fluorophenyl)-7-[(4-fluorophenyl) methyl]-4-hydroxy-2-oxo-1,2-dihydro-1,5-naphthyridine-3-carboxylate (368 mg, 85% yield). $^1$H NMR (methanol-$d_4$/CDCl$_3$) δ 8.19 (s, 1 H), 7.17-7.06 (m, 4 H), 6.94-6.83 (m, 4 H), 6.58 (s, 1 H), 4.26 (q, J=7.2 Hz, 2 H), 3.81 (s, 2 H), 1.27 (t, J=7.2 Hz, 3 H); MS m/z 459 (M+23).

EXAMPLE 129

Ethyl 7-[(2,4-difluorophenyl)methyl]-4-hydroxy-2-oxo-1,2-dihydro-1,5-naphthyridine-3-carboxylate This compound was prepared from 2,4-difluorobenzaldehyde and 5-bromo-2-methoxypyridine employing methods similar to those described in Example 132, Steps 1-7. The product was obtained as an off-white solid: $^1$H NMR ($d_6$-DMSO) δ 8.38 (1H, br s), 7.47-7.43 (1H, m), 7.40 (1H, s), 7.28-7.22 (1H, m), 7.10-7.06 (1H, m), 4.18 (2H, q, J=7 Hz), 4.10 (2H, s), 1.22 (3H, t, J=7 Hz); HRMS calcd for C$_{18}$H$_{14}$F$_2$N$_2$O$_4$+H$^+$: 361.1000. Found 361.0987.

EXAMPLE 132

Ethyl 7-[(3,4-difluorophenyl)methyl]-4-hydroxy-2-oxo-1,2-dihydro-1,5-naphthyridine-3-carboxylate Step 1: Synthesis of 5-[(3,4-difluorophenyl)methyl]-3-nitro-2-pyridinol This compound was prepared from 3,4-difluorobenzaldehyde and 5-bromo-2-methoxypyridine employing methods similar to those described in Example 89, Steps 1-4. The product was obtained as a yellow solid. $^1$H NMR ($d_6$-DMSO) δ 12.79 (1H, br s), 8.35 (1H, s), 7.84 (1H, s), 7.41-7.31 (2H, m), 7.14-7.11 (1H, m), 3.77 (2H, s); ES$^+$ MS: 267 (M+H$^+$, 100).

Step 2: Synthesis of 2-chloro-5-[(3,4-difluorophenyl) methyl]-3-nitropyridine

A mixture of 5-[(3,4-difluorophenyl)methyl]-3-nitro-2-pyridinol (10.49 g, 39.40 mmol) and phosphorous oxychloride (18 ml) was heated at 110° C. for 4 h and allowed to stir at room temperature overnight. The reaction was quenched by diluting with EtOAc and carefully adding water. The organic layer was washed three times with a saturated solution of NaHCO$_3$ in water, dried and concentrated in vacuo to afford the product as an amber oil. $^1$H NMR (CDCl$_3$) δ 8.46 (1H, s), 7.95 (1H, s), 7.19-7.14 (1H, m), 7.00-6.96 (1H, m), 6.91-6.88 (1H, m), 4.03 (2H, s).

Step 3: Synthesis of 5-[(3,4-difluorophenyl)methyl]-3-nitro-2-pyridinecarbonitrile To a solution of 2-chloro-5-[(3,4-difluorophenyl)methyl]-3-nitropyridine (10.88 g, 38.22 mmol) in NMP (50 ml), was added CuCN (10.27 g, 0.115 mmol) and NaCN (1.02 g). Heated in the microwave at 170° C. for 1 h and the resulting mixture was diluted with EtOAc and filtered through Celite. Water was added to the filtrate and the organic layer was washed with water and brine, dried and concentrated in vacuo. The resulting product was purified by chromatography on silica gel, eluting with 0-25% EtOAc/hexanes to afford an amber oil. $^1$H NMR (CDCl$_3$) δ 8.82 (1H, s), 8.31 (1H, s), 7.22-7.15 (1H, m), 7.03-6.98 (1H, m), 6.94-6.90 (1H, m), 4.16 (2H, s).

Step 4: Synthesis of 5-[(3,4-difluorophenyl)methyl]-3-nitro-2-pyridinecarboxamide To a solution of 5-[(3,4-difluorophenyl)methyl]-3-nitro-2-pyridinecarbonitrile (3.39 g, 12.32 mmol) in acetone (60 ml), was added water (23 ml), urea-hydrogen peroxide complex (19.69 g, 209 mmol), and K$_2$CO$_3$ (2.04 g, 14.78 mmol). The reaction mixture was stirred at room temperature for 30 minutes and the acetone was evaporated without using heat. The resulting precipitate was collected by filtration and thoroughly washed with water to afford a yellow solid. $^1$H NMR ($d_6$-DMSO) δ 8.79 (1H, s), 8.33 (1H, s), 8.21 (1H, br s), 7.87 (1H, s), 7.49-7.40 (1H, m), 7.38-7.33 (1H, m), 7.19-7.16 (1H, m), 4.12 (2H, s).

Step 5: Synthesis of methyl 5-[(3,4-difluorophenyl) methyl]-3-nitro-2-pyridinecarboxylate To a mixture of 5-[(3,4-difluorophenyl)methyl]-3-nitro-2-pyridinecarboxamide (2.7 g, 9.21 mmol) and MeOH (100 ml), was added dimethylformamidedimethylacetal (3.29 g, 27.62 mmol). After stirring at room temperature overnight, the solvent was evaporated using no heat, EtOAc was added and the organic layer was washed three times with brine, dried and concentrated in vacuo. The product was purified by chromatography on silica gel, eluting with 20-60% EtOAc/hexanes to afford a dark brown oil. $^1$H NMR (CDCl$_3$) δ 8.71 (1H, s), 8.05 (1H, s), 7.20-7.15 (1H, m), 7.00-6.80 (2H, m), 4.10 (2H, s), 4.01 (3H, s); HRMS calcd for C$_{14}$H$_{10}$F$_2$N$_2$O$_4$+H$^+$: 309.0687. Found 309.0681.

Step 6: Synthesis of methyl 3-amino-5-[(3,4-difluorophenyl)methyl]-2-pyridinecarboxylate A mixture of methyl 5-[(3,4-difluorophenyl)methyl]-3-nitro-2-pyridinecarboxylate (1.67 g, 5.42 mmol), 10% Pd-C (1.67 g) and MeOH (170 ml) was reduced under hydrogen for 2 h. The product was filtered through Celite, concentrated in vacuo and purified by chromatography on silica gel, eluting with 50-75% EtOAc/hexanes. The product was triturated with EtOAc to afford an off-white solid collected by filtration. $^1$H NMR ($d_6$-DMSO) δ 7.77 (1H, s), 7.39-7.30 (2H, m), 7.08-7.05 (1H, m), 6.92 (1H, s), 6.62 (2H, s), 3.88 (2H, s), 3.76 (3H, s); HRMS calcd for C$_{14}$H$_{12}$F$_2$N$_2$O$_2$+H$^+$: 279.0945. Found 279.0938.

Step 7: Synthesis of ethyl 7-[(3,4-difluorophenyl) methyl]-4-hydroxy-2-oxo-1,2-dihydro-1,5-naphthyridine-3-carboxylate This compound was prepared from methyl 3-amino-5-[(3,4-difluorophenyl)methyl]-2-pyridinecarboxylate employing methods similar to those described in Example 1, Steps 9-10. The product was obtained as a beige solid: $^1$H NMR ($d_6$-DMSO) δ 11.53 (1H, br s), 8.44 (1H, s), 7.42-7.37 (3H, m), 7.12 (1H, m), 4.21 (2H, q, J=7 Hz), 4.11 (2H, s), 1.23 (3H, t, J=7 Hz); HRMS calcd for C$_{18}$H$_{14}$F$_2$N$_2$O$_4$+H$^+$: 361.1000. Found 361.1013.

EXAMPLE 139

Ethyl 1-[3-(1,3-dioxo-1,3-dihydro-2H-isoindol-2-yl)
propyl]-7-[(4-fluorophenyl)methyl]-4-hydroxy-2-
oxo-1,2-dihydro-1,5-naphthyridine-3-carboxylate Ethyl 3-{[3-(1,3-dioxo-1,3-dihydro-2H-isoindol-2-yl) propyl]amino}-5-[(4-fluorophenyl)methyl]-2-pyridinecarboxylate. A solution of ethyl 3-amino-5-(4-fluorobenzyl)-2-pyridinecarboxylate (1.00 g, 3.65 mmol) and 3-(1,3-dioxo-1,3-dihydro-2H-isoindol-2-yl)propanal (0.929 g, 4.57 mmol) under nitrogen in glacial acetic acid (10 mL) was treated with sodium triacetoxyborohydride (1.55 g, 7.31 mmol) at ambient temperature. After stirring for 20 min., the reaction was evaporated in vacuo and the residue was partitioned between EtOAc and 5% w/v aq. $K_2CO_3$. After separating the layers, the aqueous phase was diluted with sat. aq. NaCl and back-extracted with EtOAc. The combined organic layers were washed with sat. aq. NaCl, dried over $MgSO_4$, filtered and evaporated in vacuo. The residue was dissolved in warm $Et_2O$ leaving a small residue of insolubles. The $Et_2O$ was decanted and evaporated to approximately half volume where precipitation occurred. The product was collected by filtration and dried under high vacuum: $^1H$ NMR ($d_6$-DMSO) δ 7.78-7.86 (4H, m), 7.73 (1H, s), 7.65 (1H, t, J=7 Hz), 7.25-7.30 (2H, m), 7.06-7.12 (3H, m), 4.18 (2H, q, J=7 Hz), 3.90 (2H, s), 3.65 (2H, t, J=6 Hz), 3.24 (2H, q, J=5 Hz), 1.80-1.89 (2H, m), 1.24 (3H, t, 7 Hz); $ES^+$ MS: 462 (M+H$^+$).

Ethyl 3-{[3-(1,3-dioxo-1,3-dihydro-2H-isoindol-2-yl)propyl][3-(ethyloxy)-3-oxopropanoyl]amino}-5-[(4-fluorophenyl)methyl]-2-pyridinecarboxylate A solution of ethyl 3-{[3-(1,3-dioxo-1,3-dihydro-2H-isoindol-2-yl)propyl]amino}-5-[(4-fluorophenyl)methyl]-2-pyridinecarboxylate (1.40 g, 3.03 mmol) and ethyl malonyl chloride (0.78 mL, 6.07 mmol) in DCE (15 mL) was heated under nitrogen at reflux for 2.5 hrs. The mixture was cooled, diluted with $CH_2Cl_2$ and washed with sat. aq. $NaHCO_3$. The aqueous layer was separated and back-extracted with $CH_2Cl_2$. The combined organic layers were dried over anhydrous $MgSO_4$, filtered, evaporated in vacuo and purified on silica gel eluting with 25-60% EtOAc in hexanes to provide the product as an oil: $^1H$ NMR ($d_6$-DMSO) δ 8.61 (1H, s), 7.80-7.87 (5H, m), 7.27-7.33 (2H, m), 7.07 (2H, t, J=9 Hz), 4.26 (2H, q, J=7 Hz), 4.06 (2H, s), 3.84-3.96 (3H, m), 3.49-3.57 (2H, m), 3.10-3.20 (1H, m), 2.96-3.08 (2H, m), 1.63-1.71 (2H, m), 1.22 (3H, t, J=8 Hz), 1.05 (3H, t, J=7 Hz); $ES^+$ MS: 476 (M+H$^+$).

Ethyl 1-[3-(1,3-dioxo-1,3-dihydro-2H-isoindol-2-yl)
propyl]-7-[(4-fluorophenyl)methyl]-4-hydroxy-2-
oxo-1,2-dihydro-1,5-naphthyridine-3-carboxylate.

A solution of ethyl 3-{[3-(1,3-dioxo-1,3-dihydro-2H-isoindol-2-yl)propyl][3-(ethyloxy)-3-oxopropanoyl] amino}-5-[(4-fluorophenyl)methyl]-2-pyridinecarboxylate (1.17 g, 2.04 mmol) in EtOH (10 mL) under nitrogen was treated with DBU (0.45 mL, 3.05 mmol). After stirring at ambient temperature for 15 min., the reaction mixture was treated with 1N $NaHSO_4$ (3.1 mL). The resulting slurry was diluted with water, filtered and dried under high vacuum to provide the title compound as a white solid: $^1H$ NMR ($CDCl_3$) δ 13.93 (1H, b), 8.51 (1H, s), 7.82-7.86 (2H, m), 7.71-7.75 (2H, m), 7.36 (1H, s), 7.12 (2H, m), 6.99 (2H, t, J=9 Hz), 4.49 (2H, q, J=7 Hz), 4.22 (2H, t, J=7 Hz), 4.08 (2H, s), 3.79 (2H, t, J=7 Hz), 1.96-2.07 (2H, m), 1.45 (3H, t, J=7 Hz); $ES^+$ MS: 530 (M+H$^+$).

EXAMPLE 140

7-[(4-fluorophenyl)methyl]-4-hydroxy-2-oxo-N'-
(phenylcarbonyl)-1,2-dihydro-1,5-naphthyridine-3-
carbohydrazide This compound was prepared from ethyl 7-[(4-fluorophenyl)methyl]-4-hydroxy-2-oxo-1,2-dihydro-1,5-naphthyridine-3-carboxylate and benzohydrazide employing methods similar to those described in Example 9 and was obtained as a light yellow solid: $^1H$ NMR ($d_6$-DMSO) δ 12.08 (1H, br s), 11.83 (1H, br s), 11.05 (1H, br s), 8.55 (1H, br s), 7.91-7.89 (2H, m), 7.60-7.49 (4H, m), 7.34-7.30 (2H, m), 7.16-7.13 (2H, m), 4.14 (2H, m); HRMS calcd for $C_{23}H_{17}FN_4O_4$+H$^+$: 433.1312. Found 433.1311.

EXAMPLE 141

7-[(4-Fluorophenyl)methyl]-4-hydroxy-N-methyl-1-
[4-(4-morpholinyl)phenyl]-2-oxo-1,2-dihydro-1,5-
naphthyridine-3-carboxamide The title compound was prepared in a manner similar to that described in example 681 as a white solid in 91% yield. $^1H$ NMR (DMSO-$d_6$) δ 9.99 (br s, 1 H), 8.48 (s, 1 H), 7.16-7.04 (m, 8 H), 6.79 (s, 1 H), 3.99 (s, 2 H), 3.75 (m, 4 H), 3.18 (m, 4 H), 2.85 (d, J=4.8 Hz, 3 H); MS m/z 489 (M+1).

EXAMPLE 142

7-[(4-fluorophenyl)methyl]-4-hydroxy-2-oxo-N-[2-
(phenyloxy)ethyl]-1,2-dihydro-1,5-naphthyridine-3-
carboxamide This compound was prepared from ethyl 7-[(4-fluorophenyl)methyl]-4-hydroxy-2-oxo-1,2-dihydro-1,5-naphthyridine-3-carboxylate and 2-phenoxyethylamine employing methods similar to those described in Example 2 and was obtained as a white solid: $^1H$ NMR ($d_6$-DMSO) δ 11.85 (1H, br s), 10.49 (1H, br s), 8.49 (1H, br s), 7.42 (1H, br s), 7.32-7.25 (4H, m), 7.14 (2H, t, J=8.7 Hz), 6.97-6.91 (3H, m), 4.14-4.08 (4H, br m), 3.72 (2H, br); HRMS calcd for $C_{24}H_{20}FN_3O_4$+H$^+$: 434.1516. Found 434.1519.

EXAMPLE 143

7-(4-Fluorobenzyl)-4-hydroxy-N-(2-methoxyethyl)-
N-methyl-1-[4-(methylsulfonyl)benzyl]-2-oxo-1,2-
dihydro-1,5-naphthyridine-3-carboxamide The title compound was made in a manner similar to example 65 using N-(2-methoxyethylamine to give a pale yellow glass: $^1H$ NMR ($CDCl_3$) δ 9.74 (1H, br), 8.36 (1H, s), 7.82 (2H, d, J=8 Hz), 7.26 (2H, d, J=8 Hz), 7.10 (1H, s), 7.00 (4H, d, J=7 Hz), 5.43 (2H, br), 4.02 (2H, s), 3.65 (4H, m), 3.36 (3H, s), 3.17 (3H, s), 3.02 (3H, s); HRMS calcd for $C_{28}H_{28}FN_3O_6S$+H$^+$: 554.1761. Found: 554.1757.

EXAMPLE 144

7-[(4-fluorophenyl)methyl]-4 hydroxy-N-(3-hydrox-
ypropyl-2-oxo-1,2-dihydro-1,5-naphthyridine-3-
carboxamide This compound was prepared from ethyl 7-[(4-fluorophenyl)methyl]-4-hydroxy-2-oxo-1,2-dihydro-1,5-naphthyridine-3-carboxylate and 3-amino-1-propanol employing methods similar to those described in Example 2 and was obtained as a white solid: $^1$H NMR (d$_6$-DMSO) tautomers are observed δ 11.80 (1H, t, J=5.5 Hz), 10.81 (1H, br s), 10.07 (1H, br s), 8.18 (0.52H, s), 8.14 (0.48H, s), 7.35-7.23 (3H, m), 7.14-7.08 (2H, m), 4.48 (1H, br), 3.98 (2H, s), 3.48-3.42 (2H, m), 3.33-3.23 (2H, m), 1.64-1.59 (2H, m); HRMS calcd for C$_{19}$H$_{18}$FN$_3$O$_4$+H$^+$: 372.1360. Found 372.1369.

EXAMPLE 145

7-[(4-Fluorophenyl)methyl]-4-hydroxy-N-[2-(methyloxy)ethyl]-2-oxo-1-[2-oxo-2-(1-piperidinyl)ethyl]-1,2-dihydro-1,5-naphthyridine-3-carboxamide Steps 1-4: Synthesis of ethyl 7-[(4-fluorophenyl)methyl]-4-hydroxy-2-oxo-1-[2-oxo-2-(1-piperidinyl)ethyl]-1,2-dihydro-1,5-naphthyridine-3-carboxylate This compound was prepared from N-{2-[(ethyloxy)carbonyl]-5-[(4-fluorophenyl)methyl]-3-pyridinyl}glycine and piperidine employing methods similar to those described in Example 11, Steps 2-4 and was obtained as a white solid: AP$^-$ MS: 466 (M−1, 100).

Step 5: Synthesis of 7-[(4-fluorophenyl)methyl]-4-hydroxy-N-[2-(methyloxy)ethyl]-2-oxo-1-[2-oxo-2-(1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-piperidinyl)ethyl]-1,2-dihydro-1,5-naphthyridine-3-carboxylate and 2-methoxyethylamine employing methods similar to those those described in Example 9 and was purified by reverse phase preparative HPLC (C-18 stationary phase; 10-100% CH$_3$CN/water/0.1% formic acid mobile phase). The product was obtained as a white solid: $^1$H NMR (CDCl$_3$) δ 10.18 (1H, br m), 8.55 (1H, s), 7.15 (2H, dd, J=9, 5 Hz), 7.02 (2H, t, J=9 Hz), 6.96 (1H, s), 4.94 (2H, s), 4.11 (2H, s), 3.63 (2H, q, J=5 Hz), 3.56 (2H, t, J=5 Hz), 3.50 (2H, t, J=5 Hz), 3.44 (2H, t, J=5 Hz), 3.39 (3H, s), 1.68 (2H, m), 1.60-1.50 (4H, m); HRMS calcd for C$_{26}$H$_{29}$FN$_4$O$_5$+H$^+$: 497.2200. Found: 497.2183.

EXAMPLE 146

7-[(4-Fluorophenyl)methyl]-4-hydroxy-N-[2-(4-morpholinyl)ethyl]-2-oxo-1-[2-oxo-2-(1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-piperidinyl)ethyl]-1,2-dihydro-1,5-naphthyridine-3-carboxylate and 4-(2-aminoethyl)morpholine employing methods similar to those those described in Example 9 and was purified by reverse phase preparative HPLC (C-18 stationary phase; 10-100% CH$_3$CN/water/0.1% formic acid mobile phase). The product was obtained as a light yellow rigid foam: $^1$H NMR (CDCl$_3$) δ 10.41 (1H, m), 8.57 (1H, s), 7.15 (2H, dd, J=8.5, 6 Hz), 7.03 (3H, m), 4.92 (2H, s), 4.12 (2H, s), 3.99 (4H, m), 3.89 (2H, q, J=6 Hz), 3.72 (2H, m), 3.50 (2H, m), 3.46 (2H, m), 3.35 (2H, t, J=6 Hz), 2.93 (2H, br), 1.70 (2H, m), 1.61 (2H, m), 1.53 (2H, m); HRMS calcd for C$_{29}$H$_{34}$FN$_5$O$_5$+H$^+$: 552.2622. Found: 552.2618.

EXAMPLE 147

7-[(4-Fluorophenyl)methyl]-4-hydroxy-N-(2-hydroxyethyl)-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and ethanolamine employing methods similar to those described in Example 2 and was obtained as a white solid: $^1$H NMR (d$_6$-DMSO) tautomers are observed δ 11.79 (1H, t, J=5.4 Hz), 10.81 (1h, br s), 10.07 (1H, br s), 8.18 (0.61H, s), 8.15 (0.39H, s), 7.35-7.23 (3H, m), 7.14-7.08 (2H, m), 4.73 (1H, br), 3.98 (2H, s), 3.51-3.41 (2H, m), 3.35-3.20 (2H, m); HRMS calcd for C$_{18}$H$_{16}$FN$_3$O$_4$+H$^+$: 358.1203. Found 358.1194.

EXAMPLE 148

7-[(4-fluorophenyl)methyl]-4-hydroxy-N-(2-hydroxy-1-methylethyl)-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and DL-2-amino-1-propanol employing methods similar to those described in Example 2 and was obtained a white solid: $^1$H NMR (d$_6$-DMSO) tautomers are observed δ 11.73 (1H, br s), 10.73 (1H, br s), 10.02 (1H, br s), 8.18 (0.56H, s), 8.14 (0.44H, s), 7.34-7.22 (3H, m), 7.14-7.09 (2H, m), 4.78 (1H, t, J=5 Hz), 3.98 (2H, s), 3.48-3.41 (1H, m), 3.23-3.20 (2H, m), 1.14 (0.58H, d, J=6.6 Hz), 1.08 (0.42H, d, J=6.6 Hz); HRMS calcd for C$_{19}$H$_{18}$FN$_3$O$_4$+H$^+$: 372.1360. Found 372.1370.

EXAMPLE 149

7-[(4-Fluorophenyl)methyl]-4-hydroxy-N-(2-hydroxyethyl)-2-oxo-1-[2-oxo-2-(1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-piperidinyl)ethyl]-1,2-dihydro-1,5-naphthyridine-3-carboxylate and ethanolamine employing methods similar to those those described in Example 9 and was purified by reverse phase preparative HPLC (C-18 stationary phase; 10-100% CH$_3$CN/water/0.1% formic acid mobile phase). The product was obtained as a white solid: $^1$H NMR (CDCl$_3$) δ 10.32 (1H, m), 8.56 (1H, s), 7.16 (2H, dd, J=9, 6 Hz), 7.03 (2H, t, J=9 Hz), 6.97 (1H, s), 4.93 (2H, s), 4.11 (2H, s), 3.83 (2H, t, J=5 Hz), 3.62 (2H, q, J=5 Hz), 3.50 (2H, t, J=6 Hz), 3.44 (2H, t, J=5 Hz), 1.69-1.58 (6H, m); HRMS calcd for C$_{25}$H$_{27}$FN$_4$O$_5$+H$^+$: 483.2044. Found: 483.2060.

EXAMPLE 150

7-[(4-fluorophenyl)methyl]-4-hydroxy-N-(2-hydroxypropyl)-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and DL-1-amino-2-propanol employing methods similar to those described in Example 2 and was obtained as a white solid: $^1$H NMR (d$_6$-DMSO) tautomers are observed δ 11.81 (1H, t, J=5.6 Hz), 10.81 (1H, br s), 10.10

(1H, br s), 8.18 (0.48H, s), 8.14 (052.H, s), 7.36-7.23 (3H, m), 7.14-7.08 (2H, m), 4.74 (1H, t, J=4 Hz), 3.98 (2H, s), 3.75-3.65 (1H, m), 3.29-3.15 (2H, m), 1.07-1.04 (3H, m); HRMS calcd for $C_{19}H_{18}FN_3O_4+H^+$: 372.1360. Found 372.1364.

EXAMPLE 151

1-(3-Fluorophenyl)-7-[(4-fluorophenyl)methyl]-4-hydroxy-N-methyl-2-oxo-1,2-dihydro-1,5-naphthyridine-3-carboxamide The title compound was prepared in a manner similar to that described in example 681 as a white solid in 96% yield. $^1$H NMR (methanol-$d_4$/CDCl$_3$) δ 9.78 (s, 1 H), 8.45 (s, 1 H), 7.52 (m, 1 H), 7.23 (m, 1 H), 6.97-6.86 (m, 6 H), 6.67 (s, 1 H), 3.90 (s, 2 H), 2.91 (d, J=4.4 Hz, 3 H); MS m/z 422 (M+1).

EXAMPLE 152

7-[(4-Fluorophenyl)methyl]-4-hydroxy-N-[2-(methyloxy)ethyl]-1-(2-methylpropyl)-2-oxo-1,2-dihydro-1,5-naphthyridine-3-carboxamide Step 1: Synthesis of ethyl 5-[(4-fluorophenyl)methyl]-3-[(2-methylpropyl)amino]-2-pyridinecarboxylate and ethyl 5-[(4-fluorophenyl)methyl]-3-[(2-methyl-1-propen-1yl)amino]-2-pyridinecarboxylate.

To a cold (0° C.) solution of ethyl 3-amino-5-[(4-fluorophenyl)methyl]-2-pyridinecarboxylate (390 mg, 1.4 mmol) in 1,2-dichloroethane (10 mL) was added isobutyraldehyde (0.2 mL, 2.1 mmol), acetic acid (0.5 mL, 8.5 mmol) and sodium triacetoxyborohydride (602 mg, 2.8 mmol). The resultant solution was stirred at room temperature for 24 hours. The reaction mixture was quenched by the addition of saturated aqueous sodium bicarbonate. Dichloromethane was added and the layers separated. The organic layer was washed with brine. The aqueous layers were extracted with dichloromethane and the combined organics dried over sodium sulfate. Filtration and concentration followed by silica gel chromatography provided a mixture of ethyl 5-[(4-fluorophenyl)methyl]-3-[(2-methylpropyl)amino]-2-pyridinecarboxylate and ethyl 5-[(4-fluorophenyl)methyl]-3-[(2-methyl-1-propen-1-yl)amino]-2-pyridinecarboxylate (419 mg ~1.7:1). This material was used without further purification.

Step 2: Synthesis of ethyl 3-[[3-(ethyloxy)-3-oxopropanoyl](2-methylpropyl)amino]-5-[(4-fluorophenyl)methyl]-2-pyridinecarboxylate and ethyl 3-[[3-(ethyloxy)-3-oxopropanoyl](2-methyl-1-propen-1-yl)amino]-5-[(4-fluorophenyl)methyl]-2-pyridinecarboxylate.

To a solution of ethyl 5-[(4-fluorophenyl)methyl]-3-3-[(2-methylpropyl)amino]-3-2-pyridinecarboxylate and ethyl 5-[(4-fluorophenyl)methyl]-3-[(2-methyl-1-propen-1-yl)amino]-2-pyridinecarboxylate (~1.7:1 mixture, 419 mg, 1.3 mmol) in 1,2-dichloroethane (15 mL) was added ethyl 3-chloro-3-oxopropanoate (0.25 mL, 90%, 1.9 mmol). The resultant solution was heated at 85° C. for 5 hours. Upon cooling to room temperature, dichloromethane and saturated aqueous sodium bicarbonate were added and the layers separated. The organic layer was washed with brine. The aqueous layers were extracted with dichloromethane and the combined organics dried over sodium sulfate. Filtration and concentration followed by silica gel chromatography provided ethyl 3-[[3-(ethyloxy)-3-oxopropanoyl](2-methylpropyl)amino]-5-[(4-fluorophenyl)methyl]-2-pyridinecarboxylate (309 mg, 55%). $^1$H NMR (CDCl$_3$) δ 8.56 (s, 1 H), 7.45 (s, 1 H), 7.10 (m, 2 H), 6.99 (m, 2 H), 4.39 (q, J=7.2 Hz, 2 H), 4.02-3.97 (m, 5 H), 3.15 (d, J=15.6 Hz, 1 H), 3.04 (d, J=15.6 Hz, 1 H), 2.81 (dd, J=13.6, 6.0 Hz, 1 H), 1.62 (m, 1 H), 1.36 (t, J=7.2 Hz, 3 H), 1.16 (t, J=6.8 Hz, 3 H), 0.90 (d, J=6.4 Hz, 3 H), 0.81 (d, J=6.4 Hz, 3 H); MS: m/z 445 (M+1). Further elution provided ethyl 3-[[3-(ethyloxy)-3-oxopropanoyl](2-methyl-1-propen-1-yl)amino]-5-[(4-fluorophenyl)methyl]-2-pyridinecarboxylate (115 mg, 21%). $^1$H NMR (CDCl$_3$) δ 8.37 (s, 1 H), 7.32 (s, 1 H), 7.07 (m, 2 H), 6.97 (m, 2 H), 6.15 (s, 1 H), 4.39 (q, J=7.2 Hz, 2 H), 4.18 (q, J=7.2 Hz, 2 H), 3.48 (s, 2 H), 1.70 (s, 3 H), 1.59 (s, 3 H), 1.38 (t, J=7.2 Hz, 3 H), 1.25 (t, J=7.2 Hz, 3 H); MS: m/z 445 (M+1).

Step 3: Synthesis of ethyl 7-[(4-fluorophenyl)methyl]-4-hydroxy-1-(2-methylpropyl)-2-oxo-1,2-dihydro-1,5-naphthyridine-3-carboxylate.

To a cold (0° C.) solution of ethyl 3-[[3-(ethyloxy)-3-oxopropanoyl](2-methylpropyl)amino]-5-[(4-fluorophenyl)methyl]-2-pyridinecarboxylate (309 mg, 0.70 mmol) in ethanol (20 mL) was added sodium ethoxide (104 mg, 1.53 mmol). The resultant solution was warmed to room temperature as the bath warmed and stirred overnight. Solvents were removed in vacuo and the residue was taken up in water. The pH was adjusted to 5 with 1 N HCl (aq) and the aqueous layer extracted with ethyl acetate. The organics were dried over sodium sulfate filtered and concentrated to give ethyl 7-[(4-fluorophenyl)methyl]-4-hydroxy-1-(2-methylpropyl)-2-oxo-1,2-dihydro-1,5-naphthyridine-3-carboxylate (279 mg, 99%) as a clear foam. $^1$H NMR (CDCl$_3$) δ 13.77 (broad, 1 H), 8.49 (s, 1 H), 7.23 (s, 1 H), 7.15 (dd, J=8.4, 5.6 Hz, 2 H), 7.04 (dd, J=8.8, 8.4 Hz, 2 H), 4.50 (q, J=7.2 Hz, 2 H), 4.11 (s, 2 H), 3.95 (broad, 2 H), 1.97 (m, 1 H), 1.45 (t, J=7.2 Hz, 3 H), 0.87 (d, J=6.4 Hz, 6 H); HRMS calcd for $C_{22}H_{24}FN_2O_4$ 399.1720 (M+H); found 399.1720.

Step 4: Synthesis of 7-[(4-fluorophenyl)methyl]-4-hydroxy-N-[2-(methyloxy)ethyl]-1-(2-methylpropyl)-2-oxo-1,2-dihydro-1,5-naphthyridine-3-carboxamide.

A solution of 7-[(4-fluorophenyl)methyl]-4-hydroxy-1-(2-methylpropyl)-2-oxo-1,2-dihydro-1,5-naphthyridine-3-carboxylate (20 mg, 0.05 mmol) in 2-methoxyethylamine (1 mL) was heated with a microwave at 140° C. for 20 minutes. The solvent was removed in vacuo and the residue was purified by reverse phase preparative HPLC to give the title compound (17 mg, 79%) as a white solid. $^1$H NMR (400 MHz, CDCl$_3$) δ 10.35 (br, 1 H), 8.54 (s, 1 H), 7.25 (s, 1 H), 7.15 (dd, J=8.5, 5.4 Hz, 2 H), 7.03 (t, J=8.5 Hz, 2 H), 4.12 (s, 2 H), 3.97 (br, 2 H), 3.63 (m, 2 H), 3.57 (m, 2 H), 3.39 (s, 3 H), 1.95 (m, 1 H), 0.87 (d, J=6.8 Hz, 6 H); HRMS m/z calcd for $C_{23}H_{27}N_3O_4$ (M+H)$^+$ 428.1986, found 428.1977.

EXAMPLE 153

(±)-7-[(4-fluorophenyl)methyl]-4-hydroxy-N-[1-methyl-2-(methyloxy)ethyl]-2-oxo-1-[2-oxo-2-(1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-piperidinyl)ethyl]-1,2-dihydro-1,5-naphthyridine-3-carboxylate and (±)-1-(methyloxy)-2-propanamine employing methods similar to those those described in Example 9 and was purified by reverse phase preparative HPLC (C-18 stationary phase; 10-100% $CH_3CN$/water/0.1% formic acid mobile phase). The product was obtained as an off-white rigid foam: $^1H$ NMR ($CDCl_3$) δ 10.07 (1H, d, J=8 Hz), 8.55 (1H, s), 7.16 (2H, dd, J=9, 6 Hz), 7.03 (2H, t, J=9 Hz), 6.93 (1H, s), 4.97 (1H, d, J=17 Hz), 4.90 (1H, d, J=17 Hz), 4.34 (1H, m), 4.11 (2H, s), 3.50 (2H, m), 3.44 (4H, m), 3.38 (3H, s), 1.69 (2H, m), 1.57 (2H, m), 1.52 (2H, m), 1.28 (3H, d, J=7 Hz); HRMS calcd for $C_{27}H_{31}FN_4O_5+H^+$: 511.2357. Found: 511.2162.

EXAMPLE 154

(±)-7-[(4-Fluorophenyl)methyl]-4-hydroxy-N-(2-hydroxy-1-methylethyl)-2-oxo-1-[2-oxo-2-(1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-piperidinyl)ethyl]-1,2-dihydro-1,5-naphthyridine-3-carboxylate and (±)-2-amino-1-propanol employing methods similar to those those described in Example 9 and was purified by reverse phase preparative HPLC (C-18 stationary phase; 10-100% $CH_3CN$/water/0.1% formic acid mobile phase). The product was obtained as a white solid: $^1H$ NMR ($CDCl_3$) δ 14.1 (1H, br), 10.16 (1H, d, J=7 Hz), 8.56 (1H, s), 7.16 (2H, dd, J=8.5, 6 Hz), 7.03 (2H, t, J=8.5 Hz), 6.93 (1H, s), 4.96 (1H, d, J=7 Hz), 4.89 (1H, d, J=7 Hz), 4.27 (1H, m), 4.11 (2H, s), 3.74 (1H, m), 3.66 (1H, m), 3.50 (2H, t, J=5.5 Hz), 3.43 (2H, t, J=5.5 Hz), 2.23 (1H, m), 1.69 (2H, m), 1.52 (4H, m), 1.29 (3H, d, J=7 Hz); HRMS calcd for $C_{26}H_{29}FN_4O_5+H^+$: 497.2200. Found: 497.2186.

EXAMPLE 155

N-[2-(ethyloxy)ethyl]-7-[(4-fluorophenyl)methyl]-4-hydroxy-2-oxo-1-[2-oxo-2-(1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-piperidinyl)ethyl]-1,2-dihydro-1,5-naphthyridine-3-carboxylate and 2-ethoxyethylamine employing methods similar to those those described in Example 9 and was purified by reverse phase preparative HPLC (C-18 stationary phase; 10-100% $CH_3CN$/water/0.1% formic acid mobile phase). The product was obtained as a white solid: $^1H$ NMR ($CDCl_3$) δ 14.4 (1H, br), 10.18 (1H, m), 8.55 (1H, s), 7.15 (2H, dd, J=8.4, 5.5 Hz), 7.02 (2H, t, J=8.4 Hz), 6.98 (1H, s), 4.94 (2H, s), 4.11 (2H, s), 3.61 (4H, m), 3.59-3.43 (6H, m), 1.68 (2H, m), 1.54 (4H, m), 1.21 (3H, t, J=7 Hz); HRMS calcd for $C_{27}H_{31}FN_4O_5+H^+$: 511.2357. Found: 511.2366.

EXAMPLE 156

(±)-7-[(4-Fluorophenyl)methyl]-4-hydroxy-N-(2-hydroxypropyl)-2-oxo-1-[2-oxo-2-(1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-piperidinyl)ethyl]-1,2-dihydro-1,5-naphthyridine-3-carboxylate and (±)-1-amino-2-propanol employing methods similar to those those described in Example 9 and was purified by reverse phase preparative HPLC (C-18 stationary phase; 10-100% $CH_3CN$/water/0.1% formic acid mobile phase). The product was obtained as a white solid: $^1H$ NMR ($CDCl_3$) δ 10.32 (1H, m), 8.55 (1H, s), 7.16 (2H, dd, J=8.5, 5.5 Hz), 7.03 (2H, t, J=8.5 Hz), 6.97 (1H, s), 4.94 (2H, m), 4.11 (2H, s), 4.04 (1H, m), 3.62 (1H, m), 3.50 (2H, t, J=5.5 Hz), 3.44 (2H, t, J=5.5 Hz), 3.35 (1H, m), 2.21 (1H, d, J=4 Hz), 1.69 (2H, m), 1.54 (4H, m), 1.26 (3H, d, J=6 Hz); HRMS calcd for $C_{26}H_{29}FN_4O_5+H^+$: 497.2200. Found: 497.2189.

EXAMPLE 157

7-[(4-Fluorophenyl)methyl]-4-hydroxy-N-[2-(methyloxy)ethyl]-1-(2-methyl-1-propen-1-yl)-2-oxo-1,2-dihydro-1,5-naphthyridine-3-carboxamide The title compound was prepared in a similar manner to that described in example 152 as a white solid. $^1H$ NMR (400 MHz, $CDCl_3$) δ 10.22 (s, 1H), 8.54 (s, 1 H), 7.20 (s, 1 H), 7.12 (dd, J=8.5, 5.5 Hz, 2 H), 7.01 (t, J=8.7 Hz, 2 H), 6.01 (s, 1 H), 4.07 (s, 2 H), 3.63 (m, 2 H), 3.56 (m, 2 H), 3.37 (s, 3 H), 1.91 (s, 3 H), 1.30 (s, 3 H); HRMS m/z calcd for $C_{23}H_{25}FN_3O_4$ (M+H)$^+$ 426.1829, found 426.1835.

EXAMPLE 158

N-[(1-Ethyl-2-pyrrolidinyl)methyl]-7-[(4-fluorophenyl)methyl]-4-hydroxy-1-(2-methylpropyl)-2-oxo-1,2-dihydro-1,5-naphthyridine-3-carboxamide The title compound was prepared in a similar manner to that described in example 152 as a white solid as its formate salt. $^1H$ NMR (400 MHz, $CDCl_3$) δ 10.58 (s, 1 H), 8.53 (s, 1 H), 8.42 (s, 1 H), 7.26 (s, 1 H), 7.13 (dd, J=8.4, 5.4 Hz, 2 H), 7.02 (t, J=8.8 Hz, 2 H), 4.11 (s, 2 H), 3.99-3.90 (m, 3 H), 3.81-3.67 (m, 2 H), 3.48 (m, 1 H), 3.28 (m, 1 H), 2.92 (m, 1 H), 2.79 (m, 1 H), 2.25-2.06 (m, 2 H), 1.99-1.87 (m, 3 H), 1.31 (t, J=7.3 Hz, 3 H), 0.85 (d, J=6.8 Hz, 6 H); HRMS m/z calcd for $C_{27}H_{34}N_4O_3F$ (M+H)$^+$ 481.2615, found 481.2615.

EXAMPLE 159

N-[(1-Ethyl-2-pyrrolidinyl)methyl]-7-[(4-fluorophenyl)methyl]-4-hydroxy-1-(2-methyl-1-propen-1-yl)-2-oxo-1,2-dihydro-1,5-naphthyridine-3-carboxamide The title compound was prepared in a similar manner to that described in example 152 as a white solid as its formate salt. $^1H$ NMR (400 MHz, $CDCl_3$) δ 10.38 (s, 1 H), 8.55 (s, 1 H), 8.47 (s, 1 H), 7.24 (s, 1 H), 7.13 (dd, J=8.5, 5.3 Hz, 2 H), 7.02 (t, J=8.5 Hz, 2 H), 6.01 (d, J=7.3 Hz, 1 H), 4.09 (s, 2 H), 4.00-3.84 (m, 1 H), 3.65-3.50 (m, 2 H), 3.28-3.13 (m, 2 H), 2.75 (m, 1 H), 2.61 (m, 1 H), 2.20-1.81 (m, 7 H), 1.34-1.25 (m, 6 H); HRMS m/z calcd for $C_{27}H_{32}N_4O_3F$ (M+H)$^+$ 479.2458, found 479.2462.

EXAMPLE 160

N-[2-(ethyloxy)ethyl]-7-[(4-fluorophenyl)methyl]-4-hydroxy-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and 2-ethoxyethylamine employing methods similar to those described in Example 2 and was obtained as a white solid: $^1H$ NMR ($d_6$-DMSO) δ 11.82 (1H, br s), 10.58 (1H, br s), 8.19 (1H, br s), 7.35-7.26 (3H, m), 7.15-7.10 (2H, m), 4.03 (2H, br s), 3.48-3.41 (6H, m), 1.11 (3H, t, J=8.4 Hz); HRMS calcd for $C_{20}H_{20}FN_3O_4+H^+$: 386.1516. Found 386.1501.

EXAMPLE 161

N-[(2R)-2,3-Dihydroxypropyl]-1-(3-fluorophenyl)-7-[(4-fluorophenyl)methyl]-4-hydroxy-2-oxo-1,2-dihydro-1,5-naphthyridine-3-carboxamide The title compound was prepared in a manner similar to that described in example 681 as a white solid in 94% yield. $^1$H NMR (methanol-$d_4$/CDCl$_3$) δ 10.03 (br s, 1 H), 8.40 (s, 1 H), 7.49 (m, 1 H), 7.19 (m, 1 H), 6.93-6.83 (m, 6 H), 6.63 (s, 1 H), 3.88 (s, 2 H), 3.73 (m, 1 H), 3.50-3.34 (m, 4 H); MS m/z 482 (M+1).

EXAMPLE 162

1-(2-Amino-2-oxoethyl)-7-[(4-fluorophenyl)methyl]-4-hydroxy-N-[2-(methyloxy)ethyl]-2-oxo-1,2-dihydro-1,5-naphthyridine-3-carboxamide A solution of HATU (1.14 g, 3 mmol) in DMF (4 mL) was added in portions to a stirred suspension of [7-[(4-fluorophenyl)methyl]-4-hydroxy-3-({[2-(methyloxy)ethyl]amino}carbonyl)-2-oxo-1,5-naphthyridine-1(2H)-yl]acetic acid (1 g, 2.3 mmol) in 29% ammonium hydroxide (0.4 mL, 2.9 mmol), TEA (0.4 mL, 2.9 mmol) and DMF (4 mL) at 60° C. The mixture was stirred 40 min at rt and additional HATU (350 mg, 0.92 mmol), 29% ammonium hydroxide (0.15 mL, 1 mmol) and DMF (3 mL) were added. Stirring was continued 20 min and the suspension was diluted with water and filtered. The filter cake was washed with water and EtOH; then dried in a vacuum oven to afford the product as a white solid: $^1$H NMR (d$_6$-DMSO) δ 10.25 (1H, t, J=5 Hz), 8.52 (1H, d, J=1 Hz), 7.83 (1H, s), 7.64 (1H, br s), 7.33 (2H, dd, J=8.6, 5.7 Hz), 7.27 (1H, br s), 7.11 (2H, t, J=8.6 Hz), 4.83 (2H, s), 4.11 (2H, s), 3.50 (4H, m), 3.28 (3H, s); HRMS calcd for $C_{21}H_{21}FN_4O_5+H^+$: 429.1574. Found: 429.1575.

EXAMPLE 163

1-(2-Amino-2-oxoethyl)-7-[(4-fluorophenyl)methyl]-4-hydroxy-N-[2-(4-morpholinyl)ethyl]-2-oxo-1,2-dihydro-1,5-naphthyridine-3-carboxamide Steps 1-3: Synthesis of ethyl 1-(2-amino-2-oxoethyl)-7-[(4-fluorophenyl)methyl]-4-hydroxy-2-oxo-1,2-dihydro-1,5-naphthyridine-3-carboxylate This compound was prepared from N-{2-[(ethyloxy)carbonyl]-5-[(4-fluorophenyl)methyl]-3-pyridinyl}glycine and ammonium hydroxide employing methods similar to those described in Example 11, Steps 2-4 and was obtained as an off white solid: ES$^-$ MS: 398 (M−1, 100).

Step 4: Synthesis of 1-(2-amino-2-oxoethyl)-7-[(4-fluorophenyl)methyl]-4-hydroxy-N-[2-(4-morpholinyl)ethyl]-2-oxo-1,2-dihydro-1,5-naphthyridine-3-carboxamide This compound was prepared from ethyl 1-(2-amino-2-oxoethyl)-7-[(4-fluorophenyl)methyl]-4-hydroxy-2-oxo-1,2-dihydro-1,5-naphthyridine-3-carboxylate and 4-(2-aminoethyl)morpholine employing methods similar to those those described in Example 9 and was purified by reverse phase preparative HPLC (C-18 stationary phase; 10-100% CH$_3$CN/water/0.1% formic acid mobile phase). The product was obtained as an off-white rigid foam: $^1$H NMR (CDCl$_3$) δ 10.36 (1H, m), 8.56 (1H, s), 7.61 (1H, s), 7.15 (2H, dd, J=8.5, 5.5 Hz), 7.01 (2H, t, J=8.5 Hz), 6.87 (1H, br s), 5.65 (1H, br s), 4.81 (2H, s), 4.12 (2H, s), 3.98 (4H, m), 3.91 (2H, q, J=6 Hz), 3.75 (2H, m), 3.37 (2H, t, J=6 Hz), 2.92 (2H, br); HRMS calcd for $C_{24}H_{26}FN_5O_5+H^+$: 484.1996. Found: 484.1987.

EXAMPLE 164

7-[(4-Fluorophenyl)methyl]-4-hydroxy-N-(4-hydroxybutyl)-1-(2-methylpropyl)-2-oxo-1,2-dihydro-1,5-naphthyridine-3-carboxamide The title compound was prepared in a similar manner to that described in example 152 as a white solid. $^1$H NMR (400 MHz, CDCl$_3$) δ 10.27 (s, 1 H), 8.56 (s, 1 H), 7.27 (s, 1 H), 7.17 (dd, J=8.8, 5.5 Hz, 2 H), 7.05 (t, J=8.5 Hz, 2 H), 4.14 (s, 2 H), 3.97 (br, 2 H), 3.71 (t, J=6.1 Hz, 2 H), 3.50 (dd, J=12.7, 6.6 Hz, 2 H), 1.96 (m, 1 H), 1.80-1.52 (m, 6 H), 0.89 (d, J=6.9 Hz, 6 H); HRMS m/z calcd for $C_{24}H_{29}FN_3O_4$ (M+H)$^+$ 442.2142, found 442.2119.

EXAMPLE 165

7-[(4-fluorophenyl)methyl]-4-hydroxy-N-[1-methyl-2-(methyloxy)ethyl]-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and 2-methoxyisopropylamine employing methods similar to those described in Example 2 and was obtained as a white solid: $^1$H NMR (d$_6$-DMSO) tautomers are observed δ 11.80 (1H, br s), 10.80 (1H, br s), 10.05 (1H, br s), 8.18 (0.45H, s), 8.14(0.55H, s), 7.35-7.24 (3H, m), 7.15-7.08 (2H, m), 4.15-4.07 (1H, m), 3.98 (2H, s), 3.40-3.35 (5H, m), 1.15 (0.45H, d, J=6.6 Hz), 1.09 (0.55H, d, J=6.6 Hz); HRMS calcd for $C_{20}H_{20}FN_3O_4+H^+$: 386.1516. Found 386.1513.

EXAMPLE 166

Sodium 7-(4-Fluorobenzyl)-3-{[(2-hydroxyethyl)amino]carbonyl}-2-oxo-1-[2-(2-oxopyrrolidin-1-yl)ethyl]-1,2-dihydro-1,5-naphthyridine-4-olate The title compound was made by stirring the compound in example 73 with 1N NaOH in ethanol at room temperature for 1 h. Concentration gave the sodium salt as a pale lemon solid: $^1$H NMR (d$_6$-DMSO) δ 10.57 (1H, m), 8.19 (1H, s), 7.71 (1H, s), 7.34 (2H, m), 7.10 (2H, m), 4.76 (1H, br), 4.15 (2H, m), 4.01 (2H, s), 3.25-3.44 (8H, m), 2.04 (2H, m), 1.74 (2H, m).

EXAMPLE 167

7-[(4-Fluorophenyl)methyl]-4-hydroxy-1-(2-methylpropyl)-N-[3-(4-morpholinyl)propyl]-2-oxo-1,2-dihydro-1,5-naphthyridine-3-carboxamide The title compound was prepared in a similar manner to that described in example 152 as a white solid as its formate salt. $^1$H NMR (400 MHz, CDCl$_3$) δ 10.32 (s, 1 H), 8.57 (s, 1 H), 8.27 (s, 1 H), 7.27 (s, 1 H), 7.17 (dd, J=8.7, 5.4 Hz, 2 H), 7.05 (t, J=8.6 Hz, 2 H), 5.92 (br, 2 H), 4.14 (s, 2 H), 3.97 (br, 2 H), 3.81 (t, J=4.6 Hz, 4 H), 3.51 (dd, J=12.8, 6.3 Hz, 2 H), 2.67 (m, 4 H), 2.63 (t, J=7.6 Hz, 2 H), 1.94 (m, 3 H), 0.89 (d, J=6.6 Hz, 6 H); HRMS m/z calcd for $C_{27}H_{34}FN_4O_4$ (M+H)$^+$ 497.2564, found 497.2581.

EXAMPLE 168

7-(4-Fluorobenzyl)-4-hydroxy-N-(2-hydroxy-1-methylethyl)-2-oxo-1-[2-(2-oxopyrrolidin-1-yl)ethyl]-1,2-dihydro-1,5-naphthyridine-3-carboxamide The title compound was made in a similar manner to example 9 using DL-alanine to give a white solid: $^1$H NMR (CDCl$_3$) δ 10.26 (1H, d, J=7 Hz), 8.56 (1H, s), 8.10 (1H, s), 7.24 (2H, m), 7.00 (2H, m), 4.35 (3H, m), 4.14 (2H, s), 3.69 (2H, m), 3.50 (2H, m), 3.42 (2H, m), 2.30 (2H, m), 2.19 (1H, m), 1.97 (2H, m), 1.32 (3H, d, J=7 Hz); HRMS calcd for $C_{25}H_{27}FN_4O_5$+H$^+$: 483.2044. Found: 483.2054.

EXAMPLE 169

7-(4-Fluorobenzyl)-4-hydroxy-N-(2-hydroxypropyl)-2-oxo-1-[2-(2-oxopyrrolidin-1-yl)ethyl]-1,2-dihydro-1,5-naphthyridine-3-carboxamide The title compound was made in a similar manner to example 9 using DL-1-amino-2-propanol to give a white solid: $^1$H NMR (CDCl$_3$) δ 10.40 (1H, m), 8.56 (1H, s), 8.09 (1H, s), 7.26 (2H, m), 7.02 (2H, m), 4.36 (2H, m), 4.14 (2H, s), 4.08 (1H, br), 3.62 (1H, m), 3.50 (2H, m), 3.42 (3H, m), 2.32 (2H, m), 2.16 (1H, br), 1.97 (2H, m), 1.28 (3H, d, J=6 Hz); HRMS calcd for $C_{25}H_{27}FN_4O_5$+H$^+$: 483.2044. Found: 483.2028.

EXAMPLE 170

7-(4-Fluorobenzyl)-4-hydroxy-N-methyl-2-oxo-1-[2-(2-oxopyrrolidin-1-yl)ethyl]-1,2-dihydro-1,5-naphthyridine-3-carboxamide The title compound was made in a similar manner to example 9 using a solution of methylamine in methanol to give a white solid: $^1$H NMR (CDCl$_3$) δ 10.01 (1H, m), 8.56 (1H, s), 8.05 (1H, s), 7.23 (2H, m), 6.99 (2H, m), 4.35 (2H, m), 4.14 (2H, s), 3.50 (2H, m), 3.41 (2H, m), 3.02 (3H, d, J=5 Hz), 2.31 (2H, m), 1.97 (2H, m); HRMS calcd for $C_{23}H_{23}FN_4O_4$+H$^+$: 439.1782. Found: 439.1794.

EXAMPLE 171

[7-[(4-fluorophenyl)methyl]-4-hydroxy-3-({[2-(methyloxy)ethyl]amino}carbonyl)-2-oxo-1,5-naphthyridine-1(2H)-yl]acetic acid A 4N NaOH solution (22 mL) was added dropwise to a 100° C. suspension of 1-[2-(dimethylamino)-2-oxoethyl]-7-[(4-fluorophenyl)methyl]-4-hydroxy-N-[2-(methyloxy)ethyl]-2-oxo-1,2-dihydro-1,5-naphthyridine-3-carboxamide (5 g, 11 mmol; the title compound in Example 89) in DMSO (50 mL). The mixture was stirred for 1 h at 100° C., cooled to 10° C., diluted with H$_2$O (10 mL), acidified by dropwise addition of conc. HCl (7 mL), diluted with EtOH and filtered to give the product as a white solid: $^1$H NMR (d$_6$-DMSO) δ 13.22 (1H, br s), 10.18 (1H, m), 8.55 (1H, s), 8.03 (1H, s), 7.35 (2H, m), 7.11 (2H, m), 4.98 (2H, s), 4.11 (2H, s), 3.52 (4H, m), 3.28 (3H, s).

EXAMPLE 172

7-[(4-Fluorophenyl)methyl]-4-hydroxy-N-(2-hydroxyethyl-1-(2-methylpropyl)-2-oxo-1,2-dihydro-1,5-naphthyridine-3-carboxamide The title compound was prepared in a similar manner to that described in example 152 as a white solid. $^1$H NMR (400 MHz, CDCl$_3$) δ 10.48 (s, 1 H), 8.54 (s, 1 H), 7.25 (s, 1 H), 7.15 (dd, J=8.2, 5.2 Hz, 2 H), 7.03 (t, J=8.5 Hz, 2 H), 4.12 (s, 2 H), 3.95 (br, 2 H), 3.84 (t, J=5.1 Hz, 2 H), 3.62 (m, 2 H), 2.47-1.82 (m, 2 H), 1.94 (m, 1 H), 0.87 (d, J=6.3 Hz, 6 H); HRMS m/z calcd for $C_{22}H_{25}N_3O_4F$ (M+H)$^+$ 414.1829, found 414.1835.

EXAMPLE 173

7-[(4-Fluorophenyl)methyl]-4-hydroxy-1-(2-methylpropyl)-2-oxo-N-[2-(2-oxo-1-imidazolidinyl)ethyl]-1,2-dihydro-1,5-naphthyridine-3-carboxamide The title compound was prepared in a similar manner to that described in example 152 as a white solid. $^1$H NMR (400 MHz, CDCl$_3$) δ 10.38 (s, 1 H), 8.54 (s, 1 H), 7.24 (s, 1 H), 7.15 (dd, J=8.5, 5.4 Hz, 2 H), 7.03 (t, J=8.7 Hz, 2 H), 4.70 (br, 1 H), 4.12 (s, 2 H), 3.96 (br, 2 H), 3.62 (dd, J=12.3, 5.9 Hz, 2 H), 3.55 (m, 2 H), 3.45-3.39 (m, 4 H), 1.92 (m, 1 H), 0.86 (d, J=7.0 Hz, 6 H); HRMS m/z calcd for $C_{25}H_{29}N_5O_4F$ (M+H)$^+$ 482.2204, found 482.2214.

EXAMPLE 174

7-[(4-Fluorophenyl)methyl]-4-hydroxy-N-[3-(4-methyl-1-piperazinyl)propyl]-1-(2-methyl-1-propen-1-yl)-2-oxo-1,2-dihydro-1,5-naphthyridine-3-carboxamide The title compound was prepared in a similar manner to that described in example 152 as a white solid as a bis-formate salt. $^1$H NMR (400 MHz, CDCl$_3$) δ 10.24 (s, 1 H), 8.57 (s, 1 H), 8.35 (s, 2 H), 7.23 (s, 1 H), 7.13 (dd, J=8.5, 5.2 Hz, 2 H), 7.03 (t, J=8.6 Hz, 2 H), 6.27 (br, 3 H), 6.00 (s, 1 H), 4.09 (s, 2 H), 3.52 (m, 2 H), 3.12 (br, 4 H), 2.78 (br, 4 H), 2.65 (s, 3 H), 2.59 (m, 2 H), 1.92 (s, 3 H), 1.82 (m, 2 H), 1.33 (s, 3 H); HRMS m/z calcd for $C_{28}H_{35}N_5O_3F$ (M+H)$^+$ 508.2724, found 508.2713.

EXAMPLE 175

7-[(4-Fluorophenyl)methyl]-4-hydroxy-N-{1-[(methyloxy)methyl]propyl}-1-(2-methylpropyl)-2-oxo-1,2-dihydro-1,5-naphthyridine-3-carboxamide The title compound was prepared in a similar manner to that described in example 152 as a white solid. $^1$H NMR (400 MHz, CDCl$_3$) δ 10.24 (d, J=9.5 Hz, 1 H), 8.55 (s, 1 H), 7.26 (s, 1 H), 7.16 (dd, J=8.5, 5.6 Hz, 2 H), 7.05 (t, J=8.6 Hz, 2 H), 4.20 (m, 1 H), 4.13 (s, 2 H), 3.98 (br, 2 H), 3.52 (dd, J=9.7, 5.0 Hz, 1 H), 3.47 (dd, J=9.3, 4.8 Hz, 1 H), 3.39 (s, 3 H), 1.98 (m, 1 H), 1.80-1.56 (m, 2 H), 0.99 (t, J=7.2 Hz, 3 H), 0.88 (d, J=6.4 Hz, 6 H); HRMS m/z calcd for $C_{25}H_{31}N_3O_4F$ (M+H)$^+$ 456.2299, found 456.2308.

EXAMPLE 176

7-[(4-Fluorophenyl)methyl]-4-hydroxy-N-(2-hydroxyethly)-1-(2-methyl-1-propen-1-yl)-2-oxo-1,2-dihydro-1,5-naphthyridine-3-carboxamide The title compound was prepared in a similar manner to that described in example 152 as a white solid. $^1$H NMR (400

MHz, CDCl$_3$) δ 10.37 (s, 1 H), 8.54 (s, 1 H), 7.22 (s, 1 H), 7.12 (dd, J=8.3, 5.4 Hz, 2 H), 7.01 (t, J=8.8 Hz, 2 H), 5.99 (s, 1 H), 4.08 (s, 2 H), 3.83 (t, J=5.1 Hz, 2 H), 3.61 (m, 2 H), 2.20-1.43 (m, 2 H), 1.91 (s, 3 H), 1.31 (s, 3 H); HRMS m/z calcd for C$_{22}$H$_{23}$N$_3$O$_4$F (M+H)$^+$ 412.1673, found 412.1689.

EXAMPLE 177

1-(3-Fluorophenyl)-7-[(4-fluorophenyl)methyl]-4-hydroxy-N-(2-hydroxyethyl)-2-oxo-1,2-dihydro-1,5-naphthyridine-3-carboxamide The title compound was prepared in a manner similar to that described in example 681 as a white solid in 94% yield. $^1$H NMR (CDCl$_3$) δ 10.21 (br s, 1H), 8.55 (s, 1 H), 7.58 (m, 1 H), 7.29 (m, 1 H), 7.03-6.63 (m, 6 H), 6.71 (s, 1 H), 3.97 (s, 2 H), 3.82 (m, 2 H), 3.62 (m, 2 H); MS m/z 452 (M+1).

EXAMPLE 178

1-(Cyclopropylmethyl)-7-[(4-fluorophenyl)methyl]-4-hydroxy-N-[3-(methyloxy)propyl]-2-oxo-1,2-dihydro-1,5-naphthyridine-3-carboxamide The title compound was prepared in a similar manner to that described in example 152 as a white solid. $^1$H NMR (400 MHz, CDCl$_3$) δ 10.29 (s, 1 H), 8.55 (s, 1 H), 7.44 (s, 1 H), 7.15 (dd, J=8.2, 5.5 Hz, 2 H), 7.02 (t, J=8.7 Hz, 2 H), 4.13 (s, 2 H), 4.07 (d, J=7.1 Hz, 2 H), 3.53 (dd, J=12.7, 6.5 Hz, 2 H), 3.48 (t, J=6.0 Hz, 2 H), 3.35 (s, 3 H), 1.90 (m, 2 H), 0.99 (m, 1 H), 0.51-0.37 (m, 4H); HRMS m/z calcd for C$_{24}$H$_{27}$N$_3$O$_4$F (M+H)$^+$ 440.1986, found 440.1996.

EXAMPLE 179

1-(Cyclopropylmethyl)-7-[(4-fluorophenyl)methyl]-4-hydroxy-N-[2-(methyloxy)ethyl]-2-oxo-1,2-dihydro-1,5-naphthyridine-3-carboxamide The title compound was prepared in a similar manner to that described in example 152 as a white solid. $^1$H NMR (400 MHz, CDCl$_3$) δ 10.34 (s, 1 H), 8.54 (s, 1 H), 7.43 (s, 1 H), 7.15 (dd, J=8.2, 5.4 Hz, 2 H), 7.01 (t, J=8.8 Hz, 2 H), 4.12 (s, 2 H), 4.07 (d, J=7.0 Hz, 2 H), 3.63 (m, 2 H), 3.57 (m, 2 H), 3.39 (s, 3 H), 0.99 (m, 1 H), 0.47 (m, 2 H), 0.39 (m, 2 H); HRMS m/z calcd for C$_{23}$H$_{25}$N$_3$O$_4$F (M+H)$^+$ 426.1829, found 426.1830.

EXAMPLE 180

1-(Cyclopropylmethyl)-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide The title compound was prepared in a similar manner to that described in example 152 as a white solid. $^1$H NMR (400 MHz, CDCl$_3$) δ 10.32 (s, 1 H), 8.55 (s, 1 H), 7.45 (s, 1 H), 7.16 (m, 2 H), 7.03 (m, 2 H), 4.14 (s, 2 H), 4.08 (d, J=7.3 Hz, 2 H), 3.49-3.36 (m, 6 H), 2.40 (m, 2 H), 2.04 (m, 2 H), 1.88 (m, 2 H), 1.00 (m, 1 H), 0.48 (m, 2 H), 0.41 (m, 2 H); HRMS m/z calcd for C$_{27}$H$_{30}$N$_4$O$_4$F (M+H)$^+$ 493.2251, found 493.2257.

EXAMPLE 181

1-(Cyclopropylmethyl)-7-[(4-fluorophenyl)methyl]-4-hydroxy-N-(2-hydroxyethyl)-2-oxo-1,2-dihydro-1,5-naphthyridine-3-carboxamide The title compound was prepared in a similar manner to that described in example 152 as a white solid. $^1$H NMR (400 MHz, CDCl$_3$) δ 10.50 (s, 1 H), 8.57 (s, 1 H), 7.46 (s, 1 H), 7.17 (dd, J=8.5, 5.6 Hz, 2 H), 7.04 (t, J=8.6 Hz, 2 H), 4.15 (s, 2 H), 4.09 (d, J=7.0 Hz, 2 H), 3.86 (t, J=5.0 Hz, 2 H), 3.65 (dd, J=11.1, 5.3 Hz, 2 H), 1.01 (m, 1 H), 0.50 (m, 2 H), 0.41 (m, 2 H); HRMS m/z calcd for C$_{22}$H$_{23}$N$_3$O$_4$F (M+H)$^+$ 412.1673, found 412.1673.

EXAMPLE 182

1-(Cyclopropylmethyl)-7-[(4-fluorophenyl)methyl]-4-hydroxy-N-[1-methyl-2-(methyloxy)ethyl]-2-oxo-1,2-dihydro-1,5-naphthyridine-3-carboxamide The title compound was prepared in a similar manner to that described in example 152 as a white solid. $^1$H NMR (400 MHz, CDCl$_3$) δ 10.24 (d, J=7.2 Hz, 1 H), 8.55 (s, 1 H), 7.43 (s, 1 H), 7.15 (dd, J=8.4, 5.3 Hz, 2 H), 7.02 (t, J=8.7 Hz, 2 H), 4.34 (m, 1 H), 4.13 (s, 2 H), 4.07 (m, 2 H), 3.49-3.42 (m, 2 H), 3.39 (s, 3 H), 1.29 (d, J=7.0 Hz, 3 H), 1.00 (m, 1 H), 0.48 (m, 2 H), 0.39 (m, 2 H); HRMS m/z calcd for C$_{24}$H$_{27}$N$_3$O$_4$F (M+H)$^+$ 440.1986, found 440.1997.

EXAMPLE 183

1-(Cyclopropylmethyl)-7-[(4-fluorophenyl)methyl]-4-hydroxy-N-[(1S)-1-(hydroxymethyl)-3-(methylthio)propyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.39 (d, J=8.0 Hz, 1 H), 8.54 (s, 1 H), 7.43 (s, 1 H), 7.16 (dd, J=8.0, 5.6 Hz, 2 H), 7.02 (t, J=8.5 Hz, 2 H), 4.30 (m, 1 H), 4.13 (s, 2 H), 4.05 (d, J=6.9 Hz, 2 H), 3.82 (dd, J=11.1, 3.7 Hz, 1 H), 3.73 (dd, J=11.2, 5.4 Hz, 1 H), 2.65-2.53 (m, 2 H), 2.45 (br, 1 H), 2.10 (s, 3 H), 2.03-1.89 (m, 2 H), 0.99 (m, 1 H), 0.48 (m, 2 H), 0.38 (m, 2 H); HRMS m/z calcd for C$_{25}$H$_{29}$N$_3$O$_4$F (M+H)$^+$ 486.1863, found 486.18773.

EXAMPLE 184

N-(2-Ethoxyethyl)-7-(4-fluorobenzyl)-4-hydroxy-2-oxo-1-[2-(2-oxopyrrolidin-1-yl)ethyl]-1,2-dihydro-1,5-naphthyridine-3-carboxamide The title compound was made in a similar manner to example 9 using 2-ethoxyethylamine to give a white solid: $^1$H NMR (CDCl$_3$) δ 10.27 (1H, m), 8.55 (1H, s), 8.04 (1H, s), 7.24 (2H, m), 6.99 (2H, m), 4.35 (2H, m), 4.14 (2H, s), 3.63 (4H, m), 3.56 (4H, m), 3.42 (2H, m), 2.31 (2H, m), 1.96 (2H, m), 1.24 (3H, t, J=7 Hz); HRMS calcd for C$_{26}$H$_{29}$FN$_4$O$_5$+H$^+$: 497.2200. Found: 497.2213.

EXAMPLE 185

7-(4-Fluorobenzyl)-4-hydroxy-N-(2-methoxy-1-methylethyl)-2-oxo-1-[2-(2-oxopyrrolidin-1-yl)ethyl]-1,2-dihydro-1,5-naphthyridine-3-carboxamide The title compound was made in a similar manner to example 9 using 2-methoxyisopropylamine to give a glass: $^1$H NMR (CDCl$_3$) δ 10.15 (1H, m), 8.55 (1H, s), 8.06 (1H, s), 7.23 (2H, m), 6.99 (2H, m), 4.34 (3H, m), 4.13 (2H, s), 3.46 (6H, m), 3.40 (3H, s), 2.33 (2H, m), 1.97 (2H, m), 1.30 (3H, d, J=7 Hz); HRMS calcd for C$_{26}$H$_{29}$FN$_4$O$_5$+H$^+$: 497.2200. Found: 497.2188.

EXAMPLE 186

7-(4-Fluorobenzyl)-4-hydroxy-N-(3-morpholin-4-ylpropyl)-2-oxo-1-[2-(2-oxopyrrolidin-1-yl)ethyl]-1,2-dihydro-1,5-naphthyridine-3-carboxamide The title compound was made in a similar manner to example 9 using 4-(3-aminopropyl)morpholine to give a white solid: $^1$H NMR (CDCl$_3$) δ 10.33 (1H, m), 8.57 (1H, s), 8.09 (1H, s), 7.24 (2H, m), 7.00 (2H, m), 4.34 (4H, m), 4.15 (2H, s), 3.97 (2H, m), 3.58 (2H, m), 3.45 (6H, m), 3.07 (2H, m), 2.88 (2H, m), 2.33 (4H, m), 2.00 (2H, m); HRMS calcd for $C_{29}H_{34}FN_5O_5$+H$^+$: 552.2622. Found: 552.2625.

EXAMPLE 187

1-(Cyclopropylmethyl)-7-[(4-fluorophenyl)methyl]-4-hydroxy-N-[(1S)-2-hydroxy-1-(1H-indol-3-ylmethyl)ethyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.52 (d, J=7.8 Hz, 1 H), 8.53 (s, 1 H), 8.10 (s, 1 H), 7.69 (d, J=7.8 Hz, 1 H), 7.42 (s, 1 H), 7.33 (d, J=8.2 Hz, 1 H), 7.19-7.08 (m, 4 H), 7.03 (t, J=8.7 Hz, 2 H), 4.50 (m, 1 H), 4.12 (s, 2 H), 4.05 (m, 2 H), 3.82 (dd, J=11.1, 3.9 Hz, 1 H), 3.72 (dd, J=10.9, 5.0 Hz, 1 H), 3.14 (d, J=7.3 Hz, 2 H), 2.37 (br, 1 H), 1.64 (br, 1 H), 0.98 (m, 1 H), 0.47 (m, 2 H), 0.39 (m, 2 H); HRMS m/z calcd for $C_{31}H_{30}N_4O_4F$ (M+H)$^+$ 541.2251, found 541.2238.

EXAMPLE 188

N-[2-(Ethyloxy)ethyl]-7-[(4-fluorophenyl)methyl]-4-hydroxy-1-[2-(4-morpholinyl)-2-oxoethyl]-2-oxo-1,2-dihydro-1,5-naphthyridine-3-carboxamide

Steps 1-3: Synthesis of ethyl 7-[(4-fluorophenyl)methyl]-4-hydroxy-1-[2-(4-morpholinyl)-2-oxoethyl]-2-oxo-1,2-dihydro-1,5-naphthyridine-3-carboxylate This compound was prepared from N-{2-[(ethyloxy)carbonyl]-5-[(4-fluorophenyl)methyl]-3-pyridinyl}glycine and morpholine employing methods similar to those described in Example 11, Steps 2-4. The product was obtained as a white solid: $^1$H NMR (d$_6$-DMSO) δ 8.46 (1H, s), 7.61 (1H, s), 7.31 (2H, dd, J=9, 5.6 Hz), 7.12 (2H, t, J=9 Hz), 5.08 (2H, s), 4.22 (2H, q, J=7 Hz), 4.12 (2H, s), 3.65 (2H, m), 3.58 (2H, m), 3.53 (2H, m), 3.37 (2H, m), 1.23 (3H, t, J=7 Hz).

Step 4: Synthesis of N-[2-(ethyloxy)ethyl]-7-[(4-fluorophenyl)methyl]-4-hydroxy-1-[2-(4-morpholinyl)-2-oxoethyl]-2-oxo-1,2-dihydro-1,5-naphthyridine-3-carboxamide This compound was prepared from ethyl 7-[(4-fluorophenyl)methyl]-4-hydroxy-1-[2-(4-morpholinyl)-2-oxoethyl]-2-oxo-1,2-dihydro-1,5-naphthyridine-3-carboxylate and 2-ethoxyethylamine employing methods similar to those those described in Example 9 and was purified by reverse phase preparative HPLC (C-18 stationary phase; 10-100% CH$_3$CN/water/0.1% formic acid mobile phase). The product was obtained as a white solid: $^1$H NMR (CDCl$_3$) δ 10.14 (1H, m), 8.55 (1H, s), 7.15 (2H, dd, J=8.5, 5.5 Hz), 7.04 (3H, m), 4.94 (2H, s), 4.11 (2H, s), 3.73-3.52 (14H, m), 1.22 (3H, t, J=7 Hz); HRMS calcd for $C_{26}H_{29}FN_4O_6$+H$^+$: 513.2149. Found: 513.2134.

EXAMPLE 189

(±)-7-[(4-Fluorophenyl)methyl]-4-hydroxy-N-[1-methyl-2-(methyloxy)ethyl]-1-[2-(4-morpholinyl)-2-oxoethyl]-2-oxo-1,2-dihydro-1,5-naphthyridine-3-carboxamide This compound was prepared from ethyl 7-[(4-fluorophenyl)methyl]-4-hydroxy-1-[2-(4-morpholinyl)-2-oxoethyl]-2-oxo-1,2-dihydro-1,5-naphthyridine-3-carboxylate and (±)-1-(methyloxy)-2-propanamine employing methods similar to those those described in Example 9 and was purified by reverse phase preparative HPLC (C-18 stationary phase; 10-100% CH$_3$CN/water/0.1% formic acid mobile phase). The product was obtained as an off-white rigid foam: $^1$H NMR (CDCl$_3$) δ 10.01 (1H, d, J=8 Hz), 8.57 (1H, s), 7.15 (2H, dd, J=8.6, 5.5 Hz), 7.03 (3H, m), 4.98 (1H, d, J=17 Hz), 4.91 (1H, d, J=17 Hz), 4.34 (1H, m), 4.12 (2H, s), 3.73 (2H, m), 3.68 (2H, m), 3.56 (4H, m), 3.45 (2H, d, J=5 Hz), 3.39 (3H, s), 1.29 (3H, d, J=7 Hz); HRMS calcd for $C_{26}H_{29}FN_4O_6$+H$^+$: 513.2149. Found: 513.2145.

EXAMPLE: 190

(±)-7-[(4-Fluorophenyl)methyl]-4-hydroxy-N-(2-hydroxy)-1-methylethyl)-1-[2-(4-morpholinyl)-2-oxoethyl]-2-oxo-1,2-dihydro-1,5-naphthyridine-3-carboxamide This compound was prepared from ethyl 7-[(4-fluorophenyl)methyl]-4-hydroxy-1-[2-(4-morpholinyl)-2-oxoethyl]-2-oxo-1,2-dihydro-1,5-naphthyridine-3-carboxylate and (±)-2-amino-1-propanol employing methods similar to those those described in Example 9. The reaction mixture was concentrated in vacuo, dissolved in DCM, washed with a mixture of 1N HCl and brine; then dried and concentrated. The product was obtained as an off-white rigid foam: $^1$H NMR (CDCl$_3$) δ 14.15 (1H, br), 10.12 (1H, br d, J=6 Hz), 8.56 (1H, s), 7.14 (2H, m), 7.05 (3H, m), 4.98 (1H, d, J=17 Hz), 4.91 (1H, d, J=17 Hz), 4.27 (1H, m), 4.12 (2H, s), 3.69 (6H, m), 3.57 (4H, m), 2.18 (1H, m), 1.30 (3H, d, J=7 Hz); HRMS calcd for $C_{25}H_{27}FN_4O_6$+H$^+$: 499.1993. Found: 499.1993.

EXAMPLE 191

1-(Cyclopropylmethyl -7-[(4-fluorophenyl methyl]-4-hydroxy-2-oxo-N-[(3R)-tetrahydro-3-faranyl]-1,2-dihydro-1,5-naphthyridine-3-carboxamide The title compound was prepared in a similar manner to that described in example 152 using excess amine as its tosylate salt and ethanol as solvent to provide a white solid. $^1$H NMR (400 MHz, CDCl$_3$) δ 10.41 (d, J=7.1 Hz, 1 H), 8.55 (s, 1 H), 7.44 (s, 1 H), 7.15 (m, 2 H), 7.02 (m, 2 H), 4.62 (m, 1 H), 4.13 (s, 2 H), 4.06 (d, J=6.8 Hz, 2 H), 3.98 (m, 2 H), 3.89-3.76 (m, 2 H), 2.33 (m, 1 H), 1.98 (m, 1 H), 1.64 (br, 1 H), 0.99 (m, 1 H), 0.48 (m, 2 H), 0.39 (m, 2 H); HRMS m/z calcd for $C_{24}H_{25}N_3O_4F$ (M+H)$^+$ 438.1829, found 438.1804.

EXAMPLE 192

1-(Cyclopropylmethyl)-7-[(4-fluorophenyl)methyl]-4-hydroxy-N-[1-(hydroxymethyl)-2-methylpropyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.45 (d, J=8.0 Hz, 1 H), 8.55 (s, 1 H), 7.44 (s, 1 H), 7.16 (dd, J=8.6, 5.3 Hz, 2 H), 7.02 (t, J=8.5 Hz, 2 H), 4.13 (s, 2 H), 4.07 (d, J=6.2 Hz, 2 H), 3.98 (m, 1 H), 3.82 (dd, J=11.1, 3.8 Hz, 1 H), 3.75 (dd, J=11.0, 7.1 Hz, 1 H), 2.40 (br, 1 H), 2.03 (m, 1 H), 1.64 (br, 1 H), 1.05-0.99 (m, 6 H), 0.48 (m, 2 H), 0.39 (m, 2 H); HRMS m/z calcd for C$_{25}$H$_{29}$N$_3$O$_4$F (M+H)$^+$ 454.2142, found 454.2130.

EXAMPLE 193

1-(Cyclopropylmethyl)-7-[(4-fluorophenyl)methyl]-4-hydroxy-1N-[1-(hydroxymethyl)propyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.33 (d, J=7.8 Hz, 1 H), 8.54 (s, 1 H), 7.43 (s, 1 H), 7.15 (dd, J=8.2, 5.4 Hz, 2 H), 7.02 (t, J=8.6 Hz, 2 H), 4.13 (s, 2 H), 4.10-4.04 (m, 3 H), 3.79 (dd, J=11.1, 3.8 Hz, 1 H), 3.70 (dd, J=11.1, 6.2 Hz, 1 H), 1.78-1.58 (m, 2 H), 1.03-0.96 (m, 4 H), 0.47 (m, 2 H), 0.38 (m, 2 H); HRMS m/z calcd for C$_{24}$H$_{27}$N$_3$O$_4$F (M+H)$^+$ 40.1986, found 440.1978.

EXAMPLE 194

1-(Cyclopropylmethyl)-7-[(4-fluorophenyl)methyl]-4-hydroxy-N-[1-methyl-2-(phenyloxy)ethyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.38 (d, J=8.2 Hz, 1 H), 8.55 (s, 1 H), 7.44 (s, 1 H), 7.29-7.24 (m, 2 H), 7.16 (dd, J=8.4, 5.3 Hz, 2 H), 7.02 (t, J=8.6 Hz, 2 H), 6.96-6.91 (m, 3 H), 4.55 (m, 1 H), 4.13 (s, 2 H), 4.11-3.99 (m, 4 H), 1.63 (br, 1 H), 1.44 (d, J=6.9 Hz, 3 H), 1.00 (m, 1 H), 0.48 (m, 2 H), 0.39 (m, 2 H); HRMS m/z calcd for C$_{29}$H$_{29}$N$_3$O$_4$F (M+H)$^+$ 502.2142, found 502.2140.

EXAMPLE 195

1-{[4-(Acetylamino)phenyl]methyl}-7-[(4-fluorophenyl)methyl]-4-hydroxy-N-(2-hydroxyethyl)-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$/CD$_3$OD) δ 10.19 (m, 1 H), 8.24 (s, 1 H), 7.22 (d, J=8.3 Hz, 2 H), 7.11 (s, 1 H), 6.81-6.71 (m, 6 H), 5.14 (br, 2 H), 3.80 (s, 2 H), 3.55 (t, J=5.5 Hz, 2 H), 3.38 (m, 2 H), 1.90 (s, 3 H); HRMS m/z calcd for C$_{27}$H$_{26}$N$_4$O$_5$F (M+H)$^+$ 505.1887, found 505.1874.

EXAMPLE 196

1-(4-Fluorophenyl-7-[(4-fluorophenyl)methyl]-4-hydroxy-N-[2-(methyloxy)ethyl]-2-oxo-1,2-dihydro-1,5-naphthyridine-3-carboxamide Ethyl 1-(4-fluorophenyl)-7-[(4-fluorophenyl)methyl]-4-hydroxy-2-oxo-1,2-dihydro-1,5-naphthyridine-3-carboxylate (21 mg, 0.048 mmol) was dissolved in ethanol (1 mL) and [2-(methyloxy)ethyl]amine (0.05 mL) was added. This solution was heated in a microwave at 140° C. for 20 minutes. The resulting suspension was concentrated under reduced pressure and 1 N hydrochloric acid was added to bring the mixture to a pH of 3. The resulting white solid was collected by vacuum filtration to yield 1-(4-fluorophenyl)-7-[(4-fluorophenyl)methyl]-4-hydroxy-N-[2-(methyloxy)ethyl]-2-oxo-1,2-dihydro-1,5-naphthyridine-3-carboxamide (19.8 mg, 86%). $^1$H NMR (CDCl$_3$) δ 10.07 (m, 1 H), 8.52 (s, 1 H), 7.30-7.28 (m, 2 H), 7.22-7.18 (m, 2 H), 7.02-6.92 (m, 4 H), 6.70 (s, 1 H), 3.95 (s, 2 H), 3.65-3.60 (m, 2 H), 3.55-3.52 (m, 2 H), 3.33 (s, 3 H); MS m/z 459 (M+23).

EXAMPLE 197

1-{[4-(Acetylamino)phenyl]methyl}-7-[(4-fluorophenyl)methyl]-4-hydroxy-N-(4-hydroxybutyl-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.22 (s, 1 H), 8.52 (s, 1 H), 7.39 (d, J=8.4 Hz, 2 H), 7.17 (s, 1 H), 6.99-6.92 (m, 6 H), 5.31 (br, 2 H), 3.99 (s, 2 H), 3.70 (t, J=6.1 Hz, 2 H), 3.53-3.48 (m, 2 H), 2.17 (s, 3 H), 1.79-1.64 (m, 4 H); HRMS m/z calcd for C$_{29}$H$_{30}$N$_4$O$_5$F (M+H)$^+$ 533.2200, found 533.2209.

EXAMPLE 198

1-{[4-(Acetylamino)phenyl]methyl}-7-[(4-fluorophenyl)methyl]-4-hydroxy-N-[2-(methyloxy)ethyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.30 (s, 1 H), 8.56 (s, 1 H), 7.40-7.34 (m, 3 H), 6.98-6.90 (m, 6 H), 5.31 (br, 2 H), 4.00 (s, 2 H), 3.66 (m, 2 H), 3.59 (m, 2 H), 3.39 (s, 3 H), 2.17 (s, 3 H); HRMS m/z calcd for C$_{28}$H$_{28}$N$_4$O$_5$F (M+H)$^+$ 519.2044, found 519.2021.

EXAMPLE 199

1-{[4-(Acetylamino)phenyl]methyl}-7-[(4-fluorophenyl)methyl]-4-hydroxy-N-(2-hydroxy-1-methylethyl)-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.12 (br, 1 H), 8.31 (s, 1 H), 7.28 (d, J=8.4 Hz, 2 H), 7.17 (s, 1 H), 6.85-6.76 (m, 6 H), 5.18 (br, 2 H), 4.07 (m, 1 H), 3.86 (s, 2 H), 3.50 (dd, J=10.2, 4.5 Hz, 1 H), 3.47 (dd, J=10.7, 5.1 Hz, 1 H), 1.95 (s, 3 H), 1.14 (d, J=6.4 Hz, 3 H); HRMS m/z calcd for $C_{28}H_{28}N_4O_5F$ (M+H)$^+$ 519.2044, found 519.2048.

EXAMPLE 200

1-(4-Fluorophenyl)-7-[(4-fluorophenyl)methyl]-4-hydroxy-N-(2-hydroxyethyl)-2-oxo-1,2-dihydro-1,5-naphthyridine-3-carboxamide In a similar manner to that described in example 196, from ethyl 1-(4-fluorophenyl)-7-[(4-fluorophenyl)methyl]-4-hydroxy-2-oxo-1,2-dihydro-1,5-naphthyridine-3-carboxylate (26 mg, 0.0596 mmol) and 2-aminoethanol (0.05 mL), was prepared 1-(4-fluorophenyl)-7-[(4-fluorophenyl)methyl]-4-hydroxy-N-(2-hydroxyethyl)-2-oxo-1,2-dihydro-1,5-naphthyridine-3-carboxamide (24 mg, 87% yield) as a white solid. $^1$H NMR (CDCl$_3$) δ 10.14 (s, 1 H), 8.50 (s, 1 H), 7.29-7.24 (m, 2 H), 7.20-7.16 (m, 2 H), 7.01-6.90 (m, 5 H), 6.71 (s, 1 H), 3.93 (s, 2 H), 3.76-3.73 (m, 2 H), 3.59-3.73 (m, 2 H); HRMS m/z calcd for $C_{24}H_{20}F_2N_3O_4$: 452.1422. Found: 452.1424.

EXAMPLE 201

1-{[4-(Acetylamino)phenyl]methyl}-7-[(4-fluorophenyl)methyl]-4-hydroxy-N-[2-hydroxy-1-(hydroxymethyl)ethyl]-2-oxo-1,2-dihydro-1,5-naphthyridine-3-carboxamide $^1$H NMR (400 MHz, DMSO-d$_6$) δ 10.38 (d, J=8.9 Hz, 1 H), 9.90 (br, 1 H), 8.50 (s, 1 H), 7.82-7.70 (m, 3 H), 7.44 (d, J=7.9 Hz, 2 H), 7.15 (m, 2 H), 7.06-6.98 (m, 4 H), 5.39 (br, 2 H), 5.15 (br, 1 H), 4.90 (br, 2 H), 4.02 (s, 2 H), 3.96 (br, 1 H), 3.59-3.42 (m, 4 H), 1.98 (s, 3 H); HRMS m/z calcd for $C_{28}H_{28}N_4O_6F$ (M+H)$^+$ 535.1993, found 535.1987.

EXAMPLE 202

7-[(4-Fluorophenyl)methyl]-4-hydroxy-N-[2-(methyloxy)ethyl]-2-oxo-1-[3-(1-pyrrolidinylsulfonyl)propyl]-1,2-dihydro-1,5-naphthyridine-3-carboxamide Ethyl 5-[(4-fluorophenyl)methyl]-3-[(trifluoroacetyl)amino]-2-pyridinecarboxylate. To a cold (0° C.) solution containing ethyl 3-amino-5-[(4-fluorophenyl)methyl]-2-pyridinecarboxylate (300 mg, 1.09 mmol) and triethylamine (198 μL, 1.42 mmol) in dichloromethane (4 mL) was added trifluoroacetic anhydride dropwise. The reaction mixture was allowed to stir overnight at room temperature. The reaction mixture was poured onto ice and extracted with dichloromethane. The combined organic layers were washed with water and brine, then dried over sodium sulfate. Filtration and concentration, followed by flash chromatography (0 to 3% gradient, methanol in dichloromethane) provided ethyl 5-[(4-fluorophenyl)methyl]-3-[(trifluoroacetyl)amino]-2-pyridinecarboxylate as a white solid. $^1$H NMR (400 MHz, CDCl$_3$) δ 12.24 (br, 1 H), 8.85 (d, J=1.5 Hz, 1 H), 8.39 (d, J=1.8 Hz, 1 H), 7.13 (dd, J=8.5, 5.3 Hz, 2 H), 6.98 (t, J=8.7 Hz, 2 H), 4.51 (q, J=7.0 Hz, 2 H), 4.03 (s, 2 H), 1.45 (t, J=7.2 Hz, 3 H); MS m/z 371 (M+H)$^+$.

Ethyl 5-[(4-fluorophenyl)methyl]-3-{[3-(1-pyrrolidinylsulfonyl)propyl]amino}-2-pyridinecarboxylate. To a solution of ethyl 5-[(4-fluorophenyl)methyl]-3-[(trifluoroacetyl)amino]-2-pyridinecarboxylate (206 mg, 0.556 mmol) in N,N-dimethylformamide (2 mL) was added cesium carbonate (362 mg, 1.11 mmol) and 1-[(3-iodopropyl)sulfonyl]pyrrolidine (253 mg, 0.834 mmol), respectively. The reaction mixture was stirred at 80° C. for 5 hours, after which additional cesium carbonate (362 mg, 1.11 mmol) and 1-[(3-iodopropyl)sulfonyl]pyrrolidine (253 mg, 0.834 mmol) were added. The reaction mixture was stirred at 80° C. for an additional 7 hours. The reaction mixture was cooled and diluted with toluene. The resulting mixture was washed with water and brine, then dried over sodium sulfate. Filtration and concentration, followed by flash chromatography (0 to 5% gradient, methanol in dichloromethane) provided ethyl 5-[(4-fluorophenyl)methyl]-3-{[3-(1-pyrrolidinylsulfonyl)propyl]amino}-2-pyridinecarboxylate as a clear oil. $^1$H NMR (400 MHz, CDCl$_3$) δ 7.89 (d, J=1.3 Hz, 1 H), 7.79 (t, J=5.7 Hz, 1 H), 7.13 (dd, J=8.5, 5.4 Hz, 2 H), 6.97 (t, J=8.7 Hz, 2 H), 6.86 (s, 1 H), 4.41 (q, J=7.2 Hz, 2 H), 4.26 (t, J=6.2 Hz, 2 H), 3.91 (s, 2 H), 3.37-3.31 (m, 4 H), 3.03 (m, 2 H), 2.19-2.09 (m, 2 H), 1.95-1.89 (m, 4 H), 1.42 (t, J=6.9 Hz, 3 H); MS m/z 450 (M+H)$^+$.

Ethyl 3-{[3-(ethyloxy)-3-oxopropanoyl][3-(1-pyrrolidinylsulfonyl)propyl]amino}-5-[(4-fluorophenyl)methyl]-2-pyridinecarboxylate. To a solution of ethyl 5-[(4-fluorophenyl)methyl]-3-{[3-(1-pyrrolidinylsulfonyl)propyl]amino}-2-pyridinecarboxylate (32 mg, 0.0712 mmol) in 1,2 dichloromethane (250 μL) was added ethyl malonyl chloride (45 μL, 0.356 mmol). The reaction mixture was heated at 80° C. for 1 hour. The reaction mixture was cooled and diluted with dichloromethane, then washed with saturated aqueous sodium bicarbonate solution. The organic layer was dried over sodium sulfate. Filtration and concentration, followed by flash chromatography (0 to 5% methanol in dichloromethane) provided ethyl 3-{[3-(ethyloxy)-3-oxopropanoyl][3-(1-pyrrolidinylsulfonyl)propyl]amino}-5-[(4-fluorophenyl)methyl]-2-pyridinecarboxylate as a yellow oil. $^1$H NMR (400 MHz, CDCl$_3$) δ 8.62 (d, J=1.6 Hz, 1 H), 7.58 (d, J=1.5 Hz, 1 H), 7.17 (dd, J=8.4, 5.3 Hz, 2 H), 7.01 (t, J=8.7 Hz, 2 H), 4.41 (q, J=7.2 Hz, 2 H), 4.27-4.18 (m, 2 H), 4.04 (s, 2 H), 4.02-3.88 (m, 2 H), 3.38-3.29 (m, 4 H), 3.19-2.93 (m, 4 H), 1.98 (t, J=7.7 Hz, 2 H), 1.94-1.90 (m, 4 H), 1.38 (t, J=7.1 Hz, 3 H), 1.15 (t, J=7.1 Hz, 3 H); MS m/z 564.2 (M+H)$^+$.

Ethyl 7-[(4-fluorophenyl)methyl]-4-hydroxy-2-oxo-1-[3-(1-pyrrolidinylsulfonyl)propyl]-1,2-dihydro-1,5-naphthyridine-3-carboxylate. To a cold (0° C.) solution of ethyl 3-{[3-(ethyloxy)-3-oxopropanoyl][3-(1-pyrrolidinylsulfonyl)propyl]amino}-5-[(4-fluorophenyl)methyl]-2-pyridinecarboxylate (275 mg, 0.488 mmol) in ethanol (5 mL) was added sodium ethoxide (347 μL, 3.09 M in ethanol, 1.07 mmol) dropwise. The reaction mixture was warmed to room temperature and stirred 10 minutes, then poured onto ice. Once the ice had melted, the mixture was diluted with water and washed with ethyl acetate. The aqueous layer was acidified with 1 N aqueous hydrochloric acid and extracted with ethyl acetate. The organic layer was washed with water and brine, then dried over sodium sulfate. Filtration and concentration provided ethyl 7-[(4-fluorophenyl)methyl]-4-hydroxy-2-oxo-1-[3-(1-pyrrolidinylsulfonyl)propyl]-1,2-dihydro-1,5-naphthyridine-3-carboxylate as a yellow oil. $^1$H NMR (400 MHz, CDCl$_3$) δ 8.51 (s, 1 H), 7.73 (s, 1 H), 7.23 (dd, J=8.3, 5.4 Hz, 2 H), 7.02 (t, J=8.7 Hz, 2 H), 4.51 (q, J=7.1 Hz, 2 H), 4.38 (t, J=7.8 Hz, 2 H), 4.12 (s, 2 H), 3.37-3.33 (m, 4 H), 3.05 (t, J=6.5 Hz, 2 H), 2.18 (m, 2 H), 1.96-1.93 (m, 4 H), 1.48 (t, J=7.2 Hz, 3 H); MS m/z 518 (M+H)$^+$.

7-[(4-fluorophenyl)methyl]-4-hydroxy-N-[2-(methyloxy)ethyl]-2-oxo-1-[3-(1-pyrrolidinylsulfonyl)propyl]-1,2-dihydro-1,5-naphthyridine-3-carboxamide. To a solution of ethyl 7-[(4-fluorophenyl)methyl]-4-hydroxy-2-oxo-1-[3-(1-pyrrolidinylsulfonyl)propyl]-1,2-dihydro-1,5-naphthyridine-3-carboxylate (20 mg, 0.0387 mmol) in ethanol (1 mL) was added 2-methoxyethylamine (40 μL, 0.460 mmol). The reaction mixture was heated in a microwave at 140° C. for 20 minutes. The reaction mixture was concentrated in vacuo. Purification by reverse phase HPLC provided 7-[(4-fluorophenyl)methyl]-4-hydroxy-N-[2-(methyloxy)ethyl]-2-oxo-1-[3-(1-pyrrolidinylsulfonyl)propyl]-1,2-dihydro-1,5-naphthyridine-3-carboxamide as a white solid. $^1$H NMR (400 MHz, CDCl$_3$) δ 10.26 (s, 1H), 8.57 (s, 1 H), 7.75 (s, 1 H), 7.22 (dd, J=8.5, 5.4 Hz, 2 H), 7.02 (t, J=8.7 Hz, 2 H), 4.40 (t, J=8.0 Hz, 2 H), 4.13 (s, 2 H), 3.66 (q, J=5.1 Hz, 2 H), 3.59 (m, 2 H), 3.42 (s, 3 H), 3.37-3.34 (m, 4 H), 3.05 (t, J=6.6 Hz, 2 H), 2.18 (m, 2 H), 1.97-1.93 (m, 4 H); HRMS C$_{26}$H$_{31}$FN$_4$O$_6$S (M+H)$^+$ calcd 547.1948, found 547.2009.

EXAMPLE 203

7-[(4-Fluorophenyl)methyl]-4-hydroxy-N-(2-hydroxyethyl)-2-oxo-1-[3-(1-pyrrolidinylsulfonyl)propyl]-1,2-dihydro-15-naphthyridine-3-carboxamide This compound was prepared from ethyl 7-[(4-fluorophenyl)methyl]-4-hydroxy-2-oxo-1-[3-(1-pyrrolidinylsulfonyl)propyl]-1,2-dihydro-1,5-naphthyridine-3-carboxylate and ethanolamine employing methods similar to those described in Example 202 and was obtained as a white solid: $^1$H NMR (300 MHz, CDCl$_3$) δ 10.41 (t, J=5.5 Hz, 1 H), 8.58 (d, J=1.4 Hz, 1 H), 7.77 (s, 1 H), 7.23 (m, 2 H), 7.02 (t, J=8.6 Hz, 2 H), 4.41 (t, J=7.9 Hz, 2 H), 4.14 (s, 2 H), 3.87 (t, J=5.3 Hz, 2 H), 3.65 (q, J=5.3 Hz, 2 H), 3.38-3.33 (m, 4 H), 3.05 (t, J=6.6 Hz, 2 H), 2.17 (m, 2 H), 1.98-1.93 (m, 4 H); HRMS C$_{25}$H$_{29}$FN$_4$O$_6$S (M+H)$^+$ calcd 533.1792, found 533.1860.

EXAMPLE 204

7-[(4-fluorophenyl)methyl]-4-hydroxy-N-[3-(4-morpholinyl)propyl]-2-oxo-1-[3-(1-pyrrolidinylsulfonyl)propyl]-1,2-dihydro-1,5-naphthyridine-3-carboxamide This compound was prepared from ethyl 7-[(4-fluorophenyl)methyl]-4-hydroxy-2-oxo-1-[3-(1-pyrrolidinylsulfonyl)propyl]-1,2-dihydro-1,5-naphthyridine-3-carboxylate and 3-aminopropyl morpholine employing methods similar to those described in Example 202 and was obtained as a white solid: $^1$H NMR (400 MHz, CDCl$_3$) δ 10.22 (t, J=5.3 Hz, 1 H), 8.57 (s, 1 H), 7.76 (s, 1 H), 7.22 (dd, J=8.5, 5.5 Hz, 2 H), 7.02 (t, J=8.6 Hz, 2 H), 4.39 (t, J=8.0 Hz, 2 H), 4.13 (s, 2 H), 3.84-3.82 (m, 4 H), 3.53 (q, J=6.6 Hz, 2 H), 3.38-3.34 (m, 4 H), 3.06 (t, J=6.5 Hz, 2 H), 2.71-2.62 (m, 6 H), 2.17 (m, 2 H), 1.98-1.93 (m, 6 H); HRMS C$_{30}$H$_{38}$FN$_5$O$_6$S (M+H)$^+$ calcd 616.2527, found 616.2609.

EXAMPLE 205

7-[(4-Fluorophenyl)methyl]-4-hydroxy-N-[1-methyl-2-(methyloxy)ethyl]-2-oxo-1-[3-(1-pyrrolidinylsulfonyl)propyl]-1,2-dihydro-1,5-naphthyridine-3-carboxamide This compound was prepared from ethyl 7-[(4-fluorophenyl)methyl]-4-hydroxy-2-oxo-1-[3-(1-pyrrolidinylsulfonyl)propyl]-1,2-dihydro-1,5-naphthyridine-3-carboxylate and 2-methoxy isopropylamine employing methods similar to those described in Example 202 and was obtained as a white solid: $^1$H NMR (300 MHz, CDCl$_3$) δ 10.17 (d, J=8.6 Hz, 1 H), 8.56 (s, 1 H), 7.75 (s, 1 H), 7.22 (m, 2 H), 7.02 (t, J=8.7 Hz, 2 H), 4.43-4.33 (m, 3 H), 4.13 (s, 2 H), 3.48 (d, J=4.7 Hz, 2 H), 3.41 (s, 3 H), 3.38-3.33 (n, 4 H), 3.05 (t, J=6.5 Hz, 2 H), 2.17 (m, 2 H), 1.97-1.92 (m, 4 H), 1.31 (d, J=7.0 Hz, 3 H); HRMS C$_{27}$H$_{33}$FN$_4$O$_6$S (M+H)$^+$ calcd 561.2105, found 561.2189.

EXAMPLE 206

7-[(4-Fluorophenyl)methyl]-4-hydroxy-N-methyl-2-oxo-1-[2-oxo-2-(1-pyrrolidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-pyrrolidinyl)ethyl]-1,2-dihydro-1,5-naphthyridine-3-carboxylate and methylamine employing methods similar to those those described in Example 9 and was purified by reverse phase preparative HPLC (C-18 stationary phase;10-100% CH$_3$CN/water/0.1% formic acid mobile phase). The product was obtained as a white solid: $^1$H NMR (CDCl$_3$) δ 14.3 (1H, br), 9.94 (1H, m), 8.54 (1H, s), 7.14 (3H, m), 7.02 (2H, t, J=8.6 Hz), 4.86 (2H, s), 4.11 (2H, s), 3.51 (2H, t, J=7 Hz), 3.46 (2H, t, J=7 Hz), 2.99 (3H, d, J=5 Hz), 2.05 (2H, m, J=7 Hz), 1.89 (2H, m, J=7 Hz); HRMS calcd for C$_{23}$H$_{23}$FN$_4$O$_4$+H$^+$: 439.1782. Found: 439.1794.

EXAMPLE 207

7-[(4-Fluorophenyl)methyl]-4-hydroxy-N-(3-hydroxy-2,2-dimethylpropyl)-2-oxo-1-[2-oxo-2-(1-pyrrolidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-pyrrolidinyl)ethyl]-1,2-dihydro-1,5-naphthyridine-3-carboxylate and 3-amino-2,2-dimethyl-1-propanol employing methods similar to those those described in Example 9 and was purified by reverse phase preparative HPLC (C-18 stationary phase; 10-100% CH$_3$CN/water/0.1% formic acid mobile phase). The product was obtained as a white solid: $^1$H NMR (CDCl$_3$) δ 14.4 (1H, br), 10.32 (1H, m), 8.56 (1H, s), 7.15 (2H, dd, J=8.6, 5.5 Hz), 7.02 (3H, m), 4.88 (2H, s), 4.12 (2H, s), 3.49 (2H, t, J=7 Hz), 3.46 (2H, t, J=7 Hz), 3.33 (1H, t, J=7 Hz), 3.30 (2H, d, J=7 Hz), 3.24 (2H, d, J=7 Hz), 2.05 (2H, m, J=7 Hz), 1.90 (2H, m, J=7 Hz), 0.94 (6H, s); HRMS calcd for C$_{27}$H$_{31}$FN$_4$O$_5$+H$^+$: 511.2357. Found: 511.2341.

EXAMPLE 208

(±)-7-[(4-Fluorophenyl)methyl]-4-hydroxy-N-[1-methyl-2-(methyloxyethyl]-2-oxo-1-[2-oxo-2-(1-pyrrolidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-pyrrolidinyl)ethyl]-1,2-dihydro-1,5-naphthyridine-3-carboxylate and (±)-1-(methyloxy)-2-propanamine employing methods similar to those those described in Example 9 and was purified by reverse phase preparative HPLC (C-18 stationary phase; 10-100% CH$_3$CN/water/0.1% formic acid mobile phase). The product was obtained as a white solid: $^1$H NMR (CDCl$_3$) δ 14.5 (1H, br), 10.06 (1H, d, J=8 Hz), 8.54 (1H, d, J=1 Hz), 7.15 (2H, dd, J=8.6, 5.5 Hz), 7.02 (3H, m), 4.91 (1H, d, J=17 Hz), 4.84 (1H, d, J=17 Hz), 4.34 (1H , m), 4.11 (2H, s), 3.50-3.44 (6H, m), 3.39 (3H, s), 2.04 (2H, m, J=7 Hz), 1.89

(2H, m, J=7 Hz), 1.29 (3H, d, J=7 Hz); HRMS calcd for $C_{26}H_{29}FN_4O_5+H^+$: 497.2200. Found: 497.2188.

EXAMPLE 209

7-[(4-Fluorophenyl)methyl]-4-hydroxy-N-(2-hydroxypropyl)-2oxo-1-[2-oxo-2-(1-pyrrolidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-pyrrolidinyl)ethyl]-1,2-dihydro-1,5-naphthyridine-3-carboxylate and (±)-1-amino-2-propanol employing methods similar to those those described in Example 9 and was purified by reverse phase preparative HPLC (C-18 stationary phase; 10-100% $CH_3CN$/water/0.1% formic acid mobile phase). The product was obtained as a white solid: $^1H$ NMR (CDCl$_3$) δ 14.5 (1H, br), 10.32 (1H, m), 8.54 (1H, s), 7.15 (2H, dd, J=8.5, 5.5 Hz), 7.08 (1H, s), 7.02 (2H, t, J=8.5 Hz), 4.88 (2H, m), 4.11 (2H, s), 4.05 (1H, m), 3.61 (1H, m), 3.51-3.44 (4H, m), 3.35 (1H, m), 2.20 (1H, d, J=4 Hz), 2.04 (2H, m, J=7 Hz), 1.89 (2H, m, J=7 Hz), 1.26 (3H, d, J=6 Hz); HRMS calcd for $C_{25}H_{27}FN_4O_5+H^+$: 483.2044. Found: 483.2029.

EXAMPLE 210

N-[2-(Ethyloxy)ethyl]-7-[(4-fluorophenyl)methyl]-4-hydroxy-2-oxo-1-[2-oxo-2-(1-pyrrolidinyl)ethyl]-1,2-dihydro-1,5-naphthyridine-3-carboxamide This compound was prepared from ethyl 7-[(4-fluorophenyl)methyl]-4-hydroxy-2-oxo-1 -[2-oxo-2-(1-pyrrolidinyl)ethyl]-1,2-dihydro-1,5-naphthyridine-3-carboxylate and 2-ethoxyethylamine employing methods similar to those those described in Example 9 and was purified by reverse phase preparative HPLC (C-18 stationary phase; 10-100% $CH_3CN$/water/0.1% formic acid mobile phase). The product was obtained as a white solid: $^1H$ NMR (CDCl$_3$) δ 10.18 (1H, br m), 8.53 (1H, d, J=1 Hz), 7.15 (2H, dd, J=8.6, 5.5 Hz), 7.08 (1H, s), 7.02 (2H, m), 4.87 (2H, s), 4.11 (2H, s), 3.61 (4H, m), 3.59-3.44 (6H, m), 2.04 (2H, m, J=7 Hz), 1.89 (2H, m, J=7 Hz), 1.22 (3H, t, J=7 Hz); HRMS calcd for $C_{26}H_{29}FN_4O_5+H^+$: 497.2200. Found: 497.2190.

EXAMPLE 211

7-[(2,4-difluorophenyl)methyl]-4-hydroxy-N-(3-hydroxy-2,2-dimethylpropyl)-2-oxo-1,2-dihydro-1,5-naphthyridine-3-carboxamide This compound was prepared from ethyl 7-[(2,4-difluorophenyl)methyl]-4-hydroxy-2-oxo-1,2-dihydro-1,5-naphthyridine-3-carboxylate and 3-amino-2,2-dimethylpropanol employing methods similar to those described in Example 9 and was obtained as a white solid: $^1H$ NMR (d$_6$-DMSO) tautomers are observed δ 11.80 (1H, br s ), 10.93 (1H, br s), 10.22 (1H, br s), 8.18 (0.29H, s), 8.13 (0.71H, s), 7.45-7.38 (1H, m), 7.30 (1H, s), 7.27-7.21 (1H, m), 7.09-7.05 (1H, m), 4.59 (1H, m), 4.02 (2H, s), 3.17-3.05 (4H, m), 0.81 (6H, s); HRMS calcd for $C_{21}H_{21}F_2N_3O_4+H^+$: 418.1578. Found 418.1569.

EXAMPLE 212

1-{[4-(Acetylamino)phenyl]methyl}-7-[(4-fluorophenyl)methyl]-4-hydroxy-N-[3-(4-morpholinyl)propyl]-2-oxo-1,2-dihydro-1,5-naphthyridine-3-carboxamide The title compound was prepared in a similar manner to that described in example 152 using excess amine and ethanol as solvent to provide a white solid as a formate salt. $^1H$ NMR (400 MHz, CDCl$_3$) δ 10.27 (s, 1 H), 8.51 (s, 1 H), 8.27 (s, 1 H), 7.42 (s, 1 H), 7.37 (d, J=8.1 Hz, 2 H), 7.16 (s, 1 H), 6.97-6.91 (m, 6 H), 5.94 (br, 2 H), 5.29 (br, 2 H), 3.98 (s, 2 H), 3.77 (m, 4 H), 3.51 (m, 2 H), 2.68-2.60 (m, 6 H), 2.16 (s, 3 H), 1.91 (m, 2 H); HRMS m/z calcd for $C_{32}H_{35}FN_5O_5$ (M+H)$^+$ 588.2622, found 588.2613.

EXAMPLE 213

1-{[4-(Acetylamino)phenyl]methyl}-7-[(4-fluorophenyl)methyl]-4-hydroxy-N-[1-(hydroxymethyl)butyl]-2-oxo-1,2-dihydro-1,5-naphthyridine-3-carboxamide The title compound was prepared in a similar manner to that described in example 152 using excess amine and ethanol as solvent to provide a white solid . $^1H$ NMR (400 MHz, CDCl$_3$) δ 10.29 (d, J=8.2 Hz, 1 H), 8.52 (s, 1 H), 7.39-7.36 (m, 3 H), 7.16 (s, 1 H), 6.97-6.89 (m, 6 H), 5.28 (br, 2 H), 4.18 (m, 1 H), 3.98 (s, 2 H), 3.80 (dd, J=11.1, 3.5 Hz, 1 H), 3.69 (dd, J=11.4, 6.4 Hz, 1 H), 2.31 (br, 2 H), 2.16 (s, 3 H), 1.62 (m, 2 H), 1.43 (m, 2 H), 0.94 (t, J=7.3 Hz, 3 H); HRMS m/z calcd for $C_{30}H_{32}FN_4O_5$ (M+H)$^+$ 547.2357, found 547.2342.

EXAMPLE 214

1-{[4-(Acetylamino)phenyl]methyl}-N-butyl-7-[(4-fluorophenyl)methyl]-4-hydroxy-2-oxo-1,2-dihydro-1,5-naphthyridine-3-carboxamide The title compound was prepared in a similar manner to that described in example 152 using excess amine and ethanol as solvent to provide a white solid . $^1H$ NMR (400 MHz, CDCl$_3$) δ 10.16 (s, 1 H), 8.49 (s, 1 H), 7.41 (s, 1 H), 7.37 (d, J=8.2 Hz, 2 H), 7.15 (s, 1 H), 6.96-6.90 (m, 6 H), 5.30 (br, 2 H), 3.97 (s, 2 H), 3.44 (m, 2 H), 2.15 (s, 3 H), 1.62 (m, 2 H), 1.41 (m, 2 H), 0.94 (t, J=7.5 Hz, 3 H); HRMS m/z calcd for $C_{29}H_{30}N_4O_4F$ (M+H)$^+$ 517.2251, found 517.2241.

EXAMPLE 215

7-[(4-Fluorophenyl)methyl]-4-hydroxy-N-(2-hydroxyethyl)-2-oxo-1-{[4-(1-pyrrolidinyl)phenyl]methyl}-1,2-dihydro-1,5-naphthyridine-3-carboxamide The title compound was prepared in a similar manner to that described in example 152 using excess amine and ethanol as solvent to provide a white solid as its hydrochloride salt. $^1H$ NMR (400 MHz, DMSO-d$_6$) δ 10.48 (s, 1 H), 8.45 (s, 1 H), 7.72 (s, 1 H), 7.17 (m, 2 H), 7.02 (m, 2 H), 6.95 (d, J=7.3 Hz, 2 H), 6.35 (d, J=7.8 Hz, 2 H), 5.28 (m, 2 H), 4.89 (br, 1 H), 4.00 (s, 2 H), 3.52 (m, 2 H), 3.40 (m, 2 H), 3.12 (m, 4 H), 1.89 (m, 4 H); HRMS m/z calcd for $C_{29}H_{30}N_4O_4F$ (M+H)$^+$ 517.2251, found 517.2257.

EXAMPLE 216

7-[(2,4-Difluorophenyl)methyl]-4-hydroxy-N-[3-(4-morpholinyl)propyl]-2-oxo-1,2-dihydro-1,5-naphthyridine-3-carboxamide This compound was prepared from ethyl 7-[(2,4-difluorophenyl)methyl]-4-hydroxy-2-oxo-1,2-dihydro-1,5-naphthyridine-3-carboxylate and 4-(3-aminopropyl)morpholine employing methods similar to those described in Example 2

EXAMPLE 217

7-[(4-Fluorophenyl)methyl]-4-hydroxy-1-(2-methylpropyl)-N-4-morpholinyl-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 11.05 (s, 1 H), 8.57 (s, 1 H), 7.28 (s, 1 H), 7.16 (dd, J=8.3, 5.3 Hz, 2 H), 7.05 (t, J=8.5 Hz, 2 H), 4.14 (s, 2 H), 3.97 (br, 2 H), 3.87 (m, 4 H), 2.99 (m, 4 H), 1.97 (m, 1 H), 0.89 (d, J=6.8 Hz, 6 H); HRMS m/z calcd for C$_{24}$H$_{28}$N$_4$O$_4$F (M+H)$^+$ 455.2095, found 455.2096.

EXAMPLE 218

7-[(4-Fluorophenyl)methyl]-4-hydroxy-1-(2-methylpropyl)-2-oxo-N-4H-1,2,4-triazol-4-yl-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 12.92 (s, 1 H), 8.65 (s, 1 H), 8.32 (s, 2 H), 7.34 (s, 1 H), 7.19 (dd, J=8.5, 5.3 Hz, 2 H), 7.08 (m, 2 H), 4.18 (s, 2 H), 4.03 (br, 2 H), 1.98 (m, 1 H), 0.92 (d, J=8.1 Hz, 6 H); MS m/z 437 (M+1).

EXAMPLE 219

1-{4-[(Dimethylamino)carbonyl]phenyl}-7-[(4-fluorophenyl)methyl]-4-hydroxy-N-(2-hydroxyethyl)-2-oxo-1,2-dihydro-1,5-naphthyridine-3-carboxamide Step 1: Synthesis of 3-({4-[(dimethylamino)carbonyl]phenyl}amino)-5-[(4-fluorophenyl)methyl]-2-pyridinecarboxylic acid.

To a dry 100 mL flask under a nitrogen atmosphere was added ethyl 3-amino-5-(4-fluorobenzyl)pyridine-2-carboxylate (89 mg, 0.325 mmol) described in example 1, Cs$_2$CO$_3$ (148 mg, 0.455 mmol), Pd$_2$dba$_3$ (1.5 mg, 0.0016 mmol), and Xantphos (2.8 mg, 0.0049 mmol). Dioxane (15 mL) and 4-amino-N,N-dimethylbenzamide (1.25 mL of a 0.78 M solution in dioxane, 0.975 mmol) were added and the resulting solution was refluxed for 2 hrs. Sodium tert-butoxide (94 mg, 0.975 mmol) was added and the mixture was stirred for 10 minutes. The mixture was cooled to ambient temperature, diluted with dichloromethane, filtered through Celite and concentrated under reduced pressure. Water was added and the aqueous layer was washed with ethyl acetate and then acidified with 1 N hydrochloric acid to a pH of 4. The resulting yellow precipitate was collected by vacuum filtration to yield 3-({4-[(dimethylamino)carbonyl]phenyl}amino)-5-[(4-fluorophenyl)methyl]-2-pyridinecarboxylic acid (120 mg, 94% yield). $^1$H NMR (CDCl$_3$) δ 7.82 (s, 1 H), 7.46 (s, 1 H), 7.38 (d, J=8.4 Hz, 2 H), 7.13 (d, J=8.4 Hz, 2 H), 7.09-7.05 (m, 2 H), 6.97-6.93 (m, 2 H), 3.88 (s, 2 H), 3.07 (s, 3 H), 2.99 (s, 3 H); MS m/z 392 (M−1).

Step 2: Synthesis of methyl 3-({4-[(dimethylamino)carbonyl]phenyl}amino)-5-[(4-fluorophenyl)methyl]-2-pyridinecarboxylate.

3-({4-[(dimethylamino)carbonyl]phenyl} amino)-5-[(4-fluorophenyl)methyl]-2-pyridinecarboxylic acid (79 mg, 0.201 mmol) was dissolved in a 9:1 acetonitrile:methanol solution (5 mL) and trimethylsilyldiazomethane (0.3 mL, 0.603 mmol) was added and the reaction was stirred at ambient temperature until complete by TLC (10% methanol/dichloromethane). The mixture was concentrated under reduced pressure, aqueous sodium bicarbonate was added, and the aqueous layer was extracted with chloroform. The combined organics were washed with brine and dried over sodium sulfate to yield methyl 3-({4-[(dimethylamino)carbonyl]phenyl}amino)-5-[(4-fluorophenyl)methyl]-2-pyridinecarboxylate (40.5 mg, 49% yield). $^1$H NMR (CDCl$_3$) δ 9.49 (s, 1 H), 8.00 (s, 1 H), 7.34-7.36 (m, 3 H), 7.12-7.05 (m, 4 H), 6.97-6.94 (m, 2 H), 3.97 (s, 3 H), 3.87 (s, 2 H), 3.07 (br s, 3 H), 3.02 (br s, 3 H); MS m/z 408 (M+1).

Step 3: Synthesis of methyl 1-{4-[(dimethylamino)carbonyl]phenyl}-7-[(4-fluorophenyl)methyl]-4-hydroxy-2-oxo-1,2-dihydro-1,5-naphthyridine-3-carboxylate.

In a manner similar to that described in step 2 of example 128, from methyl 3-({4-[(dimethylamino)carbonyl]phenyl}amino)-5-[(4-fluorophenyl)methyl]-2-pyridinecarboxylate (40 mg, 0.098 mmol), and methyl 3-chloro-3-oxopropanoate (0.02 mL, 0.187 mmol) was prepared methyl 3-{{4-[(dimethylamino)carbonyl]phenyl}[3-(methyloxy)-3-oxopropanoyl]amino}-5-[(4-fluorophenyl)methyl]-2-pyridinecarboxylate as a yellow oil. MS m/z 508 (M+1).

In a manner similar to that described in step 2 of example 128, from methyl 3-{{4-[(dimethylamino)carbonyl]phenyl}[3-(methyloxy)-3-oxopropanoyl]amino}1-5-[(4-fluorophenyl)methyl]-2-pyridinecarboxylate (28 mg, 0.055 mmol), methanol (10 mL), and sodium methoxide (0.04 mL of a 6.2 M solution in methanol) was prepared methyl 1-{4-[(dimethylamino)carbonyl]phenyl}-7-[(4-fluorophenyl)methyl]-4-hydroxy-2-oxo-1,2-dihydro-1,5-naphthyridine-3-carboxylate (32 mg, 68% yield over 2 steps) as a yellow solid. $^1$H NMR (CDCl$_3$) δ 8.45 (s, 1 H), 7.60 (d, J=8.4 Hz, 2 H), 7.26 (d, J=8.4 Hz, 2 H), 7.02-6.99, (m, 2 H), 6.95-6.92 (m, 2 H), 6.82 (s, 1 H), 3.99 (s, 3 H), 3.92 (s, 2 H), 3.14 (s, 3 H), 2.99 (s, 3 H); MS m/z 476 (M+1).

Step 4: Synthesis of 1-(4-fluorophenyl)-7-[(4-fluorophenyl)methyl]-4-hydroxy-N-(2-hydroxyethyl)-2-oxo-1,2-dihydro-1,5-naphthyridine-3-carboxamide.

In a similar manner to that described in example 196, from methyl 1-{4-[(dimethylamino)carbonyl]phenyl}-7-[(4-fluorophenyl)methyl]-4-hydroxy-2-oxo-1,2-dihydro-1,5-naphthyridine-3-carboxylate (20 mg, 0.0421 mmol), 2-aminoethanol (0.05 mL) and methanol (2 mL), was prepared 1-(4-fluorophenyl)-7-[(4-fluorophenyl)methyl]-4-hydroxy-N-(2-hydroxyethyl)-2-oxo-1,2-dihydro-1,5-naphthyridine-3-carboxamide (14.64 mg, 69% yield) as a white solid after purification by reverse phase HPLC. $^1$H NMR (CDCl$_3$) δ 10.19 (m, 1 H), 8.51 (s, 1 H), 7.64 (d, J=8.4 Hz, 2 H), 7.27 (d, J=8.4 Hz, 2 H), 7.02-6.99 (m, 2 H), 6.95-6.90 (m, 2 H), 6.78

(s, 1 H), 3.93 (s, 2 H), 3.79 (t, J=5.2 Hz, 2 H), 3.59 (q, J=10.4, 5.2, 2 H), 3.15 (s, 3 H), 3.04 (s, 3 H).

EXAMPLE 220

N-[2-(acetylamino)ethyl]-1-{4-[(dimethylamino) carbonyl]phenyl}-7-[(4-fluorophenyl)methyl]4-hydroxy-2-oxo-1,2-dihydro-1,5-naphthyridine-3-carboxamide In a similar manner to that described in example 196, from from methyl 1-{4-[(dimethylamino)carbonyl]phenyl}-7-[(4-fluorophenyl)methyl]-4-hydroxy-2-oxo-1,2-dihydro-1,5-naphthyridine-3-carboxylate (8 mg, 0.0168 mmol), N-(2-aminoethyl)acetamide (10 mg, 0.098 mmol) and methanol (2 mL), was prepared N-[2-(acetylamino)ethyl]-1-{4-[(dimethylamino)carbonyl]phenyl}-7-[(4-fluorophenyl)methyl]-4-hydroxy-2-oxo-1,2-dihydro-1,5-naphthyridine-3-carboxamide (4.9 mg, 54% yield) as a white solid after purification by reverse phase HPLC. $^1$H NMR (CDCl$_3$) δ 10.14 (m, 1 H), 8.52 (s, 1 H), 7.65 (d, J=8.4 Hz, 2 H), 7.27 (d, J=8.4 Hz, 2 H), 7.02-6.98 (m, 2 H), 6.95-6.90 (m, 2 H), 6.79 (s, 1 H), 6.03 (br s, 1 H), 3.94 (s, 2 H), 3.57-3.54 (m, 2 H), 3.47-3.42 (m, 2 H), 3.16 (s, 3 H), 3.04 (s, 3 H), 1.95 (s, 3 H); MS m/z 546 (M+1).

EXAMPLE 221

1-{4-[(dimethylamino)carbonyl]phenyl}-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide In a similar manner to that described in example 196, from methyl 1-{4-[(dimethylamino)carbonyl]phenyl}-7-[(4-fluorophenyl)methyl]-4-hydroxy-2-oxo-1,2-dihydro-1,5-naphthyridine-3-carboxylate (20 mg, 0.0421 mmol), 1-(3-aminopropyl)-2-pyrrolidinone (0.05 mL), and methanol (2 mL), was prepared 1-{4-[(dimethylamino)carbonyl]phenyl}-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide (20 mg, 80% yield) as a white solid after purification by reverse phase HPLC. $^1$H NMR (CDCl$_3$) δ 10.04 (t, J=6 Hz, 1 H), 8.51 (d, J=1.6 Hz, 1 H), 7.65 (d, J=8.4 Hz, 2 H), 7.28 (d, J==8.4 Hz, 2 H), 7.03-6.99 (m, 2 H), 6.96-6.91 (m, 2 H), 6.79 (d, J=1.6 Hz, 1 H), 3.94 (s, 2 H), 3.45-3.33 (m, 6 H), 3.16 (s, 3 H), 3.06 (s, 3 H), 2.36 (t, J=8 Hz, 2 H), 2.05-1.97 (m, 2 H), 1.87-1.80 (m, 2 H); MS m/z 586 (M+1).

EXAMPLE 222

7-[(4-Fluorophenyl)methyl]-4-hydroxy-2-oxo-N-[3-(2-oxo-1-pyrrolidinyl)propyl]-1-{[4-(1-pyrrolidinyl) phenyl]methyl}-1,2-dihydro-1,5-naphthyridine-3-carboxamide The title compound was prepared in a similar manner to that described in example 152 using excess amine and ethanol as solvent to provide a yellow solid. $^1$H NMR (400 MHz, CDCl$_3$) δ 10.40 (s, 1 H), 8.51 (s, 1 H), 7.37 (s, 1 H), 7.26 (m, 2 H), 7.03-6.93 (m, 2 H), 6.87 (m, 2 H), 6.40 (m, 2 H), 5.27 (s, 2 H), 4.01 (s, 2 H), 3.53-3.37 (m, 6 H), 3.24 (m, 4 H), 2.78-2.29 (m, 4 H), 2.09-1.95 (m, 4 H), 1.90 (m, 2 H); HRMS m/z calcd for C$_{34}$H$_{36}$N$_5$O$_4$FNa (M+Na)$^+$ 620.2649, found 620.2658.

EXAMPLE 223

7-[(4-Fluorophenyl)methyl]-4-hydroxy-N-(3-hydroxy-2,2-dimethylpropyl)-2-oxo-1-{[4-(1-pyrrolidinyl)phenyl]methyl}-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.59 (s, 1 H), 8.51 (s, 1 H), 7.36 (s, 1 H), 7.02-6.91 (m, 4 H), 6.86 (d, J=8.2 Hz, 2 H), 6.39 (d, J=8.3 Hz, 2 H), 5.26 (s, 2 H), 4.00 (s, 2 H), 3.40 (br, 1 H), 3.33 (m, 2 H), 3.27-3.20 (m, 6 H), 1.98 (m, 4 H), 0.96 (s, 6 H); HRMS m/z calcd for C$_{32}$H$_{35}$N$_4$O$_4$FNa (M+Na)$^+$ 581.2540, found 581.2531.

EXAMPLE 224

1-{4-[(Dimethylamino)carbonyl]phenyl}-7-[(4-fluorophenyl)methyl]-4-hydroxy-N-[2-(4-morpholinyl) ethyl]-2-oxo-1,2-dihydro-1,5-naphthyridine-3-carboxamide In a similar manner to that described in example 196, from methyl 1-{4-[(dimethylamino)carbonyl]phenyl}-7-[(4-fluorophenyl)methyl]-4-hydroxy-2-oxo-1,2-dihydro-1,5-naphthyridine-3-carboxylate (20 mg, 0.0421 mmol), [2-(4-morpholinyl)ethyl]amine (0.05 mL), and methanol (2 mL), was prepared 1-{4-[(dimethylamino)carbonyl]phenyl}-7-[(4-fluorophenyl)methyl]-4-hydroxy-N-[2-(4-morpholinyl) ethyl]-2-oxo-1,2-dihydro-1,5-naphthyridine-3-carboxamide (20 mg, 83% yield) as a tan solid after purification by reverse phase HPLC. $^1$H NMR (CDCl$_3$) δ 10.02 (br s, 1 H), 8.50 (s, 1 H), 7.64 (d, (J=8.4 Hz, 2 H), 7.26 (d, J=8.4 Hz, 2 H), 7.01-6.98 (m, 2 H), 6.94 (m, 2 H), 6.77 (s, 1 H), 3.93 (s, 2 H), 3.71-3.68 (m, 4 H), 3.58 (q, J=12.4, 6.4 Hz, 2 H), 3.15 (s, 3 H), 3.05 (s, 3 H), 2.63 (t, J=6.4 Hz, 2 H), 2.56-2.54 (m, 4 H); MS m/z 574 (M+1).

EXAMPLE 225

7-[(4-Fluorophenyl)methyl]-4-hydroxy-N-methyl-2-oxo-1-{[4-(1-pyrrolidinyl)phenyl]methyl}-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.18 (s, 1 H), 8.50 (s, 1 H), 7.36 (s, 1 H), 7.02-6.92 (m, 4 H), 6.86 (d, J=8.5 Hz, 2 H), 6.39 (d, J=8.5 Hz, 2 H), 5.25 (s, 2 H), 4.00 (s, 2 H), 3.22 (m, 4 H), 3.01 (d, J=4.5 Hz, 3 H), 1.98 (m, 4 H); HRMS m/z calcd for C$_{28}$H$_{27}$N$_4$O$_5$FNa (M+Na)$^+$ 509.1965, found 509.1947.

EXAMPLE 226

1-[2-(1,1-dioxidotetrahydro-2H-1,2-thiazin-2-yl) ethyl]-7-[(4-fluorophenyl)methyl]-4-hydroxy-N-[2-(methyloxy)ethyl]-2-oxo-1,2-dihydro-1,5-naphthyridine-3-carboxamide 2-(2-Chloroethyl)tetrahydro-2H-1,2-thiazine 1,1-dioxide To a cold (0° C.) suspension of sodium hydride (823 mg, 60% in oil, 0.0206 mol) in N,N-dimethylformamide (20 mL) was added a solution of tetrahydro-2H-1,2-thiazine 1,1-dioxide (2.53 g, 0.0187 mol) in N,N-dimethylformamide (30 mL). The resulting mixture was stirred at room temperature 1 hour. 1-Bromo-2-chloroethane was added and the reaction mixture was stirred overnight at room temperature. The reaction mixture was concentrated in vacuo, then chromatographed on silica gel (30 to 70%, ethyl acetate in hexanes). The resulting residue was triturated with ether and the solids were filtered off. The filtrate was concentrated to give 2-(2-chloroethyl) tetrahydro-2H-1,2-thiazine 1,1-dioxide, which was partially contaminated with starting material, and was taken on to the next step. $^1$H NMR (400 MHz, CDCl$_3$) δ 3.60 (t, J=6.6 Hz, 2 H), 3.47-3.42 (m, 4 H), 3.01 (t, J=6.0 Hz, 2 H), 2.18 (m, 2 H), 1.66 (m, 2 H).

2-(2-iodoethyl)tetrahydro-2H-1,2-thiazine 1,1-dioxide

To a solution of 2-(2-chloroethyl)tetrahydro-2H-1,2-thiazine 1,1-dioxide (1.3 g, 6.6 mmol) in acetone (13 mL) was added sodium iodide (4.9 g, 33 mmol). The reaction mixture was heated at 80° C. overnight. The reaction mixture was cooled to room temperature and filtered. The filtrate was concentrated in vacuo. The solids were taken up in dichloromethane and filtered. The filtrate was concentrated and chromatographed (0 to 5%, methanol in dichloromethane) to provide 2-(2-iodoethyl)tetrahydro-2H-1,2-thiazine 1,1-dioxide as an orange solid. $^1$H NMR (400 MHz, CDCl$_3$) δ 3.51-3.42 (m, 4 H), 3.25 (t, J=7.4 Hz, 2 H), 3.02 (t, J=6.0 Hz, 2 H), 2.20 (m, 2 H), 1.69 (m, 2 H).

Ethyl 3-{[2-(1,1-dioxidotetrahydro-2H-1,2-thiazin-2-yl) ethyl]amino}-5-[(4-fluorophenyl)methyl]-2-pyridinecarboxylate.

To a solution of ethyl 5-[(4-fluorophenyl)methyl]-3-[(trifluoroacetyl)amino]-2-pyridinecarboxylate (304 mg, 0.821 mmol) in N,N-dimethylformamide (3 mL) was added cesium carbonate (535 mg, 1.64 mmol) and 2-(2-iodoethyl)tetrahydro-2H-1,2-thiazine 1,1-dioxide (356 mg, 1.23 mmol), respectively. The reaction mixture was stirred at 80° C. for 5 hours. Additional cesium carbonate (535 mg, 1.64 mmol) and 2-(2-iodoethyl)tetrahydro-2H-1,2-thiazine 1,1-dioxide (356 mg, 1.23 mmol) were added and the reaction mixture was stirred overnight at 80° C. The reaction mixture was cooled and diluted with toluene. The organic layer was washed with water and brine, then dried over sodium sulfate. Filtration and concentration, followed by flash chromatography (0 to 5%, methanol in dichloromethane) to provide ethyl 3-{[2-(1,1-dioxidotetrahydro-2H-1,2-thiazin-2-yl)ethyl]amino}-5-[(4-fluorophenyl)methyl]-2-pyridinecarboxylate, which was slightly contaminated and taken on to the next step.

Ethyl 3-{[2-(1,1-dioxidotetrahydro-2H-1,2-thiazin-2-yl) ethyl][3-(ethyloxy)-3-oxopropanoyl]amino}-5-[(4-fluorophenyl)methyl]-2-pyridinecarboxylate This compound was prepared from ethyl 3-{[2-(1,1-dioxidotetrahydro-2H-1,2-thiazin-2-yl)ethyl]amino}-5-[(4-fluorophenyl)methyl]-2-pyridinecarboxylate employing methods similar to those described in Example 202. The crude material was chromatographed on silica gel (0 to 5%, methanol in dichloromethane) to provide ethyl 3-{[2-(1,1-dioxidotetrahydro-2H-1,2-thiazin-2-yl)ethyl][3-(ethyloxy)-3-oxopropanoyl]amino}-5-[(4-fluorophenyl)methyl]-2-pyridinecarboxylate which was slightly contaminated and taken on to the next step.

Ethyl 1-[2-(1,1-dioxidotetrahydro-2H-1,2-thiazin-2-yl) ethyl]-7-[(4-fluorophenyl)methyl]-4-hydroxy-2-oxo-1,2-dihydro-1,5-naphthyridine-3-carboxylate. This compound was prepared from ethyl 3-{[2-(1,1-dioxidotetrahydro-2H-1,2-thiazin-2-yl)ethyl][3-(ethyloxy)-3-oxopropanoyl]amino}-5-[(4-fluorophenyl)methyl]-2-pyridinecarboxylate employing methods similar to those described in Example 202. The procedure provided ethyl 1-[2-(1,1-dioxidotetrahydro-2H-1, 2-thiazin-2-yl)ethyl]-7-[(4-fluorophenyl)methyl]-4-hydroxy-2-oxo-1,2-dihydro-1,5-naphthyridine-3-carboxylate which was slightly contaminated and taken on to the next step. $^1$H NMR (400 MHz, CDCl$_3$) δ 8.40 (s, 1 H), 7.23 (s, 1 H), 7.10 (m, 2 H), 6.93 (m, 2 H), 4.42-3.20 (m, 10 H), 2.90 (m, 2 H), 2.10 (m, 2 H), 1.50 (m, 2 H), 1.20 (m, 3 H); MS m/z 504 (M+H)$^+$.

1-[2-(1,1-dioxidotetrahydro-2H-1,2-thiazin-2-yl)ethyl]-7-[(4-fluorophenyl)methyl]-4-hydroxy-N-[2-(methyloxy) ethyl]-2-oxo-1,2-dihydro-1,5-naphthyridine-3-carboxamide. This compound was prepared from ethyl 1-[2-(1,1-dioxidotetrahydro-2H-1,2-thiazin-2-yl)ethyl]-7-[(4-fluorophenyl)methyl]-4-hydroxy-2-oxo-1,2-dihydro-1,5-naphthyridine-3-carboxylate and 2-methoxyethylamine employing methods similar to those described in Example 202 and was obtained as a white solid: $^1$H NMR (400 MHz, CDCl$_3$) δ 10.23 (s, 1 H), 8.55 (s, 1 H), 7.85 (s, 1 H), 7.23 (m, 2 H), 6.99 (t, J=8.7 Hz, 2 H), 4.37 (t, J=7.2 Hz, 2 H), 4.10 (s, 2 H), 3.64 (q, J=5.2 Hz, 2 H), 3.58 (m, 2 H), 3.43-3.35 (m, 4 H), 3.41 (s, 3 H), 2.95 (t, J=6.1 Hz, 2 H), 2.17 (m, 2 H), 1.57 (m, 2 H); MS m/z 533 (M+H)$^+$.

EXAMPLE 227

7-[(4-Fluorophenyl)methyl]-4-hydroxy-N-(2-hydroxyethyl)-2-oxo-1-(4-pyrrdinylmethyl)-1,2-dihydro-1,5-naphthyridine-3-carboxamide The title compound was prepared in a similar manner to that described in example 152 using excess amine and ethanol as solvent to provide a white solid as a hydrochloride salt. $^1$H NMR (400 MHz, CDCl$_3$/CD$_3$OD) δ 8.31 (s, 1 H), 8.22 (d, J=5.6 Hz, 2 H), 6.92 (s, 1 H), 6.83-6.73 (m, 6 H), 5.23 (s, 2 H), 3.84 (s, 2 H), 3.58 (m, 2 H), 3.43-3.38 (m, 3 H), 2.59 (br, 1 H); HRMS m/z calcd for C$_{24}$H$_{21}$N$_4$O$_4$FNa (M+Na)$^+$ 471.1445, found 471.1453.

EXAMPLE 228

7-[(4-Fluorophenyl)methyl]-4-hydroxy-N-methyl-2-oxo-1-(4-pyridinylmethyl)-1,2-dihydro-1,5-naphthyridine-3-carboxamide The title compound was prepared in a similar manner to that described in example 152 using excess amine and ethanol as solvent to provide a white solid as a hydrochloride salt. $^1$H NMR (400 MHz, DMSO-d$_6$) δ 9.93 (s, 1 H), 8.68 (br, 2 H), 8.54 (s, 1 H), 7.73 (s, 1 H), 7.63 (br, 2 H), 7.18 (br, 2 H), 7.02 (br, 2 H), 5.67 (s, 2 H), 4.01 (s, 2 H), 2.88 (s, 3 H); HRMS m/z calcd for C$_{23}$H$_{19}$N$_4$O$_3$FNa (M+Na)$^+$ 441.1339, found 441.1336.

EXAMPLE 229

7-[(4-Fluorophenyl)methyl]-4-hydroxy-2-oxo-N-[3-(2-oxo-1-pyrrolidinyl)propyl]-1-(4-pyridinylmethyl)-1,2-dihydro-1,5-naphthyridine-3-carboxamide The title compound was prepared in a similar manner to that described in example 152 using excess amine and ethanol as solvent to provide a white solid as a formate salt. $^1$H NMR (400 MHz, CDCl$_3$) δ 10.22 (s, 1 H), 8.55 (s, 1 H), 8.48 (d, J=4.9 Hz, 2 H), 6.96-6.90 (m, 6 H), 5.36 (br, 2 H), 3.99 (s, 2

H), 3.48-3.37 (m, 6 H), 2.38 (t, J=8.2 Hz, 2 H), 2.02 (m, 2 H), 1.86 (m, 2 H); HRMS m/z calcd for $C_{29}H_{29}N_5O_4F$ (M+H)$^+$ 530.2204, found 530.2219.

EXAMPLE 230

7-[(2,4-Difluorophenyl)methyl]-4-hydroxy-N-[2-(methyloxy)ethyl]-2-oxo-1,2-dihydro-1,5-naphthyridine-3-carboxamide This compound was prepared from ethyl 7-[(2,4-difluorophenyl)methyl]-4-hydroxy-2-oxo-1,2-dihydro-1,5-naphthyridine-3-carboxylate and 2-methoxyethylamine employing methods similar to those described in Example 2 and was obtained as a white solid: $^1$H NMR (d$_6$-DMSO) tautomers are observed δ 11.70 (1H, br s), 10.79 (1H, br s), 10.19 (1H, br s), 8.18 (0.45H, s), 8.13 (0.55H, s), 7.43-7.36 (1H, m), 7.29-7.21 (2H, m) 7.08-7.05 (1H, m), 4.02 (2H, s), 3.44-3.37 (2H, m), 3.31 (3H, s), 3.26-3.20 (2H, m); HRMS calcd for $C_{19}H_{17}F_2N_3O_4$+H$^+$: 390.1265. Found 390.1255.

EXAMPLE 231

1-[2-(1,1-Dioxidotetrahydro-2H-1,2-thiazin-2-yl)ethyl]-7-[(4-fluorophenyl)methyl]-4-hydroxy-N-(2-hydroxyethyl)-2-oxo-1,2-dihydro-1,5-naphthyridine-3-carboxamide This compound was prepared from ethyl 1-[2-(1,1-dioxidotetrahydro-2H-1,2-thiazin-2-yl)ethyl]-7-[(4-fluorophenyl)methyl]-4-hydroxy-2-oxo-1,2-dihydro-1,5-naphthyridine-3-carboxylate and ethanolamine employing methods similar to those described in Example 202 and was obtained as a white solid: $^1$H NMR (300 MHz, CDCl$_3$) δ 10.40 (s, 1 H), 8.58 (s, 1 H), 7.88 (s, 1 H), 7.24 (m, 2 H), 7.01 (t, J=8.5 Hz, 2 H), 4.40 (m, 2 H), 4.13 (s, 2 H), 3.87 (m, 2 H), 3.66 (m, 2 H), 3.43-3.36 (m, 4 H), 2.97 (m, 2 H), 2.19 (m, 2 H), 1.60 (m, 2 H); MS m/z 519 (M+H)$^+$.

EXAMPLE 232

7-{[4-Fluoro-2-(trifluoromethyl)phenyl]methyl}-4-hydroxy-N-[3-(4-morpholinyl)propyl]-2-oxo-1,2-dihydro-1,5-naphthyridine-3-carboxamide Steps 1-11: Synthesis of methyl 7-{[4-fluoro-2-(trifluoromethyl)phenyl]methyl}-4-hydroxy-2-oxo-1,2-dihydro-1,5-naphthyridine-3-carboxylate This compound was prepared from 4-fluoro-2-(trifluoromethyl)benzaldehyde and 5-bromo-2-(methyloxy)pyridine employing methods similar to those described in Example 89, Steps 1-4 and Example 132, Steps 2-7. The product was obtained as a beige solid: $^1$H NMR (d$_6$-DMSO) δ 11.50 (1H, s), 8.40 (1H, d, J=1.5 Hz), 7.67 (1H, dd, J=9.3, 2.7 Hz), 7.56-7.48 (2H, m), 7.27 (1H, s), 4.29 (2H, s), 3.74 (3H, s); HRMS calcd for $C_{18}H_{12}F_4N_2O_4$+H$^+$: 397.0811. Found: 397.0818.

Step 12: Synthesis of 7-{[4-Fluoro-2-(trifluoromethyl)phenyl]methyl}-4-hydroxy-N-[3-(4-morpholinyl)propyl]-2-oxo-1,2-dihydro-1,5-naphthyridine-3-carboxamide p This compound was prepared from methyl 7-{[4-fluoro-2-(trifluoromethyl)phenyl]methyl}-4-hydroxy-2-oxo-1,2-dihydro-1,5-naphthyridine-3-carboxylate and [3-(4-morpholinyl)propyl]amine employing methods similar to those those described in Example 9 and was purified by reverse phase preparative HPLC (C-18 stationary phase; 10-100% CH$_3$CN/water/0.1% formic acid mobile phase). The product was obtained as a white solid: $^1$H NMR (d$_6$-DMSO) δ 11.74 (1H, s), 10.26 (1H, br t, J=6 Hz), 8.45 (1H, d, J=1.6 Hz), 7.67 (1H, dd, J=9.3, 2.6 Hz), 7.59-7.50 (2H, m), 7.29 (1H, s), 4.29 (2H, s), 3.55 (4H, m), 3.39 (2H, q, J=6 Hz), 2.31 (6H, m), 2.68 (2H, m, J=7 Hz); HRMS calcd for $C_{24}H_{24}F_4N_4O_4$+H$^+$: 509.1812. Found: 509.1806.

EXAMPLE 233

7-{[4-Fluoro-2-(trifluoromethyl)phenyl]methyl}-4-hydroxy-N-[2-(4-morpholinyl)ethyl]-2-oxo-1,2-dihydro-1,5-naphthyridine-3-carboxamide This compound was prepared from methyl 7-{[4-fluoro-2-(trifluoromethyl)phenyl]methyl}-4-hydroxy-2-oxo-1,2-dihydro-1,5-naphthyridine-3-carboxylate and [2-(4-morpholinyl)ethyl]amine employing methods similar to those those described in Example 9 and was purified by reverse phase preparative HPLC (C-18 stationary phase; 10-100% CH$_3$CN/water/0.1% formic acid mobile phase). The product was obtained as a white solid: $^1$H NMR (d$_6$-DMSO) δ 11.72 (1H, s), 10.34 (1H, br t, J=5 Hz), 8.45 (1H, d, J=1.2 Hz), 7.67 (1H, dd, J=9.3, 2.6 Hz), 7.59-7.50 (4H, m), 7.29 (1H, s), 4.29 (2H, s), 3.56 (4H, m), 3.46 (2H, q, J=6 Hz), 2.40 (4H, m); HRMS calcd for $C_{23}H_{22}F_4N_4O_4$+H$^+$: 495.1655. Found: 495.1659.

EXAMPLE 234

(±)-7-[(4-Fluorophenyl)methyl]-4-hydroxy-N-(2-hydroxy-1-methylethyl)-2-oxo-1-[2-oxo-2-(1-pyrrolidinyl)ethyl]-1,2-dihydro-1,5-naphthyridine-3-carboxamide This compound was prepared from ethyl 7-[(4-fluorophenyl)methyl]-4-hydroxy-2-oxo-1-[2-oxo-2-(1-pyrrolidinyl)ethyl]-1,2-dihydro-1,5-naphthyridine-3-carboxylate and (±)-2-amino-1-propanol employing methods similar to those those described in Example 9 and was purified by reverse phase preparative HPLC (C-18 stationary phase; 10-100% CH$_3$CN/water/0.1% formic acid mobile phase). The product was obtained as a white solid: $^1$H NMR (CDCl$_3$) δ 10.16 (1H, d, J=8 Hz), 8.54 (1H, s), 7.15 (2H, dd, J=8.5, 5.3 Hz), 7.04 (1H, s), 7.02 (2H, t, J=8.5 Hz), 4.90 (1H, d, J=17 Hz), 4.83 (1H, d, J=17 Hz), 4.27 (1H, m), 4.11 (2H, s), 3.76 (1H, m), 3.66 (1H, m), 3.50-3.44 (4H, m), 2.24 (1H, br), 2.05 (2H, m, J=7 Hz), 1.89 (2H, m, J=7 Hz), 1.29 (3H, d, J=7 Hz); HRMS calcd for $C_{25}H_{27}FN_4O_5$+H$^+$: 483.2044. Found: 483.2047.

EXAMPLE 235

7-{[4-Fluoro-2-(trifluoromethyl)phenyl]methyl}-4-hydroxy-N-(3-hydroxy-2,2-dimethylpropyl)-2-oxo-1,2-dihydro-1,5-naphthyridine-3-carboxamide This compound was prepared from methyl 7-{[4-fluoro-2-(trifluoromethyl)phenyl]methyl}-4-hydroxy-2-oxo-1,2-dihydro-1,5-naphthyridine-3-carboxylate and 3-amino-2,2-dimethyl-1-propanol employing methods similar to those those described in Example 9 and was purified by reverse phase preparative HPLC (C-18 stationary phase; 10-100% $CH_3CN$/water/0.1% formic acid mobile phase). The product was obtained as a white solid: $^1H$ NMR ($d_6$-DMSO) δ 11.70 (1H, s), 10.37 (1H, t, J=6 Hz), 8.47 (1H, d, J=1.5 Hz), 7.67 (1H, dd, J=9.3, 2.4 Hz), 7.59-7.51 (2H, m), 7.30 (1H, s), 4.72 (1H, t, J=5 Hz), 4.30 (2H, s), 3.23 (2H, d, J=6 Hz), 3.16 (2H, d, J=5 Hz), 0.83 (6H, s); HRMS calcd for $C_{22}H_{21}F_4N_3O_4$+$H^+$: 468.1546. Found: 468.1558.

EXAMPLE 236

7-{[4-Fluoro-2-(trifluoromethyl)phenyl]methyl}-4-hydroxy-N-[2-(methyloxy)ethyl]-2-oxo-1,2-dihydro-1,5-naphthyridine-3-carboxamide This compound was prepared from methyl 7-{[4-fluoro-2-(trifluoromethyl)phenyl]methyl}-4-hydroxy-2-oxo-1,2-dihydro-1,5-naphthyridine-3-carboxylate and 2-methoxyethylamine employing methods similar to those those described in Example 9 and was purified by recrystallization from DMSO and MeOH. The product was obtained as a white solid: $^1H$ NMR ($d_6$-DMSO) δ 11.72 (1H, s), 10.28 (1H, brt, J=5 Hz), 8.47 (1H, s), 7.67 (1H, dd, J=9.3, 2.5 Hz), 7.59-7.51 (2H, m), 7.30 (1H, s), 4.29 (2H, s), 3.52-3.46 (4H, m), 3.26 (3H, s); HRMS calcd for $C_{20}H_{17}F_4N_3O_4$+$H^+$: 440.1233. Found: 440.1224.

EXAMPLE 237

1-[2-(Dimethylamino)-2-oxoethyl]-7-(4-fluorobenzyl)-4-hydroxy-N-methyl-2-oxo-1,2-dihydro-1,5-naphthyridine-3-carboxamide The title compound was made in a similar manner to example 89 using a solution of methylamine in ethanol to give a white cotton: $^1H$ NMR ($d_6$-DMSO) δ 9.99 (1H, m), 8.51 (1H, s), 7.77 (1H, s), 7.31 (2H, m), 7.12 (2H, m), 5.11 (2H, s), 4.11 (2H, s), 3.12 (3H, s), 2.87 (3H, s), 2.81 (3H, s); HRMS calcd for $C_{21}H_{21}FN_4O_4$+$H^+$: 413.1625. Found: 413.1616.

EXAMPLE 238

Phenylmethyl 4-{[7-[(4-fluorophenyl)methyl]-4-hydroxy-3-({[2-(methyloxy)ethyl]amino}carbonyl)-2-oxo-1,5-naphthyridine-1(2H)-yl]methyl}-1-piperidinecarboxylate The title compound was prepared in a similar manner to that described in example 152 using excess amine and ethanol as solvent to provide a white solid. $^1H$ NMR (400 MHz, $CDCl_3$) δ 10.27 (m, 1 H), 8.56 (s, 1 H), 7.36-7.28 (m, 5 H), 7.18 (s, 1 H), 7.15 (dd, J=8.6, 5.4 Hz, 2 H), 7.03 (t, J=8.7 Hz, 2 H), 5.11 (s, 2 H), 4.12 (s, 2 H), 4.25-4.07 (m, 4 H), 3.62 (m, 2 H), 3.57 (m, 2 H), 3.39 (s, 3 H), 2.60 (m, 2 H), 1.74 (m, 1 H), 1.46 (m, 2 H), 1.22 (m, 2 H); HRMS m/z calcd for $C_{33}H_{36}N_4O_6FS$ (M+H)+ 603.2619, found 603.2611.

EXAMPLE 239

Phenylmethyl 4-{[7-[(4-fluorophenyl)methyl]-4-hydroxy-3-{[2-hydroxyethyl)amino]carbonyl}-2-oxo-1,5-naphthyridine-1(2H)-yl]methyl}-1-piperidinecarboxylate The title compound was prepared in a similar manner to that described in example 152 using excess amine and ethanol as solvent to provide a white solid. $^1H$ NMR (400 MHz, $CDCl_3$) δ 10.42 (m, 1 H), 8.58 (s, 1 H), 7.38-7.30 (m, 5 H), 7.20 (s, 1 H), 7.17 (dd, J=8.5, 5.4 Hz, 2 H), 7.05 (t, J=8.5 Hz, 2 H), 5.13 (s, 2 H), 4.15 (s, 2 H), 4.04 (m, 4 H), 3.86 (t, J=5.1 Hz, 2 H), 3.64 (m, 2 H), 2.61 (m, 2 H), 1.74 (m, 1 H), 1.47 (m, 2 H), 1.23 (m, 2 H); HRMS m/z calcd for $C_{32}H_{34}N_4O_6F$ (M+H)+ 589.2462, found 589.2445.

EXAMPLE 240

1-[2-(Diethylamino)-2-oxoethyl]-7-(4-fluorobenzyl)-4-hydroxy-N-(2-methoxyethyl)-2-oxo-1,2-dihydro-1,5-naphthyridine-3-carboxamide The title compound was made from ethyl 1-[2-(diethylamino)-2-oxoethyl]-7-[4-fluorophenyl)methyl]-4-hydroxy-2-oxo-1,2-dihydro-1,5-naphthyridine-3-carboxylate in a similar manner to example 237 using 2-methoxyethylamine to give a tan solid: $^1H$ NMR ($d_6$-DMSO) δ 10.20 (1H, m), 8.55 (1H, s), 7.55 (1H, s), 7.30 (2H, m), 7.11 (2H, m), 5.73 (2H, s), 4.11 (2H, s), 3.44 (6H, m), 3.30 (3H, s), 3.26 (2H, m), 1.20 (3H, t, J=7 Hz), 0.97 (3H, t, J=7 Hz); HRMS calcd for $C_{25}H_{29}FN_4O_5$+$H^+$: 485.2200. Found: 485.2186.

EXAMPLE 241

7-[(4-Fluorophenyl)methyl]-4-hydroxy-N-[2-(methyloxy)ethyl]-2-oxo-1-(4-piperidinylmethyl)-1,2-dihydro-1,5-naphthyridine-3-carboxamide To a solution of Phenylmethyl 4-{[7-[(4-fluorophenyl)methyl]-4-hydroxy-3-({[2-(methyloxy)ethyl]amino}carbonyl)-2-oxo-1,5-naphthyridine-1(2H)-yl]methyl}-1-piperidinecarboxylate (18 mg, 0.03 mmol) in methanol (3 mL) was added palladium on carbon (10 wt %, 18 mg). Hydrogen was bubbled through the reaction mixture for several minutes and then the atmosphere was maintained with a balloon of hydrogen until the reaction was judged complete by LC/MS. The resultant suspension was filtered through a pad of Celite. The filtrate was concentrated in vacuo to give the title compound (10 mg, 71%) as a white solid. $^1H$ NMR (400 MHz, $CDCl_3$) δ 10.23 (m, 1 H), 8.48 (s, 1 H), 7.36 (s, 1 H), 7.14 (dd, J=8.4, 5.4 Hz, 2 H), 6.99 (t, J=8.6 Hz, 2 H), 4.09 (s, 2 H), 4.02 (m, 2 H), 3.57 (m, 2 H), 3.53 (m, 2 H), 3.35 (s, 3 H), 3.14 (m, 2 H), 2.52 (m, 2 H), 1.78 (m, 1 H), 1.56-1.39 (m, 4 H); HRMS m/z calcd for $C_{25}H_{30}N_4O_4F$ (M+H)+ 469.2251, found 469.2252.

EXAMPLE 242

7-[(4-Fluorophenyl)methyl]-4-hydroxy-N-(2-hydroxyethyl)-2-oxo-1-(4-piperidinylmethyl)-1,2-dihydro-1,5-naphthyridine-3-carboxamide The title compound was prepared in a similar manner to that described in example 241 to provide a white solid. $^1H$ NMR (400 MHz, DMSO-d6) δ 10.42 (m, 1 H), 8.52 (s, 1 H), 7.89 (s, 1 H), 7.38 (dd, J=8.5, 5.9 Hz, 2 H), 7.14 (t, J=9.0 Hz, 2 H), 4.91 (m, 1 H), 4.16 (s, 2 H), 4.11 (m, 2 H), 3.55 (m, 2 H), 3.41 (m, 2 H), 2.97 (m, 2 H), 2.39 (m, 2 H), 1.75 (m, 1 H), 1.47 (m, 2 H), 1.23 (m, 2 H); HRMS m/z calcd for $C_{24}H_{28}N_4O_4F$ (M+H)+ 455.2095, found 455.2111.

EXAMPLE 243

7-[(3,4-difluorophenyl)methyl]-4-hydroxy-N-(3-hydroxy-2,2-dimethylpropyl)-2-oxo-1,2-dihydro-1,5-naphthyridine-3-carboxamide This compound was prepared from ethyl 7-[(3,4-difluorophenyl)methyl]-4-hydroxy-2-oxo-1,2-dihydro-1,5-naphthyridine-3-carboxylate and 3-amino-2,2-dimethylpropanol employing methods similar to those described in Example 9 and was obtained as an off-white solid: $^1$H NMR (d$_6$-DMSO) δ 8.40 (1H, br s), 7.41-7.36 (3H, m), 7.12 (1H, br s), 4.70 (1H, br s), 4.07 (2H, s), 3.20-3.15 (4H, m), 0.83 (3H, s), 0.77 (3H, s); HRMS calcd for C$_{21}$H$_{21}$F$_2$N$_3$O$_4$+H$^+$: 418.1578. Found 418.1573.

EXAMPLE 244

Sodium 1-[2-(dimethylamino)-2-oxoethyl]-7-[(4-fluorophenyl)methyl]-3-({[2-(methyloxy)ethyl]amino}carbonyl)-2-oxo-1,2-dihydro-1,5-naphthyridine-4-olate A mixture of 1-[2-(dimethylamino)-2-oxoethyl]-7-[(4-fluorophenyl)methyl]-4-hydroxy-N-[2-(methyloxy)ethyl]-2-oxo-1,2-dihydro-1,5-naphthyridine-3-carboxamide (15.5 g, 33.96 mmol) and EtOH (600 mL) was treated with 1N NaOH (39 mL, 39 mmol) and stirred 2 h at rt. The reaction mixture was partially concentrated at reduced pressure; the solid material was filtered, washed with EtOH and dried under high vacuum to afford the product as an off-white solid: $^1$H NMR (d$_6$-DMSO) δ 10.60 (1H, br), 8.14 (1H, s), 7.26 (3H, m), 7.10 (2H, t, J=8.8 Hz), 4.92 (2H, s), 3.99 (2H, s), 3.36 (4H, m), 3.24 (3H, s), 3.08 (3H, s); ES$^-$ MS: 455 (M$^-$, 100).

EXAMPLE 245

1-[2-(Dimethylamino)-2-oxoethyl]-N-[2-(ethyloxy)ethyl]-7-[(4-fluorophenyl)methyl]-4-hydroxy-2-oxo-1,2-dihydro-1,5-naphthyridine-3-carboxamide A solution of ethyl 1-[2-(dimethylamino)-2-oxoethyl]-7-[(4-fluorophenyl)methyl]-4-hydroxy-2-oxo-1,2-dihydro-1,5-naphthyridine-3-carboxylate (44 mg, 0.103 mmol) and 2-ethoxyethylamine (15 μL, 0.135 mmol) in DMF (0.9 mL) was heated at 100° C. for 1.5 h. The reaction mixture was diluted with water and the resulting precipitate was collected by filtration. The filter cake was washed water and MeOH and dried under vacuum to afford the product as a white solid: $^1$H NMR (d$_6$-DMSO) δ 10.23 (1H, br m), 8.51 (1H, s), 7.74 (1H, s), 7.31 (2H, dd, J=8.4, 5.7 Hz), 7.12 (2H, t, J~9 Hz), 5.12 (2H, s), 4.11 (2H, s), 3.51 (4H, s), 3.46 (2H, q, J=7 Hz), 3.12 (3H, s), 2.81 (3H, s), 1.10 (3H, t, J=7 Hz); HRMS calcd for C$_{24}$H$_{27}$FN$_4$O$_5$+H$^+$: 471.2044. Found: 471.2050.

EXAMPLE 246

1-[2-(Dimethylamino)-2-oxoethyl]-7-[(4-fluorophenyl)methyl]-4-hydroxy-N-(2-hydroxyethyl)-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and ethanolamine employing methods similar to those those described in Example 9 and was purified by recrystallization from DMSO and MeOH. The product was obtained as a white solid: $^1$H NMR (d$_6$-DMSO) δ 10.53 (1H, br), 8.14 (1H, s), 7.26 (3H, m), 7.10 (2H, t, J=9 Hz), 4.92 (2H, s), 4.74 (1H, br t), 3.99 (2H, s), 3.45 (2H, m), 3.27 (2H, m), 3.08 (3H,), 2.78 (3H, s); HRMS calcd for C$_{22}$H$_{23}$FN$_4$O$_5$+H$^+$: 443.1731. Found: 443.1738.

EXAMPLE 247

Phenylmethyl 4-{[7-[(4-fluorophenyl)methyl]-4-hydroxy-3-[(methylamino)carbonyl]-2-oxo-1,5-naphthyridin-1(2H)-yl]methyl}-1-piperidinecarboxylate The title compound was prepared in a similar manner to that described in example 152 using excess amine and ethanol as solvent to provide a white solid. $^1$H NMR (400 MHz, CDCl$_3$) δ 10.03 (m, 1 H), 8.57 (s, 1 H), 7.36-7.29 (m, 5 H), 7.18 (s, 1 H), 7.15 (m, 2 H), 7.03 (m, 2 H), 5.11 (s, 2 H), 4.13 (s, 2 H), 4.05 (m, 4 H), 2.99 (d, J=4.8 Hz, 3 H), 2.60 (m, 2 H), 1.71 (m, 1 H), 1.46 (m, 2 H), 1.23 (m, 2 H); HRMS m/z calcd for C$_{31}$H$_{31}$N$_4$O$_5$FNa (M+Na)$^+$ 581.2176, found 581.2164.

EXAMPLE 248

7-[(4-Fluorophenyl)methyl]-4-hydroxy-1-(1H-imidazol-2-ylmethyl)-N-methyl-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, DMSO-d$_6$) δ 11.85 (s, 1 H), 10.07 (s, 1 H), 8.52 (s, 1 H), 7.97 (s, 1 H), 7.25 (m, 2 H), 7.08 (t, J=8.8 Hz, 2 H), 6.98 (s, 1 H), 6.78 (s, 1 H), 5.48 (s, 2 H), 4.06 (s, 2 H), 2.90 (d, J=4.3 Hz, 3 H); HRMS m/z calcd for C$_{21}$H$_{18}$N$_5$O$_3$FNa (M+H)$^+$ 430.1291, found 430.1299.

EXAMPLE 249

7-[(4-Fluorophenyl)methyl]-4-hydroxy-N-(2-hydroxyethyl)-1-(1H-imidazol-2-ylmethyl)-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, DMSO-d$_6$) δ 11.89 (br, 1 H), 10.31 (m, 1 H), 8.51 (s, 1 H), 7.99 (s, 1 H), 7.25 (dd, J=8.7, 5.5 Hz, 2 H), 7.07 (t, J=8.8 Hz, 2 H), 6.97 (s, 1 H), 6.77 (s, 1 H), 5.46 (s, 2 H), 4.91 (m, 1 H), 4.06 (s, 2 H), 3.53 (m, 2 H), 3.42 (m, 2 H); HRMS m/z calcd for C$_{22}$H$_{21}$N$_5$)$_4$F (M+H)$^+$ 438.1578, found 438.1574.

EXAMPLE 250

7-[(4-Fluorophenyl)methyl]-4-hydroxy-N-methyl-2-oxo-1-(4-piperidinylmethyl)-1,2-dihydro-1,5-naphthyridine-3-carboxamide The title compound was prepared in a similar manner to that described in example 241 to provide a white solid. $^1$H NMR (400 MHz, DMSO-d$_6$/NaOD in D$_2$O) δ 8.19 (s, 1 H), 7.53 (s, 1 H), 7.29 (m, 2 H), 7.08 (m, 2 H), 4.03 (s, 2 H), 2.77 (m, 2 H), 2.68 (s, 3 H), 2.14 (m, 2 H), 1.66-1.03 (m, 7 H); HRMS m/z calcd for C$_{23}$H$_{26}$N$_4$O$_3$F (M+H)$^+$ 425.1989, found 425.1989.

EXAMPLE 251

7-[(4-Fluorophenyl)methyl]-4-hydroxy-N-[2-(4-morpholinyl)ethyl]-2-oxo-1-(4-piperidinylmethyl)-1,2-dihydro-1,5-naphthyridine-3-carboxamide The title compound was prepared in a similar manner to that described in example 241 to provide a white solid. $^1$H NMR (400 MHz, CDCl$_3$) δ 10.28 (m, 1H), 8.56 (s, 1 H), 7.23 (s, 1 H), 7.16 (m, 2 H), 7.04 (m, 2 H), 4.12 (s, 2 H), 4.04 (br, 2 H), 3.71 (m, 4 H), 3.55 (m, 2 H), 3.27-2.87 (m, 2 H), 2.60 (m, 4 H), 2.50 (m, 4 H), 1.76 (m, 1 H), 1.62-1.20 (m, 4 H); HRMS m/z calcd for C$_{28}$H$_{35}$N$_5$O$_4$F (M+H)$^+$ 524.2673, found 524.2699.

EXAMPLE 252

1-(4-fluorophenyl)-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide In a similar manner to that described in example 196, from ethyl 1-(4-fluorophenyl)-7-[(4-fluorophenyl)methyl]-4-hydroxy-2-oxo-1,2-dihydro-1,5-naphthyridine-3-carboxylate (15 mg, 0.0344 mmol) and 1-(3-aminopropyl)-2-pyrrolidinone (0.05 mL) was prepared 1-(4-fluorophenyl)-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide (10 mg, 56% yield) as a white solid after purification by reverse phase HPLC. $^1$H NMR (CDCl$_3$) δ 10.03 (t, J=5.6 Hz, 1 H), 8.50 (s, 1 H), 7.29-7.17 (m, 2 H), 7.20-7.16 (m, 2 H), 7.01-6.91 (m, 4 H), 6.69 (s, 1 H), 3.93 (s, 2 H), 3.44-3.32 (m, 6 H), 2.35 (t, J=8 Hz, 2 H), 2.04-1.96 (m, 2 H), 1.89-1.78 (m, 2 H); MS m/z 533 (M+1).

EXAMPLE 253

1-[2-(diethylamino)-2-oxoethyl]-7-(4-fluorobenzyl)-4-hydroxy-N-(2-methoxyethyl)-2-oxo-1,2-dihydro-1,5-naphthyridine-3-carboxamide The title compound was made in a similar manner to example 240 using a solution of methylamine in ethanol to give a white solid: $^1$H NMR (CDCl$_3$) δ 9.94 (1H, m), 8.54 (1H, s), 7.13 (2H, m), 7.00 (2H, m), 6.99 (1H, s), 4.92 (2H, s), 4.09 (2H, s), 3.36 (4H, m), 2.98 (3H, d, J=5 Hz), 1.22 (3H, t, J=7 Hz), 1.09 (3H, t, J=7 Hz); HRMS calcd for C$_{23}$H$_{25}$FN$_4$O$_4$+H$^+$: 441.1930. Found: 441.1957.

EXAMPLE 254

1-[2-(Diethylamino)-2-oxoethyl]-7-(4-fluorobenzyl)-4-hydroxy-N-(3-hydroxy-2,2-dimethylpropyl)-2-oxo-1,2-dihydro-1,5-naphthyridine-3-carboxamide The title compound was made in a similar manner to example 240 using 3-amino-2,2-dimethyl-1-propanol to give a tan solid: $^1$H NMR (CDCl$_3$) δ 10.32 (1H, m), 8.56 (1H, s), 7.13 (2H, m), 7.03 (2H, m), 6.95 (1H, s), 4.93 (2H, s), 4.10 (2H, s), 3.23-3.40 (8H, m), 1.21 (3H, t, J=7 Hz), 1.09 (3H, t, J=7 Hz), 0.94 (6H, s); HRMS calcd for C$_{27}$H$_{33}$FN$_4$O$_5$+H$^+$: 513.2513. Found: 513.2526.

EXAMPLE 255

7-[(4-Fluorophenyl)methyl]-4-hydroxy-1-(1H-imidazol-2-ylmethyl)-N-[2-(methyloxy)ethyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (300 MHz, DMSO-d$_6$) δ 11.95 (s, 1 H), 10.35 (m, 1 H), 8.58 (s, 1 H), 8.04 (s, 1 H), 7.31 (dd, J=8.2, 5.7 Hz, 2 H), 7.13 (t, J=8.8 Hz, 2 H), 7.04 (s, 1 H), 6.83 (s, 1 H), 5.53 (s, 2 H), 4.12 (s, 2 H), 3.63-3.52 (m, 4 H), 3.35 (s, 3 H); HRMS m/z calcd for C$_{23}$H$_{23}$N$_5$O$_4$F (M+H)$^+$ 452.1734, found 452.1728.

EXAMPLE 256

7-[(4-Fluorophenyl)methyl]-4-hydroxy-2-oxo-N-[3-(2-oxo-1-pyrrolidinyl)propyl]-1-(4-piperidinylmethyl)-1,2-dihydro-1,5-naphthyridine-3-carboxamide The title compound was prepared in a similar manner to that described in example 241 to provide a white solid. $^1$H NMR (400 MHz, CDCl$_3$) δ 10.27 (m, 1 H), 8.55 (s, 1 H), 7.26 (s, 1 H), 7.16 (dd, J=8.1, 5.6 Hz, 2 H), 7.02 (t, J=8.6 Hz, 2 H), 4.12 (s, 2 H), 4.01 (br, 2 H), 3.46-3.34 (m, 6 H), 2.98 (br, 2 H), 2.37 (m, 2 H), 2.02 (m, 2 H), 1.86 (m, 2 H), 1.86-1.10 (m, 5 H); HRMS m/z calcd for C$_{29}$H$_{35}$N$_5$)$_4$F (M+H)$^+$ 536.2673, found 536.2678.

EXAMPLE 257

7-[(4-Fluorophenyl)methyl]-4-hydroxy-1-(1H-imidazol-2-ylmethyl-2-oxo-N-[3-(2-oxo-1-pyrrolidinyl)propyl]-1,2-dihydro-1,5-naphthyridine-3-carboxamide The title compound was prepared in a similar manner to that described in example 152 using excess amine and ethanol as solvent to provide a white solid. $^1$H NMR (400 MHz, DMSO-d$_6$) δ 11.87 (s, 1 H), 10.21 (m, 1 H), 8.51 (s, 1 H), 7.95 (s, 1 H), 7.24 (dd, J=8.6, 5.5 Hz, 2 H), 7.06 (t, J=8.9 Hz, 2 H), 6.97 (s, 1 H), 6.76 (s, 1 H), 5.47 (s, 2 H), 4.05 (s, 2 H), 3.34-3.27 (m, 4 H), 3.21 (m, 2 H), 2.16 (m, 2 H), 1.87 (m, 2 H), 1.72 (m, 2 H); HRMS m/z calcd for C$_{27}$H$_{28}$N$_6$O$_4$F (M+H)$^+$ 519.2156, found 519.2152.

EXAMPLE 258

7-[(4-Fluorophenyl)methyl]-4-hydroxy-1-(1H-imidazol-2-ylmethyl)-N-[2-(4-morpholinyl)ethyl]-2-oxo-1,2-dihydro-1,5-naphthyridine-3-carboxamide The title compound was prepared in a similar manner to that described in example 152 using excess amine and ethanol as solvent to provide a white solid as a formate salt. $^1$H NMR (400 MHz, CDCl$_3$) δ 10.23 (m, 1 H), 8.51 (s, 1 H), 8.26 (s, 1 H), 8.22 (s, 1 H), 7.18 (dd, J=8.2, 5.5 Hz, 2 H), 7.01-6.97 (m, 4 H), 5.48 (s, 2 H), 4.13 (s, 2 H), 3.80 (m, 4 H), 3.65 (m, 2 H), 2.74 (m, 2 H), 2.65 (m, 4 H); HRMS m/z calcd for C$_{26}$H$_{28}$N$_6$O$_4$F (M+H)$^+$ 507.2156, found 507.2153.

EXAMPLE 259

N-Cyclobutyl-1-[2-(dimethylamino)-2-oxoethyl]-7-[(4-fluorophenyl)methyl]-4-hydroxy-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and cyclobutylamine employing methods similar to those described in Example 245. The product was obtained as a white solid: $^1$H NMR (d$_6$-DMSO) δ 10.34 (1H, br), 8.49 (1H, br), 7.77 (1H, br), 7.30 (2H, m), 7.12 (2H, t, J=8.8 Hz), 5.10 (2H, br s), 4.39 (1H, m), 4.09 (2H, br s), 3.11 (3H, s), 2.81 (3H, s), 2.27 (2H, m), 1.99 (2H, m), 1.70 (2H, m); HRMS calcd for C$_{24}$H$_{25}$FN$_4$O$_4$+H$^+$: 453.1938. Found: 453.1937.

EXAMPLE 260

1-[2-(Dimethylamino)-2-oxoethyl]-7-[(4-fluorophenyl)methyl]-4-hydroxy-N-(3-hydroxy-2,2-dimethylpropyl)-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and 3-amino-2,2-dimethyl-1-propanol employing methods similar to those described in Example 245 and was purified by reverse phase preparative HPLC (C-18 stationary phase; 10-100% $CH_3CN$/water/0.1% formic acid mobile phase). The product was obtained as a white solid: $^1$H NMR ($d_6$-DMSO) δ 10.29 (1H, t, J=6 Hz), 8.51 (1H, s), 7.72 (1H, s), 7.31 (2H, dd, J=9, 5.6 Hz), 7.12 (2H, t, J=9 Hz), 5.13 (2H, s), 4.76 (1H, t, J=5 Hz), 4.11 (2H, s), 3.25 (2H, d, J=6 Hz), 3.17 (2H, d, J=5 Hz), 3.12 (3H, s), 2.82 (3H, s), 0.83 (6H, s); HRMS calcd for $C_{25}H_{29}FN_4O_5+H^+$: 485.2200. Found: 485.2188.

EXAMPLE 261

1-[2-(Dimethylamino)-2-oxoethyl]-7-[(4-fluorophenyl)methyl]-4-hydroxy-N-(3-hydroxypropyl)-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and 3-amino-1-propanol employing methods similar to those described in Example 245 and was purified by reverse phase preparative HPLC (C-18 stationary phase; 10-100% $CH_3CN$/water/0.1% formic acid mobile phase). The product was obtained as a white solid: $^1$H NMR ($d_6$-DMSO) δ 10.56 (1H, br), 8.16 (1H, br s), 7.26 (3H, m), 7.10 (2H, t, J=8.8 Hz), 4.93 (2H, s), 4.50 (1H, br t), 3.99 (2H, s), 4.43 (2H, m), 3.27 (2H, m), 3.08 (3H, s), 2.78 (3H, s), 1.58 (2H, m, J=6 Hz); HRMS calcd for $C_{23}H_{25}FN_4O_5+H^+$: 457.1887. Found: 457.1903.

EXAMPLE 262

1-[2-(Dimethylamino)-2-oxoethyl]-7-[(4-fluorophenyl)methyl]-4-hydroxy-N-{2-[(2-hydroxyethyl)oxy]ethyl}-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and 2-[(2-aminoethyl)oxy]ethanol employing methods similar to those described in Example 245 and was purified by reverse phase preparative HPLC (C-18 stationary phase; 10-100% $CH_3CN$/water/0.1% formic acid mobile phase). The product was obtained as a white solid: $^1$H NMR ($d_6$-DMSO) δ 10.22 (1H, br t), 8.51 (1H, s), 7.74 (1H, s), 7.31 (2H, dd, J=8.4, 5.7 Hz), 7.12 (2H, t, J~9 Hz), 5.12 (2H, s), 4.59 (1H, t, J=5 Hz), 4.11 (2H, s), 3.57-3.38 (8H, m), 3.12 (3H, s), 2.82 (3H, s); HRMS calcd for $C_{24}H_{27}FN_4O_6+H$: 487.1993. Found: 487.2007.

EXAMPLE 263

1-(4-fluorophenyl)-7-[(4-fluorophenyl)methyl]-4-hydroxy-N-[2-(4-morpholinyl)ethyl]-2-oxo-1,2-dihydro-1,5-naphthyridine-3-carboxamide In a similar manner to that described in example 196, from ethyl 1-(4-fluorophenyl)-7-[(4-fluorophenyl)methyl]-4-hydroxy-2-oxo-1,2-dihydro-1,5-naphthyridine-3-carboxylate (15 mg, 0.0344 mmol) and [2-(4-morpholinyl)ethyl]amine (0.05 mL) was prepared 1-(4-fluorophenyl)-7-[(4-fluorophenyl)methyl]-4-hydroxy-N-[2-(4-morpholinyl)ethyl]-2-oxo-1,2-dihydro-1,5-naphthyridine-3-carboxamide (10 mg, 56% yield) as a yellow solid after purification by reverse phase HPLC. $^1$H NMR ($CDCl_3$) δ 10.03 (br s, 1 H), 8.51 (s, 1 H), 7.29-7.24 (m, 2 H), 7.20-7.16 (m, 2 H), 7.01-6.91 (m, 4 H), 6.69 (s, 1 H), 3.93 (s, 2 H), 3.68 (m, 4 H), 3.56 (m, 2 H), 2.59 (m, 2 H), 2.51 (m, 4 H); MS m/z 521 (M+1).

EXAMPLE 264

1-(4-fluorophenyl)-7-[(4-fluorophenyl)methyl]-4-hydroxy-N-methyl-2-oxo-1,2-dihydro-1,5-naphthyridine-3-carboxamide In a similar manner to that described in example 196, from ethyl 1-(4-fluorophenyl)-7-[(4-fluorophenyl)methyl]-4-hydroxy-2-oxo-1,2-dihydro-1,5-naphthyridine-3-carboxylate (22 mg, 0.0504 mmol) and methylamine (0.1 mL of a 8 M solution in ethanol) was prepared 1-(4-fluorophenyl)-7-[(4-fluorophenyl)methyl]-4-hydroxy-N-methyl-2-oxo-1,2-dihydro-1,5-naphthyridine-3-carboxamide (6 mg, 29% yield) as a tan solid after purification by reverse phase HPLC. $^1$H NMR ($CDCl_3$) δ 9.87 (br s, 1 H), 8.52 (s, 1 H), 7.30-7.24 (m, 2 H), 7.20-7.16 (m, 2 H), 7.01-6.91 (m, 4 H), 6.71 (s, 1 H), 3.94 (s, 2 H), 2.96 (d, J=4.8 Hz, 3 H); MS m/z 422 (M+1).

EXAMPLE 265

7-[(4-fluorophenyl)methyl]-4-hydroxy-N-[2-(methyloxy)ethyl]1-[3-(methylsulfonyl)propyl]-2-oxo-1,2-dihydro-1,5-naphthyridine-3-carboxamide Ethyl 5-[(4-fluorophenyl)methyl]-3-{[3-(methylthio)propyl]amino}-2-pyridinecarboxylate. To a solution of ethyl 3-amino-5-[(4-fluorophenyl)methyl]-2-pyridinecarboxylate (150 mg, 0.547 mmol) in 1,2 dichloroethane (2 mL) was added 3-(methylthio)propionaldehyde (82 μL, 0.821 mmol), acetic acid (156 μL, 2.74 mmol), and sodium triacetoxyborohydride (232 mg, 1.09 mmol) respectively. The reaction mixture was stirred overnight at room temperature. The reaction mixture was diluted with dichloromethane and washed with water and brine, then dried over sodium sulfate. Filtration and concentration, followed by flash chromatography (0 to 5%, methanol in dichloromethane) provided ethyl 5-[(4-fluorophenyl)methyl]-3-{[3-(methylthio)propyl]amino}-2-pyridinecarboxylate as a light yellow oil. $^1$H NMR (400 MHz, $CDCl_3$) δ 7.85 (d, J=1.5 Hz, 1 H), 7.73 (t, J=5.1 Hz, 1 H), 7.11 (dd, J=8.4, 5.5 Hz, 2 H), 6.96 (t, J=8.6 Hz, 2 H), 6.82 (s, 1 H), 4.40 (q, J=7.1 Hz, 2 H), 3.90 (s, 2 H), 3.24 (m, 2 H), 2.58 (m, 2 H), 2.07 (s, 3 H), 1.90 (m, 2 H), 1.41 (t, J=7.1 Hz, 3 H); MS m/z 363 (M+H)$^+$.

Ethyl 3-{[3-(ethyloxy)-3-oxopropanoyl][3-(methylthio)propyl]amino}-5-[(4-fluorophenyl)methyl]-2-pyridinecarboxylate. This compound was prepared from ethyl 5-[(4-fluorophenyl)methyl]-3-{[3-(methylthio)propyl]amino}-2-pyridinecarboxylate employing methods similar to those described in Example 202. The crude material was chromatographed (0 to 5%, methanol in dichloromethane) to provide ethyl 3-{[3-(ethyloxy)-3-oxopropanoyl][3-(methylthio)propyl]amino}-5-[(4-fluorophenyl)methyl]-2-pyridinecarboxylate as a clear oil. $^1$H NMR (400 MHz, $CDCl_3$) δ 8.62 (d, J=1.4 Hz, 1 H), 7.47 (d, J=1.3 Hz, 1 H), 7.13 (dd, J=8.4, 5.5 Hz, 2 H), 7.02 (t, J=8.6 Hz, 2 H), 4.42 (q, J=7.1 Hz, 2 H), 4.24 (q, J=7.2 Hz, 2 H), 4.07-3.97 (m, 2 H), 4.04 (s, 2 H), 3.38-3.01

(m, 2 H), 2.46 (m, 2 H), 2.01 (s, 3 H), 1.75 (s, 2 H), 1.41-1.15 (m, 6 H); MS m/z 477 (M+H)+.

Ethyl 7-[(4-fluorophenyl)methyl]-4-hydroxy-1-[3-(methylthio)propyl]-2-oxo-1,2-dihydro-1,5-naphthyridine-3-carboxylate. This compound was prepared from ethyl 5-[(4-fluorophenyl)methyl]-3-{[3-(methylthio)propyl]amino}-2-pyridinecarboxylate employing methods similar to those described in Example 202. Crude material appears to be a mixture of 30% S-Methyl and 70% sulfoxide products due to air oxidation. MS m/z 429 (M−H)− (for S-methyl).

Ethyl 7-[(4-fluorophenyl)methyl]-4-hydroxy-1-[3-(methylsulfonyl)propyl]-2-oxo-1,2-dihydro-1,5-naphthyridine-3-carboxylate. To a cold (0° C.) solution of 30% ethyl 7-[(4-fluorophenyl)methyl]-4-hydroxy-1-[3-(methylthio)propyl]-2-oxo-1,2-dihydro-1,5-naphthyridine-3-carboxylate and 70% ethyl 7-[(4-fluorophenyl)methyl]-4-hydroxy-1-[3-(methylsulfinyl)propyl]-2-oxo-1,2-dihydro-1,5-naphthyridine-3-carboxylate (269 mg, 0.611 mmol) in dichloromethane (10 mL) was added m-chloroperoxybenzoic acid (158 mg, 0.915 mmol). The reaction mixture was warmed to room temperature and stirred 3 hours. The reaction mixture was diluted with dichloromethane and washed with water and brine, then dried over sodium sulfate. Filtration and concentration provided ethyl 7-[(4-fluorophenyl)methyl]-4-hydroxy-1-[3-(methylsulfonyl)propyl]-2-oxo-1,2-dihydro-1,5-naphthyridine-3-carboxylate as a white solid. $^1$H NMR (400 MHz, CDCl$_3$) δ 8.55 (s, 1 H), 7.66 (s, 1 H), 7.22 (dd, J=8.5, 5.5 Hz, 2 H), 7.03 (t, J=8.5 Hz, 2 H), 4.52 (q, J=7.1 Hz, 2 H), 4.39 (t, J=7.8 Hz, 2 H), 4.13 (s, 2 H), 3.16 (t, J=6.9 Hz, 2 H), 2.95 (s, 3 H), 2.22 (m, 2 H), 1.48 (t, J=7.0 Hz, 3 H); MS m/z 461 (M−H)−.

7-[(4-Fluorophenyl)methyl]-4-hydroxy-N-[2-(methyloxy)ethyl]-1-[3-(methylsulfonyl)propyl]-2-oxo-1,2-dihydro-1,5-naphthyridine-3-carboxamide. This compound was prepared from ethyl 7-[(4-fluorophenyl)methyl]-4-hydroxy-1-[3-(methylsulfonyl)propyl]-2-oxo-1,2-dihydro-1,5-naphthyridine-3-carboxylate and 2-methoxyethylamine employing methods similar to those described in Example 202 and was obtained as a white solid. $^1$H NMR (400 MHz, CDCl$_3$) δ 10.22 (s, 1 H), 8.57 (s, 1 H), 7.67 (s, 1 H), 7.21 (dd, J=8.6, 5.5 Hz, 2 H), 7.01 (t, J=8.7 Hz, 2 H), 4.39 (t, J=7.8 Hz, 2 H), 4.12 (s, 2 H), 3.65 (m, 2 H), 3.59 (m, 2 H), 3.41 (s, 3 H), 3.14 (t, J=7.0 Hz, 2 H), 2.95 (s, 3 H), 2.21 (m, 2 H); HRMS C$_{23}$H$_{26}$FN$_3$O$_6$S (M+H)+ calcd 492.1526, found 492.1603.

EXAMPLE 266

7-[(4-fluorophenyl)methyl]-4-hydroxy-N-(2-hydroxyethyl)-1-[3-(methylsulfonyl)propyl]-2-oxo-1,2-dihydro-1,5-naphthyridine-3-carboxamide This compound was prepared from ethyl 7-[(4-fluorophenyl)methyl]-4-hydroxy-1-[3-(methylsulfonyl)propyl]-2-oxo-1,2-dihydro-1,5-naphthyridine-3-carboxylate and ethanolamine employing methods similar to those described in Example 202 and was obtained as a white solid. $^1$H NMR (400 MHz, CDCl$_3$) δ 10.33 (t, J=4.9 Hz, 1 H), 8.56 (s, 1 H), 7.67 (s, 1 H), 7.22 (dd, J=8.4, 5.4 Hz, 2 H), 7.01 (t, J=8.6 Hz, 2 H), 4.37 (t, J=7.8 Hz, 2 H), 4.12 (s, 2 H), 3.86 (t, J=5.2 Hz, 2 H), 3.63 (m, 2 H), 3.14 (t, J=6.8 Hz, 2 H), 2.95 (s, 3 H), 2.18 (m, 2 H); HRMS C$_{22}$H$_{24}$FN$_3$O$_6$S (M+H)+ calcd 478.1370, found 478.1440.

EXAMPLE 267

7-(4-Fluorobenzyl)-4-hydroxy-N-(2-isopropoxyethyl)-1-methyl-2-oxo-1,2-dihydro-1,5-naphthyridine-3-carboxamide The title compound was made in a similar manner to example 96 using 2-aminoethylisopropylether to give a white solid: $^1$H NMR (CDCl$_3$) δ 10.35 (1H, m), 8.56 (1H, s), 7.38 (1H, s), 7.15 (2H, m), 7.02 (2H, m), 4.13 (2H, s), 3.62 (5H, m), 3.58 (3H, s), 1.19 (6H, d, J=6 Hz); HRMS calcd for C$_{22}$H$_{24}$FN$_3$O$_4$+H+: 414.1829. Found: 414.1834.

EXAMPLE 268

1-(4-fluorophenyl)-7-[(4-fluorophenyl)methyl]-4-hydroxy-N-(2-hydroxypropyl)-2-oxo-1,2-dihydro-1,5-naphthyridine-3-carboxamide In a similar manner to that described in example 196, from ethyl 1-(4-fluorophenyl)-7-[(4-fluorophenyl)methyl]-4-hydroxy-2-oxo-1,2-dihydro-1,5-naphthyridine-3-carboxylate (20 mg, 0.043 mmol) and 1-amino-2-propanol (0.05 mL) was prepared 1-(4-fluorophenyl)-7-[(4-fluorophenyl)methyl]-4-hydroxy-N-(2-hydroxypropyl)-2-oxo-1,2-dihydro-1,5-naphthyridine-3-carboxamide (15 mg, 75% yield) as a white solid. $^1$H NMR (CDCl$_3$) δ 10.22 (br s, 1 H), 8.53 (s, 1 H), 7.31-7.25 (m, 2 H), 7.22-7.18 (m, 2 H), 7.03-6.92 (m, 4 H), 6.72 (s, 1 H), 4.03 (m, 1 H), 3.94 (s, 2 H), 3.56 (m, 1 H), 3.36 (m, 1 H), 1.24 (d, J=6.4 Hz, 3 H). MS m/z 466 (M+1).

EXAMPLE 269

N-[2-(acetylamino)ethyl]-1-(4-fluorophenyl)-7-[(4-fluorophenyl)methyl]-4-hydroxy-2-oxo-1,2-dihydro-1,5-naphthyridine-3-carboxamide In a similar manner to that described in example 196, from ethyl 1-(4-fluorophenyl)-7-[(4-fluorophenyl)methyl]-4-hydroxy-2-oxo-1,2-dihydro-1,5-naphthyridine-3-carboxylate (20 mg, 0.043 mmol) and N-(2-aminoethyl)acetamide (60 mg, 0.595 mmol), was prepared N-[2-(acetylamino)-1-(4-fluorophenyl)-7-[(4-fluorophenyl)methyl]-4-hydroxy-2-oxo-1,2-dihydro-1,5-naphthyridine-3-carboxamide (12 mg, 57% yield) as a white solid after purification by reverse phase HPLC. $^1$H NMR (CDCl$_3$) δ 10.17 (br s, 1 H), 8.54 (s, 1 H), 7.32-7.27 (m, 2 H), 7.22-7.18 (m, 2 H), 7.03-6.93 (m, 4 H), 6.74 (s, 1 H), 6.03 (br s, 1 H), 3.96 (s, 2 H), 3.58 (m, 2 H), 3.46 (m, 2 H), 1.97 (s, 3 H); MS m/z 493 (M+1).

EXAMPLE 270

1-(4-fluorophenyl)-7-[(4-fluorophenyl)methyl]-4-hydroxy-N-(2-hydroxy-1-methylethyl)-2-oxo-1,2-dihydro-1,5-naphthyridine-3-carboxamide In a similar manner to that described in example 196, from ethyl 1-(4-fluorophenyl)-7-[(4-fluorophenyl)methyl]-4-hydroxy-2-oxo-1,2-dihydro-1,5-naphthyridine-3-carboxylate (20 mg, 0.043 mmol) and 2-amino-1-propanol (0.05 mL), was prepared 1-(4-fluorophenyl)-7-[(4-fluorophenyl)methyl]-4-hydroxy-N-(2-hydroxy-1-methylethyl)-2-oxo-1,2-dihydro-1,5-naphthyridine-3-carboxamide (8.8 mg, 44% yield) as a white solid after purification by reverse phase HPLC. $^1$H NMR (CDCl$_3$) δ 10.06 (d, J=7.6 Hz, 1 H), 8.53 (s, 1 H), 7.31-7.27 (m, 2 H), 7.22-7.18 (m, 2 H), 7.03-6.93 (m, 4 H), 6.71 (s, 1 H), 4.29 (m, 1 H), 3.95 (s, 2 H), 3.73 (dd, J=10.8, 4 Hz, 1 H), 3.62 (dd, J=10.8, 6.4 Hz, 1 H), 1.26 (d, J=6.8 Hz, 3 H); MS m/z 466 (M+1).

EXAMPLE 271

7-[(4-fluorophenyl)methyl]-4-hydroxy-1-[3-(methylsulfonyl)propyl]-2-oxo-N-[3-(2-oxo-1-pyrrolidinyl)propyl]-1,2-dihydro-1,5-naphthyridine-3-carboxamide This compound was prepared from ethyl 7-[(4-fluorophenyl)methyl]-4-hydroxy-1-[3-(methylsulfonyl)propyl]-2- oxo-1,2-dihydro-1,5-naphthyridine-3-carboxylate and 1-(3-aminopropyl)-2-pyrrolidinone employing methods similar to those described in Example 202 and was obtained as a white solid. $^1$H NMR (400 MHz, CDCl$_3$) δ 10.23 (t, J=5.5 Hz, 1 H), 8.55 (s, 1 H), 7.65 (s, 1 H), 7.20 (dd, J=8.5, 5.4 Hz, 2 H), 7.00 (t, J=8.8 Hz, 2 H), 4.39 (t, J=7.7 Hz, 2 H), 4.11 (s, 2 H), 3.46-3.35 (m, 6 H), 3.13 (t, J=7.1 Hz, 2 H), 2.94 (s, 3 H), 2.39 (t, J=8.2 Hz, 2 H), 2.19 (m, 2 H), 2.03 (m, 2 H), 1.85 (m, 2 H); HRMS $C_{27}H_{31}FN_4O_6S$ (M+H)$^+$ calcd 559.1948, found 559.2055.

EXAMPLE 272

N-(2-Ethoxyethyl)-7-(4-fluorobenzyl)-4-hydroxy-1-methyl-2-oxo-1,2-dihydro-1,5-naphthyridine-3-carboxamide The title compound was made in a similar manner to example 96 using 2-ethoxyethylamine to give a white solid: $^1$H NMR (CDCl$_3$) δ 10.35 (1H, m), 8.57 (1H, s), 7.38 (1H, s), 7.15 (2H, m), 7.02 (2H, m), 4.13 (2H, s), 3.63 (4H, m), 3.58 (3H, s), 3.56 (2H, m), 1.23 (3H, t, J=7 Hz); HRMS calcd for $C_{21}H_{22}FN_3O_4$+H$^+$: 400.1673. Found: 400.1692.

EXAMPLE 273

7-(4-Fluorobenzyl)-4-hydroxy-1-methyl-2-oxo-N-(2-propoxyethyl)-1,2-dihydro-1,5-naphthyridine-3-carboxamide The title compound was made in a similar manner to example 96 using 2-N-propoxyethylamine to give a white solid: $^1$H NMR (CDCl$_3$) δ 10.36 (1H, m), 8.57 (1H, s), 7.38 (1H, s), 7.15 (2H, m), 7.02 (2H, m), 4.13 (2H, s), 3.63 (4H, m), 3.58 (3H, s), 3.45 (2H, m), 1.62 (2H, m), 0.94 (3H, t, J=7 Hz); HRMS calcd for $C_{22}H_{24}FN_3O_4$+H$^+$: 414.1829. Found: 414.1825.

EXAMPLE 274

7-[(4-Fluorophenyl)methyl]-4-hydroxy-N-(4-hydroxybutyl)-1-(1H-imidazol-2-ylmethyl)-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.03 (br, 1 H), 8.30 (s, 1 H), 7.95 (s, 1 H), 7.03 (dd, J=8.4, 5.3 Hz, 2 H), 6.83 (t, J=8.7 Hz, 2 H), 6.81 (s, 2 H), 5.30 (s, 2 H), 3.99 (s, 2 H), 3.50 (m, 2 H), 3.34 (m, 2 H), 1.64-1.48 (m, 4 H); HRMS m/z calcd for $C_{24}H_{25}N_5O_4$ (M+H)$^+$ 466.1891, found 466.1906.

EXAMPLE 275

7-[(4-fluorophenyl)methyl]-4-hydroxy-N-{3-[(1-methylethyl)oxy]propyl}-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and 3-isopropoxypropylamine employing methods similar to those described in Example 2 and was obtained as a white solid: $^1$H NMR (d$_6$-DMSO) δ 11.73 (1H, br s), 10.71 (1H, br s), 10.23 (1H, br s), 8.17 (1H, br s), 7.28-7.24 (3H, m), 7.15-7.10 (2H, t, J=8.4 Hz), 4.00 (2H, s), 3.52-3.46 (1H, m), 3.39 (2H, t, J=6 Hz), 3.30-3.21 (2H, m), 1.68-1.62 (2H, m), 1.06 (6H, d, J=6.1 Hz); HRMS calcd for $C_{22}H_{24}FN_3O_4$+H$^+$: 414.1829. Found 414.1810.

EXAMPLE 276

7-[(4-fluorophenyl)methyl]-4-hydroxy-N-[(2R)-2-hydroxypropyl]-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and R-(−)-1-amino-2-propanol employing methods similar to those described in Example 2 and was obtained as a white solid: $^1$H NMR (d$_6$-DMSO) tautomers are observed δ 11.81 (1H, t, J=5.7), 10.81 (1H, br s), 10.10 (1H, br s), 8.18 (0.58H, s), 8.15 (0.42H, s), 7.36-7.23 (3H, m), 7.15-7.08 (2H, m), 4,74 (1H, t, J=4.4 Hz), 3.98 (2H, s), 3.75-3.65 (1H, m), 3.26-3.15 (2H, m), 1.06 (3H, m); HRMS calcd for $C_{19}H_{18}FN_3O_4$+H$^+$: 372.1360. Found 372.1367.

EXAMPLE 277

N-[2-(Ethylthio)ethyl]-7-[(4-fluorophenyl)methyl]-4-hydroxy-1-methyl-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (15 mg, 0.042 mmol) described in example 92 and [2-(ethylthio)ethyl]amine 2-(ethylthio)ethanamine (38 mg, 0.373 mmol), was prepared N-[2-(ethylthio)ethyl]-7-[(4-fluorophenyl)methyl]-4-hydroxy-1-methyl-2-oxo-1,2-dihydro-1,5-naphthyridine-3-carboxamide (13 mg, 76% yield) as a white solid after purification by reverse phase HPLC. $^1$H NMR (CDCl$_3$) δ 10.43 (br s, 1 H), 8.57 (s, 1 H), 7.39 (s, 1 H), 7.18-7.14 (m, 2 H), 7.05-7.00 (m, 2 H), 4.14 (s, 2 H), 3.66 (m, 2 H), 3.59 (s, 3 H), 2.79 (m, 2 H), 2.61 (m, 2 H), 1.29 (m, 3 H); MS m/z 416 (M+1).

EXAMPLE 278

7-[(4-Fluorophenyl)methyl]-4-hydroxy-1-methyl-N-{[6-(methyloxy)-3-pyridinyl]methyl}-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (10 mg, 0.028 mmol) described in example 92 and {[6-(methyloxy)-3-pyridinyl]methyl}amine 1-[6-(methyloxy)-3-pyridinyl]methanamine (38 mg, 0.373 mmol), was prepared 7-[(4-fluorophenyl)methyl]-4-hydroxy-1-methyl-N-{[6-(methyloxy)-3-pyridinyl]methyl}-2-oxo-1,2-dihydro-1,5-naphthyridine-3-carboxamide (4 mg, 32% yield) as a white solid after purification by reverse phase HPLC. $^1$H NMR (CDCl$_3$) δ 10.49 (brs, 1 H), 8.57 (s, 1 H), 8.15 (d, J=2.4 Hz, 1 H), 7.59 (dd, J=8.4, 2.4 Hz, 1 H), 7.38 (s, 1 H), 7.17-7.13 (m, 2 H), 7.04-6.99 (m, 2 H), 6.72 (d, J=8.4 Hz, 1 H), 4.55 (d, J=6 Hz, 2 H), 4.13 (s, 2 H), 3.91 (s, 3 H), 3.55 (s, 3 H); HRMS m/z calcd for $C_{24}H_{22}N_4O_4F$: 449.1625 Found: 449.1626

EXAMPLE 279

7-[(4-Fluorophenyl)methyl]-4-hydroxy-1-methyl-2-oxo-N-[2-(2-oxo-1-imidazolidinyl)ethyl]-1,2-dihydro-1,5-naphthyridine-3-carboxamide In a similar manner to that described in example 196, from ethyl 7-[(4-fluorophenyl)methyl]-4-hydroxy-1-methyl-2- oxo-1,2-dihydro-1,5-naphthyridine-3-carboxylate (10 mg, 0.028 mmol) described in example 92 and 1-(2-aminoethyl)-2-imidazolidinone (47 mg, 0.364 mmol), was prepared 7-[(4-fluorophenyl)methyl]-4-hydroxy-1-methyl-2-oxo-N-[2-(2-oxo-1-imidazolidinyl)ethyl]-1,2-dihydro-1,5-naphthyridine-3-carboxamide (12 mg, 98% yield) as a white solid after purification by reverse phase HPLC. $^1$H NMR (CDCl$_3$) δ 10.33 (br s, 1 H), 8.54 (s, 1 H), 7.37 (s, 1 H), 7.16-7.13 (m, 2 H), 7.03-6.99 (m, 2 H), 4.38 (s, 1 H), 4.12 (s, 2 H), 3.62 (m, 2 H), 3.56-3.53 (m, 5 H), 3.45-3.39 (m, 4 H); HRMS m/z calcd for C$_{22}$H$_{23}$N$_5$O$_4$F: 440.1734 Found: 440.1732.

EXAMPLE 280

N-[2-(ethylamino)ethyl]-7-[(4-fluorophenyl)methyl]-4-hydroxy-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and N-ethylethylenediamine employing methods similar to those described in Example 2 and was obtained as a white solid: $^1$H NMR (d$_6$-DMSO) δ 11.72 (1H, br s), 10.68 (1H, br s), 8.17 (1H, s), 7.27 (3H, br s), 7.12 (2H, t, J=8.7 Hz), 4.00 (2H, s), 2.62-2.48 (6H, m), 0.99 (3H, t,J =7.1 Hz); HRMS calcd for C$_{20}$H$_{21}$FN$_4$O$_3$+H$^+$: 385.1676. Found 385.1685.

EXAMPLE 281

7-[(4-fluorophenyl)methyl]-4-hydroxy-1-methyl-N-(2-{[(methylamino)carbonothioyl]amino}ethyl)-2-oxo-1,2-dihydro-1,5-naphthyridine-3-carboxamide.

In a similar manner to that described in example 196, from ethyl 7-[(4-fluorophenyl)methyl]-4-hydroxy-1-methyl-2-oxo-1,2-dihydro-1,5-naphthyridine-3-carboxylate (10 mg, 0.028 mmol) described in example 92 and N-(2-aminoethyl)-N'-methylthiourea (48 mg, 0.364 mmol), was prepared 7-[(4-fluorophenyl)methyl]-4-hydroxy-1-methyl-N-(2-{[(methylamino)carbonothioyl]amino}ethyl)-2-oxo-1,2-dihydro-1,5-naphthyridine-3-carboxamide(4 mg, 33% yield) as a white solid after purification by reverse phase HPLC. $^1$H NMR (CDCl$_3$) δ 10.55 (br s, 1 H), 8.56 (s, 1 H), 7.40 (s, 1 H), 7.24-7.15 (m, 2 H), 7.05-7.00 (m, 2 H), 6.79 (br s, 1 H), 6.19 (br s, 1 H), 4.14 (s, 2 H), 3.75-3.70 (m, 4 H), 3.56 (s, 3 H), 2.95 (s, 3 H); HRMS m/z calcd for C$_{21}$H$_{23}$N$_5$O$_3$FS: 444.1506 Found: 444.1532.

EXAMPLE 282

7-[(4-Fluorophenyl)methyl]-4-hydroxy-1-methyl-2-oxo-N-[(6-oxo-1,6-dihydro-3-pyridinyl)methyl]-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate(10 mg, 0.028 mmol) described in example 92 and 5-(aminomethyl)-2(1H)-pyridinone (50 mg, 0.403 mmol), was prepared 7-[(4-fluorophenyl)methyl]-4-hydroxy-1-methyl-2-oxo-N-[(6-oxo-1,6-dihydro-3-pyridinyl)methyl]-1,2-dihydro-1,5-naphthyridine-3-carboxamide (7 mg, 58% yield) as a white solid after purification by reverse phase HPLC. $^1$H NMR (CDCl$_3$) δ 10.51 (br s, 1 H), 8.59 (s, 1 H), 7.49 (d, J=9.6 Hz, 1 H), 7.39 (s, 2 H), 7.17-7.13 (m, 2 H), 7.04-6.94 (m, 2 H), 6.56 (d, J=9.6 Hz, 1 H), 4.38 (d, J=6 Hz, 2 H), 4.13 (s, 2 H), 3.56 (s, 3 H); HRMS m/z calcd for C23H20N4O4F: 435.1469 Found: 435.1470.

EXAMPLE 283

7-[(4-Fluorophenyl)methyl]-4-hydroxy-1-methyl-2-oxo-N-[3-(1-pyrrolidinyl)propyl]-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (25 mg, 0.070 mmol) described in example 92 and [3-(1-pyrrolidinyl)propyl]amine (0.08 mL of a 4.68 M solution in chloroform, 0.0364 mmol), was prepared 7-[(4-fluorophenyl)methyl]-4-hydroxy-1-methyl-2-oxo-N-[3-(1-pyrrolidinyl)propyl]-1,2-dihydro-1,5-naphthyridine-3-carboxamide (18 mg, 60% yield) as a white solid after purification by reverse phase HPLC. $^1$H NMR (CDCl$_3$) δ 10.32 (br s, 1 H), 8.56 (s, 1 H), 8.51 (s, 1 H), 7.40 (s, 1 H), 7.17-7.14 (m, 2 H), 7.04-7.00 (m, 2 H), 4.13 (s, 2 H), 3.58 (s, 2 H), 3.54-3.52 (m, 2 H), 3.13 (br s, 4 H), 3.03-2.98 (m, 2 H), 2.19-2.06 (m, 2 H), 2.01 (br s, 4 H); HRMS m/z calcd for C$_{24}$H$_{28}$N$_4$O$_3$F: 439.2145 Found: 439.2141.

EXAMPLE 284

7-[(4-Fluorophenyl)methyl]-4-hydroxy-N-methyl-2-oxo-1-(3-pyridinylmethyl)-1,2-dihydro-1,5-naphthyridine-3-carboxamide The title compound was prepared in a similar manner to that described in example 152 using excess amine and ethanol as solvent to provide a white solid. $^1$H NMR (300 MHz, DMSO-d$_6$) δ 10.10 (m, 1 H), 8.59 (s, 1 H), 8.57 (m, 1 H), 8.51 (d, J=4.4 Hz, 1 H), 7.89 (s, 1 H), 7.60 (d, J=7.5 Hz, 1 H), 7.35 (dd, J=7.9, 4.9 Hz, 1 H), 7.25 (dd, J=8.6, 5.7 Hz, 2 H), 7.09 (t, J=8.9 Hz, 2 H), 5.57 (s, 2 H), 4.11 (s, 2 H), 2.95 (d, J=4.8 Hz, 3 H); HRMS m/z calcd for C$_{23}$H$_{20}$N$_4$O$_3$F (M+H)$^+$ 419.1519, found 419.1515.

EXAMPLE 285

7-[(4-Fluorophenyl)methyl]-4-hydroxy-N-(2-hydroxyethyl)-2-oxo-1-(3-pyrridinylmethyl)-1,2-dihydro-1,5-naphthyridine-3-carboxamide The title compound was prepared in a similar manner to that described in example 152 using excess amine and ethanol as solvent to provide a white solid. $^1$H NMR (300 MHz, DMSO-d$_6$) δ 10.37 (m, 1 H), 8.59 (s, 1 H), 8.55 (s, 1 H), 8.49 (m, 1 H), 7.89 (s, 1 H), 7.55 (m, 1 H), 7.35-7.22 (m, 3 H), 7.09 (t, J=8.2 Hz, 2 H), 5.56 (s, 2 H), 4.97 (m, 1 H), 4.11 (s, 2 H), 3.60 (m, 2 H), 3.49 (m, 2 H); HRMS m/z calcd for C$_{24}$H$_{22}$N$_4$O$_4$F (M+H)$^+$ 449.1625, found 449.1606.

EXAMPLE 286

7-[(4-Fluorophenyl)methyl]-4-hydroxy-N-(3-hydroxy-2,2-dimethylpropyl)-1-(1H-imidazol-2-ylmethyl)-2-oxo-1,2-dihydro-1,5-naphthyridine-3-carboxamide The title compound was prepared in a similar manner to that described in example 152 using excess amine and ethanol as solvent to provide a white solid. $^1$H NMR (300 MHz, DMSO-$d_6$) δ 11.94 (br, 1 H), 10.41 (m, 1 H), 8.57 (s, 1 H), 8.02 (s, 1 H), 7.30 (dd, J=8.5, 5.6 Hz, 2 H), 7.13 (t, J=8.8 Hz, 2 H), 7.05 (s, 1 H), 6.83 (s, 1 H), 5.54 (s, 2 H), 4.81 (m, 1 H), 4.12 (s, 2 H), 3.33 (m, 2 H), 3.24 (d, J=5.5 Hz, 2 H), 0.90 (s, 6 H); HRMS m/z calcd for $C_{25}H_{27}N_5O_4F$ (M+H)$^+$ 480.2047, found 480.2033.

EXAMPLE 287

7-[(4-fluorophenyl)methyl]-4-hydroxy-N-(2-hydroxypropyl)-1-[3-(methylsulfonyl)propyl]-2-oxo-1,2-dihydro-1,5-naphthyridine-3-carboxamide This compound was prepared from ethyl 7-[(4-fluorophenyl)methyl]-4-hydroxy-1-[3-(methylsulfonyl)propyl]-2-oxo-1,2-dihydro-1,5-naphthyridine-3-carboxylate and 1-amino-2-propanol employing methods similar to those described in Example 202 and was obtained as a pale yellow solid. $^1$H NMR (400 MHz, CDCl$_3$) δ 10.33 (t, J=5.1 Hz, 1 H), 8.56 (s, 1 H), 7.67 (s, 1 H), 7.21 (dd, J=8.2, 5.4 Hz, 2 H), 7.01 (t, J=8.5 Hz, 2 H), 4.37 (t, J=7.7 Hz, 2 H), 4.12 (s, 2 H), 4.08 (m, 2 H), 3.62 (m, 1 H), 3.35 (m, 1 H), 3.14 (t, J=6.7 Hz, 2 H), 2.95 (s, 3 H), 2.19 (m, 2 H), 1.27 (d, J=6.4 Hz, 3 H); HRMS $C_{23}H_{26}FN_3O_6S$ (M+H)$^+$ calcd 492.1526, found 492.1623.

EXAMPLE 288

7-[(4-fluorophenyl)methyl]-4-hydroxy-N-(2-hydroxyethyl)-1-methyl-2-oxo-1,2-dihydro-1,5-naphthyridine-3-carboxamide sodium salt Step 1: Synthesis of methyl 5-[(4-fluorophenyl)methyl]-3-(methylamino)-2-pyridinecarboxylate This compound was prepared from methyl 3-amino-5-[(4-fluorophenyl)methyl]-2-pyridinecarboxylate as described in Example 89, Steps 9-10 by reacting with trifluoroacetic anhydride, followed by alkylation with methyl iodide and subsequent deprotection upon heating in the presence of MeOH.

$^1$H NMR (CDCl$_3$) δ 7.84 (1H, s), 7.61 (1H, br s), 7.14-7.10 (2H, m), 6.99-6.94 (2H, m), 3.92 (5H, s), 2.83 (3H, d, J=5 Hz); ES$^+$ MS: 275 (M+H$^+$, 100).

Step 2: Synthesis of ethyl 7-[(4-fluorophenyl)methyl]-4-hydroxy-1-methyl-2-oxo-1,2-dihydro-1,5-naphthyridine-3-carboxylate A solution of methyl 5-[(4-fluorophenyl)methyl]-3-(methylamino)-2-pyridinecarboxylate (110.3 g, 0.402 mol) in DCE (1L) was heated to 50° C. and ethylmalonylchloride (5.7 g, 0.502 mol) was added streamwise over a period of 3 min.

The reaction mixture was heated at 85° C. for 1 h. After cooling to room temperature, added a 1N solution of K$_2$CO$_3$ (1.7 L), stirred for 15 min. and separated layers. The organic layer was washed with water (1.5L), added EtOH (3.4 L) and distilled solvents to a final volume of 1.3 L. Added streamwise a 2.68 M solution of NaOEt in EtOH (102 ml), over a period of 7 min. After 30 min, a solid precipitated, cooled to 0° C. and added conc. HCl (20 ml), followed by 1N HCl (200 ml) to pH 2-3. Extracted with CH$_2$Cl$_2$ and the organic layer was distilled to evaporate the CH$_2$Cl$_2$. $^1$H NMR (CDCl$_3$) δ 8.51 (1H, s), 7.35 (1H, s), 7.18-7.15 (2H, m), 7.05-7.01 (2H, m), 4.51 (2H, q, J=7 Hz), 4.19 (2H, s), 3.56 (3H, s), 1.23 (3H, t, J=7 Hz); ES$^+$ MS: 357 (M+H$^+$, 100).

Step 3: Synthesis of 7-[(4-fluorophenyl)methyl]-4-hydroxy-N-(2-hydroxyethyl)-1-methyl-2-oxo-1,2-dihydro-1,5-naphthyridine-3-carboxamide To a solution of ethyl 7-[(4-fluorophenyl)methyl]-4-hydroxy-1-methyl-2-oxo-1,2-dihydro-1,5-naphthyridine-3-carboxylate (143.3 g, 0.402 mol) in EtOH (1.3 L) was added NMP (0.5 L) and ethanolamine (27.75 g, 0.454 mol). Distilled EtOH over a period of 2 h and the resulting reaction mixture was heated at 110° C. for 45 min. Cooled to 60° C. and added water dropwise (0.47 L), followed by addition of 1N HCl (0.2 L) to pH 2-3. Cooled to room temperature and diluted by dropwise addition of water (1.2 L). The solids which precipitated were collected by filtration, washed with water and dried under vacuum at 70° C. to afford a tan solid. $^1$H NMR (d$_6$-DMSO) δ 10.41 (1H, t, J=5.5 Hz), 8.53 (1H, s), 8.00 (1H, s), 7.39-7.35 (2H, m), 7.15-7.10 (2H, m), 4.92 (1H, t, J=5 Hz), 4.15 (2H, s), 3.58 (3H, s), 3.55-3.53 (2H, m), 3.44-3.40 (2H, m); ES$^+$ MS: 372 (M+H$^+$, 100).

Step 4: Synthesis of: 7-[(4-fluorophenyl)methyl]-4-hydroxy-N-(2-hydroxyethyl)-1-methyl-2-oxo-1,2-dihydro-1,5-naphthyridine-3-carboxamide sodium salt.

To a suspension of 7-[(4-fluorophenyl)methyl]-4-hydroxy-N-(2-hydroxyethyl)-1-methyl-2-oxo-1,2-dihydro-1,5-naphthyridine-3-carboxamide (96 g, 0.259 mol) in EtOH (2 L) was added a solution of 1N NaOH (0.298 L) streamwise, over a period of 7 min. Stirred at room temperature for 1 h. The resulting solid was collected by filtration, washed with EtOH and dried under vacuum at 75° C. The product was obtained as a beige solid. $^1$H NMR (d$_6$-DMSO) δ 10.58 (1H, br s), 8.18 (1H, s), 7.62 (1H, s), 7.34-7.31 (2H, m), 7.12-7.08 (2H, m), 4.73 (1H, br s), 4.04 (2H, s), 3.45-3.41 (2H, m), 3.39 (3H, s), 3.27-3.23 (2H, m); ES$^+$ MS: 372 (M+H$^+$, 100.

EXAMPLE 289

7-[(4-Fluorophenyl)methyl]-4-hydroxy-N-[3-(1H-imidazol-1-yl)propyl]-1-methyl-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (10 mg, 0.028 mmol) described in example 92 and [3-(1H-imidazol-1-yl)propyl]amine (48 mg, 0.0384 mmol), was prepared 7-[(4-fluorophenyl)methyl]-4-hydroxy-N-[3-(1H-imidazol-1-yl)propyl]-1-methyl-2-oxo-1,2-dihydro-1,5-naphthyridine-3-carboxamide (4 mg, 33% yield), as a white solid after purification by reverse phase HPLC. $^1$H NMR (CDCl$_3$) δ 10.36 (br s, 1 H), 8.59 (s, 1 H), 7.74 (s, 1 H), 7.42 (s, 1 H), 7.18-7.14 (m, 2 H), 7.12 (s, 1 H), 7.05-7.01 (m, 3 H), 4.15 (s, 2 H), 4.11-4.07 (m, 2 H), 3.59 (s, 3 H), 3.51-3.45 (m, 2 H), 2.19-2.12 (m, 2 H); MS m/z 436 (M+1).

EXAMPLE 290

7-[(4-fluorophenyl)methyl]-4-hydroxy-1-methyl-N-[2-(1-methyl-1H-pyrrol-2-yl)ethyl]-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (13 mg, 0.0365 mmol) described in example 92 and [2-(1-methyl-1H- pyrrol-2-yl)ethyl]amine (45 mg, 0.364 mmol), was prepared 7-[(4-fluorophenyl)methyl]-4-hydroxy-1-methyl-N-[2-(1-methyl-1H-pyrrol-2-yl)ethyl]-2-oxo-1,2-dihydro-1,5-naphthyridine-3-carboxamide (13 mg, 86% yield) as a white solid after purification by reverse phase HPLC. $^1$H NMR (CDCl$_3$) δ 10.31 (br s, 1 H), 8.56 (s, 1 H), 7.38 (s, 1 H), 7.17-7.13 (m, 2 H), 7.04-6.99 (m, 2 H), 6.56 (m, 1 H), 6.06 (m, 1 H), 5.99 (s, 1 H), 4.12 (s, 2 H), 3.68 (m, 2 H), 3.59 (s, 3 H), 3.57 (s, 3 H), 2.90 (m, 2 H); MS m/z 435 (M+1).

EXAMPLE 291

7-[(4-fluorophenyl)methyl]-4-hydroxy-1-methyl-2-oxo-N-(1,3-thiazol-2-ylmethyl)-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate(10 mg, 0.028 mmol) described in example 92 and (1,3-thiazol-2-ylmethyl)amine (41 mg, 0.0364 mmol), was prepared 7-[(4-fluorophenyl)methyl]-4-hydroxy-1-methyl-2-oxo-N-(1,3-thiazol-2-ylmethyl)-1,2-dihydro-1,5-naphthyridine--carboxamide (12 mg, 98% yield) as a tan solid after purification by reverse phase HPLC. $^1$H NMR (CDCl$_3$) δ 10.89 (br s, 1H), 8.52 (s, 1H), 7.75 (d, J=3.2 Hz, 1H), 7.39 (s, 1H), 7.29 (d, J=3.2 Hz, 1H), 7.17-7.13 (m, 2H), 7.04-6.99 (m, 2H), 4.97 (d, J=5.6 Hz, 2H), 4.13 (s, 2H), 3.59 (s, 3H); MS m/z 425 (M+1).

EXAMPLE 292

7-[(4-Fluorophenyl)methyl]-4-hydroxy-N-(2-hydroxy-1,1-dimethylethyl)-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and 2-amino-2-methyl-1-propanol employing methods similar to those described in Example 2 and using N,N-dimethylformamide as the reaction solvent. The product was obtained as an off-white solid: $^1$H NMR (d$_6$-DMSO) tautomers are observed δ 11.95 (1H, br s), 10.95 (1H, br s), 10.01 (1H, br s), 8.17 (0.70H, s), 8.13 (0.30H, s), 7.34-7.25 (3H, m), 7.15-7.09 (2H, m), 4.86 (1H, br s), 3.98 (2H, s), 3.50-3.41 (2H, m), 1.29 (3H, s), 1.24 (3H, s); HRMS calcd for C$_{20}$H$_{20}$FN$_3$O$_4$+H$^+$: 386.1516. Found 386.1521.

EXAMPLE 293

7-[(4-Fluorophenyl)methyl]-4-hydroxy-2-oxo-N-[3-(2-oxo-1-pyrrolidinyl)propyl]-1-(3-pyridinylmethyl)-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.28 (m, 1H), 8.55 (s, 1H), 8.51 (d, J=4.6 Hz, 1H), 8.39 (s, 1H), 7.32 (d, J=8.0 Hz, 1H), 7.17 (dd, J=8.0, 4.8 Hz, 1 H), 7.13 (s, 1 H), 7.00-6.98 (m, 4 H), 5.39 (s, 2 H), 4.02 (s, 2 H), 3.47 (m, 2 H), 3.44-3.39 (m, 4 H), 2.40 (m, 2 H), 2.04 (m, 2 H), 1.88 (m, 2 H); HRMS m/z calcd for C$_{29}$H$_{29}$N$_5$O$_4$F (M+H)$^+$ 530.2204, found 530.2189.

EXAMPLE 294

7-[(4-Fluorophenyl)methyl]-4-hydroxy-2-oxo-1-(3-pyridinylmethyl)-1,2-dihydro-1,5-naphthyridine-3-carboxamide The title compound was prepared in a similar manner to that described in example 152 using ammonium hydroxide (aq) in ethanol to provide a white solid. $^1$H NMR (300 MHz, DMSO-d$_6$) δ 9.57 (br, 1 H), 8.70 (br, 1 H), 8.57 (s, 1 H), 8.54 (s, 1 H), 8.49 (d, J=4.6 Hz, 1 H), 7.86 (s, 1 H), 7.55 (d, J=7.3 Hz, 1 H), 7.31 (dd, J=7.9, 4.5 Hz, 1 H), 7.24 (m, 2 H), 7.08 (m, 2 H), 5.79 (s, 2 H), 5.55 (s, 2 H), 4.10 (s, 2 H); HRMS m/z calcd for C$_{22}$H$_{18}$N$_4$O$_3$F (M+H)$^+$ 405.1363, found 405.1348.

EXAMPLE 295

7-[(4-Fluorophenyl)methyl]-4-hydroxy-N-[(2S)-2-hydroxypropyl]-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and S-(+)-1-amino-2-propanol employing methods similar to those described in Example 2 and was obtained as a white solid: $^1$H NMR (d$_6$-DMSO) δ 11.82 (1H, br s), 10.35 (1H, br s), 8.50 (1H, s), 7.45 (1H, s), 7.31-7.27 (2H, m), 7.15 (2H, t, J=8.7 Hz), 4.93 (1H, d, J=4.2 Hz), 4.11 (2H, s), 3.80-3.75 (1H, m), 3.42-3.39 (1H, m), 3.20-3.14 (1H, m), 1.07 (3H, d, J=6.1 Hz); HRMS calcd for C$_{19}$H$_{18}$FN$_3$O$_4$+H$^+$: 372.1360. Found 372.1355.

EXAMPLE 296

N-(2,3-dihydroxypropyl)-7-[(4-fluorophenyl)methyl]-4-hydroxy-1-methyl-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (10 mg, 0.028 mmol) described in example 92 and 3-amino-1,2-propanediol (36 mg, 0.393 mmol), was prepared N-(2,3-dihydroxypropyl)-7-[(4-fluorophenyl)methyl]-4-hydroxy-1-methyl-2-oxo-1,2-dihydro-1,5-naphthyridine-3-carboxamide (10 mg, 91% yield) as a white solid after purification by reverse phase HPLC. $^1$H NMR (CDCl$_3$) δ 10.49 (br s, 1 H), 8.56 (s, 1 H), 7.39 (s, 1 H), 7.17-7.13 (m, 2 H), 7.04-6.99 (m, 2 H), 4.13 (s, 2 H), 3.92 (m, 1 H), 3.67-3.54 (m, 4 H), 3.57 (s, 3 H).

EXAMPLE 297

N-[2-(acetylamino)ethyl]-7-[(4-fluorophenyl)methyl]-4-hydroxy-1-methyl-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (20 mg, 0.056 mmol) described in example 92 and N-(2-aminoethyl)acetamide (74 mg, 0.730 mmol), was prepared N-[2-(acetylamino)ethyl]-7-[(4-fluorophenyl)methyl]-4-hydroxy-1-methyl-2-oxo-1,2-dihydro-1,5-naphthyridine-3-carboxamide (9 mg, 39% yield) as a white solid after purification by reverse phase HPLC. $^1$H NMR (CDCl$_3$) δ 10.39 (br s, 1 H), 8.56 (s, 1 H), 7.39 (s, 1 H), 7.17-7.15 (m, 2 H), 7.04-6.94 (m, 2 H), 6.09

(br s, 1 H), 4.13 (s, 2 H), 3.61-3.58 (m, 2 H), 3.57 (s, 3 H), 3.51-3.48 (m, 2 H), 1.98 (s, 3 H); MS m/z 413 (M+1).

EXAMPLE 298

7-[(4-fluorophenyl)methyl]-4-hydroxy-N-(2-hydroxyethyl)-1-{2-[(methylsulfonyl)amino]ethyl}-2-oxo-1,2-dihydro-1,5-naphthyridine-3-carboxamide Ethyl 3-{[2-({[(1,1-dimethylethyl)oxy]carbonyl}amino)ethyl]amino}-5-[(4-fluorophenyl)methyl]-2-pyridinecarboxylate. This compound was prepared from ethyl 3-amino-5-[(4-fluorophenyl)methyl]-2-pyridinecarboxylate and t-butyl N-(2-oxoethyl)carbamate employing methods similar to those described in Example 202 and was obtained as a white solid. $^1$H NMR (400 MHz, CDCl$_3$) δ 7.88 (d, J=1.4 Hz, 1 H), 7.80 (br, 1 H), 7.13 (dd, J=7.9, 5.8 Hz, 2 H), 6.98-6.93 (m, 3 H), 4.85 (br, 1 H), 4.38 (q, J=7.1 Hz, 2 H), 3.90 (s, 2 H), 3.30 (m, 4 H), 1.43-1.38 (m, 12 H); MS m/z 418 (M+H)$^+$.

Ethyl 3-[(2-aminoethyl)amino]-5-[(4-fluorophenyl)methyl]-2-pyridinecarboxylate. To a mixture of dichloromethane (2 mL) and trifluoroacetic acid (2 mL) was added ethyl 3-{[2-({[(1,1-dimethylethyl)oxy]carbonyl}amino)ethyl]amino}-5-[(4-fluorophenyl)methyl]-2-pyridinecarboxylate. The reaction mixture was stirred at room temperature for 3 hours, then concentrated in vacuo. The crude residue was partitioned between ethyl acetate and saturated aqueous sodium bicarbonate solution. The organic layer was washed with water and brine, then dried over sodium sulfate. Filtration and concentration provided ethyl 3-[(2-aminoethyl)amino]-5-[(4-fluorophenyl)methyl]-2-pyridinecarboxylate as a light yellow oil. $^1$H NMR (400 MHz, CDCl$_3$) δ 7.77 (s, 1 H), 7.72 (t, J=5.8 Hz, 1 H), 7.06 (dd, J=8.4, 5.4 Hz, 2 H), 6.90 (t, J=8.7 Hz, 2 H), 6.81 (s, 1 H), 6.63 (br, 2 H), 4.27 (q, J=7.1 Hz, 2 H), 3.79 (s, 2 H), 3.45 (m, 2 H), 3.08 (m, 2 H), 1.29 (t, J=7.2 Hz, 3 H).

Ethyl 5-[(4-fluorophenyl)methyl]-3-({2-[(methylsulfonyl)amino]ethyl}amino)-2-pyridinecarboxylate. To a cold (0° C.) solution of ethyl 3-[(2-aminoethyl)amino]-5-[(4-fluorophenyl)methyl]-2-pyridinecarboxylate (90 mg, 0.284 mmol) and triethylamine (59 μL, 0.426 mmol) in dichloromethane (1 mL) was added methanesulfonyl chloride (26 μL, 0.341 mmol) in dichloromethane (1 mL) dropwise. The reaction mixture was warmed to room temperature and stirred one hour. The reaction mixture was quenched with ice and diluted with dichloromethane. The organic layer was washed with water and brine, then dried over sodium sulfate. Filtration and concentration, followed by flash chromatography (0 to 5%, methanol in dichloromethane) provided ethyl 5-[(4-fluorophenyl)methyl]-3-({2-[(methylsulfonyl)amino]ethyl}amino)-2-pyridinecarboxylate as a clear oil. $^1$H NMR (400 MHz, CDCl$_3$) δ 7.91 (s, 1 H), 7.87 (t, J=5.6 Hz, 1 H), 7.13 (dd, J=8.3, 5.5 Hz, 2 H), 6.97 (t, J=8.7 Hz, 2 H), 6.89 (s, 1 H), 4.93 (m, 1 H), 4.39 (q, J=7.1 Hz, 2 H), 3.91 (s, 2 H), 3.38 (m, 2 H), 3.33 (m, 2 H), 2.94 (s, 3 H), 1.41 (t, J=7.1 Hz, 3 H); MS m/z 396 (M+H)$^+$.

Ethyl 3-([3-(ethyloxy)-3-oxopropanoyl]{2-[(methylsulfonyl)amino]ethyl}amino)-5-[(4-fluorophenyl)methyl]-2-pyridinecarboxylate. This compound was prepared from ethyl 5-[(4-fluorophenyl)methyl]-3-({2-[(methylsulfonyl)amino]ethyl}amino)-2-pyridinecarboxylate employing methods similar to those described in Example 202. The desired compound was separated from a di-acylated biproduct via flash chromotography and was obtained as a clear oil. $^1$H NMR (400 MHz, CDCl$_3$) δ 8.59 (d, J=1.4 Hz, 1 H), 7.71 (s, 1 H), 7.17 (dd, J=8.4, 5.4 Hz, 2 H), 7.01 (t, J=8.7 Hz, 2 H), 5.34 (t, J=5.7 Hz, 1 H), 4.43 (q, J=7.1 Hz, 2 H), 4.15 (m, 1 H), 4.04 (s, 2 H), 4.00 (m, 2 H), 3.52 (m, 1 H), 3.39 (m, 1 H), 3.31 (m, 1 H), 3.17-3.04 (m, 2 H), 2.95 (s, 3 H), 1.40 (t, J=7.1 Hz, 3 H), 1.16 (t, J=7.1 Hz, 3 H).

Ethyl 7-[(4-fluorophenyl)methyl]-4-hydroxy-1-{2-[(methylsulfonyl)amino]ethyl}-2-oxo-1,2-dihydro-1,5-naphthyridine-3-carboxylate. This compound was prepared from ethyl 3-([3-(ethyloxy)-3-oxopropanoyl]{2-[(methylsulfonyl)amino]ethyl}amino)-5-[(4-fluorophenyl)methyl]-2-pyridinecarboxylate and employing methods similar to those described in Example 202 and was obtained as a white solid. $^1$H NMR (400 MHz, CDCl$_3$) δ 8.41 (s, 1 H), 7.86 (s, 1 H), 7.19 (dd, J=8.5, 5.3 Hz, 2 H), 6.95 (t, J=8.6 Hz, 2 H), 4.45 (m, 2 H), 4.28 (m, 2 H), 4.06 (s, 2 H), 3.26 (m, 2 H), 3.12 (br, 1 H), 2.88 (s, 3 H), 1.40 (m, 3 H); MS m/z 464 (M+H)$^+$.

7-[(4-fluorophenyl)methyl]-4-hydroxy-N-(2-hydroxyethyl)-1-{2-[(methylsulfonyl)amino]ethyl}-2-oxo-1,2-dihydro-1,5-naphthyridine-3-carboxamide. This compound was prepared from ethyl 7-[(4-fluorophenyl)methyl]-4-hydroxy-1-{2-[(methylsulfonyl)amino]ethyl}-2-oxo-1,2-dihydro-1,5-naphthyridine-3-carboxylate and ethanolamine employing methods similar to those described in Example 202 and was obtained as a white solid. $^1$H NMR (400 MHz, DMSO-d$_6$) δ 10.38 (t, J=5.2 Hz, 1 H), 8.55 (s, 1 H), 8.10 (s, 1 H), 7.40 (dd, J=8.2, 5.7 Hz, 2 H), 7.27 (t, J=6.1 Hz, 1 H), 7.13 (t, J=8.8 Hz, 2 H), 4.95 (t, J=5.0 Hz, 1 H), 4.34 (t, J=6.3 Hz, 2 H), 4.14 (s, 2 H), 3.57 (m, 2 H), 3.45 (m, 2 H), 3.24 (m, 2 H), 2.89 (s, 3 H); HRMS C$_{21}$H$_{23}$FN$_4$O$_6$S (M+H)$^+$ calcd 479.1322, found 479.1400.

EXAMPLE 299

7-[(4-fluorophenyl)methyl]-4-hydroxy-N-(2-hydroxyethyl)-1-{[4-(methylsulfonyl)phenyl]methyl}-2-oxo-1,2-dihydro-1,5-naphthyridine-3-carboxamide Ethyl 5-[(4-fluorophenyl)methyl]-3-({[4-(methylsulfonyl)phenyl]methyl}amino)-2-pyridinecarboxylate. This compound was prepared from ethyl 3-amino-5-[(4-fluorophenyl)methyl]-2-pyridinecarboxylate and 4-methylsulfonyl benzaldehyde employing methods similar to those described in Example 265 and was obtained as a yellow solid.

Ethyl 3-([3-(ethyloxy)-3-oxopropanoyl]{[4-(methylsulfonyl)phenyl]methyl}amino)-5-[(4-fluorophenyl)methyl]-2-pyridinecarboxylate. This compound was prepared from ethyl 5-[(4-fluorophenyl)methyl]-3-({[4-(methylsulfonyl)phenyl]methyl}amino)-2-pyridinecarboxylate employing methods similar to those described in Example 202 and was obtained as a yellow oil.

Ethyl 7-[(4-fluorophenyl)methyl]-4-hydroxy-1-{[4-(methylsulfonyl)phenyl]methyl}-2-oxo-1,2-dihydro-1,5-naphthyridine-3-carboxylate. This compound was prepared from ethyl 3-([3-(ethyloxy)-3-oxopropanoyl]{[4-(methylsulfonyl)phenyl]methyl}amino)-5-[(4-fluorophenyl)methyl]-2-pyridinecarboxylate employing methods similar to those described in Example 202 and was obtained as a peach solid.

7-[(4-fluorophenyl)methyl]-4-hydroxy-N-(2-hydroxyethyl)-1-{[4-(methylsulfonyl)phenyl]methyl}-2-oxo-1,2-dihydro-1,5-naphthyridine-3-carboxamide. This compound was prepared from ethyl 7-[(4-fluorophenyl)methyl]-4-hydroxy-1-{[4-(methylsulfonyl)phenyl]methyl}-2-oxo-1,2-dihydro-1,5-naphthyridine-3-carboxylate and ethanolamine employing methods similar to those described in Example 202 and was obtained as a white solid. $^1$H NMR (400 MHz, CD$_3$OD) δ 8.53 (s, 1 H), 7.81 (d, J=8.2 Hz, 2 H), 7.19 (d, J=8.1 Hz, 2 H), 7.05 (s, 1 H), 6.98-6.95 (m, 4 H), 5.41 (br, 2 H), 4.00

(s, 2 H), 3.78 (t, J=5.2 Hz, 2 H), 3.60 (m, 2 H), 3.01 (s, 3 H); HRMS $C_{26}H_{24}FN_3O_6S$ (M+H)$^+$ calcd 526.1370, found 526.1434.

EXAMPLE 300

7-(4-Fluorobenzyl)-4-hydroxy-N-(3-isopropoxypropyl)-1-methyl-2-oxo-1,2-dihydro-1,5-naphthyridine-3-carboxamide The title compound was made in a similar manner to example 96 using 3-isopropoxypropylamine to give a yellow glass: $^1$H NMR (CDCl$_3$) δ 10.21 (1H, m), 8.62 (1H, s), 7.45 (1H, s), 7.16 (2H, m), 7.05 (2H, m), 4.15 (2H, s), 3.51-3.60 (8H, m), 1.89 (2H, m), 1.17 (6H, d, J=7 Hz); HRMS calcd for $C_{23}H_{26}FN_3O_4$+H$^+$: 428.1986. Found: 428.1989.

EXAMPLE 301

7-[(4-Fluorophenyl)methyl]-4-hydroxy-1-methyl-N-{2-[methyl(methylsulfonyl)amino]ethyl}-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (20 mg, 0.056 mmol) described in example 92 and N-(2-aminoethyl)-N-methylmethanesulfonamide (55 mg, 0.364 mmol), was prepared 7-[(4-fluorophenyl)methyl]-4-hydroxy-1-methyl-N-{2[methyl(methylsulfonyl)amino]ethyl}-2-oxo-1,2-dihydro-1,5-naphthyridine-3-carboxamide (24 mg, 96% yield) as a white solid after purification by reverse phase HPLC. $^1$H NMR (CDCl$_3$) δ 10.39 (br s, 1 H), 8.55 (s, 1 H), 7.38 (s, 1 H), 7.16-7.12 (m, 2 H), 7.03-6.99 (m, 2 H), 4.12 (s, 2 H), 3.68-3.63 (m, 2 H), 3.56 (s, 3 H), 3.42-3.38 (m, 2 H), 2.94 (s, 3 H), 2.82 (s, 3 H). HRMS m/z calcd for $C_{21}H_{24}N_4O_5FS$: 463.1451; Found: 463.1443.

EXAMPLE 302

7-[(4-Fluorophenyl)methyl]-4-hydroxy-N-(2-hydroxyethyl)-2-oxo-1-(2-pyridinylmethyl)-1,2-dihydro-1,5-naphthyridine-3-carboxamide The title compound was prepared in a similar manner to that described in example 152 using excess amine and ethanol as solvent to provide a white solid. $^1$H NMR (300 MHz, DMSO-d$_6$) δ 10.38 (m, 1 H), 8.58 (s, 1 H), 8.43 (d, J=4.2 Hz, 1 H), 7.84 (s, 1 H), 7.76 (td, J=7.8, 1.6 Hz, 1 H), 7.30 (m, 2 H), 7.22 (dd, J=8.4, 5.9 Hz, 2 H), 7.09 (t, J=8.8 Hz, 2 H), 5.61 (s, 2 H), 4.95 (m, 1 H), 4.08 (s, 2 H), 3.59 (m, 2 H), 3.47 (m, 2 H); HRMS m/z calcd for $C_{24}H_{22}N_4O_4F$ (M+H)$^+$ 449.1625, found 449.1637.

EXAMPLE 303

7-(4-Fluorobenzyl)-4-hydroxy-N,1-dimethyl-2-oxo-1,2-dihydro-1,5-naphthyridine-3-carboxamide The title compound was made in a similar manner to example 96 using a solution of methylamine in methanol to give a white solid: $^1$H NMR (CDCl$_3$) δ 10.09 (1H, m), 8.57 (1H, s), 7.39 (1H, s), 7.15 (2H, m), 7.02 (2H, m), 4.13 (2H, s), 3.58 (3H, s), 3.02 (3H, d, J=5 Hz); HRMS calcd for $C_{18}H_{16}FN_3O_3$+H$^+$: 342.1254. Found: 342.1254.

EXAMPLE 304

7-[(4-Fluorophenyl)methyl]-4-hydroxy-1-(1H-imidazol-4-ylmethyl)-N-methyl-2-oxo-1,2-dihydro-1,5-naphthyridine-3-carboxamide The title compound was prepared in a similar manner to that described in example 152 using excess amine and ethanol as solvent to provide a white solid as a formate salt. $^1$H NMR (400 MHz, CD$_3$OD) δ 10.04 (m, 1 H), 8.42 (s, 1 H), 8.02 (s, 1 H), 7.98 (s, 1 H), 7.91 (s, 1 H), 7.15 (m, 2 H), 6.96 (s, 1 H), 6.94 (m, 2 H), 5.41 (s, 2 H), 4.12 (s, 2 H), 2.97 (s, 3 H); MS m/z 408 (M+1).

EXAMPLE 305

1-(Cyclopropylmethyl)-7-[(4-fluorophenyl)methyl]-4-hydroxy-N-(2-hydroxypropyl)-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.49 (br, 1 H), 8.56 (s, 1 H), 7.46 (s, 1 H), 7.17 (m, 2 H), 7.04 (m, 2 H), 4.14 (s, 2 H), 4.08 (s, 2 H), 3.61 (m, 1 H), 3.38 (m, 1 H), 2.42 (m, 1 H), 1.27 (br, 3 H), 1.00 (m, 1 H), 0.49 (m, 2 H), 0.40 (m, 2 H); HRMS m/z calcd for $C_{23}H_{25}N_3O_4F$ (M+H)$^+$ 426.1829, found 426.1818.

EXAMPLE 306

7-[(4-Fluorophenyl)methyl]-4-hydroxy-N-(2-hydroxyethyl)-1-(1H-imidazol-4-ylmethyl)-2-oxo-1,2-dihydro-1,5-naphthyridine-3-carboxamide The title compound was prepared in a similar manner to that described in example 152 using excess amine and ethanol as solvent to provide a white solid as a formate salt. $^1$H NMR (400 MHz, CD$_3$OD) δ 10.42 (m, 1 H), 8.40 (s, 1 H), 8.35 (s, 1 H), 7.83 (s, 1 H), 7.47 (s, 1 H), 7.12 (dd, J=8.6, 5.2 Hz, 2 H), 6.95 (t, J=8.6 Hz, 2 H), 6.75 (s, 1 H), 5.33 (s, 2 H), 4.08 (s, 2 H), 3.73 (m, 2 H), 3.55 (m, 2 H); HRMS m/z calcd for $C_{22}H_{21}N_5O_4F$ (M+H)$^+$ 438.1578, found 438.1592.

EXAMPLE 307

1-(Cyclopropylmethyl)-7-[(4-fluorophenyl)methyl]-4-hydroxy-N-methyl-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.11 (br, 1 H), 8.56 (s, 1 H), 7.45 (s, 1 H), 7.15 (m, 2 H), 7.02 (m, 2 H), 4.13 (s, 2 H), 4.08 (d, J=6.9 Hz, 2 H), 3.00 (d, J=4.0 Hz, 3 H), 0.99 (m, 1 H), 0.49 (m, 2 H), 0.40 (m, 2 H); HRMS m/z calcd for $C_{21}H_{21}N_3O_3F$ (M+H)$^+$ 382.1567, found 382.1566.

EXAMPLE 308

7-{[4-Fluoro-2-(trifluoromethyl)phenyl]methyl}-4-hydroxy-N-(2-hydroxyethyl)-2-oxo-1,2-dihydro-1,5-naphthyridine-3-carboxamide This compound was prepared from methyl 7-{[4-fluoro-2-(trifluoromethyl)phenyl]methyl}-4-hydroxy-2-oxo-1,2-dihydro-1,5-naphthyridine-3-carboxylate and ethanolamine employing methods similar to those described in Example 245 and was purified by reverse phase preparative HPLC (C-18 stationary phase; 10-100% CH$_3$CN/water/0.1% formic acid mobile phase). The product was obtained as an off-white solid: $^1$H NMR (d$_6$-DMSO) δ 11.70 (1H, br), 10.33 (1H, m), 8.49 (1H, s), 7.70 (1H, d, J=9 Hz), 7.56 (2H, m), 7.32 (1H, s), 4.91 (1H, br t), 4.32 (2H, s), 3.56 (2H, m), 3.45 (2H, m); ES$^-$ MS: 424 (M−1, 100).

EXAMPLE 309

1-[2-(Dimethylamino)-2-oxoethyl]-7-[(4-fluorophenyl)methyl]-4-hydroxy-2-oxo-N-[2-(propyloxy)ethyl]-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and [2-(propyloxy)ethyl]amine employing methods similar to those described in Example 245 and was purified by reverse phase preparative BPLC (C-18 stationary phase; 10-100% CH$_3$CN/water/0.1% formic acid mobile phase). The product was obtained as a white solid: $^1$H NMR (d$_6$-DMSO) δ 10.63 (1H, br), 8.21 (1H, br s), 7.30 (1H, br s), 7.28 (2H, dd, J~9, 5.6 Hz), 7.11 (2H, t, J~9 Hz), 4.95 (2H, s), 4.01 (2H, s), 3.43-3.30 (6H, m), 3.08 (3H, s), 2.79 (3H, s), 1.50 (2H, m, J=7 Hz), 0.85 (3H, t, J=7 Hz); HRMS calcd for C$_{25}$H$_{29}$FN$_4$O$_5$+H$^+$: 485.2200. Found: 485.2190.

EXAMPLE 310

1-[2-(Dimethylamino)-2-oxoethyl]-7-[(4-fluorophenyl)methyl]-4-hydroxy-N-{2-[(1-methylethyl)oxy]ethyl}-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and 2-[(1-methylethyl)oxy]ethanamine employing methods similar to those described in Example 245 and was purified by reverse phase preparative HPLC (C-18 stationary phase; 10-100% CH$_3$CN/water/0.1% formic acid mobile phase). The product was obtained as a white solid: $^1$H NMR (d$_6$-DMSO) δ 10.67 (1H, br), 8.16 (1H, br s), 7.27 (3H, m), 7.10 (2H, t, J=9 Hz), 4.93 (2H, s), 4.00 (2H, s), 3.54 (1H, m, J=6 Hz), 3.40 (2H, m), 3.31 (2H, m), 3.08 (3H, s), 2.78 (3H, s), 1.08 (6H, d, J=6 Hz); HRMS calcd for C$_{25}$H$_{29}$FN$_4$O$_5$+H$^+$: 485.2200. Found: 485.2205.

EXAMPLE 311

7-{[4-Fluoro-2-(trifluoromethyl)phenyl]methyl}-4-hydroxy-N-(3-hydroxypropyl)-2-oxo-1,2-dihydro-1,5-naphthyridine-3-carboxamide This compound was prepared from methyl 7-{[4-fluoro-2-(trifluoromethyl)phenyl]methyl}-4-hydroxy-2-oxo-1,2-dihydro-1,5-naphthyridine-3-carboxylate and 3-amino-1-propanol employing methods similar to those described in Example 245 and was purified by reverse phase preparative HPLC (C-18 stationary phase; 10-100% CH$_3$CN/water/0.1% formic acid mobile phase). The product was obtained as a white solid: $^1$H NMR (d$_6$-DMSO) δ 11.74 (1H, br), 10.26 (1H, m), 8.49 (1H, s), 7.70 (1H, d, J=9 Hz), 7.56 (2H, m), 7.32 (1H, s), 4.58 (1H, t, J=5 Hz), 4.32 (2H, s), 3.51-3.40 (4H, m), 1.70 (2H, m, J=6 Hz); HRMS calcd for C$_{20}$H$_{17}$F$_4$N$_3$O$_4$+H$^+$: 440.1233. Found: 440.1241.

EXAMPLE 312

7-[(4-fluorophenyl)methyl]-4-hydroxy-N-(2-hydroxypropyl)-1-{[4-(methylsulfonyl)phenyl]methyl}-2-oxo-1,2-dihydro-1,5-naphthyridine-3-carboxamide This compound was prepared from ethyl 7-[(4-fluorophenyl)methyl]-4-hydroxy-1-{[4-(methylsulfonyl)phenyl]methyl}-2-oxo-1,2-dihydro-1,5-naphthyridine-3-carboxylate employing methods similar to those described in Example 202 and was obtained as a white solid. $^1$H NMR (400 MHz, CDCl$_3$) δ 8.51 (s, 1H), 7.80 (d, J=8.4 Hz, 2 H), 7.18 (d, J=8.2 Hz, 2 H), 7.04 (s, 1 H), 6.96-6.94 (m, 4 H), 5.41 (br, 2 H), 4.01-3.96 (m, 4 H), 3.34 (s, 1 H), 3.00 (s, 3 H), 1.21 (d, J=6.2 Hz, 3 H); HRMS C$_{27}$H$_{26}$FN$_3$O$_6$S (M+H)$^+$ calcd 540.1526, found 540.1612.

EXAMPLE 313

7-[(4-fluorophenyl)methyl]-4-hydroxy-1-{[4-(methylsulfonyl)phenyl]methyl}-2-oxo-N-[3-(2-oxo-1-pyrrolidinyl)propyl]-1,2-dihydro-1,5-naphthyridine-3-carboxamide This compound was prepared from ethyl 7-[(4-fluorophenyl)methyl]-4-hydroxy-1-{[4-(methylsulfonyl)phenyl]methyl}-2-oxo-1,2-dihydro-1,5-naphthyridine-3-carboxylate and 1-(3-aminopropyl)-2-pyrrolidinone employing methods similar to those described in Example 202 and was obtained as a white solid. $^1$H NMR (400 MHz, CDCl$_3$) δ 10.25 (t, J=5.3 Hz, 1 H), 8.57 (s, 1 H), 7.84 (d, J=8.2 Hz, 2 H), 7.20 (d, J=8.1 Hz, 2 H), 7.02-6.97 (m, 5 H), 5.45 (br, 2 H), 4.02 (s, 2 H), 3.50-3.38 (m, 6 H), 3.03 (s, 3 H), 2.39 (t, J=7.9 Hz, 2 H), 2.04 (m, 2 H), 1.88 (m, 2 H); HRMS C$_{31}$H$_{31}$FN$_4$O$_6$S (M+H)$^+$ calcd 607.1948, found 607.2043.

EXAMPLE 314

1-(Cyclopropylmethyl)-7-[(4-fluorophenyl)methyl]-4-hydroxy-2-oxo-N-[2-(2-oxo-1-imidazolidinyl)ethyl]-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.37 (m, 1 H), 8.54 (s, 1 H), 7.45 (s, 1 H), 7.15 (dd, J=8.4, 5.3 Hz, 2 H), 7.01 (t, J=8.6 Hz, 2 H), 4.71 (br, 1 H), 4.13 (s, 2 H), 4.06 (d, J=6.6 Hz, 2 H), 3.62 (m, 2 H), 3.55 (m, 2 H), 3.46-3.40 (m, 4 H), 0.98 (m, 1 H), 0.47 (m, 2 H), 0.39 (m, 2 H); HRMS m/z calcd for C$_{25}$H$_{27}$N$_5$O$_4$F (M+H)$^+$ 480.2047, found 480.2035.

EXAMPLE 315

1-(Cyclopropylmethyl)-7-[(4-fluorophenyl)methyl]-4-hydroxy-N-(2-hydroxy-1-methylethyl)-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.32 (d, J=7.8 Hz, 1 H), 8.54 (s, 1 H), 7.43 (s, 1 H), 7.15 (dd, J=8.3, 5.3 Hz, 2 H), 7.02 (t, J=8.6 Hz, 2 H), 4.26 (m, 1 H), 4.12 (s, 2 H), 4.05 (d, J=6.9 Hz, 2 H), 3.76 (dd, J=11.5, 3.9 Hz, 1 H), 3.65 (dd, J=10.7, 6.1 Hz, 1 H), 1.30 (d, J=7.2 Hz, 3 H), 0.98 (m, 1 H), 0.47 (m, 2 H), 0.38 (m, 2 H); HRMS m/z calcd for $C_{23}H_{25}N_3O_4F$ (M+H)$^+$ 426.1829, found 426.1855.

EXAMPLE 316

1-butyl-7-[(4-fluorophenyl)methyl]-4-hydroxy-N-(2-hydroxypropyl)-2-oxo-1,2-dihydro-1,5-naphthyridine-3-carboxamide Step 1: Synthesis of ethyl 1-butyl-7-[(4-fluorophenyl)methyl]-4-hydroxy-2-oxo-1,2-dihydro-1,5-naphthyridine-3-carboxylate.

Ethyl 1-butyl-7-[(4-fluorophenyl)methyl]-4-hydroxy-2-oxo-1,2-dihydro-1,5-naphthyridine-3-carboxylate (50 mg, 0.146 mmol) was dissolved in DMF (5 mL) and lithium (bis-trimethylsilyl)amide (49 mg, 0.292 mmol) and n-butyl iodide (0.1 mL, 0.876 mmol) were added. The reaction was stirred 16 hours and then concentrated under reduced pressure. Water was added and the mixture was acidified with 1 N hydrochloric acid and extracted with dichloromethane. The combined organics were dried over sodium sulfate and concentrated under reduced pressure to afford ethyl 1-butyl-7-[(4-fluorophenyl)methyl]-4-hydroxy-2-oxo-1,2-dihydro-1,5-naphthyridine-3-carboxylate (58 mg, 98% yield) as a yellow oil. $^1$H NMR (CDCl$_3$) δ 8.49 (s, 1 H), 7.22 (s, 1 H), 7.17-7.13 (m, 2 H), 7.04-6.99 (m, 2 H), 4.48 (m, 2 H), 4.11 (s, 2 H), 4.07-4.02 (m, 2 H), 1.51-1.30 (m, 4 H), 1.01-0.850 (m, 6 H); MS m/z 399 (M+1).

Step 2: Synthesis of 1-butyl-7-[(4-fluorophenyl)methyl]-4-hydroxy-N-(2-hydroxypropyl)-2-oxo-1,2-dihydro-1,5-naphthyridine-3-carboxamide.

In a similar manner to that described in example 196, from ethyl 1-butyl-7-[(4-fluorophenyl)methyl]-4-hydroxy-2-oxo-1,2-dihydro-1,5-naphthyridine-3-carboxylate (20 mg, 0.050 mmol) and 1-amino-2-propanol (0.05 mL), was prepared 1-butyl-7-[(4-fluorophenyl)methyl]-4-hydroxy-N-(2-hydroxypropyl)-2-oxo-1,2-dihydro-1,5-naphthyridine-3-carboxamide (8 mg, 38% yield) as a white solid after purification by reverse phase HPLC. $^1$H NMR (CDCl$_3$) δ 10.50 (br s, 1 H), 8.57 (s, 1 H), 7.28 (s, 1 H), 7.19-7.15 (m, 2 H), 7.07-7.02 (m, 2 H), 4.14 (s, 2 H), 4.11-4.07 (m, 3 H), 3.61 (m, 1 H), 3.39 (m, 1 H), 1.57-1.49 (m, 2 H), 1.38-1.24 (m, 6 H), 0.91 (m, 3 H); MS m/z 428 (M+1).

EXAMPLE 317

1-Butyl-7-[(4-fluorophenyl)methyl]-4-hydroxy-N-(2-hydroxyethyl)-2-oxo-1,2-dihydro-1,5-naphthyridine-3-carboxamide In a similar manner to that described in example 196, from ethyl 1-butyl-7-[(4-fluorophenyl)methyl]-4-hydroxy-2-oxo-1,2-dihydro-1,5-naphthyridine-3-carboxylate (20 mg, 0.050 mmol) and 2-aminoethanol (0.05 mL), was prepared 1-butyl-7-[(4-fluorophenyl)methyl]-4-hydroxy-N-(2-hydroxyethyl)-2-oxo-1,2-dihydro-1,5-naphthyridine-3-carboxamide (9 mg, 43% yield) as a white solid after purification by reverse phase HPLC. $^1$H NMR (CDCl$_3$) δ 10.48 (br s, 1 H), 8.55 (s, 1 H), 7.27 (s, 1 H), 7.18-7.15 (m, 2 H), 7.05-7.01 (m, 2 H), 4.14 (s, 2 H), 4.07 (m, 2 H), 3.85 (m, 2 H), 3.63 (m, 2 H), 1.51 (m, 2 H), 1.33 (m, 2 H), 0.90 (m, 3 H); MS m/z 414 (M+1).

EXAMPLE 318

7-[(4-Fluorophenyl)methyl]-4-hydroxy-2-oxo-N-[3-(2-oxo-1-pyrrolidinyl)propyl]-1-(2,2,2-trifluoroethyl)-1,2-dihydro-1,5-naphthyridine-3-carboxamide Step 1: ethyl 7-[(4-fluorophenyl)methyl]-4-hydroxy-2-oxo-1-(2,2,2-trifluoroethyl)-1,2-dihydro-1,5-naphthyridine-3-carboxylate.

In a similar manner to that described in example 316 step 1, from ethyl 7-[(4-fluorophenyl)methyl]-4-hydroxy-2-oxo-1,2-dihydro-1,5-naphthyridine-3-carboxylate (50 mg, 0.146 mmol), lithium (bis-trimethylsilyl)amide (49 mg, 0.292 mmol), and 2,2,2-trifluoroethyl trifluoromethanesulfonate (0.2 mL, 0.876 mmol) was prepared ethyl 7-[(4-fluorophenyl)methyl]-4-hydroxy-2-oxo-1-(2,2,2-trifluoroethyl)-1,2-dihydro-1,5-naphthyridine-3-carboxylate (58 mg, 95% yield) as a yellow oil. $^1$H NMR (CDCl$_3$) δ 8.54 (s, 1 H), 7.37 (s, 1 H), 7.16-7.12 (m, 2 H), 7.04-6.97 (m, 2 H), 4.83 (m, 2 H), 4.49 (m, 2 H), 4.13 (s, 2 H), 1.46 (m, 3 H); MS m/z 425 M+1).

Step 2: 7-[(4-fluorophenyl)methyl]-4-hydroxy-2-oxo-N-[3-(2-oxo-1-pyrrolidinyl)propyl]-1-(2,2,2-trifluoroethyl)-1,2-dihydro-1,5-naphthyridine-3-carboxamide.

In a similar manner to that described in example 196, from ethyl 7-[(4-fluorophenyl)methyl]-4-hydroxy-2-oxo-1-(2,2,2-trifluoroethyl)-1,2-dihydro-1,5-naphthyridine-3-carboxylate (23 mg, 0.0542 mmol) and 1-(3-aminopropyl)-2-pyrrolidinone (0.05 mL) was prepared 7-[(4-fluorophenyl)methyl]-4-hydroxy-2-oxo-N-[3-(2-oxo-1-pyrrolidinyl)propyl]-1-(2,2,2-trifluoroethyl)-1,2-dihydro-1,5-naphthyridine-3-carboxamide (15 mg, 54% yield) as a white solid after purification by reverse phase HPLC. $^1$H NMR (CDCl$_3$) δ 10.05 (br s, 1 H), 8.59 (s, 1 H), 7.38 (s, 1 H), 7.16-7.13 (m, 2 H), 7.05-7.01 (m, 2 H), 4.86 (br s, 2 H), 4.14 (s, 2 H), 3.49-3.37 (m, 6 H), 2.40 (m, 2 H), 2.04 (m, 2 H), 1.87 (m, 2 H); MS m/z 521 (M+1).

EXAMPLE 319

7-[(4-Fluorophenyl)methyl]-4-hydroxy-N-[1-(methylsulfonyl)-4-piperidinyl]-2-oxo-1-(3-pyridinylmethyl)-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.22 (d, J=6.9 Hz, 1 H), 8.57 (s, 1 H), 8.52 (d, J=4.8 Hz, 1 H), 8.40 (s, 1 H), 7.34 (d, J=7.8 Hz, 1 H), 7.20 (m, 1 H), 7.14 (s, 1 H), 7.00-6.97 (m, 4 H), 5.37 (s, 2 H), 4.11 (m, 1 H), 4.02 (s, 2 H), 3.73 (m, 2 H), 2.96 (m, 2 H), 2.80 (s, 3 H), 2.15 (m, 2 H), 1.75 (m, 2 H); HRMS m/z calcd for $C_{28}H_{29}N_5O_5FS$ (M+H)$^+$ 566.1873, found 566.1877.

EXAMPLE 320

Sodium 1-butyl-7-[(4-fluorophenyl)methyl]-2-oxo-3-({[3-(2-oxo-1-pyrrolidinyl)propyl]amino}carbonyl)-1,2-dihydro-1,5-naphthyridin-4-olate In a similar manner to that described in example 196, from ethyl 1-butyl-7-[(4-fluorophenyl)methyl]-4-hydroxy-2-oxo-1,2-dihydro-1,5-naphthyridine-3-carboxylate (20 mg, 0.050 mmol) and 1-(3-aminopropyl)-2-pyrrolidinone (0.05 mL)

was prepared 1-butyl-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide (10 mg, 40% yield) as a yellow oil after purification by reverse phase HPLC. This oil was dissolved in diethyl ether, cooled to 0° C., and sodium ethoxide (0.02 mL of a 1 M solution in ethanol, 0.02 mmol) was added. The resulting white suspension was filtered and the white solids were collected to yield sodium 1-butyl-7-[(4-fluorophenyl)methyl]-2-oxo-3-({[3-(2-oxo-1-pyrrolidinyl)propyl]amino}carbonyl)-1,2-dihydro-1,5-naphthyridin-4-olate (11 mg, 42% overall yield) as a white solid. $^1$H NMR (CDCl$_3$) δ 10.34 (br s, 1 H), 8.56 (s, 1 H), 7.27 (s, 1 H), 7.19-7.15 (m, 2 H), 7.06-7.02 (m, 2 H), 4.14 (s, 2 H), 4.09 (m, 2 H), 3.48-3.37 (m, 6 H), 2.40 (m, 2 H), 2.04 (m, 2 H), 1.88 (m, 2 H), 1.53 (m, 2 H), 1.34 (m, 2 H), 0.91 (m, 3 H); HRMS m/z calcd for: $C_{27}H_{32}N_4O_4F$: 495.2408 Found: 495.2397.

EXAMPLE 321

7-[(4-fluorophenyl)methyl]-4-hydroxy-N-(2-hydroxyethyl)-2-oxo-1-(2,2,2-trifluoroethyl)-1,2-dihydro-1,5-naphthyridine-3-carboxamide In a similar manner to that described in example 196, from ethyl 7-[(4-fluorophenyl)methyl]-4-hydroxy-2-oxo-1-(2,2,2-trifluoroethyl)-1,2-dihydro-1,5-naphthyridine-3-carboxylate (10 mg, 0.024mmol) and 2-aminoethanol (0.05 mL) was prepared 7-[(4-fluorophenyl)methyl]-4-hydroxy-N-(2-hydroxyethyl)-2-oxo-1-(2,2,2-trifluoroethyl)-1,2-dihydro-1,5-naphthyridine-3-carboxamide (3 mg, 29% yield) as a white solid after purification by reverse phase HPLC. $^1$H NMR (methanol-d$_4$/CDCl$_3$) δ 8.53 (s, 1 H), 7.42 (s, 1 H), 7.13-7.09 (m, 2 H), 7.00-6.96 (m, 2 H), 4.85 (br s, 2 H), 4.10 (s, 2 H), 3.74 (m, 2 H), 3.55 (m, 2 H); MS m/z 440 M+1).

EXAMPLE 322

7-[(4-Fluorophenyl)methyl]-4-hydroxy-N-(2-hydroxy-1-methylethyl)-2-oxo-1-(2,2,2-trifluoroethyl)-1,2-dihydro-1,5-naphthyridine-3-carboxamide In a similar manner to that described in example 196, from ethyl 7-[(4-fluorophenyl)methyl]-4-hydroxy-2-oxo-1-(2,2,2-trifluoroethyl)-1,2-dihydro-1,5-naphthyridine-3-carboxylate (20 mg, 0.050mmol) and 2-amino-1-propanol (0.05 mL) was prepared 7-[(4-fluorophenyl)methyl]-4-hydroxy-N-(2-hydroxy-1-methylethyl)-2-oxo-1-(2,2,2-trifluoroethyl)-1,2-dihydro-1,5-naphthyridine-3-carboxamide(15 mg, 65% yield) as a white solid after purification by reverse phase HPLC. $^1$H NMR (CDCl$_3$) δ 9.98 (d, J=7.6 Hz, 1 H), 8.58 (s, 1 H), 7.37 (s, 1 H), 7.15-7.12 (m, 2 H), 7.04-6.99 (m, 2 H), 4.82 (br s, 2 H), 4.26 (m, 1 H), 4.13 (s, 2 H), 3.78 (dd, J=10.8, 4 Hz, 1 H), 3.67 (dd, J=10.8, 6, 1 H), 1.30 (d, J=6.8 Hz, 3 H); MS m/z 454 M+1).

EXAMPLE 323

7-[(4-Fluorophenyl)methyl]-4-hydroxy-2-oxo-1-(3-pyridinylmethyl)-N-(tetrahydro-2H-thiopyran-4-yl)-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.17 (m, 1 H), 8.54 (s, 1 H), 8.50 (d, J=4.3 Hz, 1 H), 8.38 (s, 1 H), 7.30 (d, J=7.7 Hz, 1 H), 7.17 (m, 1 H), 7.12 (s, 1 H), 6.99-6.94 (m, 4 H), 5.35 (s, 2 H), 4.02-3.98 (m, 3 H), 2.77-1.38 (m, 8 H); HRMS m/z calcd for $C_{27}H_{26}N_4O_3FS$ (M+H)$^+$ 505.1710, found 505.1714.

EXAMPLE 324

N-(1,1-Dioxidotetrahydro-2H-thiopyran-4-yl)-7-[(4-fluorophenyl)methyl]-4-hydroxy-2-oxo-1-(3-pvridinylmethyl)-1,2-dihydro-1,5-naphthyridine-3-carboxamide To a solution of 7-[(4-fluorophenyl)methyl]-4-hydroxy-2-oxo-1-(3-pyridinylmethyl)-N-(tetrahydro-2H-thiopyran-4-yl)-1,2-dihydro-1,5-naphthyridine-3-carboxamide (24 mg, 0.05 mmol) in methanol (4 mL) was added Oxone (59.3 mg, 0.10 mmol) as a solution in water (1 mL). The resultant mixture was stirred overnight and then concentrated in vacuo. Ethyl acetate was added followed by water. The organics were washed with brine and the aqueous layer extracted with ethyl acetate. The combined organics were dried over sodium sulfate, filtered and concentrated. The residue was purified by reverse phase preparative HPLC to give the title compound (10 mg, 38%) as a white solid as a format salt. $^1$H NMR (400 MHz, CDCl$_3$) δ 10.41 (d, J=6.5 Hz, H), 8.58 (s, 1 H), 8.53 (d, J=4.3 Hz, 1 H), 8.41 (s, 1 H), 8.10 (s, 1 H), 7.36 (d, J=8.0 Hz, 1 H), 7.23 (m, 1 H), 7.16 (s, 1 H), 7.01-6.97 (m, 4 H), 5.37 (s, 2 H), 4.26 (m, 1 H), 4.04 (s, 2 H), 3.14 (m, 4 H), 2.49-2.29 (m, 4 H); HRMS m/z calcd for $C_{27}H_{26}N_4O_5FS$ (M+H)$^+$ 537.1608, found 537.1601.

EXAMPLE 325

7-[(4-fluorophenyl)methyl]-4-hydroxy-2-oxo-N-[2-(propyloxyethyl]-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and 2-propoxyethylamine employing methods similar to those described in Example 2 and was obtained as a white solid: $^1$H NMR (d$_6$-DMSO) δ 11.87 (1H, br s), 10.36 (1H, br s), 8.49 (1H, s), 7.43 (1H, s), 7.30-7.27 (2H, m), 7.16-7.11 (2H, m), 4.09 (2H, s), 3.36 (2H, t, J=6.3), 3.31 (2H, br s), 2.47-2.40 (2H, m), 1.51-1.46 (2H, m), 0.85 (3H, t, J=7.4 Hz); HRMS calcd for $C_{21}H_{22}FN_3O_4$+H$^+$: 400.1673. Found 400.1673.

EXAMPLE 326

7-[(4-Fluorophenyl)methyl]-4-hydroxy-2-oxo-N-[3-(propyloxy)propyl]-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and 3-propoxypropylamine employing methods similar to those described in Example 2 and was obtained a white solid: $^1$H NMR (d$_6$-DMSO) δ 11.83 (1H, br s), 10.26 (1H, br s), 8.48 (1H, br s), 7.43 (1H, s), 7.30-7.26 (2H, m), 7.16-7.11 (2H, m), 4.09 (2H, s), 3.42-3.38 (4H, m), 3.30-3.28 (2H, m), 1.76-1.71 (2H, m), 1.49 (2H, q, J=7 Hz), 0.83 (3H, t, J=7.3 Hz); HRMS calcd for $C_{22}H_{24}FN_3O_4$+H$^+$: 414.1829. Found 414.1844.

EXAMPLE 327

7-[(2,4-Difluorophenyl)methyl]-1-[2-(dimethylamino)-2-oxoethyl]-4-hydroxy-N-[2-(methyloxy)ethyl]-2-oxo-1,2-dihydro-1,5-naphthyridine-3-carboxamide This compound was prepared from methyl 3-amino-5-[(2,4-difluorophenyl)methyl]-2-pyridinecarboxylate employing methods similar to those described in Example 11, Steps 1-4, using N,N-dimethylamine in Step 2. Subsequent formation of the carboxamide with methoxyethylamine employing methods similar to those described in Example 2 using N,N-dimethylformamide as the reaction solvent, afforded the desired product as an off-white solid: $^1$H NMR (d$_6$-DMSO) δ 10.23 (1H, br s), 8.46 (1H, s), 7.70 (1H, s), 7.41-7.35 (1H, m), 7.25-7.20 (1H, m), 7.06-7.03 (1H, m), 5.10 (2H, s), 4.13 (2H, s), 3.53-3.50 (2H, m), 3.49-3.47 (2H, m), 3.26 (3H, s), 3.11 (3H, s), 2.80 (3H, s); HRMS calcd for $C_{23}H_{24}F_2N_4O_5+H^+$: 475.1784. Found 475.1793.

EXAMPLE 328

7-(4-Fluorobenzyl)-4-hydroxy-N-(2-hydroxy-1,1-dimethylethyl)-1-methyl-2-oxo-1,2-dihydro-1,5-naphthyridine-3-carboxamide The title compound was made in a similar manner to example 96 using 2-amino-2-methyl-1-propanol to give a white solid: $^1$H NMR (CDCl$_3$) δ 10.53 (1H, m), 8.57 (1H, s), 7.39 (1H, s), 7.16 (2H, m), 7.03 (2H, m), 4.13 (2H, s), 3.72 (2H, s), 3.58 (3H, s), 1.44 (6H, s); HRMS calcd for $C_{21}H_{22}FN_3O_4+H^+$: 400.1673. Found: 400.1686.

EXAMPLE 329

7-[(4-Fluorophenyl)methyl]-4-hydroxy-N-[(1-hydroxycyclohexyl)methyl]-1-methyl-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate(18 mg, 0.050 mmol) described in example 92, 1-(aminomethyl)cyclohexanol hydrochloride (110 mg, 0.66 mmol) and triethylamine (0.28 mL, 1.98 mmol), was prepared 7-[(4-fluorophenyl)methyl]-4-hydroxy-N-[(1-hydroxycyclohexyl)methyl]-1-methyl-2-oxo-1,2-dihydro-1,5-naphthyridine-3-carboxamide (4 mg, 18% yield) as a white solid after purification by reverse phase HPLC. $^1$H NMR (CDCl$_3$) δ 10.46 (br s, 1 H), 8.55 (s, 1 H), 7.38 (s, 1 H), 7.17-7.13 (m, 2 H), 7.04-6.94 (m, 2 H), 4.12 (s, 2 H), 3.58 (s, 3 H), 3.48 (d, J=5.6 Hz, 2 H), 1.62-1.49 (m, 1 H); MS m/z 440 (M+1).

EXAMPLE 330

7-[(4-Fluorophenyl)methyl]-4-hydroxy-N-[1-(hydroxymethyl)cyclopentyl]-1-methyl-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (18 mg, 0.050 mmol) described in example 92 and (1-aminocyclopentyl)methanol (76 mg, 0.66 mmol) was prepared 7-[(4-fluorophenyl)methyl]-4-hydroxy-N-[1-(hydroxymethyl)cyclopentyl]-1-methyl-2-oxo-1,2-dihydro-1,5-naphthyridine-3-carboxamide(10 mg, 48% yield) as a white solid after purification by reverse phase HPLC. $^1$H NMR (CDCl$_3$) δ 10.56 (br s, 1H), 8.55 (s, 1 H), 7.37 (s, 1 H), 7.17-7.14 (m, 2 H), 7.04-6.99 (m, 2 H), 4.12 (m, 2 H), 3.78 (s, 2 H), 3.56 (s, 3 H), 1.98-1.68 (m, 8 H); MS m/z 424 (M−1).

EXAMPLE 331

N-(3-Ethoxypropyl)-7-(4-fluorobenzyl)-4-hydroxy-1-methyl-2-oxo-1,2-dihydro-1,5-naphthyridine-3-carboxamide The title compound was made in a similar manner to example 96 using 3-ethoxypropylamine to give a white solid: $^1$H NMR (CDCl$_3$) δ 10.27 (1H, m), 8.56 (1H, s), 7.38 (1H, s), 7.15 (2H, m), 7.02 (2H, m), 4.13 (2H, s), 3.48-3.58 (9H, m), 1.91 (2H, m), 1.22 (3H, t, J=7 Hz); HRMS calcd for $C_{22}H_{24}FN_3O_4+H^+$: 414.1829. Found: 414.1844.

EXAMPLE 332

7-[(4-Fluorophenyl)methyl]-4-hydroxy-N-(2-hydroxycyclohexyl)-1-methyl-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (18 mg, 0.050 mmol) described in example 92, triethylamine (0.3 mL, 1.95 mmol), and 2-aminocyclohexanol hydrochloride (100 mg, 0.66 mmol), was prepared 7-[(4-fluorophenyl)methyl]-4-hydroxy-N-(2-hydroxycyclohexyl)-1-methyl-2-oxo-1,2-dihydro-1,5-naphthyridine-3-carboxamide (8 mg, 38% yield) as a white solid after purification by reverse phase HPLC. $^1$H NMR (CDCl$_3$) δ 10.29 (d, J=7.6 Hz, 1 H), 8.54 (s, 1 H), 7.37 (s, 1 H), 7.17-7.13 (m, 2 H), 7.04-6.99 (m, 2 H), 4.12 (s, 2 H), 3.86 (m, 1 H), 3.56-3.47 (m, 4 H), 2.07 (m, 2 H), 1.75 (m, 2 H), 1.42-1.23 (m, 4 H); HRMS m/z calcd for $C_{23}H_{25}N_3O_4F$: 426.1829 Found: 426.1834.

EXAMPLE 333

7-(4-Fluorobenzyl)-4-hydroxy-N-(3-hydroxypropyl)-1-methyl-2-oxo-1,2-dihydro-1,5-naphthyridine-3-carboxamide The title compound was made in a similar manner to example 96 using 3-amino-1-propanol to give a pale lemon solid: $^1$H NMR (CDCl$_3$) δ 10.33 (1H, m), 8.56 (1H, s), 7.39 (1H, s), 7.15 (2H, m), 7.02 (2H, m), 4.13 (2H, s), 3.70 (2H, m), 3.60 (2H, m), 3.57 (3H, s), 1.83 (2H, m); HRMS calcd for $C_{20}H_{20}FN_3O_4+H^+$: 386.1516. Found: 386.1501.

EXAMPLE 334

1-(2-Aminoethyl)-7-[(4-fluorophenyl)methyl]-4-hydroxy-N-(2-hydroxyethyl)-2-oxo-1,2-dihydro-1,5-naphthyridine-3-carboxamide A solution of 1-[2-(1,3-dioxo-1,3-dihydro-2H-isoindol-2-yl)ethyl]-7-[(4-fluorophenyl)methyl]-4-hydroxy-N-(2-hydroxyethyl)-2-oxo-1,2-dihydro-1,5-naphthyridine-3-carboxamide (0.255 g, 0.48 mmol) in EtOH (80 mL) under nitrogen was treated with hydrazine (0.151 mL, 4.81 mmol) for 1 h@50° C. Additional hydrazine was added (0.075 mL @1 h) after 1 and 4 hours (0.15 mL @ 4 h) and the reaction was stirred for a total of 8 h@50° C. The reaction was then capped and cooled in a refrigerator overnight. The resulting suspension was filtered then thoroughly dried under high vacuum to provide the title compound as an off-white solid: $^1$H NMR (300 MHz, DMSO-D6) δ ppm 2.8 (m, 1 H), 3.4 (m, 2 H), 3.6 (m, 2 H), 4.1 (s, 2 H), 4.2 (m, 2 H), 4.9 (bs, 1 H), 7.1

(t, J=8.7 Hz, 2 H), 7.4 (m, 2 H), 8.1 (s, 1 H), 8.5 (s, 1 H), 10.5 (m, 1 H); ES+ MS: 401 (M+H+).

EXAMPLE 335

1-[2-(1,3-dioxo-1,3-dihydro-2H-isoindol-2-yl)ethyl]-7-[(4-fluorophenyl)methyl]-4-hydroxy-N-(2-hydroxyethyl)-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.035 g, 0.068 mmol) in EtOH (3 mL) under nitrogen was treated with Ethanolamine (8 mg, 0.13 mmol) for 2 h@150° C. in a microwave vessel. The reaction was then cooled to ambient temperature and the resulting suspension was filtered, washed with EtOH and Et₂O and thoroughly dried under high vacuum to provide the title compound as an orange solid: $^1$H NMR (300 MHz, DMSO-D6) δ ppm 3.4 (m, 5 H), 3.9 (t, J=6.0 Hz, 2 H), 4.1 (s, 2 H), 4.5 (t, J=5.8 Hz, 2 H), 4.8 (t, J=5.0 Hz, 1 H), 7.1 (ddd, J=9.0, 6.7, 2.2 Hz, 2 H), 7.3 (m, 2 H), 7.8 (m, 4 H), 8.1 (d, J=1.1 Hz, 1 H), 8.5 (d, J=1.3 Hz, 1 H), 10.0 (s, 1 H); ES+ MS: 531 (M+H+).

EXAMPLE 336

1-[2-(1,3-dioxo-1,3-dihydro-2H-isoindol-2-yl)ethyl]-N-[2-(ethyloxy)ethyl]-7-[(4-fluorophenyl)methyl]-4-hydroxy-2-oxo-1,2-dihydro-1,5-naphthyridine-3-carboxamide

Step 1: Synthesis of (1,3-dioxo-1,3-dihydro-2H-isoindol-2-yl)acetaldehyde

A solution of 2-[2,2-bis(ethyloxy)ethyl]-1H-isoindole-1,3(2H)-dione (24.60 g, 93 mmol) in THF (150 mL) under nitrogen was treated with 1N HCl (aq) (75 mL, 75 mmol) and brought to reflux. After stirring for 20 h, the reaction was evaporated in vacuo and the residue was triturated with 1N HCl (100 mL). The resulting solid was collected by filtration, washed with 1N HCl, water, and Et₂O and dried under high vacuum to provide the desired product as a white solid: $^1$H NMR (d₆-DMSO, 300 MHz) δ 9.60 (1H, s), 7.87-7.95 (4H, m), 4.6 (2H, s).

Step 2: Synthesis of ethyl 3-{[2-(1,3-dioxo-1,3-dihydro-2H-isoindol-2-yl)ethyl]amino}-5-[(4-fluorophenyl)methyl]-2-pyridinecarboxylate A solution of ethyl 3-amino-5-(4-fluorobenzyl)-2-pyridinecarboxylate (1.50 g, 5.47 mmol) and (1,3-dioxo-1,3-dihydro-2H-isoindol-2-yl)acetaldehyde (2.27 g, 12 mmol) under nitrogen in glacial acetic acid (50 mL) was treated with sodium triacetoxyborohydride (2.56 g, 12.1 mmol) at ambient temperature. After stirring for 30 min., 40 mL of glacial acetic acid (40 mL) was added, to dilute the reaction, followed by 0.17 g of (1,3-dioxo-1,3-dihydro-2H-isoindol-2-yl)acetaldehyde and 0.45 g sodium triacetoxyborohydride. After stirring another 2½ h, the reaction was heated to 45° C. for another hour. The reaction was evaporated in vacuo and the residue was triturated with water (500 mL), filtered, and washed with water. The resulting solid was dissolved in CH₂Cl₂ dried over MgSO₄, filtered and evaporated in vacuo. The residue was dissolved in CH₂Cl₂ and chromatographed on silica gel eluting with 0-50% EtOAc in hexanes to provide the product as an solid. $^1$H NMR (400 MHz, DMSO-D6) δ ppm 1.2 (t, J=7.1 Hz, 3 H), 3.5 (q, J=6.2 Hz, 2 H), 3.8 (t, J=6.0 Hz, 2 H), 3.9 (s, 2 H), 4.2 (q, J=7.0 Hz, 2 H), 7.1 (ddd, J=9.1, 6.9, 1.8 Hz, 2 H), 7.3 (m, 3 H), 7.6 (t, J=6.2 Hz, 1 H), 7.7 (d, J=1.6 Hz, 1 H), 7.8 (m, 4 H); ES+MS: 447 (M+H+).

Step 3: Synthesis of ethyl 3-{[2-(1,3-dioxo-1,3-dihydro-2H-isoindol-2-yl)ethyl][3-(ethyloxy)-3-oxopropanoyl]amino}-5-[(4-fluorophenyl)methyl]-2-pyridinecarboxylate A solution of ethyl 3-{[2-(1,3-dioxo-1,3-dihydro-2H-isoindol-2-yl)ethyl]amino}-5-[(4-fluorophenyl)methyl]-2-pyridinecarboxylate (1.88 g, 4.2 mmol) and ethyl malonyl chloride (1.2 mL, 8.4 mmol) in DCE (60 mL) was heated under nitrogen at reflux for 25 hrs. An additional 0.3 mL of the ethyl malonyl chloride was added and the reaction was stirred at reflux an additional hour. The mixture was cooled, concentrated in vacuo, diluted with CH₂Cl₂ and washed with sat. aq. NaHCO₃, water, and brine. The aqueous layers were separated and the combined organic layers were dried over anhydrous MgSO₄, filtered, evaporated in vacuo and then purified on silica gel eluting with 25-60% EtOAc in hexanes to provide the product as an oil: $^1$H NMR (300 MHz, DMSO-D6) δ ppm 1.0 (t, J=7.1 Hz, 3 H), 1.2 (m, 3 H), 2.9 (m, 2 H), 3.2 (m, 1 H), 3.3 (s, 1 H), 3.7 (m, 2 H), 3.8 (qd, J=7.1, 1.0 Hz, 2 H), 4.0 (m, 1 H), 4.3 (m, 2 H), 4.4 (ddd, J=13.9, 7.4, 6.3 Hz, 1 H), 7.1 (m, 2 H), 7.3 (m, J=6.0, 6.0, 2.9, 2.8 Hz, 2 H), 7.8 (ddd, J=8.9, 6.9, 4.3 Hz, 4 H), 8.0 (d, J=2.0 Hz, 1 H), 8.6 (d, J=2.0 Hz, 1 H), ES+ MS: 561 (M+H+).

Step 4: Synthesis of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate A solution of ethyl 3-{[2-(1,3-dioxo-1,3-dihydro-2H-isoindol-2-yl)ethyl][3-(ethyloxy)-3-oxopropanoyl]amino}-5-[(4-fluorophenyl)methyl]-2-pyridinecarboxylate (2.05 g, 3.65 mmol) in EtOH (75 mL) under nitrogen was treated with DBU (0.709 mL, 4.74 mmol). After stirring at ambient temperature for 15 min., the reaction mixture was treated with 1N NaHSO₄ (5.0 mL). The resulting slurry was diluted with water, filtered, the filtered solid was washed with water, EtOH, and Et₂O and thoroughly dried under high vacuum to provide the title compound as a white solid: $^1$H NMR (400 MHz, CHLOROFORM-D) δ ppm 1.4 (t, J=7.0 Hz, 3 H), 4.0 (t, J=7.0 Hz, 4 H), 4.4 (t, J=6.5 Hz, 2 H), 4.5 (q, J=7.3 Hz, 2 H), 7.0 (t, J=8.5 Hz, 2 H), 7.1 (m, 2 H), 7.7 (dd, J=5.5, 3.1 Hz, 2 H), 7.8 (s, 1 H) 7.8 (m, 2 H), 8.4 (s, 1 H), 13.9 (none, 1 H); ES+ MS: 516 (M+H+).

Step 5: Synthesis of 1-[2-(1,3-dioxo-1,3-dihydro-2H-isoindol-2-yl)ethyl]-N-[2-(ethyloxy)ethyl]-7-[(4-fluorophenyl)methyl]-4-hydroxy-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.021 g, 0.041 mmol) in EtOH (2 mL) under nitrogen was treated with Ethoxyethylamine (0.021 mL, 0.2 mmol) for 10 min.@150° C. in a microwave vessel then@180° C. for an additional 10 min. After the reaction was cooled to ambient temperature the resulting suspension was filtered, and the filtered solid was washed with water and Et₂O then thoroughly dried under high vacuum to provide the title compound as a beige solid: $^1$H NMR (300 MHz, DMSO-d₆) δ ppm 1.07 (t, J=6.95 Hz, 4 H), 1.56-1.91 (m, 1 H), 3.34-3.41 (m, 7 H), 3.88-3.92 (m, 2 H), 4.11 (s, 2 H), 4.53-4.56 (m, 1 H), 7.12-7.13 (m, 1 H), 7.32-7.37 (m, 2 H), 7.81-7.82 (m, 4 H), 8.14-8.15 (m, 1 H), 8.52 (dd, J=1.47, 0.35 Hz, 1 H), 9.76-10.16 (m, 1 H); ES$^+$ MS: 559 (M+H$^+$).

EXAMPLE 337

N-(1,1-Dioxidotetrahydro-2H-thiopyran-4-yl)-7-[(4-fluorophenyl)methyl]-4-hydroxy-2-oxo-1,2-dihydro-1,5-naphthyridine-3-carboxamide The title compound was prepared in a similar manner to that described in example 324 to provide a white solid. $^1$H NMR (400 MHz, CDCl$_3$) δ 10.23 (d, J=7.1 Hz, 1 H), 8.29 (s, 1 H), 7.22 (s, 1 H), 7.00 (dd, J=8.6, 5.5 Hz, 2 H), 6.84 (t, J=8.7 Hz, 2 H), 4.08 (m, 1 H), 3.92 (s, 2 H), 2.99 (m, 4 H), 2.28-2.05 (m, 4 H); HRMS m/z calcd for C$_{21}$H$_{21}$N$_3$O$_5$FS (M+H)$^+$ 446.1187, found 446.1180.

EXAMPLE 338

1-[2-(Acetylamino)ethyl]-7-[(4-fluorophenyl)methyl]-4-hydroxy-N-(2-hydroxyethyl)-2-oxo-1,2-dihydro-1,5-naphthyridine-3-carboxamide A solution of 1-(2-aminoethyl)-7-[(4-fluorophenyl)methyl]-4-hydroxy-N-(2-hydroxyethyl)-2-oxo-1,2-dihydro-1,5-naphthyridine-3-carboxamide (0.019 g, 0.047 mmol) and diisopropyl ethylamine (0.075 mL, 0.43 mmol) in DMF (1 mL) under nitrogen was treated with acetic anhydride (0.004 mL, 0.042 mmol) at ambient temperature. The reaction was warmed slightly to solubilize then reacted at ambient temperature for 10 min. Water was added (2 mL) and the reaction was cooled to 0° C. and concentrated in vacuo. The resulting residue was treated with 1 N NaHSO$_4$ and filtered then triturated with Et$_2$O and dried in air to provide the title compound as an off-white solid: $^1$H NMR (300 MHz, DMSO-D6) δ ppm 1.7 (s, 3 H), 3.3 (dd, J=3.1, 1.3 Hz, 2 H), 3.4 (m, 2 H), 3.6 (m, 2 H), 4.1 (s, 2 H), 4.3 (m, 2 H), 4.9 (t, J=4.8 Hz, 1 H), 7.1 (t, J=8.8 Hz, 2 H), 7.4 (m, 2 H), 8.0 (m, 1 H), 8.2 (s, 1 H), 8.5 (s, 1 H), 10.4 (d, J=6.2 Hz, 1 H), 17.2 (s, 1 H); ES$^+$ MS: 443 (M+H$^+$).

EXAMPLE 339

1-[2-(Dimethylamino)-2-oxoethyl]-7-[(4-fluorophenyl)methyl]-4-hydroxy-N-[(2S)-2-hydroxypropyl]-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo -1,2-dihydro-1,5-naphthyridine-3-carboxylate and (2S)-1-amino-2-propanol employing methods similar to those described in Example 245 and was purified by reverse phase preparative HPLC (C-18 stationary phase; 10-100% CH$_3$CN/water/0.1% formic acid mobile phase). The product was obtained as a white solid: $^1$H NMR (d$_6$-DMSO) δ 10.28 (1H, t, J=5 Hz), 8.50 (1H, s), 7.75 (1H, s), 7.31 (2H, m), 7.12 (2H, m), 5.12 (2H, m), 4.94 (1H, d, J=5 Hz), 4.11 (2H, s), 3.78 (1H, m), 3.40 (1H, m), 3.18 (1H, m), 3.12 (3H, s), 2.82 (3H, s), 1.07 (3H, d, J=6 Hz); HRMS calcd for C$_{23}$H$_{25}$FN$_4$O$_5$+H$^+$: 457.18817. Found: 457.18875.

EXAMPLE 340

(±)-1-[2-(Dimethylamino)-2-oxoethyl]-7-[(4-fluorophenyl)methyl]-4-hydroxy-N-(2-hydroxy-1-methylethyl)-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and (±)-2-amino-1-propanol employing methods similar to those described in Example 245 and was purified by reverse phase preparative HPLC (C-18 stationary phase; 10-100% CH$_3$CN/water/0.1% formic acid mobile phase). The product was obtained as a white solid: $^1$H NMR (d$_6$-DMSO) δ 10.23 (1H, d, J=8 Hz), 8.50 (1H, s), 7.77 (1H, s), 7.32 (2H, dd, J=8.4, 5.7 Hz), 7.12 (2H, t, J~9 Hz), 5.12 (2H, m), 4.98 (1H, t, J=5 Hz), 4.11 (2H, s), 4.03 (1H, m), 3.45 (2H, m), 3.12 (3H, s), 2.82 (3H, s), 1.15 (3H, d, J=7 Hz); HRMS calcd for C$_{23}$H$_{25}$FN$_4$O$_5$+H$^+$: 457.18817. Found: 457.18872.

EXAMPLE 341

N-Ethyl-7-(4-fluorobenzyl)-4-hydroxy-1-methyl-2-oxo-1,2-dihydro-1,5-naphthyridine-3-carboxamide The title compound was made in a similar manner to example 96 using a solution of ethylamine in methanol to give a pale lemon solid: $^1$H NMR (CDCl$_3$) δ 10.12 (1H, m), 8.56 (1H, s), 7.39 (1H, s), 7.15 (2H, m), 7.02 (2H, m), 4.13 (2H, s), 3.57 (3H, s), 3.48 (2H, m), 1.27 (3H, t, J=7 Hz); HRMS calcd for C$_{19}$H$_{18}$FN$_3$O$_3$+H$^+$: 356.1405. Found: 356.1410.

EXAMPLE 342

7-(4-Fluorobenzyl)-4-hydroxy-N-(3-methoxypropyl)-1-methyl-2-oxo-1,2-dihydro-1,5-naphthyridine-3-carboxamide The title compound was made in a similar manner to example 96 using 3-methoxypropylamine to give a white solid: $^1$H NMR (CDCl$_3$) δ 10.27 (1H, m), 8.55 (1H, s), 7.38 (1H, s), 7.15 (2H, m), 7.03 (2H, m), 4.12 (2H, s), 3.57 (3H, s), 3.54 (2H, m), 3.49 (2H, m), 3.36 (3H, s), 1.90 (2H, m); HRMS calcd for C$_{21}$H$_{22}$FN$_3$O$_4$+H$^+$: 400.1667. Found: 400.1672.

EXAMPLE 343

N-{2-[(dimethylamino)sulfonyl]ethyl}-7-[(4-fluorophenyl)methyl]-4-hydroxy-1-methyl-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (30 mg, 0.084 mmol) described in example 92, 2-amino-N,N-dimethylethanesulfonamide hydrochloride (200 mg, 1.09 mmol), and triethylamine (0.5 mL, 3.27 mmol), was prepared N-{2-[(dimethylamino)sulfonyl]ethyl}-7-[(4-fluorophenyl)methyl]-4-hydroxy-1-methyl-2-oxo-1,2-dihydro-1,5-naphthyridine-3-carboxamide (19 mg, 49% yield) as a brown solid after purification by reverse phase HPLC. $^1$H NMR (CDCl$_3$) δ 10.55 (br s, 1 H), 8.55 (s, 1 H), 7.38 (s, 1 H), 7.16-7.12 (m, 2 H), 7.03-6.98 (m, 2 H), 4.12 (s, 2 H), 3.89 (m, 2 H), 3.57 (s, 3 H), 3.24 (m, 2 H), 2.89 (s, 6 H); HRMS m/z calcd for C$_{21}$H$_{24}$FN$_4$O$_5$S: 463.1446 Found: 463.1451.

EXAMPLE 344

1,1-dimethylethyl 4-{[({7-[(4-fluorophenyl)methyl]-4-hydroxy-1-methyl-2-oxo-1,2-dihydro-1,5-naphthyridine-3-ylcarbonyl)amino]methyl}cyclohexanecarboxylate In a similar manner to that described in example 196, from ethyl 7-[(4-fluorophenyl)methyl]-4-hydroxy-1-methyl-2-oxo-1,2-dihydro-1,5-naphthyridine-3-carboxylate (30 mg, 0.084 mmol) described in example 92 and 1,1-dimethylethyl 4-(aminomethyl)cyclohexanecarboxylate (221 mg, 1.04 mmol) was prepared 1,1-dimethylethyl 4-{[({7-[(4-fluorophenyl)methyl]-4-hydroxy-1-methyl-2-oxo-1,2-dihydro-1,5-naphthyridin-3 ylcarbonyl)amino]methyl}cyclohexanecarboxylate (35 mg, 80% yield) as a white solid after purification by reverse phase HPLC. $^1$H NMR (CDCl$_3$) δ 10.24 (s, 1 H), 8.55 s, 1 H), 7.38 (s, 1 H), 7.16-7.12 (m, 2 H), 7.03-6.98 (m, 2 H), 4.12 (s, 2 H), 3.57 (s, 3 H), 3.29 (m, 2 H), 2.12 (m, 2 H), 1.92 (m, 5 H), 1.60 (m, 1 H), 1.40 (s, 9 H), 1.03 (m, 2 H). HRMS m/z calcd for C$_{29}$H$_{35}$FN$_3$O$_5$: 524.2555. Found: 524.2557.

EXAMPLE 345

7-[(4-Fluorophenyl)methyl]-4-hydroxy-1-methyl-N-[2-(methylsulfonyl)ethyl]-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (30 mg, 0.084 mmol) described in example 92, triethylamine (0.05 mL, 0.364 mmol) and [2-(methylsulfonyl)ethyl]amine hydrochloride (174 mg, 1.08 mmol) was prepared 7-[(4-fluorophenyl)methyl]-4-hydroxy-1-methyl-N-[2-(methylsulfonyl)ethyl]-2-oxo-1,2-dihydro-1,5-naphthyridine-3-carboxamide (11 mg, 22% yield) as a white solid after purification by reverse phase HPLC. $^1$H NMR (CDCl$_3$) δ 10.61 (br s, 1 H), 8.56 (s, 1 H), 7.39 (s, 1 H), 7.16-7.12 (m, 2 H), 7.04-6.99 (m, 2 H), 4.13 (s, 2 H), 3.95 (m, 2 H), 3.57 (s, 3 H), 3.37 (m, 2 H), 2.98 (s, 3 H); MS m/z 434 (M+1).

EXAMPLE 346

Methyl {2-[7-[(4-fluorophenyl)methyl]-4-hydroxy-3-{[(2-hydroxyethyl)amino]carbonyl}-2-oxo-1,5-naphthyridine-1(2H)-yl]ethyl}carbamate A solution of 1-(2-aminoethyl)-7-[(4-fluorophenyl)methyl]-4-hydroxy-N-(2-hydroxyethyl)-2-oxo-1,2-dihydro-1,5-naphthyridine-3-carboxamide (0.0207 g, 0.052 mmol) and diisopropyl ethylamine (0.075 mL, 0.43 mmol) in DMF (2 mL) under nitrogen was treated with methyl chloroformate (0.0038 mL, 0.049 mmol) at ambient temperature. Water was added (2 mL) and the reaction was concentrated in vacuo. The resulting residue was purified by reversed phase HPLC to provide the title compound from pure fraction concentrated in vacuo as an off-white solid: $^1$H NMR (300 MHz, DMSO-D6) δ ppm 3.2 (m, 2 H), 3.4 (m, 5 H), 3.6 (m, 2 H), 4.1 (s, 2 H), 4.3 (t, J=6.3 Hz, 2 H), 4.9 (t, J=4.9 Hz, 1 H), 7.1 (t, J=8.9 Hz, 2 H), 7.3 (t, J=6.0 Hz, 1 H), 7.4 (m, 2 H), 8.1 (s, 1 H), 8.5 (s, 1 H), 10.4 (m, 1 H); ES$^+$ MS: 459 (M+H$^+$).

EXAMPLE 347

7-[(4-Fluorophenyl)methyl]-4-hydroxy-1-methyl-N-{2-[4-(methylsulfonyl)phenyl]ethyl}-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (30 mg, 0.084 mmol) described in example 92, triethylamine (0.5 mL, 4.08 mmol), and {2-[4-(methylsulfonyl)phenyl]ethyl}amine (250 mg, 1.25 mmol), was prepared 7-[(4-fluorophenyl)methyl]-4-hydroxy-1-methyl-N-{2-[4-(methylsulfonyl)phenyl]ethyl}-2-oxo-1,2-dihydro-1,5-naphthyridine-3-carboxamide (11 mg, 26% yield) as a white solid after purification by reverse phase HPLC. $^1$H NMR (CDCl$_3$) δ 10.28 (br s, 1 H), 8.56 (s, 1 H), 7.87 (d, J=8 Hz, 2 H), 7.44 (d, J=8 Hz, 2 H), 7.38 (s, 1 H), 7.16-7.14 (m, 2 H), 7.04-6.99 (m, 2 H), 4.13 (s, 2 H), 3.72 (m, 2 H), 3.56 (s, 3 H), 3.06-3.02 (m, 5 H); HRMS m/z calcd for: C$_{26}$H$_{25}$FN$_3$O$_5$S: 510.1493. Found: 510.1498.

EXAMPLE 348

1-(2-Aminoethyl)-N-[2-(ethyloxy)ethyl]-7-[(4-fluorophenyl)methyl]-4-hydroxy-2-oxo-1,2-dihydro-1,5-naphthyridine-3-carboxamide A solution of 1-[2-(1,3-dioxo-1,3-dihydro-2H-isoindol-2-yl)ethyl]-N-[2-(ethyloxy)ethyl]-7-[(4-fluorophenyl)methyl]-4-hydroxy-2-oxo-1,2-dihydro-1,5-naphthyridine-3-carboxamide (0.155 g, 0.277 mmol) in EtOH (6.5 mL) under nitrogen was treated with hydrazine (0.218 mL, 6.92 mmol) for 7 h@50° C. The reaction was then cooled to ambient temperature and stirred overnight. After heating an additional 6.5 h@50° C. the resulting solution was poured into water (75 mL), refrigerated and the resulting suspension was filtered and washed with cold 3:1 water:EtOH. The solid was then thoroughly dried under high vacuum to provide the title compound as an off-white solid: $^1$H NMR (400 MHz, DMSO-D6) δ ppm 1.1 (t, J=7.1 Hz, 3 H), 2.8 (t, J=7.2 Hz, 2 H), 3.5 (q, J=6.9 Hz, 2 H), 3.5 (s, 4 H), 4.2 (s, 2 H), 4.2 (t, J=7.1 Hz, 2 H), 7.1 (t, J=8.8 Hz, 2 H), 7.4 (dd, J=8.7, 5.4 Hz, 2 H), 8.1 (s, 1 H), 8.5 (s, 1 H), 10.4 (s, 1 H); ES$^+$ MS: 429 (M+H$^+$).

EXAMPLE 349

7-(4-Fluorobenzyl)-4-hydroxy-1-methyl-2-oxo-N-(3-propoxypropyl)-1,2-dihydro-1,5-naphthyridine-3-carboxamide The title compound was made in a similar manner to example 96 using 3-N-propoxypropylamine to give a white solid: $^1$H NMR (CDCl$_3$) δ 10.25 (1H, m), 8.57 (1H, s), 7.38 (1H, s), 7.15 (2H, m), 7.02 (2H, m), 4.13 (2H, s), 3.58 (3H, s), 3.55 (4H, m), 3.40 (2H, m), 1.91 (2H, m) 1.60 (2H, m), 0.92 (3H, t, J=7 Hz); HRMS calcd for C$_{23}$H$_{26}$FN$_3$O$_4$+H$^+$: 428.1980. Found: 428.1987.

EXAMPLE 350

N-(3-Butoxypropyl)-7-(4-fluorobenzyl)-4-hydroxy-1-methyl-2-oxo-1,2-dihydro-1,5-naphthyridine-3-carboxamide The title compound was made in a similar manner to example 96 using 3-butoxypropylamine to give a white solid:

¹H NMR (CDCl₃) δ 10.25 (1H, m), 8.57 (1H, s), 7.38 (1H, s), 7.15 (2H, m), 7.02 (2H, m), 4.13 (2H, s), 3.58 (3H, s), 3.52 (4H, m), 3.43 (2H, m), 1.91 (2H, m) 1.56 (2H, m), 1.38 (2H, m), 0.91 (3H, t, J=7 Hz); HRMS calcd for $C_{24}H_{28}FN_3O_4$+H⁺: 442.2137. Found: 442.2143.

EXAMPLE 351

7-[(4-fluorophenyl)methyl]-4-hydroxy-N-{2-[(1-methylethyl)oxy]ethyl}-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and 2-aminoethylisopropylether employing methods similar to those described in Example 2 and was obtained as a white solid: ¹H NMR (d₆-DMSO) δ 11.72 (1H, br s), 10.88 (1H, br s), 10.06 (1H, br s), 8.18 (1H, s), 7.30-7.25 (3H, m), 7.16-7.11 (2H, m), 3.98 (2H, br s), 3.57-3.54 (1H, m), 3.50-3.38 (4H, m), 1.08 (6H, d, J=5.7 Hz); HRMS calcd for $C_{21}H_{22}FN_3O_4$+H⁺: 400.1667. Found 400.1673.

EXAMPLE 352

1-[2-(Acetylamino)ethyl]-N-[2-(ethyloxy)ethyl]-7-[(4-fluorophenyl)methyl]-4-hydroxy-2-oxo-1,2-dihydro-1,5-naphthyridine-3-carboxamide A solution of 1-(2-aminoethyl)-N-[2-(ethyloxy)ethyl]-7-[(4-fluorophenyl)methyl]-4-hydroxy-2-oxo-1,2-dihydro-1,5-naphthyridine-3-carboxamide (0.020 g, 0.047 mmol) and diisopropyl ethylamine (0.041 mL, 0.24 mmol) in DMF (5 mL) under nitrogen was treated with acetic anhydride (0.0044 mL, 0.047 mmol) at ambient temperature. The reaction was warmed slightly to solubilize the reacted at ambient temperature for 10 min. Water was added (2 mL) and the reaction was cooled to 0° C. and concentrated in vacuo. The resulting residue was treated with 1 N NaHSO₄ and filtered then triturated with Et₂O and dried in vacuo to provide the title compound as an off-white solid: ¹H NMR (300 MHz, DMSO-D6) δ ppm 1.1 (t, J=6.9 Hz, 3 H), 1.7 (s, 3 H), 3.3 (dd, J=12.5, 5.3 Hz, 2 H), 3.5 (q, J=7.0 Hz, 2 H), 3.5 (s, 4 H), 4.1 (s, 2 H), 4.3 (t, J=6.7 Hz, 2 H), 7.1 (t, J=9.0 Hz, 2 H), 7.4 (dd, J=8.4, 5.5 Hz, 2 H), 8.0 (t, J=5.6 Hz, 1 H), 8.2 (s, 1 H), 8.6 (s, 1 H), 10.4 (s, 1 H), 17.1 (s, 1 H); ES⁺ MS: 471 (M+H⁺).

EXAMPLE 353

Methyl {2-[3-({[2-(ethyloxy)ethyl]amino}carbonyl)-7-[(4-fluorophenyl)methyl]-4-hydroxy-2-oxo-1,5-naphthyridine-1(2H)-yl]ethyl}carbamate A solution of 1-(2-aminoethyl)-N-[2-(ethyloxy)ethyl]-7-[(4-fluorophenyl)methyl]-4-hydroxy-2-oxo-1,2-dihydro-1,5-naphthyridine-3-carboxamide (0.02 g, 0.047 mmol) and diisopropyl ethylamine (0.041 mL, 0.24 mmol) in DMF (5 mL) under nitrogen was treated with methyl chloroformate (0.0036 mL, 0.047 mmol) at ambient temperature. The reaction was concentrated in vacuo and the resulting residue treated with 1 N NaHSO₄, filtered, then washed with 1 N NaHSO₄ and Et₂O before drying in vacuo to provide the title compound as an off-white solid: ¹H NMR (300 MHz, DMSO-D6) δ ppm 1.1 (t, J=7.0 Hz, 3 H), 3.3 (m, 2 H), 3.4 (s, 3 H), 3.5 (m, 7 H), 4.1 (s, 2 H), 4.3 (t, J=6.0 Hz, 2 H), 7.1 (t, J=8.8 Hz, 2 H), 7.3 (m, 1 H), 7.4 (m, 2 H), 8.1 (s, 1 H), 8.5 (s, 1 H), 17.1 (s, 1 H); ES⁺ MS: 487 (M+H⁺).

EXAMPLE 354

7-[(4-Fluorophenyl)methyl]-4-hydroxy-1-methyl-N-[1-(methylsulfonyl)-4-piperidinyl]-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (30 mg, 0.084 mmol) described in example 92, triethylamine (0.1 mL, 0.818 mmol), and 1-(methylsulfonyl)-4-piperidinamine as the trifluoroacetic acid salt (171 mg, 0.589 mmol), was prepared 7-[(4-fluorophenyl)methyl]-4-hydroxy-1-methyl-N-[-(methylsulfonyl)-4-piperidinyl]-2-oxo-1,2-dihydro-1,5-naphthyridine-3-carboxamide (15 mg, 43% yield), as a white solid after purification by reverse phase HPLC. ¹H NMR (CDCl₃) δ 10.33 (d, J=7.6 Hz, 1 H), 8.58 (s, 1 H), 7.41 (s, 1 H), 7.18-7.14 (m, 2 H), 7.05-7.00 (m, 2 H), 4.14-4.09 (m, 3 H), 3.75-3.69 (m, 2 H), 3.58 (s, 3 H), 2.97 (m, 2 H), 2.82 (s, 3 H), 2.14 (m, 2 H), 1.76 (m, 2 H); HRMS m/z calcd for $C_{23}H_{26}FN_4O_5S$: 489.1602. Found: 489.1609.

EXAMPLE 355

7-[(4-Fluorophenyl)methyl]-4-hydroxy-1-methyl-N-[3-(methylthio)propyl]-2-oxo-1,2-dihydro-15-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (30 mg, 0.084 mmol) described in example 92 and [3-(methylthio) propyl]amine (0.02 mL, 0.589 mmol) was prepared 7-[(4-fluorophenyl)methyl]-4-hydroxy-1-methyl-N-[3-(methylthio)propyl]-2-oxo-1,2-dihydro-1,5-naphthyridine-3-carboxamide (15 mg, 43% yield) as a white solid after purification by reverse phase HPLC. ¹H NMR (CDCl₃) δ 10.25 (br s, 1 H), 8.57 (s, 1 H), 7.39 (s, 1 H), 7.18-7.14 (m, 2 H), 7.05-7.00 (m, 2 H), 4.14 (s, 2 H), 3.59-3.54 (m, 5 H), 2.59 (m, 2 H), 2.12 (s, 3 H), 1.95 (m, 2 H); HRMS m/z calcd for $C_{21}H_{23}FN_3O_3S$: 416.1438. Found: 416.1447.

EXAMPLE 356

1-(2-{[[(Dimethylamino)carbonyl]amino}ethyl)-7-[(4-fluorophenyl)methyl]-4-hydroxy-N-(2-hydroxyethyl)-2-oxo-1,2-dihydro-1,5-naphthyridine-3-carboxamide A solution of 1-(2-aminoethyl)-7-[(4-fluorophenyl)methyl]-4-hydroxy-N-(2-hydroxyethyl)-2-oxo-1,2-dihydro-1,5-naphthyridine-3-carboxamide (0.019 g, 0.047 mmol) and diisopropyl ethylamine (0.15 mL, 0.86 mmol) in DMF (1.2 mL) under nitrogen was treated with N,N-dimethyl carbonyl chloride (0.0038 mL, 0.041 mmol) at ambient temperature. After 2 h, added EtOH (0.25 mL) and concentrated in vacuo. The resulting residue suspended in 1 N NaHSO₄ the refrigerated overnight. Purified by reversed phase HPLC to provide the title compound from pure fraction concentrated in vacuo as an off-white solid: ¹H NMR (300 MHz, DMSO-D6) δ ppm 2.7 (s, 6 H), 3.3 (s, 4 H), 3.4 (t, J=5.5 Hz, 2 H), 3.6 (t, J=5.3 Hz, 2 H), 4.1 (s, 2 H), 4.2 (t, J=6.0 Hz, 2 H), 4.9 (m, 1 H), 6.5 (m, 1 H), 7.1 (t, J=8.9 Hz, 2 H), 7.4 (m, 2 H), 8.3 (s, 1 H), 8.5 (s, 1 H), 10.4 (s, 1 H); ES⁻ MS: 472 (M+H⁺).

EXAMPLE 357

N-(1,1-Dioxidotetrahydro-2H-thiopyran-4-yl)-7-[(4-fluorophenyl)methyl]-4-hydroxy-2-oxo-1-(2-pyridinylmethyl)-1,2-dihydro-1,5-naphthyridine-3-carboxamide The title compound was prepared in a similar manner to that described in example 324 to provide a white solid. $^1$H NMR (400 MHz, CDCl$_3$) δ 10.51 (d, J=7.6 Hz, 1 H), 8.53 (s, 1 H), 8.44 (d, J=4.8 Hz, 1 H), 7.61-7.56 (m, 2 H), 7.18 (m, 1 H), 7.13 (d, J=7.9 Hz, 1 H), 7.00 (m, 2 H), 6.92 (m, 2 H), 5.49 (s, 2 H), 4.26 (m, 1 H), 4.02 (s, 2 H), 3.14 (m, 4 H), 2.49-2.28 (m, 4 H); HRMS m/z calcd for $C_{27}H_{26}N_4O_5FS$ (M+H)$^+$ 537.1608, found 537.1616.

EXAMPLE 358

1-(2-{[(Dimethylamino)carbonyl]amino}ethyl)-N-[2-(ethyloxy)ethyl]-7-[(4-fluorophenyl)methyl]-4-hydroxy-2-oxo-1,2-dihydro-1,5-naphthyridine-3-carboxamide A solution of 1-(2-aminoethyl)-N-[2-(ethyloxy)ethyl]-7-[(4-fluorophenyl)methyl]-4-hydroxy-2-oxo-1,2-dihydro-1,5-naphthyridine-3-carboxamide (0.02 g, 0.047 mmol) and diisopropyl ethylamine (0.041 mL, 0.24 mmol) in DMF (5 mL) under nitrogen was treated with N,N-dimethyl carbonyl chloride (0.0043 mL, 0.047 mmol) at ambient temperature. After 2 h, an additional 0.001 mL of the chloride was added and the was stirred at ambient temperature for an additional 6 h. The reaction was concentrated in vacuo and the resulting residue suspended in DMSO and water, filtered, then washed with water and Et$_2$O before drying in vacuo to provide the title compound as an off-white solid: $^1$H NMR (400 MHz, DMSO-D6) δ ppm 1.1 (t, J=7.0 Hz, 3 H), 2.7 (s, 6 H), 3.3 (d, J=7.0 Hz, 2 H), 3.5 (q, J=7.0 Hz, 2 H), 3.5 (s, 4 H), 4.1 (s, 2 H), 4.2 (t, J=6.1 Hz, 2 H), 6.6 (m, 1 H), 7.1 (t, J=8.9 Hz, 2 H), 7.4 (dd, J=8.8, 5.5 Hz, 2 H), 8.3 (s, 1 H), 8.5 (s, 1 H), 10.4 (s, 1 H); ES$^+$ MS: 500 (M+H$^+$).

EXAMPLE 359

7-(4-Fluorobenzyl)-4-hydroxy-N-[(1S)-2-hydroxy-1-methylethyl]-1-methyl-2-oxo-1,2-dihydro-1,5-naphthyridine-3-carboxamide The title compound was made in a similar manner to example 96 using (S)-(+)-2-amino-1-propanol to give a yellow solid: $^1$H NMR (CDCl$_3$) δ 10.21 (1H, d, J=7 Hz), 8.54 (1H, s), 7.40 (1H, s), 7.16 (2H, m), 7.03 (2H, m), 4.27 (1H, m), 4.13 (2H, s), 3.83 (1H, m), 3.69 (1H, m), 3.52 (3H, s), 1.30 (3H, d, J=7 Hz); HRMS calcd for $C_{20}H_{20}FN_3O_4$+H$^+$: 386.1516. Found: 386.1512.

EXAMPLE 360

7-(4-Fluorobenzyl)-4-hydroxy-N-[(1R)-2-hydroxy-1-methylethyl]-1-methyl-2-oxo-1,2-dihydro-1,5-naphthyridine-3-carboxamide The title compound was made in a similar manner to example 96 using (R)-(-)-2-amino-1-propanol to give a yellow solid: $^1$H NMR (CDCl$_3$) δ 10.20 (1H, d, J=7 Hz), 8.53 (1H, s), 7.41 (1H, s), 7.16 (2H, m), 7.02 (2H, m), 4.26 (1H, m), 4.13 (2H, s), 3.83 (1H, m), 3.69 (1H, m), 3.51 (3H, s), 1.31 (3H, d, J=7 Hz); HRMS calcd for $C_{20}H_{20}FN_3O_4$+H$^+$: 386.1516. Found: 386.1517.

EXAMPLE 361

7-(4-Fluorobenzyl)-4-hydroxy-N-[(2R)-2-hydroxypropyl]-1-methyl-2-oxo-1,2-dihydro-1,5-naphthyridine-3-carboxamide The title compound was made in a similar manner to example 96 using (R)-(-)-1-amino-propanol to give a yellow solid: $^1$H NMR (CDCl$_3$) δ 10.42 (1H, m), 8.53 (1H, s), 7.37 (1H, s), 7.16 (2H, m), 7.02 (2H, m), 4.12 (2H, s), 4.08 (1H, m), 3.62 (1H, m), 3.54 (3H, s), 3.34 (1H, m), 1.27 (3H, d, J=7 Hz); HRMS calcd for $C_{20}H_{20}FN_3O_4$+H$^+$: 386.1516. Found: 386.1518.

EXAMPLE 362

1-Ethyl-7-[(4-fluorophenyl)methyl]-4-hydroxy-N-{2-[methyl(methylsulfonyl)amino]ethyl}-2-oxo-1,2-dihydro-1,5-naphthyridine-3-carboxamide Step 1: ethyl 1-ethyl-7-[(4-fluorophenyl)methyl]-4-hydroxy-2-oxo-1,2-dihydro-1,5-naphthyridine-3-carboxylate.

In a manner similar to that described in example 316 step 1, from ethyl 7-[(4-fluorophenyl)methyl]-4-hydroxy-2-oxo-1,2-dihydro-1,5-naphthyridine-3-carboxylate (160 mg, 0.468 mmol), lithium (bis-trimethylsilyl)amide (0.94 mL of a 1 M solution in tetrahydrofuran, 0.940 mmol), and iodoethane (0.22 mL, 2.81 mmol) was prepared ethyl 1-ethyl-7-[(4-fluorophenyl)methyl]-4-hydroxy-2-oxo-1,2-dihydro-1,5-naphthyridine-3-carboxylate (170 mg, 95% yield) as a yellow oil. The product was carried on without further purification. $^1$H NMR (CDCl$_3$) δ 8.37 (s, 1 H), 7.34 (s, 1 H), 7.10-7.05 (m, 2 H), 6.95-6.91 (m, 2 H), 4.39 (m, 2 H), 4.11 (m, 2 H), 4.06 (s, 2 H), 1.35 (m, 3 H), 1.15 (m, 3 H); MS m/z 393 (M+23).

Step 2: 1-Ethyl-7-[(4-fluorophenyl)methyl]-4-hydroxy-N-{2-[methyl(methylsulfonyl)amino]ethyl}-2-oxo-1,2-dihydro-1,5-naphthyridine-3-carboxamide.

In a similar manner to that described in example 196, from ethyl 1-ethyl-7-[(4-fluorophenyl)methyl]-4-hydroxy-2-oxo-1,2-dihydro-1,5-naphthyridine-3-carboxylate (38 mg, 0.103 mmol), and N-(2-aminoethyl)-N-methylmethanesulfonamide (489 mg, 3.21 mmol), was prepared 1-ethyl-7-[(4-fluorophenyl)methyl]-4-hydroxy-N-{2-[methyl(methylsulfonyl)amino]ethyl}-2-oxo-1,2-dihydro-1,5-naphthyridine-3-carboxamide (33 mg, 67% yield) as a white solid after purification by reverse phase HPLC. $^1$H NMR (CDCl$_3$) δ 10.42 (br s, 1 H), 8.55 (s, 1 H), 7.38 (s, 1 H), 7.17-7.13 (m, 2 H), 7.04-6.99 (m, 2 H), 4.19 (m, 2 H), 4.14 (s, 2 H), 3.66 (m, 2 H), 3.41 (m, 2 H), 2.97 (s, 3 H), 2.84 (s, 3 H), 1.23 (m, 3 H); HRMS m/z calcd for $C_{22}H_{26}FN_4O_5S$: 477.1602. Found: 477.1610.

EXAMPLE 363

N-[2-(Acetylamino)ethyl]-1-ethyl-7-[(4-fluorophenyl)methyl]-4-hydroxy-2-oxo-1,2-dihydro-1,5-naphthyridine-3-carboxamide In a similar manner to that described in example 196, from ethyl 1-ethyl-7-[(4-fluorophenyl)methyl]-4-hydroxy-2-oxo- 1,2-dihydro-1,5-naphthyridine-3-carboxylate (30 mg, 0.081 mmol) and N-(2-aminoethyl)acetamide (66 mg, 0.648 mmol) was prepared N-[2-(acetylamino)ethyl]-1-ethyl-7-[(4-fluorophenyl)methyl]-4-hydroxy-2-oxo-1,2-dihydro-1,5-naphthyridine-3-carboxamide (21 mg, 60% yield) as a white solid after purification by reverse phase HPLC. $^1$H NMR (CDCl$_3$) δ 10.31 (br s, 1 H), 8.49 (s, 1 H), 7.38 (s, 1 H), 7.14-7.11 (m, 2 H), 7.01-6.96 (m, 2 H), 6.85 (br s, 1 H), 4.16 (m, 2 H), 4.10 (s, 2 H), 3.54 (m, 2 H), 3.42 (m, 2 H), 1.94 (s, 3 H), 1.20 (m, 3 H); HRMS m/z calcd for C$_{22}$H$_{24}$FN$_4$O$_4$: 427.1776 Found: 427.1783.

EXAMPLE 364

1-Ethyl-7-[(4-fluorophenyl)methyl]-4-hydroxy-2-oxo-N-[2-2-oxo-1-imidazolidinyl)ethyl]-1,2-dihydro-1,5-naphthyridine-3-carboxamide In a similar manner to that described in example 196, from ethyl 1-ethyl-7-[(4-fluorophenyl)methyl]-4-hydroxy-2-oxo-1,2-dihydro-1,5-naphthyridine-3-carboxylate (30 mg, 0.081 mmol) and 1-(2-aminoethyl)-2-imidazolidinone (0.17 mL, 0.648 mmol) was prepared 1-ethyl-7-[(4-fluorophenyl)methyl]-4-hydroxy-2-oxo-N-[2-(2-oxo-1-imidazolidinyl)ethyl]-1,2-dihydro-1,5-naphthyridine-3-carboxamide (13 mg, 35% yield) as a white solid after purification by reverse phase HPLC. $^1$H NMR (CDCl$_3$) δ 10.36 (br s, 1 H), 8.54 (s, 1 H), 7.35 (s, 1 H), 7.16-7.12 (m, 2 H), 7.04-6.94 (m, 2 H), 4.41 (s, 1 H), 4.18 (m, 2 H), 4.13 (s, 2 H), 3.62 (m, 2 H), 3.55 (m, 2 H), 3.45-3.39 (m, 4 H), 1.21 (m, 3 H); MS m/z 454 (M+1).

EXAMPLE 365

7-[(4-Fluorophenyl)methyl]-4-hydroxy-N-[(1S)-2-hydroxy-1-methylethyl]-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and S-(+)-2-amino-1-propanol employing methods similar to those described in Example 2 and using N,N-dimethylformamide as the reaction solvent. The product was obtained as an off-white solid: $^1$H NMR (d$_6$-DMSO) δ tautomers are observed 11.71 (1H, br s), 10.71 (1H, br s), 10.05 (1H, br s), 8.18 (0.59H, s), 8.14 (0.41H, s), 7.36-7.23 (3H, m), 7.14-7.08 (2H, m), 4.78 (1H, t, J=5 Hz), 3.98 (2H, s), 3.97-3.95 (1H, m), 3.49-3.41 (1H, m), 3.26-3.21 (1H, m), 1.13 (1.62H, d, J=6.6 Hz), 1.08 (1.388H, d, J=6.6 Hz); HRMS calcd for C$_{19}$H$_{18}$FN$_3$O$_4$+H$^+$: 372.1360. Found 372.1356.

EXAMPLE 366

7-[(4-Fluorophenyl)methyl]-4-hydroxy-N-[(1R)-2-hydroxy-1-methylethyl]-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and R-(−)-2-amino-1-propanol employing methods similar to those described in Example 2 and using N,N-dimethylformamide as the reaction solvent. The product was obtained as an off-white solid: $^1$H NMR (d$_6$-DMSO) tautomers are observed δ 11.72 (1H, br s), 10.70 (1H, br s), 10.04 (1H, br s), 8.17 (0.23H, s), 8.14 (0.77H, s), 7.34-7.22 (3H, m), 7.14-7.08 (2H, m), 4.79-4.77 (1H, m), 3.98 (2H, s), 3.97-3.92 (1H, m), 3.29-3.21 (1H, m), 1.13 (1.65H, d, J=6.6 Hz),1.08 (1.35H, d, J=6.6 Hz); HRMS calcd for C$_{19}$H$_{18}$FN$_3$O$_4$+H$^+$: 372.1354. Found 372.1361.

EXAMPLE 367

1-ethyl-7-[(4-fluorophenyl)methyl]-4-hydroxy-N-(2 hydroxy-1-methylethyl)-2-oxo-1,2-dihydro-1,5-naphthyridine-3-carboxamide In a similar manner to that described in example 196, from ethyl 1-ethyl-7-[(4-fluorophenyl)methyl]-4-hydroxy-2-oxo-1,2-dihydro-1,5-naphthyridine-3-carboxylate (30 mg, 0.081 mmol) and 2-amino-1-propanol (0.052 mL, 0.648 mmol) was prepared 1-ethyl-7-[(4-fluorophenyl)methyl]-4-hydroxy-N-(2-hydroxy-1-methylethyl)-2-oxo-1,2-dihydro-1,5-naphthyridine-3-carboxamide (21 mg, 66% yield) as a white solid after purification by reverse phase HPLC. $^1$H NMR (CDCl$_3$) δ 10.34 (d, J=7.2 Hz, 1 H), 8.55 (s, 1 H), 7.36 (s, 1 H), 7.18-7.14 (m, 2 H), 7.05-7.01 (m, 2 H), 4.28 (m, 1 H), 4.21-4.14 (m, 4 H), 3.79 (dd, J=10.8, 3.6 Hz, 1 H), 3.68 (dd, J=10.8, 6 Hz, 1 H), 1.32 (d, J=6.8 Hz, 3 H), 1.24 (t, J=6.8 Hz, 3 H); HRMS m/z calcd for C$_{21}$H$_{23}$FN$_3$O$_4$: 400.1667. Found: 400.1674.

EXAMPLE 368

1-Ethyl-7-[(4-fluorophenyl)methyl]-4-hydroxy-N-(2-hydroxyethyl)-2-oxo-1,2-dihydro-1,5-naphthyridine-3-carboxamide In a similar manner to that described in example 196, from ethyl 1-ethyl-7-[(4-fluorophenyl)methyl]-4-hydroxy-2-oxo-1,2-dihydro-1,5-naphthyridine-3-carboxylate (30 mg, 0.081 mmol) and 2-aminoethanol (0.05 mL) was prepared 1-ethyl-7-[(4-fluorophenyl)methyl]-4-hydroxy-N-(2-hydroxyethyl)-2-oxo-1,2-dihydro-1,5-naphthyridine-3-carboxamide (18 mg, 58% yield) as a white solid after purification by reverse phase HPLC. $^1$H NMR (CDCl$_3$) δ 10.47 (br s, 1 H), 8.53 (s, 1 H), 7.35 (s, 1 H), 7.17-7.13 (m, 2 H), 7.04-6.99 (m, 2 H), 4.20-4.13 (m, 4 H), 3.85 (m, 2 H), 3.63 (m, 2 H), 1.22 (m, 3 H); HRMS m/z calcd for C$_{20}$H$_{21}$FN$_3$O$_4$: 386.1510. Found: 386.1517.

EXAMPLE 369

1-Ethyl-7-[(4-fluorophenyl)methyl]-4-hydroxy-N-(2-hydroxypropyl)-2-oxo-1,2-dihydro-1,5-naphthyridine-3-carboxamide In a similar manner to that described in example 196, from ethyl 1-ethyl-7-[(4-fluorophenyl)methyl]-4-hydroxy-2-oxo-1,2-dihydro-1,5-naphthyridine-3-carboxylate (30 mg, 0.081 mmol) and 1-amino-2-propanol (0.05 mL) was prepared 1-ethyl-7-[(4-fluorophenyl)methyl]-4-hydroxy-N-(2-hydroxypropyl)-2-oxo-1,2-dihydro-1,5-naphthyridine-3-carboxamide (12 mg, 38% yield) as a white solid after purification by reverse phase HPLC. $^1$H NMR (CDCl$_3$) δ 10.49 (s, 1 H), 8.56 (s, 1 H), 7.37 (s, 1 H), 7.18 (m, 2 H), 7.05-7.07 (m, 2 H), 4.23-4.06 (m, 5 H), 3.62 (m, 1 H), 3.38 (m, 1 H), 1.29-1.22 (m, 6 H); HRMS m/z calcd for C$_{21}$H$_{23}$FN$_3$O$_4$: 400.1667. Found: 400.1673.

EXAMPLE 370

1-[3-(1,3-Dioxo-1,3-dihydro-2H-isoindol-2-yl)propyl]-7-[(4-fluorophenol)methyl]-4-hydroxy-N-(2-hydroxyethyl)-2-oxo-1,2-dihydro-1,5-naphthyridine-3-carboxamide A mixture of ethyl 1-[3-(1,3-dioxo-1,3-dihydro-2H-isoindol-2-yl)propyl]-7-[(4-fluorophenyl)methyl]-4-hydroxy-2- oxo-1,2-dihydro-1,5-naphthyridine-3-carboxylate (50 mg, 0.095 mmol) and ethanolamine (28 μL, 0.46 mmol) was combined in ethanol (3 mL) and heated in a microwave tube twice for 10 min. at 150° C. The mixture was stirred at ambient temperature and the crude product was filtered and washed with 1N NaHSO₄. Purification by reverse phase chromatography eluting with 10-90% aqueous CH₃CN containing 0.1% formic acid provided a white solid: $^1$H NMR (d₆-DMSO) δ 10.36 (1H, b), 8.53 (1H, s), 7.81-7.86 (2H, m), 7.71-7.75 (2H, m), 7.34 (1H, s), 7.12-7.17 (2H, m), 6.99 (2H, t, J=9 Hz), 4.24 (2H, t, J=8 Hz), 4.08 (2H, s), 3.81-3.87 (2H, m), 3.76 (2H, t, J=6 Hz), 3.58-3.64 (2H, m), 2.44 (1H, b), 2.01-2.09 (2H, m); ES⁺ MS: 545 (M+H⁺).

EXAMPLE 371

1-[2-(1,1-dioxido-2-isothiazolidinyl)ethyl]-7-[(4-fluorophenyl)methyl]-4-hydroxy-N-(2-hydroxyethyl)-2-oxo-1,2-dihydro-1,5-naphthyridine-3-carboxamide N-[2,2-bis(methyloxy)ethyl]-3-chloro-1-propanesulfonamide. To a cold (0° C.) solution of aminoacetaldehyde dimethyl acetal (2.22 mL, 20.4 mmol) and triethylamine (3.54 mL, 25.4 mmol) in dichloromethane (60 mL) was added 3-chloropropanesulfonyl chloride (2.06 mL, 16.9 mmol) in dichloromethane (40 mL) dropwise. The reaction mixture was warmed to room temperature and stirred one hour. The reaction mixture was quenched with water. The organic phase was washed with water and brine, then dried over sodium sulfate. Filtration and concentration, followed by trituration with ether provided N-[2,2-bis(methyloxy)ethyl]-3-chloro-1-propanesulfonamide as a white solid. $^1$H NMR (400 MHz, CDCl₃) δ 4.56 (s, 1 H), 4.42 (t, J=5.0 Hz, 1 H), 3.68 (t, J=6.1 Hz, 2 H), 3.42 (s, 6 H), 3.25-3.21 (m, 4 H), 2.28 (m, 2 H).

2-[2,2-bis(methyloxy)ethyl]isothiazolidine 1,1-dioxide. To a cold (0° C.) suspension of sodium hydride (267 mg, 60% in oil, 6.67 mmol) in N,N-dimethylformamide (30 mL) was added N-[2,2-bis(methyloxy)ethyl]-3-chloro-1-propanesulfonamide (1.49 g, 6.06 mmol) in N,N-dimethylformamide (10 mL) dropwise. The reaction mixture was warmed to room temperature and stirred one hour. The reaction mixture was poured onto ice and extracted with toluene. The organic layer was washed with water and brine, then dried over sodium sulfate. Filtration and concentration provided 2-[2,2-bis(methyloxy)ethyl]isothiazolidine 1,1-dioxide as a clear oil. $^1$H NMR (400 MHz, CDCl₃) δ 4.51 (t, J=5.3 Hz, 1 H), 3.41-3.37 (m, 8 H), 3.17-3.11 (m, 4 H), 2.35 (m, 2 H).

(1,1-dioxido-2-isothiazolidinyl)acetaldehyde. To a solution of 2-[2,2-bis(methyloxy)ethyl]isothiazolidine 1,1-dioxide (1.00 g, 4.77 mmol) in acetone (5 mL) was added hydrochloric acid (600 μL, 1 M aqueous, 0.600 mmol). The reaction mixture was heated at 60° C. for 10 hours, then cooled to room temperature. The excess acetone was removed in vacuo and the resulting residue was partitioned between water and dichloromethane. The organic layer was separated and dried over sodium sulfate. Filtration and concentration, followed by flash chromatography (0 to 5%, methanol in dichloromethane) provided (1,1-dioxido-2-isothiazolidinyl)acetaldehyde as a brown oil. $^1$H NMR (400 MHz, CDCl₃) δ 9.64 (s, 1 H), 3.91 (s, 2 H), 3.39 (m, 2 H), 3.20 (t, J=7.7 Hz, 2 H), 2.44 (m, 2 H).

Ethyl 3-{[2-(1,1-dioxido-2-isothiazolidinyl)ethyl]amino}-5-[(4-fluorophenyl)methyl]-2-pyridinecarboxylate. This compound was prepared from ethyl 3-amino-5-[(4-fluorophenyl)methyl]-2-pyridinecarboxylate and (1,1-dioxido-2-isothiazolidinyl)acetaldehyde employing methods similar to those described in Example 265 and was obtained as a brownish oil. $^1$H NMR (400 MHz, CDCl₃) δ 7.92 (s, 1 H), 7.89 (br, 1 H), 7.14 (dd, J=8.4, 5.4 Hz, 2 H), 6.98 (t, J=8.6 Hz, 2 H), 6.92 (s, 1 H), 4.41 (q, J=7.2 Hz, 2 H), 3.91 (s, 2 H), 3.41 (m, 2 H), 3.29-3.24 (m, 4 H), 3.13 (t, J=7.7 Hz, 2 H), 2.31 (m, 2 H), 1.41 (t, J=7.0 Hz, 3 H); MS m/z 422 (M+H)⁺.

Ethyl 3-{[2-(1,1-dioxido-2-isothiazolidinyl)ethyl][3-(ethyloxy)-3-oxopropanoyl]amino}-5-[(4-fluorophenyl)methyl]-2-pyridinecarboxylate. This compound was prepared from ethyl 3-{[2-(1,1-dioxido-2-isothiazolidinyl)ethyl]amino}-5-[(4-fluorophenyl)methyl]-2-pyridinecarboxylate employing methods similar to those described in Example 202 and was obtained as a brown oil. $^1$H NMR (400 MHz, CDCl₃) δ 8.59 (d, J=1.5 Hz, 1 H), 7.94 (d, J=1.5 Hz, 1 H), 7.20 (dd, J=8.5, 5.5 Hz, 2 H), 7.00 (t, J=8.6 Hz, 2 H), 4.71-2.88 (m, 1 H), 4.04 (s, 2 H), 2.48-2.22 (m, 2 H), 1.48-1.13 (m, 6 H); MS m/z 536 (M+H)⁺.

Ethyl 1-[2-(1,1-dioxido-2-isothiazolidinyl)ethyl]-7-[(4-fluorophenyl)methyl]-4-hydroxy-2-oxo-1,2-dihydro-1,5-naphthyridine-3-carboxylate. This compound was prepared from ethyl 3-{[2-(1,1-dioxido-2-isothiazolidinyl)ethyl][3-(ethyloxy)-3-oxopropanoyl]amino}-5-[(4-fluorophenyl)methyl]-2-pyridinecarboxylate employing methods similar to those described in Example 202 and was obtained as an orange solid. $^1$H NMR (400 MHz, CDCl₃) δ 8.53 (s, 1 H), 7.85 (s, 1 H), 7.24 (m, 2 H), 7.01 (t, J=8.6 Hz, 2 H), 4.52 (q, J=7.0 Hz, 2 H), 4.40 (t, J=7.2 Hz, 2 H), 4.12 (s, 2 H), 3.37 (t, J=7.3 Hz, 2 H), 3.30 (t, J=6.6 Hz, 2 H), 3.09 (t, J=7.6 Hz, 2 H), 2.27 (m, 2 H), 1.47,(t, J=7.1 Hz, 3 H); MS m/z 490 (M+H)⁺.

1-[2-(1,1-dioxido-2-isothiazolidinyl)ethyl]-7-[(4-fluorophenyl)methyl]-4-hydroxy-N-(2-hydroxyethyl)-2-oxo-1,2-dihydro-1,5-naphthyridine-3-carboxamide. This compound was prepared from ethyl 1-[2-(1,1-dioxido-2-isothiazolidinyl)ethyl]-7-[(4-fluorophenyl)methyl]-4-hydroxy-2-oxo-1,2-dihydro-1,5-naphthyridine-3-carboxylate and ethanolamine employing methods similar to those described in Example 202 and was obtained as an white solid. $^1$H NMR (400 MHz, CDCl₃) δ 10.37 (t, J=5.3 Hz, 1 H), 8.59 (s, 1 H), 7.87 (s, 1 H), 7.24 (m, 2 H), 7.02 (t, J=8.6 Hz, 2 H), 4.42 (t, J=7.0 Hz, 2 H), 4.13 (s, 2 H), 3.87 (t, J=5.2 Hz, 2 H), 3.65 (m, 2 H), 3.36 (t, J=7.0 Hz, 2 H), 3.26 (t, J=6.5 Hz, 2 H), 3.08 (t, J=7.5 Hz, 2 H), 2.25 (m, 2 H); HRMS C₂₃H₂₅FN₄O₆S (M+H)⁺ calcd 505.1479, found 505.1558.

EXAMPLE 372

1-[3-(1,3-Dioxo-1,3-dihydro-2H-isoindol-2-yl)propyl]-N-[2-(ethyloxy)ethyl]-7-[(4-fluorophenyl)methyl]-4-hydroxy-2-oxo-1,2-dihydro-1,5-naphthyridine-3-carboxamide This compound was prepared from ethyl 1-[3-(1,3-dioxo-1,3-dihydro-2H-isoindol-2-yl)propyl]-7-[(4-fluorophenyl)methyl]-4-hydroxy-2-oxo-1,2-dihydro-1,5-naphthyridine-3-carboxylate and 2-(ethyloxy)ethanamine employing methods similar to those described in Example 370 and was obtained as a white solid: ES⁺ MS: 573 (M+H⁺).

EXAMPLE 373

Methyl {3-[3-({[2-(ethyloxy)ethyl]amino}carbonyl)-7-[(4-fluorophenyl)methyl]-4-hydroxy-2-oxo-1,5-naphthyridine-1(2H)-yl]propyl}carbamate Step 1: Synthesis of 1-(3-aminopropyl)-N-[2-(ethyloxy)ethyl]-7-[(4-fluorophenyl)methyl]-4-hydroxy-2-oxo-1,2-dihydro-1,5-naphthyridine-3-carboxamide A mixture of 1-[3-(1,3-dioxo-1,3-dihydro-2H-isoindol-2-yl)propyl]-N-[2-(ethyloxy)ethyl]-7-[(4-fluorophenyl)methyl]-4-hydroxy-2-oxo-1,2-dihydro-1,5-naphthyridine-3-carboxamide (261 mg, 0.46 mmol) and anhydrous hydrazine (286 μL, 9.1 mmol) in ethanol (20 mL) was heated at 50° C. for 5 hours. Water (40 mL) was added and the resulting slurry was cooled to 0-5° C. and collected by filtration to provide the product as a white solid: $^1$H NMR (CDCl$_3$) δ 10.52 (1H, b), 8.44 (1H, s), 7.93 (1H, s), 7.33-7.39 (2H, m), 7.09-7.16 (2H, m), 4.22 (2H, t, J=7 Hz), 4.13 (2H, s), 3.42-3.50 (6H, m), 2.61 (2H, t, J=7 Hz), 1.65-1.73 (2H, m), 1.11 (3H, t, J=7 Hz); ES$^+$ MS: 443 (M+H$^+$).

Methyl {3-[3-({[2-(ethyloxy)ethyl]amino}carbonyl)-7-[(4-fluorophenyl)methyl]-4-hydroxy-2-oxo-1,5-naphthyridin-1(2H)-yl]propyl}carbamate. A mixture of 1-(3-aminopropyl)-N-[2-(ethyloxy)ethyl]-7-[(4-fluorophenyl)methyl]-4-hydroxy-2-oxo-1,2-dihydro-1,5-naphthyridine-3-carboxamide (15 mg, 0.034 mmol), methyl chloroformate (2.6 μL, 034 mmol) and diisopropylethyl amine (30 μL, 0.17 mmol) in anhydrous DMF (1.5 mL) was stirred under nitrogen at ambient temperature overnight. The crude reaction mixture was evaporated in vacuo and purified by reverse phase chromatography eluting with 10-90% aqueous CH$_3$CN containing 0.1% formic acid to provide the product as a white solid: $^1$H NMR (CDCl$_3$) δ 10.29 (2H, b), 8.57 (1H, s), 7.36 (1H, s), 7.13-7.18 (2H, m), 7.00-7.05 (2H, m), 5.60 (2H, b), 4.23 (2H, t, J=7 Hz), 4.13 (2H, s), 3.67 (3H, s), 3.63 (2H, b), 3.56 (2H, q, J=7 Hz), 3.11 (2H, b), 1.74-1.81 (2H, m), 1.24 (3H, t, J=7 Hz); ES$^+$ MS: 501 (M+H$^+$).

EXAMPLE 374

1-(3-Aminopropyl)-N-[2-(ethyloxy)ethyl]-7-[(4-fluorophenyl)methyl]-4-hydroxy-2-oxo-1,2-dihydro-1,5-naphthyridine-3-carboxamide A mixture of 1-[3-(1,3-dioxo-1,3-dihydro-2H-isoindol-2-yl)propyl]-N-[2-(ethyloxy)ethyl]-7-[(4-fluorophenyl)methyl]-4-hydroxy-2-oxo-1,2-dihydro-1,5-naphthyridine-3-carboxamide (261 mg, 0.46 mmol) and anhydrous hydrazine (286 μL, 9.1 mmol) in ethanol (20 mL) was heated at 50° C. for 5 hours. Water (40 mL) was added and the resulting slurry was cooled to 0-5° C. and collected by filtration to provide the product as a white solid: $^1$H NMR (CDCl$_3$) δ 10.52 (1H, b), 8.44 (1H, s), 7.93 (1H, s), 7.33-7.39 (2H, m), 7.09-7.16 (2H, m), 4.22 (2H, t, J=7 Hz), 4.13 (2H, s), 3.42-3.50 (6H, m), 2.61 (2H, t, J=7 Hz), 1.65-1.73 (2H, m), 1.11 (3H, t, J=7 Hz); ES$^+$ MS: 443 (M+H$^+$).

EXAMPLE 375

1-[3-(acetylamino)propyl]-N-[2-(ethyloxy)ethyl]-7-[(4-fluorophenyl)methyl]-4-hydroxy-2-oxo-1,2-dihydro-1,5-naphthyridine-3-carboxamide This compound was prepared from 1-(3-aminopropyl)-N-[2-(ethyloxy)ethyl]-7-[(4-fluorophenyl)methyl]-4-hydroxy-2-oxo-1,2-dihydro-1,5-naphthyridine-3-carboxamide and acetic anhydride employing methods similar to those described in Step 2 of Example 373 and was obtained as a white solid: ES$^+$ MS: 485 (M+H$^+$).

EXAMPLE 376

1-(3-{[(dimethylamino)carbonyl]amino}propyl)-N-[2-(ethyloxy)ethyl]-7-[(4-fluorophenyl)methyl]-4-hydroxy-2-oxo-1,2-dihydro-1,5-naphthyridine-3-carboxamide This compound was prepared from 1-(3-aminopropyl)-N-[2-(ethyloxy)ethyl]-7-[(4-fluorophenyl)methyl]-4-hydroxy-2-oxo-1,2-dihydro-1,5-naphthyridine-3-carboxamide and dimethylcarbamyl chloride employing methods similar to those described in Step 2 of Example 373 and was obtained as a lyophile: ES$^+$ MS: 514 (M+H$^+$).

EXAMPLE 377

7-[(4-Fluorophenyl)methyl]-4-hydroxy-N-(2-hydroxyethyl)-1-(3-hydroxypropyl)-2-oxo-1,2-dihydro-1,5-naphthyridine-3-carboxamide Ethyl 7-[(4-Fluorophenyl)methyl]-4-hydroxy-1-(3-hydroxypropyl)-2-oxo-1,2-dihydro-1,5-naphthyridine-3-carboxylate. In a similar manner to that described in example 316 step 1, from ethyl 7-[(4-fluorophenyl)methyl]-4-hydroxy-2-oxo-1,2-dihydro-1,5-naphthyridine-3-carboxylate (20 mg, 0.0584 mmol), lithium (bis-trimethylsilyl)amide (0.18 mL of a 1 M tetrahydrofuran solution, 0.18 mmol), and 3-iodo-1-propanol (0.03 mL, 0.350 mmol) was prepared ethyl 7-[(4-fluorophenyl)methyl]-4-hydroxy-1-(3-hydroxypropyl)-2-oxo-1,2-dihydro-1,5-naphthyridine-3-carboxylate (22 mg, 95% yield) as a yellow oil. The product was carried on without further purification. MS m/z 423 (M+23).

S7-[(4-Fluorophenyl)methyl]-4-hydroxy-N-(2-hydroxyethyl)-1-(3-hydroxypropyl)-2-oxo-1,2-dihydro-1,5-naphthyridine-3-carboxamide. In a similar manner to that described in example 196, from ethyl 7-[(4-fluorophenyl)methyl]-4-hydroxy-1-(3-hydroxypropyl)-2-oxo-1,2-dihydro-1,5-naphthyridine-3-carboxylate (27 mg, 0.0675 mmol) and 2-aminoethanol (0.05 mL) was prepared 7-[(4-fluorophenyl)methyl]-4-hydroxy-N-(2-hydroxyethyl)-1-(3-hydroxypropyl)-2-oxo-1,2-dihydro-1,5-naphthyridine-3-carboxamide (13 mg, 46% yield) as a white solid after purification by reverse phase HPLC. $^1$H NMR (CDCl$_3$) δ 10.28 (br s, 1 H), 8.52 (s, 1 H), 7.51 (1 H), 7.15-7.11 (m, 2 H), 7.01-6.96 (m, 2 H), 4.27 (m, 2 H), 4.10 (s, 2 H), 3.76 (m, 2 H), 3.57 (m, 2 H), 3.49 (m, 2 H), 1.79 (m, 2 H); HRMS m/z calcd for C$_{21}$H$_{23}$N$_3$O$_5$F: 416.1622. Found: 416.1634.

EXAMPLE 378

1-[2-(1,1-Dioxido-2-isothiazolidinyl)ethyl]-7-[(4-fluorophenyl)methyl]-4-hydroxy-N-[2-(methyloxy)ethyl]-2-oxo-1,2-dihydro-1,5-naphthyridine-3-carboxamide This compound was prepared from ethyl 1-[2-(1,1-dioxido-2-isothiazolidinyl)ethyl]-7-[(4-fluorophenyl)methyl]-4-hydroxy-2-oxo-1,2-dihydro-1,5-naphthyridine-3-carboxylate and 2-methoxyethylamine employing methods similar to those described in Example 202 and was obtained as a white solid. $^1$H NMR (400 MHz, CDCl$_3$) δ 10.24 (s, 1 H), 8.58 (s, 1 H), 7.86 (s, 1 H), 7.24 (m, 2 H), 7.01 (t, J=8.6 Hz, 2 H), 4.42 (t, J=7.0 Hz, 2 H), 4.12 (s, 2 H), 3.65 (m, 2 H), 3.59 (m, 2 H), 3.42 (s, 3 H), 3.36 (t, J=6.9 Hz, 2 H), 3.26 (t, J=6.7 Hz, 2 H), 3.07 (t, J=7.5 Hz, 2 H), 2.24 (m, 2 H); HRMS C$_{24}$H$_{27}$FN$_4$O$_6$S (M+H)$^+$ calcd 519.1635, found 519.1718.

EXAMPLE 379

1-[2-(1,1-Dioxido-2-isothiazolidinyl)ethyl]-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide This compound was prepared from ethyl 1-[2-(1,1-dioxido-2-isothiazolidinyl)ethyl]-7-[(4-fluorophenyl)methyl]-

4-hydroxy-2-oxo-1,2-dihydro-1,5-naphthyridine-3-carboxylate and 1-(3-aminopropyl)-2-pyrrolidinone employing methods similar to those described in Example 202. The free phenol existed as an oil and was therefore treated with aqueous sodium hydroxide solution and concentrated to give the corresponding sodium phenolate as a white solid. $^1$H NMR (400 MHz, CDCl$_3$) δ 10.22 (t, J=5.2 Hz, 1 H), 8.57 (s, 1 H), 7.85 (s, 1 H), 7.23 (dd, J=8.5, 5.4 Hz, 2 H), 7.00 (t, J=8.7 Hz, 2 H), 4.42 (t, J=7.0 Hz, 2 H), 4.12 (s, 2 H), 3.47-3.33 (m, 8 H), 3.26 (t, J=6.8 Hz, 2 H), 3.07 (t, J=7.6 Hz, 2 H), 2.40 (t, J=7.9 Hz, 2 H), 2.24 (m, 2 H), 2.04 (m, 2 H), 1.87 (m, 2 H); HRMS C$_{28}$H$_{32}$FN$_5$O$_6$S (M+H)$^+$ calcd 586.2057, found 586.2133.

EXAMPLE 380

7-[(4-fluorophenyl)methyl]-4-hydroxy-N-{2-[methyl(methylsulfonyl)amino]ethyl}-1-[2-(methyloxy)ethyl]-2-oxo-1,2-dihydro-1,5-naphthyridine-3-carboxamide In a manner similar to that described in example 316, from ethyl 7-[(4-fluorophenyl)methyl]-4-hydroxy-1-[2-(methyloxy)ethyl]-2-oxo-1,2-dihydro-1,5-naphthyridine-3-carboxylate (10 mg, 0.025 mmol) and N-(2-aminoethyl)-N-methylmethanesulfonamide (50 mg, 0.329 mmol) was prepared 7-[(4-fluorophenyl)methyl]-4-hydroxy-N-{2-[methyl(methylsulfonyl)amino]ethyl}-1-[2-(methyloxy)ethyl]-2-oxo-1,2-dihydro-1,5-naphthyridine-3-carboxamide (8 mg, 62% yield) as a white solid after purification by reverse phase HPLC. $^1$H NMR (CDCl$_3$) δ 10.36 (br s, 1 H), 8.53 (s, 1 H), 7.69 (s, 1 H), 7.16-7.13 (m, 2 H), 7.02-6.98 (m, 2 H), 4.33 (m, 2 H), 4.10 (s, 2 H), 3.68-3.61 (m, 4 H), 3.39 (m, 2 H), 3.18 (s, 3 H), 2.95 (s, 3 H), 2.82 (s, 3 H); MS m/z 507 M+1).

EXAMPLE 381

7-[(4-Fluorophenyl)methyl]-4-hydroxy-1-(3-hydroxypropyl)-N-{2-[methyl(methylsulfonyl)amino]ethyl}-2-oxo-1,2-dihydro-1,5-naphthyridine-3-carboxamide In a similar manner to that described in example 196, from ethyl 7-[(4-fluorophenyl)methyl]-4-hydroxy-1-(3-hydroxypropyl)-2-oxo-1,2-dihydro-1,5-naphthyridine-3-carboxylate (60 mg, 0.15 mmol) and N-(2-aminoethyl)-N-methylmethanesulfonamide (100 mg, 0.657 mmol) was prepared 7-[(4-fluorophenyl)methyl]-4-hydroxy-1-(3-hydroxypropyl)-N-{2-[methyl(methylsulfonyl)amino]ethyl}-2-oxo-1,2-dihydro-1,5-naphthyridine-3-carboxamide (18 mg, 24% yield) as a white solid after purification by reverse phase HPLC. $^1$H NMR (CDCl$_3$) δ 10.31 (br s, 1 H), 8.58 (s, 1 H), 7.49 (s, 1 H), 7.18-7.14 (m, 2 H), 7.05-6.99 (m, 2 H), 4.37 (m, 2 H), 4.14 (s, 2 H), 3.67 (m, 2 H), 3.51 (m, 2 H), 3.41 (m, 2 H), 2.95 (s, 3 H), 2.83 (s, 3 H), 1.83 (m, 2 H); HRMS m/z calcd for C$_{23}$H$_{28}$N$_4$O$_6$FS: 507.1714. Found: 507.1712.

EXAMPLE 382

1-[2-(Dimethylamino)-2-oxoethyl]-7-[(4-fluorophenyl)methyl]-4-hydroxy-N-[1-(hydroxymethyl)cyclopentyl]-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and (1-aminocyclopentyl)methanol employing methods similar to those described in Example 245 and was purified by reverse phase preparative HPLC (C-18 stationary phase; 10-100% CH$_3$CN/water/0.1% formic acid mobile phase). The product was obtained as a cream-colored solid: $^1$H NMR (d$_6$-DMSO) δ 10.32 (1H, s), 8.50 (1H, s), 7.74 (1H, s), 7.32 (2H, dd, J=8.5, 6 Hz), 7.12 (2H, t, J~9 Hz), 5.12 (2H, s), 5.04 (1H, br), 4.11 (2H, s), 3.51 (2H, s), 3.12 (3H, s), 2.82 (3H, s), 1.91 (2H, m), 1.74 (4H, m), 1.56 (2H, m); HRMS calcd for C$_{26}$H$_{29}$FN$_4$O$_5$+H$^+$: 497.2200. Found: 497.2200.

EXAMPLE 383

1-[2-(Dimethylamino)-2-oxoethyl]-7-[(4-fluorophenyl)methyl]-4-hydroxy-N-(2-hydroxy-1,1-dimethylethyl)-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and 2-amino-2-methyl-1-propanol employing methods similar to those described in Example 245 and was purified by reverse phase preparative HPLC (C-18 stationary phase; 10-100% CH$_3$CN/water/0.1% formic acid mobile phase). The product was obtained as a cream-colored solid: $^1$H NMR (d$_6$-DMSO) δ 10.35 (1H, s), 8.49 (1H, d, J=1.3 Hz), 7.74 (1H, s), 7.32 (2H, dd, J=8.6, 5.6 Hz), 7.12 (2H, t, J~9 Hz), 5.11 (2H, s), 5.09 (1H, m), 4.10 (2H, s), 3.44 (2H, d, J=5 Hz), 3.12 (3H, s), 2.82 (3H, s), 1.32 (6H, s); HRMS calcd for C$_{24}$H$_{27}$FN$_4$O$_5$+H$^+$: 471.2044. Found: 471.2040.

Example 384

1-[2-(Dimethylamino)-2-oxoethyl]-7-[(4-fluorophenyl)methyl]-4-hydroxy-N-{2-[methyl(methylsulfonyl)amino]ethyl}-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and N-(2-aminoethyl)-N-methylmethanesulfonamide employing methods similar to those described in Example 245 and was purified by reverse phase preparative HPLC (C-18 stationary phase; 10-100% CH$_3$CN/water/0.1% formic acid mobile phase). The product was obtained as a cream-colored solid: $^1$H NMR (d$_6$-DMSO) δ 10.20 (1H, br t, J=6 Hz), 8.51 (1H, s), 7.76 (1H, s), 7.31 (2H, dd, J=8.3, 6 Hz), 7.12 (2H, t, J~9 Hz), 5.12 (2H, s), 4.11 (2H, s), 3.55 (2H, q, J=6 Hz), 3.25 (2H, m), 3.12 (3H, s), 2.85 (3H, s), 2.81 (3H, s), 2.79 (3H, s); HRMS calcd for C$_{24}$H$_{28}$FN$_5$O$_6$+H$^+$: 534.1823. Found: 534.1812.

EXAMPLE 385

1-[2-(Dimethylamino)-2-oxoethyl]-7-[(4-fluorophenyl)methyl]-4-hydroxy-N-[(1R)-2-hydroxy-1-methylethyl]-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and (2R)-2-amino-1-propanol employing methods similar to those described in Example 245 and was purified by reverse phase preparative HPLC (C-18 stationary phase; 10-100% CH$_3$CN/water/0.1% formic acid mobile phase). The product was obtained as an off-white solid: $^1$H NMR (d$_6$-DMSO) δ 10.23 (1H, d, J=8 Hz), 8.50 (1H, s), 7.77 (1H, s), 7.32 (2H, dd, J=8.6, 6 Hz), 7.12 (2H, t, J=8.6 Hz), 5.12 (2H, m), 5.00 (1H, br), 4.11 (2H, s), 4.03 (1H, m), 3.44 (2H, m), 3.12 (3H, s), 2.82 (3H, s), 1.15 (3H, d, J=7 Hz); HRMS calcd for C$_{23}$H$_{25}$FN$_4$O$_5$+H$^+$: 457.1887. Found: 457.1881.

EXAMPLE 386

1-[2-(Dimethylamino)-2-oxoethyl]-7-[(4-fluorophenyl)methyl]-4-hydroxy-N-[(1S)-2-hydroxy-1-methylethyl]-2-oxo-1,2-dihydro-1,5-naphthyridine-3-carboxamide This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and (2S)-2-amino-1-propanol employing methods similar to those described in Example 245 and was purified by reverse phase preparative HPLC (C-18 stationary phase; 10-100% CH$_3$CN/water/0.1% formic acid mobile phase). The product was obtained as an off-white solid: $^1$H NMR (d$_6$-DMSO) δ 10.23 (1H, d, J=8 Hz), 8.50 (1H, s), 7.77 (1H, s), 7.32 (2H, dd, J=8.6, 6 Hz), 7.12 (2H, t, J=8.6 Hz), 5.12 (2H, m), 4.98 (1H, t, J=5 Hz), 4.11 (2H, s), 4.03 (1H, m), 3.44 (2H, m), 3.12 (3H, s), 2.82 (3H, s), 1.15 (3H, d, J=7 Hz); HRMS calcd for C$_{23}$H$_{25}$FN$_4$O$_5$+H$^+$: 457.1887. Found: 457.1879.

EXAMPLE 387

Sodium 1-[2-(dimethylamino)-2-oxoethyl]-7-[(4-fluorophenyl)methyl]-3-({[(2R)-2-hydroxypropyl]amino}carbonyl)-2-oxo-1,2-dihydro-1,5-naphthyridine-4-olate This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and (2R)-1-amino-2-propanol employing methods similar to those described in Example 245 and was purified by reverse phase preparative HPLC (C-18 stationary phase; 10-100% CH$_3$CN/water/0.1% formic acid mobile phase). The resulting material was treated with 1.3 equivalents of 1N NaOH solution and triturated with CH$_3$CN to afford the product as a white solid: $^1$H NMR (d$_6$-DMSO) δ 10.59 (1H, br), 8.14 (1H, s), 7.26 (3H, m), 7.10 (2H, m), 4.92 (2H, s), 4.80 (1H, br), 3.99 (2H, s), 3.67 (1H, br), 3.15 (2H, m), 3.08 (3H, s), 2.78 (3H, s), 1.04 (3H, br d, J~5 Hz); HRMS calcd for C$_{23}$H$_{25}$FN$_4$O$_5$+H$^+$: 457.1887. Found: 457.1882.

EXAMPLE 388

1-(2-Aminoethyl)-7-[(4-fluorophenyl)methyl]-4-hydroxy-N-{2-[(1-methylethyl)oxy]ethyl}-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.143 g, 0.28 mmol) in EtOH (3 mL) under nitrogen was treated with 2-[(1-methylethyl)oxy]ethanamine (0.102 mL, 0.83 mmol) for 50 min. (130° C. in a microwave vessel. The reaction was transferred to a test tube, diluted with EtOH (35 mL), and treated with hydrazine (0.174 mL, 5.55 mmol) for 4 h@50° C. After the reaction was cooled to ambient temperature the resulting suspension was diluted with water (150 mL) and refrigerated overnight. The resulting suspension was filtered, washed with 3:1 water:EtOH and thoroughly dried under high vacuum to provide the title compound as an off-white solid: $^1$H NMR (400 MHz, DMSO-D6) δ ppm 1.1 (d, J=6.2 Hz, 6 H), 2.8 (bs, 2 H), 3.3 (s, 2 H), 3.5 (m, 4 H), 3.6 (m, 1 H), 4.2 (s, 2 H), 7.1 (t, J=9.3 Hz, 2 H), 7.4 (dd, J=8.5, 5.4 Hz, 2 H), 8.1 (s, 1 H), 8.5 (s, 1 H), 10.4 (s, 1 H); ES$^+$ MS: 443 (M+H$^+$).

EXAMPLE 389

1-[2-(1,3-Dioxo-1,3-dihydro-2H-isoindol-2-yl)ethyl]-7-[(4-fluorophenyl)methyl]-4-hydroxy-N-[3-(4-morpholinyl)propyl]-2-oxo-1,2-dihydro-1,5-naphthyridine-3-carboxamide-[3-(4-morpholinyl)propyl]amine (1:1)

A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (2.5 mL) under nitrogen was treated with [3-(4-morpholinyl)propyl]amine (0.035 mL, 0.24 mmol) for 40 min.@130° C. in a microwave vessel. The reaction was then cooled to ambient temperature and the resulting suspension was filtered, washed with EtOH and Et$_2$O then thoroughly dried under high vacuum to provide the title compound as a white solid: $^1$H NMR (300 MHz, DMSO-D6) δ ppm 1.5 (m, 4 H), 2.2 (t, J=7.0 Hz, 2 H), 2.3 (m, 1 H), 2.6 (t, J=6.9 Hz, 2 H), 3.2 (q, J=6.5 Hz, 2 H), 3.5 (q, J=4.9 Hz, 8 H), 3.9 (t, J=5.5 Hz, 2 H), 4.1 (s, 2 H), 4.5 (t, J=5.6 Hz, 2 H), 7.1 (ddd, J=9.1, 6.7, 2.1 Hz, 2 H), 7.3 (m, 2 H), 7.8 (m, 4 H), 8.1 (s, 1 H), 8.4 (t, J=1.1 Hz, 1 H), 10.0 (t, J=6.0 Hz, 1 H); ES$^+$ MS: 614 (M+H$^+$).

EXAMPLE 390

1-[2-(1,3-dioxo-1,3-dihydro-2H-isoindol-2-yl)ethyl]-7-[(4-fluorophenyl)methyl]-4-hydroxy-2-oxo-N-(tetrahydro-2-furanylmethyl)-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (2.5 mL) under nitrogen was treated with 1-(tetrahydro-2-furanyl)methanamine (0.025 mL, 0.24 mmol) for 40 min. (130° C. in a microwave vessel. The reaction was then cooled to ambient temperature and the resulting suspension was filtered, washed with EtOH and Et$_2$O then thoroughly dried under high vacuum to provide the title compound as a white solid: $^1$H NMR (300 MHz, DMSO-D6) δ ppm 1.7 (m, 4 H), 3.2 (m, 2 H), 3.6 (m, 2 H), 3.8 (m, 1 H), 3.9 (t, J=5.7 Hz, 2 H), 4.1 (s, 2 H), 4.6 (m, 1 H), 7.1 (m, 2 H), 7.3 (m, 2 H), 7.8 (s, 4 H), 8.2 (s, 1 H), 8.5 (d, J=1.4 Hz, 1 H), 10.0 (t, J=5.8 Hz, 1 H); ES$^+$ MS: 571 (M+H$^+$).

EXAMPLE 391

1-[2-(Acetylamino)ethyl]-7-[(4-fluorophenyl)methyl]-4-hydroxy-N-{2-[(1-methylethyl)oxy]ethyl}-2-oxo-1,2-dihydro-1,5-naphthyridine-3-carboxamide A solution of 1-(2-aminoethyl)-7-[(4-fluorophenyl)methyl]-4-hydroxy-N-{2-[(1-methylethyl)oxy]ethyl}-2-oxo-1,2-dihydro-1,5-naphthyridine-3-carboxamide (0.021 g, 0.046 mmol) and diisopropyl ethylamine (0.04 mL, 0.23 mmol) in DMF (5 mL) under nitrogen was treated with acetic anhydride (0.0046 mL, 0.048 mmol) at ambient temperature. The reaction was concentrated in vacuo and the resulting residue was treated with 1 N NaHSO₄. Extracted the mixture twice with EtOAc, combined the organics, dried over MgSO₄, filtered and concentrated the filtrate. The residue was then triturated with Et₂O, filtered, and dried in vacuo to provide the title compound as an off-white solid: ¹H NMR (300 MHz, DMSO-D6) δ ppm 1.1 (d, J=6.0 Hz, 6 H), 1.7 (s, 3 H), 3.3 (q, J=6.1, 2 H), 3.5 (m, 3 H), 3.6 (m, 2 H), 4.1 (s, 2 H), 4.3 (t, J=6.5 Hz, 2 H), 7.1 (m, 2 H), 7.4 (ddd, J=12.1, 5.5, 3.2 Hz, 2 H), 8.0 (d, J=6.0 Hz, 1 H), 8.2 (d, J=1.3 Hz, 1 H), 8.5 (d, J=1.5 Hz, 1 H), 10.4 (t, J=5.1 Hz, 1 H), 17.1 (s, 1 H); ES⁺ MS: 485 (M+H⁺).

EXAMPLE 392

Methyl {2-[7-[(4-fluorophenyl)methyl]-4-hydroxy-3-[({2-[(1-methylethyl)oxy]ethyl}amino)carbonyl]-2-oxo-1,5-naphthyridine-1(2H)-yl]ethyl}carbamate A solution of 1-(2-aminoethyl)-7-[(4-fluorophenyl)methyl]-4-hydroxy-N-{2-[(1-methylethyl)oxy]ethyl}-2-oxo-1,2-dihydro-1,5-naphthyridine-3-carboxamide (0.020 g, 0.045 mmol) and diisopropyl ethylamine (0.04 mL, 0.23 mmol) in DMF (5 mL) under nitrogen was treated with methyl chloroformate (0.0036 mL, 0.047 mmol) at ambient temperature. The reaction was concentrated in vacuo and the resulting residue was treated with 1N NaHSO₄. The resulting suspension was filtered, washed with EtOH and Et₂O, and dried in vacuo to provide the title compound as a beige solid: ¹H NMR (300 MHz, DMSO-d₆) δ ppm 1.12 (d, J=6.18 Hz, 6 H), 3.22-3.31 (m, 2 H), 3.45 (s, 3 H), 3.49-3.56 (m, 4 H), 3.61 (dt, J=12.07, 6.04 Hz, 1 H), 4.14 (s, 2 H), 4.29 (t, J=6.32 Hz, 2 H), 7.11-7.19 (m, 2 H), 7.26 (t, J=5.62 Hz, 1 H), 7.39 (dd, J=8.56, 5.48 Hz, 2 H), 8.12 (s, 1 H), 8.53 (s, 1 H), 10.38 (t, J=5.48 Hz, 1 H), 17.12 (s, 1 H); ES⁺ MS: 501 (M+H⁺).

EXAMPLE 393

N-[2-(Acetylamino)ethyl]-7-[(4-fluorophenyl)methyl]-4-hydroxy-1-(3-hydroxypropyl)-2-oxo-1,2-dihydro-1,5-naphthyridine-3-carboxamide In a similar manner to that described in example 196, from ethyl 7-[(4-fluorophenyl)methyl]-4-hydroxy-1-(3-hydroxypropyl)-2-oxo-1,2-dihydro-1,5-naphthyridine-3-carboxylate (60 mg, 0.15 mmol) and N-(2-aminoethyl)acetamide (100 mg, 0.99 mmol) was prepared N-[2-(acetylamino)ethyl]-7-[(4-fluorophenyl)methyl]-4-hydroxy-1-(3-hydroxypropyl)-2-oxo-1,2-dihydro-1,5-naphthyridine-3-carboxamide (21 mg, 31% yield) as a tan solid after purification by reverse phase HPLC. ¹H NMR (methanol-d₄/CDCl₃) δ 10.18 (br s, 1 H), 8.40 (s, 1 H), 7.56 (s, 1 H), 7.09-7.05 (m, 2 H), 6.94-6.88 (m, 2 H), 4.21 (m, 2 H), 4.04 (s, 2 H), 7.70 (m, 2 H), 3.46 (m, 2 H), 3.33 (m, 2 H), 1.86 (s, 3 H), 1.74 (m, 2 H); MS m/z 457 M+1).

EXAMPLE 394

7-[(4-Fluorophenyl)methyl]-4-hydroxy-N-(2-hydroxy-1-methylethyl-1-(3-hydroxypropyl)-2-oxo-1,2-dihydro-1,5-naphthyridine-3-carboxamide In a similar manner to that described in example 196, from ethyl 7-[(4-fluorophenyl)methyl]-4-hydroxy-1-(3-hydroxypropyl)-2-oxo-1,2-dihydro-1,5-naphthyridine-3-carboxylate (60 mg, 0.15 mmol) and 2-amino-1-propanol (0.07 mL) was prepared 7-[(4-fluorophenyl)methyl]-4-hydroxy-N-(2-hydroxy-1-methylethyl)-1-(3-hydroxypropyl)-2-oxo-1,2-dihydro-1,5-naphthyridine-3-carboxamide (20 mg, 31% yield) as a white solid after purification by reverse phase HPLC. ¹H NMR (CDCl₃) δ 10.16 (d, J=7.2 Hz, 1 H), 8.55 (s, 1 H), 7.47 (s, 1 H), 7.17-7.13 (m, 2 H), 7.03-6.98 (m, 2 H), 4.29-4.24 (m, 3 H), 4.11 (s, 2 H), 3.76 (dd, J=11.2, 4 Hz, 1 H), 3.65 (dd, J=11.2, 6 Hz, 1 H), 3.50 (m, 2 H), 1.81 (m, 2 H), 1.29 (d, J=6.8 Hz, 3 H); HRMS m/z calcd for C₂₂H₂₅N₃O₅F: 430.1778. Found: 430.1786.

EXAMPLE 395

7-[(4-Fluorophenyl)methyl]-4-hydroxy-1-(3-hydroxypropyl)-2-oxo-N-[2-(2-oxo-1-imidazolidinyl)ethyl]-1,2-dihydro-1,5-naphthyridine-3-carboxamide In a similar manner to that described in example 196, from ethyl 7-[(4-fluorophenyl)methyl]-4-hydroxy-1-(3-hydroxypropyl)-2-oxo-1,2-dihydro-1,5-naphthyridine-3-carboxylate (60 mg, 0.15 mmol) and 1-(2-aminoethyl)-2-imidazolidinone (0.4 mL) was prepared 7-[(4-fluorophenyl)methyl]-4-hydroxy-1-(3-hydroxypropyl)-2-oxo-N-[2-(2-oxo-1-imidazolidinyl)ethyl]-1,2-dihydro-1,5-naphthyridine-3-carboxamide (22 mg, 31% yield) as a white solid after purification by reverse phase HPLC. ¹H NMR (CDCl₃) δ 10.25 (br s, 1 H), 8.55 (s, 1 H), 7.46 (s, 1 H), 7.16-7.12 (m, 2 H), 7.03-7.12 (m, 2 H), 4.73 (br s, 1 H), 4.29 (br s, 2 H), 4.11 (s, 2 H), 3.64-3.39 (m, 10 H), 1.79 (m, 2 H); HRMS m/z calcd for C₂₄H₂₇N₅O₅F: 484.1996. Found: 484.1997.

EXAMPLE 396

1-[2-(1,3-Dioxo-1,3-dihydro-2H-isoindol-2-yl)ethyl]-7-[(4-fluorophenyl)methyl]-4-hydroxy-N-(2-hydroxy-1-methylethyl)-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (1 mL) under nitrogen was treated with 2-amino-1-propanol (0.0041 mL, 0.051 mmol) for 10 min. (150° C. in a microwave vessel. An additional 0.001 mL of the amine was added to the reaction and it was further microwaved for 20 min.@150° C. The reaction was then cooled to ambient temperature and the resulting suspension was filtered, washed with EtOH and then thoroughly dried under high vacuum to provide the title compound as a white solid: ¹H NMR (400 MHz, DMSO-d₆) δ ppm 0.97 (d, J=6.59 Hz, 3 H), 3.25-3.31 (m, 2 H), 3.86-3.95 (m, 3 H), 4.11 (s, 2 H), 4.43-4.52 (m, 1 H), 4.57-4.65 (m, 1 H), 4.90 (t, J=5.31 Hz, 1 H), 7.10-7.16 (m, 2 H), 7.31-7.38 (m, 2 H), 7.80-7.85 (m, 4 H), 8.15-8.18 (m, 1 H), 8.52 (d, J=1.46 Hz, 1 H), 9.96 (d, J=7.87 Hz, 1 H), 17.25 (s, 1 H); ES⁺ MS: 545 (M+H⁺).

EXAMPLE 397

1-[2-(1,3-Dioxo-1,3-dihydro-2H-isoindol-2-yl)ethyl]-7-[(4-fluorophenyl)methyl]-4-hydroxy-N-{2-[(2-hydroxyethyl)oxy]ethyl}-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (1 mL) under nitrogen was treated with 2-[(2-aminoethyl)oxy]ethanol (0.0042 mL, 0.058 mmol) for 10 min.@150° C. in a microwave vessel. An additional 0.001 mL of the amine was added to the reaction and it was further microwaved for 20 min.@150° C. The reaction was then cooled to ambient temperature and the resulting suspension was filtered, washed with 1:1 water:EtOH and then thoroughly dried under high vacuum to provide the title compound as a white solid: $^1$H NMR (300 MHz, DMSO-$d_6$) δ ppm 3.35-3.44 (m, 6 H), 3.44-3.51 (m, 2 H), 3.90 (t, J=5.05 Hz, 2 H), 4.11 (s, 2 H), 4.50-4.62 (m, 3 H), 7.08-7.17 (m, 2 H), 7.30-7.38 (m, 2 H), 7.82 (s, 4 H), 8.14 (s, 1 H), 8.52 (s, 1 H), 10.02 (m, 1 H), 17.11 (s, 1 H); ES$^+$ MS: 575 (M+H$^+$).

EXAMPLE 398

1-[2-(1,3-dioxo-1,3-dihydro-2H-isoindol-2-yl)ethyl]-7-[(4-fluorophenyl)methyl]-4-hydroxy-N-(3-hydroxy-2,2-dimethylpropyl)-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (1 mL) under nitrogen was treated with 3-amino-2,2-dimethyl-1-propanol (0.008 mL, 0.078 mmol) for 20 min. (160° C. in a microwave vessel. The reaction was further microwaved for 40 min.@160° C., cooled to ambient temperature, and the resulting suspension was filtered, washed with EtOH and then thoroughly dried under high vacuum to provide the title compound as a white solid: $^1$H NMR (300 MHz, DMSO-$d_6$) δ ppm 0.57 (s, 6 H), 1.93 (s, 1 H), 2.91 (d, J=5.19 Hz, 2 H), 3.08 (d, J=5.62 Hz, 2 H), 3.92 (t, J=5.33 Hz, 2 H), 4.16 (s, 2 H), 4.56-4.68 (m, 3 H), 7.11-7.18 (m, 2 H), 7.35-7.41 (m, 2 H), 7.80 (s, 4 H), 8.22 (d, J=0.84 Hz, 1 H), 8.55 (d, J=0.56 Hz, 1 H), 10.02 (t, J=6.32 Hz, 1 H); ES$^+$ MS: 573 (M+H$^+$).

EXAMPLE 399

N-[2-(Ethyloxy)ethyl]-7-[(4-fluorophenyl)methyl]-4-hydroxy-1-{3-[(4-morpholinylcarbonyl)amino]propyl}-2-oxo-1,2-dihydro-1,5-naphthyridine-3-carboxamide This compound was prepared from 1-(3-aminopropyl)-N-[2-(ethyloxy)ethyl]-7-[(4-fluorophenyl)methyl]-4-hydroxy-2-oxo-1,2-dihydro-1,5-naphthyridine-3-carboxamide and 4-morpholinecarbonyl chloride employing methods similar to those described in Step 2 of Example 373 and was obtained as a white solid: ES$^+$ MS: 556 (M+H$^+$).

EXAMPLE 400

N-[2-(ethyloxy)ethyl]-7-[(4-fluorophenyl)methyl]-1-{3-[(2-furanylcarbonyl)amino]propyl}-4-hydroxy-2-oxo-1,2-dihydro-1,5-naphthyridine-3-carboxamide A mixture of 1-(3-aminopropyl)-N-[2-(ethyloxy)ethyl]-7-[(4-fluorophenyl)methyl]-4-hydroxy-2-oxo-1,2-dihydro-1,5-naphthyridine-3-carboxamide (25 mg, 0.057), 2-furancarbonyl chloride (5.8 μL, 0.059 mmol) and DIEA (49 μL, 0.282 mmol) was combined in anhydrous DMF (1.5 mL). After stirring under nitrogen at ambient temperature for 0.5 hrs, the reaction mixture was evaporated in vacuo and partitioned between EtOAc and 1N NaHSO$_4$. The aqueous layer was separated and back-extracted with EtOAc. The combined organic layers were washed with brine, dried over MgSO$_4$, filtered, and evaporated in vacuo. The product was crystallized from MeOH/Et$_2$O and collected by filtration providing a white solid: ES$^+$ MS: 537 (M+H$^+$).

EXAMPLE 401

N-[2-(ethyloxy)ethyl]-7-[(4-fluorophenyl)methyl]-4-hydroxy-2-oxo-1-{3-[(2-thienylcarbonyl)amino]propyl}-1,2-dihydro-1,5-naphthyridine-3-carboxamide This compound was prepared from 1-(3-aminopropyl)-N-[2-(ethyloxy)ethyl]-7-[(4-fluorophenyl)methyl]-4-hydroxy-2-oxo-1,2-dihydro-1,5-naphthyridine-3-carboxamide and 2-thiophenecarbonyl chloride employing methods similar to those described in Example 400 and was obtained as a white solid: ES$^+$ MS: 553 (M+H$^+$).

EXAMPLE 402

N-[2-(ethyloxy)ethyl]-7-[(4-fluorophenyl)methyl]-4-hydroxy-2-{3-[(methylsulfonyl)amino]propyl}-2-oxo-1,2-dihydro-1,5-naphthyridine-3-carboxamide This compound was prepared from 1-(3-aminopropyl)-N-[2-(ethyloxy)ethyl]-7-[(4-fluorophenyl)methyl]-4-hydroxy-2-oxo-1,2-dihydro-1,5-naphthyridine-3-carboxamide and methanesulphonyl chloride employing methods similar to those described in Example 400 and was obtained as a tan solid: ES$^+$ MS: 521 (M+H$^+$).

EXAMPLE 403

1-[2-(1,3-dioxo-1,3-dihydro-2H-isoindol-2-yl)ethyl]-2-[(4-fluorophenyl)methyl]-4-hydroxy-N-[1-methyl-2-(methyloxy)ethyl]-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (1 mL) under nitrogen was treated with 1-(methyloxy)-2-propanamine (0.0069 mL, 0.078 mmol) for 20 min.@160° C. and for 40 min@150° C. in a microwave vessel. The reaction was further microwaved for 30 min.@150° C. after the addition of an additional equivalent (0.0069 mL) of the propanamine, cooled to ambient temperature, and the resulting suspension was filtered, washed with EtOH and then thoroughly dried under high vacuum to provide the title compound as an off-white solid: $^1$H NMR (400 MHz, DMSO-$d_6$) δ ppm 0.99 (d, J=6.59 Hz, 3 H), 2.09 (s, 1 H), 3.16-3.27 (m, 5 H), 3.90 (t, J=5.31 Hz, 2 H), 4.02-4.11 (m, 1 H), 4.13 (s, 2 H), 4.49-4.60 (m, 2 H), 7.13 (t, J=8.88 Hz, 2 H), 7.36 (dd, J=8.70, 5.77 Hz, 2 H), 7.79-7.85 (m, 4 H), 8.18 (s, 1 H), 8.54 (d, J=1.28 Hz, 1 H), 9.96 (d, J=8.42 Hz, 1 H); ES$^+$ MS: 559 (M+H$^+$).

EXAMPLE 404

1-[2-(1,3-dioxo-1,3-dihydro-2H-isoindol-2-yl)ethyl]-7-[(4-fluorophenyl)methyl]-4-hydroxy-N-[2-(4-morpholinyl)ethyl]-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (1 mL) under nitrogen was treated with 2-(4-morpholinyl)ethanamine (0.008 mL, 0.061 mmol) for 30 min.@150° C. The reaction was further microwaved for 30 min.@150° C. after the addition of an additional equivalent (0.008 mL) of the amine, cooled to ambient temperature, and the resulting suspension was filtered, washed with EtOH and then thoroughly dried under high vacuum to provide the title compound as an off-white solid: $^1$H NMR (300 MHz, DMSO-d$_6$) δ ppm 2.26-2.34 (m, 6 H), 3.33-3.37 (m, 2 H), 3.48-3.54 (m, 4 H), 3.91 (t, J=5.69 Hz, 2 H), 4.13 (s, 2 H), 4.56 (t, J=5.62 Hz, 2 H), 7.10-7.17 (m, 2 H), 7.33-7.40 (m, 2 H), 7.82 (s, 4 H), 8.16 (d, J=1.12 Hz, 1 H), 8.53 (d, J=0.84 Hz, 1 H), 10.04 (t, J=6.18 Hz, 1 H); ES$^+$ MS: 600 (N+H$^+$).

EXAMPLE 405

1-[2-(1,3-dioxo-1,3-dihydro-2H-isoindol-2-yl)ethyl]-7-[(4-fluorophenyl)methyl]-4-hydroxy-N-[3-(1H-imidazol-1-yl)propyl]-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (1 mL) under nitrogen was treated with 3-(1H-imidazol-1-yl)-1-propanamine (0.0072 mL, 0.061 mmol) for 30 min.@150° C. The reaction was further microwaved for 30 min.@150° C. after the addition of an additional equivalent (0.0072 mL) of the amine, cooled to ambient temperature, and the resulting suspension was filtered, washed with EtOH and then thoroughly dried under high vacuum to provide the title compound as a white solid: $^1$H NMR (300 MHz, DMSO-d$_6$) δ ppm 1.74-1.84 (m, 2 H), 3.18 (q, J=6.60 Hz, 2 H), 3.83 (t, J=6.95 Hz, 2 H), 3.91 (t, J=5.48 Hz, 2 H), 4.14 (s, 2 H), 4.57 (t, J=5.55 Hz, 2 H), 6.90 (t, J=1.05 Hz, 1 H) 7.09-7.18 (m, 3 H), 7.37 (td, J=6.00, 2.32 Hz, 2 H), 7.57 (t, J=1.12 Hz, 1 H), 7.70-7.75 (m, 2 H), 7.78-7.83 (m, 2 H), 8.19 (s, 1 H), 8.54 (s, 1 H), 9.93 (t, J=6.04 Hz, 1 H), 17.12 (bs, 1 H); ES$^+$ MS: 595 (M+H$^+$).

EXAMPLE 406

Sodium 1-(2-Amino-2-oxoethyl)-7-(4-fluorobenzyl)-3-{[(2-methoxyethyl)amino]carbonyl}-2-oxo-1,2-dihydro-1,5-naphthyridin-4-olate The compound in example 162 was treated in a similar manner to example 166 to give a white solid: $^1$H NMR (d$_6$-DMSO) δ 10.49 (1H, m), 8.17 (1H, s), 7.45 (1H, s), 7.41 (1H, s), 7.26 (2H, m), 7.08 (3H, m), 4.68 (2H, s), 3.99 (2H, s), 3.37 (4H, m), 3.24 (3H, s).

EXAMPLE 407

7-[(4-Fluorophenyl)methyl]-4-hydroxy-1-(3-hydroxypropyl)-N-2-(methyloxy)ethyl-2-oxo-1,2-dihydro-1,5-naphthyridine-3-carboxamide In a similar manner to that described in example 196, from ethyl 7-[(4-fluorophenyl)methyl]-4-hydroxy-1-(3-hydroxypropyl)-2-oxo-1,2-dihydro-1,5-naphthyridine-3-carboxylate (60 mg, 0.15 mmol) and [2-(methyloxy)ethyl]amine (0.05 mL) was prepared 7-[(4-fluorophenyl)methyl]-4-hydroxy-1-(3-hydroxypropyl)-N-[2-(methyloxy)ethyl]-2-oxo-1,2-dihydro-1,5-naphthyridine-3-carboxamide (21 mg, 33% yield) as a yellow solid after purification by reverse phase HPLC. $^1$H NMR (CDCl$_3$) δ 10.22 (br s, 1 H), 8.56 (s, 1 H), 7.46 (s, 1 H), 7.16-7.16 (m, 2 H), 7.03-6.99 (m, 2 H), 4.31 (m, 2 H), 4.12 (s, 2 H), 3.64 (m, 2 H), 3.57 (m, 2 H), 3.49 (m, 2 H), 3.39 (s, 3 H), 1.82 (m, 2 H); HRMS m/z calcd for C$_{22}$H$_{25}$N$_3$O$_5$F: 430.1778. Found: 430.1778.

EXAMPLE 408

7-[(4-Fluorophenyl)methyl]-4-hydroxy-1-(3-hydroxypropyl)-N-{2-[(1-methylethyl)sulfonyl]ethyl}-2-oxo-1,2-dihydro-1,5-naphthyridine-3-carboxamide In a similar manner to that described in example 196, from ethyl 7-[(4-fluorophenyl)methyl]-4-hydroxy-1-(3-hydroxypropyl)-2-oxo-1,2-dihydro-1,5-naphthyridine-3-carboxylate (60 mg, 0.15 mmol), triethylamine (0.2 mL, 1.41 mmol), and 2-amino-N,N-dimethylethanesulfonamide hydrochloride (89 mg, 0.47 mmol), was prepared 7-[(4-fluorophenyl)methyl]-4-hydroxy-1-(3-hydroxypropyl)-N-{2-[(1-methylethyl)sulfonyl]ethyl}-2-oxo-1,2-dihydro-1,5-naphthyridine-3-carboxamide (14 mg, 18% yield) as a white solid after purification by reverse phase HPLC. $^1$H NMR (CDCl$_3$) δ 10.40 (br s, 1 H), 8.49 (s, 1 H), 7.54 (s, 1 H), 7.13-7.09 (m, 2 H), 6.99-6.94 (m, 2 H), 4.26 (m, 2 H), 4.08 (s, 2 H), 3.84 (m, 2 H), 3.49 (m, 2 H), 3.22 (m, 2 H), 2.84 (s, 6 H), 1.78 (m, 2 H).

EXAMPLE 409

7-[(4-Fluorophenyl)methyl]-4-hydroxy-1-(3-hydroxypropyl)-N-methyl-2-oxo-1,2-dihydro-1,5-naphthyridine-3-carboxamide In a similar manner to that described in example 196, from ethyl 7-[(4-fluorophenyl)methyl]-4-hydroxy-1-(3-hydroxypropyl)-2-oxo-1,2-dihydro-1,5-naphthyridine-3-carboxylate (60 mg, 0.15 mmol) and methylamine (0.11 mL of a 8M solution in ethanol) was prepared 7-[(4-fluorophenyl)methyl]-4-hydroxy-1-(3-hydroxypropyl)-N-methyl-2-oxo-1,2-dihydro-1,5-naphthyridine-3-carboxamide (10 mg, 17% yield) as a white solid after purification by reverse phase HPLC. $^1$H NMR (CDCl$_3$) δ 9.97 (br s, 1 H), 8.58 (s, 1 H), 7.46 (s, 1 H), 7.17-7.13 (m, 2 H), 7.04-6.99 (m, 2 H), 4.32 (m, 2 H), 4.13 (s, 2 H), 3.49 (m, 2 H), 3.21 (m, 1 H), 3.01 (d, J=4.8 Hz, 3 H), 1.83 (m, 2 H); HRMS m/z calcd for C$_{20}$H$_{21}$N$_3$O$_4$F: 386.1516. Found: 386.1517.

EXAMPLE 410

7-[(4-Fluorophenyl)methyl]-4-hydroxy-N-(2-hydroxypropyl)-1-(3-hydroxypropyl)-2-oxo-1,2-dihydro-1,5-naphthyridine-3-carboxamide In a similar manner to that described in example 196, from ethyl 7-[(4-fluorophenyl)methyl]-4-hydroxy-1-(3-hydroxypropyl)-2-oxo-1,2-dihydro-1,5-naphthyridine-3-carboxylate (60 mg, 0.15mmol) and 1-amino-2-propanol (0.05 mL) was prepared 7-[(4-fluorophenyl)methyl]-4-hydroxy-N-(2-hydroxypropyl)-1-(3-hydroxypropyl)-2-oxo-1,2-dihydro-1,5-naphthyridine-3-carboxamide (22 mg, 34% yield) as a yellow solid after purification by reverse phase HPLC. $^1$H NMR (CDCl$_3$) δ 10.27 (br s, 1 H), 8.49 (s, 1 H), 7.52 (s, 1 H), 7.14-7.10 (m, 2 H), 6.99-6.94 (m, 2 H), 4.26 (m, 2 H), 4.09 (s, 2 H), 3.95 (m, 1 H), 3.55-3.47 (m, 3 H), 3.29 (m, 1 H), 1.79 (m, 2 H), 1.19 (d, J=6 Hz, 3 H); MS m/z 430 (M+1).

EXAMPLE 411

7-[(4-Fluorophenyl)methyl]-4-hydroxy-1-(1H-imidazol-4-ylmethyl)-N-[2-(methyloxy)ethyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, DMSO-d$_6$) δ 11.93 (br, 1 H), 10.38 (m, 1 H), 8.50 (s, 1 H), 8.15 (s, 1 H), 7.51 (s, 1 H), 7.28 (dd, J=8.5, 5.6 Hz, 2 H), 7.08 (t, J=8.9 Hz, 2 H), 6.92 (s, 1 H), 5.33 (s, 2 H), 4.08 (s, 2 H), 3.55-3.47 (m, 4 H), 3.27 (s, 3 H); HRMS m/z calcd for C$_{23}$H$_{23}$N$_5$O$_4$F (M+H)$^+$ 452.1734, found 452.1734.

EXAMPLE 412

1-[2-(1,3-dioxo-1,3-dihydro-2H-isoindol-2-yl)ethyl]-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (1 mL) under nitrogen was treated with 1-(3-aminopropyl)-2-pyrrolidinone (0.0085 mL, 0.061 mmol) for 30 min.@150° C. The reaction was further microwaved for 30 min.@150° C. after the addition of an additional equivalent (0.0085 mL) of the amine, cooled to ambient temperature, and treated with 1N NaHSO$_4$. The resulting suspension was filtered, washed with EtOH and the filtrate was concentrated in vacuo. The filtrate residue was purified by reversed phase HPLC. Pure fractions were combined and concentrated to afford the title compound as an off-white solid: $^1$H NMR (400 MHz, DMSO-d$_6$) δ ppm 1.51-1.59 (m, 2 H), 1.89-1.96 (m, 2 H), 2.21 (t, J=8.24 Hz, 2 H), 3.08 (t, J=6.59 Hz, 2 H), 3.15-3.21 (m, 2 H), 3.27-3.31 (m, 2 H), 3.87-3.93 (m, 2 H), 4.11 (s, 2 H), 4.55 (s, 2 H), 7.11-7.16 (m, 2 H), 7.35 (td, J=6.46, 2.29 Hz, 2 H), 7.78-7.85 (m, 4 H), 8.15 (s, 1 H), 8.51 (s, 1 H), 9.95 (s, 1 H); ES$^+$ MS: 612 (M+H$^+$).

EXAMPLE 413

N-{2-[7-[(4-fluorophenyl)methyl]-4-hydroxy-2-oxo-3-({[2-(2-oxo-1-imidazolidinyl)ethyl]amino}carbonyl)-1,5-naphthyridine-1(2H)-yl]ethyl}-N'-[2-(2-oxo-1-imidazolidinyl)ethyl]-1,2-benzenedicarboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (1 mL) under nitrogen was treated with 1-(2-aminoethyl)-2-imidazolidinone (0.0078 g, 0.03 mmol, 50% W/W in IPA) for 30 min.@150° C. The reaction was further microwaved for 30 min. (150° C. after the addition of an additional 0.6 equivalents (0.015 mL) of the amine, cooled to ambient temperature, and treated with 1N NaHSO$_4$. The resulting suspension was filtered and the filtrate was concentrated in vacuo. The filtrate residue was purified by reversed phase HPLC. Pure fractions were combined and concentrated to afford the title compound as a yellow solid: $^1$H NMR (400 MHz, DMSO-d$_6$) δ ppm 3.16-3.22 (m, 6 H), 3.26-3.38 (m, 11 H), 3.49 (dq, J=12.61, 6.42 Hz, 3 H), 4.11 (s, 3 H), 4.38 (t, J=6.41 Hz, 2 H), 6.29 (s, 1 H), 6.37 (s, 1 H), 7.09 (t, J=8.88 Hz, 1 H), 7.28-7.39 (m, 2 H), 7.41 -7.47 (m, 2 H), 8.32 (s, 1 H), 8.35-8.40 (m, 1 H), 8.43-8.47 (m, 1 H), 8.51 (s, 1 H), 10.37 (s, 1 H); ES$^+$ MS: 728 (M+H$^+$).

EXAMPLE 414

1-(2-Amino-2-oxoethyl)-7-(4-fluorobenzyl)-4-hydroxy-N-(2-hydroxyethyl)-2-oxo-1,2-dihydro-1,5-naphthyridine-3-carboxamide The title compound was made in a similar manner to example 162 using ethanolamine to give an off-white solid: $^1$H NMR (d$_6$-DMSO) δ 10.30 (1H, m), 8.49 (1H, s), 7.78 (1H, s), 7.62 (1H, s), 7.32 (2H, m), 7.25 (1H, s), 7.10 (2H, m), 4.92 (1H, t, J=5 Hz), 4.81 (2H, s), 4.10 (2H, s), 3.52 (2H, m), 3.39 (2H, m); HRMS calcd for C$_{20}$H$_{19}$FN$_4$O$_5$+H$^+$: 415.1418. Found: 415.1416.

EXAMPLE 415

1-(2-aminoethyl)-7-[(4-fluorophenyl)methyl]-4-hydroxy-2-oxo-N-[2-(2-oxo-1-imidazolidinyl)ethyl]-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (1 mL) under nitrogen was treated with 1-(2-aminoethyl)-2-imidazolidinone (0.0078 g, 0.03 mmol, 50% W/W in IPA) for 30 min. (150° C. The reaction was further microwaved for 30 min.@150° C. after the addition of an additional 0.6 equivalents (0.015 mL) of the amine, cooled to ambient temperature, and treated with 1N NaHSO$_4$. The resulting suspension was filtered and the filtrate was concentrated in vacuo. The filtrate residue was purified by reversed phase HPLC. Pure fractions were combined and concentrated to afford the title compound as an off-white solid: ES$^+$ MS: 469 (M+H$^+$).

EXAMPLE 416

1-[2-(1,3-dioxo-1,3-dihydro-2H-isoindol-2-yl)ethyl]-7-[(4-fluorophenyl)methyl]-4-hydroxy-2-oxo-N-[2-(2-oxo-1-imidazolidinyl)ethyl]-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (1 mL) under nitrogen was treated with 1-(2-aminoethyl)-2-imidazolidinone (0.0078 g, 0.03 mmol, 50% W/W in IPA) for 30 min.@150° C. The reaction was further microwaved for 30 min.@150° C. after the addition of an additional 0.6 equivalents (0.015 mL) of the amine, cooled to ambient temperature, and treated with 1N NaHSO$_4$. The resulting suspension was filtered and the filtrate was concentrated in vacuo. The filtrate residue was purified by reversed phase HPLC. Pure fractions were combined and concentrated to afford the title compound as a pale yellow glass: $^1$H NMR (300 MHz, CHLOROFORM-d) δ ppm 1.82 (s, 1 H), 3.38-3.51 (m, 4 H), 3.52-3.65 (m, 4 H), 4.00 (t, J=6.67 Hz, 2 H), 4.04-4.10 (m, 2 H), 4.26 (s, 1 H), 4.46 (t, J=6.74 Hz, 2 H), 6.91-7.04 (m, 2 H), 7.10-7.21 (m, 2 H), 7.70-7.78 (m, 3 H), 7.79-7.85 (m, 2 H), 8.51 (d, J=1.26 Hz, 1 H), 10.24 (t, J=6.04 Hz, 1 H); ES$^+$ MS: 599 (M+H$^+$).

EXAMPLE 417

N-{2-[7-[(4-Fluorophenyl)methyl]-4-hydroxy-2-oxo-3-({[3-(2-oxo-1-pyrrolidinyl)propyl]amino}carbonyl)-1,5-naphthyridine-1(2H)-yl]ethyl}-N'-[3-(2-oxo-1-pyrrolidinyl)propyl]-1,2-benzenedicarboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.025 g, 0.049 mmol) in EtOH (1 mL) under nitrogen was treated with 1-(3-aminopropyl)-2-pyrrolidinone (0.0085 mL, 0.061 mmol) for 30 min. 150° C. The reaction was further microwaved for 30 min.@150° C. after the addition of an additional equivalent (0.0085 mL) of the amine, cooled to ambient temperature, and treated with 1N NaHSO$_4$. The resulting suspension was filtered, washed with EtOH and the filtrate was concentrated in vacuo. The filtrate residue was purified by reversed phase HPLC. Pure fractions were combined and concentrated to afford the title compound as a pale yellow glass: $^1$H NMR (300 MHz, CHLOROFORM-d) δ ppm 1.74 (ddd, J=12.42, 6.11, 5.90 Hz, 2 H), 1.84-1.95 (m, 2 H), 1.99-2.12 (m, 4 H), 2.41 (td, J=8.14, 2.25 Hz, 4 H), 3.21-3.32 (m, 2 H), 3.35-3.50 (m, 10 H), 3.61-3.73 (m, 2 H), 4.07 (s, 2 H), 4.48 (t, J=6.74 Hz, 2 H), 6.91-7.01 (m, 2 H), 7.17-7.23 (m, 2 H), 7.47-7.62 (m, 4 H), 7.71 (dd, J=5.26, 3.44 Hz, 1 H), 7.77 (t, J=5.90 Hz, 1 H), 8.18 (s, 1 H), 8.49 (s, 1 H), 10.31 (t, J=5.76 Hz, 1 H); ES$^+$ MS: 754 (M+H$^+$).

EXAMPLE 418

7-[(4-Fluorophenyl)methyl]-4-hydroxy-N-(2-hydroxy-1-methylethyl)-1-(1H-imidazol-4-ylmethyl)-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.22 (d, J=7.4 Hz, 1 H), 8.40 (s, 1 H), 7.75 (s, 1 H), 7.42 (s, 1 H), 7.07 (dd, J=8.1, 5.6 Hz, 2 H), 6.91 (t, J=8.5 Hz, 2 H), 6.70 (s, 1 H), 5.34 (d, J=15.8 Hz, 1 H), 5.16 (d, J=15.6 Hz, 1 H), 4.16 (m, 1 H), 4.03 (s, 2 H), 3.64 (dd, J=11.4, 4.1 Hz, 1 H), 3.55 (dd, J=11.1, 5.6 Hz, 1 H), 1.23 (d, J=7.2 Hz, 3 H); HRMS m/z calcd for C$_{23}$H$_{23}$N$_5$O$_4$F (M+H)$^+$ 452.1734, found 452.1738.

EXAMPLE 419

1-(2-aminoethyl)-7-[(4-fluorophenyl)methyl]-4-hydroxy-2-oxo-N-(tetrahydro-2-furanylmethyl)-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.252 g, 0.49 mmol) in EtOH (15 mL) under nitrogen was treated with 1-(tetrahydro-2-furanyl)methanamine (0.252 mL, 2.44 mmol) for 15 min.@150° C. in a microwave vessel. The reaction was transferred to a test tube, diluted with EtOH (30 mL), and treated with hydrazine (0.4 mL, 13 mmol)@50° C. overnight. After the reaction was cooled to ambient temperature the resulting suspension was diluted with water (120 mL) and refrigerated overnight. The resulting suspension was filtered, washed with 2:1 water:EtOH and thoroughly dried under high vacuum to provide the title compound as an off-white solid: $^1$H NMR (300 MHz, DMSO-d$_6$) δ ppm 1.49-1.61 (m, 1H), 1.80-2.00 (m, 3H), 2.78 (t, J=6.46 Hz, 2H), 3.25-3.41 (m, 1H), 3.49-3.59 (m, 1H), 3.68 (t, J=6.81 Hz, 1H), 3.75-3.86 (m, 1H), 3.95-4.05 (m, 1H), 4.16 (s, 2H), 4.18-4.26 (m, 2H), 7.14 (ddd, J=8.95, 6.91, 1.82 Hz, 2H), 7.35-7.43 (m, 2H), 8.15 (d, J=1.40 Hz, 1H), 8.51 (s, 1H), 10.44-10.53 (m, 1H); ES$^+$ MS: 441 (M+H$^+$).

EXAMPLE 420

1-(2-aminoethyl)-7-[(4-fluorophenyl)methyl]-4-hydroxy-N-[3-(4-morpholinyl)propyl]-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.252 g, 0.49 mmol) in EtOH (15 mL) under nitrogen was treated with 3-(4-morpholinyl)-1-propanamine (0.357 mL, 2.44 mmol) for 15 min. (150° C. in a microwave vessel. The reaction was transferred to a test tube, diluted with EtOH (30 mL), and treated with hydrazine (0.4 mL, 13 mmol)@50° C. overnight. After the reaction was cooled to ambient temperature the resulting suspension was diluted with water (120 mL) and refrigerated overnight. The resulting suspension was filtered, washed with 2:1 water:EtOH and thoroughly dried under high vacuum to provide the title compound as a pale yellow solid: $^1$H NMR (300 MHz, DMSO-d$_6$) δ ppm 1.68-1.76 (m, 2 H), 2.31-2.38 (m, 7 H), 2.78 (t, J=6.81 Hz, 2 H), 3.35-3.46 (m, 3 H), 3.55-3.62 (m, 5 H), 4.16 (s, 2 H), 4.22 (t, J=6.81 Hz, 2 H), 7.10-7.17 (m, 2 H), 7.38 (ddd, J=9.02, 5.79, 3.02 Hz, 2 H), 8.15 (s, 1 H), 8.50 (d, J=1.26 Hz, 1 H), 10.41 (d, J=3.93 Hz, 1 H); ES$^+$ MS: 484 (M+H$^+$).

EXAMPLE 421

1-(2-aminoethyl)-7-[(4-fluorophenyl)methyl]-4-hydroxy-N-{2-[(2-hydroxyethyl)oxy]ethyl}-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate (0.252 g, 0.49 mmol) in EtOH (15 mL) under nitrogen was treated with 2-[(2-aminoethyl)oxy]ethanol (0.176 mL, 2.44 mmol) for 15 min.@150° C. in a microwave vessel. Transferred the mixture to a test tube, diluted with EtOH (30 mL), and treated with hydrazine (0.4 mL, 13 mmol)@50° C. overnight. After the reaction was cooled to ambient temperature the resulting suspension was diluted with water (120 mL) and refrigerated overnight. The resulting suspension was filtered, washed with 2:1 water:EtOH and thoroughly dried under high vacuum to provide the title compound as an off-white solid: $^1$H NMR (300 MHz, DMSO-d$_6$) δ ppm 2.27 (s, 1 H), 2.79 (t, J=6.81 Hz, 2 H), 3.45-3.61 (m, 8 H), 4.12-4.17 (m, 2 H), 4.22 (t, J=6.74 Hz, 2 H), 4.62 (s, 1 H), 7.10-7.18 (m, 2 H), 7.33-7.42 (m, 2 H), 8.07-8.16 (m, 1 H), 8.46-8.54 (m, 1 H), 10.44 (t, J=5.19 Hz, 1 H); ES$^+$ MS: 445 (M+H$^+$).

EXAMPLE 422

1-(2-aminoethyl)-7-[(4-fluorophenyl)methyl]-4-hydroxy-N-[2-(4-morpholinyl)ethyl]-2-oxo-1,2-dihydro-1,5-naphthyridine-3-carboxamide A solution of ethyl 1-[2-(1,3-dioxo-1,3-dihydro-2H-isoindol-2-yl)ethyl]-7-[(4-fluorophenyl)methyl]-4-hydroxy-2- oxo-1,2-dihydro-1,5-naphthyridine-3-carboxylate (0.252 g, 0.49 mmol) in EtOH (15 mL) under nitrogen was treated with 2-(4-morpholinyl)ethanamine (0.321 mL, 2.44 mmol) for 30 min. (150° C. in a microwave vessel. The reaction was further microwaved for an additional 30 min.@150° C. after the addition of another equivalent (0.064 mL) of the amine. The reaction was transferred to a test tube, diluted with EtOH (30 mL), and treated with hydrazine (0.4 mL, 13 mmol)@50° C. overnight. After the reaction was cooled to ambient temperature the resulting suspension was diluted with water (120 mL) and refrigerated overnight. The resulting suspension was filtered, washed with 2:1 water:EtOH and thoroughly dried under high vacuum to provide the title compound as a pale yellow solid: $^1$H NMR (300 MHz, DMSO-$d_6$) δ ppm 2.27 (s, 1 H), 2.39-2.46 (m, 5 H), 2.70-2.81 (m, 2 H), 3.40-3.53 (m, 1 H), 3.57-3.61 (m, 6 H), 4.16 (s, 2 H), 4.18-4.26 (m, 2 H), 7.10-7.17 (m, 2 H), 7.35-7.41 (m, 2 H), 8.13-8.15 (m, 1 H), 8.50-8.51 (m, 1 H), 10.36-10.43 (m, 1 H); ES$^+$ MS: 470 (M+H$^+$).

EXAMPLE 423

1-(3-Fluorophenyl)-7-[(4-fluorophenyl)methyl]-4-hydroxy-N-[2-(methyloxy)ethyl]-2-oxo-1,2-dihydro-1,5-naphthyridine-3-carboxamide The title compound was prepared in a manner similar to that described in example 681 as a white solid in 94% yield. $^1$H NMR (CDCl$_3$) δ 10.03 (br s, 1 H), 8.52 (s, 1 H), 7.55 (m, 1 H), 7.24 (m, 1 H), 7.01-6.91 (m, 6 H), 6.67 (s, 1 H), 3.94 (s, 2 H), 3.62 (m, 2 H), 3.53 (m, 2 H), 3.33 (s, 3 H); MS m/z 466 (M+1).

EXAMPLE 424

1-[3-(2,5-Dioxo-1-pyrrolidinyl)propyl]-7-[(4-fluorophenyl)methyl]-4-hydroxy-N-[2-(methyloxy)ethyl]-2-oxo-1,2-dihydro-1,5-naphthyridine-3-carboxamide Ethyl 1-(3-chloropropyl)-7-[(4-fluorophenyl)methyl]-4-hydroxy-2-oxo-1,2-dihydro-1,5-naphthyridine-3-carboxylate. To a solution of ethyl 7-[(4-fluorophenyl)methyl]-4-hydroxy-2-oxo-1,2-dihydro-1,5-naphthyridine-3-carboxylate (40 mg, 0.117 mmol) in N,N-dimethylformamide was added lithium bis(trimethylsilyl)amide (234 µL, 1.0 M in tetrahydrofuran, 0.234 mmol) dropwise. 1-Chloro-3-iodopropane (50 µL, 0.468 mmol) was added dropwise and stirred 4 hours at room temperature. The reaction mixture was acidified with cold 1 N aqueous hydrochloric acid and extracted with toluene. The organic layer was washed with water and brine, then dried over sodium sulfate. Filtration and concentration provided ethyl 1-(3-chloropropyl)-7-[(4-fluorophenyl)methyl]-4-hydroxy-2-oxo-1,2-dihydro-1,5-naphthyridine-3-carboxylate as a light yellow solid. $^1$H NMR (400 MHz, CDCl$_3$) δ 8.53 (d, J=1.1 Hz, 1 H), 7.50 (s, 1 H), 7.18 (dd, J=8.6, 5.3 Hz, 2 H), 7.03 (t, J=8.6 Hz, 2 H), 4.50 (q, J=7.1 Hz, 2 H), 4.27 (t, J=7.6 Hz, 2 H), 4.13 (s, 2 H), 3.61 (t, J=5.9 Hz, 2 H), 2.09 (m, 2 H), 1.47 (t, J=7.3 Hz, 3 H); MS m/z 417 (M−H)$^-$.

Ethyl 1-[3-(2,5-dioxo-1-pyrrolidinyl)propyl]-7-[(4-fluorophenyl)methyl]-4-hydroxy-2-oxo-1,2-dihydro-1,5-naphthyridine-3-carboxylate. To a solution of ethyl 1-(3-chloropropyl)-7-[(4-fluorophenyl)methyl]-4-hydroxy-2-oxo-1,2-dihydro-1,5-naphthyridine-3-carboxylate (24 mg, 0.057 mmol) in N,N-dimethylformamide (700 µL) was added succinimide (23 mg, 0.23 mmol), potassium carbonate (32 mg, 0.23 mmol), and possium iodide (38 mg, 0.23 mmol), respectively. The reaction mixture was stirred at 70° C. overnight. The reaction mixture was cooled and quenched with cold 1 N aqueous hydrochloric acid and extracted with toluene. The organic layer was washed with water and brine, then dried over sodium sulfate. Filtration and concentration provided ethyl 1-[3-(2,5-dioxo-1-pyrrolidinyl)propyl]-7-[(4-fluorophenyl)methyl]-4-hydroxy-2-oxo-1,2-dihydro-1,5-naphthyridine-3-carboxylate as a light yellow oil. $^1$H NMR (400 MHz, CDCl$_3$) δ 8.51 (s, 1 H), 7.31 (s, 1 H), 7.19 (dd, J=8.5, 5.3 Hz, 2 H), 7.04 (t, J=8.6 Hz, 2 H), 4.50 (q, J=7.1 Hz, 2 H), 4.17-4.12 (m, 4 H), 3.58 (t, J=7.1 Hz, 2 H), 2.71 (s, 4 H), 1.90 (m, 2 H), 1.47 (t, J=7.1 Hz, 3 H); MS m/z 504 (M+Na)$^+$.

1-[3-(2,5-Dioxo-1-pyrrolidinyl)propyl]-7-[(4-fluorophenyl)methyl]-4-hydroxy-N-[2-(methyloxy)ethyl]-2-oxo-1,2-dihydro-1,5-naphthyridine-3-carboxamide. This compound was prepared from ethyl 1-[3-(2,5-dioxo-1-pyrrolidinyl)propyl]-7-[(4-fluorophenyl)methyl]-4-hydroxy-2-oxo-1,2-dihydro-1,5-naphthyridine-3-carboxylate and 2-methoxyethylamine employing methods similar to those described in Example 202 and was obtained as a white solid. $^1$H NMR (400 MHz, CDCl$_3$) δ 10.27 (s, 1 H), 8.56 (s, 1 H), 7.34 (s, 1 H), 7.19 (dd, J=8.4, 5.4 Hz, 2 H), 7.04 (t, J=8.6 Hz, 2 H), 4.18-4.12 (m, 4 H), 3.64 (m, 2 H), 3.61-3.57 (m, 4 H), 3.42 (s, 3 H), 2.73 (s, 4 H), 1.91 (m, 2 H); HRMS $C_{26}H_{27}FN_4O_6$ (M+H)$^+$ calcd 511.1915, found 511.1988.

EXAMPLE 425

7-[(4-Fluorophenyl)methyl]-4-hydroxy-N-{2[-methyl(methylsulfonyl)amino]ethyl}-2-oxo-1,2-dihydro-1,5-naphthyridine-3-carboxamide This compound was prepared from ethyl 7-[(4-fluorophenyl)methyl]-4-hydroxy-2-oxo-1,2-dihydro-1,5-naphthyridine-3-carboxylate and N-(2-aminoethyl)-N-methylmethanesulfonamide employing methods similar to those described in Example 2 and using N,N-dimethylformamide as the reaction solvent. The product was obtained as an off-white solid: $^1$H NMR (d$_6$-DMSO) δ 11.93 (1H, br s), 10.91 (1H, br s), 9.99 (1H, br s), 8.10 (1H, br s), 7.35-7.25 (3H, m), 7.18-7.08 (2H, m), 3.98 (2H, br s), 3.46 (2H, br s), 3.21 (2H, br s), 2.85 (3H, s), 2.81 (3H, s); HRMS calcd for $C_{20}H_{21}FN_4O_5S+H^+$: 449.1295. Found 449.1292.

EXAMPLE 426

1-(2-{[(dimethylamino)carbonyl]amino}ethyl)-7-[(4-fluorophenyl)methyl]-4-hydroxy-2-oxo-N-(tetrahydro-2-furanylmethyl)-1,2-dihydro-1,5-naphthyridine-3-carboxamide A solution of 1-(2-aminoethyl)-7-[(4-fluorophenyl)methyl]-4-hydroxy-2-oxo-N-(tetrahydro-2-furanylmethyl)-1,2-dihydro-1,5-naphthyridine-3-carboxamide (0.025 g, 0.057 mmol) and diisopropyl ethylamine (0.05 mL, 0.29 mmol) in DMF (3 mL) under nitrogen was treated with N,N-dimethyl carbonyl chloride (0.0055 mL, 0.06 mmol) (40° C. After 2½ h the reaction was cooled, concentrated in vacuo, and the resulting residue treated with 1N NaHSO$_4$, filtered, washed with water, and dried in vacuo to provide the title compound as an orange solid: $^1$H NMR (300 MHz, DMSO-d$_6$) δ ppm 0.98-1.34 (m, 1 H), 1.48-1.67 (m, 1 H), 1.67-2.12 (m, 3 H), 2.70 (s, 6 H), 3.32-3.41 (m, 1 H), 3.57 (d, J=18.81 Hz, 1 H), 3.63-3.71 (m, 1 H), 3.78-3.85 (m, 1 H), 4.00 (d, J=1.97 Hz, 2 H), 4.12 (s, 3 H), 4.26 (t, J=6.04 Hz, 2 H), 6.52-6.57 (m, 1 H), 7.14 (t, J=8.70 Hz, 2 H), 7.35-7.43 (m, 2 H), 8.28 (s, 1 H), 8.53 (s, 1 H), 10.46 (s, 1 H); ES+ MS: 512 (M+H+).

EXAMPLE 427

1-(2-{[(dimethylamino)carbonyl]amino}ethyl)-7-[(4-fluorophenyl)methyl]-4-hydroxy-N-{2-[(2-hydroxyethyl)oxy]ethyl}-2-oxo-1,2-dihydro-1,5-naphthyridine-3-carboxamide A solution of 1-(2-aminoethyl)-7-[(4-fluorophenyl)methyl]-4-hydroxy-N-{2-[(2-hydroxyethyl)oxy]ethyl}-2-oxo-1,2-dihydro-1,5-naphthyridine-3-carboxamide (0.025 g, 0.057 mmol) and diisopropyl ethylamine (0.05 mL, 0.29 mmol) in DMF (3 mL) under nitrogen was treated with N,N-dimethyl carbonyl chloride (0.0055 mL, 0.06 mmol) (40° C. After 2½ h the reaction was cooled, concentrated in vacuo, and the resulting residue treated with 1N NaHSO$_4$, filtered, washed with water, and dried in vacuo to provide the title compound as a pale yellow solid: $^1$H NMR (300 MHz, DMSO-d$_6$) δ ppm 1.73 (s, 1 H), 2.70 (s, 6 H), 3.24-3.30 (m, 3 H), 3.46-3.62 (m, 7 H), 4.12 (s, 2 H), 4.25 (t, J=6.32 Hz, 2 H), 4.62 (t, J=5.19 Hz, 1 H), 6.56 (t, J=5.76 Hz, 1 H), 7.10-7.18 (m, 2 H), 7.37-7.44 (m, 2 H), 8.30 (s, 1 H), 8.53 (d, J=1.69 Hz, 1 H), 10.41 (t, J=5.26 Hz, 1 H); ES+ MS: 516 (M+H+).

EXAMPLE 428

7-(4-Fluorobenzyl)-4-hydroxy-N-[(2S)-2-hydroxypropyl]-2-oxo-1-[2-(2-oxopyrrolidin-1-yl)ethyl]-2-dihydro-1,5-naphthyridine-3-carboxamide The title compound was made in a similar manner to example 9 using (S)-(+)-1-amino-2-propanol to give a beige solid: $^1$H NMR (CDCl$_3$) δ 10.32 (1H, m), 8.53 (1H, s), 8.03 (1H, s), 7.22 (2H, m), 6.98 (2H, m), 4.31 (2H, m), 4.13 (2H, s), 4.07 (1H, m), 3.62 (1H, m), 3.31-3.49 (5H, m), 3.13 (2H, br), 2.32 (2H, m), 1.96 (2H, m), 1.27 (3H, d, J=7 Hz); HRMS calcd for C$_{25}$H$_{27}$FN$_4$O$_5$+H+: 483.2044. Found: 483.2046.

EXAMPLE 429

7-(4-Fluorobenzyl)-4-hydroxy-N-[(2R)-2-hydroxypropyl]-2-oxo-1-[2-(2-oxopyrrolidin-1-yl)ethyl]-1,2-dihydro-1,5-naphthyridine-3-carboxamide The title compound was made in a similar manner to example 9 using (R)-(−)-1-amino-2-propanol to give a beige solid: $^1$H NMR (CDCl$_3$) δ 10.32 (1H, m), 8.54 (1H, s), 8.02 (1H, s), 7.22 (2H, m), 6.98 (2H, m), 4.63 (2H, br), 4.31 (2H, m), 4.13 (2H, s), 4.08 (1H, m), 3.62 (1H, m), 3.30-3.49 (5H, m), 2.34 (2H, m), 1.97 (2H, m), 1.27 (3H, d, J=7 Hz); HRMS calcd for C$_{25}$H$_{27}$FN$_4$O$_5$+H+: 483.2044. Found: 483.2038.

EXAMPLE 430

1-[2-(acetylamino)ethyl]-7-[(4-fluorophenyl)methyl]-4-hydroxy-2-oxo-N-(tetrahydro-2-furanylmethyl)-1,2-dihydro-1,5-naphthyridine-3-carboxamide A solution of 1-(2-aminoethyl)-7-[(4-fluorophenyl)methyl]-4-hydroxy-2-oxo-N-(tetrahydro-2-furanylmethyl)-1,2-dihydro-1,5-naphthyridine-3-carboxamide (0.025 g, 0.057 mmol) and diisopropyl ethylamine (0.05 mL, 0.29 mmol) in DMF (3 mL) under nitrogen was treated with acetic anhydride (0.06 mL, 0.63 mmol) at 40° C. The reaction was concentrated in vacuo and the resulting residue was treated with 1 N NaHSO$_4$, filtered, washed with water, and dried in vacuo to provide the title compound as a pale yellow solid: $^1$H NMR (400 MHz, DMSO-d$_6$) δ ppm 1.56 (ddd, J=15.28, 11.80, 7.14 Hz, 1 H), 1.67 (s, 3 H), 1.79-1.89 (m, 2 H), 1.90-2.00 (m, 1 H), 3.26-3.31 (m, 2 H), 3.33-3.40 (m, 1 H), 3.56 (ddd, J=13.91, 5.95, 4.30 Hz, 1 H), 3.64-3.71 (m, 1 H), 3.76-3.84 (m, 1 H), 3.96-4.04 (m, 1 H), 4.15 (s, 2 H), 4.27 (t, J=6.77 Hz, 2 H), 7.11-7.17 (m, 2 H), 7.38-7.44 (m, 2 H), 8.03 (t, J=5.85 Hz, 1 H), 8.19 (d, J=1.46 Hz, 1 H), 8.56 (d, J=1.46 Hz, 1 H), 10.42 (t, J=5.58 Hz, 1 H); ES+ MS: 483 (M+H+).

EXAMPLE 431

7-(4-Fluorobenzyl)-4-hydroxy-N-(3-methoxypropyl)-2-oxo-1-[2-(2-oxopyrrolidin-1-yl)ethyl]-1,2-dihydro-1,5-naphthyridine-3-carboxamide The title compound was made in a similar manner to example 9 using 3-methoxypropylamine to give a glass: $^1$H NMR (CDCl$_3$) δ 10.15 (1H, m), 8.58 (1H, s), 8.03 (1H, s), 7.21 (2H, m), 6.98 (2H, m), 6.19 (1H, br), 4.34 (2H, m), 4.13 (2H, s), 3.43-3.55 (8H, m), 3.36 (3H, s), 2.37 (2H, m), 1.99 (2H, m), 1.90 (2H, m); HRMS calcd for C$_{26}$H$_{29}$FN$_4$O$_5$+H+: 497.2200. Found: 497.2197.

EXAMPLE 432

7-[(4-Fluorophenyl)methyl]-4-hydroxy-N-(2-hydroxypropyl)-1-(1H-imidazol-4-ylmethyl)-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.24 (br, 1 H), 8.21 (s, 1 H), 7.63 (s, 1 H), 7.28 (s, 1 H), 6.92 (dd, J=8.5, 5.5 Hz, 2 H), 6.76 (t, J=8.7 Hz, 2 H), 6.56 (s, 1 H), 5.17 (d, J=15.6 Hz, 1 H), 5.12 (d, J=15.8 Hz, 1 H), 3.89 (s, 2 H), 3.77 (m, 1 H), 3.34 (m, 1 H), 3.13 (m, 1 H), 1.02 (d, J=6.2 Hz, 3 H); HRMS m/z calcd for C$_{23}$H$_{23}$N$_5$O$_4$F (M+H)+ 452.1734, found 452.1728.

EXAMPLE 433

7-[(4-Fluorophenyl)methyl]-4-hydroxy-N-(2-hydroxy-1,1-dimethylethyl)-1-(1H-imidazol-4-ylmethyl)-2-oxo-1,2-dihydro-1,5-naphthyridine-3-carboxamide The title compound was prepared in a similar manner to that described in example 152 using excess amine and ethanol as solvent to provide a white solid as a formate salt. $^1$H NMR (400 MHz, CDCl$_3$) δ 10.25 (br, 1 H), 8.25 (s, 1 H), 7.91 (s, 1 H), 7.64 (s, 1 H), 7.34 (s, 1 H), 6.95 (dd, J=8.5, 5.5 Hz, 2 H), 6.79 (t, J=8.6 Hz, 2 H), 6.60 (s, 1 H), 5.17 (s, 2 H), 3.92 (s, 2 H), 3.50 (s, 2 H), 1.25 (s, 6 H); HRMS m/z calcd for C$_{24}$H$_{25}$N$_5$O$_4$F (M+H)+ 466.1891, found 466.1884.

EXAMPLE 434

7-(4-Fluorobenzyl)-4-hydroxy-N-(3-hydroxypropyl)-2-oxo-1-[2-(2-oxopyrrolidin-1-yl)ethyl]-1,2-dihydro-1,5-naphthyridine-3-carboxamide The title compound was made in a similar manner to example 9 using 3-amino-1-propanol to give a viscous oil: $^1$H NMR (CDCl$_3$) δ 10.22 (1H, m), 8.60 (1H, s), 8.04 (1H, s), 7.22 (2H, m), 6.99 (2H, m), 5.03 (2H, br), 4.34 (2H, m), 4.15

(2H, s), 3.72 (2H, m), 3.60 (2H, m), 3.46 (4H, m), 2.39 (2H, m), 2.01 (2H, m), 1.84 (2H, m); HRMS calcd for $C_{25}H_{27}FN_4O_5+H^+$: 483.2044. Found: 483.2047.

EXAMPLE 435

7-[(4-Fluorophenyl)methyl]-4-hydroxy-N-methyl-2-oxo-1-(2-pyridinylmethyl)-1,2-dihydro-1,5-naphthyridine-3-carboxamide The title compound was prepared in a similar manner to that described in example 152 using excess amine and ethanol as solvent to provide a white solid. $^1$H NMR (400 MHz, DMSO-$d_6$) δ 10.05 (m, 1 H), 8.51 (d, J=1.4 Hz, 1 H), 8.37 (dd, J=5.5, 1.6 Hz, 1 H), 7.78 (s, 1 H), 7.69 (td, J=7.8, 1.7 Hz, 1 H), 7.23 (m, 2 H), 7.15 (dd, J=8.5, 5.6 Hz, 2 H), 7.02 (t, J=8.9 Hz, 2 H), 5.54 (s, 2 H), 4.02 (s, 2 H), 2.87 (d, J=4.8 Hz, 3 H); HRMS m/z calcd for $C_{23}H_{20}N_4O_3F$ (M+H)$^+$ 419.1519, found 419.1524.

EXAMPLE 436

1-(2-Amino-2-oxoethyl)-7-(4-fluorobenzyl)-4-hydroxy-N-[(2S)-2-hydroxypropyl]-2-oxo-1,2-dihydro-1,5-naphthyridine-3-carboxamide The title compound was made in a similar manner to example 162 using (S)-(+)-1-amino-2-propanol to give an off-white solid: $^1$H NMR ($d_6$-DMSO) δ 10.29 (1H, m), 8.52 (1H, s), 7.82 (1H, s), 7.64 (1H, s), 7.33 (2H, m), 7.26 (1H, s), 7.11 (2H, m), 4.95 (1H, m), 4.83 (2H, s), 4.11 (2H, s), 3.78 (1H, m), 3.41 (1H, m), 3.18 (1H, m), 1.08 (3H, d, J=6 Hz); HRMS calcd for $C_{21}H_{21}FN_4O_5+H^+$: 429.1574. Found: 429.1580.

EXAMPLE 437

7-[(4-fluorophenyl)methyl]-4-hydroxy-1-{2-[(methylsulfonyl)amino]ethyl}-N-[3-(4-morpholinyl)propyl]-2-oxo-1,2-dihydro-1,5-naphthyridine-3-carboxamide A solution of 1-(2-aminoethyl)-7-[(4-fluorophenyl)methyl]-4-hydroxy-N-[3-(4-morpholinyl)propyl]-2-oxo-1,2-dihydro-1,5-naphthyridine-3-carboxamide (0.025 g, 0.052 mmol) and diisopropyl ethylamine (0.05 mL, 0.29 mmol) in DMF (5 mL) under nitrogen was treated with methanesulfonyl chloride (0.0053 mL, 0.068 mmol) at 40° C. for 1 h then 3½ h at ambient temperature. The reaction was concentrated in vacuo and the resulting residue was triturated with Et$_2$O: MeOH, filtered, washed with 2:1 Et$_2$O:MeOH, and dried in vacuo to provide the title compound as a pale yellow solid: $^1$H NMR (300 MHz, DMSO-$d_6$) δ ppm 1.67 (s, 1 H), 1.99 (br. s., 2 H), 2.90 (s, 3 H), 3.07 (d, J=12.07 Hz, 2 H), 3.12-3.28 (m, 4 H), 3.39-3.51 (m, 4 H), 3.59-3.72 (m, 2 H), 3.92-4.04 (m, 1 H), 4.15 (s, 2 H), 4.35 (t, J=7.23 Hz, 2 H), 7.09-7.17 (m, 2 H), 7.29 (t, J=6.60 Hz, 1 H), 7.35-7.44 (m, 2 H), 8.13 (s, 1 H), 8.56 (d, J=1.40 Hz, 1 H), 9.80 (br. s., 1 H), 10.31 (t, J=5.83 Hz, 1 H); ES$^+$ MS: 562 (M+H$^+$).

EXAMPLE 438 methyl {2-[7-[(4-fluorophenyl)methyl]-4-hydroxy-3-({[2-(4-morpholinyl)ethyl]amino}carbonyl)-2-oxo-1,5-naphthyridine-1(2H)-yl]ethyl}carbamate A solution of 1-(2-aminoethyl)-7-[(4-fluorophenyl)methyl]-4-hydroxy-N-[2-(4-morpholinyl)ethyl]-2-oxo-1,2-dihydro-1,5-naphthyridine-3-carboxamide (0.025 g, 0.052 mmol) and diisopropyl ethylamine (0.05 mL, 0.29 mmol) in DMF (5 mL) under nitrogen was treated with methyl chloroformate (0.0087 mL, 0.11 mmol) at 40° C. for 1 h then 3½ h at ambient temperature. The reaction was concentrated in vacuo and the resulting residue was triturated with Et$_2$O: MeOH, filtered, washed with 2:1 Et$_2$O:MeOH, and dried in vacuo to provide the title compound as a pale yellow solid: $^1$H NMR (300 MHz, DMSO-$d_6$) δ ppm 1.23 (s, 1 H), 3.06-3.20 (m, 2 H), 3.25-3.32 (m, 2 H), 3.36-3.43 (m, 2 H), 3.45 (s, 3 H), 3.55 (d, J=10.95 Hz, 2 H), 3.69 (t, J=12.2 Hz, 2 H), 3.78 (d, J=6.74 Hz, 2 H), 4.00 (d, J=12.35 Hz, 2 H), 4.15 (s, 2 H), 4.31 (t, J=5.76 Hz, 2 H), 7.12-7.19 (m, 2 H), 7.38-7.45 (m, 2 H), 8.16 (s, 1 H), 8.55 (s, 1 H), 9.91 (br. s., 1 H), 10.39 (t, J=6.60 Hz, 1 H); ES$^+$ MS: 528 (M+H$^+$).

EXAMPLE 439

7-[(4-fluorophenyl)methyl]-4-hydroxy-1-{2-[(methylsulfonyl)amino]ethyl}-N-[2-(4-morpholinyl)ethyl]-2-oxo-1,2-dihydro-1,5-naphthyridine-3-carboxamide A solution of 1-(2-aminoethyl)-7-[(4-fluorophenyl)methyl]-4-hydroxy-N-[2-(4-morpholinyl)ethyl]-2-oxo-1,2-dihydro-1,5-naphthyridine-3-carboxamide (0.025 g, 0.052 mmol) and diisopropyl ethylamine (0.05 mL, 0.29 mmol) in DMF (5 mL) under nitrogen was treated with methanesulfonyl chloride (0.0053 mL, 0.068 mmol) at 40° C. for 1 h then 3½ h at ambient temperature. The reaction was concentrated in vacuo and the resulting residue was triturated with Et$_2$O: MeOH, filtered, washed with 2:1 Et$_2$O:MeOH, and dried in vacuo to provide the title compound as an off-white solid: $^1$H NMR (300 MHz, DMSO-$d_6$) δ ppm 2.35-2.46 (m, 2 H), 2.90 (s, 3 H), 3.06-3.20 (m, 1 H), 3.21-3.29 (m, 2 H), 3.34-3.45 (m, 2 H), 3.52-3.68 (m, 4 H), 3.72-3.83 (m, 2 H), 3.97-4.02 (m, 1 H), 4.15 (d, J=0.56 Hz, 2 H), 4.30-4.41 (m, 2 H), 7.13 (t, J=8.98 Hz, 2 H), 7.29 (s, 1 H), 7.41 (dd, J=8.84, 5.62 Hz, 2 H), 8.13 (s, 1 H), 8.56 (s, 1 H), 9.83 (br. s., 1 H), 10.32-10.41 (m, 1 H); ES$^+$ MS: 548 (M+H$^+$).

EXAMPLE 440

7-[(4-fluorophenyl)methyl]-4-hydroxy-1-{2-[(4-morpholinylcarbonyl)amino]ethyl}-N-[2-(4-morpholinyl)ethyl]-2-oxo-1,2-dihydro-1,5-naphthyridine-3-carboxamide A solution of 1-(2-aminoethyl)-7-[(4-fluorophenyl)methyl]-4-hydroxy-N-[2-(4-morpholinyl)ethyl]-2-oxo-1,2-dihydro-1,5-naphthyridine-3-carboxamide (0.025 g, 0.052 mmol) and diisopropyl ethylamine (0.05 mL, 0.29 mmol) in DMF (5 mL) under nitrogen was treated with 4-morpholinecarbonyl chloride (0.008 mL, 0.068 mmol) at 40° C. for 1 h then 3½ h at ambient temperature. The reaction was concentrated in vacuo and the resulting residue was triturated with Et$_2$O:MeOH, filtered, washed with 2:1 Et$_2$O:MeOH, and dried in vacuo to provide the title compound as an off-white solid: $^1$H NMR (300 MHz, DMSO-$d_6$) δ ppm 1.3 (s, 1 H), 3.10 (s, 2 H), 3.13-3.22 (m, 8 H), 3.27-3.33 (m, 1 H), 3.42-3.50 (m, 4 H), 3.55 (d, J=10.67 Hz, 2 H), 3.63-3.73 (m, 2 H), 3.78 (d, J=4.49 Hz, 1 H), 3.93-4.05 (m, 2 H), 4.14 (s, 2 H), 4.30 (t, J=6.67 Hz, 2 H), 7.11-7.19 (m, 2 H), 7.39-7.47 (m, 2

H), 8.34 (s, 1 H), 8.57 (d, J=1.12 Hz, 1 H), 9.88 (br. s., 1 H), 10.38-10.48 (m, 1 H); ES+ MS: 583 (M+H+).

EXAMPLE 441

7-[(4-fluorophenyl)methyl]-4-hydroxy-N-{2-[(2-hydroxyethyl)oxy]ethyl}-1-{2-[(methylsulfonyl)amino]ethyl}-2-oxo-1,2-dihydro-1,5-naphthyridine-3-carboxamide A solution of 1-(2-aminoethyl)-7-[(4-fluorophenyl)methyl]-4-hydroxy-N-{2-[(2-hydroxyethyl)oxy]ethyl}-2-oxo-1,2-dihydro-1,5-naphthyridine-3-carboxamide (0.025 g, 0.052 mmol) and diisopropyl ethylamine (0.05 mL, 0.29 mmol) in DMF (5 mL) under nitrogen was treated with methanesulfonyl chloride (0.0053 mL, 0.068 mmol) at 40° C. for 1 h then 3½ h at ambient temperature. The reaction was concentrated in vacuo and the resulting residue was triturated with Et$_2$O:MeOH, filtered, washed with 2:1 Et$_2$O:MeOH. A second crop was obtained by filtration from the filtrate, dried in vacuo to provide the title compound as an off-white solid: $^1$H NMR (300 MHz, DMSO-d$_6$) δ ppm 2.90 (s, 3 H), 3.19-3.30 (m, 2 H), 3.46-3.61 (m, 8 H), 4.14 (s, 2 H), 4.34 (t, J=6.53 Hz, 2 H), 4.60-4.64 (m, 1 H), 7.09-7.16 (m, 2 H), 7.23-7.29 (m, 1 H), 7.37-7.44 (m, 2 H), 8.11 (d, J=0.84 Hz, 1 H), 8.55 (d, J=1.54 Hz, 1 H), 10.35 (t, J=5.48 Hz, 1 H), 17.12 (s, 1 H); ES+ MS: 523 (M+H+).

EXAMPLE 442 methyl {2-[7-(4-fluorophenyl)methyl]-4-hydroxy-3-({[3-(4-morpholinyl)propyl]amino}carbonyl)-[2-oxo-1,5-naphthyridine-1(2H)-yl]ethyl}carbamate A solution of 1-(2-aminoethyl)-7-[(4-fluorophenyl)methyl]-4-hydroxy-N-[3-(4-morpholinyl)propyl]-2-oxo-1,2-dihydro-1,5-naphthyridine-3-carboxamide (0.025 g, 0.052 mmol) and diisopropyl ethylamine (0.05 mL, 0.29 mmol) in DMF (5 mL) under nitrogen was treated with methyl chloroformate (0.0087 mL, 0.11 mmol) at 40° C. for 1 h then 3½ h at ambient temperature. The reaction was concentrated in vacuo and the resulting residue was triturated with Et$_2$O:MeOH, filtered, washed with 2:1 Et$_2$O:MeOH, and dried in vacuo to provide the title compound as an orange solid: $^1$H NMR (300 MHz, DMSO-d$_6$) δ ppm 1.56-1.76 (m, 1 H), 1.99 (s, 2 H), 2.99-3.12 (m, 2 H), 3.17 (s, 2 H), 3.29 (d, J=6.32 Hz, 2 H), 3.39-3.51 (m, 7 H), 3.66 (t, J=12.42 Hz, 2 H), 3.97 (d, J=11.23 Hz, 2 H), 4.15 (s, 2 H), 4.30 (t, J=5.90 Hz, 2 H), 7.15 (ddd, J=8.91, 6.74, 2.18 Hz, 2 H), 7.30 (t, J=5.97 Hz, 1 H), 7.40 (td, J=5.86, 2.18 Hz, 2 H), 8.15 (s, 1 H), 8.54 (d, J=0.98 Hz, 1 H), 10.34 (t, J=5.97 Hz, 1 H); ES+ MS: 542 (M+H+).

EXAMPLE 443

7-[(4-fluorophenyl)methyl]-4-hydroxy-1-{2-[(methylsulfonyl)amino]ethyl}-2-oxo-N-(tetrahydro-2-furanylmethyl)-1,2-dihydro-1,5-naphthyridine-3-carboxamide A solution of 1-(2-aminoethyl)-7-[(4-fluorophenyl)methyl]-4-hydroxy-2-oxo-N-(tetrahydro-2-furanylmethyl)-1,2-dihydro-1,5-naphthyridine-3-carboxamide (0.025 g, 0.052 mmol) and diisopropyl ethylamine (0.05 mL, 0.29 mmol) in DMF (5 mL) under nitrogen was treated with methanesulfonyl chloride (0.0053 mL, 0.068 mmol) at 40° C. for 1 h then 3½ h at ambient temperature. The reaction was concentrated in vacuo and the resulting residue was triturated with Et$_2$O: MeOH, filtered, washed with 2:1 Et$_2$O:MeOH, and dried in vacuo to provide the title compound as a pale yellow solid: $^1$H NMR (300 MHz, DMSO-d$_6$) δ ppm 1.44-1.67 (m, 1 H), 1.80-1.89 (m, 3 H), 2.90 (s, 3 H), 3.19-3.29 (m, 2 H), 3.34-3.41 (m, 1 H), 3.53-3.61 (m, 1 H), 3.64-3.71 (m, 1 H), 3.77-3.87 (m, 1 H), 3.97-4.08 (m, 1 H), 4.14 (s, 2 H), 4.35 (t, J=6.18 Hz, 2 H), 7.10-7.18 (m, 2 H), 7.26 (t, J=5.76 Hz, 1 H), 7.40 (dd, J=8.14, 5.48 Hz, 2 H), 8.11 (s, 1 H), 8.55 (s, 1 H), 10.39 (t, J=5.97 Hz, 1 H), 17.10 (s, 1 H); ES+ MS: 519 (M+H+).

EXAMPLE 444

7-[(4-fluorophenyl)methyl]-4-hydroxy-1-{2-[(4-morpholinylcarbonyl)amino]ethyl}-N-[3-(4-morpholinyl)propyl]-2-oxo-1,2-dihydro-1,5-naphthyridine-3-carboxamide A solution of 1-(2-aminoethyl)-7-[(4-fluorophenyl)methyl]-4-hydroxy-N-[3-(4-morpholinyl)propyl]-2-oxo-1,2-dihydro-1,5-naphthyridine-3-carboxamide (0.025 g, 0.052 mmol) and diisopropyl ethylamine (0.05 mL, 0.29 mmol) in DMF (5 mL) under nitrogen was treated with methyl chloroformate (0.008 mL, 0.07 mmol) at 40° C. for 1 h then 3½ h at ambient temperature. The reaction was concentrated in vacuo and the resulting residue was triturated with Et$_2$O:MeOH, and concentrated again in vacuo, before triturating again with EtOAc. Filtered the resulting suspension and dried in vacuo to provide the title compound as an orange solid: $^1$H NMR (400 MHz, DMSO-d$_6$) δ ppm 1.23-1.29 (m, 2 H), 1.99-2.05 (m, 1 H), 3.04-3.08 (m, 2 H), 3.10-3.19 (m, 7 H), 3.42 (s, 2 H), 3.44-3.49 (m, 6 H), 3.70 (t, J=11.81 Hz, 2 H), 3.96 (d, J=13.19 Hz, 2 H), 4.14 (s, 2 H), 4.29 (t, J=6.59 Hz, 2 H), 6.81 (t, J=4.67 Hz, 1 H), 7.14 (t, J=8.79 Hz, 2 H), 7.42 (dd, J=8.70, 5.59 Hz, 2 H), 8.32 (s, 1 H), 8.55 (d, J=1.28 Hz, 1 H), 10.15 (s, 1 H), 10.37 (t, J=6.50 Hz, 1 H); ES+ MS: 597 (M+H+).

EXAMPLE 445

7-[(4-fluorophenyl)methyl]-4-hydroxy-1-{2-[(4-morpholinylcarbonyl)amino]ethyl}-2-oxo-N-(tetrahydro-2-furanylmethyl)-1,2-dihydro-1,5-naphthyridine-3-carboxamide This compound was prepared from 1-(2-aminoethyl)-7-[(4-fluorophenyl)methyl]-4-hydroxy-2-oxo-N-(tetrahydro-2-furanylmethyl)-1,2-dihydro-1,5-naphthyridine-3-carboxamide employing methods similar to those described in Example 391 and was obtained as an off-white solid: ES+ MS: 554 (M+H+).

EXAMPLE 446

1-[2-(acetylamino)ethyl]-7-[(4-fluorophenyl)methyl]-4-hydroxy-N-[3-(4-morpholinyl)propyl]-2-oxo-1,2-dihydro-1,5-naphthyridine-3-carboxamide This compound was prepared from 1-(2-aminoethyl)-7-[(4-fluorophenyl)methyl]-4-hydroxy-N-[3-(4-morpholinyl)propyl]-2-oxo-1,2-dihydro-1,5-naphthyridine-3-carboxamide employing methods similar to those described in Example 391 and was obtained as an off-white solid: ES+ MS: 526 (M+H+).

EXAMPLE 447

1-(2-{[(dimethylamino)carbonyl]amino}ethyl)-7-[(4-fluorophenyl)methyl]-4-hydroxy-N-[3-(4-morpholinyl)propyl]-2-oxo-1,2-dihydro-1,5-naphthyridine-3-carboxamide A solution of 1-(2-aminoethyl)-7-[(4-fluorophenyl)methyl]-4-hydroxy-N-[3-(4-morpholinyl)propyl]-2-oxo-1,2-dihydro-1,5-naphthyridine-3-carboxamide (0.025 g, 0.057 mmol) and diisopropyl ethylamine (0.05 mL, 0.29 mmol) in DMF (3 mL) under nitrogen was treated with N,N-dimethyl carbonyl chloride (0.0055 mL, 0.06 mmol)@40° C. After 2½ h the reaction was cooled, concentrated in vacuo, and the resulting residue treated with 1N NaHSO$_4$. Extracted the mixture 3× with EtOAc and concentrated the organics. The residue was then dissolved in EtOAc and washed with saturated NaHCO$_3$ (aqueous) then concentrated the organics. Triturated the residue with Et$_2$O, filtered, and dried in vacuo to provide the title compound as an orange solid: $^1$H NMR (300 MHz, DMSO-d$_6$) δ ppm 1.66-1.79 (m, 2 H), 1.76-1.93 (m, 1 H), 2.35 (t, J=6.18 Hz, 6 H), 2.70 (s, 6 H), 3.19-3.31 (m, 2 H), 3.40-3.48 (m, 2 H), 3.53-3.63 (m, 4 H), 4.11 (s, 2 H), 4.25 (s, 2 H), 6.54-6.59 (m, 1 H), 7.14 (t, J=8.84 Hz, 2 H), 7.37-7.44 (m, 2 H), 8.17-8.39 (m, 1 H), 8.52 (s, 1 H), 10.38 (s, 1 H); ES$^+$ MS: 555 (M+H$^+$).

EXAMPLE 448 methyl {2-[7-[(4-fluorophenyl)methyl]-4-hydroxy-2-oxo-3-{[(tetrahydro-2-furanylmethyl)amino]carbonyl}-1,5-naphthyridine-1(2H)-yl]ethyl}carbamate This compound was prepared from 1-(2-aminoethyl)-7-[(4-fluorophenyl)methyl]-4-hydroxy-2-oxo-N-(tetrahydro-2-furanylmethyl)-1,2-dihydro-1,5-naphthyridine-3-carboxamide employing methods similar to those described in Example 391 and was obtained as an orange solid: ES$^+$ MS: 499 (M+H$^+$).

EXAMPLE 449

1-[2-(acetylamino)ethyl]-7-[(4-fluorophenyl)methyl]-4-hydroxy-N-[2-(4-morpholinyl)ethyl]-2-oxo-1,2-dihydro-1,5-naphthyridine-3-carboxamide This compound was prepared from 1-(2-aminoethyl)-7-[(4-fluorophenyl)methyl]-4-hydroxy-N-[2-(4-morpholinyl)ethyl]-2-oxo-1,2-dihydro-1,5-naphthyridine-3-carboxamide employing methods similar to those described in Example 391 and was obtained as an off-white solid: $^1$H NMR (300 MHz, DMSO-d$_6$) δ ppm 1.68 (s, 3 H), 2.36 (s, 1 H), 2.40-2.54 (m, 6 H), 3.29 (s, 1 H), 3.50 (q, J=6.13 Hz, 2 H), 3.61 (s, 4 H), 4.14 (s, 2 H), 4.27 (t, J=6.39 Hz, 2 H), 7.10-7.18 (m, 2 H), 7.38-7.45 (m, 2 H), 8.04 (t, J=6.25 Hz, 1 H), 8.20 (d, J=1.12 Hz, 1 H), 8.55 (d, J=1.40 Hz, 1 H), 10.37 (t, J=5.69 Hz, 1 H), 17.21 (s, 1 H); ES$^+$ MS: 512 (M+H$^+$).

EXAMPLE 450

1-(2-{[(dimethylamino)carbonyl]amino}ethyl)-7-[(4-fluorophenyl)methyl]-4-hydroxy-N-[2-(4-morpholinyl)ethyl]-2-oxo-1,2-dihydro-1,5-naphthyridine-3-carboxamide A solution of 1-(2-aminoethyl)-7-[(4-fluorophenyl)methyl]-4-hydroxy-N-[2-(4-morpholinyl)ethyl]-2-oxo-1,2-dihydro-1,5-naphthyridine-3-carboxamide (0.025 g, 0.057 mmol) and diisopropyl ethylamine (0.05 mL, 0.29 mmol) in DMF (3 mL) under nitrogen was treated with N,N-dimethyl carbonyl chloride (0.0055 mL, 0.06 mmol) (40° C. After 2½ h the reaction was cooled, concentrated in vacuo, and the resulting residue was triturated with EtOAc and water, filtered, and dried in vacuo to provide the title compound as an off-white solid: $^1$H NMR (300 MHz, DMSO-d$_6$) δ ppm 1.84 (s, 1 H), 2.39-2.47 (m, 4 H), 2.52-2.57 (m, 2 H), 2.71 (s, 6 H), 3.23-3.31 (m, 2 H), 3.44-3.55 (m, 2 H), 3.56-3.62 (m, 4 H), 4.12 (s, 2 H), 4.25 (t, J=6.32 Hz, 2 H), 6.57 (t, J=5.55 Hz, 1 H), 7.09-7.18 (m, 2 H), 7.41 (dd, J=8.70, 5.62 Hz, 2 H), 8.30 (s, 1 H), 8.53 (s, 1 H), 10.40 (t, J=5.90 Hz, 1 H); ES$^+$ MS: 541 (M+H$^+$).

EXAMPLE 451

7-[(4-Fluorophenyl)methyl]-4-hydroxy-N-(2-hydroxy-1-methylethyl)-2-oxo-1-(2-pyridinylmethyl)-1,2-dihydro-1,5-naphthyridine-3-carboxamide The title compound was prepared in a similar manner to that described in example 152 using excess amine and ethanol as solvent to provide a white solid. $^1$H NMR (400 MHz, DMSO-d$_6$) δ 10.27 (d, J=7.4 Hz, 1 H), 8.51 (s, 1 H), 8.37 (d, J=4.4 Hz, 1 H), 7.76 (s, 1 H), 7.70 (t, J=7.6 Hz, 1 H), 7.23 (m, 2 H), 7.15 (dd, J=8.5, 5.7 Hz, 2 H), 7.02 (t, J=8.9 Hz, 2 H), 5.54 (s, 2 H), 4.96 (t, J=5.3 Hz, 1 H), 4.03 (m, 1 H), 4.01 (s, 2 H), 3.44 (m, 2 H), 1.15 (d, J=7.0 Hz, 3 H); HRMS m/z calcd for C$_{25}$H$_{24}$N$_4$O$_4$F (M+H)$^+$ 463.1782, found 463.1786.

EXAMPLE 452

7-[(4-Fluorophenyl)methyl]-4-hydroxy-N-[2-(methyloxy)ethyl]-2-oxo-1-(2-pyridinylmethyl)-1,2-dihydro-1,5-naphthyridine-3-carboxamide The title compound was prepared in a similar manner to that described in example 152 using excess amine and ethanol as solvent to provide a white solid. $^1$H NMR (400 MHz, DMSO-d$_6$) δ 10.30 (m, 1 H), 8.53 (s, 1 H), 8.38 (d, J=5.1 Hz, 1 H), 7.78 (s, 1 H), 7.71 (t, J=7.7 Hz, 1 H), 7.25 (m, 1 H), 7.16 (dd, J=8.7, 5.7 Hz, 2 H), 7.04 (t, J=8.9 Hz, 2 H), 5.56 (s, 2 H), 4.03 (s, 2 H), 3.55-3.47 (m, 4 H), 3.30 (s, 3 H); HRMS m/z calcd for C$_{25}$H$_{24}$N$_4$O$_4$F (M+H)$^+$ 463.1782, found 463.1775.

EXAMPLE 453

7-[(4-Fluorophenyl)methyl]-4-hydroxy-N-(2-hydroxypropyl)-2-oxo-1-(2-pyridinylmethyl)-1,2-dihydro-1,5-naphthyridine-3-carboxamide The title compound was prepared in a similar manner to that described in example 152 using excess amine and ethanol as solvent to provide a white solid. $^1$H NMR (400 MHz, DMSO-d$_6$) δ 10.33 (m, 1 H), 8.51 (s, 1 H), 8.37 (d, J=5.2 Hz, 1 H), 7.76 (s, 1 H), 7.69 (t, J=7.9 Hz, 1 H), 7.25 (s, 1 H), 7.23 (m, 1 H), 7.15 (dd, J=8.4, 5.6 Hz, 2 H), 7.02 (t, J=8.9 Hz, 2 H), 5.55 (s, 2 H), 4.91 (d, J=4.8 Hz, 1 H), 4.02 (s, 2 H), 3.77 (m, 1 H), 3.42 (m, 1 H), 3.16 (m, 1 H), 1.06 (d, J=6.5 Hz, 3 H); HRMS m/z calcd for C$_{25}$H$_{24}$N$_4$O$_4$F (M+H)$^+$ 463.1782, found 463.1784.

EXAMPLE 454

7-[(4-Fluorophenyl)methyl]-4-hydroxy-N-(2-hydroxy-1,1-dimethylethyl)-2-oxo-1-(2-pyridinylmethyl-1,2-dihydro-1,5-naphthyridine-3-carboxamide The title compound was prepared in a similar manner to that described in example 152 using excess amine and ethanol as solvent to provide a white solid. $^1$H NMR (400 MHz, CDCl$_3$) δ 10.48 (s, 1 H), 8.51 (s, 1 H), 8.43 (d, J=4.6 Hz, 1 H), 7.55 (t, J=7.8 Hz, 1 H), 7.47 (s, 1 H), 7.15 (m, 1 H), 7.06 (d, J=7.8 Hz, 1 H), 6.98 (m, 2 H), 6.90 (m, 2 H), 5.48 (s, 2 H), 3.99

(s, 2 H), 3.73 (s, 2 H), 1.44 (s, 6 H); HRMS m/z calcd for $C_{26}H_{26}N_4O_4F$ (M+H)$^+$ 477.1938, found 477.1939.

EXAMPLE 455

7-[(4-fluorophenyl)methyl]-4-hydroxy-N-{2-[(2-hydroxyethyl)oxy]ethyl}-1-{2-[(4-morpholinylcarbonyl)amino]ethyl}-2-oxo-1,2-dihydro-1,5-naphthyridine-3-carboxamide A solution of 1-(2-aminoethyl)-7-[(4-fluorophenyl)methyl]-4-hydroxy-N-{2-[(2-hydroxyethyl)oxy]ethyl}-2-oxo-1,2-dihydro-1,5-naphthyridine-3-carboxamide (0.025 g, 0.057 mmol) and diisopropyl ethylamine (0.05 mL, 0.29 mmol) in DMF (3 mL) under nitrogen was treated with N,N-dimethyl carbonyl chloride (0.06 mL, 0.63 mmol)@40° C. After 2½ h the reaction was cooled, concentrated in vacuo, and the resulting residue treated with 1N NaHSO$_4$. Extracted the mixture 3× with EtOAc and concentrated the organics. The residue was then purified on silica gel by prep TLC (9:1 CH$_2$Cl$_2$:MeOH). Pure bands were collected to provide the title compound as an off-white solid: $^1$H NMR (400 MHz, DMSO-d$_6$) δ ppm 3.17 (d, J=5.31 Hz, 6 H), 3.43-3.50 (m, 4 H), 3.54 (dt, J=14.83, 5.22 Hz, 4 H), 3.60 (q, J=5.25 Hz, 2 H), 4.13 (s, 2 H), 4.24-4.33 (m, 2 H), 4.62 (t, J=4.85 Hz, 2 H), 6.79 (t, J=5.95 Hz, 2 H), 7.14 (t, J=8.79 Hz, 2 H), 7.42 (dd, J==8.61, 5.86 Hz, 2 H), 8.28 (s, 1 H), 8.48-8.60 (m, 1 H), 10.28-10.48 (m, 1 H); ES$^+$ MS: 558 (M+H$^+$).

EXAMPLE 456

1-[2-(acetylamino)ethyl]-7-[(4-fluorophenyl)methyl]-4-hydroxy-N-{2-[(2-hydroxyethyl)oxy]ethyl}-2-oxo-1,2-dihydro-1,5-naphthyridine-3-carboxamide A solution of 1-(2-aminoethyl)-7-[(4-fluorophenyl)methyl]-4-hydroxy-N-{2-[(2-hydroxyethyl)oxy]ethyl}-2-oxo-1,2-dihydro-1,5-naphthyridine-3-carboxamide (0.025 g, 0.057 mmol) and diisopropyl ethylamine (0.05 mL, 0.29 mmol) in DMF (3 mL) under nitrogen was treated with N,N-dimethyl carbonyl chloride (0.06 mL, 0.63 mmol) (40° C. After 2½ h the reaction was cooled, concentrated in vacuo, and the resulting residue treated with 1N NaHSO$_4$. Extracted the mixture 3× with EtOAc and concentrated the organics. The residue was then purified on silica gel by prep TLC (9:1 CH$_2$Cl$_2$:MeOH). Pure bands were collected to provide the title compound as an off-white solid: $^1$H NMR (400 MHz, CHLOROFORM-d) δ ppm 1.98 (s, 3 H), 3.46-3.54 (m, 2 H), 3.68 (d, J=4.76 Hz, 2 H), 3.71 (s, 4 H), 3.77-3.88 (m, 2 H), 4.17 (s, 2 H), 4.36 (t, J=7.23 Hz, 2 H), 5.31 (s, 1 H), 6.14 (s, 1 H), 7.02 (t, J=8.79 Hz, 2 H), 7.22-7.25 (m, 2 H), 8.07 (s, 1 H), 8.58 (s, 1 H), 10.51 (s, 1 H); ES$^+$ MS: 487 (M+H$^+$).

EXAMPLE 457 sodium 7-[(4-fluorophenyl)methyl]-3-({[2-(methyloxy)ethyl]amino}carbonyl)-2-oxo-1-[2-(2-oxo-1-pyrrolidinyl)ethyl]-1,2-dihydro-1,5-naphthyridine-4-olate (2-oxo-1-pyrrolidinyl)acetaldehyde. A mixture of N-(2-Hydroxyethyl)-2-pyrrolidone (5.00 g, 38.8 mmol) and triacetoxyperiodinane (24.6 g, 58.0 mmol) in CH$_2$Cl$_2$ was stirred at ambient temperature for approximately 64 hours. The reaction mixture was evaporated in vacuo and the residue was triturated with Et$_2$O. After filtration of the solids, the mother liquor was evaporated in vacuo to provide the product as a crude oil: $^1$H NMR (CDCl$_3$) δ 9.60 (1H, s), 4.16 (2H, s), 3.46 (2H, t, J=7 Hz), 2.45 (2H, t, J=8 Hz), 2.11 (2H, m).

Ethyl 5-(4-fluorobenzyl)-3-{[2-(2-oxopyrrolidin-1-yl)ethyl]amino}pyridine-2-carboxylate. (2-Oxopyrrolidin-1-yl)acetaldehyde (2.00 g, 15.7 mmol) and ethyl 3-amino-5-(4-fluorobenzyl)-2-pyridinecarboxylate (2.00 g, 7.32 mmol) were combined in 1:1 dichloroethane/acetic acid (10 mL) and cooled under nitrogen to 0-5° C. Sodium triacetoxyborohydride (3.10 g, 14.6 mmol) was added and the reaction was stirred for 15 min. Two additional portions of aldehyde (1.0 g, 7.8 mmol) plus sodium triacetoxyborohydride (1.65 g, 7.8 mmol) separated by 15 min. increments were made. The reaction mixture was evaporated in vacuo, dissolved in CH$_2$Cl$_2$, and treated with aqueous K$_2$CO$_3$ (5% w/v). After separating the layers, the aqueous phase was back-extracted twice with CH$_2$Cl$_2$. The combined organic phases were dried over MgSO$_4$, filtered, evaporated in vacuo and purified on silica gel eluting with 0-3% MeOH in EtOAc to provide an oil: $^1$H NMR (CDCl$_3$) δ 7.89 (1H, d, J=1.4 Hz), 7.83 (1H, br t, J~6 Hz), 7.15 (2H, dd, J~9, 6 Hz), 6.98 (2H, t, J~9 Hz), 6.92 (1H, s), 4.42 (2H, q, J=7 Hz), 3.92 (2H, s), 3.49 (2H, m), 3.41 (2H, t, J=7 Hz), 3.35 (2H, q, J=6 Hz), 2.36 (2H, t, J=8 Hz), 1.99 (2H, m), 1.42 (3H, t, J=7 Hz); ES$^+$ MS: 386 (M+H$^+$).

Ethyl 3-{[3-(ethyloxy)-3-oxopropanoyl][2-(2-oxo-1-pyrrolidinyl)ethyl]amino}-5-[(4-fluorophenyl)methyl]-2-pyridinecarboxylate. A solution of ethyl 5-(4-fluorobenzyl)-3-{[2-(2-oxopyrrolidin-1-yl)ethyl]amino}pyridine-2-carboxylate (2.445 g, 6.34 mmol) and ethyl malonyl chloride (1.25 mL, 9.5 mmol) was heated under nitrogen at reflux for 1 hour. Additional ethyl malonyl chloride (0.25 mL, 1.9 mmol) was added and the reaction was maintained for another hour at reflux. The reaction mixture was cooled, diluted with CH$_2$Cl$_2$, and treat with saturated aqueous NaHCO$_3$. After phase separation, the aqueous phase was extracted twice with CH$_2$Cl$_2$. The combined organic layers were dried over MgSO$_4$, filtered, evaporated in vacuo and purified on silica gel eluting with 3% MeOH in CH$_2$Cl$_2$ to provide an oil: $^1$H NMR (CDCl$_3$) δ 8.57 (1H, d, J=2 Hz), 8.23 (1H, d, J=2 Hz), 7.23 (2H, dd, J=6, 8 Hz), 7.00 (2H, t, J=8 Hz), 4.66-4.76 (1H, m), 4.41 (2H, q, J=7 Hz), 3.98-4.08 (4H, m), 3.80-3.90 (2H, m), 3.24-3.31 (1H, m), 3.02 (2H, dd, J=16, 32 Hz), 2.86-2.96 (2H, m), 2.30-2.48 (2H, m), 1.92-2.11 (2H, m), 1.38 (3H, t, J=7 Hz), 1.17 (3H, t, J=Hz); ES$^+$ MS: 500 (M+H$^+$).

Ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate. A solution of ethyl 3-{[3-(ethyloxy)-3-oxopropanoyl][2-(2-oxo-1-pyrrolidinyl)ethyl]amino}-5-[(4-fluorophenyl)methyl]-2-pyridinecarboxylate (1.80 g, 3.98 mmol) in ethanol (20 mL) was treated with DBU (1.53 mL, 10.3 mmol). After stirring under nitrogen for 20 min., the reaction was quenched with 1N HCl (7.8 mL) and evaporated in vacuo. Trituration with water and filtration provided the product as a white solid: $^1$H NMR (CDCl$_3$) δ 8.50 (1H, d, J=1.4 Hz), 8.11 (1H, s), 7.26 (2H, m), 7.00 (2H, ddd, J~9, 9, 2 Hz), 4.52 (2H, q, J=7 Hz), 4.33 (2H, br t, J~7 Hz), 4.14 (2H, s), 3.52-3.44 (4H, m), 2.35 (2H, t, J=8 Hz), 2.00 (2H, m), 1.48 (3H, t, J=7 Hz); ES$^+$ MS: 476 (M+Na$^+$).

7-(4-Fluorobenzyl)-4-hydroxy-N-(2-methoxyethyl)-2-oxo-1-[2-(2-oxopyrrolidin-1-yl)ethyl]-1,2-dihydro-1,5-naphthyridine-3-carboxamide. A mixture of ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate (1.13 g, 2.50 mmol) and 2-methoxyethylamine (1.1 mL, 12.5 mmol) in isopropanol (20 mL) was heated at reflux for 3 hrs. After cooling, the resulting slurry was diluted with isopropanol (10 mL) and filtered. The precipitate was partitioned between CH$_2$Cl$_2$ and 1N NaHSO$_4$. After separating the layers, the aqueous phase was back-extracted with CH$_2$Cl$_2$ and the combined organics were dried over Na$_2$SO$_4$, filtered and evaporated in vacuo to provide the product as a white solid. The isopropanol was evaporated in vacuo and the residue was partitioned between CH$_2$Cl$_2$ and 1N NaHSO$_4$. After separating the layers, the aqueous phase was back-extracted with CH$_2$Cl$_2$ and the combined organics were dried over Na$_2$SO$_4$, filtered and evaporated in vacuo to provide an additional crop of the product as a white solid: $^1$H NMR (CDCl$_3$) δ 10.27 (1H, br m), 8.55 (1H, s), 8.06 (1H, s), 7.24 (2H, m), 6.99 (2H, t, J=8.6 Hz), 4.35 (2H, t, J=7 Hz), 4.14 (2H, s), 3.65 (2H, m), 3.59 (2H, m), 3.50 (2H, t, J=7 Hz), 3.44 (2H, m), 3.42 (3H, s), 2.31 (2H, t, J=8 Hz), 1.97 (2H, m); ES$^+$ MS: 483 (M+H$^+$).

Sodium 7-[(4-fluorophenyl)methyl]-3-({[2-(methyloxy) ethyl]amino}carbonyl)-2-oxo-1-[2-(2-oxo-1-pyrrolidinyl) ethyl]-1,2-dihydro-1,5-naphthyridine-4-olate. A solution of 7-(4-Fluorobenzyl)-4-hydroxy-N-(2-methoxyethyl)-2-oxo-1-[2-(2-oxopyrrolidin-1-yl)ethyl]-1,2-dihydro-1,5-naphthyridine-3-carboxamide (693 mg, 1.436 mmol) in ethanol (20 mL) was treated with 1.009 M NaOH (1.423 mL, 1.436 mmol). The solution was evaporated in vacuo, triturated with Et$_2$O, filtered and dried under high vacuum to provide the product as a white solid: $^1$H NMR (d$^6$-DMSO) δ 10.65 (1H, s), 8.20 (1H, s), 7.73 (1H, s), 7.35 (2H, dd, J=5, 9 Hz), 7.11 (2H, t, J=9 Hz), 4.16 (2H, t, J=9 Hz), 4.02 (2H, s), 3.24-3.39 (8H, m), 3.25 (3H, s), 2.05 (2H, t, J~9 Hz), 1.69-1.79 (2H, m); ES$^-$ MS: 483 (M−H$^+$).

EXAMPLE 458

1-[2-(1,3-dioxo-1,3-dihydro-2H-isoindol-2-yl)ethyl]-7-[(4-fluorophenyl)methyl]-4-hydroxy-N-[2-(methyloxy)ethyl]-2-oxo-1,2-dihydro-1,5-naphthyridine-3-carboxamide This compound was prepared from ethyl 1-[2-(1,3-dioxo-1,3-dihydro-2H-isoindol-2-yl)ethyl]-7-[(4-fluorophenyl) methyl]-4-hydroxy-2-oxo-1,2-dihydro-1,5-naphthyridine-3-carboxylate employing methods similar to those described in Example 336 and was obtained as an orange solid: ES$^+$ MS: 545 (M+H$^+$).

EXAMPLE 459

1-(2-aminoethyl)-7-[(4-fluorophenyl)methyl]-4-hydroxy-N-[2-(methyloxy)ethyl]-2-oxo-1,2-dihydro-1,5-naphthyridine-3-carboxamide This compound was prepared from 1-[2-(1,3-dioxo-1,3-dihydro-2H-isoindol-2-yl)ethyl]-7-[(4-fluorophenyl)methyl]-4-hydroxy-N-[2-(methyloxy)ethyl]-2-oxo-1,2-dihydro-1,5-naphthyridine-3-carboxamide employing methods similar to those described in Example 348 and was obtained as an orange solid: ES$^+$ MS: 415 (M+H$^+$).

EXAMPLE 460

1-[2-(1,3-dioxo-1,3-dihydro-2H-isoindol-2-yl)ethyl]-7-[(4-fluorophenyl)methyl]-4-hydroxy-N-{3-[(1-methylethyl)oxy]propyl}-2-oxo-1,2-dihydro-1,5-naphthyridine-3-carboxamide This compound was prepared from ethyl 1-[2-(1,3-dioxo-1,3-dihydro-2H-isoindol-2-yl)ethyl]-7-[(4-fluorophenyl) methyl]-4-hydroxy-2-oxo-1,2-dihydro-1,5-naphthyridine-3-carboxylate employing methods similar to those described in Example 336 and was obtained as an off-white solid: ES$^+$ MS: 587 (M+H$^+$).

EXAMPLE 461

1-[2-(1,3-dioxo-1,3-dihydro-2H-isoindol-2-yl)ethyl]-7-[(4-fluorophenyl)methyl]-4-hydroxy-N-{2-[(1-methylethyl)oxy]ethyl}-2-oxo-1,2-dihydro-1,5-naphthyridine-3-carboxamide This compound was prepared from ethyl 1-[2-(1,3-dioxo-1,3-dihydro-2H-isoindol-2-yl)ethyl]-7-[(4-fluorophenyl) methyl]-4-hydroxy-2-oxo-1,2-dihydro-1,5-naphthyridine-3-carboxylate employing methods similar to those described in Example 336 and was obtained as an off-white solid: ES$^+$ MS: 573 (M+H$^+$).

EXAMPLE 462

Sodium 1-[2-(Dimethylamino)-2-oxoethyl]-7-(4-fluorobenzyl)-3-[(methylamino)carbonyl]-2-oxo-1,2-dihydro-1,5-naphthyridine-4-olate The compound in example 237 was treated in a similar manner to example 166 to give a white solid: $^1$H NMR (d$_6$-DMSO) δ 10.34 (1H, m), 8.15 (1H, s), 7.30 (1H, s), 7.25 (2H, m), 7.10 (2H, m), 4.92 (2H, s), 3.98 (2H, s), 3.07 (3H, s), 2.78 (3H, s), 2.70 (3H, d, J=5 Hz).

EXAMPLE 463

1-{2-[Acetyl(methyl)amino]ethyl}-7-[(4-fluorophenyl)methyl]-4-hydroxy-N-methyl-2-oxo-1,2-dihydro-1,5-naphthyridine-3-carboxamide This compound was prepared from ethyl 1-{2-[acetyl(methyl)amino]ethyl}-7-[(4-fluorophenyl)methyl]-4-hydroxy-2-oxo-1,2-dihydro-1,5-naphthyridine-3-carboxylate and methylamine in ethanol using methods similar to Example 574: step 2 to provide an off-white solid: $^1$H NMR (400 MHz, DMSO-d$_6$ (90° C.) δ ppm 1.80-1.87 (m, 3 H), 2.95 (d, J=4.94 Hz, 6 H), 3.53 (t, J=6.79 Hz, 2 H), 4.18 (s, 2 H), 4.36 (s, 2 H), 7.12 (t, J=8.44 Hz, 2 H), 7.35-7.40 (m, 2 H), 8.05 (s, 1 H), 8.54 (s, 1 H), 10.07 (s, 1 H), 17.05 (br. s., 1 H); ES$^+$ MS: 427 (M+H$^+$).

EXAMPLE 464

1-(2-aminoethyl)-7-[(4-fluorophenyl)methyl]-4-hydroxy-N-[1-(hydroxymethyl)-2-methylpropyl]-2-oxo-1,2-dihydro-1,5-naphthyridine-3-carboxamide This compound was prepared from ethyl 1-[2-(1,3-dioxo-1,3-dihydro-2H-isoindol-2-yl)ethyl]-7-[(4-fluorophenyl) methyl]-4-hydroxy-2-oxo-1,2-dihydro-1,5-naphthyridine-3-carboxylate employing methods similar to those described in Example 388 and was obtained as an off-white solid: ES$^+$ MS: 443 (M+H$^+$).

EXAMPLE 465

7-[(4-Fluorophenyl)methyl]-4-hydroxy-1-[2-(methylamino)-2-oxoethyl]-N-[2-(methyloxy)ethyl]-2-oxo-1,2-dihydro-1,5-naphthyridine-3-carboxamide This compound was prepared from ethyl 3-amino-5-[(4-fluorophenyl)methyl]-2-pyridinecarboxylate employing methods similar to those described in Example 11 Steps 1-4, using methylamine in Step 2 and subsequent formation of the carboxamide with 2-methoxyethylamine employing methods similar to those described in Example 2 using N,N-dimethylformamide as the reaction solvent. The product was obtained as an off-white solid: $^1$H NMR (d$_6$-DMSO) δ 10.61 (1H, br s), 8.21 (1H, s), 7.85-7.80 (1H, m), 7.35 (1H, s), 7.29-7.25 (2H, m), 7.12-7.08 (2H, m), 4.67 (2H, s), 4.00 (2H, s), 3.38 (3H, s), 3.31 (2H, s), 3.25 (3H, s), 2.52 (3H, d, J=4.5 Hz); HRMS calcd for C$_{22}$H$_{23}$FN$_4$O$_5$+H$^+$: 443.1731. Found 443.1729.

EXAMPLE 466

7-[(4-Fluorophenyl)methyl]-4-hydroxy-N-(4-hydroxybutyl)-1-[(1-methyl-1H-imidazol-2-yl)methyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CD$_3$OD/CDCl$_3$) δ 10.17 (s, 1 H), 8.43 (s, 1 H), 8.00 (s, 1 H), 7.14 (dd, J=8.5, 5.3 Hz, 2 H), 6.95 (t, J=8.7 Hz, 2 H), 6.89 (s, 1 H), 6.83 (s, 1 H), 5.53 (s, 2 H), 4.10 (s, 2 H), 3.67 (s, 3 H), 3.59 (t, J=6.2 Hz, 2 H), 3.46 (m, 2 H), 1.74-1.58 (m, 4 H); HRMS m/z calcd for C$_{25}$H$_{27}$N$_5$O$_4$F (M+H)$^+$ 480.2047, found 480.2040.

EXAMPLE 467

7-[(4-Fluorophenyl)methyl]-4-hydroxy-1-[(1-methyl-1H-imidazol-2-yl)methyl]-N-[2-(methyloxy)ethyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, DMSO-d$_6$) δ 10.26 (m, 1 H), 8.51 (s, 1 H), 8.10 (s, 1 H), 7.27 (dd, J=8.5, 5.6 Hz, 2 H), 7.08 (t, J=8.9 Hz, 2 H), 7.05 (s, 1 H), 6.66 (s, 1 H), 5.49 (s, 2 H), 4.07 (s, 2 H), 3.68 (s, 3 H), 3.53-3.46 (m, 4 H), 3.26 (s, 3 H); HRMS m/z calcd for C$_{24}$H$_{25}$N$_5$O$_4$F (M+H)$^+$ 466.1891, found 466.1885.

EXAMPLE 468

7-[(4-Fluorophenyl)methyl]-4-hydroxy-N-(2-hydroxyethyl)-1-[(1-methyl-1H-imidazol-2-yl)methyl]-2-oxo-1,2-dihydro-1,5-naphthyridine-3-carboxamide The title compound was prepared in a similar manner to that described in example 152 using excess amine and ethanol as solvent to provide a white solid as a formate salt. $^1$H NMR (400 MHz, DMSO-d$_6$/CD$_3$OD) δ 8.50 (s, 1 H), 8.25 (s, 1 H), 8.12 (s, 1 H), 7.27 (dd, J=8.7, 5.7 Hz, 2 H), 7.06 (t, J=9.0 Hz, 2 H), 7.03 (s, 1 H), 6.67 (s, 1 H), 5.49 (s, 2 H), 4.07 (s, 2 H), 3.69 (s, 3 H), 3.52 (t, J=5.3 Hz, 2 H), 3.40 (t, J=5.5 Hz, 2 H); HRMS m/z calcd for C$_{23}$H$_{23}$N$_5$O$_4$F (M+H)$^+$ 452.1734, found 452.1727.

EXAMPLE 469

7-[(4-Fluorophenyl)methyl]-4-hydroxy-N-methyl-1-[(1-methyl-1H-imidazol-2-yl)methyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, DMSO-d$_6$) δ 10.01 (m, 1 H), 8.51 (s, 1 H), 8.17 (s, 1 H), 7.28 (dd, J=8.6, 5.7 Hz, 2 H), 7.08 (t, J=8.8 Hz, 2 H), 7.04 (s, 1 H), 6.68 (s, 1 H), 5.49 (s, 2 H), 4.07 (s, 2 H), 3.68 (s, 3 H), 2.88 (d, J=4.9 Hz, 3 H); HRMS m/z calcd for C$_{22}$H$_{21}$N$_5$O$_3$F (M+H)$^+$ 422.1628, found 422.1622.

EXAMPLE 470

N-Cyclobutyl-1-[2-(cyclopropylamino)-2-oxoethyl]-7-[(4-fluorophenyl)methyl]-4-hydroxy-2-oxo-1,2-dihydro-1,5-naphthyridine-3-carboxamide Steps 1-3: Synthesis of ethyl 1-[2-(cyclopropylamino)-2-oxoethyl]-7-[(4-fluorophenyl)methyl]-4-hydroxy-2-oxo-1,2-dihydro-1,5-naphthyridine-3-carboxylate This compound was prepared from N-{2-[(ethyloxy)carbonyl]-5-[(4-fluorophenyl)methyl]-3-pyridinyl}glycine and cyclopropylamine employing methods similar to those described in Example 11, Steps 2-4. The product was obtained as a white solid: $^1$H NMR (d$_6$-DMSO) δ 8.47 (1H, s), 8.26 (1H, d, J=4 Hz), 7.65 (1H, s), 7.31 (2H, dd, J=8.4, 6 Hz), 7.11 (2H, t, J=9 Hz), 4.73 (2H, s), 4.22 (2H, q, J=7 Hz), 4.11 (2H, s), 2.56 (1H, m), 1.23 (3H, t, J=7 Hz), 0.59 (2H, m), 0.35 (2H, m); ES$^+$ MS: 440 (M+H$^+$, 100).

Step 4: Synthesis of N-cyclobutyl-1-[2-(cyclopropylamino)-2-oxoethyl]-7-[(4-fluorophenyl)methyl]-4-hydroxy-2-oxo-1,2-dihydro-1,5-naphthyridine-3-carboxamide This compound was prepared from ethyl 1-[2-(cyclopropylamino)-2-oxoethyl]-7-[(4-fluorophenyl)methyl]-4-hydroxy-2-oxo-1,2-dihydro-1,5-naphthyridine-3-carboxylate and cyclobutylamine by methods similar to those described in Example 245. The crude material was triturated with a mixture of MeOH and 1N HCl to afford the product as a white solid: $^1$H NMR (d$_6$-DMSO) δ 10.30 (1H, d, J=7 Hz), 8.54 (1H, s), 8.24 (1H, d, J=4 Hz), 7.74 (1H, s), 7.32 (2H, dd, J=8.4, 5.7 Hz), 7.11 (2H, t, J~9 Hz), 4.80 (2H, s), 4.40 (1H, m, J=8 Hz), 4.11 (2H, s), 2.56 (1H, m), 2.29 (2H, m), 2.03 (2H, m), 1.71 (2H, m), 0.59 (2H, m), 0.36 (2H, m); HRMS calcd for C$_{25}$H$_{25}$FN$_4$O$_4$+H$^+$: 465.1938. Found: 465.1934.

EXAMPLE 471

1-[2-(Cyclopropylamino)-2-oxoethyl]-7-[(4-fluorophenyl)methyl]-4-hydroxy-N-[2-(methyloxy)ethyl]-2-oxo-1,2-dihydro-1,5-naphthyridine-3-carboxamide This compound was prepared from ethyl 1-[2-(cyclopropylamino)-2-oxoethyl]-7-[(4-fluorophenyl)methyl]-4-hydroxy-2-oxo-1,2-dihydro-1,5-naphthyridine-3-carboxylate and 2-methoxyethylamine by methods similar to those described in Example 245. The crude material was triturated with a mixture of MeOH and 1N HCl to afford the product as a white solid: $^1$H NMR (d$_6$-DMSO) δ 10.22 (1H, br), 8.54 (1H, br s), 8.24 (1H, br s), 7.74 (1H, br s), 7.32 (2H, m), 7.11 (2H, m), 4.80 (2H, s), 4.11 (2H, s), 3.51 (4H, m), 3.27 (3H, s), 2.56 (1H, m), 0.59 (2H, m), 0.34 (2H, m); HRMS calcd for C$_{24}$H$_{25}$FN$_4$O$_5$+H$^+$: 469.1887. Found: 469.1882.

EXAMPLE 472

1-[2-(Cyclopropylamino)-2-oxoethyl]-7-[(4-fluorophenyl)methyl]-4-hydroxy-N-(2-hydroxyethyl)-2-oxo-1,2-dihydro-1,5-naphthyridine-3-carboxamide This compound was prepared from ethyl 1-[2-(cyclopropylamino)-2-oxoethyl]-7-[(4-fluorophenyl)methyl]-4-hydroxy-2-oxo-1,2-dihydro-1,5-naphthyridine-3-carboxylate and ethanolamine employing methods similar to those described in Example 245. The crude material was triturated with a mixture of MeOH and 1N HCl to afford the product as a white solid: $^1$H NMR (d$_6$-DMSO) δ 10.25 (1H, t, J=5 Hz), 8.54 (1H, s), 8.25 (1H, d, J=4 Hz), 7.74 (1H, s), 7.32 (2H, dd, J=8.5, 5.7 Hz), 7.11 (2H, t, J~9 Hz), 4.92 (1H, br m), 4.80 (2H, s), 4.11 (2H, s), 3.54 (2H, t, J=5 Hz), 3.42 (2H, q, J~5 Hz), 2.57 (1H, m), 0.59 (2H, m), 0.35 (2H, m); HRMS calcd for C$_{23}$H$_{23}$FN$_4$O$_5$+H$^+$: 455.1731. Found: 455.1728.

EXAMPLE 473

1-[2-(Cyclopropylamino)-2-oxoethyl]-7-[(4-fluorophenyl)methyl]-4-hydroxy-N-methyl-2-oxo-1,2-dihydro-1,5-naphthyridine-3-carboxamide This compound was prepared from ethyl 1-[2-(cyclopropylamino)-2-oxoethyl]-7-[(4-fluorophenyl)methyl]-4-hydroxy-2-oxo-1,2-dihydro-1,5-naphthyridine-3-carboxylate and methanolic methylamine employing methods similar to those described in Example 245. The crude material was triturated with a mixture of MeOH and 1N HCl to afford the product as a white solid: $^1$H NMR (d$_6$-DMSO) δ 9.99 (1H, d, J=5 Hz), 8.53 (1H, s), 8.23 (1H, d, J=4 Hz), 7.74 (1H, s), 7.32 (2H, dd, J=8.6, 5.7 Hz), 7.11 (2H, t, J~9 Hz), 4.79 (2H, s), 4.13 (2H, s), 2.88 (3H, d, J=5 Hz), 2.57 (1H, m), 0.59 (2H, m), 0.34 (2H, m); HRMS calcd for C$_{22}$H$_{21}$FN$_4$O$_4$+H$^+$: 425.1625. Found: 425.1623.

EXAMPLE 474

Sodium 1-(4-fluorophenyl)-7-[(4-fluorophenyl)methyl]-3-{[(2-hydroxyethyl)amino]carbonyl}-2-oxo-1,2-dihydro-1,5-naphthyridine-4-olate 1-(4-fluorophenyl)-7-[(4-fluorophenyl)methyl]-4-hydroxy-N-(2-hydroxyethyl)-2-oxo-1,2-dihydro-1,5-naphthyridine-3-carboxamide (311 mg, 0.690 mmol) described in example 200 was suspended in ethanol (10 mL) and 1 N sodium hydroxide was added (0.68 mL) and the resulting white suspension was stirred for 1 hour. The mixture was diluted with diethyl ether (50 mL) and the solid was collected by vacuum filtration to afford sodium 1-(4-fluorophenyl)-7-[(4-fluorophenyl)methyl]-3-{[(2-hydroxyethyl)amino]carbonyl}-2-oxo-1,2-dihydro-1,5-naphthyridine-4-olate (300 mg, 92% yield) as a white solid. $^1$H NMR (DMSO-d$_6$) δ 10.53 (br s, 1 H), 8.15 (s, 1 H), 7.31 (m, 2 H), 7.19 (m, 2 H), 7.11 (m, 2 H), 7.03 (m, 2 H), 6.48 (s, 1 H), 4.71 (br s, 1 H), 3.85 (s, 2 H), 3.41 (m, 2 H), 3.26 (m, 2 H); MS m/z 452 (M+1).

EXAMPLE 475

Phenylmethyl {2-[7-[(4-fluorophenyl)methyl]-4-hydroxy-3-{[(2-hydroxyethyl)amino]carbonyl}-2-oxo-1,5-naphthyridine-1(2H)-yl]ethyl}methylcarbamate—2-aminoethanol (1:1)

Step 1: Synthesis of phenylmethyl (2-hydroxyethyl)methylcarbamate

A solution of 2-methylaminoethanol (24.59 g, 327 mmol) and triethylamine (64 mL, 459 mmol) in CH$_2$Cl$_2$ (100 mL) under nitrogen was cooled in an ice/water bath and treated with phenylmethyl chloridocarbonate (50 mL, 350 mmol) over 1½ h. Let warm to ambient temperature after the addition was complete and stirred an additional 2 h. Poured the reaction into a separatory funnel and partitioned between 1N HCl (200 mL) and CH$_2$Cl$_2$ (200 mL). Back extracted the aqueous with CH$_2$Cl$_2$ (200 mL), washed the organics with water and brine, dried over MgSO$_4$, filtered, and evaporated in vacuo to provide the desired material as a clear viscous oil: $^1$H NMR (300 MHz, CHLOROFORM-d) δ ppm 2.34 (s, 1 H), 3.01 (s, 3 H), 3.47 (t, J=5.26 Hz, 2 H), 3.78 (s, 2 H), 5.14 (s, 2 H), 7.30-7.41 (m, 5 H); ES$^+$ MS: 232 (M+Na$^+$).

Step 2: Synthesis of phenylmethyl methyl(2-oxoethyl)carbamate

A solution of phenylmethyl (2-hydroxyethyl)methylcarbamate (2.02 g, 9.64 mmol) and Dess Martin's Reagent (6.36 g, 15.6 mmol) in CH$_2$Cl$_2$ (100 mL) were combined under nitrogen and stirred for 4 h at ambient temperature. Added CH$_2$Cl$_2$ (100 mL) and washed the organics with 2M Na$_2$CO$_3$ (aq.), saturated NaHCO$_3$, water, and brine, dried over Na$_2$SO$_4$, filtered and evaporated in vacuo. Purified the residue by flash chromatography using silica gel and a gradient between 0 and 10% MeOH in CH$_2$Cl$_2$ over 20 minutes to provide the desired material, after combining and concentrating pure fractions in vacuo, as a yellow viscous oil: $^1$H NMR (400 MHz, CHLOROFORM-d) δ ppm 3.03 (d, J=6.59 Hz, 3 H), 4.06 (s, 1 H), 4.13 (s, 1 H), 5.12-5.21 (m, 2 H), 7.29-7.40 (m, 5 H), 9.63 (d, J=16.28 Hz, 1 H); ES$^+$ MS: 230 (M+Na$^+$).

Step 3: Synthesis of ethyl 5-[(4-fluorophenyl)methyl]-3-{[2-(methyl{[(phenylmethyl)oxy]carbonyl}amino)ethyl]amino}-2-pyridinecarboxylate A solution of ethyl 3-amino-5-(4-fluorobenzyl)-2-pyridinecarboxylate (1.78 g, 6.5 mmol) and phenylmethyl methyl (2-oxoethyl)carbamate (2.58 g, 12.4 mmol) under nitrogen in glacial acetic acid (300 mL) was treated with sodium triacetoxyborohydride (2.56 g, 12.1 mmol) at ambient temperature overnight. Concentrated the reaction in vacuo then redissolved in glacial acetic acid (100 mL) and treated with another 1 g of sodium triacetoxyborohydride at ambient temperature for 2 h. The reaction was evaporated in vacuo and the residue was chromatographed on silica gel eluting with 98:2-95:5 CH$_2$Cl$_2$:EtOAc to provide a clear viscous oil. The oil was dissolved in CH$_2$Cl$_2$, washed with saturated K$_2$CO$_3$, water, and brine, dried over Na$_2$SO$_4$, filtered and evaporated in vacuo to afford the product as a yellow viscuos oil. $^1$H NMR (300 MHz, DMSO-d$_6$) δ ppm 1.27 (t, J=7.09 Hz, 3 H), 2.87 (d, J=5.90 Hz, 3 H), 3.34-3.51 (m, 4 H), 3.89 (d, J=20.22 Hz, 2 H), 4.24 (q, J=7.16 Hz, 2 H), 5.02 (d, J=23.16 Hz, 2 H), 7.09 (t, J=8.84 Hz, 2 H), 7.18-7.39 (m, 7 H), 7.66 (d, J=16.00 Hz, 1 H), 7.77 (s, 1 H); ES$^+$ MS: 466 (M+H$^+$).

Step 4: Synthesis of ethyl 3-{[3-(ethyloxy)-3-oxopropanoyl][2-(methyl{[(phenylmethyl)oxy]carbonyl}amino)ethyl]amino}-5-[(4-fluorophenyl)methyl]-2-pyridinecarboxylate A solution of ethyl 5-[(4-fluorophenyl)methyl]-3-{[2-(methyl {[(phenylmethyl)oxy]carbonyl}amino)ethyl]amino}-2-pyridinecarboxylate (1.62 g, 3.5 mmol) and ethyl malonyl chloride (1.24 mL, 8.7 mmol) in DCE (50 mL) was heated under nitrogen at reflux for 2 hrs. An additional 0.5 mL of the ethyl malonyl chloride was added and the reaction was stirred at reflux an additional ½ hour. The mixture was cooled, treated with EtOH (25 mL), and then concentrated in vacuo. The residue was purified on silica gel eluting with a gradient between 0 and 100% EtOAc in CH$_2$Cl$_2$ to provide after combination and concentration in vacuo of pure fractions the product as an yellow viscous oil: $^1$H NMR (400 MHz, DMSO-d$_6$@90° C.) δ ppm 1.11 (t, J=6.77 Hz, 2 H), 1.28 (t, J=7.14 Hz, 3 H), 2.82 (s, 3 H), 3.03 (s, 3 H), 3.34-3.43 (m, 2 H), 3.96 (d, J=5.85 Hz, 2 H), 4.02-4.07 (m, 4 H), 4.27-4.35 (m, 2 H), 5.02 (s, 2H), 7.08 (t, J=8.87 Hz, 2 H), 7.23-7.34 (m, 7 H), 7.70 (s, 1 H), 8.59 (s, 1 H); ES$^+$ MS: 580 (M+H$^+$).

Step 5: Synthesis of ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate A solution of ethyl 3-{[3-(ethyloxy)-3-oxopropanoyl][2-(methyl {[(phenylmethyl)oxy]carbonyl}amino)ethyl]amino}-5-[(4-fluorophenyl)methyl]-2-pyridinecarboxylate (1.32 g, 2.3 mmol) in EtOH (25 mL) under nitrogen was treated with DBU (0.54 mL, 3.55 mmol). After stirring at ambient temperature for 5 min., the reaction mixture was treated with 1N NaHSO$_4$ (3.6 mL). The resulting slurry was diluted with water, filtered, the filtered solid was washed with 1:1 water:EtOH, and Et$_2$O and thoroughly dried under high vacuum to provide the title compound as a white solid: $^1$H NMR (400 MHz, DMSO-d$_6$) δ ppm 1.25 (q, J=6.96 Hz, 3 H), 2.84 (d, J=15.02 Hz, 3 H), 3.42-3.50 (m, 1 H), 3.54 (t, J=4.94 Hz, 1 H), 4.03 (s, 1 H), 4.14 (s, 1 H), 4.19-4.27 (m, 2 H), 4.32-4.38 (m, 2 H), 4.72 (s, 1 H), 4.93 (s, 1 H), 7.00 (d, J=4.21 Hz, 1 H), 7.10 (t, J=8.79 Hz, 2 H), 7.19-7.30 (m, 4 H), 7.30-7.39 (m, 2 H), 8.04 (s, 1 H), 8.41 (s, 1 H), 8.49 (s, 1 H); ES$^+$ MS: 534 (M+H$^+$).

Step 6: Synthesis of phenylmethyl {2-[7-[(4-fluorophenyl)methyl]-4-hydroxy-3-{[(2-hydroxyethyl)amino]carbonyl}-2-oxo-1,5-naphthyridine-1(2H)-yl]ethyl}methylcarbamate -2-aminoethanol (1:1)

A solution of ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate (0.022 g, 0.041 mmol) in EtOH (3 mL) under nitrogen was treated with Ethoxyethylamine (0.012 mL, 0.20 mmol) for 15 min.@150° C. in a microwave vessel then@150° C. for an additional 1 h. After the reaction was cooled to ambient temperature the resulting suspension was filtered, and the filtered solid was washed with EtOH and Et$_2$O then thoroughly dried under high vacuum to provide the title compound as a white solid: $^1$H NMR (400 MHz, DMSO-d$_6$ (90° C.) δ ppm 2.62 (t, J=5.67 Hz, 2 H), 2.87 (s, 3 H), 3.38 (t, J=7.14 Hz, 2 H), 3.43-3.49 (m, 2 H), 3.55 (t, J=5.95 Hz, 2 H), 3.60 (s, 3 H), 4.07-4.15 (m, 3 H), 4.41 (t, J=5.67 Hz, 3 H), 4.64 (s, 1 H), 4.87 (s, 2 H), 7.08 (t, J=8.97 Hz, 2 H), 7.16 (s, 2 H), 7.28 (d, J=2.20 Hz, 2 H), 7.29-7.34 (m, 3 H), 7.87 (s, 1 H), 8.48 (s, 1 H), 10.30 (s, 1 H); ES$^+$ MS: 549 (M+H$^+$).

EXAMPLE 476

1-{2-[[(Dimethylamino)carbonyl](methyl)amino]ethyl}-7-[(4-fluorophenyl)methyl]-4-hydroxy-N-(2-hydroxyethyl)-2-oxo-1,2-dihydro-1,5-naphthyridine-3-carboxamide Step 1: Synthesis of ethyl 1-{2-[[(dimethylamino)carbonyl](methyl)amino]ethyl}-7-[(4-fluorophenyl)methyl]-4-hydroxy-2-oxo-1,2-dihydro-1,5-naphthyridine-3-carboxylate A solution of ethyl 7-[(4-fluorophenyl)methyl]-4-hydroxy-1-[2-(methyl {[(phenylmethyl)oxy]carbonyl}amino)ethyl]-2-oxo-1,2-dihydro-1,5-naphthyridine-3-carboxylate (0.255 g, 0.48 mmol) in CH$_2$Cl$_2$ (20 mL) was combined with diisopropylethylamine (0.42 mL, 2.4 mmol), dimethylcarbamic chloride (0.22 mL, 2.4 mmol) and Pd/C (0.030 g, 10% w/w). The resulting suspension was flushed with nitrogen and evacuated several times the charged with hydrogen under a balloon and stirred at ambient temperature overnight. The reaction mixture was filtered, washed with CH$_2$Cl$_2$, and concentrated in vacuo. The residue was washed with EtOAc: Hexanes 1:1, filtered and the filtrate was concentrated in vacuo. The residue was triturated with water and the resulting suspension was filtered to afford the title compound as an off-white crystalline solid: $^1$H NMR (300 MHz, DMSO-d$_6$) δ ppm 1.25 (t, J=7.05 Hz, 3 H), 2.59 (s, 6 H), 2.80 (s, 3 H), 3.26-3.30 (m, 2 H), 4.17 (s, 2 H), 4.23 (q, J=7.16 Hz, 2 H), 4.32 (t, J=6.21 Hz, 2 H), 7.11-7.18 (m, 2 H), 7.38-7.43 (m, 2 H), 8.11 (s, 1 H), 8.50 (d, J=1.47 Hz, 1 H); ES$^+$ MS: 471 (M+H$^+$).

Step 2: Synthesis of 1-{2-[[(dimethylamino)carbonyl](methyl)amino]ethyl}-7-[(4-fluorophenyl)methyl]-4-hydroxy-N-(2-hydroxyethyl)-2-oxo-1,2-dihydro-1,5-naphthyridine-3-carboxamide This compound was prepared from ethyl 1-{2-[acetyl(methyl)amino]ethyl}-7-[(4-fluorophenyl)methyl]-4-hydroxy-2-oxo-1,2-dihydro-1,5-naphthyridine-3-carboxylate and methylamine in ethanol using methods similar to Example 574: step 2 to provide an off-white solid: $^1$H NMR (400 MHz, DMSO-d$_6$@90° C.) δ ppm 2.61-2.64 (m, 6 H), 2.81 (s, 3 H), 3.35 (dd, J=7.07, 6.52 Hz, 2 H), 3.48 (q, J=5.53 Hz, 2 H), 3.61 (q, J=5.31 Hz, 2 H), 4.18 (s, 2 H), 4.35-4.42 (m, 2 H), 4.64 (t, J=4.67 Hz, 1 H), 7.12 (ddd, J=8.99, 6.66, 2.20 Hz, 2 H), 7.36-7.41 (m, 2 H), 8.03-8.07 (m, 1 H), 8.54 (d, J=1.65 Hz, 1 H), 10.32 (s, 1 H); ES$^+$ MS: 486 (M+H$^+$).

EXAMPLE 477

1-[3-(2,5-dioxo-1-pyrrolidinyl)propyl]-7-[(4-fluorophenyl)methyl]-4-hydroxy-N-(2-hydroxyethyl)-2-oxo-1,2-dihydro-1,5-naphthyridine-3-carboxamide This compound was prepared from ethyl1-[3-(2,5-dioxo-1-pyrrolidinyl)propyl]-7-[(4-fluorophenyl)methyl]-4-hydroxy-2-oxo-1,2-dihydro-1,5-naphthyridine-3-carboxylate and ethanolamine employing methods similar to those described in Example 202 and was obtained as a white solid. $^1$H NMR (400 MHz, CDCl$_3$) δ 10.36 (t, J=5.3 Hz, 1 H), 8.55 (d, J=1.2 Hz, 1 H), 7.34 (s, 1 H), 7.19 (dd, J=8.5, 5.4 Hz, 2 H), 7.04 (t, J=8.5 Hz, 2 H), 4.17-4.13 (m, 4 H), 3.85 (t, J=5.0 Hz, 2 H), 3.63 (m, 2 H), 3.56 (t, J=7.1 Hz, 2 H), 2.72 (s, 4 H), 1.92 (m, 2 H); HRMS C$_{25}$H$_{25}$FN$_4$O$_6$ (M+H)$^+$ calcd 497.1758, found 497.1832.

EXAMPLE 478 phenylmethyl {2-[7-[(4-fluorophenyl)methyl]-4-hydroxy-2-oxo-3-[(propylamino)carbonyl]-1,5-naphthyridine-1(2H)-yl]ethyl}methylcarbamate—1-propanamine (1:1)

This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as a white solid: ES$^+$ MS: 547 (M+H$^+$).

EXAMPLE 479 phenylmethyl {2-[7-[(4-fluorophenyl)methyl]-4-hydroxy-3-[(methylamino)carbonyl]-2-oxo-1,5-naphthyridine-1(2H)-yl]ethyl}methylcarbamate-methanamine(1:1)

This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as a white solid: ES+ MS: 519 (M+H+).

EXAMPLE 480

1-Butyl-7-[(4-fluorophenyl)methyl]-4-hydroxy-N-[(2R)-2-hydroxypropyl]-2-oxo-1,2-dihydro-1,5-naphthyridine-3-carboxamide In a similar manner to that described in example 196, from ethyl 1-butyl-7-[(4-fluorophenyl)methyl]-4-hydroxy-2-oxo-1,2-dihydro-1,5-naphthyridine-3-carboxylate (30 mg, 0.075 mmol) and (2R)-1-amino-2-propanol (0.05 mL) was prepared 1-butyl-7-[(4-fluorophenyl)methyl]-4-hydroxy-N-[(2R)-2-hydroxypropyl]-2-oxo-1,2-dihydro-1,5-naphthyridine-3-carboxamide (20 mg, 63% yield) as a white solid after purification by reverse phase HPLC. $^1$H NMR (CDCl$_3$) δ 10.48 (br s, 1 H), 8.56 (s, 1 H), 7.27 (s, 1 H), 7.19-7.15 (m, 2 H), 7.06-7.02 (m, 2 H), 4.14 (s, 2 H), 4.10-4.06 (m, 3 H), 3.61 (m, 1 H), 3.66 (m, 1 H), 1.52 (m, 2 H), 1.34 (m, 2 H), 1.27 (d, J=6.4 Hz, 3 H), 0.91 (m, 3 H); MS m/z 428 (M+1).

EXAMPLE 481

1-Butyl-7-[(4-fluorophenyl)methyl]-4-hydroxy-N-[2S)-2-hydroxypropyl]-2-oxo-1,2-dihydro-1,5-naphthyridine-3-carboxamide In a similar manner to that described in example 196, from ethyl 1-butyl-7-[(4-fluorophenyl)methyl]-4-hydroxy-2-oxo-1,2-dihydro-1,5-naphthyridine-3-carboxylate (30 mg, 0.075 mmol) and (2S)-1-amino-2-propanol (0.05 mL) was prepared 1-butyl-7-[(4-fluorophenyl)methyl]-4-hydroxy-N-[(2S)-2-hydroxypropyl]-2-oxo-1,2-dihydro-1,5-naphthyridine-3-carboxamide (20 mg, 63% yield) as a white solid after purification by reverse phase HPLC. $^1$H NMR (CDCl$_3$) δ 10.45 (br s, 1 H), 8.53 (s, 1 H), 7.25 (s, 1 H), 7.17-7.13 (m, 2 H), 7.05-7.00 (m, 2 H), 4.12 (s, 2 H), 4.09-4.04 (m, 3 H), 3.59 (m, 1 H), 3.35 (m, 1 H), 1.49 (m, 2 H), 1.32 (m, 2 H), 1.25 (d, J=6.4 Hz, 3 H), 0.89 (m, 3 H); MS m/z 428 (M+1).

EXAMPLE 482 phenylmethyl {2-[7-[(4-fluorophenyl)methyl]-4-hydroxy-3-{[(2-methylpropyl)amino]carbonyl}-2-oxo-1,5-naphthyridine-1(2H)-yl]ethyl}methylcarbamate This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as a tan solid: ES+ MS: 561 (M+H+).

EXAMPLE 483 phenylmethyl {2-[3-[(ethylamino)carbonyl]-7-[(4-fluorophenyl)methyl]-4-hydroxy-2-oxo-1,5-naphthyridine-1(2H)-yl]ethyl}methylcarbamate—ethanamine (1:1)

This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as a white solid: ES− MS: 533 (M+H+).

EXAMPLE 484

N-[2-(acetylamino)ethyl]-1-butyl-7-[(4-fluorophenyl)methyl]-4-hydroxy-2-oxo-1,2-dihydro-1,5-naphthyridine-3-carboxamide In a similar manner to that described in example 196, from ethyl 1-butyl-7-[(4-fluorophenyl)methyl]-4-hydroxy-2-oxo-1,2-dihydro-1,5-naphthyridine-3-carboxylate (30 mg, 0.075 mmol) and N-(2-aminoethyl)acetamide (27 mg, 0.264 mmol) was prepared N-[2-(acetylamino)ethyl]-1-butyl-7-[(4fluorophenyl)methyl]-4-hydroxy-2-oxo-1,2-dihydro-1,5-naphthyridine-3-carboxamide (20 mg, 59% yield) as a white solid after purification by reverse phase HPLC. $^1$H NMR (CDCl$_3$) δ 10.41 (br s, 1 H), 8.55 (s, 1 H), 7.27 (s, 1 H), 8.17-7.13 (m, 2 H), 7.05-7.01 (m, 2 H), 6.18 (br s, 1 H), 4.13 (s, 2 H), 4.06 (m, 2 H), 3.59 (m, 2 H), 3.47 (m, 2 H), 1.97 (s, 3 H), 1.52 (m, 2 H), 1.33 (m, 2 H), 0.90 (m, 3 H); MS m/z 455 (M+1).

EXAMPLE 485

1-butyl-7-[(4-fluorophenyl)methyl]-4-hydroxy-N-{2-[methyl(methylsulfonyl)amino]ethyl}-2-oxo-1,2-dihydro-1,5-naphthyridine-3-carboxamide In a similar manner to that described in example 196, from ethyl 1-butyl-7-[(4-fluorophenyl)methyl]-4-hydroxy-2-oxo-1,2-dihydro-1,5-naphthyridine-3-carboxylate (30 mg, 0.075 mmol) and N-(2-aminoethyl)-N-methylmethanesulfonamide (excess) was prepared 1-butyl-7-[(4-fluorophenyl)methyl]-4-hydroxy-N-{2-[methyl(methylsulfonyl)amino]ethyl}-2-oxo-1,2-dihydro-1,5-naphthyridine-3-carboxamide (21 mg, 55% yield) as a white solid after purification by reverse phase HPLC. $^1$H NMR (CDCl$_3$) δ 10.41 (br s, 1 H), 8.55 (s, 1 H), 7.27 (s, 1 H), 7.17-7.13 (m, 2 H), 7.05-7.00 (m, 2 H), 4.13 (s, 2 H), 4.08 (m, 2 H), 3.65 (m, 2 H), 3.39 (m, 2 H), 2.94 (s, 3 H), 2.82(s, 3 H), 1.50 (m, 2 H), 1.33 (m, 2 H), 0.89 (m, 3 H); MS m/z 505 (M+1).

EXAMPLE 486

1-butyl-7-[(4-fluorophenyl)methyl]-4-hydroxy-N-(3-hydroxy-2,2-dimethylpropyl)-2-oxo-1,2-dihydro-1,5-naphthyridine-3-carboxamide In a similar manner to that described in example 196, from ethyl 1-butyl-7-[(4-fluorophenyl)methyl]-4-hydroxy-2-oxo-1,2-dihydro-1,5-naphthyridine-3-carboxylate (30 mg, 0.075 mmol) and 3-amino-2,2-dimethyl-1-propanol (0.05 mL) was prepared 1-butyl-7-[(4-fluorophenyl)methyl]-4-hydroxy-N-(3-hydroxy-2,2-dimethylpropyl)-2-oxo-1,2-dihydro-1,5-naphthyridine-3-carboxamide (18 mg, 53% yield) as a white solid after purification by reverse phase HPLC. $^1$H NMR (CDCl$_3$) δ 10.51 (br s, 1 H), 8.56 (s, 1 H), 7.27 (s, 1 H), 7.17-7.13 (m, 2 H), 7.05-7.01 (m, 2 H), 4.14 (s, 2 H), 4.08 (m, 2 H), 3.39 (m, 1 H), 3.30 (m, 2 H), 3.22 (m, 2 H), 1.51 (m, 2 H), 1.33 (m, 2 H), 0.94 (s, 6 H), 0.90 (m, 3 H); MS m/z 456 M+1).

EXAMPLE 487 phenylmethyl {2-[3-({[2-(ethyloxy)ethyl]amino}carbonyl)-7-[(4-fluorophenyl)methyl]-4-hydroxy-2-oxo-1,5-naphthyridine-1(2H)-yl]ethyl}methylcarbamate This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as a tan solid: ES$^+$ MS: 577 (M+H$^+$).

EXAMPLE 488 phenylmethyl {2-[7-[(4-fluorophenyl)methyl]-4-hydroxy-3-({[1-methyl-2-(methyloxy)ethyl]amino}carbonyl)-2-oxo-1,5-naphthyridine-1(2H-yl]ethyl}methylcarbamate This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as a tan solid: ES$^+$ MS: 577 (M+H$^+$).

EXAMPLE 489 phenylmethyl {2-[7-[(4-fluorophenyl)methyl]-4-hydroxy-3-({[3-(1H-imidazol-1-yl)propyl]amino}carbonyl)-2-oxo-1,5-naphthyridine-1(2H)-yl]ethylmethyl}carbamate This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as a tan solid: ES$^+$ MS: 613 (M+H$^+$).

EXAMPLE 490

Sodium 1-[2-(dimethylamino)-2-oxoethyl]-7-[(4-fluorophenyl)methyl]-3-{[(3-hydroxypropyl)amino]carbonyl}-2-oxo-1,2-dihydro-1,5-naphthyridine-4-olate This compound was prepared from ethyl 1-[2-(dimethylamino)-2-oxoethyl]-7-[(4-fluorophenyl)methyl]-4-hydroxy-2-oxo-1,2-dihydro-1,5-naphthyridine-3-carboxylate and 3-amino-1-propanol employing methods similar to those described in Example 245. The resulting material was triturated with water, covered with EtOH and treated with 1 equivalent of 1N NaOH solution. Concentration in vacuo afforded the product as a white solid: $^1$H NMR (d$_6$-DMSO) δ 10.53 (1H, br), 8.14 (1H, s), 7.25 (3H, m), 7.10 (2H, t, J=9 Hz), 4.92 (2H, s), 4.49 (1H, br), 3.98 (2H, s), 3.43 (2H, m), 3.25 (2H, m), 3.07 (3H, s), 2.78 (3H, s), 1.58 (2H, m, J=6 Hz); AP$^+$ MS: 457 (M+H$^+$, 100).

EXAMPLE 491

7-[(4-Fluorophenyl)methyl]-4-hydroxy-N-(3-hydroxypropyl)-1-[(1-methyl-1H-imidazol-2-yl)methyl]-2-oxo-1,2-dihydro-1,5-naphthyridine-3-carboxamide The title compound was prepared in a similar manner to that described in example 152 using excess amine and ethanol as solvent to provide a white solid. $^1$H NMR (400 MHz, CD$_3$OD) δ 10.19 (s, 1 H), 8.42 (s, 1 H), 8.04 (s, 1 H), 7.11 (m, 2 H), 6.92 (m, 2 H), 6.82 (s, 2 H), 5.50 (s, 2 H), 4.07 (s, 2 H), 3.63 (s, 3 H), 3.63 (m, 2 H), 3.52 (m, 2 H), 1.82 (m, 2 H); HRMS m/z calcd for C$_{24}$H$_{25}$N$_5$O$_4$F (M+H)$^+$ 466.1897, found 466.1896.

EXAMPLE 492 phenylmethyl {2-[7-[(4-fluorophenyl)methyl]-4-hydroxy-3-({[2-(4-morpholinyl)ethyl]amino}carbonyl)-2-oxo-1,5-naphthyridine-1(2H)-yl]ethyl}methylcarbamate hydrochloride This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as an orange solid: ES$^+$ MS: 618 (M+H$^+$).

EXAMPLE 493 phenylmethyl {2-[7-[(4-fluorophenyl)methyl]-4-hydroxy-3-({[3-(4-morpholinyl)propyl]amino}carbonyl)-2-oxo-1,5-naphthyridin-1(2H)-yl]ethyl}methylcarbamate hydrochloride This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as an orange solid: ES$^+$ MS: 632 (M+H$^+$).

EXAMPLE 494

1-[2-(acetylamino)ethyl]-7-[(4-fluorophenyl)methyl]-4-hydroxy-N-(2-hydroxy-1-methylethyl)-2-oxo-1,2-dihydro-1,5-naphthyridine-3-carboxamide Step 1: Synthesis of 1-(2-aminoethyl)-7-[(4-fluorophenyl)methyl]-4-hydroxy-N-(2-hydroxy-1-methylethyl)-2-oxo-1,2-dihydro-1,5-naphthyridine-3-carboxamide This compound was prepared from 1-[2-(1,3-dioxo-1,3-dihydro-2H-isoindol-2-yl)ethyl]-7-[(4-fluorophenyl)methyl]-4-hydroxy-N-(2-hydroxy-1-methylethyl)-2-oxo-1,2-dihydro-1,5-naphthyridine-3-carboxamide employing methods similar to those described in Example 334 and was obtained as an off-white solid: $^1$H NMR (400 MHz, DMSO-d$_6$) δ ppm 1.18 (d, J=6.78 Hz, 3 H), 2.77 (t, J=6.87 Hz, 2 H), 3.42-3.49 (m, 2 H), 3.99-4.09 (m, 2 H), 4.15 (s, 2 H), 4.20 (t, J=6.96 Hz, 2 H), 5.00 (t, J=4.85 Hz, 1 H), 7.09-7.17 (m, 2 H), 7.39 (dd, J=8.61, 5.68 Hz, 2 H), 8.13 (s, 1 H), 8.49 (s, 1 H), 10.41 (d, J=7.69 Hz, 1 H); ES$^+$ MS: 415 (M+H$^+$).

Step 2: Synthesis of 1-[2-(acetylamino)ethyl]-7-[(4-fluorophenyl)methyl]-4-hydroxy-N-(2-hydroxy-1-methylethyl)-2-oxo-1,2-dihydro-1,5-naphthyridine-3-carboxamide This compound was prepared from 1-(2-aminoethyl)-7-[(4-fluorophenyl)methyl]-4-hydroxy-N-(2-hydroxy-1-methylethyl)-2-oxo-1,2-dihydro-1,5-naphthyridine-3-carboxamide employing methods similar to those described in Example 338 and was obtained as an off-white solid: $^1$H NMR (400 MHz, DMSO-$d_6$) δ ppm 1.19 (d, J=6.59 Hz, 3 H), 1.67 (s, 3 H), 3.26-3.31 (m, 2 H), 3.48 (t, J=5.04 Hz, 2 H), 4.01-4.11 (m, 1 H), 4.14 (s, 2 H), 4.25 (t, J=6.68 Hz, 2 H), 5.01 (t, J=5.22 Hz, 1 H), 7.11-7.17 (m, 2 H), 7.38-7.44 (m, 2 H), 8.04 (t, J=5.86 Hz, 1 H), 8.20 (d, J=1.10 Hz, 1 H), 8.56 (d, J=1.46 Hz, 1 H), 10.37 (d, J=7.87 Hz, 1 H); ES$^+$ MS: 457 (M+H$^+$).

EXAMPLE 495

1-[2-(acetylamino)ethyl]-7-[(4-fluorophenyl)methyl]-4-hydroxy-N-[2-(methyloxy)ethyl]-2-oxo-1,2-dihydro-1,5-naphthyridine-3-carboxamide This compound was prepared from 1-(2-aminoethyl)-7-[(4-fluorophenyl)methyl]-4-hydroxy-N-[2-(methyloxy)ethyl]-2-oxo-1,2-dihydro-1,5-naphthyridine-3-carboxamide employing methods similar to those described in Example 456 and was obtained as a tan solid: $^1$H NMR (400 MHz, DMSO-$d_6$) δ ppm 1.67 (s, 3 H), 3.27-3.32 (m, 5 H), 3.49-3.58 (m, 4 H), 4.14 (s, 2 H), 4.26 (t, J=6.50 Hz, 2 H), 7.08-7.17 (m, 2 H), 7.41 (dd, J=8.61, 5.68 Hz, 2 H), 8.04 (t, J=5.95 Hz, 1 H), 8.20 (s, 1 H), 8.56 (d, J=1.28 Hz, 1 H), 10.38 (t, J=5.22 Hz, 1 H), 17.08 (s, 1 H); ES$^+$ MS: 457 (M+H$^+$).

EXAMPLE 496

1-[2-(acetylamino)ethyl]-7-[(4-fluorophenyl)methyl]-4-hydroxy-N-{3-[(1-methylethyl)oxy]propyl}-2-oxo-1,2-dihydro-1,5-naphthyridine-3-carboxamide Step 1: Synthesis of 1-(2-aminoethyl)-7-[(4-fluorophenyl)methyl]-4-hydroxy-N-{3-[(1-methylethyl)oxy]propyl}-2-oxo-1,2-dihydro-1,5-naphthyridine-3-carboxamide This compound was prepared from 1-[2-(1,3-dioxo-1,3-dihydro-2H-isoindol-2-yl)ethyl]-7-[(4-fluorophenyl)methyl]-4-hydroxy-N-{3-[(1-methylethyl)oxy]propyl}-2-oxo-1,2-dihydro-1,5-naphthyridine-3-carboxamide employing methods similar to those described in Example 334 and was obtained as a tan solid: ES$^+$ MS: 457 (M+H$^+$).

Step 2: Synthesis of 1-[2-(acetylamino)ethyl]-7-[(4-fluorophenyl)methyl]-4-hydroxy-N-{3-[(1-methylethyl)oxy]propyl}-2-oxo-1,2-dihydro-1,5-naphthyridine-3-carboxamide This compound was prepared from 1-(2-aminoethyl)-7-[(4-fluorophenyl)methyl]-4-hydroxy-N-{3-[(1-methylethyl)oxy]propyl}-2-oxo-1,2-dihydro-1,5-naphthyridine-3-carboxamide employing methods similar to those described in Example 338 and was obtained as an off-white solid: ES$^+$ MS: 499 (M+H$^+$).

EXAMPLE 497

Phenylmethyl {3-[7-[(4-fluorophenyl)methyl]-4-hydroxy-3-{[(2-hydroxyethyl)amino]carbonyl}-2-oxo-1,5-naphthyridine-1(2H)-yl]propyl}methylcarbamate Phenylmethyl [3,3-bis(ethyloxy)propyl]methylcarbamate. A solution of phenylmethyl [3,3-bis(ethyloxy)propyl]carbamate (4.17 g, 14.8 mmol, J. Med. Chem. 1998 41, 3919-3922) in anhydrous DMF (15 mL) under nitrogen at ambient temperature was treated LiHMDS (1.0 M in THF, 17.8 mL, 17.8 mmol). After stirring 5 min., methyl iodide (1.11 mL, 17.8 mmol) was added. After stirring an additional 15 min., the reaction mixture was quenched by addition of saturated brine, water and Et$_2$O. After separation of the phases, the aqueous layer was back-extracted with Et$_2$O. The combined organic phases were washed with brine, dried over anhydrous MgSO$_4$, filtered, evaporated in vacuo and purified on silica gel eluting with 25% EtOAc in Hexanes to provide the product as an oil: $^1$H NMR (CDCl$_3$) δ 7.28-7.38 (5H, m), 5.12 (2H, s), 4.45-4.56 (1H, m), 3.29-3.68 (6H, m), 2.92 (3H, s), 1.81-1.90 (2H, m), 1.11-1.23 (6H, m); ES$^+$ MS: 318 (M+Na$^+$).

Phenylmethyl methyl(3-oxopropyl)carbamate. A mixture of phenylmethyl [3,3-bis(ethyloxy)propyl]methylcarbamate (2.982 g, 10.1 mmol) and TFA (15 mL) was stirred at ambient temperature for 30 min. The reaction was evaporated in vacuo and the residue was purified on silica gel eluting with 30% EtOAc in hexanes to provide the product as an oil: $^1$H NMR (d$^6$-DMSO) δ 9.63 (1H, s), 7.26-7.36 (5H, m), 5.02 (2H, b), 3.48 (2H, b), 2.75-2.85 (3H, m), 2.64 (2H, b); ES$^+$ MS: 244 (M+Na$^+$).

Ethyl 5-[(4-fluorophenyl)methyl]-3-{[3-(methyl{[(phenylmethyl)oxy]carbonyl}amino)propyl]amino}-2-pyridinecarboxylate. A mixture of ethyl 3-amino-5-(4-fluorobenzyl)-2-pyridinecarboxylate (1.21 g, 4.10 mmol) and phenylmethyl methyl(3-oxopropyl)carbamate (1.63 g, 7.39 mmol) in glacial acetic acid (15 mL) was treated with sodium trisacetoxyborohydride (1.74 g, 8.21 mmol) and stirred under nitrogen at ambient temperature. After approximately 1 hour, additional sodium triacetoxyborohydride (1.00 g, 4.72 mmol) was added. After an additional 3-4 hours, additional phenylmethyl methyl(3-oxopropyl)carbamate (1.00 g, 4.52 mmol) and sodium triacetoxyborohydride (1.00 g, 4.72 mmol) was added. The reaction mixture was evaporated in vacuo and the residue was dissolved in CH$_2$Cl$_2$ and treated with 2N KOH. After separating the layers, the aqueous phase was back-extracted with CH$_2$Cl$_2$ and the combined organic layers were washed with water, dried over MgSO$_4$, filtered, evaporated in vacuo and purified on silica eluting with 3% MeOH in CH$_2$Cl$_2$ to provide the product as an oil: $^1$H NMR (CDCl$_3$) δ 7.88 (1H, s), 7.77 (1H, s), 7.26-7.37 (5H, m), 7.11 (2H, b), 6.97 (2H, t, J=8.8), 6.74 (1H, d, J=31 Hz), 5.12 (2H, s), 4.42 (2H, q, J=7 Hz), 3.90 (2H, s), 3.41 (2H, t, J=7), 3.06-3.20 (2H, m), 2.92 (3H, s), 1.86 (2H, b), 1.42 (3H, t, J=7 Hz); ES$^+$ MS: 480 (M+H$^+$).

Ethyl 7-[(4-fluorophenyl)methyl]-4-hydroxy-1-[3-(methyl{[(phenylmethyl)oxy]carbonyl}amino)propyl]-2-oxo-1,2-dihydro-1,5-naphthyridine-3-carboxylate. This compound was prepared in two steps from ethyl 5-[(4-fluorophenyl)methyl]-3-{[3-(methyl{[(phenylmethyl)oxy]carbonyl}amino)propyl]amino}-2-pyridinecarboxylate and ethyl 3-chloro-3-oxopropionate employing methods similar to those described in Example 457, Steps 3-4. The product was obtained as a white solid: $^1$H NMR (d$^6$-DMSO, 80° C.) δ 8.65 (1H, b), 7.73 (1H, b), 7.23-7.39 (7H, m), 7.10 (2H, t, J=7

Hz), 5.05 (2H, s), 3.90-4.12 (4H, m), 3.40 (2H, q, J=7 Hz), 3.32 (2H, b), 2.85 (3H, s), 1.74 (2H, b), 1.09 (3H, t, J=7 Hz); ES+ MS: 470 (M+Na+).

Phenylmethyl {3-[7-[(4-fluorophenyl)methyl]-4-hydroxy-3-{[(2-hydroxyethyl)amino]carbonyl}-2-oxo-1,5-naphthyridine-1(2H)-yl]propyl}methylcarbamate. A mixture of ethyl 7-[(4-fluorophenyl)methyl]-4-hydroxy-1-[3-(methyl{[(phenylmethyl)oxy]carbonyl}amino)propyl]-2-oxo-1,2-dihydro-1,5-naphthyridine-3-carboxylate (20 mg, 0.036 mmol) and 2-aminoethanol (13 µL, 0.22 mmol) were combined in EtOH (2 mL) and heated for 15 min. at 125° C. in a microwave vessel. Additional 2-aminoethanol (50 µL, 0.84 mmol) was added and the reaction was heated at 150° C. for 20 min. The mixture was evaporated in vacuo and partitioned between CH$_2$Cl$_2$ and 1N NaHSO$_4$. After separating the layers, the aqueous phase was back-extracted with CH$_2$Cl$_2$. The combined organic layers were dried over MgSO$_4$, filtered, evaporated in vacuo and triturated with Et$_2$O to provide the product as a white solid: $^1$H NMR (d$^6$-DMSO) δ 10.37 (1H, b), 8.54 (1H, s), 7.93-8.03 (1H, m), 7.17-7.40 (7H, m), 7.11 (2H, t, J=9 Hz), 4.89-5.09 (3H, m), 4.12-4.22 (4H, m), 3.52-3.58 (2H, m), 3.40-3.45 (2H, m), 3.29 (3H, s), 2.81-2.88 (2H, m), 1.78 (b, 2H); ES+ MS: 563 (M+H+).

EXAMPLE 498 phenylmethyl {3-[7-[(4-fluorophenyl)methyl]-4-hydroxy-3-{[(2-hydroxy-1-methylethyl)amino]carbonyl}-2-oxo-1,5-naphthyridine-1(2H)-yl] propyl}methylcarbamate This compound was prepared from ethyl 7-[(4-fluorophenyl)methyl]-4-hydroxy-1-[3-(methyl{[(phenylmethyl)oxy]carbonyl}amino)propyl]-2-oxo-1,2-dihydro-1,5-naphthyridine-3-carboxylate and 2-amino-1-propanol using conditions similar to Step 5 from Example 497 and obtained as a white solid: ES+ MS: 577 (M+H+).

EXAMPLE 499 phenylmethyl {3-[7-[(4-fluorophenyl)methyl]-4-hydroxy-2-oxo-3-{[(tetrahydro-2-furanylmethyl)amino]carbonyl}-1,5-naphthyridine-1(2H)-yl] propyl}methylcarbamate This compound was prepared from ethyl 7-[(4-fluorophenyl)methyl]-4-hydroxy-1-[3-(methyl{[(phenylmethyl)oxy]carbonyl}amino)propyl]-2-oxo-1,2-dihydro-1,5-naphthyridine-3-carboxylate and (tetrahydro-2-furanylmethyl)amine using conditions similar to Example 497: ES+ MS: 603 (M+H+).

EXAMPLE 500

Phenylmethyl {3-[3-({[2-(ethyloxy)ethyl] amino}carbonyl)-7-[(4-fluorophenyl)methyl]-4-hydroxy-2-oxo-1,5-naphthyridin-1(2H)-yl] propyl}methylcarbamate This compound was prepared from ethyl 7-[(4-fluorophenyl)methyl]-4-hydroxy-1-[3-(methyl{[(phenylmethyl)oxy]carbonyl}amino)propyl]-2-oxo-1,2-dihydro-1,5-naphthyridine-3-carboxylate and 2-(ethyloxy)ethanamine using conditions similar to Step 5 from Example 497 and obtained as a white solid: ES+ MS: 591 (M+H+).

EXAMPLE 501

Phenylmethyl {3-[7-[(4-fluorophenyl)methyl]-4-hydroxy-3-{[(2-hydroxypropyl)amino]carbonyl}-2-oxo-1,5-naphthyridine-1(2H)-yl] propyl}methylcarbamate This compound was prepared from ethyl 7-[(4-fluorophenyl)methyl]-4-hydroxy-1-[3-(methyl{[(phenylmethyl)oxy]carbonyl}amino)propyl]-2-oxo-1,2-dihydro-1,5-naphthyridine-3-carboxylate and 1-amino-2-propanol using conditions similar to Step 5 from Example 497 and obtained as a white solid: ES+ MS: 577 (M+H+).

EXAMPLE 502

Phenylmethyl {3-[7-[(4-fluorophenyl)methyl]-4-hydroxy-3-[{2-[(1-methylethyl)oxy]ethyl}amino) carbonyl]-2-oxo-1,5-naphthyridine-1(2H)-yl] propyl}methylcarbamate This compound was prepared from ethyl 7-[(4-fluorophenyl)methyl]-4-hydroxy-1-[3-(methyl{[(phenylmethyl)oxy]carbonyl}amino)propyl]-2-oxo-1,2-dihydro-1,5-naphthyridine-3-carboxylate and 2-[(1-methylethyl)oxy]ethanamine using conditions similar to step 5 from Example 497 and obtained as a white solid: ES+ MS: 605 (M+H+).

EXAMPLE 503

Phenylmethyl {3-[7-[(4-fluorophenyl)methyl]-4-hydroxy-3-{[(4-hydroxybutyl)amino]carbonyl}-2-oxo-1,5-naphthyridine-1(2H)-yl] propyl}methylcarbamate This compound was prepared from ethyl 7-[(4-fluorophenyl)methyl]-4-hydroxy-1-[3-(methyl{[(phenylmethyl)oxy]carbonyl}amino)propyl]-2-oxo-1,2-dihydro-1,5-naphthyridine-3-carboxylate and 4-amino-1-butanol using conditions similar to Step 5 from Example 497 and obtained as a white solid: ES+ MS: 591 (M+H+).

EXAMPLE 504 phenylmethyl {2-[7-[(4-fluorophenyl)methyl]-4-hydroxy-3-[({3-[(1-methylethyl)oxy]propyl}amino) carbonyl]-2-oxo-1,5-naphthyrdin-1(2H)-yl] ethyl}methylcarbamate—{3-[(1-methylethyl)oxy] propyl}amine (1:1)

This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as a white solid: ES+ MS: 605 (M+H+).

EXAMPLE 505 phenylmethyl {2-[7-[(4-fluorophenyl)methyl]-4-hydroxy-3-[({2-[(2-hydroxyethyl)oxy]ethyl}amino) carbonyl]-2-oxo-1,5-naphthyridine-1(2H)-yl] ethyl}methylcarbamate—2-[(2H)-aminoethyl)oxy] ethanol (1:1)

This compound was prepared from ethyl 7-[(4-fluorophenyl)methyl]-4-hydroxy-1-[2-(methyl{[(phenylmethyl)oxy]

carbonyl}amino)ethyl]-2-oxo-1,2-dihydro-1,5-naphthyridine-3-carboxylate employing methods similar to those described in Example 475: step 6 and was obtained as a white solid: ES+ MS: 593 (M+H+).

EXAMPLE 506 phenylmethyl {2-[7-[(4-fluorophenyl)methyl]-4-hydroxy-3-{([2-hydroxy-1-methylethyl)amino]carbonyl}-2-oxo-1,5-naphthyridine-1(2H)-yl]ethyl}methylcarbamate—2-amino-1-propanol (1:1)

This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5- naphthyridine-3-carboxylate employing methods similar to those described in Example 475: step 6 and was obtained as a white solid: ES+ MS: 563 (M+H+).

EXAMPLE 507 phenylmethyl {2-[7-[(4-fluorophenyl)methyl]-4-hydroxy-3-[({2-[(1-methylethyl)oxy]ethyl}amino)carbonyl]-2-oxo-1,5-naphthyridine-1(2H)-yl]ethyl}methylcarbamate—{2-[(1-methylethyl)oxy]ethyl}amine (1:1)

This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as a tan solid: $^1$H NMR (400 MHz, DMSO-d$_6$) δ ppm 1.08 (td, J=6.86, 4.39 Hz, 12 H), 2.84 (d, J=5.85 Hz, 3 H), 3.36 (q, J=6.95 Hz, 4 H), 3.46-3.53 (m, 6 H), 3.55-3.58 (m, 1 H), 4.04 (s, 1 H), 4.12 (s, 1 H), 4.42 (t, J=5.40 Hz, 2 H), 4.58 (s, 1 H), 4.84 (s, 1 H), 6.91 (d, J=4.94 Hz, 1 H), 7.05-7.15 (m, 3 H), 7.16-7.19 (m, 1 H), 7.25-7.36 (m, 4 H), 7.99 (d, J=65.68 Hz, 1 H), 8.50 (d, J=24.52 Hz, 1 H), 8.47 (s, 1 H), 10.35 (d, J=25.62 Hz, 1 H); ES+ MS: 591 (M+H+).

EXAMPLE 508 phenylmethyl {2-[7-[(4-fluorophenyl)methyl]-4-hydroxy-2-oxo-3-({[2-(2-oxo-1-imidazolidinyl)ethyl]amino}carbonyl)-1,5-naphthyridin-1(2H)-yl]ethyl}methylcarbamate—1-(2-aminoethyl-2-imidazolidinone (1:1)

This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as a white solid: $^1$H NMR (400 MHz, DMSO-d$_6$@90° C.) δ ppm 2.67 (t, J=6.50 Hz, 2 H), 2.86 (s, 3 H), 3.05 (t, J=6.50 Hz, 2 H), 3.19-3.25 (m, 3 H), 3.28 (t, J=6.40 Hz, 3 H), 3.34-3.43 (m, 4 H), 3.50-3.57 (m, 4 H), 4.11 (s, 2 H), 4.41 (t, J=6.04 Hz, 2 H), 4.85 (br. s., 2 H), 5.89 (s, 1 H), 6.00 (s, 1 H), 7.05-7.11 (m, 2 H), 7.13-7.16 (m, 2 H), 7.26-7.33 (m, 5 H), 7.88 (s, 1 H), 8.48 (s, 1 H), 10.25-10.31 (m, 1 H); ES+ MS: 617 (M+H+).

EXAMPLE 509 phenylmethyl {2-[7-[(4-fluorophenyl)methyl]-4-hydroxy-2-oxo-3-{[(tetrahydro-2-furanylmethyl)amino]carbonyl}-1,5-naphthyridin-1(2H)-yl]ethyl}methylcarbamate—(tetrahydro-2-furanylmethyl)amine (1:1)

This compound was prepared from ethyl 7-[(4-fluorophenyl)methyl]-4-hydroxy-1-[2-(methyl{[(phenylmethyl)oxy]carbonyl}amino)ethyl]-2-oxo-1,2-dihydro-1,5-naphthyridine-3-carboxylate employing methods similar to those described in Example 475: step 6 and was obtained as a white solid: ES+ MS: 589 (M+H+).

EXAMPLE 510

1-[2-(acetylamino)ethyl]-7-[(4-fluorophenyl)methyl]-4-hydroxy-N-[1-methyl-2-(methyloxy)ethyl]-2-oxo-1,2-dihydro-1,5-naphthyridine-3-carboxamide Step 1: Synthesis of 1-(2-aminoethyl)-7-[(4-fluorophenyl)methyl]-4-hydroxy-N-[1-methyl-2-(methyloxy)ethyl]-2-oxo-1,2-dihydro-1,5-naphthyridine-3-carboxamide This compound was prepared from ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate employing methods similar to those described in Example 422 and was obtained as an orange solid: $^1$H NMR (400 MHz, DMSO-d$_6$) δ ppm 1.09-1.21 (m, 5 H), 3.26-3.29 (m, 3 H), 3.39 (d, J=4.94 Hz, 2 H), 4.08-4.14 (m, 2 H), 4.14-4.23 (m, 1 H), 4.28 (s, 2 H), 7.02-7.13 (m, 2 H), 7.26-7.37 (m, 2 H), 8.11 (s, 1 H), 8.49 (s, 1 H), 10.36 (d, J=7.87 Hz, 1 H); ES+ MS: 429 (M+H+).

Step 2: Synthesis of 1-[2-(acetylamino)ethyl]-7-[(4-fluorophenyl)methyl]-4-hydroxy-N-[1-methyl-2-(methyloxy)ethyl]-2-oxo-1,2-dihydro-1,5-naphthyridine-3-carboxamide This compound was prepared from 1-(2-aminoethyl)-7-[(4-fluorophenyl)methyl]-4-hydroxy-N-[1-methyl-2-(methyloxy)ethyl]-2-oxo-1,2-dihydro-1,5-naphthyridine-3-carboxamide employing methods similar to those described in Example 338 and was obtained as an off-white solid: $^1$H NMR (300 MHz, DMSO-d$_6$) δ ppm 1.20 (d, J=6.74 Hz, 3 H), 1.67 (s, 3 H), 3.24-3.30 (m, 2 H), 3.31 (s, 3 H), 3.43 (d, J=4.91 Hz, 2 H), 4.14 (s, 2 H), 4.18-4.29 (m, 3 H), 7.10-7.18 (m, 2 H), 7.38-7.44 (m, 2 H), 8.04 (t, J=5.97 Hz, 1 H), 8.18 (s, 1 H), 8.55 (s, 1 H), 10.40 (d, J=8.42 Hz, 1 H); ES+ MS: 471 (M+H+).

EXAMPLE 511

1-[2-(acetylamino)ethyl]-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide Step 1: Synthesis of 1-(2-aminoethyl)-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide This compound was prepared from 1-[2-(1,3-dioxo-1,3-dihydro-2H-isoindol-2-yl)ethyl]-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide employing methods similar to those described in Example 334 and was obtained as an orange solid: $^1$H NMR (400 MHz, DMSO-d$_6$) δ ppm 1.69-1.79 (m, 2 H), 1.88-1.96 (m, 2 H), 2.22 (t, J=7.97 Hz, 2 H), 2.93 (s, 2 H), 3.20-3.27 (m, 4 H), 3.34-3.39 (m, 4 H), 4.16 (s, 2 H), 4.35 (s, 2 H), 7.14 (t, J=8.70 Hz, 2 H), 7.30-7.41 (m, 2 H), 8.14 (s, 1 H), 8.53 (s, 1 H), 10.29 (s, 1 H); ES+ MS: 482 (M+H+).

Step 2: Synthesis of 1-[2-(acetylamino)ethyl]-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide This compound was prepared from 1-(2-aminoethyl)-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide employing methods similar to those described in Example 338 and was obtained as an off-white solid: $^1$H NMR (300 MHz, DMSO-$d_6$) δ ppm 1.68 (s, 3 H), 1.69-1.81 (m, J=6.91, 6.91, 6.91, 6.91 Hz, 2 H), 1.92 (qd, J=7.58, 7.44 Hz, 2 H), 2.22 (t, J=7.93 Hz, 2 H), 3.21-3.29 (m, 4 H), 3.34-3.39 (m, 4 H), 4.14 (s, 2 H), 4.26 (t, J=6.25 Hz, 2 H), 7.10-7.18 (m, 2 H), 7.38-7.46 (m, 2 H), 8.05 (t, J=5.62 Hz, 1 H), 8.19 (s, 1 H), 8.54 (s, 1 H), 10.33 (t, J=5.76 Hz, 1 H); ES$^+$ MS: 524 (M+H$^+$).

EXAMPLE 512

1-[2-(acetylamino)ethyl]-7-[(4-fluorophenyl)methyl]-4-hydroxy-N-[1-(hydroxymethyl)-2-methylpropyl]-2-oxo-1,2-dihydro-1,5-naphthyridine-3-carboxamide Step 1: Synthesis of 1-(2-aminoethyl)-7-[(4-fluorophenyl)methyl]-4-hydroxy-N-[1-(hydroxymethyl)-2-methylpropyl]-2-oxo-1,2-dihydro-1,5-naphthyridine-3-carboxamide This compound was prepared from ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate employing methods similar to those described in Example 422 and was obtained as an off-white solid: $^1$H NMR (400 MHz, DMSO-$d_6$) δ ppm 0.85-0.95 (m, 8 H), 1.96-2.01 (m, 1 H), 2.83 (t, J=6.87 Hz, 2 H), 3.48 (d, J=9.89 Hz, 2 H), 3.57 (d, J=13.55 Hz, 1 H), 3.82-3.88 (m, 1 H), 4.17 (s, 2 H), 4.20-4.31 (m, 2 H), 4.88 (s, 1 H), 7.15 (t, J=8.88 Hz, 2 H), 7.34-7.43 (m, 2 H), 8.16 (s, 1 H), 8.52 (d, J=1.28 Hz, 1 H), 10.44 (d, J=7.88 Hz, 1 H); ES$^+$ MS: 443 (M+H$^+$).

Step 2: Synthesis of 1-[2-(acetylamino)ethyl]-7-[(4-fluorophenyl)methyl]-4-hydroxy-N-(3-hydroxy-2,2-dimethylpropyl)-2-oxo-1,2-dihydro-1,5-naphthyridine-3-carboxamide This compound was prepared from 1-(2-aminoethyl)-7-[(4-fluorophenyl)methyl]-4-hydroxy-N-[1-(hydroxymethyl)-2-methylpropyl]-2-oxo-1,2-dihydro-1,5-naphthyridine-3-carboxamide employing methods similar to those described in Example 338 and was obtained as an off-white solid: $^1$H NMR (400 MHz, DMSO-$d_6$) δ ppm 0.89-1.00 (m, 8 H), 1.27 (s, 1 H), 2.04 (dd, J=13.54, 6.77 Hz, 1 H), 2.99 (s, 2 H), 3.35 (q, J=6.28 Hz, 2 H), 3.51-3.62 (m, 3 H), 3.87-3.94 (m, 1 H), 4.17 (s, 2 H), 4.28-4.33 (m, 1 H), 7.04-7.14 (m, 2 H), 7.38 (dd, J=8.42, 5.49 Hz, 2 H), 7.76 (s, 1 H), 8.10 (s, 1 H), 8.52 (s, 1 H), 10.34 (d, J=7.68 Hz, 1 H); ES$^+$ MS: 485 (M+H$^+$).

EXAMPLE 513

1-[2-(acetylamino)ethyl]-7-[(4-fluorophenyl)methyl]-4-hydroxy-2-oxo-N-[2-(2-oxo-1-imidazolidinyl)ethyl]-1,2-dihydro-1,5-naphthyridine-3-carboxamide This compound was prepared from 1-(2-aminoethyl)-7-[(4-fluorophenyl)methyl]-4-hydroxy-2-oxo-N-[2-(2-oxo-1-imidazolidinyl)ethyl]-1,2-dihydro-1,5-naphthyridine-3-carboxamide employing methods similar to those described in Example 338 and was obtained as an off-white solid: ES$^+$ MS: 511 (M+H$^+$).

EXAMPLE 514

1-[2-(acetylamino)ethyl]-7-[(4-fluorophenyl)methyl]-4-hydroxy-N-(3-hydroxy-2,2-dimethylpropyl)-2-oxo-1,2-dihydro-1,5-naphthyridine-3-carboxamide Step 1: Synthesis of 1-(2-aminoethyl)-7-[(4-fluorophenyl)methyl]-4-hydroxy-N-(3-hydroxy-2,2-dimethylpropyl)-2-oxo-1,2-dihydro-1,5-naphthyridine-3-carboxamide This compound was prepared from ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate employing methods similar to those described in Example 422 and was obtained as an off-white solid: $^1$H NMR (400 MHz, DMSO-$d_6$) δ ppm 0.87 (s, 6 H), 2.94 (t, J=6.23 Hz, 2 H), 3.21 (d, J=4.58 Hz, 2 H), 3.28 (d, J=6.04 Hz, 4 H), 4.17 (s, 2 H), 4.36 (t, J=6.23 Hz, 2 H), 4.78 (t, J=5.13 Hz, 1 H), 7.12-7.17 (m, 2 H), 7.39 (dd, J=8.70, 5.40 Hz, 2 H), 8.12 (s, 1 H), 8.54 (s, 1 H), 10.43 (s, 1 H); ES$^+$ MS: 443 (M+H$^+$).

Step 2: Synthesis of 1-[2-(acetylamino)ethyl]-7-[(4-fluorophenyl)methyl]-4-hydroxy-N-(3-hydroxy-2,2-dimethylpropyl)-2-oxo-1,2-dihydro-1,5-naphthyridine-3-carboxamide This compound was prepared from 1-(2-aminoethyl)-7-[(4-fluorophenyl)methyl]-4-hydroxy-N-(3-hydroxy-2,2-dimethylpropyl)-2-oxo-1,2-dihydro-1,5-naphthyridine-3-carboxamide employing methods similar to those described in Example 338 and was obtained as a white solid: $^1$H NMR (400 MHz, DMSO-$d_6$) δ ppm 0.87 (s, 6 H), 1.68 (s, 3 H), 3.20 (d, J=5.12 Hz, 2 H), 3.24-3.32 (m, 4 H), 4.14 (s, 2 H), 4.27 (t, J=6.40 Hz, 2 H), 4.80 (t, J=5.12 Hz, 1 H), 7.14 (ddd, J=8.97, 6.59, 2.20 Hz, 2 H), 7.38-7.43 (m, 2 H), 8.03 (t, J=6.13 Hz, 1 H), 8.19 (d, J=10 Hz, 1 H), 8.55 (s, 1 H), 10.47 (s, 1 H); ES$^+$ MS: 485 (M+H$^+$).

EXAMPLE 515

1-[2-(acetylamino)ethyl]-7-[(4-fluorophenyl)methyl]-4-hydroxy-N-(2-hydroxy-1,1-dimethylethyl)-2-oxo-1,2-dihydro-1,5-naphthyridine-3-carboxamide Step 1: Synthesis of 1-(2-aminoethyl)-7-[(4-fluorophenyl)methyl]-4-hydroxy-N-(2-hydroxy-1,1-dimethylethyl)-2-oxo-1,2-dihydro-1,5-naphthyridine-3-carboxamide This compound was prepared from ethyl 1-[2-(1,3-dioxo-1,3-dihydro-2H-isoindol-2-yl)ethyl]-7-[(4-fluorophenyl)methyl]-4-hydroxy-2-oxo-1,2-dihydro-1,5-naphthyridine-3-carboxylate employing methods similar to those described in Example 422 and was obtained as an off-white solid: $^1$H NMR (400 MHz, DMSO-$d_6$) δ ppm 1.35 (s, 6 H), 2.76-2.85 (m, 2 H), 3.29 (s, 2 H), 3.47 (s, 2 H), 4.16 (s, 2 H), 4.24 (t, J=6.96 Hz, 2 H), 5.14 (s, 1 H), 7.14 (t, J=8.88 Hz, 2 H), 7.39 (dd, J=8.61, 5.49 Hz, 2 H), 8.15 (d, J=1.46 Hz, 1 H), 8.51 (d, J=1.65 Hz, 1 H), 10.51 (s, 1 H); ES$^+$ MS: 429 (M+H$^+$).

Step 2: Synthesis of 1-[2-(acetylamino)ethyl]-7-[(4-fluorophenyl)methyl]-4-hydroxy-N-(2-hydroxy-1,1-dimethylethyl)-2-oxo-1,2-dihydro-1,5-naphthyridine-3-carboxamide This compound was prepared from 1-(2-aminoethyl)-7-[(4-fluorophenyl)methyl]-4-hydroxy-N-(2-hydroxy-1,1-dimethylethyl)-2-oxo-1,2-dihydro-1,5-naphthyridine-3-carboxamide employing methods similar to those described in Example 338 and was obtained as an orange solid: $^1$H NMR (400 MHz, DMSO-d$_6$) δ ppm 1.34 (s, 6 H), 1.66 (s, 3 H), 3.23-3.29 (m, 2 H), 3.46 (s, 2 H), 4.12 (s, 2 H), 4.22 (t, J=6.22 Hz, 2 H), 5.13 (s, 1 H), 7.10-7.15 (m, 2 H), 7.37-7.43 (m, 2 H), 8.03 (t, J=5.85 Hz, 1 H), 8.17 (d, J=1.46 Hz, 1 H), 8.53 (d, J=1.46 Hz, 1 H), 10.48 (s, 1 H); ES$^+$ MS: 471 (M+H$^+$).

EXAMPLE 516

N-[(2R)-2,3-Dihydroxypropyl]-7-[(4-fluorophenyl)methyl]-4-hydroxy-1-methyl-2-oxo-1,2-dihydro-1,5-naphthyridine-3-carboxamide In a similar manner to that described in example 196, from ethyl 7-[(4-fluorophenyl)methyl]-4-hydroxy-1-methyl-2-oxo-1,2-dihydro-1,5-naphthyridine-3-carboxylate (50 mg, 0.140 mmol) and (2R)-3-amino-1,2-propanediol (0.03 mL, 0.42 mmol) was prepared N-[(2R)-2,3-dihydroxypropyl]-7-[(4-fluorophenyl)methyl]-4-hydroxy-1-methyl-2-oxo-1,2-dihydro-1,5-naphthyridine-3-carboxamide (39 mg, 68% yield) as a white solid. $^1$H NMR (DMSO-d$_6$) δ 10.44 (br s, 1 H), 8.53 (s, 1 H), 8.01 (s, 1 H), 7.40-7.36 (m, 2 H), 7.15-7.10 (m, 2 H), 5.06 (m, 1 H), 4.77 (m, 1 H), 4.16 (s, 2 H), 3.61-3.55 (m, 4 H), 3.39 (m, 1 H), 3.24 (m, 1 H); MS m/z 402 (M+1).

EXAMPLE 517

Sodium 1-[2-(Dimethylamino)-2-oxoethyl]-7-(4-fluorobenzyl)-3-({[(2S)-2-hydroxypropyl]amino}carbonyl)-2-oxo-1,2-dihydro-1,5-naphthyridine-4-olate The compound in example 339 was treated in a similar manner to example 166 to give a white solid: $^1$H NMR (d$_6$-DMSO) δ 10.48 (1H, m), 8.15 (1H, s), 7.30 (1H, s), 7.26 (2H, m), 7.10 (2H, m), 4.93 (2H, s), 4.76 (1H, m), 3.99 (2H, s), 3.68 (1H, m), 3.17 (2H, m), 3.08 (3H, s), 2.78 (3H, s), 1.04 (3H, d, J=6 Hz).

EXAMPLE 518

1-(2-{[(dimethylamino)carbonyl]amino}ethyl)-7-[(4-fluorophenyl)methyl]-4-hydroxy-2-oxo-N-[2-(2-oxo-1-imidazolidinyl)ethyl]-1,2-dihydro-1,5-naphthyridine-3-carboxamide This compound was prepared from 1-(2-aminoethyl)-7-[(4-fluorophenyl)methyl]-4-hydroxy-2-oxo-N-[2-(2-oxo-1-imidazolidinyl)ethyl]-1,2-dihydro-1,5-naphthyridine-3-carboxamide employing methods similar to those described in Example 450 and was obtained as a tan solid: $^1$H NMR (300 MHz, DMSO-d$_6$) δ ppm 2.70 (s, 6 H), 3.19-3.31 (m, 6 H), 3.34-3.44 (m, 2 H), 3.52 (q, J=6.22 Hz, 2 H), 4.12 (s, 2 H), 4.25 (t, J=6.53 Hz, 2 H), 6.38 (s, 1 H), 6.53-6.59 (m, 1 H), 7.14 (t, J=8.91 Hz, 2 H), 7.40 (dd, J=8.84, 5.48 Hz, 2 H), 8.29 (s, 1 H), 8.53 (d, J=1.40 Hz, 1 H), 10.33 (t, J=6.60 Hz, 1 H), 17.07 (s, 1 H); ES$^+$ MS: 540 (M+H$^+$).

EXAMPLE 519

1-(2-{[(dimethylamino)carbonyl]amino}ethyl)-7-[(4-fluorophenyl)methyl]-4-hydroxy-N-[2-(methyloxy)ethyl]-2-oxo-1,2-dihydro-1,5-naphthyridine-3-carboxamide This compound was prepared from 1-(2-aminoethyl)-7-[(4-fluorophenyl)methyl]-4-hydroxy-N-[2-(methyloxy)ethyl]-2-oxo-1,2-dihydro-1,5-naphthyridine-3-carboxamide employing methods similar to those described in Example 450 and was obtained as an off-white solid: $^1$H NMR (300 MHz, DMSO-d$_6$) δ ppm 1.71 (s, 1 H), 2.70 (s, 6 H), 3.22-3.30 (m, 2 H), 3.31 (s, 3 H), 3.49-3.58 (m, 4 H), 4.12 (s, 2 H), 4.25 (t, J=6.46 Hz, 2 H), 6.55 (t, J=5.55 Hz, 1 H), 7.11-7.18 (m, 2 H), 7.37-7.43 (m, 2 H), 8.28 (d, J=1.40 Hz, 1 H), 8.53 (d, J=1.40 Hz, 1 H), 10.43 (t, J=4.98 Hz, 1 H); ES$^+$ MS: 486 (MH$^+$).

EXAMPLE 520

1-(2-{[(dimethylamino)carbonyl]amino}ethyl)-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide This compound was prepared from 1-(2-aminoethyl)-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide employing methods similar to those described in Example 450 and was obtained as an off-white solid: $^1$H NMR (300 MHz, DMSO-d$_6$) δ ppm 1.70-1.81 (m, 2 H), 1.88-1.97 (m, 2 H), 2.22 (t, J=8.07 Hz, 2 H), 2.70 (s, 6 H), 3.22-3.31 (m, 6 H), 3.33-3.39 (m, 2 H), 4.12 (s, 2 H), 4.25 (t, J=6.04 Hz, 2 H), 6.56 (t, J=5.40 Hz, 1 H), 7.11-7.17 (m, 2 H), 7.37-7.43 (m, 2 H), 8.28 (s, 1 H), 8.52 (s, 1 H), 10.35 (s, 1 H); ES$^+$ MS: 553 (M+H$^+$).

EXAMPLE 521

1-(2-{[(dimethylamino)carbonyl]amino}ethyl)-7-[(4-fluorophenyl)methyl]-4-hydroxy-N-(2-hydroxy-1-methylethyl)-2-oxo-1,2-dihydro-1,5-naphthyridine-3-carboxamide This compound was prepared from 1-(2-aminoethyl)-7-[(4-fluorophenyl)methyl]-4-hydroxy-N-(2-hydroxy-1-methylethyl)-2-oxo-1,2-dihydro-1,5-naphthyridine-3-carboxamide employing methods similar to those described in Example 450 and was obtained as a tan solid: $^1$H NMR (300 MHz, DMSO-d$_6$) δ ppm 1.19 (d, J=6.60 Hz, 3 H), 2.70 (s, 6 H), 3.19-3.31 (m, 2 H), 3.48 (t, J=4.84 Hz, 2 H), 3.99-4.11 (m, 1 H), 4.12 (s, 2 H), 4.25 (t, J=6.81 Hz, 2 H), 5.01 (t, J=5.33 Hz, 1 H), 6.53 (t, J=5.55 Hz, 1 H), 7.11-7.18 (m, 2 H), 7.37-7.43 (m, 2 H), 8.25 (d, J=1.54 Hz, 1 H), 8.52 (d, J=1.40 Hz, 1 H), 10.42 (d, J=7.44 Hz, 1 H), 17.20 (s, 1 H); ES$^+$ MS: 486 (M+H$^+$).

EXAMPLE 522

1-(2-{[(dimethylamino)carbonyl]amino}ethyl)-7-[(4-fluorophenyl)methyl]-4-hydroxy-N-[1-(hydroxymethyl)-2-methylpropyl]-2-oxo-1,2-dihydro-1,5-naphthyridine-3-carboxamide This compound was prepared from 1-(2-aminoethyl)-7-[(4-fluorophenyl)methyl]-4-hydroxy-N-[1-(hydroxymethyl)-2-methylpropyl]-2-oxo-1,2-dihydro-1,5-naphthyridine-3-carboxamide employing methods similar to those described in Example 450 and was obtained as an off-white solid: $^1$H NMR (300 MHz, DMSO-d$_6$) δ ppm 0.93 (t, J=6.46 Hz, 6 H), 1.91 (s, 1 H), 1.93-2.07 (m, 1 H), 2.70 (s, 6 H), 3.23-3.30 (m, 2 H), 3.44-3.60 (m, 2 H), 3.80-3.91 (m, 1 H), 4.12 (s, 2 H), 4.19-4.33 (m, 2 H), 4.88 (t, J=4.91 Hz, 1 H), 6.54 (t, J=5.40 Hz, 1 H), 7.14 (t, J=8.91 Hz, 2 H), 7.41 (dd, J=8.77, 5.55 Hz, 2 H), 8.26 (s, 1 H), 8.53 (d, J=1.40 Hz, 1 H), 10.45 (d, J=9.55 Hz, 1 H); ES$^+$ MS: 514 (M+H$^+$).

EXAMPLE 523

1-(2-{[(dimethylamino)carbonyl]amino}ethyl)-7-[(4-fluorophenyl)methyl]-4-hydroxy-N-(3-hydroxy-2,2-dimethylpropyl)-2-oxo-1,2-dihydro-1,5-naphthyridine-3-carboxamide This compound was prepared from 1-(2-aminoethyl)-7-[(4-fluorophenyl)methyl]-4-hydroxy-N-(3-hydroxy-2,2-dimethylpropyl)-2-oxo-1,2-dihydro-1,5-naphthyridine-3-carboxamide employing methods similar to those described in Example 450 and was obtained as a white solid: $^1$H NMR (300 MHz, DMSO-d$_6$) δ ppm 0.87 (s, 6 H), 2.71 (s, 6 H), 3.24 (dd, J=19.51, 5.48 Hz, 6 H), 4.12 (s, 2 H), 4.27 (t, J=6.32 Hz, 2 H), 4.78 (t, J=5.05 Hz, 1 H), 6.55 (t, J=5.40 Hz, 1 H), 7.11-7.17 (m, 2 H), 7.38-7.43 (m, 2 H), 8.27 (d, J=1.26 Hz, 1 H), 8.53 (d, J=1.40 Hz, 1 H), 10.50 (t, J=6.25 Hz, 1 H), 17.20 (s, 1 H); ES$^+$ MS: 514 (M+H$^+$).

EXAMPLE 524

1-(2-{[(dimethylamino)carbonyl]amino}ethyl)-7-[(4-fluorophenyl)methyl]-4-hydroxy-N-[1-methyl-2-(methyloxy)ethyl]-2-oxo-1,2-dihydro-1,5-naphthyridine-3-carboxamide This compound was prepared from 1-(2-aminoethyl)-7-[(4-fluorophenyl)methyl]-4-hydroxy-N-[1-methyl-2-(methyloxy)ethyl]-2-oxo-1,2-dihydro-1,5-naphthyridine-3-carboxamide employing methods similar to those described in Example 450 and was obtained as an off-white solid: $^1$H NMR (300 MHz, DMSO-d$_6$) δ ppm 1.21 (d, J=6.74 Hz, 3 H), 1.73 (s, 1 H), 2.70 (s, 6 H), 3.19-3.30 (m, 3 H), 3.33-3.35 (m, 2 H), 3.43 (d, J=4.91 Hz, 2 H), 4.12 (s, 2 H), 4.18-4.29 (m, 3 H), 6.53 (t, J=5.55 Hz, 1 H), 7.10-7.19 (m, 2 H), 7.40 (ddd, J=12.18, 5.51, 3.37 Hz, 2 H), 8.26 (d, J=1.40 Hz, 1 H), 8.53 (d, J=1.40 Hz, 1 H), 10.43 (d, J=8.98 Hz, 1 H); ES$^+$ MS: 500 (M+H$^+$).

EXAMPLE 525

1-(2-{[(dimethylamino)carbonyl]amino}ethyl)-7-[(4-fluorophenyl)methyl]-4-hydroxy-N-(2-hydroxy-1,1-dimethylethyl)-2-oxo-1,2-dihydro-1,5-naphthyridine-3-carboxamide This compound was prepared from 1-(2-aminoethyl)-7-[(4-fluorophenyl)methyl]-4-hydroxy-N-(2-hydroxy-1,1-dimethylethyl)-2-oxo-1,2-dihydro-1,5-naphthyridine-3-carboxamide employing methods similar to those described in Example 450 and was obtained as an off-white solid: $^1$H NMR (300 MHz, DMSO-d$_6$) δ ppm 1.36 (s, 6 H), 2.70 (s, 6 H), 3.27 (q, J=6.55 Hz, 2 H), 3.48 (d, J=5.33 Hz, 2 H), 4.11 (s, 2 H), 4.24 (t, J=5.90 Hz, 2 H), 5.12 (t, J=4.77 Hz, 1 H), 6.52-6.57 (m, 1 H), 7.11-7.18 (m, 2 H), 7.38-7.43 (m, 2 H), 8.25-8.27 (m, 1 H), 8.52 (s, 1 H), 10.54 (s, 1 H), 17.31 (s, 1 H); ES$^+$ MS: 500 (M+H$^+$).

EXAMPLE 526

1-(2-{[(dimethylamino)carbonyl]amino}ethyl)-7-[(4-fluorophenyl)methyl]-4-hydroxy-N-{3-[(1-methylethyl)oxy]propyl}-2-oxo-1,2-dihydro-1,5-naphthyridine-3-carboxamide This compound was prepared from 1-(2-aminoethyl)-7-[(4-fluorophenyl)methyl]-4-hydroxy-N-{3-[(1-methylethyl)oxy]propyl}-2-oxo-1,2-dihydro-1,5-naphthyridine-3-carboxamide employing methods similar to those described in Example 450 and was obtained as an off-white solid: $^1$H NMR (300 MHz, DMSO-d$_6$) δ ppm 1.10 (d, J=6.18 Hz, 6 H), 1.72-1.81 (m, 2 H), 2.70 (s, 6 H), 3.28 (d, J=5.90 Hz, 2 H), 3.41-3.49 (m, 4 H), 3.51-3.57 (m, 1 H), 4.11 (s, 2 H), 4.25 (t, J=6.11 Hz, 2 H), 6.55 (t, J=5.62 Hz, 1 H), 7.10-7.18 (m, 2 H), 7.37-7.43 (m, 2 H), 8.28 (d, J=1.12 Hz, 1 H), 8.52 (d, J=1.40 Hz, 1 H), 10.33-10.38 (m, 1 H); ES$^+$ MS: 528 (M+H$^+$).

EXAMPLE 527

7-[(4-Fluorophenyl)methyl]-4-hydroxy-N-[2-(methyloxy)ethyl]-2-oxo-1-[3-(2-oxo-1-pyrrolidinyl)propyl]-1,2-dihydro-1,5-naphthyridine-3-carboxamide Ethyl 5-[(4-fluorophenyl)methyl]-3-{[3-(2-oxo-1-pyrrolidinyl)propyl]amino}-2-pyridinecarboxylate. This compound was prepared from ethyl 3-amino-5-[(4-fluorophenyl)methyl]-2-pyridinecarboxylate and 3-(2-oxo-1-pyrrolidinyl)propanal employing methods similar to those described in Example 265 and was obtained as a clear oil. $^1$H NMR (400 MHz, CDCl$_3$) δ 7.81 (d, J=1.6 Hz, 1 H), 7.71 (br, 1 H), 7.07 (dd, J=8.5, 5.4 Hz, 2 H), 6.92 (t, J=8.6 Hz, 2 H), 6.74 (d, J=1.3 Hz, 1 H), 4.35 (q, J=7.1 Hz, 2 H), 3.86 (s, 2 H), 3.35-3.29 (m, 4 H), 3.10 (m, 2 H), 2.33 (t, J=8.2 Hz, 2 H), 1.96 (m, 2 H), 1.79 (m, 2 H), 1.35 (t, J=7.2 Hz, 3 H); MS m/z 400 (M+H)$^+$.

Ethyl 3-{[3-(ethyloxy)-3-oxopropanoyl][3-(2-oxo-1-pyrrolidinyl)propyl]amino}-5-[(4-fluorophenyl)methyl]-2-pyridinecarboxylate. This compound was prepared from ethyl 5-[(4-fluorophenyl)methyl]-3-{[3-(2-oxo-1-pyrrolidinyl)propyl]amino}-2-pyridinecarboxylate employing methods similar to those described in Example 202 and was obtained as a pale yellow oil. $^1$H NMR (400 MHz, CDCl$_3$) δ 8.58 (s, 1 H), 7.64 (s, 1 H), 7.15 (m, 2 H), 7.00 (m, 2 H), 4.41 (m, 2 H), 4.05 (s, 2 H), 4.03-3.94 (m, 4 H), 3.36 (m, 2 H), 3.26-3.01 (m, 2 H), 2.35 (m, 2 H), 2.00 (m, 2 H), 1.69 (m, 2 H), 1.37 (m, 3 H), 1.17 (m, 3 H); MS m/z 514 (M+H)$^+$.

Ethyl 7-[(4-fluorophenyl)methyl]-4-hydroxy-2-oxo-1-[3-(2-oxo-1-pyrrolidinyl)propyl]-1,2-dihydro-1,5-naphthyridine-3-carboxylate. This compound was prepared from ethyl 3-{[3-(ethyloxy)-3-oxopropanoyl][3-(2-oxo-1-pyrrolidinyl)propyl]amino}-5-[(4-fluorophenyl)methyl]-2-pyridinecarboxylate employing methods similar to those described in Example 202 and was obtained as a yellow solid. $^1$H NMR (400 MHz, CDCl$_3$) δ 8.50 (d, J=1.2 Hz, 1 H), 7.41 (s, 1 H), 7.18 (dd, J=8.5, 5.4 Hz, 2 H), 7.03 (t, J=8.6 Hz, 2 H), 4.52 (q, J=7.1 Hz, 2 H), 4.15-4.10 (m, 4 H), 3.41 (m, 2 H), 2.39 (t, J=7.9 Hz, 2 H), 2.04 (m, 2 H), 1.85 (m, 2 H), 1.48 (t, J=7.1 Hz, 3 H); MS m/z 468 (M+H)$^+$.

7-[(4-Fluorophenyl)methyl]-4-hydroxy-N-[2-(methyloxy)ethyl]-2-oxo-1-[3-(2-oxo-1-pyrrolidinyl)propyl]-1,2-dihydro-1,5-naphthyridine-3-carboxamide. This compound was prepared from ethyl 7-[(4-fluorophenyl)methyl]-4-hydroxy-2-oxo-1-[3-(2-oxo-1-pyrrolidinyl)propyl]-1,2-dihydro-1,5-naphthyridine-3-carboxylate and 2-methoxyethylamime employing methods similar to those described in Example 202 and was obtained as a white solid. $^1$H NMR (400 MHz, CDCl$_3$) δ 10.30 (t, J=5.2 Hz, 1 H), 8.55 (d, J=0.9 Hz, 1 H), 7.42 (s, 1 H), 7.18 (dd, J=8.6, 5.3 Hz, 2 H), 7.03 (t, J=8.6 Hz, 2 H), 4.17-4.12 (m, 4 H), 3.65 (m, 2 H), 3.59 (m, 2 H), 3.42-3.37 (m, 7 H), 2.40 (t, J=8.0 Hz, 2 H), 2.05 (m, 2 H), 1.84 (m, 2 H); HRMS C$_{26}$H$_{29}$FN$_4$O$_5$ (M+Na)$^+$ calcd 519.2122, found 519.2023.

EXAMPLE 528

7-[(3,4-Difluorophenyl)methyl]-1-[2-(dimethylamino)-2-oxoethyl]-4-hydroxy-N-[2-(methyloxy)ethyl]-2-oxo-1,2-dihydro-1,5-naphthyridine-3-carboxamide This compound was prepared from methyl 3-amino-5-[(3,4-difluorophenyl)methyl]-2-pyridinecarboxylate employing methods similar to those described in Example 11, Steps 1-4, using N,N-dimethylamine in Step 2. Subsequent formation of the carboxamide with methoxyethylamine employing methods similar to those described in Example 2 using N,N-dimethylformamide as the reaction solvent, afforded the desired product as an off-white solid: $^1$H NMR (d$_6$-DMSO) δ 10.23 (1H, t, J=5.2 Hz), 8.54 (1H, s), 7.77 (1H, s), 7.42-7.33 (2H, m), 7.15 (1H, br s), 5.14 (2H, s), 4.12 (2H, s), 3.53-3.48 (4H, m), 3.27 (3H, s), 3.14 (3H, s), 2.82 (3H, s); HRMS calcd for C$_{23}$H$_{24}$F$_2$N$_4$O$_5$+H$^+$: 475.1793. Found 475.1793.

EXAMPLE 529

7-[(4-Fluorophenyl)methyl]-4-hydroxy-1-{2-[(methylsulfonyl)amino]ethyl}-2-oxo-N-[3-(2-oxo-1-pyrrolidinyl)propyl]-1,2-dihydro-1,5-naphthyridine-3-carboxamide This compound was prepared from 1-(2-aminoethyl)-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide employing methods similar to those described in Example 441 and was obtained as an off-white solid: ES$^+$ MS: 560 (M+H$^+$).

EXAMPLE 530

7-[(4-fluorophenyl)methyl]-4-hydroxy-N-[2-(methyloxy)ethyl]-1-{2-[(methylsulfonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-[2-(methyloxy)ethyl]-2-oxo-1,2-dihydro-1,5-naphthyridine-3-carboxamide employing methods similar to those described in Example 441 and was obtained as an off-white solid: ES$^+$ MS: 493 (M+H$^+$).

EXAMPLE 531

7-[(4-fluorophenyl)methyl]-4-hydroxy-1-{2-[(methylsulfonyl)amino]ethyl}-2-oxo-N-[2-(2-oxo-1-imidazolidinyl)ethyl]-1,2-dihydro-1,5-naphthyridine-3-carboxamide This compound was prepared from 1-(2-aminoethyl)-7-[(4-fluorophenyl)methyl]-4-hydroxy-2-oxo-N-[2-(2-oxo-N-1 imidazolidinyl)ethyl]-1,2-dihydro-1,5-naphthyridine-3-carboxamide employing methods similar to those described in Example 441 and was obtained as an off-white solid: ES$^+$ MS: 547 (M+H$^+$).

EXAMPLE 532

7-[(4-fluorophenyl)methyl]-4-hydroxy-N-[1-methyl-{2-(methyloxy)ethyl]-1-2-[(methylsulfonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-[1-methyl-2-(methyloxy)ethyl]-2-oxo-1,2-dihydro-1,5-naphthyridine-3-carboxamide employing methods similar to those described in Example 441 and was obtained as an off-white solid: ES$^+$ MS: 507 (M+H$^+$).

EXAMPLE 533

7-[(4-fluorophenyl)methyl]-4-hydroxy-N-(3-hydroxy-2,2-dimethylpropyl)-1-{2-[(methylsulfonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-(3-hydroxy-2,2-dimethylpropyl)-2-oxo-1,2-dihydro-1,5-naphthyridine-3-carboxamide employing methods similar to those described in Example 441 and was obtained as an off-white solid: ES$^+$ MS: 521 (M+H$^+$).

EXAMPLE 534

7-[(4-fluorophenyl)methyl]-4-hydroxy-N-(2-hydroxy-1-methylethyl)-1-{2-[(methylsulfonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-(2-hydroxy-1-methylethyl)-2-oxo-1,2-dihydro-1,5-naphthyridine-3-carboxamide employing methods similar to those described in Example 441 and was obtained as an off-white solid: ES$^+$ MS: 493 (M+H$^+$).

EXAMPLE 535

7-[(3,4-difluorophenyl)methyl]-1-[2-(dimethylamino)-2-oxoethyl]-4-hydroxy-N-[(2S)-2-hydroxypropyl]-2-oxo-1,2-dihydro-1,5-naphthyridine-3-carboxamide This compound was prepared from methyl 3-amino-5-[(3,4-difluorophenyl)methyl]-2-pyridinecarboxylate employing methods similar to those described in Example 11, Steps 1-4, using N,N-dimethylamine in Step 2. Subsequent formation of the carboxamide with S-(+)-1-amino-2-propanol employing methods similar to those described in Example 2 using N,N-dimethylformamide as the reaction solvent, afforded the desired product as a light yellow solid: $^1$H NMR (d$_6$-DMSO) δ 10.29 (1H, t, J=5.4 Hz), 8.54 (1H, s), 7.77 (1H, s), 7.42-7.33 (2H, m), 7.15 (1H, br s), 5.14 (2H, s), 4.95 (1H, d, J=4.3 Hz), 4.12 (2H, s), 3.81-3.75 (1H, m), 3.46-3.40 (1H, m), 3.22-3.16

(1H, m), 3.14 (3H, s), 2.83 (3H, s), 1.08 (3H, d, J=6.1 Hz); HRMS calcd for $C_{23}H_{24}F_2N_4O_5+H^+$: 475.1793. Found 475.1805.

EXAMPLE 536

7-[(4-fluorophenyl)methyl]-4-hydroxy-1-{2-[(4-morpholinylcarbonyl)amino]ethyl}-2-oxo-N-[2-(2-oxo-1-imidazolidinyl)ethyl]-1,2-dihydro-1,5-naphthyridine-3-carboxamide This compound was prepared from 1-(2-aminoethyl)-7-[(4-fluorophenyl)methyl]-4-hydroxy-2-oxo-N-[2-(2-oxo-1-imidazolidinyl)ethyl]-1,2-dihydro-1,5-naphthyridine-3-carboxamide and 4-morpholinecarbonyl chloride employing methods similar to those described in Example 450 and was obtained as an orange solid: ES$^+$ MS: 582 (M+H$^+$).

EXAMPLE 537

7-[(4-fluorophenyl)methyl]-4-hydroxy-N-(2-hydroxy-1,1-dimethylethyl)-1-{2-[(methylsulfonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-(2-hydroxy-1,1-dimethylethyl)-2-oxo-1,2-dihydro-1,5-naphthyridine-3-carboxamide employing methods similar to those described in Example 441 and was obtained as an orange solid: ES$^+$ MS: 507 (M+H$^+$).

EXAMPLE 538

7-[(4-fluorophenyl)methyl]-4-hydroxy-N-[2-(methyloxy)ethyl]-1-{2-[(4-morpholinylcarbonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-[2-(methyloxy)ethyl]-2-oxo-1,2-dihydro-1,5-naphthyridine-3-carboxamide and 4-morpholinecarbonyl chloride employing methods similar to those described in Example 450 and was obtained as an off-white solid: $^1$H NMR (300 MHz, DMSO-d$_6$) δ ppm 1.72 (s, 1 H), 3.13-3.20 (m, 3 H), 3.31 (s, 4 H), 3.45-3.50 (m, 5 H), 3.50-3.58 (m, 5 H), 4.13 (s, 2 H), 4.28 (t, J=6.39 Hz, 2 H), 6.77 (t, J=5.40 Hz, 1 H), 7.14 (t, J=8.84 Hz, 2 H), 7.41 (dd, J=8.49, 5.55 Hz, 2 H), 8.26 (s, 1 H), 8.55 (d, J=0.70 Hz, 1 H), 10.42 (t, J=5.62 Hz, 1 H); ES$^+$ MS: 528 (M+H$^+$).

EXAMPLE 539

7-[(4-fluorophenyl)methyl]-4-hydroxy-1-{2-[(4-morpholinylcarbonyl)amino]ethyl}-2-oxo-N-[3-(2-oxo-1-pyrrolidinyl)propyl]-1,2-dihydro-1,5-naphthyridine-3-carboxamide This compound was prepared from 1-(2-aminoethyl)-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide and 4-morpholinecarbonyl chloride employing methods similar to those described in Example 450 and was obtained as an orange solid: ES$^+$ MS: 595 (M+H$^+$).

EXAMPLE 540

7-[(4-fluorophenyl)methyl]-4-hydroxy-N-[1-(hydroxymethyl)-2-methylpropyl]-1-{2-[(methylsulfonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-[1-(hydroxymethyl)-2-methylpropyl]-2-oxo-1,2-dihydro-1,5-naphthyridine-3-carboxamide employing methods similar to those described in Example 441 and was obtained as an off-white solid: ES$^+$ MS: 521 (M+H$^+$).

EXAMPLE 541

7-[(4-fluorophenyl)methyl]-4-hydroxy-N-{3-[(1-methylethyl)oxy]propyl}-1-{2-[(methylsulfonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-{3-[(1-methylethyl)oxy]propyl}-2-oxo-1,2-dihydro-1,5-naphthyridine-3-carboxamide employing methods similar to those described in Example 441 and was obtained as an off-white solid: ES$^+$ MS: 535 (M+H$^+$).

EXAMPLE 542

7-[(4-fluorophenyl)methyl]-4-hydroxy-N-(2-hydroxy-1-methylethyl)-1-{2-[(4-morpholinylcarbonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-(2-hydroxy-1-methylethyl)-2-oxo-1,2-dihydro-1,5-naphthyridine-3-carboxamide and 4-morpholinecarbonyl chloride employing methods similar to those described in Example 450 and was obtained as an orange solid: ES$^+$ MS: 528 (M+H$^+$).

EXAMPLE 543

7-[(4-fluorophenylmethyl]-4-hydroxy-N-[1-methyl-2-(methyloxy)ethyl]-1-{2-[(4-morpholinylcarbonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-[1-methyl-2-(methyloxy)ethyl]-2-oxo-1,2-dihydro-1,5-naphthyridine-3-carboxamide and 4-morpholinecarbonyl chloride employing methods similar to those described in Example 450 and was obtained as an off-white solid: $^1$H NMR (300 MHz, DMSO-d$_6$) δ ppm 1.21 (d, J=6.60 Hz, 3 H), 1.74 (s, 1 H), 3.12-3.19 (m, 4 H), 3.30 (s, 2 H), 3.32 (s, 3 H), 3.43 (d, J=4.77 Hz, 2 H), 3.45-3.50 (m, 4 H), 4.14 (s, 2 H), 4.17-4.32(m, 3 H), 6.74(t, J=5.76 Hz, 1 H), 7.11-7.18(m, 2 H), 7.39-7.44(m, 2 H), 8.24 (s, 1 H), 8.55 (d, J=1.40 Hz, 1 H), 10.43 (d, J=8.00 Hz, 1 H); ES$^+$ MS: 542 (M+H$^+$).

EXAMPLE 544

7-[(4-fluorophenol)methyl]-4-hydroxy-N-{3-[(1-methylethyl)oxy]propyl}-1-{2-[(4-morpholinylcarbonyl(amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-{3-[(1-methylethyl)oxy]propyl}-2-oxo-1,2-dihydro-1,5-naphthyridine-3-carboxamide and 4-morpholinecarbonyl chloride employing methods similar to those described in Example 450 and was obtained as an off-white solid: ES$^+$ MS: 570 (M+H$^+$).

EXAMPLE 545

7-[(4-fluorophenyl)methyl]-4-hydroxy-N-[1-(hydroxymethyl)-2-methylpropyl]-1-{2-[(4-morpholinylcarbonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-[1-(hydroxymethyl)-2-methylpropyl]-2-oxo-1,2-dihydro-1,5-naphthyridine-3-carboxamide and 4-morpholinecarbonyl chloride employing methods similar to those described in Example 450 and was obtained as an off-white solid: $^1$H NMR (300 MHz, DMSO-d$_6$) δ ppm 0.88-0.96 (m, 6 H), 1.92-2.04 (m, 2 H), 3.12-3.21 (m, 4 H), 3.27-3.31 (m, 2 H), 3.44-3.51 (m, 5 H), 3.51-3.61 (m, 1 H), 3.86 (ddd, J=14.64, 5.30, 5.19 Hz, 1 H), 4.14 (s, 2 H), 4.29 (t, J=6.25 Hz, 2 H), 4.88 (t, J=5.05 Hz, 1 H), 6.77 (t, J=5.76 Hz, 1 H), 7.11-7.18 (m, 2 H), 7.39-7.45 (m, 2 H), 8.25 (d, J=1.54 Hz, 1 H), 8.54 (d, J=0.98 Hz, 1 H), 10.44 (d, J=9.13 Hz, 1 H); ES$^+$ MS: 556 (M+H$^+$).

EXAMPLE 546

7-[(4-fluorophenyl)methyl]-4-hydroxy-N-(2-hydroxy-1,1-dimethylethyl)-1-{2-[(4-morpholinylcarbonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-(2-hydroxy-1,1-dimethylethyl)-2-oxo-1,2-dihydro-1,5-naphthyridine-3-carboxamide and 4-morpholinecarbonyl chloride employing methods similar to those described in Example 450 and was obtained as an orange solid: $^1$H NMR (300 MHz, DMSO-d$_6$) δ ppm 1.36 (s, 6 H), 2.03 (s, 1 H), 3.13-3.20 (m, 4 H), 3.27-3.30 (m, 2 H), 3.48 (dt, J=4.56, 2.35 Hz, 6 H), 4.13 (s, 2 H), 4.27 (t, J=6.04 Hz, 2 H), 5.09-5.15 (m, 1 H), 6.75 (t, J=5.76 Hz, 1 H), 7.10-7.18 (m, 2.04 Hz, 2 H), 7.39-7.44 (m, 2 H), 8.23 (d, J=1.54 Hz, 1 H), 8.53 (d, J=1.26 Hz, 1 H), 10.53 (s, 1 H); ES$^+$ MS: 542 (M+H$^+$).

EXAMPLE 547

7-[(4-fluorophenyl)methyl]-4-hydroxy-N-(3-hydroxy-2,2-dimethylpropyl)-1-{2-[(4-morpholinylcarbonyl)amino]ethyl}-2-oxo-1,2-dihydro-1,5-naphthyridine-3-carboxamide This compound was prepared from 1-(2-aminoethyl)-7-[(4-fluorophenyl)methyl]-4-hydroxy-N-(3-hydroxy-2,2-dimethylpropyl)-2-oxo-1,2-dihydro-1,5-naphthyridine-3-carboxamide and 4-morpholinecarbonyl chloride employing methods similar to those described in Example 450 and was obtained as a white solid: ES$^+$ MS: 556 (M+H$^+$).

EXAMPLE 548

7-[(4-Fluorophenyl)methyl]-4-hydroxy-N-(2-hydroxyethyl)-2-oxo-1-[3-(2-oxo-1-pyrrolidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxo-1-pyrrolidinyl)propyl]-1,2-dihydro-1,5-naphthyridine-3-carboxylate and ethanolamine employing methods similar to those described in Example 202 and was obtained as a white solid. $^1$H NMR (400 MHz, CDCl$_3$) δ 10.36 (t, J=5.7 Hz, 1 H), 8.53 (s, 1 H), 7.41 (s, 1 H), 7.18 (dd, J=8.3, 5.5 Hz, 2 H), 7.03 (t, J=8.6 Hz, 2 H), 4.16-4.11 (m, 4 H), 3.85 (t, J=5.0 Hz, 2 H), 3.63 (m, 2 H), 3.38-3.33 (m, 4 H), 2.40 (t, J=8.0 Hz, 2 H), 2.03 (m, 2 H), 1.82 (m, 2 H); HRMS C$_{25}$H$_{27}$FN$_4$O$_5$ (M+H)$^+$ calcd 483.2044, found 483.2046.

EXAMPLE 549

7-[(4-Fluorophenyl)methyl]-4-hydroxy-N-methyl-2-oxo-1-[3-(2-oxo-1-pyrrolidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxo-1-pyrrolidinyl)propyl]-1,2-dihydro-1,5-naphthyridine-3-carboxylate and methylamine (8 M in ethanol) employing methods similar to those described in Example 202 and was obtained as a white solid. $^1$H NMR (400 MHz, CDCl$_3$) δ 10.04 (m, 1 H), 8.55 (s, 1 H), 7.41 (s, 1 H), 7.17 (dd, J=8.5, 5.3 Hz, 2 H), 7.02 (t, J=8.6 Hz, 2 H), 4.16-4.11 (m, 4 H), 3.41-3.37 (m, 4 H), 3.01 (d, J=4.9 Hz, 3 H), 2.39 (t, J=8.0 Hz, 2 H), 2.05 (m, 2 H), 1.83 (m, 2 H); HRMS C$_{24}$H$_{25}$FN$_4$O$_4$ (M+H)$^+$ calcd 453.1938, found 453.1945.

EXAMPLE 550 methyl {2-[7-[(4-fluorophenyl)methyl]-4-hydroxy-3-({[2-(methyloxy)ethyl]amino}carbonyl)-2-oxo-1,5-naphthyridine-1(2H)-yl]ethyl}carbamate This compound was prepared from 1-(2-aminoethyl)-7-[(4-fluorophenyl)methyl]-4-hydroxy-N-[2-(methyloxy)ethyl]-2-oxo-1,2-dihydro-1,5-naphthyridine-3-carboxamide employing methods similar to those described in Example 442 and was obtained as an orange solid: ES$^+$ MS: 473 (+H$^+$).

EXAMPLE 551 methyl {2-[7-[(4-fluorophenyl)methyl]-4-hydroxy-3-[({3-[(1-methylethyl)oxy]propyl}amino)carbonyl]-2-oxo-1,5-naphthyridine-1(2H)-yl]ethyl}carbamate This compound was prepared from 1-(2-aminoethyl)-7-[(4-fluorophenyl)methyl]-4-hydroxy-N-{3-[(1-methylethyl)oxy]propyl}-2-oxo-1,2-dihydro-1,5-naphthyridine-3-carboxamide employing methods similar to those described in Example 442 and was obtained as an off-white solid: ES$^+$ MS: 515 (M+H$^+$).

EXAMPLE 552 methyl {2-[7-[(4-fluorophenyl)methyl]-4-hydroxy-3-{[1-methyl-2-(methyloxy)ethyl]amino}carbonyl)-2-oxo-1,5-naphthyridine-1(2H)-yl]ethyl}carbamate This compound was prepared from 1-(2-aminoethyl)-7-[(4-fluorophenyl)methyl]-4-hydroxy-N-[1-methyl-2-(methyloxy)ethyl]-2-oxo-1,2-dihydro-1,5-naphthyridine-3-carboxamide employing methods similar to those described in Example 442 and was obtained as an off-white solid: $^1$H NMR (300 MHz, DMSO-$d_6$) δ ppm 1.20 (d, J=6.84 Hz, 3 H), 3.22-3.30 (m, 2 H), 3.31 (s, 3 H), 3.43 (d, J=5.34 Hz, 2 H), 3.46 (s, 3 H), 4.14 (s, 2 H), 4.20-4.31 (m, 3 H), 7.12-7.18 (m, 2 H), 7.27 (t, J=6.41 Hz, 1 H), 7.37-7.44 (m, 2 H), 8.11 (s, 1 H), 8.53 (s, 1 H), 10.37 (d, J=7.48 Hz, 1 H), 17.12 (s, 1 H); ES$^+$ MS: 486 (M+H$^+$).

EXAMPLE 553 methyl {2-[7-[(4-fluorophenyl)methyl]-4-hydroxy-3-({[1-(1-methylethyl)ethenyl]amino}carbonyl)-2-oxo-1,5-naphthyridine-1(2H)-yl]ethyl}carbamate This compound was prepared from 1-(2-aminoethyl)-7-[(4-fluorophenyl)methyl]-4-hydroxy-N-[1-(hydroxymethyl)-2-methylpropyl]-2-oxo-1,2-dihydro-1,5-naphthyridine-3-carboxamide employing methods similar to those described in Example 442 and was obtained as an orange solid: ES$^+$ MS: 482 (M+H$^+$).

EXAMPLE 554 methyl {2-[7-[(4-fluorophenyl)methyl]-4-hydroxy-2-oxo-3-({[3-(2-oxo-1-pyrrolidinyl)propyl]amino}carbonyl)-1,5-naphthyridine-1(2H)-yl]ethyl}carbamate This compound was prepared from 1-(2-aminoethyl)-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide employing methods similar to those described in Example 442 and was obtained as an orange solid: $^1$H NMR (300 MHz, DMSO-$d_6$) δ ppm 1.75 (qd, J=6.84, 6.62 Hz, 2 H), 1.86-1.99 (m, 2 H), 2.22 (t, J=8.01 Hz, 2 H), 3.19-3.28 (m, 4 H), 3.34-3.38 (m, 4 H), 3.46 (s, 3 H), 4.13 (s, 2 H), 4.29 (d, J=7.05 Hz, 2 H), 7.11-7.18 (m, 2 H), 7.29 (t, J=7.26 Hz, 1 H), 7.37-7.44 (m, 2 H), 8.11 (s, 1 H), 8.52 (s, 1 H), 10.05-10.53 (m, 1 H), 17.07-17.32 (m, 1 H); ES$^+$ MS: 540 (M+H$^+$).

EXAMPLE 555

7-[(4-fluorophenyl)methyl]-4-hydroxy-2-oxo-N,1-bis[3-(2-oxo-1-pyrrolidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxo-1-pyrrolidinyl)propyl]-1,2-dihydro-1,5-naphthyridine-3-carboxylate and 1-(3-aminopropyl)-2-pyrrolidinone employing methods similar to those described in Example 202. The free phenol existed as an oil and was therefore treated with aqueous sodium hydroxide solution and concentrated to give the corresponding sodium phenolate as a white solid. $^1$H NMR (300 MHz, CDCl$_3$) δ 10.27 (t, J=5.9 Hz, 1 H), 8.55 (d, J=1.3 Hz, 1 H), 7.43 (s, 1 H), 7.18 (dd, J=8.6, 5.4 Hz, 2 H), 7.03 (t, J=8.6 Hz, 2 H), 4.18-4.12 (m, 4 H), 3.49-3.36 (m, 10 H), 2.43-2.37 (m, 4 H), 2.10-2.00 (m, 4 H), 1.92-1.80 (m, 4 H); MS m/z 564 (M+H)$^+$.

EXAMPLE 556

Sodium 7-[(4-fluorophenyl)methyl]-3-({[(2R)-2-hydroxypropyl]amino}carbonyl)-2-oxo-1-[2-(2-oxo-1-pyrrolidinyl)ethyl]-1,2-dihydro-1,5-naphthyridine-4-olate This compound was prepared in two steps from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and (2R)-1-amino-2-propanol using conditions similar to Steps 5 & 6 from Example 457: $^1$H NMR (D$_2$O) δ 8.24 (1H, s), 7.51 (1H, s), 7.17 (2H, dd, J=6, 7 Hz), 6.94 (2H, t, J=7 Hz), 4.16 (2H, t, J=6 Hz), 3.98 (2H, s), 3.86-3.92 (1H, m), 3.35 (2H, t, J=5 Hz), 3.28 (1H, dd, J=4, 14 Hz), 3.13 (1H, dd, J=8, 14 Hz), 3.06 (2H, t, J=7 Hz), 1.86 (2H, t, J=8 Hz), 1.43-1.52 (2H, m), 1.07 (3H, d, J=6 Hz); ES$^+$ MS: 483 (M+H$^+$).

EXAMPLE 557

N-[(2S)-2,3-Dihydroxypropyl]-7-[(4-fluorophenyl)methyl]-4-hydroxy-1-methyl-2-oxo-1,2-dihydro-1,5-naphthyridine-3-carboxamide In a manner similar to that described in example 516, N-[(2S)-2,3-dihydroxypropyl]-7-[(4-fluorophenyl)methyl]-4-hydroxy-1-methyl-2-oxo-1,2-dihydro-1,5-naphthyridine-3-carboxamide was prepared as a white solid in 88% yield as a white solid. Analytical data was identical to that of example 516.

EXAMPLE 558

1-[2-(Cyclobutylamino)-2-oxoethyl]-7-(4-fluorobenzyl)-4-hydroxy-N-(2-methoxyethyl)-2-oxo-1,2-dihydro-1,5-naphthyridine-3-carboxamide O-(7-Azabenzotriazol-1-yl)-N,N,N',N',-tetramethyluronium hexafluorophosphate (57 mg, 0.15 mmol) was added to a mixture of [7-[(4-fluorophenyl)methyl]-4-hydroxy-3-({[2-(methyloxy)ethyl]amino}carbonyl)-2-oxo-1,5-naphthyridine-1(2H)-yl]acetic acid, the title compound in Example 171 (50 mg, 0.12 mmol), triethylamine (0.02 mL, 0.15 mmol) and cyclobutylamine (0.012 mL, 0.15 mmol) in DMF (1 mL) at rt. After 1 h, the mixture was diluted with H$_2$O (4 mL) and the title compound was collected by filtration to give a white solid: $^1$H NMR (d$_6$-DMSO) δ 10.22 (1H, m), 8.54 (1H, s), 8.42 (1H, m), 7.75 (1H, s), 7.31 (2H, m), 7.10 (2H, m), 4.81 (2H, s), 4.13 (1H, m), 4.10 (2H, s), 3.52 (4H, m), 3.27 (3H, s), 2.09 (2H, m), 1.84 (2H, m), 1.59 (2H, m); HRMS calcd for C$_{25}$H$_{27}$FN$_4$O$_5$+H$^+$: 483.2044. Found: 483.2049.

EXAMPLE 559

7-(4-Fluorobenzyl)-4-hydroxy-1-[2-(isopropylamino)-2-oxoethyl]-N-(2-methoxyethyl)-2-oxo-1,2-dihydro-1,5-naphthyridine-3-carboxamide The title compound was made in a similar manner to example 558 using isopropylamine to give a white solid: $^1$H NMR (d$_6$-DMSO) δ 10.24 (1H, m), 8.55 (1H, s), 8.04 (1H, m), 7.66 (1H, s), 7.30 (2H, m), 7.10 (2H, m), 4.81 (2H, s), 4.11

(2H, s), 3.76 (1H, m), 3.49 (4H, m), 3.27 (3H, s), 1.00 (6H, d, J=6 Hz); HRMS calcd for $C_{24}H_{27}FN_4O_5+H^+$: 471.2044. Found: 471.2039.

EXAMPLE 560

7-[(4-fluorophenyl)methyl]-4-hydroxy-N-{3-[(1-methylethyl)oxy]propyl}-2-oxo-1-[2-(2-oxo-1-pyrrolidinyl)ethyl]-1,2-dihydro-1,5-naphthyridine-3-carboxamide This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 3-[(1-methylethyl)oxy]-1-propanamine using conditions similar to those employed in Example 563 to provide a white solid: $ES^+$ MS: 525 $(M+H^+)$.

EXAMPLE 561

7-[(4-fluorophenyl)methyl]-4-hydroxy-2-oxo-N-[2-(2-oxo-1-imidazolidinyl)ethyl]-1-[2-(2-oxo-1-pyrrolidinyl)ethyl]-1,2-dihydro-1,5-naphthyridine-3-carboxamide This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 1-(2-aminoethyl)-2-imidazolidinone using conditions similar to those employed in Example 563 to provide a white solid: $ES^+$ MS: 537 $(M+H^+)$.

EXAMPLE 562

7-[(4-fluorophenyl)methyl]-4-hydroxy-2-oxo-1-[2-(2-oxo-1-pyrrolidinyl)ethyl]-N-(tetrahydro-2-furanylmethyl)-1,2-dihydro-1,5-naphthyridine-3-carboxamide This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and (tetrahydro-2-furanylmethyl)amine using conditions similar to those employed in Example 563 to provide a white solid: $^1$H NMR ($d^6$-DMSO) δ 10.39 (1H, t, J=6 Hz), 8.55 (1H, s), 8.12 (1H, s), 7.40 (2H, dd, J=6, 9 Hz), 7.13 (2H, t, J=9 Hz), 4.38 (2H, b), 4.15 (2H, s), 3.95-4.02 (1H, m), 3.80 (1H, q, J=8 Hz), 3.66 (1H, q, J=8 Hz), 3.50-3.57 (1H, m), 3.32-3.46 (5H, m), 1.89-1.99 (3H, m), 1.78-1.87 (2H, m), 1.70-1.78 (2H, m), 1.49-1.58 (1H, m); $ES^+$ MS: 509 $(+H^+)$.

EXAMPLE 563

7-[(4-fluorophenyl)methyl]-4-hydroxy-N-{2-[(2-hydroxyethyl)oxy]ethyl}-2-oxo-1-[2-(2-oxo-1-pyrrolidinyl)ethyl]-1,2-dihydro-1,5-naphthyridine-3-carboxamide A mixture of ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate (30 mg, 0.066 mmol) and 2-[(2-aminoethyl)oxy]ethanol (100 μL) was heated in EtOH (3 mL) at 175° C. for 45 min. in a microwave. The reaction mixture was evaporated in vacuo and partitioned between 1N $NaHSO_4$ and $CH_2Cl_2$. The aqueous phase was back-extracted with $CH_2Cl_2$ and the combined organic layers were dried over $MgSO_4$, filtered, evaporated in vacuo and triturated with $Et_2O$ to provide the product as a white solid: $^1$H NMR ($d^6$-DMSO) δ 10.35 (1H, t, J=5 Hz), 8.54 (1H, s), 8.09 (1H, s), 7.39 (2H, dd, J=5, 9 Hz), 7.11 (2H, t, J=9 Hz), 4.59 (1H, t, J=5 Hz), 4.36 (2H, t, J=6 Hz), 4.14 (2H, s), 3.33-3.56 (12H, m), 1.93 (2H, t, J=8 Hz), 1.74 (2H, t, J=7 Hz); $ES^+$ MS: 513 $(M+H^+)$.

EXAMPLE 564

7-[(4-fluorophenyl)methyl]-4-hydroxy-2-oxo-1-[2-(2-oxo-1-pyrrolidinyl)ethyl]-N-[3-(2-oxo-1-pyrrolidinyl)propyl]-1,2-dihydro-1,5-naphthyridine-3-carboxamide This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 1-(3-aminopropyl)-2-pyrrolidinone using conditions similar to those employed in Example 563 to provide a white solid: $^1$H NMR ($d^6$-DMSO) δ 10.28 (1H, t, J=6 Hz), 8.55 (1H, s), 8.10 (1H, s), 7.40 (2H, dd, J=6, 9 Hz), 7.13 (2H, t, J=9 Hz), 4.37 (2H, t, J=6 Hz), 4.15 (2H, s), 3.43 (2H, t, J=6 Hz), 3.31-3.39 (6H, m), 3.22 (2H, t, J=7 Hz), 2.22 (2H, t, J=8 Hz), 1.87-2.00 (4H, m), 1.70-1.78 (4H, m); $ES^+$ MS: 550 $(M+H^+)$.

EXAMPLE 565

N-(2,3-dihydroxypropyl)-7-[(4-fluorophenyl)methyl]-4-hydroxy-2-oxo-1-[2-(2-oxo-1-pyrrolidinyl)ethyl]-1,2-dihydro-1,5-naphthyridine-3-carboxamide This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 3-amino-1,2-propanediol using conditions similar to those employed in Example 563 to provide a white solid: $ES^+$ MS: 499 $(M+H^+)$.

EXAMPLE 566

7-[(4-fluorophenyl)methyl]-4-hydroxy-N-{1-[(methyloxy)methyl]propyl}-2-oxo-1-[2-(2-oxo-1-pyrrolidinyl)ethyl]-1,2-dihydro-1,5-naphthyridine-3-carboxamide This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 1-(methyloxy)-2-butanamine using conditions similar to those employed in Example 563 to provide a white solid: $^1$H NMR ($d^6$-DMSO) δ 10.32 (1H, d, J=9 Hz), 8.53 (1H, s), 8.11 (1H, s), 7.38 (2H, dd, J=6, 9 Hz), 7.11 (2H, t, J=9 Hz), 4.37 (2H, b), 4.14 (2H, s), 4.05 (1H, b), 3.32-3.47 (6H, m), 3.26 (3H, s), 1.95 (2H, t, J=8 Hz), 1.69-1.80 (2H, m), 1.56-1.66 (1H, m), 1.42-1.56 (1H, m), 0.86 (3H, t, J=8 Hz); $ES^+$ MS: 511 $(M+H^+)$.

EXAMPLE 567

7-[(4-fluorophenyl)methyl]-4-hydroxy-N-[2-hydroxy-1-(hydroxymethyl)ethyl]-2-oxo-1-[2-(2-oxo-1-pyrrolidinyl)ethyl]-1,2-dihydro-1,5-naphthyridine-3-carboxamide This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 2-amino-1,

EXAMPLE 568

7-[(4-fluorophenyl)methyl]-4-hydroxy-N-[1-(hydroxymethyl)-2-methylpropyl]-2-oxo-1-[2-(2-oxo-1-pyrrolidinyl)ethyl]-1,2-dihydro-1,5-naphthyridine-3-carboxamide This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 2-amino-3-methyl-1-butanol using conditions similar to those employed in Example 563 to provide a white solid: $^1$H NMR (d$^6$-DMSO) δ 10.38 (1H, d, J=9 Hz), 8.55 (1H, s), 8.14 (1H, s), 7.40 (2H, dd, J=6, 9 Hz), 7.13 (2H, t, J=9 Hz), 4.87 (1H, t, J=5 Hz), 4.30-4.50 (2H, m), 4.16 (2H, s), 3.79-3.87 (1H, m), 3.32-3.60 (7H, m), 1.89-2.04 (2H, m), 1.71-1.81 (2H, m), 0.90 (6H, dd, J=7, 9 Hz); ES$^+$ MS: 511 (M+H$^+$).

EXAMPLE 569

7-[(4-fluorophenyl)methyl]-4-hydroxy-N-[1-(hydroxymethyl)butyl]-2-oxo-1-[2-(2-oxo-1-pyrrolidinyl)ethyl]-1,2-dihydro-1,5-naphthyridine-3-carboxamide This compound was prepared from ethyl 7-(4-fluorobenzyl)-4-hydroxy-2-oxo-1-[2-(2-oxopyrrolidin-1-yl)ethyl]-1,2-dihydro-1,5-naphthyridine-3-carboxylate and 2-amino-1-pentanol using conditions similar to those employed in Example 563 to provide a white solid: $^1$H NMR (d$^6$-DMSO) δ 10.31 (1H, d, J=8 Hz), 8.55 (1H, s), 8.12 (1H, s), 7.40 (2H, dd, J=6, 9 Hz), 7.13 (2H, t, J=9 Hz), 4.93 (1H, t, J=5 Hz), 4.30-4.46 (2H, m), 4.15 (2H, s), 3.94-4.03 (1H, m), 3.32-3.53 (6H, m), 1.88-2.05 (2H, m), 1.68-1.82 (2H, m), 1.42-1.64 (2H, m), 1.25-1.36 (2H, m), 0.88 (3H, t, J=7 Hz); ES$^+$ MS: 511 (M+H$^+$).

EXAMPLE 570

7-(4-Fluorobenzyl)-4-hydroxy-1-[2-(3-hydroxyazetidin-1-yl)-2-oxoethyl]-N-(2-methoxyethyl)-2-oxo-1,2-dihydro-1,5-naphthyridine-3-carboxamide The title compound was made in a similar manner to example 558 using azetidine-3-ol to give a beige solid: $^1$H NMR (d$_6$-DMSO) δ 10.22 (1H, m), 8.53 (1H, s), 7.82 (1H, s), 7.33 (2H, m), 7.14 (2H, m), 4.91 (2H, m), 4.55 (1H, m), 4.47 (1H, m), 4.12 (2H, s), 4.06 (2H, m), 3.63 (1H, m), 3.50 (4H, m), 3.28 (3H, s); HRMS calcd for $C_{24}H_{25}FN_4O_6$+H$^+$: 485.1836. Found: 485.1836.

EXAMPLE 571

7-[(4-fluorophenyl)methyl]-4-hydroxy-N-[(1S)-2-hydroxy-1-methylethyl]-2-oxo-1-(2,2,2-trifluoroethyl)-1,2-dihydro-1,5-naphthyridine-3-carboxamide In a manner similar to that described in 321, from ethyl 7-[(4-fluorophenyl)methyl]-4-hydroxy-2-oxo-1-(2,2,2-trifluoroethyl)-1,2-dihydro-1,5-naphthyridine-3-carboxylate (38 mg, 0.089 mmol) and (2S)-2-amino-1-propanol (0.05 mL) was prepared 7-[(4-fluorophenyl)methyl]-4-hydroxy-N-[(1 S)-2-hydroxy-1-methylethyl]-2-oxo-1-(2,2,2-trifluoroethyl)-1,2-dihydro-1,5-naphthyridine-3-carboxamide (34 mg, 85% yield) as a white solid. $^1$H NMR (DMSO-d$_6$) δ 10.07 (d, J=8 Hz, 1 H), 8.58 (s, 1 H), 8.19 (s, 1 H), 7.37-7.33 (m, 2 H), 7.14-7.09 (m, 2 H), 5.19 (m, 2 H), 5.01 (m, 1 H), 4.12 (s, 2 H), 4.03 (m, 1 H), 3.43 (m, 2 H), 1.16 (d, J=6.8 Hz, 3 H); HRMS m/z calcd for $C_{21}H_{20}F_4N_3O_4$: 454.1385. Found: 454.1391.

EXAMPLE 572

7-[(4-fluorophenyl)methyl]-4-hydroxy-N-[(1R)-2-hydroxy-1-methylethyl]-2-oxo-1-(2,2,2-trifluoroethyl)-1,2-dihydro-1,5-naphthyridine-3-carboxamide In a manner similar to that described in example 571, from from ethyl 7-[(4-fluorophenyl)methyl]-4-hydroxy-2-oxo-1-(2,2,2-trifluoroethyl)-1,2-dihydro-1,5-naphthyridine-3-carboxylate (38 mg, 0.089 mmol) and (2R)-2-amino-1-propanol (0.05 mL) was prepared 7-[(4-fluorophenyl)methyl]-4-hydroxy-N-[(1R)-2-hydroxy-1-methylethyl]-2-oxo-1-(2,2,2-trifluoroethyl)-1,2-dihydro-1,5-naphthyridine-3-carboxamide (40 mg, 95% yield) as a white solid. Analytical data was identical to example 571.

EXAMPLE 573 sodium 7-[(4-fluorophenyl)methyl]-3-({[(1S)-2-hydroxy-1-methylethyl]amino}carbonyl)-1-methyl-2-oxo-1,2-dihydro-1,5-naphthyridine-4-olate In a manner similar to that described in example 474, from 7-[(4-fluorophenyl)methyl]-4-hydroxy-N-[(1S)-2-hydroxy-1-methylethyl]-1-methyl-2-oxo-1,2-dihydro-1,5-naphthyridine-3-carboxamide (436 mg, 1.13 mmol described in example 359) and sodium hydroxide (1.08 mL of a 1 N solution) was prepared sodium 7-[(4-fluorophenyl)methyl]-3-({[(1S)-2-hydroxy-1-methylethyl]amino}carbonyl)-1-methyl-2-oxo-1,2-dihydro-1,5-naphthyridine-4-olate (331 mg, 72% yield) as a white solid. $^1$H NMR (DMSO-d$_6$) δ 10.41 (d, J=7.2 Hz, 1 H), 8.16 (s, 1 H), 7.59 (s, 1 H), 7.33-7.29 (m, 2 H), 7.11-7.07 (m, 2 H), 4.79 (m, 1 H), 3.93 (m, 1 H), 3.41 (m, 1 H), 3.28 (s, 3 H), 3.24 (m, 1 H), 1.03 (d, J=6.8 Hz, 3 H); MS m/z 386 (M+1).

EXAMPLE 574

1-{2-[acetyl(methyl)amino]ethyl}-7-[(4-fluorophenyl)methyl]-4-hydroxy-N-(2-hydroxy-1-methylethyl)-2-oxo-1,2-dihydro-1,5-naphthyridine-3-carboxamide Step 1: Synthesis of ethyl 1-{2-[acetyl(methyl)amino]ethyl}-7-[(4-fluorophenyl)methyl]-4-hydroxy-2-oxo-1,2-dihydro-1,5-naphthyridine-3-carboxylate A solution of ethyl 7-[(4-fluorophenyl)methyl]-4-hydroxy-1-[2-(methyl {[(phenylmethyl)oxy]carbonyl}amino)ethyl]-2-oxo-1,2-dihydro-1,5-naphthyridine-3-carboxylate (0.023 g, 0.043 mmol) in CH$_2$Cl$_2$ (1.5 mL) was combined with diisopropylethylamine (0.0038 mL, 0.22 mmol), acetic anhydride (0.021 mL, 0.22 mmol) and Pd/C (0.012 g, 10% w/w). The resulting suspension was flushed with nitrogen and evacuated several times the charged with hydrogen under a balloon and stirred at ambient temperature overnight. The reaction mixture was filtered, washed with CH$_2$Cl$_2$, and concentrated in vacuo. The residue was dissolved in CH$_2$Cl$_2$, washed with 1N NaHSO$_4$, and brine, concentrated the organics to afford the title compound as an oil: $^1$H NMR (400 MHz, DMSO-d$_6$) δ ppm 1.22 (d, J=6.59 Hz, 3 H), 1.86 (s, 3 H), 2.94 (s, 3 H), 3.50 (t, J=6.86 Hz, 2 H), 4.18 (s, 2 H), 4.28 (q, J=6.83 Hz, 4 H), 7.12 (t, J=8.69 Hz, 2 H), 7.35-7.40 (m, 2 H), 8.02 (d, J=6.40 Hz, 1 H), 8.47 (s, 1 H); ES$^+$ MS: 442 (M+H$^+$).

Step 2: Synthesis of 1-{2-[acetyl(methyl)amino] ethyl}-7-[(4-fluorophenyl)methyl]-4-hydroxy-N-(2-hydroxy-1-methylethyl)-2-oxo-1,2-dihydro-1,5-naphthyridine-3-carboxamide A solution of ethyl 1-{2-[acetyl(methyl)amino]ethyl}-7-[(4-fluorophenyl)methyl]-4-hydroxy-2-oxo-1,2-dihydro-1,5-naphthyridine-3-carboxylate (0.019 g, 0.039 mmol) in EtOH (3 mL) under nitrogen was treated with 2-amino-1-propanol (0.02 mL, 0.27 mmol) for 30 min. (160° C. in a microwave vessel. After the reaction was cooled to ambient temperature the resulting suspension was concentrated in vacuo, triturated with Et$_2$O:MeOH, filtered, and the filtered solid was washed with Et$_2$O then thoroughly dried under high vacuum to provide the title compound as an off-white solid: $^1$H NMR (400 MHz, DMSO-d$_6$ (90° C.) δ ppm 1.23 (d, J=6.86 Hz, 3 H), 1.85 (s, 3 H), 2.95 (s, 3 H), 3.50-3.55 (m, 4 H), 4.08-4.11 (m, 1 H), 4.18 (s, 2 H), 4.35 (s, 2 H), 4.69-4.72 (m, 1 H), 7.10-7.15 (m, 2 H), 7.37-7.42 (m, 2 H), 8.08 (s, 1 H), 8.55 (s, 1 H), 10.29 (d, J=4.53 Hz, 1 H), 17.15 (s, 1 H); ES$^+$ MS: 471 (M+H$^+$).

EXAMPLE 575

7-[(4-Fluorophenyl)methyl]-4-hydroxy-N-(2-hydroxypropyl)-2-oxo-1-[3-(2-oxo-1-pyrrolidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxo-1-pyrrolidinyl) propyl]-1 ,2-dihydro-1,5-naphthyridine-3-carboxylate and 1-amino-2-propanol employing methods similar to those described in Example 202. $^1$H NMR (400 MHz, CDCl$_3$) δ 10.36 (t, J=5.8 Hz, 1 H), 8.52 (s, 1 H), 7.38 (s, 1 H), 7.16 (dd, J=8.2, 5.5 Hz, 2 H), 7.01 (t, J=8.7 Hz, 2 H), 4.20-4.00 (m, 6 H), 3.60 (m, 1 H), 3.43-3.25 (m, 5 H), 2.39 (m, 2 H), 2.01 (m, 2 H), 1.80 (m, 2 H), 1.25 (d, J=6.4 Hz, 3 H); MS m/z 497 (M+H)$^+$.

EXAMPLE 576

1-Ethyl-7-[(4-fluorophenyl)methyl]-4-hydroxy-N-[(1S)-2-hydroxy-1-methylethyl]-2-oxo-1,2-dihydro-1,5-naphthyridine-3-carboxamide In a similar manner to that described in example 196, from ethyl 1-ethyl-7-[(4-fluorophenyl)methyl]-4-hydroxy-2-oxo-1,2-dihydro-1,5-naphthyridine-3-carboxylate (60 mg, 0.162 mmol) and (2S)-2-amino-1-propanol (0.05 mL) was prepared 1-ethyl-7-[(4-fluorophenyl)methyl]-4-hydroxy-N-[(1S)-2-hydroxy-1-methylethyl]-2-oxo-1,2-dihydro-1,5-naphthyridine-3-carboxamide (33 mg, 51% yield) as a white solid after purification by reverse phase HPLC. $^1$H NMR (CDCl$_3$) δ 10.27 (d, J=7.6 Hz, 1 H), 8.50 (s, 1 H), 7.33 (s, 1 H), 7.16-7.12 (m, 2 H), 7.04-6.98 (m, 2 H), 4.27 (m, 6 H), 3.78 (dd, J=11.2, 3.6 Hz, 1 H), 3.65 (dd, J=11.2, 6 Hz, 1 H), 1.29 (d, J=6.8 Hz, 3 H), 1.19 (m, 3 H); MS m/z 400 (M+1).

EXAMPLE 577

7-[(4-Fluorophenyl)methyl]-4-hydroxy-N-[(2S)-2-hydroxypropyl]-1-(3-hydroxypropyl)-2-oxo-1,2-dihydro-1,5-naphthyridine-3-carboxamide In a similar manner to that described in example 196, from ethyl 7-[(4-fluorophenyl)methyl]-4-hydroxy-1-(3-hydroxypropyl)-2-oxo-1,2-dihydro-1,5-naphthyridine-3-carboxylate (60 mg, 0.15 mmol) and (2S)-1-amino-2-propanol (0.05 mL), was prepared 7-[(4-fluorophenyl)methyl]-4-hydroxy-N-[(2S)-2-hydroxypropyl]-1-(3-hydroxypropyl)-2-oxo-1,2-dihydro-1,5-naphthyridine-3-carboxamide (16 mg, 25% yield) as a white solid after purification by reverse phase HPLC. Analytical data was identical to that described in example 578.

EXAMPLE 578

7-[(4-fluorophenyl)methyl]-4-hydroxy-N-[(2R)-2-hydroxypropyl]-1-(3-hydroxypropyl)-2-oxo-1,2-dihydro-1,5-naphthyridine-3-carboxamide In a similar manner to that described in example 196, from ethyl 7-[(4-fluorophenyl)methyl]-4-hydroxy-1-(3-hydroxypropyl)-2-oxo-1,2-dihydro-1,5-naphthyridine-3-carboxylate (60 mg, 0.15 mmol) and (2R)-1-amino-2-propanol (0.05 mL) was prepared 7-[(4-fluorophenyl)methyl]-4-hydroxy-N-[(2R)-2-hydroxypropyl]-1-(3-hydroxypropyl)-2-oxo-1,2-dihydro-1,5-naphthyridine-3-carboxamide (16 mg, 25% yield) as a white solid after purification by reverse phase HPLC. $^1$H NMR (CDCl$_3$) δ 10.02 (s, 1 H), 8.35 (s, 1 H), 7.56 (s, 1 H), 7.06-7.03 (m, 2 H), 6.89-6.84 (m, 2 H), 4.17 (m, 2 H), 4.01 (s, 2 H), 3.89 (m, 1 H), 3.45-3.39 (m, 3 H), 3.19 (m, 1 H),1.71 (m, 2 H), 1.09 (m, 3 H); MS m/z 430 (M+1).

EXAMPLE 579

1-Ethyl-7-[(4-fluorophenyl)methyl]-4-hydroxy-N-[(1R)-2-hydroxy-1-methylethyl]-2-oxo-1,2-dihydro-1,5-naphthyridine-3-carboxamide In a similar manner to that described in example 196, from ethyl 1-ethyl-7-[(4-fluorophenyl)methyl]-4-hydroxy-2-oxo-1,2-dihydro-1,5-naphthyridine-3-carboxylate (60 mg, 0.162 mmol) and (2R)-2-amino-1-propanol (0.05 mL) was prepared 1-ethyl-7-[(4-fluorophenyl)methyl]-4-hydroxy-N-[(1R)-2-hydroxy-1-methylethyl]-2-oxo-1,2-dihydro-1,5-naphthyridine-3-carboxamide (50 mg, 85% yield) as a white solid after purification by reverse phase HPLC. Analytical data was identical to that described in example 576.

EXAMPLE 580

7-[(4-fluorophenyl)methyl]-4-hydroxy-N-(2-hydroxyethyl)-2-oxo-1-[2-(2-oxo-1-piperidinyl)ethyl]-1,2-dihydro-1,5-naphthyridine-3-carboxamide Ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate. This compound was prepared in 3 steps from ethyl 3-amino-5-[(4-fluorophenyl)methyl]-2-pyridinecarboxylate and (2-oxo-1-piperidinyl)acetaldehyde (WO 01/90081A1) employing methods similar to Steps 2-4 of Example 457 to provide the product as a white solid: ¹H NMR (CDCl₃) δ 8.50 (1H, s), 8.35 (1H, s), 7.23-7.28 (2H, m), 6.99 (2H, t, J=9 Hz), 4.53 (2H, q, J=7 Hz), 4.36 (2H, t, J=8 Hz), 4.16 (2H, s), 3.54 (2H, t, J=7), 3.41 (2H, b), 2.39 (2H, b), 1.76-1.81 (4H, m), 1.49 (3H, t, J=7 Hz); ES⁺ MS: 490 (M+Na⁺).

7-[(4-Fluorophenyl)methyl]-4-hydroxy-N-(2-hydroxyethyl)-2-oxo-1-[2-(2-oxo-1-piperidinyl)ethyl]-1,2-dihydro-1,5-naphthyridine-3-carboxamide. This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 2-aminoethanol using methods similar to Example 563 to provide a white solid: ¹H NMR (CDCl₃) δ 10.42 (1H, b), 8.53 (1H, s), 8.25 (1H, s), 7.21-7.26 (2H, m), 6.97 (2H, t, J=8 Hz), 4.38 (2H, t, J=7 Hz), 4.15 (2H, s), 3.86 (2H, t, J=5 Hz), 3.49-3.66 (4H, m), 3.35 (2H, b), 2.85 (1H, t, J=5 Hz), 2.35 (2H, b), 1.72-1.76 (4H, m); ES⁺ MS: 483 (M+H⁺).

EXAMPLE 581

7-[(4-Fluorophenyl)methyl]-4-hydroxy-N-[2-(methyloxy)ethyl]-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 2-(methyloxy)ethanamine using methods similar to Example 563 to provide a white solid: ¹H NMR (CDCl₃) δ 10.29 (1H, b), 8.54 (1H, s), 8.26 (1H, s), 7.24 (2H, dd, J=6, 9 Hz), 6.99 (2H, t, J=9 Hz), 4.39 (2H, t, J=8 Hz), 4.15 (2H, s), 3.50-3.69 (6H, m), 3.42 (3H, s), 3.36 (2H, b), 2.36 (2H, b), 1.75 (4H, b); ES⁺ MS: 497 (M+H⁺).

EXAMPLE 582

7-[(4-Fluorophenyl)methyl]-4-hydroxy-N-(2-hydroxy-1-methylethyl)-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 2-amino-1-propanol using methods similar to Example 563 to provide a white solid: ¹H NMR (CDCl₃) δ 10.28 (1H, d, J=7 Hz), 8.55 (1H, s), 8.28 (1H, s), 7.25 (2H, dd, J=6, 8 Hz), 6.99 (2H, t, J=8 Hz), 4.38 (2H, t, J=8 Hz), 4.25-4.34 (1H, m), 4.16 (2H, s), 3.80 (1H, dd, J=4, 11 Hz), 3.68 (1H, dd, J=6, 11 Hz), 3.53 (2H, t, J=7 Hz), 3.37 (2H, b), 2.36 (2H, b), 1.76 (4H, b), 1.33 (3H, d, J=7 Hz); ES⁺ MS: 497 (M+H⁺).

EXAMPLE 583

7-[(4-Fluorophenyl)methyl]-4-hydroxy-N-(2-hydroxypropyl)-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 1-amino-2-propanol using methods similar to Example 563 to provide a white solid: ¹H NMR (CDCl₃) δ 10.42 (1H, b), 8.56 (1H, s), 8.30 (1H, s), 7.25 (2H, dd, J=5, 9 Hz), 6.99 (2H, dd, J=9 Hz), 4.39 (2H, t, J=7 Hz), 4.16 (2H, s), 4.04-4.12 (1H, m), 3.60-3.67 (1H, m), 3.54 (2H, t, J=8 Hz), 3.34-3.42 (3H, m), 2.36 (2H, b), 1.73-1.80 (4H, m), 1.28 (3H, d, J=6 Hz); ES⁺ MS: 497 (M+H⁺).

EXAMPLE 584

7-[(4-Fluorophenyl)methyl]-4-hydroxy-N-[1-methyl-2-(methyloxy)ethyl]-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 1-(methyloxy)-2-propanamine using methods similar to Example 563 to provide a white solid: ¹H NMR (CDCl₃) δ 10.17 (1H, d, J=8 Hz), 8.54 (1H, s), 8.27 (1H, s), 7.23 (2H, dd, J=5, 8 Hz), 6.98 (2H, t, J=8 Hz), 4.31-4.43 (3H, m), 4.15 (2H, s), 3.53 (2H, b), 3.47 (2H, d, J=5 Hz), 3.40 (3H, s), 3.36 (2H, b), 2.35 (2H, b), 1.75 (4H, b), 1.30 (3H, d, J=7 Hz); ES⁺ MS: 511 (M+H⁺).

EXAMPLE 585

N-[2-(Ethyloxy)ethyl]-7-[(4-fluorophenyl)methyl]-4-hydroxy-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 2-(ethyloxy)ethanamine using methods similar to Example 563 to provide a white solid: ¹H NMR (CDCl₃) δ 10.36 (1H, b), 8.53 (1H, s), 8.16 (1H, s), 7.37 (2H, dd, J=6, 8 Hz), 7.11 (2H, t, J=9 Hz), 4.37 (2H, t, J=6 Hz), 4.13 (2H, s), 3.42-3.50 (8H, m), 3.24 (2H, t, J=6 Hz), 1.99 (2H, t, J=6 Hz), 1.48-1.62 (4H, m), 1.10 (3H, t, J=7 Hz); ES⁺ MS: 511 (M+H⁺).

EXAMPLE 586

7-[(4-Fluorophenyl)methyl]-4-hydroxy-N-{3-[(1-methylethyl)oxy]propyl}-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 3-[(1-methylethyl)oxy]-1-propanamine using methods similar to Example 563 to provide a white solid: ES⁺ MS: 539 (M+H⁺).

EXAMPLE 587

7-[(4-Fluorophenyl)methyl]-4-hydroxy-N-{2-[(1-methylethyl)oxy]ethyl}1-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 2-[(1-methylethyl)oxy]ethanamine using methods similar to Example 563 to provide a white solid: ¹H NMR (d⁶-DMSO) δ 10.37 (1H, b), 8.53 (1H, s), 8.15 (1H, s), 7.37 (2H, dd, J=6, 8 Hz), 7.11 (2H, t, J=9 Hz), 4.37 (2H, b), 4.13 (2H, s), 3.53-3.62 (1H, m), 3.45-3.53 (6H, m), 3.24 (2H, t, J=6 Hz), 1.98 (2H, t, J=6 Hz), 1.48-1.63 (4H, m), 1.09 (6H, d, J=6 Hz); ES+ MS: 525 (M+H+).

EXAMPLE 588

7-[(4-Fluorophenyl)methyl]-4-hydroxy-2-oxo-1-[2-(2-oxo-1-piperidinyl)ethyl]-N-[3-(2-oxo-1-pyrrolidinyl)propyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 1-(3-aminopropyl)-2-pyrrolidinone using methods similar to Example 563 to provide a white solid: $^1$H NMR (d$^6$-DMSO) δ 10.28 (1H, t, J=6 Hz), 8.53 (1H, s), 8.16 (1H, s), 7.38 (2H, dd, J=6, 8 Hz), 7.11 (2H, t, J=9 Hz), 4.35 (2H, t, J=6 Hz), 4.13 (2H, s), 3.47 (2H, t, J=7 Hz), 3.18-3.35 (8H, m), 2.19 (2H, t, J=9 Hz), 2.02 (2H, t, J=5 Hz), 1.84-1.94 (2H, m), 1.69-1.76 (2H, m), 1.49-1.62 (4H, m); ES+ MS: 564 (M+H+).

EXAMPLE 589

7-[(4-Fluorophenyl)methyl]-4-hydroxy-N-(4-hydroxybutyl)-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 4-amino-1-butanol using methods similar to Example 563 to provide a white solid: $^1$H NMR (d$^6$-DMSO) δ 10.28 (1H, t, J=7 Hz), 8.53 (1H, s), 8.17 (1H, s), 7.38 (2H, dd, J=6, 8 Hz), 7.11 (2H, t, J=9 Hz), 4.42 (1H, t, J=5 Hz), 4.36 (2H, t, J=5 Hz), 4.13 (2H, s), 3.47 (2H, t, J=7 Hz), 3.21-3.42 (6H, m), 2.00 (2H, t, J=6 Hz), 1.41-1.82 (8H, m); ES+ MS: 511 (M+H+).

EXAMPLE 590

7-[(4-Fluorophenyl)methyl]-4-hydroxy-N-[2-hydroxy-1-(hydroxymethyl)ethyl]-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 2-amino-1,3-propanediol using methods similar to Example 563 to provide a white solid: ES+ MS: 513 (M+H+).

EXAMPLE 591

7-[(4-fluorophenyl)methyl]-4-hydroxy-N-methyl-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and methylamine using methods similar to Example 563 to provide a white solid: $^1$H NMR (d$^6$-DMSO) δ 10.10 (1H, b), 8.53 (1H, s), 8.15 (1H, s), 7.37 (2H, dd, J=6, 8 Hz), 7.11 (2H, t, J=9 Hz), 4.34 (2H, t, J=7 Hz), 4.12 (2H, s), 3.46 (2H, t, J=7 Hz), 3.22 (2H, t, J=6 Hz), 2.88 (3H, d, J=5 Hz), 2.01 (2H, t, J=7 Hz), 1.48-1.62 (4H, m); ES+ MS: 553 (M+H+).

EXAMPLE 592

1-(Cyanomethyl)-7-[(4-fluorophenyl)methyl]-4-hydroxy-N-[2-(methyloxyethyl]-2-oxo-1,2-dihydro-1,5-naphthyridine-3-carboxamide Ethyl 1-(cyanomethyl)-7-[(4-fluorophenyl)methyl]-4-hydroxy-2-oxo-1,2-dihydro-1,5-naphthyridine-3-carboxylate. In a similar manner to that described in example 316 step 1, from ethyl 7-[(4-fluorophenyl)methyl]-4-hydroxy-2-oxo-1,2-dihydro-1,5-naphthyridine-3-carboxylate (29 mg, 0.085 mmol) lithium (bis-trimethylsilyl)amide (0.17 mL of a 1 M solution in tetrahydrofuran) and iodoacetonitrile (0.04 mL, 0.51 mmol) was prepared ethyl 1-(cyanomethyl)-7-[(4-fluorophenyl)methyl]-4-hydroxy-2-oxo-1,2-dihydro-1,5-naphthyridine-3-carboxylate (33 mg, 95% yield) as a yellow oil. Product was carried on without further purification. $^1$H NMR (CDCl$_3$) δ 8.51 (s, 1 H), 7.40 (s, 1 H), 7.15-7.09 (m, 2 H), 7.01-6.96 (m, 2 H), 5.10 (s, 2 H), 4.46 (m, 2 H), 4.13 (s, 2 H), 1.41 (m, 3 H); MS m/z 404 (M+23).

1-(Cyanomethyl)-7-[(4-fluorophenyl)methyl]-4-hydroxy-N-[2-(methyloxy)ethyl]-2-oxo-1,2-dihydro-1,5-naphthyridine-3-carboxamide. In a similar manner to that described in example 196, from ethyl 1-(cyanomethyl)-7-[(4-fluorophenyl)methyl]-4-hydroxy-2-oxo-1,2-dihydro-1,5-naphthyridine-3-carboxylate (33 mg, 0.087 mmol) and [2-(methyloxy)ethyl]amine (0.05 mL) was prepared 1-(cyanomethyl)-7-[(4-fluorophenyl)methyl]-4-hydroxy-N-[2-(methyloxy)ethyl]-2-oxo-1,2-dihydro-1,5-naphthyridine-3-carboxamide (14 mg, 40% yield) as a white solid after purification by reverse phase HPLC. $^1$H NMR (CDCl$_3$) δ 9.95 (s, 1 H), 8.62 (s, 1 H), 7.38 (s, 1 H), 7.18-7.15 (m, 2 H), 7.05-7.01 (m, 2 H), 5.12 (s, 2 H), 4.17 (s, 2 H), 3.63 (m, 2 H), 3.57 (m, 2 H), 3.41 (s, 3 H); MS m/z 411 (M+1).

EXAMPLE 593

7-(4-Fluorobenzyl)-4-hydroxy-N-(2-methoxyethyl)-2-oxo-1-{2-oxo-2-[(2,2,2-trifluoroethyl)amino]ethyl}-1,2-dihydro-1,5-naphthyridine-3-carboxamide The title compound was made in a similar manner to example 558 using 2,2,2-trifluoroethylamine to give a white solid: $^1$H NMR (d$_6$-DMSO) δ 10.18 (1H, m), 8.88 (1H, m), 8.54 (1H, s), 7.77 (1H, s), 7.30 (2H, m), 7.10 (2H, m), 4.96 (2H, s), 4.09 (2H, s), 3.89 (2H, m), 3.49 (4H, m), 3.28 (3H, s); HRMS calcd for C$_{23}$H$_{22}$F$_4$N$_4$O$_5$+H+: 511.1600. Found: 511.1598.

EXAMPLE 594

7-(4-Fluorobenzyl)-1-{2-[(4-fluorophenyl)amino]-2-oxoethyl}-4-hydroxy-N-(2-methoxyethyl)-2-oxo-1,2-dihydro-1,5-naphthyridine-3-carboxamide The title compound was made in a similar manner to example 558 using 4-fluoroaniline to give an off-white solid: $^1$H NMR (d$_6$-DMSO) δ 10.43 (1H, m), 10.20 (1H, m), 8.55 (1H, s), 7.98 (1H, s), 7.54 (2H, m), 7.30 (2H, m), 7.14 (2H, m), 7.03 (2H, m), 5.08 (2H, s), 4.10 (2H, s), 3.49 (4H, m), 3.26 (3H, s); HRMS calcd for C$_{27}$H$_{24}$F$_2$N$_4$O$_5$+H+: 523.1790. Found: 523.1787.

EXAMPLE 595

7-(4-Fluorobenzyl)-4-hydroxy-N-(2-methoxyethyl)-2-oxo-1-(2-oxo-2-thiomorpholin-4-ylethyl)-1,2-dihydro-1,5-naphthyridine-3-carboxamide The title compound was made in a similar manner to example 558 using thiomorpholine to give an off-white solid:

¹H NMR (d₆-DMSO) δ 10.21 (1H, m), 8.53 (1H, s), 7.65 (1H, s), 7.31 (2H, m), 7.12 (2H, m), 5.16 (2H, s), 4.13 (2H, s), 3.83 (2H, m), 3.66 (2H, m), 3.49 (4H, m), 3.26 (3H, s), 2.86 (1H, m), 2.70 (3H, m); HRMS calcd for $C_{25}H_{27}FN_4O_5S+H^+$: 515.1760. Found: 515.1759.

EXAMPLE 596

7-(4-Fluorobenzyl)-4-hydroxy-N-(2-methoxyethyl)-2-oxo-1-[2-oxo-2-(1,3-thiazolidin-3-yl)ethyl]-1,2-dihydro-1,5-naphthyridine-3-carboxamide The title compound was made in a similar manner to example 558 using thiazolidine to give a lemon solid: ¹H NMR (d₆-DMSO) δ 10.21 (1H, m), 8.52 (1H, s), 7.84 (1H, s), 7.31 (2H, m), 7.12 (2H, m), 5.16 (2H, s), 4.76 (1H, s), 4.43 (1H, s), 4.11 (2H, s), 3.92 (1H, m), 3.63 (1H, m), 3.52 (4H, m), 3.26 (3H, s), 3.22 (1H, m), 3.02 (1H, m); HRMS calcd for $C_{24}H_{25}FN_4O_5S+H^+$: 501.1600. Found: 501.1600.

EXAMPLE 597

7-(4-Fluorobenzyl)-4-hydroxy-N-(2-methoxyethyl)-2-oxo-1-[2-oxo-2-(pyridin-3-ylamino)ethyl]-1,2-dihydro-1,5-naphthyridine-3-carboxamide The title compound was made in a similar manner to example 558 using 3-aminopyridine to give a white solid: ¹H NMR (d₆-DMSO) δ 10.66 (1H, s), 10.19 (1H, m), 8.72 (1H, s), 8.56 (1H, m), 8.28 (1H, m), 8.01 (2H, m), 7.38 (1H, m), 7.31 (2H, m), 7.03 (2H, m), 5.13 (2H, s), 4.11 (2H, s), 3.52 (4H, m), 3.26 (3H, s); HRMS calcd for $C_{26}H_{24}FN_5O_5+H^+$: 506.1830. Found: 506.1833.

EXAMPLE 598

1-{2-[Ethyl(methyl)amino]-2-oxoethyl}-7-[(4-fluorophenyl)methyl]-4-hydroxy-N-[2-(methyloxyethyl]-2-oxo-1,2-dihydro-5-naphthyridine-3-carboxamide This compound was prepared from [7-[(4-fluorophenyl)methyl]-4-hydroxy-3-({[2-(methyloxy)ethyl]amino}carbonyl)-2-oxo-1,5-naphthyridine-1(2H)-yl]acetic acid and N-ethylmethylamine employing methods similar to those described in Example 558 and was obtained as a white solid: ¹H NMR (d₆-DMSO) δ mixture of rotamers 10.22 (1H, m), 8.52 (1H, s), 7.69 and 7.64 (1H, s), 7.31 (2H, m), 7.11 (2H, m), 5.12 and 5.10 (2H, s), 4.11 and 4.10 (2H, s), 3.53-3.45 (4H, m), 3.27 (2H, m), 3.26 (3H, s), 3.09 and 2.78 (3H, s), 1.20 and 0.97 (3H, t, J=7 Hz); AP⁺ MS: 471 (M+H⁺, 100).

EXAMPLE 599

7-[(4-Fluorophenyl)methyl]-4-hydroxy-1-{2-[methyl(methyloxy)amino]-2-oxoethyl}-N-[2-(methyloxy)ethyl]-2-oxo-1,2-dihydro-1,5-naphthyridine-3-carboxamide This compound was prepared from [7-[(4-fluorophenyl)methyl]-4-hydroxy-3-({[2-(methyloxy)ethyl]amino}carbonyl)-2-oxo-1,5-naphthyridine-1(2H)-yl]acetic acid and N,O-dimethylhydroxylamine hydrochloride employing methods similar to those described in Example 558 and was obtained as a white solid: ¹H NMR (d₆-DMSO) δ 10.17 (1H, br t, J=5 Hz), 8.53 (1H, s), 7.82 (1H, s), 7.32 (2H, t, J~8 Hz), 7.12 (2H, t, J~9 Hz), 5.19 (2H, s), 4.12 (2H, s), 3.83 (3H, s), 3.53-3.48 (4H, m), 3.26 (3H, s), 3.12 (3H, s); AP⁺ MS: 473 (M+H⁺, 100).

EXAMPLE 600

7-[(4-fluorophenyl)methyl]-4-hydroxy-2-oxo-1-[2-(2-oxo-1-piperidinyl)ethyl]-N-(tetrahydro-2H-pyran-4-yl)-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and tetrahydro-2H-pyran-4-amine using methods similar to Example 563 to provide a white solid: ES⁺ MS: 523 (M+H⁺).

EXAMPLE 601

7-[(4-fluorophenyl)methyl]-4-hydroxy-N-[(2R)-2-hydroxypropyl]-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and (2R)-1-amino-2-propanol using methods similar to Example 563 to provide an off-white solid: ¹H NMR (300 MHz, DMSO-d₆) δ ppm 1.10 (d, J=6.32 Hz, 3 H), 1.55-1.65 (m, 4 H), 2.04 (t, J=5.79 Hz, 2 H), 3.15-3.28 (m, 2 H), 3.40-3.53 (m, 4 H), 3.81 (br. s., 1 H), 4.16 (s, 2 H), 4.39 (t, J=6.42 Hz, 2 H), 4.95 (d, J=3.58 Hz, 1 H), 7.11-7.17 (m, 2 H), 7.38-7.43 (m, 2 H), 8.20 (d, J=1.47 Hz, 1 H), 8.56 (d, J=1.68 Hz, 1 H), 10.42 (t, J=5.16 Hz, 1 H), 17.23 (s, 1 H); ES⁺ MS: 497 (M+H⁺).

EXAMPLE 602

7-[(4-fluorophenyl)methyl]-4-hydroxy-N-(3-hydroxypropyl)-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 3-aminopropanol using methods similar to Example 563 to provide an off-white solid: ¹H NMR (300 MHz, DMSO-d₆) δ ppm 1.09 (t, J=7.05 Hz, 2 H), 1.52-1.65 (m, 4 H), 1.65-1.75 (m, 2 H), 2.04 (t, J=6.42 Hz, 2 H), 3.26 (t, J=5.48 Hz, 2 H), 3.39-3.53 (m, 4 H), 4.16 (s, 2 H), 4.39 (t, J=6.42 Hz, 2 H), 4.55-4.63 (m, 1 H), 7.11-7.17 (m, 2 H), 7.38-7.43 (m, 2 H), 8.20 (s, 1 H), 8.56 (d, J=1.47 Hz, 1 H), 10.32 (t, J=5.58 Hz, 1 H), 17.25 (s, 1 H); ES⁺ MS: 497 (M+H⁺).

EXAMPLE 603

7-[(4-fluorophenyl)methyl]-4-hydroxy-N-(2-hydroxybutyl)-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 1-amino-2-butanol using methods similar to Example 563 to provide an off-white solid: ¹H NMR (300 MHz, DMSO-d₆) δ ppm 0.83-0.93 (m, 3 H), 1.38-1.45 (m, 2 H), 1.54-1.65 (m, 4 H), 2.04 (t, J=6.00 Hz, 2 H), 3.18-3.30 (m, 3 H), 3.44-3.57 (m, 4 H), 4.16 (s, 2 H), 4.31-4.45 (m, 2 H), 4.95 (d, J=5.26 Hz, 1

H), 7.11-7.18 (m, 2 H), 7.38-7.44 (m, 2 H), 8.20 (s, 1 H), 8.56 (d, J=1.68 Hz, 1 H), 10.42 (t, J=5.58 Hz, 1 H), 17.23 (s, 1 H); ES+ MS: 511 (M+H+).

EXAMPLE 604

7-[(4-fluorophenyl)methyl]-4-hydroxy-N-[(1R)-1-(hydroxymethyl)-3-methylbutyl]-2-oxo-1-[2-(2-oxo-1-piperidinyl)ethyl]-1,2-dihydro-1,5-naphthyridine-3-carboxamide A mixture of ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate (30 mg, 0.064 mmol) and (2R)-2-amino-4-methyl-1-pentanol (75 µL, 0.64 mmol) was heated in EtOH (3 mL) at 175° C. for 45 min. in a microwave. The reaction mixture was cooled to rt and let stand overnight. Added 1N NaHSO$_4$ (2 mL) filtered the resulting suspension, washed with EtOH:water 1:1, and Et$_2$O then concentrated the filtrate in vacuo. Dissolved the residue in CH$_2$Cl$_2$, washed with 0.5N NaHSO$_4$, water, and brine then dried the organics over Na$_2$SO$_4$, filtered and concentrated in vacuo. Triturated the residue with Et$_2$O, filtered and dried in vacuo to provide the product as an off-white solid: $^1$H NMR (300 MHz, DMSO-d$_6$) δ ppm 0.91 (d, J=6.53 Hz, 6 H), 1.40-1.50 (m, 2 H), 1.53-1.67 (m, 6 H), 1.99-2.11 (m, 2 H), 3.18-3.29 (m, 2 H), 3.35-3.50 (m, 4 H), 3.53-3.59 (m, 1 H), 4.09 (dd, J=4.32, 3.26 Hz, 1 H), 4.17 (s, 2 H), 4.93 (t, J=5.16 Hz, 1 H), 7.10-7.18 (m, 2 H), 7.37-7.44 (m, 2 H), 8.21 (d, J=1.47 Hz, 1 H), 8.56 (d, J=1.69 Hz, 1 H), 10.31 (d, J=9.06 Hz, 1 H), 17.27 (s, 1 H); ES+ MS: 539 (M+H+).

EXAMPLE 605

7-[(4-fluorophenyl)methyl]-4-hydroxy-2-oxo-1-[2-(2-oxo-1-piperidinyl)ethyl]-N-[(3R)-tetrahydro-3-furanyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl) ethyl]-1,2-dihydro-1,5-naphthyridine-3-carboxylate and (3R)-tetrahydro-3-furanamine using methods similar to Example 563 to provide an off-white solid: $^1$H NMR (300 MHz, DMSO-d$_6$) δ ppm 1.54-1.65 (m, 4 H), 1.88 (d, J=8.42 Hz, 1 H), 2.04 (t, J=5.69 Hz, 2 H), 2.23-2.32 (m, 1 H), 3.25-3.30 (m, 2 H), 3.45-3.54 (m, 2 H), 3.65 (dd, J=9.16, 2.84 Hz, 1 H), 3.72-3.88 (m, 3 H), 4.17 (s, 2 H), 4.39 (t, J=7.16 Hz, 2 H), 4.55 (s, 1 H), 7.11-7.17 (m, 2 H), 7.38-7.43 (m, 2 H), 8.23 (s, 1 H), 8.58 (d, J=1.47 Hz, 1 H), 10.50 (d, J=7.16 Hz, 1 H), 16.83 (s, 1 H); ES+ MS: 509 (M+H+).

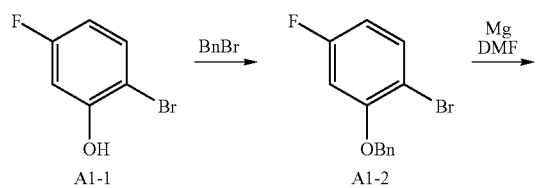

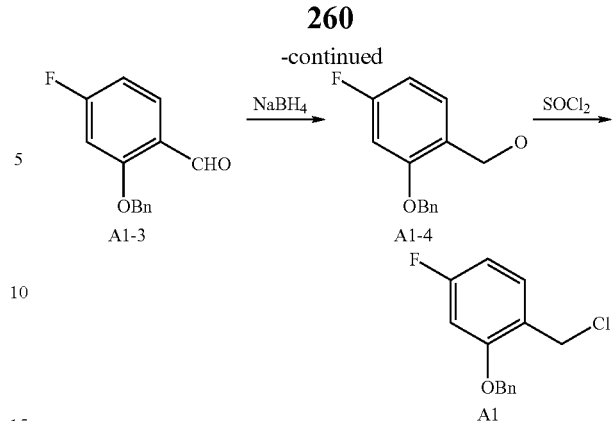

Compound A 1-2: 2-Benzyloxy-1-bromo-4-fluoro-benzene

To a solution of compound A1-1 (50.0 g, 131 mmol) in acetone (250 mL) were added potassium carbonate (37.8 g, 137 mmol) and benzyl bromide (31.0 mL, 131 mmol) at rt, and the mixture was refluxed at 80° C. for 2 h. Then, the mixture was treated with ice crushes and 1N HCl (300 mL) and extracted with EtOAc. The extract was washed with water and brine. After dried over Na$_2$SO$_4$, the solvent was concentrated in vacuo to give 72.2 g of compound A1-2 (yield=98.0%) as pale yellow oil.
$^1$H NMR (CDCl$_3$) δ 7.51-7.30(m, 6H), 6.68 (dd, J=10.5 Hz, 2.7 Hz, 1H), 6.62-6.50 (m, 1H), 5.13 (s, 2H).

Compound A1-3: 2-Benzyloxy-4-fluoro-benzaldehyde

To a suspension of magnesium (6.36 g) in THF (40 mL) was added dropwise a solution of A1-2 (70.1 g, 249 mmol) in THF (240 mL) at 65° C. during 90 min period with stirring under N$_2$ atmosphere. After stirring at 65° C. for 30 min, the reaction mixture was treated with sat. NH$_4$Cl solution (500 mL). Then the mixture was extracted with EtOAc. The combined organic layers were washed with water, and dried over Na$_2$SO$_4$. The solvent was concentrated in vacuo to give 57.5 g of compound A1-3 (quant) as brown oil.
$^1$H NMR (CDCl$_3$) δ 10.44 (s, 1H), 7.88 (t, 7.5 Hz, 1H), 7.42 (m, 5H), 6.74 (m, 2H), 5.17 (s, 2H).

Compound A1-4: (2-Benzyloxy-4-fluoro-phenyl)-methanol

To a solution of compound A1-3 (57.1 g, 248 mmol ) in EtOH (170 mL) was added NaBH$_4$ (4.69 g) at 0° C. and stirred for 1 h. The reaction mixture was treated with sat. NH$_4$Cl solution (300 mL), and then the mixture was extracted with EtOAc. The combined organic layers were washed with water and brine. After dried over Na$_2$SO$_4$, the solvent was concentrated in vacuo. The product mixture was purified by silica gel column chromatography (eluent: EtOAc/n-Hexane=1/5 to 1/3 v/v) to afford 43.4 g of compound A1-4 (yield=74%) as pale yellow oil.
$^1$H NMR (CDCl$_3$) δ 7.41-7.33 (m, 5H), 7.25 (t, J=8.1 Hz, 1H), 6.70-6.62 (m, 2H), 5.08 (s, 2H), 4.68 (s, 2H), 2.10 (br s, 1H).

Compound A1: 2-Benzyloxy-1-chloromethyl-4-fluoro-benzene

To a solution of compound A1-4 (42.4 g, 182 mmol) in CH$_2$Cl$_2$ (210 mL) was added dropwise thionyl chloride (15.6 mL, 219 mmol) at 0° C. during 7 min period, and then added DMF (1 drop). After stirring at rt for 30 min, the solvent was concentrated in vacuo. To the resulting residue were added cold-water (100 mL) and $Et_2O$ (200 mL), and the mixture was neutralized to pH 7.2 with sat. $NaHCO_3$ solution. After neutralizing, the mixture was extracted with $Et_2O$ several times. The combined organic layers were washed with water and brine, then dried over $Na_2SO_4$. The solvent was concentrated in vacuo to give a crude product. The crude product was purified by crystallization with n-Hexane to give 41.7 g of compound A-1 (yield=89.0%) as a pale yellow powder.

$^1$H NMR ($CDCl_3$) δ 7.47-7.29 (m, 6H), 6.65 (m, 2H), 5.12 (s, 2H), 4.66 (s, 2H).

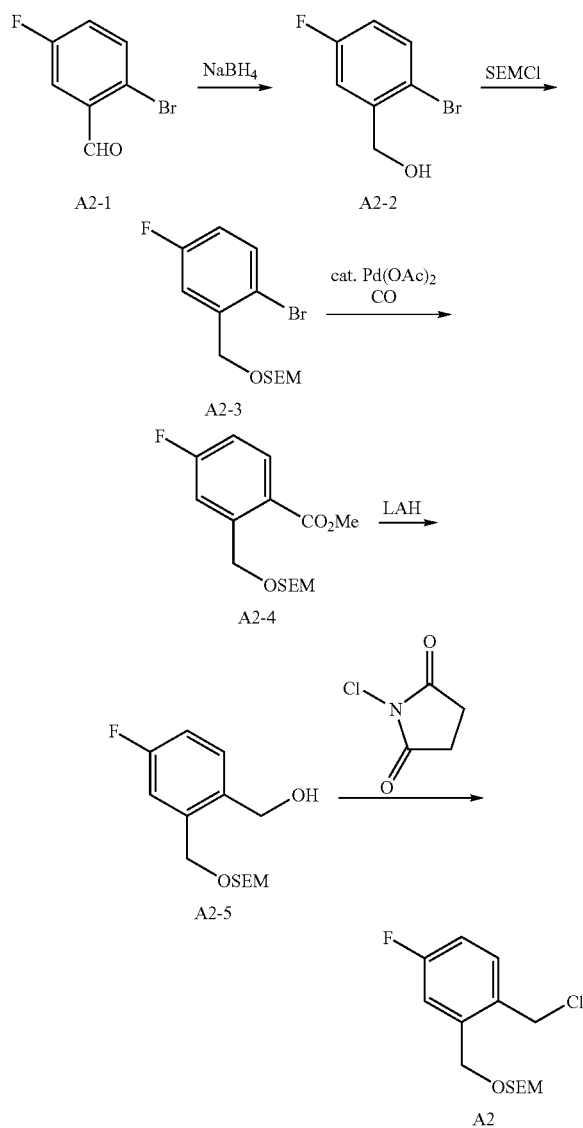

Compound A2-2: (2-Bromo-5-fluoro-phenyl)-methanol

To a solution of compound A2-1 (75.0 g, 369 mmol) in EtOH (375 mL) was added a solution of $NaBH_4$ (4.47 g, 118 mmol) in water (9 mL) at 0° C., and the mixture was stirred at rt for 1 h. The mixture was treated with water and EtOAc, and extracted with EtOAc. The extract was washed with brine, dried over $Na_2SO_4$. The solvent was concentrated in vacuo to give 75.6 g of compound A2-2 (yield=99.8%) as a colorless solid.

$^1$H NMR ($CDCl_3$) δ 7.50-7.46(1H, m), 7.29-7.25(1H, m), 6.92-6.85(1H, m), 4.72(2H, s).

Compound A2-3: [2-(2-Bromo-5-fluoro-benzyloxymethoxy)-ethyl]-trimethyl-silane To a solution of compound A2-2 (75.6 g, 369 mmol) and diisopropylamine (57.7 g, 446 mmol) in $CH_2Cl_2$ (770 mL) was added SEMCl (73.8 g, 443 mmol) under $N_2$ atmosphere at 0° C. After stirring at rt for 45 min, the mixture was treated with cold-water, and stirred for 10 min. The resulting mixture was extracted with n-Hexane, and washed with water and brine. After dried over $Na_2SO_4$, the solvent was concentrated in vacuo to give 131.0 g of compound A2-3 (quant).

$^1$H NMR ($CDCl_3$) δ 7.48-7.43(1H, m), 7.24-7.20(1H, m), 6.88-6.82(1H, m), 4.79(2H, s), 4.60(2H, s), 3.69-3.63(2H, m), 0.97-0.91(2H, m), 0.00(9H, s).

Compound A2-4: 4-Fluoro-2-(2-trimethylsilanyl-ethoxymethoxymethyl)-benzoic acid methyl ester To a solution of compound A2-3 (65.4 g, 184 mmol) in DMF (464 mL) and MeOH (186 mL) were added $Et_3N$ (257 ml, 1844 mmol), $Pd(OAc)_2$ (8.28 g, 36.9 mmol) and diphenyl (phosphino) propane (19.0 g, 46.1 mmol) at rt. The mixture was stirred at 80° C. for 18 h under CO atmosphere. After the reaction mixture was treated with $NH_4Cl$ solution and EtOAc, the insoluble materials were filtered off. The filtrate was washed with water, dried over $Na_2SO_4$. The solvent was concentrated in vacuo to afford the crude product. After adding acetone and n-Hexane, the resulting precipitates were filtered off. The filtrate was concentrated in vacuo to give 59.6 g of compound A2-4 (quant) as a red oil.

$^1$H NMR ($CDCl_3$) δ 8.01-7.97(1H, m), 7.44-7.40(1H, m), 7.01-6.95(1H, m), 5.00(2H, s), 4.81(2H, s), 3.86(3H, s), 3.70-3.63(2H, m), 0.97-0.91(2H, m), 0.00(9H, s).

Compound A2-5: [4-Fluoro-2-(2-trimethylsilanyl-ethoxymethoxymethyl)-phenyl]-methanol To a suspension of $LiAlH_4$ (14.0 g, 369 mmol) in $Et_2O$ (1000 mL) was added dropwise a solution of compound A2-4 (119 g, 184 mmol) in $Et_2O$ (200 mL) during 70 min period at 0° C., and stirred for 75 min. After water (14 mL) and 2N NaOH solution (14 mL) were added to the reaction mixture, $Et_2O$ layer was separated. The $Et_2O$ layer was dried over $Na_2SO_4$, the solvent was concentrated in vacuo to give 100 g of compound A2-5 (yield=95%) as a red oil.

$^1$H NMR ($CDCl_3$) δ 7.35-7.31(1H, m), 7.10-7.06(1H, m), 7.00-6.94(1H, m), 4.72(2H, s), 4.65(2H, s), 4.61(2H, s), 3.64-3.58(2H, m), 0.94-0.88(2H, m), 0.00(9H, s).

Compound A2: [2-(2-Chloromethyl-5-fluoro-benzyloxymethoxy)-ethyl]-trimethyl-silane To a solution of compound A2-5 (100 g, 350 mmol) in THF (1000 mL) was added $P(Ph)_3$ (96.5 g, 368 mmol) with stirring. NCS (49.1 g, 368 mmol) was added to the solution, and the mixture was stirred at rt for 1 h. The resulting precipitates were filtered off, and the filtrate was concentrated in vacuo. The residual oil was purified by distillation (148-154° C./2 mmHg) to give 93.2 g of compound A2 (yield=87.0%) as a colorless oil.

$^1$H NMR (CDCl$_3$) δ 7.34-7.29(1H, m), 7.16-7.12(1H, m), 6.98-6.92(1H, m), 4.75(2H, s), 4.70(2H, s), 4.62(2H, s), 3.67-3.62(2H, m), 0.96-0.91(2H, m), 0.00(9H, s).

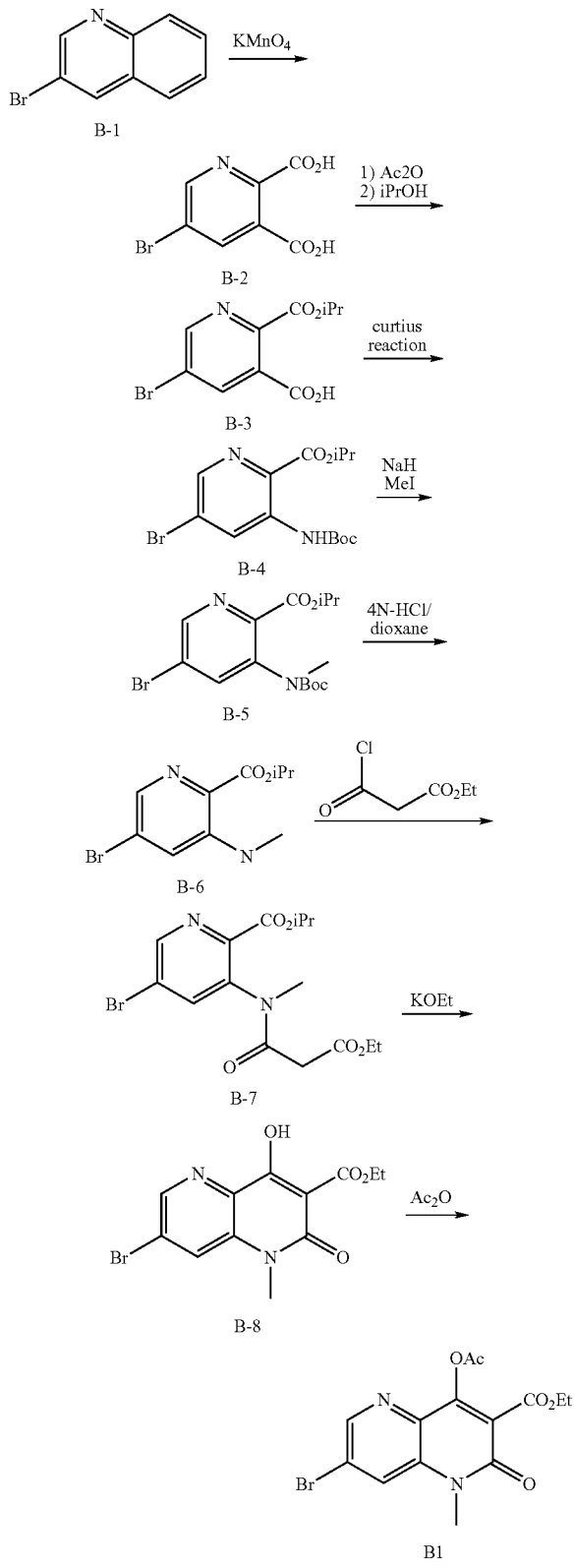

Compound B-2: 5-Bromo-pyridine-2,3-dicarboxylic acid

To a mixture of 3-bromoquinoline (10 ml, 72.7 mmol) and water (200 mL) was added KMnO$_4$ (69.0 g, 436 mmol) at 6 portion each 15 min at 80° C. with stirring. After allowing the reaction to cool to rt, MeOH (20 mL) was added to the solution. The resulting mixture was washed with toluene (100 mL), and the aqueous layer was adjusted to pH 1 with conc. HCl. The mixture was extracted twice with EtOAc/THF (100 mL/50 mL). The combined extracts were washed with brine, dried over Na$_2$SO$_4$, and the solvent was removed in vacuo. Water was added to the residue, the resulting insoluble materials were filtered off. Isobutyl acetate was added to the filtrate, and then water was removed in vacuo. The resulting precipitates were collected by filtration, and dried to give 4.45 g of compound B-2 (yield=25%) as a colorless crystal.

$^1$H NMR (DMSO-d6) δ 12.50(1H, s), 8.90(1H, d, J=2.1 Hz), 8.43(1H, d, J=2.1 Hz).

Compound B-3: 5-Bromo-pyridine-2,3-dicarboxylic acid 2-isopropyl ester

A mixture of compound B-2 (179 g, 728 mmol) and acetic anhydride (1250 mL) was heated at 120° C. for 1.5 h. After allowing the reaction to cool, acetic anhydride was removed in vacuo. After 2-propanol was added to the residue, the resulting mixture was heated at reflux for 13 h. After allowing the reaction to cool, the solvent was removed in vacuo. The crude product was purified by crystallization with acetone/($^i$Pr)$_2$O to give 77.8 g of compound B-4 (yield=37.0%) as a brown crystal.

$^1$H NMR (CDCl$_3$) δ 8.88(1H, d, J=2.1 Hz), 8.44(1, d, J=2.1 Hz), 7.70(1H, bs), 5.41-5.28(1H, m), 1.40(6H, d, J=6.3 Hz).

Compound B-4: 5-Bromo-3-tert-butoxycarbonylamino-pyridine-2-carboxylic acid isopropyl ester To a solution of compound B-3 (101 g, 352 mmol) in $^t$-BuOH (1014 mL) were added Et$_3$N (147 ml, 1055 mmol) and diphenyl(phosphoryl) azide (94.6 ml, 422 mmol) at rt under N$_2$ atmosphere with stirring. After the mixture was heated at reflux for 2.5 h, allowed cooling to rt. The reaction mixture was extracted with EtOAc, and washed with sat. NaHCO$_3$ solution and brine. After the solvent was concentrated in vacuo, a mixture of acetone/n-Hexane was added to the residue. The resulting insoluble materials were removed, and then the solvent was concentrated in vacuo. The resulting product was purified by crystallization with ($^i$Pr)$_2$O/n-Hexane to give 104 g of compound B-4 (yield=82.0%) as a off-brown crystal $^1$H NMR (CDCl$_3$) δ 10.31(1H, s), 9.12(1H, d, J=2.0 Hz), 8.39(1H, d, J=2.0 Hz), 5.36-5.29(1H, m), 1.54(9H, s), 1.45 (6H, d, J=6.3 Hz).

Compound B-5: 5-Bromo-3-(tert-butoxycarbonyl-methyl-amino)-pyridine-2-carboxylic acid isopropyl ester NaH (60%, 13.9 g, 347 mmol) was added at 7 portions to a solution of compound B-4 (104 g, 289 mmol) in THF/DMF (416 mL/623 mL) at 9° C. under N$_2$ atmosphere. After MeI (27 ml, 434 mmol) was added dropwise to the mixture, the reaction mixture was stirred at rt for 75 min. The resulting mixture was treated with NH$_4$Cl solution, extracted twice with EtOAc. The extract was washed with water and brine, dried over Na₂SO₄, and then the solvent was concentrated in vacuo to give 116 g of compound B-5 (quant) as red oil.

$^1$H NMR (CDCl₃) δ 8.64(1H, s), 7.76(1H, s), 5.29-5.23 (1H, m), 3.23(3H, s), 1.39(6H, d, J=6.3 Hz), 1.34(9H, s).

Compound B-6:
5-Bromo-3-methylamino-pyridine-2-carboxylic acid isopropyl ester

A solution of compound B-5 (116 g, 289 mmol) in 4N HCl (1,4 dioxane solution) was stirred at rt for 1.5 h. After removal of the solvent, ice crushes and sat. NaHCO₃ solution were added to the residue. The resulting mixture was extracted twice with EtOAc, washed with brine, dried over Na₂SO₄. The solvent was concentrated in vacuo, and then the resulting product was purified by crystallization with n-Hexane to give 71.9 g of compound B-6 (yield=91.0%) as a yellow crystal.

$^1$H NMR (CDCl₃) δ 8.03(1H, d, J=1.8 Hz), 7.80(1H, brs), 7.20(1H, d, J=1.8 Hz), 5.32-5.24(1H, m), 2.90(3H, d, J=5.0 Hz), 1.43(6H, d, J=6.4 Hz).

Compound B-7: 5-Bromo-3-[(2-ethoxycarbonyl-acetyl)-methyl-amino]-pyridine-2-carboxylic acid isopropyl ester To a suspension of compound B-6 (2.33 g, 8.53 mmol) in THF (14 mL) was added ethyl-3-chloro-3-oxo-propionate (1.20 ml, 9.37 mmol). The mixture was heated at 120° C. in a sealed tube in a microwave for 5 min. After cooling, sat. NaHCO₃ solution was added to the mixture, and the mixture was extracted twice with EtOAc. The extract was washed with brine, dried over Na₂SO₄, and then the solvent was concentrated in vacuo. The residue was purified by crystallization with n-Hexane to give 2.81 g of compound B-7 (yield=85%) as a pale brown crystal.

$^1$H NMR (CDCl₃) δ 8.80(1H, d, J=1.8 Hz), 7.93(1H, d, J=1.8 Hz), 5.35-5.27(1H, m), 4.16-4.10(2H, m), 3.24(3H, s), 3.15 (2H, d, J=10.8 Hz), 1.37(6H, d, J=6.4 Hz), 1.24(3H, J=7.2 Hz).

Compound B-8: 7-Bromo-4-hydroxy-1-methyl-2-oxo-1,2-dihydro)[1,5]naphthyridine-3-carboxylic acid ethyl ester To a solution of compound B-7 (88.0 g, 227 mmol) in DMF (880 mL) was added dropwise KOEt in EtOH (178 ml, 24 wt %, 454 mmol) at 0° C. under N₂ atmosphere, and the mixture was stirred at rt for 1 h. The reaction mixture was adjusted to pH 4 with 2N HCl at 0° C., and extracted several times with EtOAc. The combined extracts were dried over Na₂SO₄, and then concentrated in vacuo. The resulting product was triturated with Et₂O to give 68.3 g of compound B-8 (yield=92.0%) as a pale brown crystal.

$^1$H NMR (CDCl₃) δ 13.98(1H, bs), 8.66(1H, d, J=1.8 Hz), 7.85(1H, d, J=1.8 Hz), 4.53(2H, q, J=7.2 Hz), 3.63(3H, s), 1.49(3H, t, J=7.2 Hz).

Compound B 1: 4-Acetoxy-7-bromo-1-methyl-2-oxo-1,2-dihydro-[1,5]naphthyridine-3-carboxylic acid ethyl ester A mixture of compound B-8 (26.1 g) and acetic anhydride (200 mL) was heated at 130° C. for 1.5 hr with stirring. After removal of the solvent, furthermore residual solvent was evaporated twice with toluene at reduced pressure. The resulting product was triturated with Et₂O to give 27.4 g of compound B1 (yield=93.0%) as a pale brown crystal.

$^1$H NMR (CDCl₃) δ 8.58(1H, d, J=1.8 Hz), 7.87(1H, d, J=1.8 Hz), 4.44(2H, q, J=7.2 Hz), 3.68(3H, s), 2.43(3H, s), 1.39(3H, t, J=7.2 Hz).

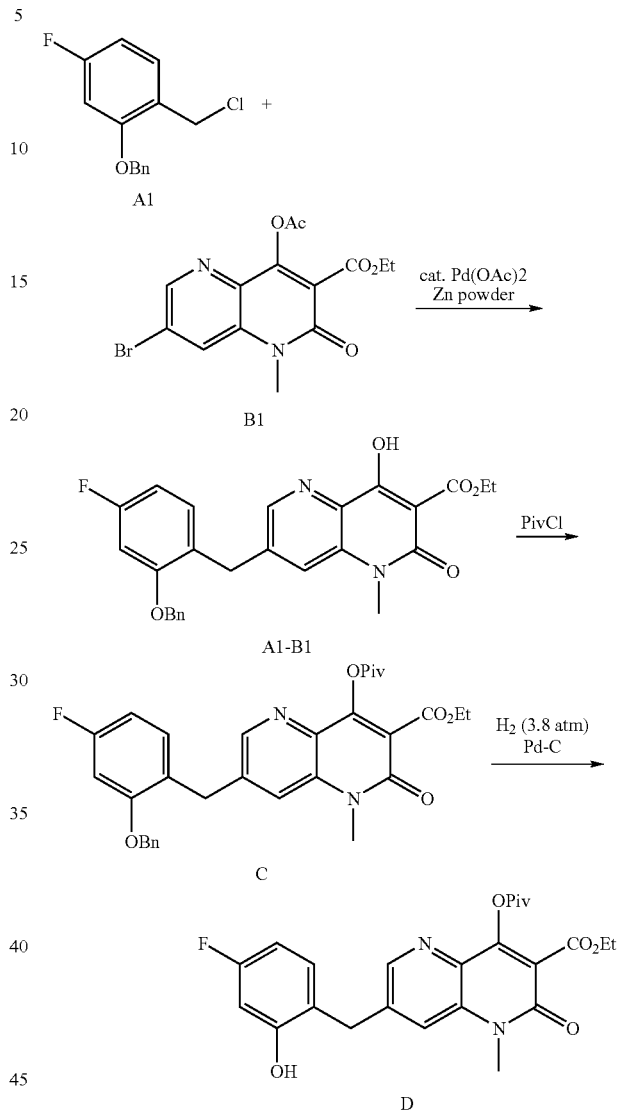

Compound A1-B 1: 7-(2-Benzyloxy-4-fluoro-benzyl)-4-hydroxy-1-methyl-2-oxo-1,2-dihydro-[1,5]naphthyridine-3-carboxylic acid ethyl ester To a suspension of Zn (8.21 g, 125.5 mmol) in THF (200 mL) was added dropwise compound A1 (26.2 g, 104.5 mmol) at rt, and then were added 1,2-dibromethane (0.50 ml) and trimethylsilyl chloride (0.50 ml). After the reaction mixture was heated at 60° C. for 90 min, the mixture was cooled to rt. To the reaction mixture were added P(Ph)₃ (1.37 g, 5.23 mmol), Pd(OAc)₂ (587 mg, 2.62 mmol) and compound B1 (19.3 g, 52.3 mmol), and heated at 60° C. for 30 min with stirring. After the reaction mixture was cooled to rt, the mixture was treated with 2N HCl (20 mL), extracted with EtOAc. The extract was washed with water and brine, and dried over Na₂SO₄. The solvent was concentrated in vacuo to afford 30.5 g of crude compound A1-B1.

Compound C: 7-(2-Benzyloxy-4-fluoro-benzyl)-4-(2,2-dimethyl-propionyloxy)-1-methyl-2-oxo-1,2-dihydro-[1,5]naphthyridine-3-carboxylic acid ethyl ester To a solution of compound A1-B1 in pyridine (103 mL) was added pivaloyl chloride (5.5 ml, 44.6 mmol) at 0° C. and stirred at rt for 1 h. The resulting mixture was treated with water, extracted twice with EtOAc and dried over $Na_2SO_4$. The solvent was concentrated in vacuo to afford the crude product, the product mixture was purified by silicagel column chromatography (eluent: n-Hexane/EtOAc=3/2 v/v) to give 9.32 g of compound C (yield=77.0% from compound B1).

$^1$H NMR (CDCl$_3$) δ 8.34(1H, d, J=1.4 Hz), 7.36-7.33(4H, m), 7.26-7.17(3H, m), 6.70-6.64(2H, m), 4.94(2H, s), 4.39 (2H, q, J=7.2 Hz), 4.03(2H, s), 3.31(3H, s), 1.41(9H, s), 1.37(3H, t, J=7.2 Hz).

Compound D: 4-(2,2-Dimethyl-propionyloxy)-7-(4-fluoro-2-hydroxy-benzyl)-1-methyl-2-oxo-1,2-dihydro-[1,5]naphthyridine-3-carboxylic acid ethyl ester To a solution of compound C (10.9 g, 19.9 mmol) in 1,4-dioxane was added 10% Pd—C (4.36 g) at rt. The suspension were stirred for 18 h at 3.5 atm under H$_2$ atmosphere. After filtration through Celite, the filtrate was concentrated in vacuo. The residue was washed with EtOAc to give 8.99 g of compound D (yield=99.0%) as a colorless crystal.

$^1$H NMR (CDCl$_3$) δ 9.25(1H, bs), 8.44(1H, d, J=1.7 Hz), 7.54(1H, d, J=1.7 Hz), 7.07-7.02(1H, m), 6.66-6.62(1H, m), 6.55-6.50(1H, m), 4.38(2H, q, J=7.2 Hz), 4.03(2H, s), 3.63 (3H, s), 1.41(9H, s), 1.36(3H, t, J=7.2 Hz).

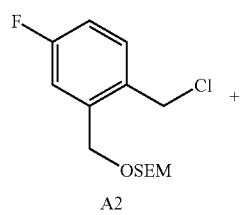

A2

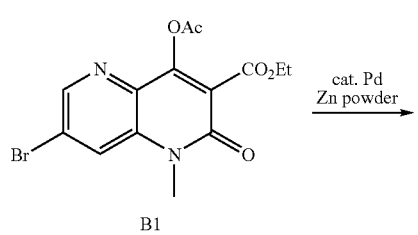

B1

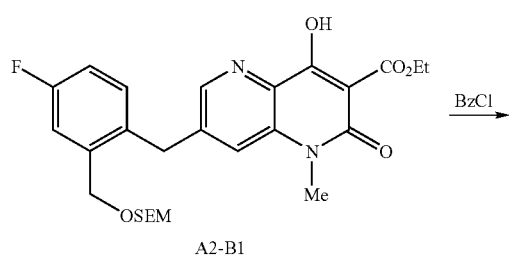

A2-B1

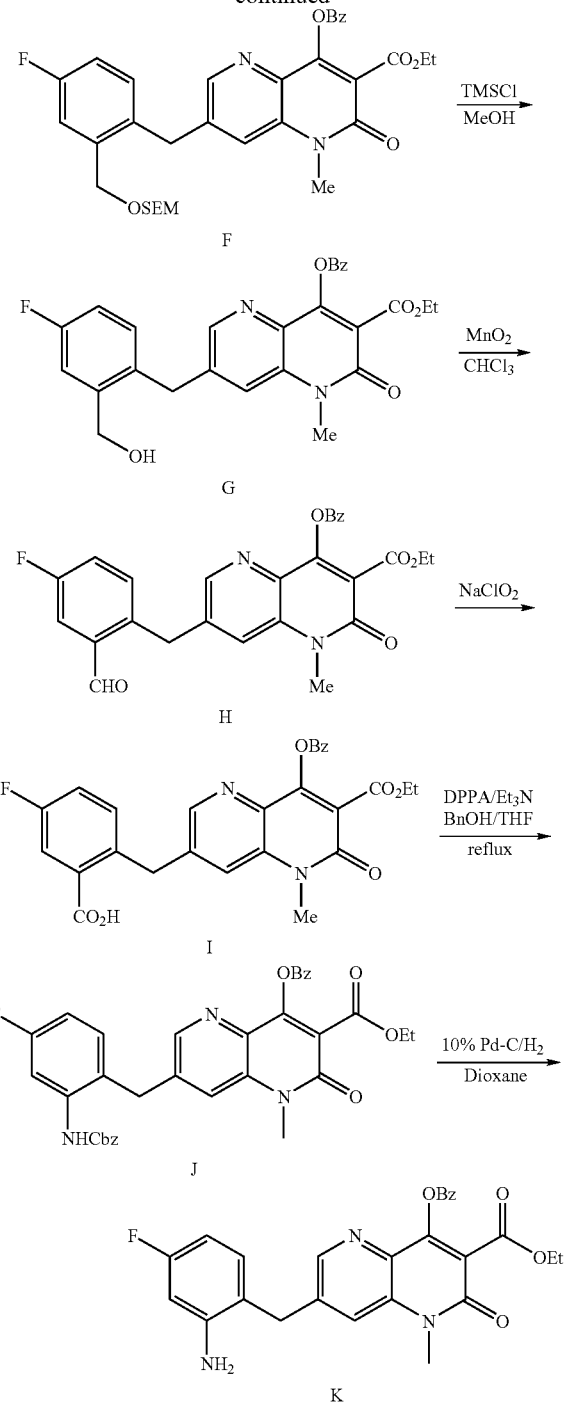

Compound A2-B 1: 7-[4-Fluoro-2-(2-trimethylsilanyl-ethoxymethoxymethyl)-benzyl-]-4-hydroxy-1-methyl-2-oxo-1,2-dihydro-[1,5]naphthyridine-3-carboxylic acid ethyl ester To a suspension of Zn (6.40 g, 97.5 mmol) in THF (120 mL) was added dropwise a solution of compound A2 (24.8 g, 81.1 mmol) in THF (24 mL) at rt, and then were added THF (6 mL), 1,2-dibromoethan (0.30 ml) and trimethylsilylchloride (0.30 ml). After the reaction mixture was heated at 50-55° C. for 3 h, P(Ph)$_3$ (1.07 g, 4.08 mmol) and Pd(OAc)$_2$ (456 mg, 2.03 mmol) were added to the mixture with stirring. To a reaction mixture was added dropwise a solution of compound B1 (15.0 g, 40.6 mmol) in THF (135 mL) during 30 min period with stirring. After additional THF (15 mL) was added and heated at 50° C. for 30 min with stirring. After the reaction mixture was cooled to rt, the mixture was treated with 2N HCl (97.5 mL) and water (90 mL) and extracted with EtOAc (450 mL). The extract was washed with water (200 ml) and brine (100 mL), and dried over $Na_2SO_4$. The solvent was concentrated in vacuo to afford 41.6 g of crude compound A2-B1.

Compound F: 4-Benzoyloxy-7-[4-fluoro-2-(2-triemethylsilanyl-ethoxymethoxymethyl)-benzyl]-1-methyl-2-oxo-1,2-dihydro-[1,5]naphthyridine-3-carboxylic acid ethyl ester To a solution of crude compound A2-B1 (41.64 g) in $CH_2Cl_2$ (300 ml) were added $Et_3N$ (11.5 ml, 82.5 mmol) and benzoyl chloride (7.0 ml, 60.3 mmol) at 0° C. After stirring for 1 h at rt, the reaction mixture was treated with 1N HCl (62 ml) and water (248 mL). The organic layer was separated, and washed with water (200 ml) and brine (100 ml). After dried over $MgSO_4$, the solvent was concentrated in vacuo to afford the crude product. The product mixture was purified by silicagel column chromatography (eluent: n-Hexane/EtOAc=3/2 v/v) to give 15.8 g of compound F (yield=62.4% from compound B1).

$^1$H NMR ($CDCl_3$) δ 8.35(1H, d, J=1.8 Hz), 8.20-8.24(2H, m), 7.50-7.70(3H, m), 7.43(1H, d, J=1.8 Hz), 6.95-7.18(3H, m), 4.69(2H, s), 4.54(2H, s), 4.32(2H, q, J=7.2 Hz), 4.17(2H, s), 3.58-3.64(5H, m), 1.18(3H, t, J=7.2 Hz), 0.91(2H, t, J=8.4 Hz), 0.00(9H, s).

Compound G: 4-Benzoyloxy-7-(4-fluoro-2-hydroxymethyl-benzyl)-1-methyl-2-oxo-1,2-dihydro-[1,5]naphthyridine-3-carboxylic acid ethyl ester To a solution of compound F (15.75 g, 25.37 mmol) in MeOH (120 mL) was added dropwise trimethylsilyl chloride (16.1 ml, 127 mmol) for 15 min. After addition of MeOH (6 mL), the mixture was stirring at 30-40° C. for 1 h. The mixture was treated with water (80 mL), the resulting mixture was stirring for 20 min at 0° C. The resulting precipitates were collected by filtration washing with water (40 mL×2) to afford 9.5 g of compound G (yield=76.6%) as a pale yellow crystal.

$^1$H NMR ($CDCl_3$) δ 8.34(1H, d, J=1.8 Hz), 8.20-8.23(2H, m), 7.50-7.70(3H, m), 7.46(1H, d, J=1.8 Hz), 6.95-7.19(3H, m), 4.63(2H, s), 4.32(2H, q, J=7.2 Hz), 4.17(2H, s), 3.63(3H, s), 1.18(3H, t, J=7.2 Hz).

Compound H: 4-Benzoyloxy-7-(4-fluoro-2-formyl-benzyl)-1-methyl-2-oxo-1,2-dihydro-[1,5]naphthyridine-3-carboxylic acid ethyl ester To a solution of compound G (9.25 g, 18.86 mmol) in $CHCl_3$ (270 mL) was added $MnO_2$ (27.75 g, 319 mmol), and the mixture was heated at reflux for 3 h. After cooling to rt, the insoluble materials were filtered off. The filtrate was concentrated in vacuo to afford the crude product, and the crude product was purified by recrystallization with $CHCl_3/(^iPr)_2O$ to give 8.86 g of compounds H (yield=96.2%) as a colorless crystal.

$^1$H NMR ($CDCl_3$) δ 10.05(1H, s), 8.32(1H, d, J=1.8 Hz), 8.19-8.22(2H, m), 7.50-7.69 (5H, m), 7.28-7.31(2H, m), 4.54 (2H, s), 4.32(2H, q, J=7.2 Hz), 3.69(3H, s), 1.18(3H, t, J=7.2 Hz).

Compound I: 4-Benzoyloxy-7-(2-carboxy-4-fluoro-benzyl)-1-methyl-2-oxo-1,2-dihydro-[1,5]naphthyridine-3-carboxylic acid ethyl ester To a solution of $NaClO_4$ (2.24 g, 24.77 mmol) and sulfamide (2.41 g, 24.82 mmol) in water (100 mL) was added a solution of compound H (5.50 g, 11.26 mmol) in THF (350 mL) at rt, and the mixture was stirred for 1 h at 40° C. Additionally, to a reaction mixture was added a solution of $NaClO_4$ (1.12 g, 12.38 mmol) and sulfamide (1.21 g, 12.46 mmol) in water (50 mL), and stirred for 30 min at 40° C. The solvent was removed in vacuo to afford the crude residue, and the residue was treated with water (300 mL). The resulting precipitate was collected by filtration washing with water (100 mL) to give 5.33 g of compound I (yield=94.1%) as a colorless crystal.

$^1$H NMR (DMSO-d6) δ 8.34(1H, s), 8.10-8.13(2H, m), 7.98(1H, s), 7.79-7.84(1H, m), 7.59-7.67(3H, m), 7.36-7.50 (2H, m), 4.52(2H, s), 4.22(2H, q, J=7.2 Hz), 3.64(3H, s), 1.08(3H, t, J=7.2 Hz).

Compound J: 4-Benzoyloxy-7-(2-benzyloxycarbonylamino-4-fluoro-benzyl)-1-methyl-2-oxo-1,2-dihydro-[1,5]naphthyridine-3-carboxylic acid ethyl ester To a suspension of $I_2$ (2.424 g, 4.80 mmol) in THF (50 mL) were added successively diphenylphosphoryl azide (1.20 ml, 5.57 mmol), $Et_3N$ (2.07 ml, 14.8 mmol) and benzyl alcohol (2.50 ml, 24.05 mmol) under $N_2$ atmosphere at rt with stirring, and the mixture was heated at reflux for 2 h. The reaction mixture was poured into ice/water (300 mL), extracted with EtOAc (150 mL) and washed with sat. $NaHCO_3$ solution and water. After dried over $Na_2SO_4$, the solvent was concentrated in vacuo. The resulting solid (5.9 g) was washed with a mixture of $Et_2O$ (10 mL) and $(^iPr)_2O$ (10 mL) to give 2.54 g of compound J (yield=86.9%).

$^1$H NMR ($CDCl_3$) δ 8.33-8.30(1H, m), 8.23-8.19(2H, m), 7.70-7.64(2H, m), 7.56-7.50(3H, m), 7.32(5H, m), 7.09-7.04 (1H, m), 6.88-6.82(1H, m), 6.41(1H, bs), 5.12(2H, s), 4.32 (2H, quart, J=7.2 Hz), 4.05(2H, s), 3.50(3H, s), 1.19(3H, trip, J=7.2 Hz).

Compound K: 7-(2-Amino-4-fluoro-benzyl)-4-benzoyloxy-1-methyl-2-oxo-1,2-dihydro-[1,5]naphthyridine-3-carboxylic acid ethyl ester To a suspension of 10% Pd—C (1.11 g) in 1,4 dioxane (100 mL) was added a solution of compound J (5.525 g, 9.06 mmol) in 1,4 dioxane (350 mL), and rinsed with 1,4 dioxane (20 mL). The mixture was stirring at rt under $H_2$ atmosphere for 1.5 h. After the mixture was filtered washing with THF, the filtrate was concentrated in vacuo to afford the crude product (4.71 g). The crude product was dissolved in $CH_2Cl_2$ (20 mL), the resulting precipitate was collected by filtration washing with $CH_2Cl_2$ to give 3.26 g of compound K (yield=75.8%) as a pale yellow crystal.

$^1$H NMR ($CDCl_3$) δ 8.39(1H, d, J=1.5 Hz), 8.22-8.19(2H, m), 7.70-7.65(1H, m), 7.55-7.50(2H, m), 7.45(1H, bs), 6.98-6.93(1H, m), 6.53-6.47(2H, m), 4.32(2H, quart, J=7.2 Hz), 4.00(2H, s), 3.63(3H, s), 1.18(3H, trip, J=7.2 Hz).

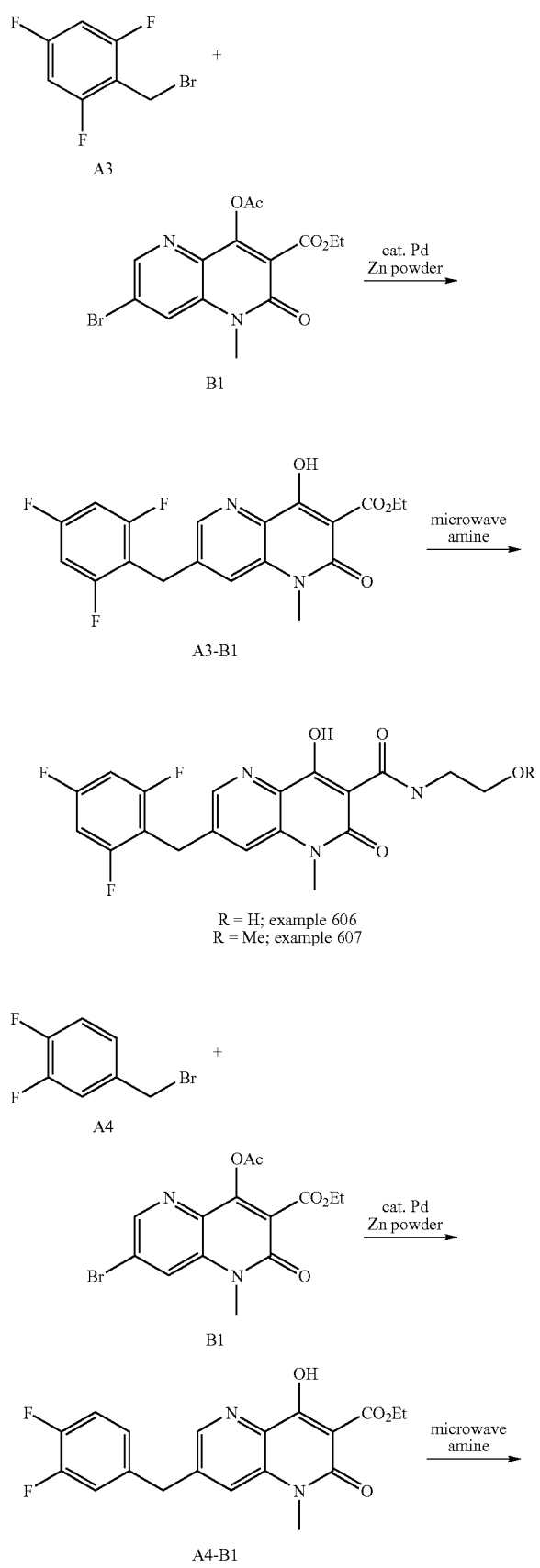

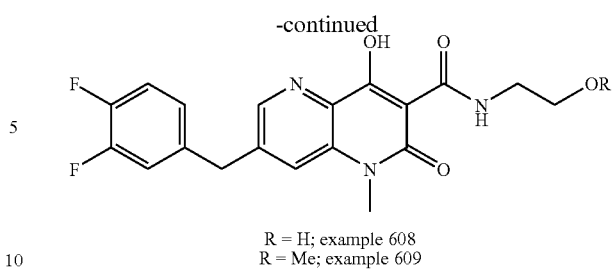

R = H; example 608
R = Me; example 609

Compound A3-B 1: 4-Hydroxy-1-methyl-2-oxo-7-(2,4,6-trifluoro-benzyl)-1,2-dihydro-[1,5]naphthyridine-3-carboxylic acid ethyl ester To a suspension of Zn (424 mg, 6.28 mmol) in THF (9 mL) was added dropwise compound A3 (1.22 g, 5.42 mmol) at rt, and then were added THF (1 mL), 1,2-dibromoethan (0.02 ml) and trimethylsilyl chloride (0.02 ml). After the reaction mixture was heated at 50° C. for 15 min, the mixture was cooled to rt. To the reaction mixture were added P(Ph)$_3$ (72 mg, 0.27 mmol), Pd(OAc)$_2$ (60 mg, 0.27 mmol) and a solution of compound B1 (1.0 g, 2.71 mmol) in THF (10 mL), and heated at 50° C. for 1 h with stirring. After the reaction mixture was cooled to rt, the mixture was treated with 2N HCl (20 mL), extracted with EtOAc. The extract was washed with water and brine, and dried over Na$_2$SO$_4$. The solvent was concentrated in vacuo to afford the crude product. The crude product was purified by crystallization with acetone/Et$_2$O to give 603 mg of compound A3-B1 (yield=56.7%) as a colorless crystal.

$^1$H NMR (CDCl$_3$) δ 8.57(1H, s), 7.48(1H, s), 6.72(2H, t, J=8.1 Hz), 4.51(2H, q, J=7.2 Hz), 4.13(2H, s), 3.60(3H, s), 1.48(3H, t, J=7.2 Hz).

EXAMPLE 606

4-Hydroxy-1-methyl-2-oxo-7-(2,4,6-trifluoro-benzyl-1,2-dihydro-[1,5]naphthyridine-3-carboxylic acid (2-hydroxy-ethyl)-amide A mixture of compound A3-B1 (196 mg, 0.500 mmol) in EtOH (4 mL) and 2-amino ethanol (69 μL, 1.00 mmol) was heated at 140° C. in a sealed tube in a microwave for 10 min. After cooling to rt, the resulting precipitate was collected by filtration. The crude product was purified by crystallization with with acetone/EtOH to give Example A3-B1-1 (yield=80.0%). m.p.: 202-203° C.; Elemental Analysis: C$_{19}$H$_{16}$F$_3$N$_3$O$_4$; Calcd (%): C, 56.02; H, 3.96; N, 10.32; F, 13.99.; Found (%): C, 56.03; H, 3.98; N, 10.35; F, 13.71; $^1$H NMR (DMSO-d6) δ 10.42(1H, bs), 8.46(1H, s), 7.87(1H, s), 7.29-7.23(2H, m), 4.96-4.92(1H, m), 4.21(2H, s), 3.58(3H, s), 3.60-3.54(2H, m), 3.47-3.42(2H, m).

EXAMPLE 607

4-Hydroxy-1-methyl-2-oxo-7-(2,4,6-trifluoro-benzyl)-1,2-dihydro-[1,5]naphthyridine-3-carboxylic acid (2-methoxy-ethyl)-amide This compound was prepared from compound A3-B1 in a manner similar to that described in Example A3-B1-1 and was obtained at 53.0% yield: m.p.: 166-168° C.; Elemental Analysis: C$_{20}$H$_{18}$F$_3$N$_3$O$_4$; Calcd (%): C, 57.01; H, 4.31; N, 9.97; F, 13.53; Found (%): C, 56.94; H, 4.14; N, 9.99; F, 13.32; $^1$H NMR (DMSO-d6) δ 10.41-10.37 (1H, m), 8.44 (1H, s), 7.86(1H, s), 7.28-7.20(2H, m), 4.19(2H, s), 3.56(3H, s), 3.56-3.50(4H, m), 3.29(3H, s).

Compound A4-B 1: 7-(3,4-Difluoro-benzyl)-4-hydroxy-1-methyl-2-oxo-1,2-dihydro-[1,5]naphthyridine-3-carboxylic acid ethyl ester The crude compound A4-B1 was prepared from compound B1 (750 mg, 2.03 mmol) and compound A4 (841 mg, 4.06 mmol) in a manner similar to that described in Example A3-B1.
A mixture of above-mentioned crude compound A4-B1 and acetic anhydride was heated at 120° C. for 2 h. After removal of the solvent, the residue was purified by silicagel column chromatography (eluent: n-Hexane/EtOAc=1/2 v/v) to afford 378 mg of compound A4-B1-1 as a colorless crystal. A mixture of compound A4-B1-1 (375 mg, 0.901 mmol) in EtOH (7.5 mL) and KOEt in EtOH (0.53 ml, 24 wt % 1.35 mmol) was stirred at rt for 15 min. After cooling to 0° C., 10% citric acid solution (5 mL) and water (50 mL) were added to the reaction mixture with stirring, and then the resulting mixture was stirred for 15 min. The resulting precipitates were collected by filtration with washing water (20 mL×3) to give 340 mg of compound A4-B1 (yield=44.7% from compound B1). $^1$H NMR (CDCl$_3$) δ 8.51(1H, s), 7.38(1H, s), 6.92-7.19 (3H, m), 4.77(1H, bs), 4.50(2H, q, J=7.2 Hz), 4.12(2H, s), 3.58(3H, s), 1.49(3H, t, J=7.2 Hz).

EXAMPLE 608

7-(3,4-Difluoro-benzyl)-4-hydroxy-1-methyl-2-oxo-1,2-dihydro-[1,5]naphthyridine-3-carboxylic acid (2-hydroxy-ethyl)-amide This compound was prepared from compound A4-B1 (160 mg, 0.427 mmol) in a manner similar to that described in Example A4-B1-1 and was obtained at 69.8% yield: m.p.: 187-189° C.; Elemental Analysis: C$_{19}$H$_{17}$F$_2$N$_3$O$_4$; Calcd (%): C, 58.61; H, 4.40; N, 10.79; F, 9.76; Found (%): C, 58.48; H, 4.43; N, 10.79; F, 9.39; $^1$H NMR (DMSO-d6) δ 10.44(1H, bs), 8.58(1H, s), 8.04(1H, s), 7.52-7.19 (3H, m), 4.94(1H, bs), 4.17(2H, s), 3.61-3.42(7H, m).

EXAMPLE 609

7-(3,4-Difluoro-benzyl)-4-hydroxy-1-methyl-2-oxo-1,2-dihydro-[1,5]naphthyridine-3-carboxylic acid (2-methoxy-ethyl)-amide This compound was prepared from compound A4-B1 (160 mg, 0.427 mmol) in a manner similar to that described in Example A4-B1-1 and was obtained at 66.2% yield: m.p.: 180-181° C.; Elemental Analysis: C$_{20}$H$_{19}$F$_2$N$_3$O$_4$; Calcd (%): C, 59.55; H, 4.75; N, 10.42; F, 9.42; Found (%): C, 59.52; H, 4.73; N, 10.41; F, 9.05; $^1$H NMR (DMSO-d6) δ 10.41(1H, bs), 8.57(1H, s), 8.04(1H, s), 7.51-7.19 (3H, m), 4.17(2H, s), 3.61(3H, s), 3.58-3.27(7H, m).

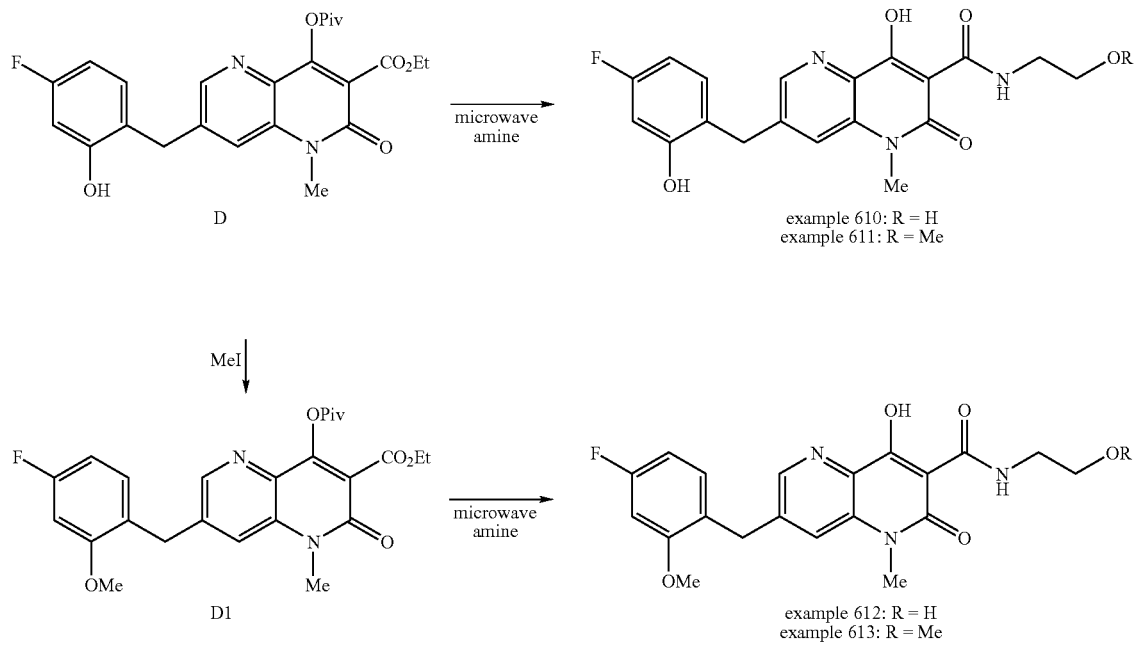

EXAMPLE 610

7-(4-Fluoro-2-hydroxy-benzyl)-4-hydroxy-1-methyl-2-oxo-1,2-dihydro-[1,5]naphthyridine-3-carboxylic acid (2-hydroxy-ethyl)-amide This compound was prepared from compound D in a manner similar to that described in Example A3-B1-1: m.p.: 281-283° C.; Elemental Analysis: C$_{19}$H$_{18}$F$_1$N$_3$O$_5$; Calcd (%): C, 58.91; H, 4.68; N, 10.85; F, 4.90; Found (%): C, 58.75; H, 4.67; N, 10.87; F, 4.59; $^1$H NMR (DMSO-d6) δ 10.43(1H, bs), 8.51(1H, s), 7.91(1H, s), 7.23-7.18(1H, m), 6.63-6.59 (1H, m), 4.93(1H, bs), 4.05(2H, s), 3.57-3.53(5H, m), 3.47-3.43(2H, m).

EXAMPLE 611

7-(4-Fluoro-2-hydroxy-benzyl)-4-hydroxy-1-methyl-2-oxo-1,2-dihydro-[1,5]naphthyridine-3-carboxylic acid (2-methoxy-ethyl)-amide This compound was prepared from compound D in a manner similar to that described in Example A3-B1-1: m.p.: 268-270° C.; Elemental Analysis: $C_{20}H_{20}F_1N_3O_5$; Calcd (%): C, 59.85; H, 5.02; N, 10.47; F, 4.73; Found (%): C, 59.94; H, 5.05; N, 10.44; F, 4.36; $^1$H NMR (DMSO-d6) δ 10.41(1H, bs), 10.14(1H, bs), 8.51(1H, s), 7.91(1H, s), 7.23-7.18(1H, m), 6.64-6.58(1H, m), 4.05(2H, s), 3.57-3.51(7H, m), 3.30 (3H, s).

Compound D1: 4-(2,2-Dimethyl-propionyloxy)-7-(4-fluoro-2-methoxy-benzyl)-1-methyl-2-oxo-1,2-dihydro-[1,5]naphthyridine-3-carboxylic acid ethyl ester To a solution of compound D (500 mg, 1.10 mmol) in DMF (12 mL) were added potassium carbonate (167 mg, 1.21 mmol) and MeI (75 μL, 1.21 mmol) at rt, and stirred for 3 h. The mixture was treated with water and extracted with EtOAc. The combined organic layers were washed with water and dried over $Na_2SO_4$. The solvent was concentrated in vacuo to give 480 mg of compound D1 (yield=93.0%) as a colorless solid. $^1$H NMR (CDCl$_3$) δ 8.40 (d, 1.8 Hz, 1H), 7.42 (d, 1.8 Hz, 1H), 7.11-7.06 (m, 1H), 6.66-6.61 (m, 2H), 4.40 (q, 6.90 Hz, 2H), 4.12 (s, 2H), 3.79 (s, 3H), 3.63 (s, 3H), 1.41 (s, 9H), 1.37 (t, 6.9 Hz, 3H).

EXAMPLE 612

7-(4-Fluoro-2-methoxy-benzyl)-4-hydroxy-1-methyl-2-oxo-1,2-dihydro-[1,5]naphthyridine-3-carboxylic acid (2-hydroxy-ethyl)-amide This compound was prepared from D1 in a manner similar to that described in Example A3-B1-1 and was obtained at 70% yield: m.p.: 240-242° C. Elemental Analysis: $C_{20}H_{20}FN_3O_5$; Calcd (%): C, 59.85; H, 5.02; N, 10.47; F, 4.73; Found (%): C, 59.64; H, 4.96; N, 10.46; F, 4.50; $^1$H NMR (DMSO-d$_6$) δ 10.43 (s, 1H), 8.48 (s, 1H), 7.89 (s, 1H), 7.29 (dd, J=8.1 Hz, 6.9 Hz, 1H), 6.91 (dd, J=11.1 Hz, 2.4 Hz, 1H), 6.74 (dt, J=8.4 Hz, 2.7 Hz, 1H), 4.94 (t, J=4.8 Hz, 1H), 4.07 (s, 2H), 3.82 (s, 3H), 3.57 (s, 3H), 3.43 (m, 4H).

EXAMPLE 613

7-(4-Fluoro-2-methoxy-benzyl)-4-hydroxy-1-methyl-2-oxo-1,2-dihydro-[1,5]naphthyridine-3-carboxylic acid (2-methoxy-ethyl)-amide This compound was prepared from D1 in a manner similar to that described in Example A3-B1-1 and was obtained at 51% yield: m.p.: 191-192° C.; Elemental Analysis: $C_{20}H_{20}FN_3O_5$; Calcd (%): C, 60.72; H, 5.34; N, 10.12; F, 4.57; Found (%): C, 60.68; H, 5.30; N, 10.09; F, 4.36; $^1$H NMR (DMSO-d$_6$) δ 10.40 (s, 1H), 8.46 (d, 1.5 Hz, 1H), 7.88 (s, 1H), 7.27 (dd, J=8.4 Hz, 6.9 Hz, 1H), 6.89 (dd, J=11.7 Hz, 2.7 Hz, 1H), 6.71 (dt, J=8.4 Hz, 2.7 Hz, 1H), 4.05 (s, 2H), 3.80 (s, 3H), 3.55 (s, 3H), 3.50 (m, 4H), 3.28 (s, 3H).

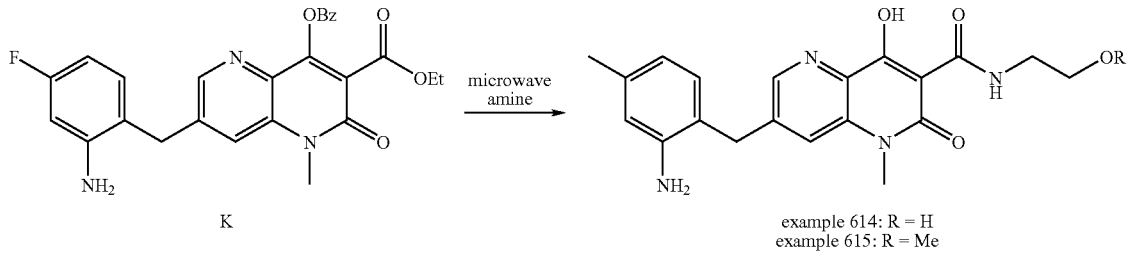

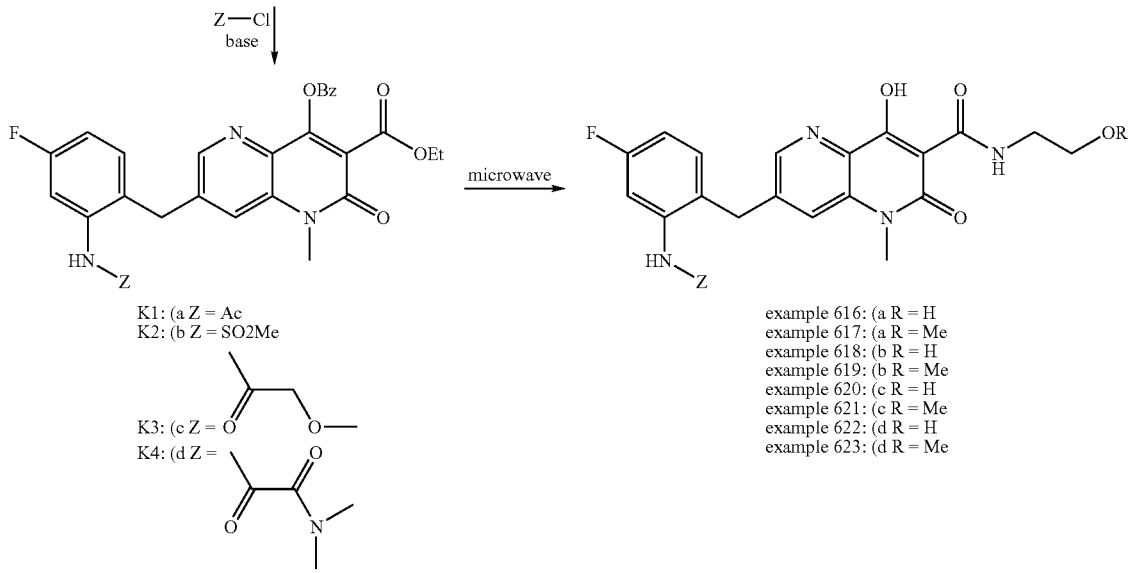

EXAMPLE 614

7-(2-Amino-4-fluoro-benzyl)-4-hydroxy-1-methyl-2-oxo-1,2-dihydro-[1,5]naphthyridine-3-carboxylic acid (2-hydroxy-ethyl)-amide This compound was prepared from compound K in a manner similar to that described in Example A3-B1-1 and was obtained at 50.0% yield: m.p.: 200-201° C.; $^1$H NMR (DMSO-$d_6$) δ 10.42 (t, J=8.1 Hz, 1H), 8.43 (s, 1H), 7.88 (s, 1H), 6.97 (dd, J=8.1 Hz, 6.9 Hz, 1H), 6.42 (dd, J=11.7 Hz, 2.7 Hz, 1H), 6.28 (dt, J=8.7 Hz, 3.6 Hz, 1H), 5.39 (s, 2H), 3.96 (s, 2H), 3.59 (s, 3H), 3.56-3.30 (m, 4H).

EXAMPLE 615

7-(2-Amino-4-fluoro-benzyl)-4-hydroxy-1-methyl-2-oxo-1,2-dihydro-[1,5]naphthyridine-3-carboxylic acid (2-methoxy-ethyl)-amide This compound was prepared from compound K in a manner similar to that described in Example A3-B1-1 and was obtained at 56.0% yield: m.p.: 196-197° C.;

Elemental Analysis: $C_{20}H_{21}FN_4O_4$; Calcd (%): C, 59.99; H, 5.29; N, 13.99; F, 4.74; Found (%): C, 59.70; H, 5.29; N, 13.70; F, 4.34. $^1$H NMR (DMSO-$d_6$) δ 10.40 (s, 1H), 8.47 (s, 1H), 7.94 (s, 1H), 6.96 (dd, J=8.1 Hz, 6.9 Hz, 1H), 6.41 (dd, J=11.4 Hz, 2.4 Hz, 1H), 6.27 (dt, J=8.7 Hz, 2.7 Hz, 1H), 5.39 (s, 2H), 3.97 (s, 2H), 3.55 (s, 3H), 3.50-3.30 (m, 4H), 3.29 (s, 3H).

Compound K1: 7-(2-Acetylamino-4-fluoro-benzyl)-4-benzoyloxy-1-methyl-2-oxo-1,2-dihydro-[1,5]naphthyridine-3-carboxylic acid ethyl ester To a mixture of compound K (500 mg) and $Et_3N$ (176 μL) in THF was added acetyl chloride (83 μL) at 0° C. And the mixture was stirred for 1 h. After adding a $NH_4Cl$ solution, the resulting precipitate was collected by filtration to give 369 mg of compound K2 (yield=69.0%) as a colorless solid. $^1$H NMR (DMSO-d6) δ 8.33(1H, d, J=1.5 Hz), 8.11(2H, d, J=7.5 Hz), 7.91(1H, m), 7.81(1H, t, J=7.5 Hz), 7.64(2H, t, J=7.5 Hz), 7.33-7.24(2H, m), 7.04-6.96(1H, m), 7.03(1H, br), 4.22(2H, q, J=7.2 Hz), 4.17(2H, s), 3.63(3H, s), 2.01(3H, s), 1.08(3H, t, J=7.2 Hz).

EXAMPLE 616

7-(2-Acetylamino-4-fluoro-benzyl)-4-hydroxy-1-methyl-2-oxo-1,2-dihydro-[1,5]naphthyridine-3-carboxylic acid (2-hydroxy-ethyl)-amide This compound was prepared from compound K1 in a manner similar to that described in Example A3-B1-1: m.p.: 285-286° C.; Elemental Analysis: $C_{21}H_{21}F_1N_4O_5$; Calcd (%): C, 58.87; H, 4.94; N, 13.08; F, 4.43; Found (%): C, 58.74; H, 4.91; N, 12.78; F, 4.13; MS (FAB) m/z: 429 [(M+H)+]; $^1$H NMR (DMSO-d6) δ 10.42(1H, brt, J=5.1 Hz), 9.59 (1H, brs), 8.44(1H, d, J=1.8 Hz), 7.81(1H, d, J=1.8 Hz), 7.34-7.27(2H, m), 7.01(1H, ddd, J=2.9 Hz, 8.7 Hz, 8.7 Hz), 4.93(1H, brt, J=5.1 Hz), 4.19(2H, s), 3.59-3.54(2H, m), 3.55 (3H, s), 3.47-3.42(2H, m), 2.01(3H, s).

EXAMPLE 617

7-(2-Acetylamino-4-fluoro-benzyl)-4-hydroxy-1-methyl-2-oxo-1,2-dihydro-[1,5]naphthyridine-3-carboxylic acid (2-methoxy-ethyl)-amide This compound was prepared from compound K1 in a manner similar to that described in Example A3-B1-1: MS (FAB) m/z: 432 [(M+H)+], 885 [(2M+H)+]; HRMS (FAB): $C_{22}H_{23}FN_4O_5+H$. Calcd: 443.1731. Found: 443.1738 (Int. 97.8%); $^1$H NMR (CDCl$_3$) δ 10.34(1H, brt, J=3.9 Hz), 8.19 (1H, d, J=1.8 Hz), 7.32-7.38(3H, m), 7.14(1H, m), 6.97(1H, m), 4.08(2H, s), 3.70-3.58(4H, m), 3.54(3H, s), 3.43(3H, s), 2.12(3H, s).

Compound K2: 4-Benzoyloxy-7-(4-fluoro-2-methanesulfonylamino-benzyl)-1-methyl-2-oxo-1,2-dihydro-[1,5]naphthyridine-3-carboxylic acid ethyl ester To a solution of compound K (371.0 mg, 0.78 mmol) were added MsCl (362 μl, 4.68 mmol) and pyridine (631 μl, 7.8 mmol), and the mixture was stirred at rt for 5 h. After the reaction mixture was quenched with brine, the resulting mixture was extracted with EtOAc, dried over $Na_2SO_4$. The solvent was concentrated in vacuo, the residue was purified by silicagel column chromatography (eluent: CHCl$_3$) to give 367.1 mg of compound K3 (yield=85.0%) as a colorless solid. $^1$H NMR (CDCl$_3$) δ 8.28 (1H, d, J=1.4 Hz), 8.18 (2H, dd, J=7.0, 1.4 Hz), 7.67 (1H, dd, J=7.5, 7.5 Hz), 7.61 (1H, s), 7.52 (2H, dd, 7.9, 7.4 Hz), 7.20(1H, dd, J=7.0, 2.4 Hz), 7.09 (1H, dd, 6.3, 2.4 Hz), 6.93 (1H, dd, 7.9, 2.4 Hz), 6.89(1H, s), 4.32(2H, q, J=7.2 Hz), 4.21(2H, s), 3.59(3H, s), 2.98(3H, s), 1.18 (3H, t, J=7.2 Hz).

EXAMPLE 618

7-(4-Fluoro-2-methanesulfonylamino-benzyl)-4-hydroxy-1-methyl-2-oxo-1,2-dihydro-[1,5]naphthyridine-3-carboxylic acid (2-hydroxy-ethyl)-amide This compound was prepared from compound K2 in a manner similar to that described in Example A3-B1-1: $^1$H NMR (DMSO d-6) δ 10.45(1H, bs), 8.50(1H, s), 7.97(1H, s), 7.27-7.14(2H, m), 6.90(1H, m), 4.98 (1H, brs), 4.23(2H, s), 3.58(3H, s), 3.65-3.55(2H, m), 3.46-3.39(2H, m), 2.93 (3H, s).

EXAMPLE 619

7-(4-Fluoro-2-methanesulfonylamino-benzyl)-4-hydroxy-1-methyl-2-oxo-1,2-dihydro-[1,5]naphthyridine-3-carboxylic acid (2-methoxy-ethyl)-amide This compound was prepared from compound K2 in a manner similar to that described in Example A3-B1-1: $^1$H NMR (CDCl$_3$) δ 10.32(1H, bs), 8.17(1H, s), 7.68(1H, s), 7.27-7.20(1H, m), 7.18-7.10(2H, m), 4.17 (2H, s), 3.70-3.60 (4H, m), 3.56(3H, s), 3.45(3H, s), 3.14 (3H, s).

Compound K3: 4-Benzoyloxy-7-[4-fluoro-2-(2-methoxy-acetylamino)-benzyl]-1-methyl-2-oxo-1,2-dihydro-[1,5]naphthyridine-3-carboxylic acid ethyl ester To a solution of compound K (500 mg, 1.05 mmol) in THF (20 mL) wee added pyridine (0.187 ml, 2.31 mmol) at rt and methoxyacetyl chloride (0.106 ml, 1.16 mmol) at 0° C., and the mixture was stirred for 10 min. The reaction mixture was poured into 2N HCl (5 mL), the resulting solution was extracted with EtOAc. The extract was washed twice with water and dried over $Na_2SO_4$. The solvent was concentrated in vacuo to afford the crude product. The crude product were purified by crystallization with EtOAc/$Et_2O$ to give 477.0 mg of compound K4 (yield=82.8%) as a colorless crystal. $^1H$ NMR ($CDCl_3$) δ 8.40(1H, s), 8.19-8.21(2H, m), 8.10(1H, bs), 7.51-7.84(4H, m), 7.40(1H, s), 7.15-7.22(1H, m), 6.87-6.93 (1H, m), 4.32(2H, q, J=7.2 Hz), 4.09(2H, s), 3.92(2H, s), 3.63(3H, s), 3.33(3H, s), 1.19(3H, t, J=7.2 Hz).

EXAMPLE 620

7-[4-Fluoro-2-(2-methoxy-acetylamino)-benzyl]-4-hydroxy-1-methyl-2-oxo-1,2-dihydro-[1,5]naphthyridine-3-carboxylic acid (2-hydroxy-ethyl)-amide This compound was prepared from compound K3 (230 mg, 0.42 mmol) in a manner similar to that described in Example A3-B1-1 and was obtained at 22.3% yield: m.p.: 205-206° C.; Elemental Analysis: $C_{22}H_{23}F_1N_4O_6$; Calcd (%): C, 57.64; H, 5.06; N, 12.22; F, 4.14; Found (%): C, 57.47; H, 4.83; N, 12.05; F, 3.90; $^1H$ NMR ($CDCl_3$) δ 10.46(1H, bs), 8.62(1H, s), 8.15(1H, bs), 7.78-7.82(1H, m), 7.35(1H, s), 7.18-7.23 (1H, m), 6.89-6.96 (1H, m), 4.13(2H, s), 3.93(2H, s), 3.85-3.93(2H, m), 3.63-3.68 (2H, m), 3.54(3H, s), 3.38(3H, s).

EXAMPLE 621

7-[4-Fluoro-2-(2-methoxy-acetylamino)-benzyl]-4-hydroxy-1-methyl-2-oxo-1,2-dihydro-[1,5]naphthyridine-3-carboxylic acid (2-methoxy-ethyl)-amide This compound was prepared from compound K3 (230 mg, 0.42 mmol) in a manner similar to that described in Example A3-B1-1 and was obtained at 57.4% yield: m.p.: 194-195° C.; Elemental Analysis: $C_{23}H_{25}F_1N_4O_6$; Calcd (%): C, 58.47; H, 5.33; N, 11.86; F, 4.02; Found (%): C, 58.35; H, 5.11; N, 11.85; F, 3.83; $^1H$ NMR ($CDCl_3$) δ 10.34(1H, bs), 8.62(1H, s), 8.14(1H, bs), 7.79-7.83(1H, m), 7.34(1H, s), 7.18-7.22 (1H, m), 6.89-6.96 (1H, m), 4.13(2H, s), 3.92(2H, s), 3.54-3.69(7H, m), 3.42(3H, s), 3.37(3H, s).

Compound K4: 4-Benzoyloxy-7-[2-(dimethylaminooxalyl-amino)-4-fluoro-benzyl]-1-methyl-2-oxo-1,2-dihydro-[1,5]naphthyridine-3-carboxylic acid ethyl ester This compound was prepared from compound K in a manner similar to that described in compound K3 : $^1H$ NMR (DMSO-d6) δ 8.31(1H, s), 8.09(2H, d, J=7.2 Hz), 7.94(1H, s), 7.78(1H, t, J=7.5 Hz), 7.62(2H, t, J=7.5 Hz), 7.42-7.40 (1H, m), 7.33-7.29(1H, m), 7.10-7.05(1H, m), 4.22-4.17(4H, m), 3.64(3H, s), 2.89(3H, s), 2.88(3H, s), 1.06(3H, t, J=6.9 Hz).

EXAMPLE 622

N-{5-Fluoro-2-[8-hydroxy-7-(2-hydroxy-ethylcarbamoyl)-5-methyl-6-oxo-5,6-dihydro-[1,5]naphthyridine-3-ylmethyl]-phenyl}-N',N'-dimethyl-oxalamide This compound was prepared from compound K4 in a manner similar to that described in Example A3-B1-1: m.p.: 263-265° C.; Elemental Analysis: $C_{23}H_{24}F_1N_3O_5$; Calcd (%): C, 56.90; H, 4.98; N, 14.43; F, 3.91; Found (%): C, 56.82; H, 4.93; N, 14.35; F, 3.66; $^1H$ NMR (DMSO-d6) δ 10.42(2H, bs), 8.45(1H, s), 7.85(1H, s), 7.43-7.32(2H, m), 7.13-7.08(1H, m), 4.92(1H, t, J=5.5 Hz), 4.21(2H, s), 3.57-3.54(5H, m), 3.46-3.43(2H, m), 2.92(3H, s), 2.90(3H, s).

EXAMPLE 623

N-{5-Fluoro-2-[8-hydroxy-7-(2-methoxy-ethylcarbamoyl)-5-methyl-6-oxo-5,6-dihydro-[1,5]naphthyridine-3-ylmethyl]-phenyl}-N',N'-dimethyl-oxalamide This compound was prepared from compound K4 in a manner similar to that described in Example A3-B1-1: m.p.: 239-241° C.; Elemental Analysis: $C_{24}H_{26}F_1N_5O_6$; Calcd (%): C, 57.71; H, 5.25; N, 14.02; F, 3.80; Found (%): C, 57.94; H, 5.43; N, 14.16; F, 3.56; $^1H$ NMR (DMSO-d6) δ 10.48(1H, bs), 10.40(1H, bs), 8.46(1H, s), 7.85(1H, s), 7.43-7.32(2H, m), 7.14-7.08(1H, m), 4.21(2H, s), 3.57-3.51(7H, m), 3.29(3H, s), 2.92(3H, s), 2.90(3H, s).

EXAMPLE 624

7-[(4-Fluorophenyl)methyl]-4-hydroxy-N-[(2S)-2-hydroxypropyl]-1-[3-(methyloxy)propyl]-2-oxo-1,2-dihydro-1,5-naphthyridine-3-carboxamide The title compound was prepared in a similar manner to that described in example 647 to provide a white solid. $^1H$ NMR (400 MHz, $CDCl_3$) δ 10.45 (m, 1H), 8.53 (s, 1H), 7.58 (s, 1H), 7.15 (dd, J=8.5, 5.3 Hz, 2H), 7.01 (t, J=8.6 Hz, 2H), 4.21 (m, 2H), 4.11 (s, 2H), 4.07 (m, 1H), 3.60 (ddd, J=13.7, 6.2, 3.4 Hz, 1H), 3.39-3.31 (m, 3H), 3.28 (s, 3H), 1.86 (m, 2H), 1.25 (d, J=6.5 Hz, 3H); MS m/z 444 (M+1).

EXAMPLE 625

7-[(4-Fluorophenyl)methyl]-4-hydroxy-N-[(2R)-2-hydroxypropyl]-1-[3-(methyloxy)propyl]-2-oxo-1,2-dihydro-1,5-naphthyridine-3-carboxamide Synthesis of the title compound and spectral data were identical to the enantiomer described in example 624.

EXAMPLE 626

7-[(4-Fluorophenyl)methyl]-4-hydroxy-N-[(1R)-2-hydroxy-1-methylethyl]-1-[3-(methyloxy)propyl]-2-oxo-1,2-dihydro-1,5-naphthyridine-3-carboxamide The title compound was prepared in a similar manner to that described in example 647 to provide a white solid. $^1H$ NMR (400 MHz, $CDCl_3$) δ 10.29 (d, J=8.4 Hz, 1 H), 8.53 (s, 1 H), 7.59 (s, 1 H), 7.17 (dd, J=8.6, 5.3 Hz, 2 H), 7.02 (t, J=8.6 Hz, 2 H), 4.27 (m, 1 H), 4.20 (m, 2 H), 4.12 (s, 2 H), 3.79 (dd, J=11.2, 3.9 Hz, 1 H), 3.67 (dd, J=10.7, 6.1 Hz, 1 H), 3.37 (t, J=5.4 Hz, 2 H), 3.29 (s, 3 H), 1.87 (m, 1 H), 1.31 (d, J=7.1 Hz, 3 H); MS m/z 444 (M+1).

EXAMPLE 627

7-[(4-Fluorophenyl)methyl]-4-hydroxy-N-[(1S)-2-hydroxy-1-methylethyl]-1-[3-(methyloxy)propyl]-2-oxo-1,2-dihydro-1,5-naphthyridine-3-carboxamide Synthesis of the title compound and spectral data were identical to the enantiomer described in example 626.

EXAMPLE 628

1-{2-[Acetyl(methyl)amino]ethyl}-7-[(4-fluorophenyl)methyl]-4-hydroxy-N-[(2R)-2-hydroxypropyl]-2-oxo-1,2-dihydro-1,5-naphthyridine-3-carboxamide This compound was prepared from ethyl 1-{2-[acetyl(methyl)amino]ethyl}-7-[(4-fluorophenyl)methyl]-4-hydroxy-2-oxo-1,2-dihydro-1,5-naphthyridine-3-carboxylate and (2R)-1-amino-2-propanol using methods similar to Example 574: step 2 to provide an off-white solid: $^1$H NMR (400 MHz, DMSO-d$_6$@90° C.) δ ppm 1.14 (d, J=6.17 Hz, 3 H), 1.84 (s, 3 H), 2.91-2.98 (m, 3 H), 3.23-3.33 (m, 1 H), 3.40-3.50 (m, 1 H), 3.54 (t, J=6.72 Hz, 2 H), 3.85-3.88 (m, 1 H), 4.18 (s, 2 H), 4.37 (d, J=7.55 Hz, 2 H), 4.65 (d, J=5.90 Hz, 1 H), 7.12 (t, J=8.51 Hz, 2 H), 7.36-7.43 (m, 2 H), 8.07 (s, 1 H), 8.55 (s, 1 H), 10.35 (s, 1 H), 16.97-17.20 (m, 1 H); ES$^+$ MS: 471 (M+H$^+$).

EXAMPLE 629

1-{2-[Acetyl(methyl)amino]ethyl}-7-[(4-fluorophenyl)methyl]-4-hydroxy-N-[(1S)-2-hydroxy-1-methylethyl]-2-oxo-1,2-dihydro-1,5-naphthyridine-3-carboxamide This compound was prepared from ethyl 1-{2-[acetyl(methyl)amino]ethyl}-7-[(4-fluorophenyl)methyl]-4-hydroxy-2-oxo-1,2-dihydro-1,5-naphthyridine-3-carboxylate and (2S)-2-amino-1-propanol using methods similar to Example 574: step 2 to provide an off-white solid: $^1$H NMR (400 MHz, DMSO-d$_6$@90° C.) δ ppm 1.23 (d, J=6.72 Hz, 3 H), 1.85 (s, 3 H), 2.95 (s, 2 H), 3.50-3.55 (m, 5 H), 4.07-4.12 (m, 1 H), 4.18 (s, 2 H), 4.36 (d, J=4.80 Hz, 2 H), 4.70 (t, J=5.63 Hz, 1 H), 7.12 (t, J=8.78 Hz, 2 H), 7.37-7.41 (m, 2 H), 8.08 (s, 1 H), 8.55 (s, 1 H), 10.27 (s, 1 H), 17.14 (s, 1 H); ES$^+$ MS: 471 (M+H$^+$).

EXAMPLE 630

1,1-dimethylethyl (3R)-3-[({7-[(4-fluorophenyl)methyl]-4-hydroxy-2-oxo-1-[2-(2-oxo-1-piperidinyl)ethyl]-1,2-dihydro-1,5-naphthyridin-3-yl}carbonyl)amino]butanoate This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 1,1-dimethylethyl (3R)-3-aminobutanoate using methods similar to Example 563 to provide an orange solid: ES$^+$ MS: 581 (M+H$^+$).

EXAMPLE 631

7-[(4-fluorophenyl)methyl]-4-hydroxy-N-(3-hydroxybutyl)-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 4-amino-2-butanol using methods similar to Example 563 to provide a white solid: $^1$H NMR (300 MHz, DMSO-d$_6$) δ ppm 1.06-1.12 (m, 3 H), 1.53-1.68 (m, 6 H), 2.04 (t, J=5.90 Hz, 2 H), 3.22-3.30 (m, 2 H), 3.48 (dt, J=13.48, 6.74 Hz, 4 H), 3.62-3.76 (m, 1 H), 4.16 (s, 2 H), 4.39 (t, J=6.21 Hz, 2 H), 4.64 (d, J=4.63 Hz, 1 H), 7.11-7.18 (m, 2 H), 7.38-7.44 (m, 2 H), 8.19 (s, 1 H), 8.56 (d, J=1.26 Hz, 1 H), 10.33 (t, J=5.48 Hz, 1 H), 17.27 (s, 1 H); ES$^+$ MS: 511 (M+H$^+$).

EXAMPLE 632

1,1-dimethylethyl (3S)-3-[({7-[(4-fluorophenyl)methyl]-4-hydroxy-2-oxo-1-[2-(2-oxo-1-piperidinyl)ethyl]-1,2-dihydro-1,5-naphthyridin-3-yl]carbonyl)amino}butanoate This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 1,1-dimethylethyl (3S)-3-aminobutanoate using methods similar to Example 563 to provide an orange solid: $^1$H NMR (300 MHz, DMSO-d$_6$) δ ppm 1.25 (d, J=6.74 Hz, 3 H), 1.39 (s, 9 H), 1.52-1.67 (m, 4 H), 1.99-2.11 (m, 2 H), 2.52-2.58 (m, 2 H), 3.19-3.30 (m, 2 H), 3.49 (t, J=6.84 Hz, 2 H), 4.16 (s, 2 H), 4.35-4.42 (m, 3 H), 7.11-7.17 (m, 2 H), 7.41 (m, 2 H), 8.20 (d, J=1.47 Hz, 1 H), 8.57 (d, J=1.68 Hz, 1 H), 10.41 (d, J=8.21 Hz, 1 H), 17.06 (d, J=5.26 Hz, 1 H); ES$^+$ MS: 581 (M+H$^+$).

EXAMPLE 633

1-{2-[Acetyl(methyl)amino]ethyl}-7-[(4-fluorophenyl)methyl]-4-hydroxy-N-(2-hydroxyethyl)-2-oxo-1,2-dihydro-1,5-naphthyridine-3-carboxamide This compound was prepared from ethyl 1-{2-[acetyl(methyl)amino]ethyl}-7-[(4-fluorophenyl)methyl]-4-hydroxy-2-oxo-1,2-dihydro-1,5-naphthyridine-3-carboxylate and ethanolamine using methods similar to Example 574: step 2 to provide an off-white solid: $^1$H NMR (400 MHz, DMSO-d$_6$90° C.) δ ppm 1.85 (s, 3 H), 2.95 (s, 2 H), 3.49 (q, J=5.58 Hz, 3 H), 3.53 (d, J=13.58 Hz, 2 H), 3.58-3.66 (m, 2 H), 4.18 (s, 2 H), 4.36 (d, J=6.04 Hz, 2 H), 4.62-4.65 (m, 1 H), 7.12 (t, J=8.92 Hz, 2 H), 7.37-7.43 (m, 2 H), 8.07 (s, 1 H), 8.55 (s, 1 H), 10.32 (s, 1 H), 17.08 (s, 1 H); ES$^+$ MS: 457 (M+H$^+$).

EXAMPLE 634

7-[(4-fluorophenyl)methyl]-4-hydroxy-N-(3-hydroxy-2-methylpropyl)-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)ethyl]-1,2-dihydro-1,5-naphthyridine-3-carboxylate and 3-amino-2-methyl-1-propanol using methods similar to Example 563 to provide an orange solid: $^1$H NMR (300 MHz, DMSO-d$_6$) δ ppm 0.89 (d, J=6.95 Hz, 3 H), 1.52-1.65 (m, 4 H), 1.79-1.88 (m, 1 H), 2.03 (t, J=6.00 Hz, 2 H), 3.20-3.47 (m, 6 H), 3.51 (t, J=6.00 Hz, 2 H), 4.16 (s, 2 H), 4.40 (t, J=6.11 Hz, 2 H), 4.64 (s, 1 H), 7.11-7.17 (m, 2 H), 7.38-7.43 (m, 2 H), 8.20 (d, J=1.47 Hz, 1 H), 8.56 (d, J=1.47 Hz, 1 H), 10.38 (t, J=5.90 Hz, 1 H), 17.24 (s, 1 H); ES$^+$ MS: 511 (M+H$^+$).

EXAMPLE 635

N-(1-cyclopropyl-3-hydroxypropyl)-7-[(4-fluorophenyl)methyl]-4-hydroxy-2-oxo-1-[2-(2-oxo-1-piperidinyl)ethyl]-1,2-dihydro-1,5-naphthyridine-3-carboxamide This compound was prepared from ethyl 7-[(4-fluorophenyl)methyl]-4-hydroxy-2-oxo-1-[2-(2-oxo-1-piperidinyl)

ethyl]-1,2-dihydro-1,5-naphthyridine-3-carboxylate and 3-amino-3-cyclopropyl-1-propanol using methods similar to Example 563 to provide an off-white solid: $^1$H NMR (300 MHz, DMSO-$d_6$) δ ppm 0.24-0.34 (m, 2 H), 0.38-0.46 (m, 1 H), 0.52 (t, J=8.74 Hz, 1 H), 1.00-1.11 (m, 1 H), 1.54-1.67 (m, 4 H), 1.75-1.88 (m, 2 H), 2.04 (s, 2 H), 3.28 (t, J=5.69 Hz, 3 H), 3.46-3.60 (m, 5 H), 4.17 (s, 2 H), 4.41 (t, J=6.95 Hz, 2 H), 7.11-7.17 (m, 2 H), 7.38-7.45 (m, 2 H), 8.22 (s, 1 H), 8.56 (d, J=1.47 Hz, 1 H), 10.36 (d, J=8.63 Hz, 1 H), 17.23 (s, 1 H); ES$^+$ MS: 537 (M+H$^+$).

EXAMPLE 636

7-[(4-Fluorophenyl)methyl]-4-hydroxy-N-methyl-1-[2-(methylamino)-2-oxoethyl]-2-oxo-1,2-dihydro-1,5-naphthyridine-3-carboxamide This compound was prepared from [7-[(4-fluorophenyl)methyl]-4-hydroxy-3-[(methylamino)carbonyl]-2-oxo-1,5-naphthyridine-1 (2H)-yl]acetic acid and methylamine employing methods similar to those described in example 558. The product was obtained as a white solid: $^1$H NMR ($d_6$-DMSO) δ 10.00 (1H, br s), 8.53 (1H, s), 8.03 (1H, br s), 7.79 (1H, s), 7.33-7.30 (2H, m), 7.15-7.05 (2H, m), 4.83 (2H, s), 4.11 (2H, s), 2.88 (3H, d, J=3.8 Hz), 2.52 (3H, d, J=4.4 Hz); HRMS calcd for $C_{20}H_{19}FN_4O_4$+H$^+$: 399.1463. Found 399.1465.

EXAMPLE 637

7-(4-Fluorobenzyl)-4-hydroxy-N-methyl-2-oxo-1-{2-oxo-2-[(2,2,2-trifluoroethyl)amino]ethyl}-1,2-dihydro-1,5-naphthyridine-3-carboxamide The title compound was made from 1-[2-(dimethylamino)-2-oxoethyl]-7-[(4-fluorophenyl)methyl]-4-hydroxy-N-methyl-2-oxo-1,2-dihydro-1,5-naphthyridine-3-carboxamide in a similar manner to example 558 using 2,2,2-trifluoroethylamine to give a white solid: $^1$H NMR ($d_6$-DMSO) δ 9.94 (1H, m), 8.87 (1H, t, J=6 Hz), 8.53 (1H, s), 7.78 (1H, s), 7.31 (2H, m), 7.10 (2H, m), 4.96 (2H, s), 4.09 (2H, s), 3.88 (2H, m), 2.87 (3H, d, J=4 Hz); HRMS calcd for $C_{21}H_{18}F_4N_4O_4$+H$^+$: 467.1340. Found: 467.1340.

EXAMPLE 638

7-(4-Fluorobenzyl)-4-hydroxy-1-[2-(isopropylamino)-2-oxoethyl]-N-methyl-2-oxo-1,2-dihydro-1,5-naphthyridine-3-carboxamide The title compound was made from 1-[2-(dimethylamino)-2-oxoethyl]-7-[(4-fluorophenyl)methyl]-4-hydroxy-N-methyl-2-oxo-1,2-dihydro-1,5-naphthyridine-3-carboxamide in a similar manner to example 558 using isopropylamine to give a white solid: $^1$H NMR ($d_6$-DMSO) δ 9.99 (1H, m), 8.54 (1H, s), 8.02 (1H, d, J=7 Hz), 7.67 (1H, s), 7.30 (2H, m), 7.12 (2H, m), 4.81 (2H, s), 4.10 (2H, s), 3.77 (1H, m), 2.88 (3H, d, J=4 Hz), 0.99 (6H, d, J=7 Hz); HRMS calcd for $C_{22}H_{23}FN_4O_4$+H$^+$: 427.1780. Found: 427.1777.

EXAMPLE 639

1-(2-{[2-(Dimethylamino)ethyl]amino}-2-oxoethyl)-7-(4-fluorobenzyl)-4-hydroxy-N-methyl-2-oxo-1,2-dihydro-1,5-naphthyridine-3-carboxamide The title compound was made from 1-[2-(dimethylamino)-2-oxoethyl]-7-[(4-fluorophenyl)methyl]-4-hydroxy-N-methyl-2-oxo-1,2-dihydro-1,5-naphthyridine-3-carboxamide in a similar manner to example 558 using N,N-dimethylethylenediamine to give a white solid: $^1$H NMR ($d_6$-DMSO) δ 9.99 (1H, m), 8.52 (1H, s), 8.08 (1H, m), 7.71 (1H, s), 7.30 (2H, m), 7.10 (2H, m), 4.84 (2H, s), 4.10 (2H, s), 3.08 (2H, m), 2.88 (3H, d, J=4 Hz), 2.20 (2H, t, J=7 Hz), 2.10 (6H, s); HRMS calcd for $C_{23}H_{26}FN_5O_4$+H$^+$: 456.2040. Found: 456.2043.

EXAMPLE 640

1-(2-Amino-2-oxoethyl)-7-(4-fluorobenzyl)-4-hydroxy-N-methyl-2-oxo-1,2-dihydro-1,5-naphthyridine-3-carboxamide The title compound was made from 1-[2-(dimethylamino)-2-oxoethyl]-7-[(4-fluorophenyl)methyl]-4-hydroxy-N-methyl-2-oxo-1,2-dihydro-1,5-naphthyridine-3-carboxamide in a similar manner to example 558 using ammonium hydroxide to give a white solid: $^1$H NMR ($d_6$-DMSO) δ 10.00 (1H, m), 8.52 (1H, s), 7.82 (1H, s), 7.63 (1H, s), 7.33 (2H, m), 7.26 (1H, s), 7.10 (2H, m), 4.83 (2H, s), 4.11 (2H, s), 2.88 (3H, d, J=4 Hz); HRMS calcd for $C_{19}H_{17}FN_4O_4$+H$^+$: 385.1310. Found: 385.1309.

EXAMPLE 641

Sodium 1-[2-(cyclopropylamino)-2-oxoethyl]-7-[(4-fluorophenyl)methyl]-3-[(methylamino)carbonyl]-2-oxo-1,2-dihydro-1,5-naphthyridine-4-olate This compound was prepared by treating a mixture of the product from Example 473 with 1.5 equivalents of 1N NaOH solution. The mixture was stirred 4 h at rt and filtered to afford the product as a white solid: $^1$H NMR ($d_6$-DMSO) δ 10.15 (1H, br), 8.25 (1H, s), 7.69 (1H, br), 7.27 (3H, m), 7.08 (2H, t, J=9 Hz), 4.70 (2H, br s), 4.05 (2H, s), 2.79 (3H, d, J=5 Hz), 2.60 (1H, m), 0.61 (2H, m), 0.40 (2H, m).

EXAMPLE 642

7-[(4-fluorophenyl)methyl]-4-hydroxy-N-methyl-1-{2-[(methyloxy)amino]-2-oxoethyl}-2-oxo-1,2-dihydro-1,5-naphthyridine-3-carboxamide This compound was prepared from [7-[(4-fluorophenyl)methyl]-4-hydroxy-3-[(methylamino)carbonyl]-2-oxo-1,5-naphthyridine-1(2H)-yl]acetic acid and methoxylamine employing methods similar to those described in example 558. The product was obtained as a white solid: $^1$H NMR ($d_6$-DMSO) δ 11.39 (1H, br s), 9.96 (1H, br s), 8.55 (1H, s), 7.88 (1H, s), 7.36-7.31 (2H, m), 7.14-7.09 (2H, m), 4.80 (2H, s), 4.11 (2H, s), 3.52 (3H, s), 2.88 (3H, d, J=4.8 Hz); HRMS calcd for $C_{20}H_{19}FN_4O_5$+H$^+$: 415.1412. Found 415.1416.

EXAMPLE 643

1-{2-[(Cyclopropylmethyl)amino]-2-oxoethyl}-7-(4-fluorobenzyl)-4-hydroxy-N-methyl-2-oxo-1,2-dihydro-1,5-naphthyridine-3-carboxamide The title compound was made from 1-[2-(dimethylamino)-2-oxoethyl]-7-[(4-fluorophenyl)methyl]-4-hydroxy-N-methyl-2-oxo-1,2-dihydro-1,5-naphthyridine-3-carboxamide in a similar manner to example 558 using (aminomethyl)cyclopropane to give a white solid: $^1$H NMR ($d_6$-DMSO) δ 10.08 (1H, m), 8.45 (1H, s), 8.17 (1H, m), 7.61 (1H, s), 7.29 (2H, m), 7.09 (2H, m), 4.81 (2H, s), 4.07 (2H, s), 2.89 (2H, m), 2.83

(3H, d, J=4 Hz), 0.84 (1H, m), 0.35 (2H, m), 0.10 (2H, m); HRMS calcd for $C_{23}H_{23}FN_4O_4+H^+$: 439.1780. Found: 439.1779.

EXAMPLE 644

7-(4-Fluorobenzyl)-4-hydroxy-N-methyl-2-oxo-1-[2-oxo-2-(propylamino)ethyl]-1,2-dihydro-1,5-naphthyridine-3-carboxamide The title compound was made from 1-[2-(dimethylamino)-2-oxoethyl]-7-[(4-fluorophenyl)methyl]-4-hydroxy-N-methyl-2-oxo-1,2-dihydro-1,5-naphthyridine-3-carboxamide in a similar manner to example 558 using n-propylamine to give a white solid: $^1$H NMR ($d_6$-DMSO) δ 9.98 (1H, m), 8.54 (1H, s), 8.08 (1H, t, J=6 Hz), 7.72 (1H, s), 7.31 (2H, m), 7.12 (2H, m), 4.83 (2H, s), 4.10 (2H, s), 2.95 (2H, m), 2.87 (3H, d, J=4 Hz), 1.32 (2H, m), 0.77 (3H, t, J=7 Hz); HRMS calcd for $C_{22}H_{23}FN_4O_4+H^+$: 427.1780. Found: 427.1781.

EXAMPLE 645

Sodium 7-[(4-fluorophenyl)methyl]-1-[(1-methyl-1H-imidazol-2-yl)methyl]-3-({[2-(methyloxy)ethyl]amino}carbonyl)-2-oxo-1,2-dihydro-1,5-naphthyridine-4-olate In a manner similar to that described in example 474, from 7-[(4-fluorophenyl)methyl]-4-hydroxy-1-[(1-methyl-1H-imidazol-2-yl)methyl]-N-[2-(methyloxy)ethyl]-2-oxo-1,2-dihydro-1,5-naphthyridine-3-carboxamide (506 mg, 1.09 mmol described in example 467) and 1 N sodium hydroxide (1.06 mL) was prepared sodium 7-[(4-fluorophenyl)methyl]-1-[(1-methyl-1H-imidazol-2-yl)methyl]-3-({[2-(methyloxy)ethyl]amino}carbonyl)-2-oxo-1,2-dihydro-1,5-naphthyridine-4-olate (473 mg, 89% yield) as a white solid. $^1$H NMR (DMSO-$d_6$) δ 10.72 (s, 1 H), 8.14 (s, 1 H), 7.92 (s, 1 H), 7.27-7.23 (m, 2 H), 7.08-7.03 (m, 2 H), 6.96 (s, 1 H), 6.71 (s, 1 H), 5.34 (s, 2 H), 3.94 (s, 2 H), 3.59 (s, 3 H), 3.38-3.33 (m, 4 H), 3.23 (s, 3 H); MS m/z 466 (M+1).

EXAMPLE 646

7-(4-Fluorobenzyl)-4-hydroxy-1-{2-[(2-methoxyethyl)amino]-2-oxoethyl}-N-methyl-2-oxo-1,2-dihydro-1,5-naphthyridine-3-carboxamide The title compound was made from 1-[2-(dimethylamino)-2-oxoethyl]-7-[(4-fluorophenyl)methyl]-4-hydroxy-N-methyl-2-oxo-1,2-dihydro-1,5-naphthyridine-3-carboxamide in a similar manner to example 558 using 2-methoxyethylamine to give a white solid: $^1$H NMR ($d_6$-DMSO) δ 9.99 (1H, m), 8.52 (1H, s), 8.27 (1H, t, J=6 Hz), 7.73 (1H, s), 7.31 (2H, m), 7.11 (2H, m), 4.86 (2H, s), 4.10 (2H, s), 3.28 (2H, m), 3.21 (3H, s), 3.18 (2H, m), 2.88 (3H, d, J=4 Hz); HRMS calcd for $C_{22}H_{23}FN_4O_5+H^+$: 443.1730. Found: 443.1729.

EXAMPLE 647

1-Cyclopropyl-7-[(4-fluorophenyl)methyl]-4-hydroxy-N-(2-hydroxyethyl)-2-oxo-1,2-dihydro-1,5-naphthyridine-3-carboxamide 3-Fluoro-4-iodo-2-pyridinecarbonitrile. Modified from WO 2004/019868. To a cold (0° C.) solution of diisopropylamine (4.84 mL, 32 mmol) in THF (82.3 mL) was added n-butyllithium (12.8 mL, 2.5 M in hexanes, 32 mmol) dropwise. The resultant solution was stirred at 0° C. for 15 minutes to give a 0.32 M stock solution of LDA. To a cold (−78° C.) solution of LDA (74 mL, 0.32 M in THF, 23.7 mmol) in THF (50 mL) was added 3-fluoro-2-pyridinecarbonitrile (2.4 g, 19.7 mmol) (Sakamoto et. al. *Chem. Pharm. Bull.* 1985, 33, 565) as a solution in THF (20 mL). After 15 minutes, a solution of $I_2$ (5.49 g, 21.6 mmol) in THF (20 mL) was added rapidly and the resultant suspension was stirred for 20 minutes at −78° C. The reaction mixture was quenched by the addition of water and warmed to ambient temperature. Ethyl acetate was added and the organic layer was washed successively with sodium thiosulfate, and brine. The aqueous layer was extracted with ethyl acetate and the combined organics were dried over sodium sulphate. Filtration and concentration followed by purification by silica gel chromatography provided 3-fluoro-4-iodo-2-pyridinecarbonitrile (3.6 g, 73%) as a white solid. $^1$H NMR (400 MHz, CDCl$_3$) δ 8.14 (d, J=4.8 Hz, 1 H), 7.98 (t, J=4.8 Hz, 1 H).

3-Fluoro-5-iodo-2-pyridinecarbonitrile. Modified from WO 2004/019868. To a cold (−78° C.) solution of freshly prepared LDA (39 mL, 0.5 M in THF, 19.5 mmol) in 100 mL of THF was added a precooled (0° C.) solution of 3-fluoro-4-iodo-2-pyridinecarbonitrile (3.72 g, 15.0 mmol) in THF dropwise. The resultant solution was stirred at −78° C. for 2.5 hours. Water was added followed by ethyl acetate and the mixture was warmed to ambient temperature. The layers were separated and the organic layer was washed with brine. The aqueous layer was extracted with ethyl acetate and the combined organics were dried over sodium sulphate. Filtration and concentration followed by purification by silica gel chromatography provided 3-fluoro-5-iodo-2-pyridinecarbonitrile (2.35 g, 63%) as a white solid along with recovered starting material (456 mg). $^1$H NMR (300 MHz, CDCl$_3$) δ 8.82 (s, 1 H), 8.06 (dd, J=7.5, 1.5 Hz, 1 H).

3-Fluoro-5-[(4-fluorophenyl)methyl]-2-pyridinecarbonitrile. To a solution of 3-fluoro-5-iodo-2-pyridinecarbonitrile (2.31 g, 9.3 mmol) in THF (100 mL) was added 4-fluorobenzyl zinc chloride (27.9 mL, 0.5 M in THF, 14.0 mmol) followed by Pd(PPh$_3$)$_4$ (538 mg, 0.47 mmol). The resultant solution was heated at 75° C. (bath temperature) for 3 hours. After cooling to room temperature, water and ethyl acetate were added. The layers were separated and the organic layer was washed with brine. The aqueous layer was acidified with 1 N HCl until it cleared and extracted with ethyl acetate. The combined organics were dried over sodium sulphate. Filtration and concentration followed by purification by silica gel chromatography provided 3-fluoro-5-[(4-fluorophenyl)methyl]-2-pyridinecarbonitrile (1.6 g, 75%) as a yellow solid. $^1$H NMR (400 MHz, CDCl$_3$) δ 8.40 (s, 1 H), 7.28 (d, J=8.8 Hz, 1 H), 7.12 (dd, J=8.4, 5.2 Hz, 2 H), 7.03 (t, J=8.4 Hz, 2 H), 4.04 (s, 2 H). MS m/z 231 (M+1).

3-(Cyclopropylamino)-5-[(4-fluorophenyl)methyl]-2-pyridinecarbonitrile. 3-Fluoro-5-[(4-fluorophenyl)methyl]-2-pyridinecarbonitrile (546 mg, 2.4 mmol) was taken up in cyclopropylamine (8 mL) and heated at 75° C. in a microwave for 10 minutes and then again for 12 minutes. The mixture was concentrated in vacuo and the residue was purified by silica gel chromatography to give 3-(cyclopropylamino)-5-[(4-fluorophenyl)methyl]-2-pyridinecarbonitrile (417 mg, 66%) as a white solid. $^1$H NMR (300 MHz, CDCl$_3$) δ 7.93 (d, J=1.9 Hz, 1 H), 7.19 (dd, J=8.2, 5.9 Hz, 2 H), 7.19 (d, J=2.4 Hz, 1 H), 7.06 (t, J=8.6 Hz, 2 H), 5.02 (s, 1 H), 4.00 (s, 2 H), 2.48 (m, 1 H), 0.86 (m, 2 H), 0.61 (m, 2 H).

3-(Cyclopropylamino)-5-[(4-fluorophenyl)methyl]-2-pyridinecarboxylic acid. A solution of 3-(cyclopropylamino)-5-[(4-fluorophenyl)methyl]-2-pyridinecarbonitrile (360 mg, 1.34 mmol) in ethanol (25 mL) was treated with sodium hydroxide (2 mL, 50% aqueous) and heated at 100° C. (bath temperature) for 14 hours. The reaction mixture was concentrated in vacuo and the residue taken up in water and cooled in an ice bath. The solution was acidified by the slow addition of 6 NHCl (final pH~3). The aqueous layer was extracted with ethyl acetate and the organics dried over sodium sulfate. Filtration and concentration gave 3-(cyclopropylamino)-5-[(4-fluorophenyl)methyl]-2-pyridinecarboxylic acid (385 mg, 99%) as a white powder. $^1$H NMR (400 MHz, CDCl$_3$) δ 8.94 (br, 1 H), 7.93 (s, 1 H), 7.74 (s, 1 H), 7.30 (s, 1 H), 7.15 (dd, J=8.5, 5.5 Hz, 2 H), 7.00 (t, J=8.7 Hz, 2 H), 3.97 (s, 2 H), 2.40 (m, 1 H), 0.77 (m, 2 H), 0.54 (m, 2 H); MS m/z 287 M+1).

Methyl 3-(cyclopropylamino)-5-[(4-fluorophenyl)methyl]-2-pyridinecarboxylate. To a solution of 3-(cyclopropylamino)-5-[(4-fluorophenyl)methyl]-2-pyridinecarboxylic acid (298 mg, 1.1 mmol) in DMF (10 mL) was added potassium carbonate (316 mg, 2.3 mmol) followed by methyl iodide (0.15 mL, 2.3 mmol). The resultant suspension was stirred for 1.5 hours at which time water and ethyl acetate were added. The layers were separated and the organic layer was washed with brine. The aqueous layer was extracted with ethyl acetate and the combined organics were dried over sodium sulphate. Filtration and concentration followed by purification by silica gel chromatography provided methyl 3-(cyclopropylamino)-5-[(4-fluorophenyl)methyl]-2-pyridinecarboxylate (234 mg, 77%) as a white crystalline solid upon standing. $^1$H NMR (400 MHz, CDCl$_3$) δ 7.90 (d, J=1.9 Hz, 1 H), 7.78 (br, 1 H), 7.24 (s, 1 H), 7.15 (dd, J=8.5, 5.4 Hz, 2 H), 7.00 (t, J=8.7 Hz, 2 H), 3.96 (s, 2 H), 3.93 (s, 3 H), 2.39 (m, 1 H), 0.77 (m, 2 H), 0.52 (m, 2 H); MS m/z 301 (M+1).

Ethyl 1-cyclopropyl-7-[(4-fluorophenyl)methyl]-4-hydroxy-2-oxo-1,2-dihydro-1,5-naphthyridine-3-carboxylate. A solution of methyl 3-(cyclopropylamino)-5-[(4-fluorophenyl)methyl]-2-pyridinecarboxylate (234 mg, 0.78 mmol) and ethyl 3-chloro-3-oxopropanoate (0.13 mL, 90%, 1.0 mmol) was heated at 85° C. for 3 hours. Upon cooling to room temperature, dichloromethane and saturated aqueous sodium bicarbonate were added and the layers separated. The organic layer was washed with brine. The aqueous layers were extracted with dichloromethane and the combined organics dried over sodium sulfate. Filtration and concentration followed by silica gel chromatography provided methyl 3-{cyclopropyl[3-(ethyloxy)-3-oxopropanoyl]amino}-5-[(4-fluorophenyl)methyl]-2-pyridinecarboxylate (285 mg, 88%) as an oil.

A solution of methyl 3-{cyclopropyl[3-(ethyloxy)-3-oxopropanoyl]amino}-5-[(4-fluorophenyl)methyl]-2-pyridinecarboxylate (402 mg, 0.97 mmol) in ethanol (20 mL) at 0° C. was treated with sodium ethoxide (165 mg, 2.4 mmol). The reaction mixture was allowed to warm to room temperature as the bath warmed overnight. Solvents were removed in vacuo and the residue was taken up in water. The pH was adjusted to ~5 with 1 N HCl (aq) and the aqueous layer extracted with ethyl acetate. The organics were dried over sodium sulfate filtered and concentrated to give ethyl 1-cyclopropyl-7-[(4-fluorophenyl)methyl]-4-hydroxy-2-oxo-1,2-dihydro-1,5-naphthyridine-3-carboxylate (362 mg, 98%) as a solid. $^1$H NMR (400 MHz, CDCl$_3$) δ 8.50 (d, J=1.6 Hz, 1 H), 7.78 (s, 1 H), 7.18 (dd, J=8.7, 5.4 Hz, 2 H), 7.04 (t, J=8.7 Hz, 2 H), 4.50 (q, J=7.1 Hz, 2 H), 4.13 (s, 2 H), 2.77 (m, 1 H), 1.46 (t, J=7.3 Hz, 3 H), 1.22 (m, 2 H), 0.76 (m, 2 H); MS m/z 383 (M+1).

1-Cyclopropyl-7-[(4-fluorophenyl)methyl]-4-hydroxy-N-(2-hydroxyethyl)-2-oxo-1,2-dihydro-1,5-naphthyridine-3-carboxamide. A solution of ethyl 1-cyclopropyl-7-[(4-fluorophenyl)methyl]-4-hydroxy-2-oxo-1,2-dihydro-1,5-naphthyridine-3-carboxylate (24 mg, 0.06 mmol) and 2-aminoethanol (0.05 mL) in ethanol (1 mL) was heated in a microwave for 20 minutes. The reaction mixture was concentrated in vacuo and the residue taken up in water. The solution was acidified with 1 N HCl to a final pH~4. The precipitate was filtered through a Teflon filter and the solids collected. This material was azeotroped with methanol to provide the title compound (16 mg, 64%) as a yellow solid. $^1$H NMR (400 MHz, CDCl$_3$) δ 10.38 (s, 1 H), 8.54 (s, 1 H), 7.80 (s, 1 H), 7.17 (m, 2 H), 7.03 (m, 2 H), 4.13 (s, 2 H), 3.84 (m, 2 H), 3.62 (m, 2 H), 2.82 (m, 1 H), 1.23 (m, 2 H), 0.76 (m, 2 H); HRMS m/z calcd for C$_{21}$H$_{21}$N$_3$O$_4$F (M+H)$^+$ 398.1517, found 398.1512.

EXAMPLE 648

Sodium 7-[(4-fluorophenyl)methyl]-3-{[(2-hydroxyethyl)amino]carbonyl}-1-[(1-methyl-1H-imidazol-2-ylmethyl]-2-oxo-1,2-dihydro-1,5-naphthyridine-4-olate In a manner similar to that described in example 474, from 7-[(4-fluorophenyl)methyl]-4-hydroxy-N-(2-hydroxyethyl)-1-[(1-methyl-1H-imidazol-2-yl)methyl]-2-oxo-1,2-dihydro-1,5-naphthyridine-3-carboxamide (336 mg, 0.744 mmol described in example 468) and 1 N sodium hydroxide was prepared sodium 7-[(4-fluorophenyl)methyl]-3-{[(2-hydroxyethyl)amino]carbonyl}-1-[(1-methyl-1H-imidazol-2-yl)methyl]-2-oxo-1,2-dihydro-1,5-naphthyridine-4-olate (324 mg, 92% yield) as a white solid. $^1$H NMR (DMSO-d$_6$) δ 10.61 (s, 1 H), 8.16 (s, 1 H), 7.95 (s, 1 H), 7.27 (m, 2 H), 7.08 (m, 2 H), 6.98 (s, 1 H), 6.73 (s, 1 H), 5.36 (s, 2 H), 4.76 (br s, 1 H), 3.95 (s, 2 H), 3.62 (s, 3 H), 3.46 (br s, 2 H), 3.30 (br s, 2 H); MS m/z 452 (M+1).

EXAMPLE 649

1-Cyclopropyl-7-[(4-fluorophenyl)methyl]-4-hydroxy-N-methyl-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 10.04 (s, 1 H), 8.57 (s, 1 H), 7.82-7.18 (m, 2 H), 7.05 (m, 2 H), 4.15 (s, 2 H), 3.01 (d, J=4.0 Hz, 3 H), 2.83 (br, 1 H), 1.25 (m, 2 H), 0.78 (m, 2 H); HRMS m/z calcd for C$_{20}$H$_{19}$N$_3$O$_3$F (M+H)$^+$ 368.1411, found 368.1404.

EXAMPLE 650

1-Cyclopropyl-7-[(4-fluorophenyl)methyl]-4-hydroxy-N-[2-(methyloxy)ethyl]-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 10.25 (m, 1 H), 8.55 (s, 1 H), 7.80 (s, 1 H), 7.17 (dd, J=8.4, 5.5 Hz, 2 H), 7.03 (t, J=8.6 Hz, 2 H), 4.13 (s, 2 H), 3.63 (m, 2 H), 3.57 (m, 2 H), 3.39 (s, 3 H), 2.80 (m, 1 H), 1.23 (m, 2 H), 0.77 (m, 2 H); HRMS m/z calcd for C$_{22}$H$_{23}$N$_3$O$_4$F (M+H)$^+$ 412.1673, found 412.1668.

EXAMPLE 651

1-cyclopropyl-7-[(4-fluorophenyl)methyl]-4-hydroxy-N-[(2R)-2-hydroxypropyl]-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 10.38 (m, 1 H), 8.52 (s, 1 H), 7.79 (s, 1 H), 7.17 (dd, J=8.2, 5.4 Hz, 2 H), 7.03 (t, J=8.5 Hz, 2 H), 4.13 (s, 2 H), 4.06 (m, 1 H), 3.58 (ddd, J=13.8, 6.1, 3.4 Hz, 1 H), 3.36 (m, 1 H), 2.79 (m, 1 H), 1.26-1.17 (m, 5 H), 0.75 (m, 2 H); HRMS m/z calcd for C$_{22}$H$_{23}$N$_3$O$_4$F (M+H)$^+$ 412.1673, found 412.1668.

EXAMPLE 652

1-Cyclopropyl-7-[(4-fluorophenyl)methyl]-4-hydroxy-N-[(1S)-2-hydroxy-1-methylethyl]-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 10.22 (d, J=7.1 Hz, 1 H), 8.52 (s, 1 H), 7.79 (s, 1 H), 7.17 (m, 2 H), 7.03 (t, J=8.4 Hz, 2 H), 4.26 (m, 1 H), 4.13 (s, 2 H), 3.76 (dd, J=10.9, 3.4 Hz, 1 H), 3.65 (dd, J=10.6, 6.5 Hz, 1 H), 2.79 (m, 1 H), 1.29 (d, J=6.9 Hz, 3 H), 1.23 (m, 2 H), 0.76 (m, 2 H); HRMS m/z calcd for C$_{22}$H$_{23}$N$_3$O$_4$F (M+H)$^+$ 412.1673, found 412.1665.

EXAMPLE 653

1-cyclopropyl-7-[(4-fluorophenyl)methyl]-4-hydroxy-N-[(2S)-2-hydroxypropyl]-2-oxo-1,2-dihydro-1,5-naphthyridine-3-carboxamide Synthesis of the title compound and spectral data were identical to the enantiomer described in example 651. HRMS m/z calcd for C$_{22}$H$_{23}$N$_3$O$_4$F (M+H)$^+$ 412.1673, found 412.1668.

EXAMPLE 654

1-Cyclopropyl-7-[(4-fluorophenyl)methyl]-4-hydroxy-N-[(1R)-2-hydroxy-1-methylethyl]-2-oxo-1,2-dihydro-1,5-naphthyridine-3-carboxamide Synthesis of the title compound and spectral data were identical to the enantiomer described in example 652. HRMS m/z calcd for C$_{22}$H$_{23}$N$_3$O$_4$F (M+H)$^+$ 412.1673, found 412.1664.

EXAMPLE 655

Sodium 1-[2-(Cyclopropylamino)-2-oxoethyl]-7-[(4-fluorophenyl)methyl]-3-({[2-(methyloxy)ethyl]amino}carbonyl)-2-oxo-1,2-dihydro-1,5-naphthyridine-4-olate The title compound was made by treating the compound in example 471 in a manner similar to example 166 to give a yellow solid: $^1$H NMR (d$_6$-DMSO) δ 10.51 (1H, m), 8.19 (1H, s), 8.08 (1H, d, J=4 Hz), 7.30 (1H, s), 7.25 (2H, m), 7.09 (2H, m), 4.64 (2H, s), 3.99 (2H, s), 3.37 (4H, m), 3.24 (3H, s), 2.53 (1H, m), 0.56 (2H, m), 0.34 (2H, m).

EXAMPLE 656

Sodium 3-({[(2R)-2,3-dihydroxypropyl]amino}carbonyl)-7-[(4-fluorophenyl)methyl]-1-methyl-2-oxo-1,2-dihydro-1,5-naphthyridine-4-olate In a manner similar to that described in example 474, from N-[(2R)-2,3-dihydroxypropyl]-7-[(4-fluorophenyl)methyl]-4-hydroxy-1-methyl-2-oxo-1,2-dihydro-1,5-naphthyridine-3-carboxamide (395 mg, 0.985 mmol described in example 516) and 1 N sodium hydroxide (0.99 mL) was prepared sodium 3-({[(2R)-2,3-dihydroxypropyl]amino}carbonyl)-7-[(4-fluorophenyl)methyl]-1-methyl-2-oxo-1,2-dihydro-1,5-naphthyridine-4-olate (390 mg, 94% yield) as a white solid. $^1$H NMR (DMSO-d$_6$) δ 10.61 (s, 1 H), 8.17 (s, 1 H), 7.60 (s, 1 H), 7.33-7.29 (m, 2 H), 7.11-7.06 (m, 2 H), 4.85 (m, 1 H), 4.57 (m, 1 H), 4.02 (s, 2 H), 3.50 (m, 1 H), 3.38 (s, 3 H), 3.40-3.25 (m, 3 H), 3.16 (m, 1 H); MS m/z 402 (M+1).

EXAMPLE 657

1-{2-[Acetyl(methyl)amino]ethyl}-7-[(4-fluorophenyl)methyl]-4-hydroxy-N-[(1R)-2-hydroxy-1-methylethyl]-2-oxo-1,2-dihydro-1,5-naphthyridine-3-carboxamide This compound was prepared from ethyl 1-{2-[acetyl(methyl)amino]ethyl}-7-[(4-fluorophenyl)methyl]-4-hydroxy-2-oxo-1,2-dihydro-1,5-naphthyridine-3-carboxylate and (2R)-2-amino-1-propanol using methods similar to Example 574: step 2 to provide an off-white solid: $^1$H NMR (400 MHz, DMSO-d$_6$@90° C.) δ ppm 1.23 (d, J=6.72 Hz, 3 H), 1.85 (s, 3 H), 2.80 (s, 1 H), 2.95 (s, 2 H), 3.50-3.55 (m, 4 H), 4.05-4.14 (m, 1 H), 4.18 (d, J=0.82 Hz, 2 H), 4.35 (s, 2 H), 4.70 (t, J=5.56 Hz, 1 H), 7.09-7.15 (m, 2 H), 7.36-7.42 (m, 2 H), 8.08 (s, 1 H), 8.55 (s, 1 H), 10.06-10.42 (m, 1 H), 17.06-17.18 (m, 1 H); ES$^-$ MS: 471 (M+H$^+$).

EXAMPLE 658

1-Cyclopropyl-N-[(2S)-2,3-dihydroxypropyl]-7-[(4-fluorophenyl)methyl]-4-hydroxy-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 10.40 (m, 1 H), 8.53 (s, 1 H), 7.80 (s, 1 H), 7.17 (dd, J=8.5, 5.5 Hz, 2 H), 7.03 (t, J=8.6 Hz, 2 H), 4.13 (s, 1 H), 3.91 (m, 1 H), 3.70-3.49 (m, 4 H), 2.80 (m, 1 H), 3.20-2.20 (br, 2 H), 1.23 (m, 2 H), 0.76 (m, 2 H); HRMS m/z calcd for C$_{22}$H$_{23}$N$_3$O$_5$F (M+H)$^+$ 428.1623, found 428.1618.

EXAMPLE 659

1-Cyclopropyl-7-[(4-fluorophenyl)methyl]-4-hydroxy-2-oxo-N-[3-(2-oxo-1-pyrrolidinyl)propyl]-1,2-dihydro-1,5-naphthyridine-3-carboxamide The title compound was prepared in a similar manner to that described in example 647 to provide a white solid. $^1$H NMR (400 MHz, CDCl$_3$) δ 10.22 (m, 1H), 8.53 (d, J=1.6 Hz, 1H), 7.79 (d, J=1.3 Hz, 1H), 7.15 (dd, J=8.6, 5.4 Hz, 2H), 7.02 (t, J=8.7 Hz, 2H), 4.12 (s, 2H), 3.45-3.34 (m, 6H), 2.79 (m, 1H), 2.38 (t, J=7.9 Hz, 2H), 2.02.(t, J=7.4 Hz, 2H), 1.86 (m, 2H), 1.22 (m, 2H), 0.76 (m, 2H); HRMS m/z calcd for C$_{26}$H$_{28}$N$_4$O$_4$F (M+H)$^+$ 479.2095, found 479.2090.

EXAMPLE 660

1-Cyclopropyl-N-[(2R)-2,3-dihydroxypropyl]-7-[(4-fluorophenyl)methyl]-4-hydroxy-2-oxo-1,2-dihydro-1,5-naphthyridine-3-carboxamide Synthesis of the title compound and spectral data were identical to the enantiomer described in example 658. HRMS m/z calcd for C$_{22}$H$_{23}$N$_3$O$_5$F (M+H)$^+$ 428.1623, found 428.1618.

EXAMPLE 661

1-Cyclopropyl-7-[(4-fluorophenyl)methyl]-4-hydroxy-2-oxo-N-[2-(2-oxo-1-imidazolidinyl)ethyl]1,2-dihydro-1,5-naphthyridine-3-carboxamide The title compound was prepared in a similar manner to that described in example 647 to provide a white solid. $^1$H NMR (400 MHz, CDCl$_3$) δ 10.27 (m, 1 H), 8.54 (s, 1 H), 7.80 (s, 1 H), 7.17 (dd, J=8.4, 5.3 Hz, 2 H), 7.03 (t, J=8.6 Hz, 2 H), 4.13 (s, 2 H), 3.61 (m, 2 H), 3.54 (m, 2 H), 3.44-3.39 (m, 4 H), 2.81 (m, 1 H), 1.23 (m, 2 H), 0.77 (m, 2 H); HRMS m/z calcd for C$_{24}$H$_{25}$N$_5$O$_4$F (M+H)$^+$ 466.1891, found 466.1886.

EXAMPLE 662

1-[2-(Ethylamino)-2-oxoethyl]-7-(4-fluorobenzyl)-4-hydroxy-N-methyl-2-oxo-1,2-dihydro-1,5-naphthyridine-3-carboxamide The title compound was made from 1-[2-(dimethylamino)-2-oxoethyl]-7-[(4-fluorophenyl)methyl]-4-hydroxy-N-methyl-2-oxo-1,2-dihydro-1,5-naphthyridine-3-carboxamide in a similar manner to example 558 using a solution of ethylamine in THF to give a white solid: $^1$H NMR (d$_6$-DMSO) δ 9.99 (1H, m), 8.54 (1H, s), 8.10 (1H, t, J=6 Hz), 7.74 (1H, s), 7.31 (2H, m), 7.12 (2H, m), 4.82 (2H, s), 4.10 (2H, s), 3.02 (2H, m), 2.88 (3H, d, J=4 Hz), 0.94 (3H, t, J=7 Hz); HRMS calcd for C$_{21}$H$_{21}$FN$_4$O$_4$+H$^+$: 413.1620. Found: 413.1622.

EXAMPLE 663

1-[2-(tert-Butylamino)-2-oxoethyl]-7-(4-fluorobenzyl)-4-hydroxy-N-methyl-2-oxo-1,2-dihydro-1,5-naphthyridine-3-carboxamide The title compound was made from 1-[2-(dimethylamino)-2-oxoethyl]-7-[(4-fluorophenyl)methyl]-4-hydroxy-N-methyl-2-oxo-1,2-dihydro-1,5-naphthyridine-3-carboxamide in a similar manner to example 558 using tert-butylamine to give a white solid: $^1$H NMR (d$_6$-DMSO) δ 10.01 (1H, m), 8.55 (1H, s), 7.88 (1H, s), 7.60 (1H, s), 7.31 (2H, m), 7.09 (2H, m), 4.81 (2H, s), 4.10 (2H, s), 2.88 (3H, d, J=4 Hz), 1.19 (9H, s); HRMS calcd for C$_{23}$H$_{25}$FN$_4$O$_4$+H$^+$: 441.1930. Found: 441.1935.

EXAMPLE 664

1-Cyclopropyl-7-[(4-fluorophenyl)methyl]-4-hydroxy-N-(4-hydroxybutyl)-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 10.15 (m, 1 H), 8.53 (s, 1 H), 7.79 (s, 1 H), 7.15 (dd, J=8.3, 5.3 Hz, 2 H), 7.01 (t, J=8.7 Hz, 2 H), 4.11 (s, 2 H), 3.68 (m, 2 H), 3.46 (m, 2 H), 2.79 (m, 1 H), 2.00 (br, 1 H), 1.75-1.63 (m, 4 H), 1.22 (m, 2 H), 0.76 (m, 2 H); HRMS m/z calcd for C$_{23}$H$_{25}$N$_3$O$_4$F (M+H)$^+$ 426.1830, found 426.1826.

EXAMPLE 665

7-[(4-Fluorophenyl)methyl]-4-hydroxy-N-(2-hydroxyethyl)-1-[2-(methyloxy)ethyl]-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 10.44 (m, 1 H), 8.55 (s, 1 H), 7.70 (s, 1 H), 7.15 (dd, J=8.2, 5.4 Hz, 2 H), 7.01 (t, J=8.8 Hz, 2 H), 4.34 (t, J=5.3 Hz, 2 H), 4.11 (s, 2 H), 3.85 (t, J=5.0 Hz, 2 H), 3.65-3.61 (m, 4 H), 3.18 (s, 3 H); HRMS m/z calcd for C$_{21}$H$_{23}$N$_3$O$_5$F (N+H)$^+$ 416.1623, found 416.1618.

EXAMPLE 666

7-[(4-Fluorophenyl)methyl]-4-hydroxy-N,1-bis[2-(methyloxy)ethyl]-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 10.29 (m, 1 H), 8.54 (s, 1 H), 7.70 (s, 1 H), 7.15 (dd, J=8.3, 5.5 Hz, 2 H), 7.01 (t, J=8.6 Hz, 2 H), 4.33 (t, J=5.3 Hz, 2 H), 4.10 (s, 2 H), 3.66-3.63 (m, 4 H), 3.58 (t, J=5.4 Hz, 2 H), 3.40 (s, 3 H), 3.18 (s, 3 H); HRMS m/z calcd for C$_{22}$H$_{25}$N$_3$O$_5$F (M+H)$^+$ 430.1779, found 430.1772.

EXAMPLE 667

7-[(4-Fluorophenyl)methyl]-4-hydroxy-N-methyl-1-[2-(methyloxy)ethyl]-2-oxo-1,2-dihydro-1,5-naphthyridine-3-carboxamide The title compound was prepared in a similar manner to that described in example 647 to provide a white solid. $^1$H NMR (400 MHz, CDCl$_3$) δ 10.07 (m, 1 H), 8.56 (s, 1 H), 7.70 (s, 1 H), 7.16 (dd, J=8.4, 5.3 Hz, 2 H), 7.02 (t, J=8.7 Hz, 2 H), 4.35 (t, J=5.2 Hz, 2 H), 4.12 (s, 2 H), 3.65 (t, J=5.3 Hz, 2 H), 3.21 (s, 3 H), 3.02 (d, J=4.8 Hz, 3 H); HRMS m/z calcd for C$_{20}$H$_{21}$N$_3$O$_4$F (M+H)$^+$ 386.1517, found 386.1512.

EXAMPLE 668

7-[(4-Fluorophenyl)methyl]-4-hydroxy-N-[2-(methyloxy)ethyl]-2-oxo-1-[2-(2-oxo-1-imidazolidinyl)ethyl]-1,2-dihydro-1,5-naphthyridine-3-carboxamide The title compound was prepared in a similar manner to that described in example 647 to provide a white solid. $^1$H NMR (400 MHz, CDCl$_3$) δ 10.27 (m, 1 H), 8.54 (s, 1 H), 8.03 (s, 1 H), 7.22 (m, 2 H), 6.98 (t, J=8.4 Hz, 2 H), 4.39-4.34 (m, 3 H), 4.11 (s, 2 H), 3.64 (m, 2 H), 3.58 (m, 2 H), 3.46-3.39 (m, 4 H), 3.40 (s, 3 H), 3.29 (m, 2 H); HRMS m/z calcd for C$_{24}$H$_{27}$N$_5$O$_5$F (M+H)$^+$ 484.1997, found 484.1991.

EXAMPLE 669

7-[(4-fluorophenyl)methyl]-4-hydroxy-N-(2-hydroxyethyl)-2-oxo-1-[3-(2-oxo-1-piperidinyl)propyl]-1,2-dihydro-1,5-naphthyridine-3-carboxamide

Step 1: Synthesis of N-[3,3-bis(ethyloxy)propyl]-5-chloropentanamide

A solution of [3,3-bis(ethyloxy)propyl]amine (9.02 g, 61 mmol) and diisopropylethylamine (13.3 mL, 76.4 mmol) in CH$_2$Cl$_2$ (50 mL) was added dropwise to a cooled (0° C.) solution of 5-chloropentanoyl chloride (10.35 g, 61 mmol) in CH$_2$Cl$_2$ (50 mL) over 2 h. After addition was complete the mixture was treated with 1N NaHSO$_4$ (75 mL) and separated the layers in a separatory funnel. Back extracted the aqueous with CH$_2$Cl$_2$ then combined the organics, washed them with brine, dried them over MgSO$_4$, filtered, and concentrated in vacuo. The resulting oil was chromatographed on silica gel using a gradient between 50 and 100% EtOAC in Hexanes over 100 min. Collected, combined, and concentrated in vacuo pure fractions to provide the desired product as a yellow viscous oil: $^1$H NMR (300 MHz, DMSO-d$_6$) δ ppm 1.10 (t, J=7.09 Hz, 6 H), 1.44-1.55 (m, 2 H), 1.59-1.75 (m, 4 H), 2.04 (t, J=7.23 Hz, 2 H), 3.01-3.08 (m, 2 H), 3.41 (dq, J=9.55, 7.07 Hz, 2 H), 3.50-3.64 (m, 4 H), 4.48 (t, J=5.69 Hz, 1 H), 7.74 (t, J=4.98 Hz, 1 H); ES$^+$ MS: 288 (M+Na$^+$).

Step 2: Synthesis of 1-[3,3-bis(ethyloxy)propyl]-2-piperidinone

A solution of N-[3,3-bis(ethyloxy)propyl]-5-chloropentanamide (10 g, 38 mmol) in THF (400 mL) was treated with lithium hexamethyl disilazide (LiHMDS, 1.0 M in THF) (40 mL, 40 mmol) at ambient temperature. After stirring for 15 min., an additional 10 mL of LiHMDS was added and the reaction was stirred an additional 30 min. After TLC (EtOAc) showed the absence of starting material, the reaction was poured into a sep. funnel containing EtOAc (500 mL) and 1N NaHSO$_4$ (500 mL). Back extracted the aqueous with EtOAc then combined the organics, washed them with brine, dried over MgSO$_4$, filtered, and concentrated in vacuo to provide the product as a clear viscous oil. $^1$H NMR (300 MHz, DMSO-d$_6$) δ ppm 1.10 (t, J=7.02 Hz, 6 H), 1.63-1.74 (m, 6 H), 2.17 (t, J=6.11 Hz, 2 H), 3.20-3.28 (m, 4 H), 3.42 (dq, J=9.55, 7.07 Hz, 2 H), 3.56 (dq, J=9.55, 7.07 Hz, 2 H), 4.47 (t, J=5.62 Hz, 1 H).

Step 3: Synthesis of 3-(2-oxo-1-piperidinyl)propanal

A solution of 1-[3,3-bis(ethyloxy)propyl]-2-piperidinone (1.52 g, 6.61 mmol) in CH$_2$Cl$_2$ (100 mL) under nitrogen was treated with trifluoroacetic acid (TFA) (1.5 mL, 19.5 mmol) and stirred at ambient temperature for 1 h. After adding an additional 1.5 mL of TFA and monitoring by TLC (EtOAc, KMnO$_4$ stain) for complete consumption of starting materials the reaction mixture was partitioned between CH$_2$Cl$_2$ and 1:1 Sat. NaHCO$_3$:water (150 mL) solution. Extracted the aqueous with CH$_2$Cl$_2$ two additional times before combining the organics, washing them with brine, drying over MgSO$_4$, filtering, and concentrating in vacuo to provide the desired product as a clear oil: $^1$H NMR (300 MHz, CHLOROFORM-d) δ ppm 1.78-1.91 (m, 4 H), 2.67 (t, J=6.11 Hz, 2 H), 2.85 (td, J=6.42, 0.91 Hz, 2 H), 3.50 (t, J=5.48 Hz, 2 H), 3.71 (t, J=6.32 Hz, 2 H), 9.53-9.58 (m, 1 H); ES$^+$ MS: 156 (M+H$^+$).

Step 4: Synthesis of ethyl 5-[(4-fluorophenyl)methyl]-3-{[3-(2-oxo-1-piperidinyl)propyl]amino}-2-pyridinecarboxylate A solution of ethyl 3-amino-5-(4-fluorobenzyl)-2-pyridinecarboxylate (0.79 g, 2.9 mmol) and 3-(2-oxo-1-piperidinyl)propanal (0.56 g, 3.6 mmol) under nitrogen in glacial acetic acid (10 mL) was treated with sodium triacetoxyborohydride (1.21 g, 5.7 mmol) at 0° C. for 30 min. After stirring for an additional 30 min., an additional 0.23 g of 3-(2-oxo-1-piperidinyl)propanal and 0.36 g sodium triacetoxyborohydride were added. After stirring another 1 h, an additional 0.145 g of 3-(2-oxo-1-piperidinyl)propanal and 0.3 g sodium triacetoxyborohydride were added and stirred at 0° C. for another ½ hour. The reaction was evaporated in vacuo and the residue was dissolved in CH$_2$Cl$_2$, washed with 2N Na$_2$CO$_3$, and back extracted the aqueous 2× with CH$_2$Cl$_2$. The organics were combined, washed with brine, dried over MgSO$_4$, filtered and evaporated in vacuo. The residue was dissolved in CH$_2$Cl$_2$ and chromatographed on silica gel eluting with 10-100% acetone in hexanes to provide, after combining pure fractions and concentrating them in vacuo, the product as a clear viscous oil. $^1$H NMR (300 MHz, DMSO-d$_6$) δ ppm 1.25-1.31 (m, 3 H), 1.63-1.77 (m, 6 H), 2.19 (t, J=5.90 Hz, 2 H), 3.12-3.25 (m, 4 H), 3.24-3.39 (m, 2 H), 3.94 (s, 2 H), 4.26 (q, J=7.11 Hz, 2 H), 7.08-7.16 (m, 3 H), 7.31 (ddd, J=12.00, 5.33, 3.02 Hz, 2 H), 7.61 (t, J=5.69 Hz, 1 H), 7.76 (d, J=1.82 Hz, 1 H); ES$^+$ MS: 414 (M+H$^+$).

Step 5: Synthesis of ethyl 3-{[3-(ethyloxy)-3-oxopropanoyl][3-(2-oxo-1-piperidinyl)propyl]amino}-5-[(4-fluorophenyl)methyl]-2-pyridinecarboxylate This compound was prepared from ethyl 5-[(4-fluorophenyl)methyl]-3-{[3-(2-oxo-1-piperidinyl)propyl]amino}-2-pyridinecarboxylate using methods similar to Example 336: step 3 to provide a red viscous oil: $^1$H NMR (300 MHz, DMSO-d$_6$) δ ppm 1.08 (t, J=7.16 Hz, 3 H), 1.23-1.28 (m, 3 H), 1.43-1.59 (m, 2 H), 1.60-1.70 (m, 4 H), 2.16 (t, J=4.91 Hz, 1 H), 2.96-3.19 (m, 6 H), 3.34-3.40 (m, 2 H), 3.83-3.98 (m, 2 H), 4.01-4.16 (m, 2 H), 4.29 (q, J=7.16 Hz, 2 H), 7.08-7.17 (m, 2 H), 7.30-7.39 (m, 2 H), 7.90 (d, J=1.82 Hz, 1 H), 8.65 (d, J=1.82 Hz, 1 H), 12.71 (br. s., 1 H); ES$^+$ MS: 528 (M+H$^+$).

Step 6: Synthesis of ethyl 7-[(4-fluorophenyl)methyl]-4-hydroxy-2-oxo-1-[3-(2-oxo-1-piperidinyl)propyl]-1,2-dihydro-1,5-naphthyridine-3-carboxylate This compound was prepared from ethyl 3-{[3-(ethyloxy)-3-oxopropanoyl][3-(2-oxo-1-piperidinyl)propyl]amino}-5-[(4-fluorophenyl)methyl]-2-pyridinecarboxylate using methods similar to Example 336: step 4 to provide a tan solid: $^1$H NMR (400 MHz, DMSO-d$_6$) δ ppm 1.26 (t, J=7.07 Hz, 3 H), 1.65-1.77 (m, 6 H), 2.19 (t, J=6.39 Hz, 2 H), 3.21 (t, J=5.56 Hz, 2 H), 3.34-3.39 (m, 2 H), 4.08-4.16 (m, 2 H), 4.18 (s, 2 H), 4.24 (q, J=7.14 Hz, 2 H), 7.10-7.17 (m, 2 H), 7.36-7.42 (m, 2 H), 7.94-7.97 (m, 1 H), 8.49 (d, J=1.37 Hz, 1 H); ES$^+$ MS: 482 (M+H$^+$).

Step 7: Synthesis of 7-[(4-fluorophenyl)methyl]-4-hydroxy-N-(2-hydroxyethyl)-2-oxo-1-[3-(2-oxo-1-piperidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxo-1-piperidinyl)propyl]-1,2-dihydro-1,5-naphthyridine-3-carboxylate and ethanolamine using methods similar to Example 563 to provide an off-white solid: $^1$H NMR (300 MHz, DMSO-d$_6$) δ ppm 1.64-1.79 (m, 6 H), 2.19 (t, J=6.42 Hz, 2 H), 3.21 (t, J=5.58 Hz, 2 H), 3.33-3.48 (m, 4 H), 3.50-3.61 (m, 2 H), 4.15-4.25 (m, 4 H), 4.93 (t, J=5.05 Hz, 1 H), 7.10-7.18 (m, 2 H), 7.37-7.44 (m, 2 H), 8.00 (d, J=1.26 Hz, 1 H), 8.55 (d, J=1.26 Hz, 1 H), 10.41 (t, J=5.90 Hz, 1 H); ES$^+$ MS: 497 (M+H$^+$).

EXAMPLE 670

7-[(4-fluorophenyl)methyl]-4-hydroxy-N-[(2S)-2-hydroxypropyl]-2-oxo-1-[3-(2-oxo-1-piperidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxo-1-piperidinyl)propyl]-1,2-dihydro-1,5-naphthyridine-3-carboxylate and (2S)-1-amino-2-propanol using methods similar to Example 563 to provide an off-white solid: $^1$H NMR (300 MHz, DMSO-$d_6$) δ ppm 1.11 (d, J=5.90 Hz, 3 H), 1.64-1.80 (m, 6 H), 2.19 (t, J=5.69 Hz, 2 H), 3.16-3.27 (m, 4 H), 3.34-3.49 (m, 2 H), 3.78-3.84 (m, 1 H), 4.16-4.25 (m, 4 H), 4.96 (d, J=4.84 Hz, 1 H), 7.11-7.19 (m, 2 H), 7.38-7.45 (m, 2 H), 8.00 (s, 1 H), 8.56 (s, 1 H), 10.43 (t, J=5.48 Hz, 1 H), 17.23 (s, 1 H); ES$^+$ MS: 511 (M+H$^+$).

EXAMPLE 671

7-[(4-fluorophenyl)methyl]-4-hydroxy-N-methyl-2-oxo-1-[3-(2-oxo-1-piperidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxo-1-piperidinyl)propyl]-1,2-dihydro-1,5-naphthyridine-3-carboxylate and methylamine using methods similar to Example 563 to provide an off-white solid: $^1$H NMR (300 MHz, DMSO-$d_6$) δ ppm 1.65-1.81 (m, 6 H), 2.19 (t, J=6.21 Hz, 2 H), 2.91 (d, J=4.84 Hz, 3 H), 3.20 (t, J=5.79 Hz, 2 H), 3.38 (q, J=7.09 Hz, 2 H), 4.16-4.25 (m, 4 H), 7.11-7.18 (m, 2 H), 7.37-7.44 (m, 2 H), 8.01 (s, 1 H), 8.55 (d, J=1.68 Hz, 1 H), 10.14 (d, J=4.63 Hz, 1 H), 17.23 (s, 1 H); ES$^+$ MS: 467 (M+H$^+$).

EXAMPLE 672

7-[(4-fluorophenyl)methyl]-4-hydroxy-N-[(2R)-2-hydroxypropyl]-2-oxo-1-[3-(2-oxo-1-piperidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxo-1-piperidinyl)propyl]-1,2-dihydro-1,5-naphthyridine-3-carboxylate and (2R)-1-amino-2-propanol using methods similar to Example 563 to provide a white solid: $^1$H NMR (300 MHz, DMSO-$d_6$) δ ppm 1.09 (t, J=6.63 Hz, 3 H), 1.66-1.80 (m, 6 H), 2.19 (t, J=5.79 Hz, 2 H), 3.16-3.25 (m, 4 H), 3.34-3.48 (m, 2 H), 3.73-3.87 (m, 1 H), 4.17-4.24 (m, 4 H), 4.96 (d, J=4.63 Hz, 1 H), 7.11-7.17 (m, 2 H), 7.38-7.43 (m, 2 H), 8.00 (s, 1 H), 8.56 (s, 1 H), 10.43 (s, 1 H), 16.84 (s, 1 H); ES$^+$ MS: 511 (M+H$^+$).

EXAMPLE 673

7-[(4-fluorophenyl)methyl]-4-hydroxy-N-[(1R)-2-hydroxy-1-methylethyl]-2-oxo-1-[3-(2-oxo-1-piperidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxo-1-piperidinyl)propyl]-1,2-dihydro-1,5-naphthyridine-3-carboxylate and (2R)-2-amino-1-propanol using methods similar to Example 563 to provide a tan solid: $^1$H NMR (300 MHz, DMSO-$d_6$) δ ppm 1.19 (d, J=6.74 Hz, 3 H), 1.65-1.81 (m, 6 H), 2.19 (t, J=5.79 Hz, 2 H), 3.21 (t, J=5.90 Hz, 2 H), 3.37 (t, J=6.95 Hz, 2 H), 3.48 (t, J=5.05 Hz, 2 H), 4.05 (t, J=6.00 Hz, 1 H), 4.14-4.23 (m, 4 H), 5.00 (t, J=5.16 Hz, 1 H), 7.10-7.18 (m, 2 H), 7.37-7.44 (m, 2 H), 7.98 (s, 1 H), 8.56 (d, J=1.26 Hz, 1 H), 10.31-10.39 (m, 1 H), 17.24 (s, 1 H); ES$^+$ MS: 511 (M+H$^+$).

EXAMPLE 674

7-[(4-fluorophenyl)methyl]-4-hydroxy-N-[(1S)-2-hydroxy-1-methylethyl]-2-oxo-1-[3-(2-oxo-1-piperidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxo-1-piperidinyl)propyl]-1,2-dihydro-1,5-naphthyridine-3-carboxylate and (2S)-2-amino-1-propanol using methods similar to Example 563 to provide a tan solid: $^1$H NMR (300 MHz, DMSO-$d_6$) δ ppm 1.19 (d, J=6.74 Hz, 3 H), 1.65-1.80 (m, 6 H), 2.19 (t, J=5.79 Hz, 2 H), 3.21 (t, J=5.16 Hz, 2 H), 3.37 (t, J=7.79 Hz, 2 H), 3.48 (t, J=5.16 Hz, 2 H), 4.00-4.12 (m, 1 H), 4.16-4.28 (m, 4 H), 5.00 (t, J=5.16 Hz, 1 H), 7.11-7.18 (m, 2 H), 7.41 (dd, J=8.74, 5.58 Hz, 2 H), 7.99 (s, 1 H), 8.56 (d, J=1.47 Hz, 1 H), 10.37 (d, J=8.63 Hz, 1 H), 17.26 (s, 1 H); ES$^+$ MS: 511 (M+H$^+$).

EXAMPLE 675

7-[(4-Fluorophenyl)methyl]-4 hydroxy-N-[2-(methyloxy)ethyl]-2-oxo-1-[2-oxo-2-(propylamino)ethyl]-1,2-dihydro-1,5-naphthyridine-3-carboxamide The title compound was made in a similar manner to example 558 using n-propylamine to give a white solid: $^1$H NMR ($d_6$-DMSO) δ 10.23 (1H, m), 8.54 (1H, s), 8.10 (1H, m), 7.72 (1H, s), 7.31 (2H, m), 7.10 (2H, m), 4.84 (2H, s), 4.10 (2H, s), 3.50 (4H, m), 3.27 (3H, s), 2.96 (2H, m), 1.32 (2H, m), 0.77 (3H, t, J=7 Hz); HRMS calcd for $C_{24}H_{27}FN_4O_5$+H$^+$: 471.2040. Found: 471.2041.

EXAMPLE 676

1-(2-{[2-(Dimethylamino)ethyl]amino}-2-oxoethyl)-7-[(4-fluorophenyl)methyl]-4-hydroxy-N-[2-(methyloxy)ethyl]-2-oxo-1,2-dihydro-1,5-naphthyridine-3-carboxamide The title compound was made in a similar manner to example 558 using N,N-dimethylethylenediamine to give a white solid: $^1$H NMR ($d_6$-DMSO) δ 10.23 (1H, m), 8.53 (1H, s), 8.10 (1H, m), 7.71 (1H, s), 7.31 (2H, m), 7.10 (2H, m), 4.85 (2H, s), 4.10 (2H, s), 3.49 (4H, m), 3.27 (3H, s), 3.10 (2H, m), 2.21 (2H, t, J=7 Hz), 2.10 (6H, s); HRMS calcd for $C_{25}H_{30}FN_5O_5$+H$^+$: 500.2300. Found: 500.2307.

EXAMPLE 677

1-{2-[(Cyclopropylmethyl)amino]-2-oxoethyl}-7-[(4-fluorophenol)methyl]-4-hydroxy-N-[2-(methyloxy)ethyl]-2-oxo-1,2-dihydro-1,5-naphthyridine-3-carboxamide The title compound was made in a similar manner to example 558 using (aminomethyl)cyclopropane to give a white solid: $^1$H NMR ($d_6$-DMSO) δ 10.23 (1H, m), 8.53 (1H, s), 8.24 (1H, t, J=5 Hz), 7.73 (1H, s), 7.31 (2H, m), 7.10 (2H, m), 4.86 (2H, s), 4.10 (2H, s), 3.52 (4H, m), 3.27 (3H, s), 2.91 (2H, t, J=7 Hz), 0.80 (1H, m), 0.36 (2H, m), 0.10 (2H, m); HRMS calcd for $C_{25}H_{27}FN_4O_5$+H$^+$: 483.2040. Found: 483.2040.

EXAMPLE 678

1-{2-[(1,1-Dimethylethyl)amino]-2-oxoethyl}-7-[(4-fluorophenyl)methyl]-4-hydroxy-N-[2-(methyloxy)ethyl]-2-oxo-1,2-dihydro-1,5-naphthyridine-3-carboxamide The title compound was made in a similar manner to example 558 using tert-butylamine to give a white solid: $^1$H NMR ($d_6$-DMSO) δ 10.26 (1H, m), 8.56 (1H, s), 7.89 (1H, s), 7.58 (1H, s), 7.31 (2H, m), 7.10 (2H, m), 4.81 (2H, s), 4.10

(2H, s), 3.52 (4H, m), 3.27 (3H, s), 1.19 (9H, s); HRMS calcd for $C_{25}H_{29}FN_4O_5$+H$^+$: 485.2190. Found: 485.2195.

EXAMPLE 679

7-[(4-Fluorophenyl)methyl]-4-hydroxy-N-(3-hydroxypropyl)-2-oxo-1-[3-(2-oxo-1-piperidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxo-1-piperidinyl)propyl]-1,2-dihydro-1,5-naphthyridine-3-carboxylate and 3-amino-1-propanol using methods similar to Example 563 to provide a grey solid: $^1$H NMR (400 MHz, DMSO-d$_6$) δ ppm 1.69-1.79 (m, 8 H), 2.21 (t, J=6.31 Hz, 2 H), 2.82-2.87 (m, 1 H), 3.20-3.24 (m, 2 H), 3.37 (t, J=7.23 Hz, 2 H), 3.45-3.56 (m, 4 H), 4.17-4.25 (m, 3 H), 4.26-4.32 (m, 1 H), 7.09-7.15 (m, 2 H), 7.35-7.40 (m, 2 H), 7.86 (s, 1 H), 8.53 (s, 1 H), 10.29 (s, 1 H); ES$^+$ MS: 511 (M+H$^+$).

EXAMPLE 680

7-[(4-Fluorophenyl)methyl]-4-hydroxy-N-[2-(methyloxy)ethyl]-1-(2-{[2-(methyloxy)ethyl]amino}-2-oxoethyl)-2-oxo-1,2-dihydro-1,5-naphthyridine-3-carboxamide The title compound was made in a similar manner to example 558 using 2-methoxyethylamine to give a white solid: $^1$H NMR (d$_6$-DMSO) δ 10.23 (1H, m), 8.53 (1H, s), 8.28 (1H, m), 7.73 (1H, s), 7.31 (2H, m), 7.10 (2H, m), 4.86 (2H, s), 4.10 (2H, s), 3.52 (4H, m), 3.30 (2H, m), 3.27 (3H, s), 3.22 (3H, s), 3.19 (2H, m); HRMS calcd for $C_{24}H_{27}FN_4O_6$+H$^+$: 487.1990. Found: 487.1989.

EXAMPLE 681

7-[(4-fluorophenyl)methyl]-4-hydroxy-N-(2-hydroxyethyl)-1-[4-(methyloxy)phenyl]-2-oxo-1,2-dihydro-1,5-naphthyridine-3-carboxamide 3,5-Dibromo-2-pyridinecarbonitrile. 3,5-Dibromopyridine (30.5 g, 0.12 mol) was dissolved in dichloromethane (80 mL) and methyltrioxorhenium (150 mg, 0.603 mmol) was added 30% hydrogen peroxide (27 mL) was added slowly over 5 minutes and the mixture was stirred at ambient temperature for 3 hours. An additional 40 mL of hydrogen peroxide was added and the reaction was stirred 16 hours. Manganese dioxide (100 mg) was added and the suspension was stirred 40 minutes. The mixture was extracted with dichloromethane, dried over sodium sulfate, filtered, and concentrated under reduced pressure. Ethyl acetate was added and the suspension was refluxed for 30 minutes until solids dissolved and then the mixture was allowed to cool to ambient temperature and aged 48 hours. 3,5-dibromopyridine 1-oxide (25.09 g, 82% yield) was collected by vacuum filtration as pale yellow needles. $^1$H NMR (CDCl$_3$) δ 8.27 (s, 2 H), 7.56 (s, 1 H).

3,5-dibromopyridine 1-oxide (25.09g, 0.099 mol) was dissolved in acetonitrile (200 mL) and triethylamine (28 mL, 0.198 mol) and trimethylsilylcyanide (40 mL, 0.297 mol) were added. The reaction was stirred 16 hours and then diluted with dichloromethane, aqueous sodium carbonate, water, and then filtered through Celite eluting with dichloromethane. The mixture was extracted with dichloromethane and purified by silica gel chromatography (3:2 hexanes:ethyl acetate gradient elution) to afford 3,5-dibromo-2-pyridinecarbonitrile (18.98 g, 73% yield) as a tan solid. $^1$H NMR (CDCl$_3$) δ 8.68 (d, J=2 Hz, 1 H), 8.20 (d, J=2 Hz, 1 H); MS m/z 262 M+1).

3-Bromo-5-[(4-fluorophenyl)methyl]-2-pyridinecarbonitrile. 3,5-dibromo-2-pyridinecarbonitrile (4.52g, 15.34 mmol) was dissolved in tetrahydrofuran (75 mL) and palladium tetrakis(triphenylphosphine) (0.887g, 0.767 mmol) and 4-fluorobenyl zinc chloride (46.02 mL, 0.5 M in tetrahydrofuran) were added. The mixture was heated at 85° C. for 1 hour. An additional 12.3 mL of 4-fluorobenyl zinc chloride was added and the reaction was heated 40 minutes and allowed to cool to ambient temperature. The mixture was diluted with water and ethyl acetate and several drops of 1 N hydrochloric acid were added and the reaction was extracted with ethyl acetate. The organics were washed with brine, dried over sodium sulfate and concentrated under reduced pressure. Purification by silica gel chromatography (0-100% ethyl acetate/hexanes gradient elution) gave 3-bromo-5-[(4-fluorophenyl)methyl]-2-pyridinecarbonitrile (2.54g, 57% yield) as a pale yellow solid. $^1$H NMR (CDCl$_3$) δ 8.48 (s, 1 H), 7.74 (s, 1 H), 7.15-7.11 (m, 2 H), 7.07-7.02 (m, 2 H), 4.02 (s, 2 H); MS m/z 292 (M+1).

5-[(4-Fluorophenyl)methyl]-3-{[4-(methyloxy)phenyl]amino}-2-pyridinecarbonitrile. A dry 50 mL flask was charged with 3-bromo-5-[(4-fluorophenyl)methyl]-2-pyridinecarbonitrile (55.3 mg, 0.190 mmol), cesium carbonate (87 mg, 0.266 mmol), palladium acetate (2.1 mg, 0.0095 mmol), rac-BINAP (8.9 mg, 0.0143 mmol), 4-(methyloxy)aniline (28 mg, 0.228 mmol) and toluene (5 mL). The mixture was refluxed for 5 hours, cooled to ambient temperature, filtered through Celite eluting with dichloromethane, and concentrated under reduced pressure. Purification by silica gel chromatography (0-100% ethyl acetate/hexanes gradient elution) gave 5-[(4-fluorophenyl)methyl]-3-{[4-(methyloxy)phenyl]amino}-2-pyridinecarbonitrile (52.2 mg, 83% yield) as a white solid. $^1$H NMR (CDCl$_3$) δ 7.88 (s, 1 H), 7.07-7.02 (m, 4 H), 6.98-6.88 (m, 5 H), 6.21 (br s, 1 H), 3.82 (s, 2 H); MS m/z 334 (M+1).

Methyl 5-[(4-fluorophenyl)methyl]-3-{[4-(methyloxy)phenyl]amino}-2-pyridinecarboxylate. 5-[(4-fluorophenyl)methyl]-3-{[4-(methyloxy)phenyl]amino}-2-pyridinecarbonitrile (505 mg, 1.52 mmol) was dissolved in ethanol (50 mL) and 50% sodium hydroxide was added and the mixture was heated at 100° C. for 1 hour. The reaction was cooled to ambient temperature, concentrated under reduced pressure, and acidified with 6 N hydrochloric acid. The aqueous layer was extracted with ethyl acetate and the organics were dried over sodium sulfate and concentrated under reduced pressure to yield 5-[(4-fluorophenyl)methyl]-3-{[4-(methyloxy)phenyl]amino}-2-pyridinecarboxylic acid (560 mg, 95% yield). $^1$H NMR (CDCl$_3$/methanol-d$_4$) δ 7.95 (s, 1 H), 7.32 (s, 1 H), 7.01-6.98 (m, 4 H), 6.93-6.83 (m, 4 H), 3.86 (s, 2 H), 3.75 (s, 3 H); MS m/z 353 (M+1).

5-[(4-fluorophenyl)methyl]-3-{[4-(methyloxy)phenyl]amino}-2-pyridinecarboxylic acid (560 mg, 1.59 mmol) was dissolved in N,N-dimethylformamide (50 mL) and potassium carbonate (483 mg, 3.50 mmol) and iodomethane (0.15 mL, 2.39 mmol) were added. The reaction was stirred at ambient temperature for 3 hours, diluted with ethyl acetate and water, and extracted with ethyl acetate. The organics were dried over sodium sulfate and concentrated under reduced pressure. Purification by silica gel chromatography (20-100% ethyl acetate/hexanes gradient elution) gave methyl 5-[(4-fluorophenyl)methyl]-3-{[4-(methyloxy)phenyl]amino}-2-pyridinecarboxylate (373 mg, 64% yield) as a white solid. $^1$H NMR (CDCl$_3$) δ 9.22 (s, 1 H), 7.89 (s, 1 H), 7.09-7.02 (m, 4 H), 6.96-6.86 (m, 4 H), 3.97 (s, 2 H), 3.82 (s, 3 H), 3.80 (s, 3 H); MS m/z 367 (M+1).

Methyl 7-[(4-fluorophenyl)methyl]-4-hydroxy-1-[4-(methyloxy)phenyl]-2-oxo-1,2-dihydro-1,5-naphthyridine-3-carboxylate. In a manner similar to example 128, from methyl 5-[(4-fluorophenyl)methyl]-3-{[4-(methyloxy)phenyl]amino}-2-pyridinecarboxylate (385 mg, 1.05 mmol) was prepared methyl 7-[(4-fluorophenyl)methyl]-4-hydroxy-1-[4-(methyloxy)phenyl]-2-oxo-1,2-dihydro-1,5-naphthyridine-3-carboxylate (418 mg, 92% yield over 2 steps). $^1$H NMR (CDCl$_3$) δ 8.44 (s, 1 H), 7.09-6.93 (m, 8 H), 6.74 (s, 1 H), 3.99 (s, 3 H), 3.92 (s, 2 H), 3.87 (s, 3 H); MS m/z 435 (M+1).

7-[(4-Fluorophenyl)methyl]-4-hydroxy-N-(2-hydroxyethyl)-1-[4-(methyloxy)phenyl]-2-oxo-1,2-dihydro-1,5-naphthyridine-3-carboxamide. In a similar manner to that described in example 196, from methyl 7-[(4-fluorophenyl)methyl]-4-hydroxy-1-[4-(methyloxy)phenyl]-2-oxo-1,2-dihydro-1,5-naphthyridine-3-carboxylate (50 mg, 0.115 mmol) and 2-aminoethanol (0.03 mL) was prepared 7-[(4-fluorophenyl)methyl]-4-hydroxy-N-(2-hydroxyethyl)-1-[4-(methyloxy)phenyl]-2-oxo-1,2-dihydro-1,5-naphthyridine-3-carboxamide (47 mg, 89% yield) as a white solid. $^1$H NMR (CDCl$_3$) δ 10.18 (s, 1 H), 8.44 (s, 1 H), 7.08-7.02 (m, 4 H), 6.98-6.94 (m, 2 H), 6.91-6.87 (m, 2 H), 6.74 (s, 1 H), 3.90 (s, 2 H), 3.85 (s, 3 H), 3.71 (m, 2 H), 3.53 (m, 2 H); HRMS m/z calcd for C$_{25}$H$_{23}$FN$_3$O$_5$: 464.1616 Found: 464.1617.

EXAMPLE 682

7-[(4-fluorophenol)methyl]-4-hydroxy-N-methyl-1-[4-(methyloxy)phenyl]-2-oxo-1,2-dihydro-1,5-naphthyridine-3-carboxamide In a similar manner to that described in example 196, from methyl 7-[(4-fluorophenyl)methyl]-4-hydroxy-1-[4-(methyloxy)phenyl]-2-oxo-1,2-dihydro-1,5-naphthyridine-3-carboxylate (50 mg, 0.115 mmol) and methylamine was prepared 7-[(4-fluorophenyl)methyl]-4-hydroxy-N-methyl-1-[4-(methyloxy)phenyl]-2-oxo-1,2-dihydro-1,5-naphthyridine-3-carboxamide (48 mg, 97% yield) as a white solid. $^1$H NMR (CDCl$_3$) δ 9.96 (s, 1 H), 8.48 (s, 1 H), 7.11-7.05 (m, 4 H), 7.01-6.98 (m, 4 H), 6.77 (s, 1 H), 3.92 (s, 2 H), 3.87 (s, 3 H), 2.95 (d, J=4.8 Hz, 3 H); HRMS m/z calcd for C$_{24}$H$_{21}$FN$_3$O$_4$: 434.1511 Found: 434.1512.

EXAMPLE 683

7-[(4-fluorophenyl)methyl]-4-hydroxy-N-[2-(methyloxy)ethyl]-1-[4-(methyloxy)phenyl]-2-oxo-1,2-dihydro-1,5-naphthyridine-3-carboxamide In a similar manner to that described in example 196, from methyl 7-[(4-fluorophenyl)methyl]-4-hydroxy-1-[4-(methyloxy)phenyl]-2-oxo-1,2-dihydro-1,5-naphthyridine-3-carboxylate (50 mg, 0.115 mmol) and [2-(methyloxy)ethyl]amine was prepared 7-[(4-fluorophenyl)methyl]-4-hydroxy-N-[2-(methyloxy)ethyl]-1-[4-(methyloxy)phenyl]-2-oxo-1,2-dihydro-1,5-naphthyridine-3-carboxamide (47 mg, 89% yield) as a white solid. $^1$H NMR (CDCl$_3$) δ 10.14 (s, 1 H), 8.47 (s, 1 H), 7.12-7.04 (m, 4 H), 7.00-6.96 (m, 2 H), 6.93-6.89 (m, 2 H), 6.74 (s, 1 H), 3.91 (s, 2 H), 3.86 (s, 3 H), 3.59 (m, 2 H), 3.51 (m, 2 H), 3.31 (s, 3 H); HRMS m/z calcd for C$_{26}$H$_{25}$FN$_3$O$_5$: 478.1773. Found: 478.1773.

EXAMPLE 684

1-[2-(Ethylamino)-2-oxoethyl]-7-[(4-fluorophenyl)methyl]-4-hydroxy-N-[2-(methyloxy)ethyl]-2-oxo-1,2-dihydro-1,5-naphthyridine-3-carboxamide The title compound was made in a similar manner to example 558 using a solution of ethylamine in THF to give a white solid: $^1$H NMR (d$_6$-DMSO) δ 10.23 (1H, m), 8.54 (1H, s), 8.12 (1H, t, J=5 Hz), 7.74 (1H, s), 7.31 (2H, m), 7.10 (2H, m), 4.82 (2H, s), 4.11 (2H, s), 3.50 (4H, m), 3.27 (3H, s), 3.03 (2H, m), 0.95 (3H, t, J=7 Hz); HRMS calcd for C$_{23}$H$_{25}$FN$_4$O$_5$+H$^+$: 457.1880. Found: 457.1885.

EXAMPLE 685

7-[(4-Fluorophenyl)methyl]-4-hydroxy-N-(2-hydroxyethyl)-2-oxo-1-(tetrahydro-2-furanylmethyl)-1,2-dihydro-1,5-naphthyridine-3-carboxamide The title compound was prepared in a similar manner to that described in example 647 to provide a white solid. $^1$H NMR (400 MHz, CDCl$_3$) δ 10.41 (m, 1 H), 8.53 (s, 1 H), 7.69 (s, 1 H), 7.16 (dd, J=8.3, 5.5 Hz, 2 H), 7.01 (t, J=8.8 Hz, 2 H), 4.44 (dd, J=14.7, 2.3 Hz, 1 H), 4.12 (m, 1 H), 4.10 (s, 2 H), 3.98 (dd, J=14.7, 7.5 Hz, 1 H), 3.84 (m, 2 H), 3.64-3.55 (m, 4 H), 2.04 (m, 1 H), 1.87-1.79 (m, 2 H), 1.59 (m, 1 H); HRMS m/z calcd for C$_{23}$H$_{25}$N$_3$O$_5$F (M+H)$^+$ 442.1779, found 442.1773.

EXAMPLE 686

7-[(4-Fluorophenyl)methyl]-4-hydroxy-N-[2-(methyloxy)ethyl]-2-oxo-1-(tetrahydro-2-furanylmethyl)-1,2-dihydro-1,5-naphthyridine-3-carboxamide The title compound was prepared in a similar manner to that described in example 647 to provide a white solid. $^1$H NMR (400 MHz, CDCl$_3$) δ 10.29 (s, 1 H), 8.52 (s, 1 H), 7.69 (s, 1 H), 7.15 (m, 2 H), 7.00 (m, 2 H), 4.47 (d, J=14.4 Hz, 1 H), 4.13 (m, 1 H), 4.09 (s, 2 H), 3.98 (dd, J=13.9, 7.4 Hz, 1 H), 3.65-3.54 (m, 6 H), 3.38 (s, 3 H), 2.04 (m, 2 H), 1.85-1.78 (m, 4 H), 1.60 (m, 1 H); HRMS m/z calcd for C$_{24}$H$_{27}$N$_3$O$_5$F (M+1 H)$^+$ 456.1936, found 456.1929.

EXAMPLE 687

7-[(4-Fluorophenyl)methyl]-4-hydroxy-N-methyl-2-oxo-1-(tetrahydro-2-furanylmethyl)-1,2-dihydro-1,5-naphthyridine-3-carboxamide The title compound was prepared in a similar manner to that described in example 647 to provide a white solid. $^1$H NMR (400 MHz, CDCl$_3$) δ 10.08 (s, 1 H), 8.54 (s, 1 H), 7.71 (s, 1 H), 7.17 (m, 2 H), 7.02 (m, 2 H), 4.46 (d, J=14.2 Hz, 1 H), 4.17-4.00 (m, 2 H), 4.11 (s, 2 H), 3.60 (m, 2 H), 3.00 (s, 3 H), 2.05 (m, 1 H), 1.88-1.81 (m, 2 H), 1.62 (m, 1 H); HRMS m/z calcd for C$_{22}$H$_{23}$N$_3$O$_4$F (M+H)$^+$ 412.1673, found 412.1665.

EXAMPLE 688

7-[(4-fluorophenyl)methyl]-4-hydroxy-N-[(2S)-2-hydroxypropyl]-2-oxo-1-[3-(2-oxohexahydro-1H-azepin-1-yl)propyl]-1,2-dihydro-1,5-naphthyridine-3-carboxamide Step 1: Synthesis of N-[3,3-bis(ethyloxy)propyl]-6-chlorohexanamide This compound was prepared from [3,3-bis(ethyloxy)propyl]amine and 6-chlorohexanoyl chloride using methods similar to Example 669: step 1 to provide a yellow viscous oil: $^1$H NMR (300 MHz, DMSO-d$_6$) δ ppm 1.10 (t, J=7.09 Hz, 6 H), 1.28-1.40 (m, 4 H), 1.44-1.56 (m, 2 H), 1.59-1.75 (m, 4 H), 2.04 (t, J=7.23 Hz, 2 H), 3.01-3.09 (m, 2 H), 3.41 (dq, J=9.55, 7.07 Hz, 2 H), 3.50-3.64 (m, 4 H), 4.48 (t, J=5.69 Hz, 1 H), 7.74 (t, J=5.33 Hz, 1 H); ES$^+$ MS: 302 (M+Na$^+$).

Step 2: Synthesis of 1-[3,3-bis(ethyloxy)propyl]hexahydro-2H-azepin-2-one

This compound was prepared from [3,3-bis(ethyloxy)propyl]amine using methods similar to Example 669: step 2 to provide a yellow viscous oil: $^1$H NMR (300 MHz, DMSO-d6) δ ppm 1.10 (t, J=7.02 Hz, 6 H), 1.52 (td, J=10.28, 5.40 Hz, 4 H), 1.58-1.71 (m, 4 H), 2.36-2.41 (m, 2 H), 3.24-3.30 (m, 2 H), 3.30 (s, 1 H), 3.33 (s, 1 H), 3.42 (dq, J=9.53, 7.03 Hz, 2 H), 3.55 (dq, J=9.49, 7.08 Hz, 2 H), 4.45 (t, J=5.62 Hz, 1 H); ES$^+$ MS: 266 (M+Na$^+$).

Step 3: Synthesis of 3-(2-oxohexahydro-1H-azepin-1-yl)propanal

This compound was prepared 1-[3,3-bis(ethyloxy)propyl]hexahydro-2H-azepin-2-one using methods similar to Example 669: step 3 to provide a yellow oil: $^1$H NMR (400 MHz, DMSO-d$_6$) δ ppm 1.46-1.56 (m, 4 H), 1.58-1.66 (m, 2 H), 2.38 (td, J=4.99, 1.74 Hz, 2 H), 2.58 (td, J=6.63, 2.10 Hz, 2 H), 3.34-3.37 (m, 2 H), 3.53-3.57 (m, 2 H), 9.62 (t, J=2.10 Hz, 1 H); ES$^+$ MS: 170 (M+H$^+$).

Step 4: Synthesis of ethyl 5-[(4-fluorophenyl)methyl]-3-{[3-(2-oxohexahydro-1H-azepin-1-yl)propyl]amino}-2-pyridinecarboxylate This compound was prepared from ethyl 3-amino-5-(4-fluorobenzyl)-2-pyridinecarboxylate and 3-(2-oxohexahydro-1H-azepin-1-yl)propanal using methods similar to Example 669: step 4 to provide a clear oil: $^1$H NMR (300 MHz, DMSO-d$_6$) δ ppm 1.28 (t, J=7.09 Hz, 3 H), 1.47-1.58 (m, 4 H), 1.58-1.74 (m, 4 H), 2.36-2.44 (m, 2 H), 3.15 (q, J=6.74 Hz, 2 H), 3.28-3.38 (m, 4 H), 3.94 (s, 2 H), 4.26 (q, J=7.07 Hz, 2 H), 7.07-7.16 (m, 3 H), 7.27-7.34 (m, 2 H), 7.62 (t, J=5.62 Hz, 1 H), 7.77 (d, J=1.82 Hz, 1 H); ES$^+$ MS: 428 (M+H$^+$).

Step 5: Synthesis of ethyl 3-{[3-(ethyloxy)-3-oxopropanoyl][3-(2-oxohexahydro-1H-azepin-1-yl)propyl]amino}-5-[(4-fluorophenyl)methyl]-2-pyridinecarboxylate This compound was prepared from ethyl 5-[(4-fluorophenyl)methyl]-3-{[3-(2-oxohexahydro-1H-azepin-1-yl)propyl]amino}-2-pyridinecarboxylate using methods similar to Example 336: step 3 to provide an orange viscous oil: $^1$H NMR (300 MHz, DMSO-d$_6$) δ ppm 1.06-1.11 (m, 3 H), 1.22-1.29 (m, 3 H), 1.34-1.65 (m, 8 H), 2.33-2.41 (m, 2 H), 3.02-3.07 (m, 2 H), 3.24 (d, J=7.02 Hz, 2 H), 3.36 (s, 1 H), 3.47 (s, 3 H), 3.83-3.98 (m, 2 H), 4.05-4.15 (m, 2 H), 4.21-4.34 (m, 2 H), 7.07-7.18 (m, 2 H), 7.30-7.41 (m, 2 H), 7.90 (d, J=1.83 Hz, 1 H), 8.65 (d, J=1.97 Hz, 1 H); ES$^+$ MS: 542 (M+H$^+$).

Step 6: Synthesis of ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate This compound was prepared from ethyl 3-{[3-(ethyloxy)-3-oxopropanoyl][3-(2-oxohexahydro-1H-azepin-1-yl)propyl]amino}-5-[(4-fluorophenyl)methyl]-2-pyridinecarboxylate using methods similar to Example 336: step 4 to provide a tan solid: $^1$H NMR (300 MHz, DMSO-d$_6$) δ ppm 1.26 (t, J=7.16 Hz, 3 H), 1.47-1.60 (m, 4 H), 1.60-1.73 (m, 4 H), 2.34-2.45 (m, 2 H), 3.34 (dd, J=11.48, 8.11 Hz, 4 H), 3.39 (s, 1 H), 4.06-4.17 (m, 2 H), 4.19 (s, 2 H), 4.24 (q, J=7.16 Hz, 2 H), 7.11-7.18 (m, 2 H), 7.37-7.44 (m, 2 H), 7.96 (s, 1 H), 8.49 (d, J=1.47 Hz, 1 H); ES$^+$ MS: 496 (M+H$^+$).

Step 7: Synthesis of 7-[(4-fluorophenyl)methyl]-4-hydroxy-N-[(2S)-2-hydroxypropyl]-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and (2S)-1-amino-2-propanol using methods similar to Example 563 to provide an off-white solid: $^1$H NMR (300 MHz, DMSO-d$_6$) δ ppm 1.08-1.13 (m, 3 H), 1.55 (d, J=2.74 Hz, 4 H), 1.63 (s, 2 H), 1.65-1.78 (m, 2 H), 2.41 (d, J=10.11 Hz, 2 H), 3.19 (s, 1 H), 3.38 (d, J=6.95 Hz, 5 H), 3.81 (s, 1 H), 4.16-4.25 (m, 4 H), 4.96 (d, J=4.63 Hz, 1 H), 7.11-7.17 (m, 2 H), 7.38-7.44 (m, 2 H), 8.00 (s, 1 H), 8.56 (d, J=1.47 Hz, 1 H), 10.44 (t, J=6.21 Hz, 1 H), 17.21 (s, 1 H); ES$^+$ MS: 525 (M+H$^+$).

EXAMPLE 689

7-[(4-fluorophenyl)methyl]-4-hydroxy-N-(4-hydroxybutyl)-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and 4-amino-1-butanol using methods similar to Example 563 to provide an off-white solid: $^1$H NMR (300 MHz, DMSO-d$_6$) δ ppm 1.25-1.85 (m, 12 H), 2.35-2.45 (m, 2 H), 3.40 (ddd, J=18.53, 12.53, 6.42 Hz, 8 H), 4.15-4.23 (m, 4 H), 4.44 (t, J=5.16 Hz, 1 H), 7.14 (t, J=8.95 Hz, 2 H), 7.37-7.43 (m, 2 H), 7.99 (s, 1 H), 8.56 (d, J=1.47 Hz, 1 H), 10.31 (t, J=6.11 Hz, 1 H), 17.21 (s, 1 H); ES$^+$ MS: 539 (M+H$^+$).

EXAMPLE 690

7-[(4-fluorophenyl)methyl]-4-hydroxy-N-(3-hydroxypropyl)-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and 3-amino-1-propanol using methods similar to Example 563 to provide an off-white solid: $^1$H NMR (300 MHz, DMSO-d$_6$) δ ppm 1.54 (d, J=4.42 Hz, 4 H), 1.60-1.76 (m, 6 H), 2.36-2.44 (m, 2 H), 3.33-3.39 (m, 4 H), 3.39-3.52 (m, 4 H), 4.15-4.24 (m, 4 H), 4.60 (t, J=5.05 Hz, 1 H), 7.14 (ddd, J=9.00, 6.69, 2.00 Hz, 2 H), 7.38-7.44 (m, 2 H), 7.99 (d, J=1.47 Hz, 1 H), 8.56 (d, J=1.47 Hz, 1 H), 10.33 (t, J=5.90 Hz, 1 H), 17.23 (s, 1 H); ES+ MS: 525 (M+H+).

EXAMPLE 691

7-[(4-fluorophenyl)methyl]-4-hydroxy-N-[(2R)-2-hydroxypropyl]-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and (2R)-1-amino-2-propanol using methods similar to Example 563 to provide an off-white solid: $^1$H NMR (300 MHz, DMSO-$d_6$) δ ppm 1.06-1.12 (m, 4 H), 1.54 (d, J=5.05 Hz, 4 H), 1.60-1.75 (m, 4 H), 2.36-2.45 (m, 2 H), 3.15-3.25 (m, 1 H), 3.32-3.47 (m, 4 H), 3.82 (ddd, J=10.84, 6.63, 4.42 Hz, 1 H), 4.15-4.24 (m, 4 H), 4.96 (d, J=4.84 Hz, 1 H) 7.10-7.18 (m, 2 H), 7.38-7.44 (m, 2 H), 8.00 (d, J=1.26 Hz, 1 H), 8.56 (d, J=1.47 Hz, 1 H), 10.44 (t, J=5.58 Hz, 1 H), 17.21 (s, 1 H); ES+ MS: 525 (M+H+).

EXAMPLE 692

7-[(4-fluorophenyl)methyl]-4-hydroxy-N-[3-(methyloxy)propyl]-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and [3-(methyloxy)propyl]amine using methods similar to Example 563 to provide an orange solid: $^1$H NMR (300 MHz, DMSO-$d_6$) δ ppm 1.54 (d, J=3.58 Hz, 4 H), 1.64 (d, J=7.16 Hz, 2 H), 1.69-1.75 (m, 2 H), 1.77-1.82 (m, 2 H), 2.38-2.44 (m, 2 H), 3.24-3.26 (m, 3 H), 3.34-3.47 (m, 8 H), 4.15-4.25 (m, 4 H), 7.11-7.18 (m, 2 H), 7.40 (dd, J=8.63, 5.69 Hz, 2 H), 8.00 (s, 1 H), 8.56 (d, J=1.26 Hz, 1 H), 10.34 (t, J=5.90 Hz, 1 H), 17.19 (s, 1 H); ES+ MS: 539 (M+H+).

EXAMPLE 693

7-[(4-fluorophenyl)methyl]-4-hydroxy-N-(3-hydroxybutyl)-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and 4-amino-2-butanol using methods similar to Example 563 to provide an off-white solid: $^1$H NMR (300 MHz, DMSO-$d_6$) δ ppm 1.10 (d, J=6.32 Hz, 3 H), 1.37-1.87 (m, 10 H), 2.36-2.45 (m, 2 H), 3.32-3.48 (m, 5 H), 3.63-3.77 (m, 2 H), 4.12-4.23 (m, 4 H), 4.62 (br. s., 1 H), 7.14 (ddd, J=9.05, 6.63, 2.21 Hz, 2 H), 7.37-7.44 (m, 2 H), 7.99 (d, J=1.05 Hz, 1 H), 8.56 (d, J=1.26 Hz, 1 H), 10.35 (t, J=5.69 Hz, 1 H), 17.26 (s, 1 H); ES+ MS: 539 (M+H+).

EXAMPLE 694

7-[(4-fluorophenyl)methyl]-4-hydroxy-N-[(1S)-2-hydroxy-1-methylethyl]-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and (2S)-2-amino-1-propanol using methods similar to Example 563 to provide an off-white solid: $^1$H NMR (300 MHz, DMSO-$d_6$) δ ppm 1.19 (d, J=6.53 Hz, 3 H), 1.47-1.58 (m, 4 H), 1.61-1.74 (m, 4 H), 2.41 (d, J=11.58 Hz, 2 H), 3.38 (t, J=6.95 Hz, 4 H), 3.48 (t, J=5.05 Hz, 2 H), 3.97-4.12 (m, 1 H), 4.15-4.27 (m, 4 H), 4.98-5.02 (m, 1 H), 7.14 (t, J=8.95 Hz, 2 H), 7.41 (dd, J=8.84, 5.69 Hz, 2 H), 7.99 (s, 1 H), 8.56 (d, J=1.47 Hz, 1 H), 10.37 (d, J=8.00 Hz, 1 H), 17.24 (s, 1 H); ES+ MS: 525 (M+H+).

EXAMPLE 695

7-[(4-fluorophenyl)methyl]-4-hydroxy-2-oxo-1-[3-(2-oxohexahydro-1H-azepin-1-yl)propyl]-N-[3-(2-oxo-1-pyrrolidinyl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and 1-(3-aminopropyl)-2-pyrrolidinone using methods similar to Example 563 to provide an off-white solid: $^1$H NMR (300 MHz, DMSO-$d_6$) δ ppm 1.54 (d, J=3.58 Hz, 4 H), 1.59-1.65 (m, 2 H), 1.65-1.81 (m, 4 H), 1.84-1.97 (m, 2 H), 2.21 (t, J=8.21 Hz, 2 H), 2.35-2.47 (m, 2 H), 3.24 (t, J=6.74 Hz, 2 H), 3.35 (td, J=7.05, 2.95 Hz, 8 H), 4.15-4.25 (m, 4 H), 7.14 (t, J=8.95 Hz, 2 H), 7.31-7.54 (m, 2 H), 8.00 (s, 1 H), 8.56 (d, J=1.47 Hz, 1 H), 10.31 (t, J=5.90 Hz, 1 H), 17.15 (s, 1 H); ES+ MS: 592 (M+H+).

EXAMPLE 696

7-[(4-fluorophenyl)methyl]-4-hydroxy-N-(2-hydroxyethyl)-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and ethanolamine using methods similar to Example 563 to provide an off-white solid: $^1$H NMR (300 MHz, DMSO-$d_6$) δ ppm 1.54 (d, J=5.05 Hz, 4 H), 1.60-1.75 (m, 4 H), 2.41 (d, J=11.16 Hz, 2 H), 3.34-3.42 (m, 4 H), 3.45 (t, J=5.58 Hz, 2 H), 3.53-3.63 (m, 2 H), 4.16-4.24 (m, 4 H), 4.93 (t, J=4.21 Hz, 1 H), 7.11-7.18 (m, 2 H), 7.37-7.45 (m, 2 H), 8.00 (s, 1 H), 8.56 (d, J=1.47 Hz, 1 H), 10.41 (t, J=6.00 Hz, 1 H), 17.20 (s, 1 H); ES+ MS: 511 (M+H+).

EXAMPLE 697

7-[(4-fluorophenyl)methyl]-4-hydroxy-N-methyl-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and N-methylamine in ethanol using methods similar to Example 563 to provide an off-white solid: $^1$H NMR (300 MHz, DMSO-d6) δ ppm 1.54 (d, J=4.42 Hz, 4 H), 1.61-1.77 (m, 4 H), 2.35-2.44 (m, 2 H), 2.91 (d, J=4.84 Hz, 3 H), 3.34-3.42 (m, 4 H), 4.14-4.23 (m, 4 H), 7.14 (t, J=8.95 Hz, 2 H), 7.40 (dd, J=8.84, 5.48 Hz, 2 H), 7.99 (s, 1 H), 8.56 (d, J=1.47 Hz, 1 H), 10.14 (d, J=4.63 Hz, 1 H), 17.22 (s, 1 H); ES+ MS: 481 (M+H+).

EXAMPLE 698

7-[(4-fluorophenyl)methyl]-4-hydroxy-N-[(1R)-2-hydroxy-1-methylethyl]-2-oxo-1-[3-(2-oxohexahydro-1H-azepin-1-yl)propyl]-1,2-dihydro-1,5-naphthyridine-3-carboxamide This compound was prepared from ethyl 7-[(4-fluorophenyl)methyl]-4-hydroxy-2-oxo-1-[3-(2-oxohexahydro-1H-azepin-1-yl)propyl]-1,2-dihydro-1,5-naphthyridine-3-carboxylate and (2R)-2-amino-1-propanol using methods similar to Example 563 to provide an off-white solid: $^1$H NMR (300 MHz, DMSO-d$_6$) δ ppm 1.19 (d, J=6.74 Hz, 3 H), 1.48-1.59 (m, 4 H), 1.59-1.75 (m, 4 H), 2.35-2.47 (m, 2 H), 3.33-3.42 (m, 4 H), 3.48 (t, J=5.05 Hz, 2 H), 3.99-4.12 (m, 1 H), 4.14-4.23 (m, 4 H), 4.97-5.02 (m, 1 H), 7.14 (ddd, J=8.95, 6.63, 2.11 Hz, 2 H), 7.24-7.54 (m, 2 H), 7.98 (s, 1 H), 8.56 (d, J=1.47 Hz, 1 H), 10.37 (d, J=8.00 Hz, 1 H), 17.24 (s, 1 H); ES$^+$ MS: 525 (M+H$^+$).

EXAMPLE 699

7-[(4-Fluorophenyl)methyl]-4-hydroxy-N-(2-hydroxyethyl-2-oxo-1-(3-pyridinyl)-1,2-dihydro-1,5-naphthyridine-3-carboxamide The title compound was prepared in a manner similar to that described in example 681 as a white solid in 98% yield. $^1$H NMR (CDCl$_3$) δ 10.10 (m, 1 H), 8.78 (d, J=4.8 Hz, 1 H), 8.52 (s, 1 H), 8.49 (d, J=2.4 Hz, 1 H), 7.59 (d, J=8 Hz, 1 H), 7.53 (dd, J=8, 4.8 Hz, 1 H), 7.00-6.90 (m, 4 H), 6.65 (s, 1 H), 3.93 (s, 2 H), 3.79 (m, 2 H), 3.58 (m, 2 H); MS m/z 435 M+1).

EXAMPLE 700

N-[(2R)-2,3-Dihydroxypropyl]-7-[(4-fluorophenyl)methyl]-4-hydroxy-2-oxo-1-(3-pyridinyl)-1,2-dihydro-1,5-naphthyridine-3-carboxamide The title compound was prepared in a manner similar to that described in example 681 as a white solid in 93% yield. $^1$H NMR (methanol-d$_4$/CDCl$_3$) δ 10.00 (m, 1 H), 8.72 (d, J=4.8 Hz, 1 H), 8.46 (s, 1 H), 8.43 (s, 1 H), 7.58 (d, J=8 Hz, 1 H), 7.53 (dd, J=8, 4.8 Hz, 1 H), 6.96-6.85 (m, 4 H), 6.62 (s, 1 H), 3.90 (s, 2 H), 3.76 (m, 1 H), 3.56-3.42 (m, 4 H); MS m/z 465 (M+1).

EXAMPLE 701

7-[(4-Fluorophenyl)methyl]-4-hydroxy-N-methyl-2-oxo-1-(3-pyridinyl)-1,2-dihydro-1,5-naphthyridine-3-carboxamide The title compound was prepared in a manner similar to that described in example 681 as a white solid in 92% yield. $^1$H NMR (CDCl$_3$) δ 9.77 (br s, 1 H), 8.79 (d, J=4.8 Hz, 1 H), 8.53 (d, J=1.2 Hz, 1 H), 8.51 (d, J=2 Hz, 1 H), 7.60 (d, J=8 Hz, 1 H), 7.54 (dd, J=8, 4.8 Hz, 1 H), 7.00-6.90 (m, 4 H), 6.67 (s, 1 H), 3.94 (s, 2 H), 2.97 (d, J=4.8 Hz, 3 H); MS m/z 405 (M+1).

EXAMPLE 702

7-[(4-Fluorophenyl)methyl]-4-hydroxy-N-[2-(methyloxy)ethyl]-2-oxo-1-(3-pyridinyl)-1,2-dihydro-1,5-naphthyridine-3-carboxamide The title compound was prepared in a manner similar to that described in example 681 as a white solid in 97% yield. $^1$H NMR (CDCl$_3$) δ 9.97 (br s, 1 H), 8.78 (d, J=4.8 Hz, 1 H), 8.52-8.50 (m, 2 H), 7.60 (d, J=8 Hz, 1 H), 7.53 (dd, J=8, 4.8 Hz, 1 H), 6.99-6.90 (m, 4 H), 6.64 (s, 1 H), 3.93 (s, 2 H), 3.61 (m, 2 H), 3.52 (m, 2 H), 3.33 (s, 3 H); MS m/z 449 (M+1).

EXAMPLE 703

N-[2-(Acetylamino)ethyl]-7-[(4-fluorophenyl)methyl]-4-hydroxy-2-oxo-1-(3-pyridinyl-1,2-dihydro-1,5-naphthyridine-3-carboxamide The title compound was prepared in a manner similar to that described in example 681 as a white solid in 98% yield. $^1$H NMR (CDCl$_3$) δ 10.03 (br s, 1 H), 8.80 (br s, 1 H), 8.54 (s, 1 H), 8.52 (s, 1 H), 7.63 (d, J=8 Hz, 1 H), 7.57 (m, 1 H), 7.00-6.91 (m, 4 H), 6.67 (s, 1 H), 6.01 (br s, 1 H), 3.95 (s, 2 H), 3.57 (m, 2 H), 3.45 (m, 2 H), 1.95 (s, 3 H); MS m/z 476 (M+1).

EXAMPLE 704

7-[(4-Fluorophenyl)methyl]-4-hydroxy-N-(2-hydroxyethyl-2-oxo-1-[3-(1-piperidinylsulfonyl)phenyl]-1,2-dihydro-1,5-naphthyridine-3-carboxamide The title compound was prepared in a manner similar to that described in example 681 as a white solid in 98% yield. $^1$H NMR (CDCl$_3$) δ 10.11 (br s, 1 H), 8.53 (s, 1 H), 7.90 (d, J=7.6 Hz, 1 H), 7.74 (t, J=7.6 Hz, 1 H), 7.63 (s, 1 H), 7.44 (d, J=8.4 Hz, 1 H), 7.01-6.91 (m, 4 H), 6.62 (s, 1 H), 3.94 (s, 2 H), 3.81 (m, 2 H), 3.59 (m, 2 H), 3.03 (m, 4 H), 1.63 (m, 4 H), 1.44 (m, 2 H); MS m/z 581 (M+1).

EXAMPLE 705

N-(2,3-Dihydroxypropyl)-7-[(4-fluorophenyl)methyl]-4-hydroxy-2-oxo-1-[3-(1-piperidinylsulfonyl)phenyl]-1,2-dihydro-1,5-naphthyridine-3-carboxamide The title compound was prepared in a manner similar to that described in example 681 as a white solid in 91% yield. $^1$H NMR (methanol-d$_4$/CDCl$_3$) δ 9.90 (br s, 1 H), 8.32 (s, 1 H), 7.75 (d, J=8 Hz, 1 H), 7.62 (t, J=8 Hz, 1 H), 7.46 (s, 1 H), 7.31 (d, J=7.6 Hz, 1 H), 6.86-6.74 (m, 4 H), 6.51 (s, 1 H), 3.80 (s, 2 H), 3.64 (br s, 1 H), 3.46-3.28 (m, 4 H), 2.85 (m, 4 H), 1.47 (br s, 4 H), 1.28 (m, 2 H); MS m/z 611 (M+1).

EXAMPLE 706

7-[(4-Fluorophenyl)methyl]-4-hydroxy-N-[2-(methyloxy)ethyl]-2-oxo-1-[3-(1-piperidinylsulfonyl)phenyl]-1,2-dihydro-1,5-naphthyridine-3-carboxamide The title compound was prepared in a manner similar to that described in example 681 as a white solid in 98% yield. $^1$H NMR (CDCl$_3$) δ 9.98 (br s, 1 H), 8.52 (s, 1 H), 7.90 (d, J=8 Hz, 1 H), 7.73 (t, J=8 Hz, 1 H), 7.64 (s, 1 H), 7.44 (d, J=8 Hz, 1 H), 7.01-6.91 (m, 4 H), 6.62 (s, 1 H), 3.93 (s, 2 H), 3.62 (m, 2 H), 3.54 (m, 2 H), 3.34 (s, 3 H), 3.03 (m, 4 H), 1.63 (m, 4 H), 1.45 (m, 2 H); MS m/z 595 (M+1).

EXAMPLE 707

7-[(4-Fluorophenyl)methyl]-4-hydroxy-N-methyl-2-oxo-1-[3-(1-piperidinylsulfonyl)phenyl]-1,2-dihydro-1,5-naphthyridine-3-carboxamide The title compound was prepared in a manner similar to that described in example 681 as a white solid in 85% yield.

¹H NMR (CDCl₃) δ 9.77 (br s, 1 H), 8.53 (s, 1 H), 7.91 (d, J=7.6 Hz, 1 H), 7.74 (t, J=7.6 Hz, 1 H), 7.64 (s, 1 H), 7.44 (d, J=7.6 Hz, 1 H), 6.99-6.91 (m, 4 H), 6.63 (s, 1 H), 3.93 (s, 2 H), 3.03-2.96 (m, 7 H), 1.64 (br s, 4 H), 1.44 (m, 2 H); MS m/z 551 (M+1).

EXAMPLE 708

N-[2-(Acetylamino)ethyl]-7-[(4-fluorophenyl)methyl]-4-hydroxy-2-oxo-1-[3-(1-piperidinylsulfonyl)phenyl]-1,2-dihydro-1,5-naphthyridine-3-carboxamide The title compound was prepared in a manner similar to that described in example 681 as a white solid in 77% yield. ¹H NMR (CDCl₃) δ 10.05 (br s, 1 H), 8.53 (s, 1 H), 7.91 (d, J=7.6, 1 H), 7.75 (t, J=8 Hz, 1 H), 7.64 (s, 1 H), 7.44 (d, J=7.6 Hz, 1 H), 7.01-6.91 (m, 4 H), 6.64 (s, 1 H), 6.05 (br s, 1 H), 3.94 (s, 2 H), 3.57 (m, 2 H), 3.46 (m, 2 H), 3.03 (m, 4 H), 1.95 (s, 3 H), 1.64 (m, 4 H), 1.45 (m, 2 H); MS m/z 622 (M+1).

EXAMPLE 709

7-[(4-Fluorophenyl)methyl]-4-hydroxy-1-(2-hydroxyethyl)-N-methyl-2-oxo-1,2-dihydro-1,5-naphthyridine-3-carboxamide The title compound was prepared in a similar manner to that described in example 647 to provide a white solid. ¹H NMR (400 MHz, CDCl₃) δ 10.00 (br, 1 H), 8.43 (s, 1 H), 7.60 (s, 1 H), 7.12 (m, 2 H), 6.99 (m, 2 H), 4.35 (m, 2 H), 4.06 (s, 2 H), 3.97 (m, 2 H), 2.99 (d, J=4.8 Hz, 3 H); MS m/z 372 M+1).

EXAMPLE 710

7-[(4-Fluorophenyl)methyl]-4-hydroxy-1-(2-hydroxyethyl)-N-[2-(methyloxy)ethyl]-2-oxo-1,2-dihydro-1,5-naphthyridine-3-carboxamide The title compound was prepared in a similar manner to that described in example 647 to provide a white solid. ¹H NMR (400 MHz, CDCl₃) δ 10.24 (br, 1 H), 8.47 (s, 1 H), 7.59 (s, 1 H), 7.13 (m, 2 H), 6.99 (m, 2 H), 4.36 (m, 2 H), 4.08 (s, 2 H), 3.96 (m, 2 H), 3.63 (m, 2 H), 3.58 (m, 2 H), 3.40 (s, 3 H); MS m/z 416 M+1).

EXAMPLE 711

N-[2-(Acetylamino)ethyl]-7-[(4-fluorophenyl)methyl]-4-hydroxy-1-(2-hydroxyethyl)-2-oxo-1,2-dihydro-1,5-naphthyridine-3-carboxamide The title compound was prepared in a similar manner to that described in example 647 to provide a white solid. ¹H NMR (400 MHz, CDCl₃) δ 10.24 (br, 1 H), 8.40 (s, 1 H), 7.70 (s, 1 H), 7.11 (m, 2 H), 6.95 (m, 2 H), 4.27 (m, 2 H), 4.05 (s, 2 H), 3.82 (m, 2 H), 3.50 (m, 2 H), 3.39 (m, 2 H), 1.91 (s, 3 H); MS m/z 443 (M+1).

EXAMPLE 712

7-[(4-Fluorophenyl)methyl]-4-hydroxy-N 1-bis(2-hydroxyethyl)-2-oxo-1,2-dihydro-1,5-naphthyridine-3-carboxamide The title compound was prepared in a similar manner to that described in example 647 to provide a white solid. ¹H NMR (400 MHz, CDCl₃/CD₃OD) δ 10.28 (br, 1 H), 8.43 (s, 1 H), 7.69 (s, 1 H), 7.10 (m, 2 H), 6.95 (m, 2 H), 4.28 (m, 2 H), 4.06 (s, 2 H), 3.80 (m, 2 H), 3.72 (m, 2 H), 3.53 (m, 2 H); MS m/z 402 M+1).

EXAMPLE 713

1-(2,3-Dihydroxypropyl)-7-[(4-fluorophenyl)methyl]-4-hydroxy-N-(2-hydroxyethyl)-2-oxo-1,2-dihydro-1,5-naphthyridine-3-carboxamide The title compound was prepared in a similar manner to that described in example 647 to provide a white solid. ¹H NMR (400 MHz, CDCl₃) δ 10.32 (br, 1 H), 8.42 (s, 1 H), 7.96 (s, 1 H), 7.18 (m, 2 H), 6.98 (m, 2 H), 4.40 (m, 1 H), 4.23 (dd, J=14.4, 6.8 Hz, 1 H), 4.11 (s, 2 H), 3.94 (m, 2 H), 3.62-3.51 (m, 4 H); MS m/z 432 (M+1).

EXAMPLE 714

1-(2,3-Dihydroxypropyl)-7-[(4-fluorophenyl)methyl]-4-hydroxy-N-[2-(methyloxy)ethyl]-2-oxo-1,2-dihydro-1,5-naphthyridine-3-carboxamide The title compound was prepared in a similar manner to that described in example 647 to provide a white solid. ¹H NMR (400 MHz, CDCl₃) δ 10.13 (br, 1 H), 8.51 (s, 1 H), 7.66 (s, 1 H), 7.13 (m, 2 H), 7.00 (m, 2 H), 4.42 (dd, J=14.8, 6.0 Hz, 1 H), 4.17 (dd, J=14.8, 6.0 Hz, 1 H), 4.05 (s, 2 H), 3.95 (m, 1 H), 3.66-3.50 (m, 6 H), 3.39 (s, 3 H); MS m/z 446 M+1).

EXAMPLE 715

1-(2,3-Dihydroxypropyl)-7-[(4-fluorophenyl)methyl]-4-hydroxy-N-methyl-2-oxo-1,2-dihydro-1,5-naphthyridine-3-carboxamide The title compound was prepared in a similar manner to that described in example 647 to provide a white solid. ¹H NMR (400 MHz, CDCl₃) δ 9.90 (br, 1 H), 8.52 (s, 1 H), 7.66 (s, 1 H), 7.13 (m, 2 H), 7.00 (m, 2 H), 4.43 (dd, J=14.8, 6.4 Hz, 1 H), 4.17 (dd, J=14.8, 6.0 Hz, 1 H), 4.10 (s, 2 H), 3.94 (m, 1 H), 3.62 (dd, J=12.0, 3.6 Hz, 1 H), 3.51 (dd, J=12.0, 2.8 Hz, 1 H), 3.00 (d, J=4.8 Hz, 3 H); MS m/z 402 (M+1).

The invention claimed is:
1. A compound selected from the group consisting of:
7-(4-Fluorobenzyl)-4-hydroxy-N-(2-methoxyethyl)-2-oxo-1,2-dihydro-1,5-naphthyridine-3-carboxamide;
N-Cyclopropyl-7-(4-fluorobenzyl)-4-hydroxy-2-oxo-1-[2-(2-oxopyrrolidin-1-yl)ethyl]-1,2-dihydro-1,5-naphthyridine-3-carboxamide;
7-(4-Fluorobenzyl)-4-hydroxy-N-(2-morpholin-4-ylethyl)-2-oxo-1-[2-(2-oxopyrrolidin-1-yl)ethyl]-1,2-dihydro-1,5-naphthyridine-3-carboxamide;
7-Benzyl-4-hydroxy-N-(2-methoxyethyl)-1-(2-morpholin-4-yl-2-oxoethyl)-2-oxo-1,2-dihydro-1,5-naphthyridine-3-carboxamide;
4-Hydroxy-N-[2-(methyloxy)ethyl]-2-oxo-7-(phenylmethyl)-1,2-dihydro-1,5-naphthyridine-3-carboxamide;
7-[(4-Fluorophenyl)methyl]-4-hydroxy-2-oxo-N-[3-(2-oxo-1-pyrrolidinyl)propyl]-1,2-dihydro-1,5-naphthyridine-3-carboxamide;
7-[(4-Fluorophenyl)methyl]-4-hydroxy-N-[2-(4-morpholinyl)ethyl]-2-oxo-1,2-dihydro-1,5-naphthyridine-3-carboxamide;

7-[(5-Fluoro-2-pyridinyl)methyl]-4-hydroxy-N-[3-(4-morpholinyl)propyl]-2-oxo-1,2-dihydro-1,5-naphthyridine-3-carboxamide;

7-Benzyl-4-hydroxy-N-(2-methoxyethyl)-1-[4-(methylsulfonyl)benzyl]-2-oxo-1,2-dihydro-1,5-naphthyridine-3-carboxamide;

7-(4-Fluorobenzyl)-4-hydroxy-N-(2-methoxyethyl)-2-oxo-1-[2-(2-oxopyrrolidin-1-yl)ethyl]-1,2-dihydro-1,5-naphthyridine-3-carboxamide;

7-Benzyl-4-hydroxy-N-(2-methoxyethyl)-1-[(1-methyl-1H-imidazol-2-yl)methyl]-2-oxo-1,2-dihydro-1,5-naphthyridine-3-carboxamide;

7-Benzyl-1-(cyclopropylmethyl)-4-hydroxy-N-(2-methoxyethyl)-2-oxo-1,2-dihydro-1,5-naphthyridine-3-carboxamide;

7-Benzyl-4-hydroxy-N-(2-methoxyethyl)-2-oxo-1-(1,3-thiazol-2-ylmethyl)-1,2-dihydro-1,5-naphthyridine-3-carboxamide;

7-(4-Fluorobenzyl)-4-hydroxy-N-(2-methoxyethyl)-1-[4-(methylsulfonyl)benzyl]-2-oxo-1,2-dihydro-1,5-naphthyridine-3-carboxamide;

7-[(4-Fluorophenyl)methyl]-4-hydroxy-N-[2-(4-morpholinyl)ethyl]-1-[2-(4-morpholinyl)-2-oxoethyl]-2-oxo-1,2-dihydro-1,5-naphthyridine-3-carboxamide;

7-[(4-Fluorophenyl)methyl]-4-hydroxy-N-[2-(methyloxy)ethyl]-1-[2-(4-morpholinyl)-2-oxoethyl]-2-oxo-1,2-dihydro-1,5-naphthyridine-3-carboxamide;

7-[(4-Fluorophenyl)methyl]-4-hydroxy-N-(3-hydroxy-2,2-dimethylpropyl)-2-oxo-1,2-dihydro-1,5-naphthyridine-3-carboxamide;

7-[(4-Fluorophenyl)methyl]-4-hydroxy-N-{2-[(2-hydroxyethyl)oxy]ethyl}-2-oxo-1,2-dihydro-1,5-naphthyridine-3-carboxamide;

1-[2-(Dimethylamino)-2-oxoethyl]-7-[(4-fluorophenyl)methyl]-4-hydroxy-N-[2-(methyloxy)ethyl]-2-oxo-1,2-dihydro-1,5-naphthyridine-3-carboxamide;

1-[2-(Dimethylamino)-2-oxoethyl]-7-[(4-fluorophenyl)methyl]-4-hydroxy-N-[2-(4-morpholinyl)ethyl]-2-oxo-1,2-dihydro-1,5-naphthyridine-3-carboxamide;

7-[(Fluorophenyl)methyl]-4-hydroxy-1-[2-(4-morpholinyl)-2-oxoethyl]-N-[3-(4-morpholinyl)propyl]-2-oxo-1,2-dihydro-1,5-naphthyridine-3-carboxamide;

7-[(4-Fluorophenyl)methyl]-4-hydroxy-1-[2-(4-morpholinyl)-2-oxoethyl]-2-oxo-N-[3-(2-oxo-1-pyrrolidinyl)propyl]-1,2-dihydro-1,5-naphthyridine-3-carboxamide;

7-[(4-Fluorophenyl)methyl]-4-hydroxy-N-(2-hydroxyethyl)-1-[2-(4-morpholinyl)-2-oxoethyl]-2-oxo-1,2-dihydro-1,5-naphthyridine-3-carboxamide;

7-[(4-Fluorophenyl)methyl]-4-hydroxy-1-methyl-N-[2-(4-morpholinyl)ethyl]-2-oxo-1,2-dihydro-1,5-naphthyridine-3-carboxamide;

7-[(4-Fluorophenyl)methyl]-4-hydroxy-1-methyl-N-[3-(4-morpholinyl)propyl]-2-oxo-1,2-dihydro-1,5-naphthyridine-3-carboxamide;

7-[(4-Fluorophenyl)methyl]-4-hydroxy-1-methyl-2-oxo-N-[3-(2-oxo-1-pyrrolidinyl)propyl]-1,2-dihydro-1,5-naphthyridine-3-carboxamide;

7-[(4-Fluorophenyl)methyl]-4-hydroxy-N-(2-hydroxyethyl)-1-methyl-2-oxo-1,2-dihydro-1,5-naphthyridine-3-carboxamide;

7-[(4-Fluorophenyl)methyl]-4-hydroxy-N-[2-(methyloxy)ethyl]-1-[2-(4-methyl-1-piperazinyl)-2-oxoethyl]-2-oxo-1,2-dihydro-1,5-naphthyridine-3-carboxamide;

7-[(4-Fluorophenyl)methyl]-4-hydroxy-1-(2-{methyl[2-(methyloxy)ethyl]amino}-2-oxoethyl)-N-[2-(methyloxy)ethyl]-2-oxo-1,2-dihydro-1,5-naphthyridine-3-carboxamide;

(±)-7-[(4-Fluorophenyl)methyl]-4-hydroxy-N-[2-hydroxy-1-methylethyl]-1-(2-{methyl[2-(methyloxy)ethyl]amino}-2-oxoethyl)-2-oxo-1,2-dihydro-1,5-naphthyridine-3-carboxamide;

(±)-7-[(4-Fluorophenyl)methyl]-4-hydroxy-N-[(2-hydroxypropyl]-1-(2-{methyl[2-(methyloxy)ethyl]amino}-2-oxoethyl)-2-oxo-1,2-dihydro-1,5-naphthyridine-3-carboxamide;

N-[2-(ethyloxy)ethyl]-7-[(4-fluorophenyl)methyl]-4-hydroxy-1-(2-{methyl[2-(methyloxy)ethyl]amino}-2-oxoethyl)-2-oxo-1,2-dihydro-1,5-naphthyridine-3-carboxamide;

1-[2-(Dimethylamino)-2-oxoethyl]-7-(4-fluorobenzyl)-4-hydroxy-N-methyl-2-oxo-1,2-dihydro-1,5-naphthyridine-3-carboxamide;

or a pharmaceutically acceptable salt thereof.

2. A compound according claim 1 wherein the pharmaceutically acceptable salt is a sodium salt.

3. A method of treatment of an HIV infection in a human comprising administering to said human an antiviral effective amount of a compound according to claim 1.

4. A pharmaceutical composition comprising an effective amount of a compound according to claim 1 together with a pharmaceutically acceptable carrier.

5. A pharmaceutical composition according to claim 4 in the form of a tablet or capsule.

6. A pharmaceutical composition according to claim 4 in the form of a liquid or suspension.

7. A method of treatment of an HIV infection in a human comprising administering to said human a composition comprising a compound according to claim 1 and another therapeutic agent.

8. 7-[(4-Fluorophenyl)methyl]-4-hydroxy-N-(2-hydroxyethyl)-1-methyl-2-oxo-1,2-dihydro-1,5-naphthyridine-3-carboxamide or a pharmaceutically acceptable salt thereof.

9. 7-[(4-Fluorophenyl)methyl]-4-hydroxy-N-(2-hydroxyethyl)-1-methyl-2-oxo-1,2-dihydro-1,5-naphthyridine-3-carboxamide sodium salt.

10. A method of treatment of an HIV infection in a human comprising administering to said human an antiviral effective amount of 7-[(4-fluorophenyl)methyl]-4-hydroxy-N-(2-hydroxyethyl)-1-methyl-2-oxo-1,2-dihydro-1,5-naphthyridine-3-carboxamide or a pharmaceutically acceptable salt thereof.

11. A pharmaceutical composition comprising an effective amount of 7-[(4-fluorophenyl)methyl]-4-hydroxy-N-(2-hydroxyethyl)-1-methyl-2-oxo-1,2-dihydro-1,5-naphthyridine-3-carboxamide, or a pharmaceutically acceptable salt thereof, together with a pharmaceutically acceptable carrier.

12. A pharmaceutical composition according to claim 11 in the form of a tablet or capsule.

13. A pharmaceutical composition according to claim 11 in the form of a liquid or suspension.

14. A method of treatment of an HIV infection in a human comprising administering to said human a composition comprising 7-[(4-fluorophenyl)methyl]-4-hydroxy-N-(2-hydroxyethyl)-1-methyl-2-oxo-1,2-dihydro-1,5-naphthyridine-3-carboxamide, or a pharmaceutically acceptable salt thereof, and another therapeutic agent.

15. A pharmaceutical composition according to claim 11 wherein said composition comprises at least one additional therapeutic agent.

16. A compound selected from the group consisting of:
- sodium 1-ethyl-7-[(4-fluorophenyl)methyl]-3-({[(1S)-2-hydroxy-1-methylethyl]amino}carbonyl)-2-oxo-1,2-dihydro-1,5-naphthyridin-4-olate;
- 1-(2-Amino-2-oxoethyl)-7-[(4-fluorophenyl)methyl]-4-hydroxy-N-[2-(methyloxy)ethyl]-2-oxo-1,2-dihydro-1,5-naphthyridine-3-carboxamide;
- 1-(4-Fluorophenyl)-7-[(4-fluorophenyl)methyl]-4-hydroxy-N-(2-hydroxyethyl)-2-oxo-1,2-dihydro-1,5-naphthyridine-3-carboxamide;
- 7-(4-Fluorobenzyl)-4-hydroxy-N-[(2S)-2-hydroxypropyl]-2-oxo-1-[2-(2-oxopyrrolidin-1-yl)ethyl]-1,2-dihydro-1,5-naphthyridine-3-carboxamide;
- 7-(4-Fluorobenzyl)-4-hydroxy-N-[(2R)-2-hydroxypropyl]-2-oxo-1-[2-(2-oxopyrrolidin-1-yl)ethyl]-1,2-dihydro-1,5-naphthyridine-3-carboxamide;
- 7-[(4-Fluorophenyl)methyl]-4-hydroxy-1-[2-(methylamino)-2-oxoethyl]-N-[2-(methyloxy)ethyl]-2-oxo-1,2-dihydro-1,5-naphthyridine-3-carboxamide;
- 7-[(4-Fluorophenyl)methyl]-4-hydroxy-1-[(1-methyl-1H-imidazol-2-yl)methyl]-N-[2-(methyloxy)ethyl]-2-oxo-1,2-dihydro-1,5-naphthyridine-3-carboxamide;
- N-[(2R)-2,3-Dihydroxypropyl]-7-[(4-fluorophenyl)methyl]-4-hydroxy-1-methyl-2-oxo-1,2-dihydro-1,5-naphthyridine-3-carboxamide;
- 1-Ethyl-7-[(4-fluorophenyl)methyl]-4-hydroxy-N-[(1S)-2-hydroxy-1-methylethyl]-2-oxo-1,2-dihydro-1,5-naphthyridine-3-carboxamide;

or a pharmaceutically acceptable salt thereof.

17. A compound according claim 16 wherein the pharmaceutically acceptable salt is a sodium salt.

18. A method of treatment of an HIV infection in a human comprising administering to said human an antiviral effective amount of a compound according to claim 16.

19. A pharmaceutical composition comprising an effective amount of a compound according to claim 16 together with a pharmaceutically acceptable carrier.

20. A pharmaceutical composition according to claim 19 in the form of a tablet or capsule.

21. A pharmaceutical composition according to claim 19 in the form of a liquid or suspension.

22. A method of treatment of an HIV infection in a human comprising administering to said human a composition comprising a compound according to claim 16 and another therapeutic agent.

* * * * *